US007598226B2

(12) United States Patent
Jiang et al.

(10) Patent No.: US 7,598,226 B2
(45) Date of Patent: Oct. 6, 2009

(54) COMPOSITIONS AND METHODS FOR THE THERAPY AND DIAGNOSIS OF BREAST CANCER

(75) Inventors: Yuqiu Jiang, San Diego, CA (US); Davin C. Dillon, Issaquah, WA (US); Jennifer L. Mitcham, Redmond, WA (US); Jiangchun Xu, Bellevue, WA (US); Susan L. Harlocker, Seattle, WA (US)

(73) Assignee: Corixa Corporation, Wilmington, DE (US)

( * ) Notice: Subject to any disclaimer, the term of this patent is extended or adjusted under 35 U.S.C. 154(b) by 907 days.

(21) Appl. No.: 10/007,805

(22) Filed: Dec. 7, 2001

(65) Prior Publication Data

US 2002/0150581 A1 Oct. 17, 2002

Related U.S. Application Data

(63) Continuation-in-part of application No. 09/834,759, filed on Apr. 13, 2001, now Pat. No. 6,680,197, which is a continuation-in-part of application No. 09/620,405, filed on Jul. 20, 2000, now Pat. No. 6,528,054, which is a continuation-in-part of application No. 09/604,287, filed on Jun. 22, 2000, now Pat. No. 6,586,572, which is a continuation-in-part of application No. 09/590,751, filed on Jun. 8, 2000, now Pat. No. 6,756,477, which is a continuation-in-part of application No. 09/551,621, filed on Apr. 17, 2000, now Pat. No. 6,844,325, which is a continuation-in-part of application No. 09/433,826, filed on Nov. 3, 1999, now Pat. No. 6,579,973.

(51) Int. Cl.
*A01N 43/04* (2006.01)
*A61K 31/70* (2006.01)
*C07H 21/02* (2006.01)
*C07H 21/04* (2006.01)
*C12N 15/00* (2006.01)
*C12N 5/00* (2006.01)

(52) U.S. Cl. ............... 514/44; 435/320.1; 435/325; 536/23.1; 536/23.5

(58) Field of Classification Search ............ 536/23.1, 536/24.3, 24.31, 24.33, 23.5; 435/6, 320.1, 435/325; 514/44
See application file for complete search history.

(56) References Cited

U.S. PATENT DOCUMENTS

| | | | |
|---|---|---|---|
| 4,962,187 A | 10/1990 | Pant | 530/350 |
| 5,215,926 A | 6/1993 | Etchells, III et al. | 436/501 |
| 5,240,856 A | 8/1993 | Goffe et al. | 435/299 |
| 5,478,556 A | 12/1995 | Elliott et al. | 424/852 |
| 5,668,267 A | 9/1997 | Watson et al. | 536/23.15 |
| 5,843,435 A | 12/1998 | Slavin | 424/93.71 |
| 5,855,889 A | 1/1999 | Watson et al. | 424/185.1 |
| 5,861,381 A | 1/1999 | Chambon et al. | 514/44 |
| 5,891,857 A | 4/1999 | Holt et al. | |
| 5,922,836 A | 7/1999 | Watson et al. | 530/300 |
| 5,968,754 A | 10/1999 | Watson et al. | 435/7.23 |
| 5,981,731 A * | 11/1999 | Monia | 536/24.5 |
| 5,986,170 A | 11/1999 | Subjeck | 800/2 |
| 6,004,756 A | 12/1999 | Watson et al. | 435/6 |
| 6,150,168 A | 11/2000 | Woo et al. | 435/440 |
| 6,153,386 A * | 11/2000 | Lalouel et al. | 435/6 |
| 6,387,697 B1 | 5/2002 | Yuqiu et al. | 435/325 |
| 6,518,237 B1 | 2/2003 | Yuqiu et al. | 514/2 |
| 6,528,054 B1 | 3/2003 | Jiang et al. | 424/130.1 |
| 6,573,368 B2 | 6/2003 | Yuqiu et al. | 536/23.1 |
| 6,579,973 B1 | 6/2003 | Yuqiu et al. | 530/806 |
| 6,586,572 B2 | 7/2003 | Jiang et al. | 530/350 |
| 6,590,076 B1 | 7/2003 | Yuqiu et al. | 530/350 |
| 6,680,197 B2 | 1/2004 | Jiang et al. | 435/325 |
| 6,756,477 B1 | 6/2004 | Jiang et al. | 530/350 |
| 6,844,325 B2 * | 1/2005 | Jiang et al. | 514/44 |
| 6,958,361 B2 | 10/2005 | Houghton et al. | 514/885 |
| 6,969,518 B2 | 11/2005 | Houghton et al. | 424/138.1 |
| 2002/0009738 A1 | 1/2002 | Houghton et al. | 435/6 |
| 2002/0150581 A1 | 10/2002 | Jiang et al. | 424/155.1 |
| 2003/0170631 A1 | 9/2003 | Houghton et al. | 435/6 |

FOREIGN PATENT DOCUMENTS

| | | |
|---|---|---|
| CA | 2226901 A1 | 7/1998 |
| CA | 2226910 A1 | 10/1998 |
| CA | 2284642 A1 | 10/1998 |
| WO | WO 89/06280 | 7/1989 |
| WO | WO 91/16116 | 10/1991 |

(Continued)

OTHER PUBLICATIONS

Adams et al. GenBank Accession No. B15703. 1997.*
Adams et al. GenBank Accession No. B17512. 1997.*
Chen et al. GenBank Accession No. X88318.1.*
Adams et al. GenBank Accession No. AQ280806.*
Nyberg et al. Workshop on Long-Term Follow-up of Participants in Human Gene Transfer Research. Molecular Therapy. vol. 10., No. 6, Dec. 2004, pp. 976-980.*
Gura (Science, 1997, vol. 278, pp. 1041-1042).*
Hartwell et al. (Science, 1997, vol. 278, pp. 1064-1068).*

(Continued)

*Primary Examiner*—Janet L Epps-Smith
(74) *Attorney, Agent, or Firm*—Seed IP Law Group PLLC

(57) ABSTRACT

Compositions and methods for the therapy and diagnosis of cancer, particularly breast cancer, are disclosed. Illustrative compositions comprise one or more breast tumor polypeptides, immunogenic portions thereof, polynucleotides that encode such polypeptides, antigen presenting cell that expresses such polypeptides, and T cells that are specific for cells expressing such polypeptides. The disclosed compositions are useful, for example, in the diagnosis, prevention and/or treatment of diseases, particularly breast cancer.

4 Claims, 2 Drawing Sheets

FOREIGN PATENT DOCUMENTS

| WO | WO 91/16629 | 10/1991 |
|---|---|---|
| WO | WO 92/07243 | 4/1992 |
| WO | WO 96/29430 | 9/1996 |
| WO | WO 97/02280 | 1/1997 |
| WO | WO 97/22349 | 6/1997 |
| WO | WO 97/25426 | 7/1997 |
| WO | WO 97/25431 | 7/1997 |
| WO | WO 98/04742 | 2/1998 |
| WO | WO 98/21331 | 5/1998 |
| WO | WO 98/24928 | 6/1998 |
| WO | WO 98/33915 | 8/1998 |
| WO | WO 98/45328 | 10/1998 |
| WO | WO 98/54963 | 12/1998 |
| WO | WO 99/09155 | 2/1999 |
| WO | WO 99/14230 | 3/1999 |
| WO | WO 00/08210 | 2/2000 |
| WO | WO 00/37643 | 6/2000 |
| WO | WO 00/43420 | 7/2000 |
| WO | WO 00/60076 | 10/2000 |
| WO | WO 00/73801 | 12/2000 |
| WO | WO 01/37779 | 5/2001 |
| WO | WO 01/47959 | 7/2001 |
| WO | WO 01/51628 | 7/2001 |
| WO | WO 01/57270 | 8/2001 |
| WO | WO 01/75171 | 10/2001 |
| WO | WO 01/79286 | 10/2001 |
| WO | WO 02/059377 | 8/2002 |
| WO | WO 02/083956 | 10/2002 |

OTHER PUBLICATIONS

GenBank Accession No. AI951118. (First appeared in GenBank-NCBI on Aug. 19, 1999).*
Anderson, W. French. Human Gene Therapy. Apr. 30, 1998, Nature, vol. 392, pp. 25-30.*
Mullins JJ et al. Hypertension 22:630-633, 1993.*
Cameron ER. Molecular Biotechnology 7:253-265, 1997.*
Hammer RE et al. Cell 63:1099-1112. 1990.*
Smith. Journal of Biotechnology 99: 1-22, 2002.*
Gardner et al. International Journal of Developmental Biology. (1997), vol. 41, pp. 235-243.*
GenBank Accession No. AI687645, May 27, 1999.
GenBank Accession No. AQ280806, Nov. 22, 1998.
Genseq (Derwent) Accession No. AAV90219, Feb. 15, 1999.
GenBank Accession No. AC069200, May 24, 2000.
Sulston et al., "Toward a complete human genome sequence," *Genome Research* 8(11):1097-1108, 1998.
GenBank Accession No. AL157387, Feb. 18, 2000.
GenBank Accession No. AC036170, Apr. 9, 2000.
Chang and Shu, "Current status of adoptive immunotherapy of cancer," *Critical Reviews in Oncology/Hematology* 22(3):213-228, Apr. 1996.
Cheever and Chen, "Therapy with cultured T cells: principles revisited," *Immunological Reviews*, 157: 177-194, 1997.
Cheever et al., "Potential uses of interleukin 2 in cancer therapy," *Immunobiol*, 172:365-382, 1986.
Chen et al., "T-cells for tumor therapy can be obtained from antigen-loaded sponge implants," *Cancer Research* 54(4):1065-1070, Feb. 15, 1994.
Cole et al., "Characterization of the functional specificity of a cloned T-cell receptor heterodimer recognizing the MART-1 melanoma antigent," *Cancer Research*, 55:748-752, Feb. 15, 1995.
Durrant L., "Cancer vaccines," *Anti-Cancer Drugs*, 8:727-733, 1997.
Eshhar Z., "Tumor-specific T-bodies: toward clinical application," *Cancer Immunol Immnother*, 45:131-136, 1997.
GenBank Accession No. AF269087, Mar. 28, 2001.
GenBank Accession No. AAK27325, Mar. 28, 2001.
GenBank Accession No. AA864891, Feb. 20, 1998.
GenBank Accession No. AA398925, Apr. 25, 1997.
Genseq Accession No. V84525 (Dec. 10, 1998).

Hwu et al., "In vivo antitumor activity of T cells redirected with chimeric antibody/T-cell receptor genes," *Cancer Research*, 55:3369-3373, Aug. 1, 1995.
Porter-Jordan and Lippman, "Overview of the biologic markers of breast cancer," *Breast Cancer* 8:(1):73-100, Feb. 1994.
Prilliman et al., "HLA-B15 peptide ligands are preferentially anchored at their c termini," *The Journal of Immunology* 162(12):7277-7284, Jun. 15, 1999.
Stratagene 1991 product catalog, Prime-It™ Random Labeling Kit, catalog No. 300387, p. 66.
Wei et al., "Protection against mammary tumor growth by vaccination with full-length, modified human *ErbB-2* DNA," *Int. J. Cancer*, 81:748-754, 1999.
GenBank Accession No. AL359312, Dec. 7, 2001.
Jäger et al., "Identification of a tissue-specific putative transcription factor in breast tissue by serological screening of a breast cancer library," *Cancer Research* 61(5):2055-2061, Mar. 1, 2001.
GenBank Accession No. AF269087, Mar. 28, 2001.
Alberts et al. Mol. Biol. Cell, 3$^{rd}$ ed., p. 455, 1994.
Anderson and Seilhamer, "A comparison of selected MRNA and protein abundances in human liver", *Electrophoresis* 18: 533-537, 1997.
Boon, T., "Toward a Genetic Analysis of Tumor Rejection Antigens", *Adv. Cancer Res.* 58: 177-210, 1992.
Bork, P., "Powers and Pitfalls in Sequence Analysis: The 70% Hurdle", *Genome Research* 10(4): 398-400, Apr. 2000.
Burgess, W.H. et al., "Possible Dissociation of the Heparin-binding and Mitogenic Activities of Heparin-binding (Acidic Fibroblast) Growth Factor-1 from Its Receptor-binding Activities by Site-directed Mutagenesis of a Single Lysine Residue", *Journal of Cell Biology* 111:2129-2138, Nov. 1990.
Cheli et al., *Clin Chem.* 44(4): 765-72, 1998.
Conner et al., *Mol Brain Res.* 42: 1-17, 1996.
Curti, B.D., "Physical barriers to drug delivery in tumors", *Critical Reviews in Oncology/Hematology* 14: 29-39, 1993.
Dermer., *Bio/Technol.* 12: 320, 1994.
Doerks, T. et al., "Protein annotation: detective work for function prediction", *Trends in Genetics* 14(6): 248-250, Jun. 1998.
Ezzell, C., "Cancer 'Vaccines': An Idea Whose Time Has Come?" *The Journal of NIH Research* 7: 46-49, Jan. 1995.
Freshney, Cult. Animal Cells, A Manual of Basic Technique, Alan R. Lisc. Inc. p. 4, 1983.
Fu et al., *EMBO J.* 15: 4392-4401, 1996.
Gaubin et al., *J Immunol.* 1999, 162(5): 2631-8.
GenBank Database, Accession No. AA219147, Feb. 7, 1997.
GenBank Database, Accession No. AI272025, Nov. 17, 1998.
GenBank Database, Accession No. AL049911, Oct. 22, 1999.
Geneseq (Derwent) Database, Accession No. AAV41453, Oct. 12, 1998.
Geneseq (Derwent) Database, Accession No. V90219, 1998.
Geneseq Database (Derwent), Accession No. AAL25059, Dec. 7, 2001.
Gillies and Wesolowski, "Antigen binding and biological activities of engineered mutant chimeric antibodies with human tumor specificities", *Hum Antibod. Hybridomas* 1(1): 47-54, 1990.
Greenbaum et al, *Genome Biology* 4(9): 117.1-117.8), 2003.
Hell et al, *Laboratory Investigation* 73: 492-496, 1995.
Jain, R.K., "Barriers to Drug Delivery in Solid Tumors", *Scientific American* 271(1): 58-65, Jul. 1994.
Kawakami et al., *Cancer Science* 95(10): 784-791, Oct. 2004.
Lazar, E. et al., "Transforming Growth Factor α: Mutation of Aspartic Acid 47 and Leucine 48 Results in Different Biological Activities", *Molecular and Cellular Biology* 8(3): 1247-1252, Mar. 1988.
Lewin, B, ed., 1983, Genes, John Wiley & Sons, New York, pp. 72-74.
McClean et al., *Eur. J. Cancer* 29A(16): 2243-2248, 1993.
Moutsopoulos et al., *Molecular Medicine* 6(3): 141-151, 2000.
MPSRCH search report, 2006, pp. 1-3.
Russel and Barton, "Structural Features can be Unconserved in Proteins with Similar Folds. An Analysis of Side-chain to Side-chain Contacts Secondary Structure and Accessability", *J. Mol. Biol.* 244: 332-350, 1994.
Schmid S et al, 2001, J Comparative Neurology, 430(2): 160-171.

Shantz. et al., J. Biochem. Cell Biol. 31: 107-122, 1999.
Skolnick and Fetrow, "From genes to protein structure and function: novel applications of computational approaches in the genomic era", *Trends in Biotechnology* 18: 34-39, Jan. 2000.
Spitler, L.E., "Cancer Vaccines: The Interferon Analogy", *Cancer Biotherapy* 10(1): 1-3, 1995.
Tao et al., *J. Immunol.* 143(8): 2595-2601, 1989.
Wang et al., *J Immunol* 161(7): 3598-3606, 1998.
Watson et al., Methods of Creating Recombinant DNA Molecules, (Recombinant DNA Second Edition, pp. 63-77) 1994.
White et al., *Ann Rev Med 52*: 125-145, 2001.
Wright et al., *Genome Biology* vol. 2(7): research0025.1-0025.18, Jul. 2001.
Yokota, J et al., *Oncogene* 3: 471-475, 1988.
GenBank Database, Accession No. XP_035844, Jul. 16, 2001.
Kang, D.-C. et al., "Reciprocal subtraction differential RNA display: An efficient and rapid procedure for isolating differentially expressed gene sequences," *Proc. Natl. Acad. Sci. USA* 95:13788-13793, Nov. 1998.
Goto, Y. et al., "A Novel Human Insulinoma-associated cDNA, IA-1, Encodes a Protein with 'Zinc-finger' DNA-binding Motifs," *The Journal of Biological Chemistry* 267(21):15252-15257, Jul. 25, 1992.
Lucas, S. et al., "Identification of a New *MAGE* Gene with Tumor-specific Expression by Representational Difference Analysis," *Cancer Research* 58:743-752, Feb. 15, 1998.
Schweinfest, C.W. et al., "Subtraction Hybridization cDNA Libraries From Colon Carcinoma and Hepatic Cancer," *Genetic Analysis, Techniques and Applications* 7(3):64-70. May 1990.
Thompson, T.N., "Optimization of Metabolic Stability as a Goal of Modern Drug Design," *Medicinal Research Reviews* 21(5):412-449, 2001.
Xie, H. et al., "IA-2, a Transmembrane Protein Tyrosine Phosphatase, Is Expressed in Human Lung Cancer Cell Lines with Neuroendocrine Phenotype," *Cancer Research* 56:2742-2744, Jun. 15, 1996.
Bodey, B. et al., "Failure of Cancer Vaccines: The Significant Limitation of the Approach to Immunotherapy," *Anticancer Research* 20:2665-2676, 2000.
Burmer, G.C. et al., "Frequency and Spectrum of c-Ki-*ras* Mutations in Human Sporadic Colon Carcinoma, Carcinomas Arising in Ulcerative Colitis, and Pancreatic Adenocarcinoma," *Environmental Health Perspectives* 93:27-31, 1991.
Buskens, C. et al., "Adenocarcinomas of the Gastro-Esophageal Junction: A Comparative Study of the Gastric Cardia and the Esophagus with Respect to Cyclooxygenase-2 Expression," *Digestive Disease Week Abstracts and Itinerary Planner*, Abstract No. 850, 2003.
Geneseq Database, Accession No. AAA59007, Nov. 7, 2000.
Geneseq Database, Accession No. AAA59008, Nov. 7, 2000.
Geneseq Database, Accession No. AAA59009, Nov. 7, 2000.
Geneseq Database, Accession No. AAA59010, Nov. 7, 2000.
Geneseq Database, Accession No. AAA59011, Nov. 7, 2000.
Geneseq Database, Accession No. AAA59012, Nov. 7, 2000.
Geneseq Database, Accession No. AAA59013, Nov. 7, 2000.
Geneseq Database, Accession No. AAA59014, Nov. 7, 2000.
Geneseq Database, Accession No. AAA59015, Nov. 7, 2000.
Geneseq Database, Accession No. AAB07638, Nov. 7, 2000.
Geneseq Database, Accession No. AAB07639, Nov. 7, 2000.
Geneseq Database, Accession No. AAB07640, Nov. 7, 2000.
Geneseq Database, Accession No. AAB07641, Nov. 7, 2000.
Geneseq Database, Accession No. AAB07642, Nov. 7, 2000.
Geneseq Database, Accession No. AAB63900, Mar. 26, 2001.
Geneseq Database, Accession No. AAB63901, Mar. 26, 2001.
Geneseq Database, Accession No. AAB63903, Mar. 26, 2001.
Geneseq Database, Accession No. AAB63905, Mar. 26, 2001.
Geneseq Database, Accession No. AAB63906, Mar. 26, 2001.
Geneseq Database, Accession No. AAB63907, Mar. 26, 2001.
Geneseq Database, Accession No. AAB63909, Mar. 26, 2001.
Geneseq Database, Accession No. AAB63911, Mar. 26, 2001.
Geneseq Database, Accession No. AAB63913, Mar. 26, 2001.
Geneseq Database, Accession No. AAB63915, Mar. 26, 2001.
Geneseq Database, Accession No. AAB63916, Mar. 26, 2001.
Geneseq Database, Accession No. AAB63917, Mar. 26, 2001.
Geneseq Database, Accession No. AAB63918, Mar. 26, 2001.
Geneseq Database, Accession No. AAB63919, Mar. 26, 2001.
Geneseq Database, Accession No. AAB63922, Mar. 26, 2001.
Geneseq Database, Accession No. AAB63925, Mar. 26, 2001.
Geneseq Database, Accession No. AAB63926, Mar. 26, 2001.
Geneseq Database, Accession No. AAB63929, Mar. 26, 2001.
Geneseq Database, Accession No. AAB63931, Mar. 26, 2001.
Geneseq Database, Accession No. AAB63933, Mar. 26, 2001.
Geneseq Database, Accession No. AAB63935, Mar. 26, 2001.
Geneseq Database, Accession No. AAB63938, Mar. 26, 2001.
Geneseq Database, Accession No. AAB63939, Mar. 26, 2001.
Geneseq Database, Accession No. AAB63942, Mar. 26, 2001.
Geneseq Database, Accession No. AAB63943, Mar. 26, 2001.
Geneseq Database, Accession No. AAB63945, Mar. 26, 2001.
Geneseq Database, Accession No. AAB63965, Mar. 26, 2001.
Geneseq Database, Accession No. AAB84701, Sep. 17, 2001.
Geneseq Database, Accession No. AAB84702, Sep. 17, 2001.
Geneseq Database, Accession No. AAD06847, Aug. 6, 2001.
Geneseq Database, Accession No. AAF22978, Mar. 26, 2001.
Geneseq Database, Accession No. AAF22993, Mar. 26, 2001.
Geneseq Database, Accession No. AAH28489, Sep. 17, 2001.
Geneseq Database, Accession No. AAI03961, Oct. 9, 2001.
Geneseq Database, Accession No. AAM05199, Oct. 9, 2001.
Geneseq Database, Accession No. AAZ91768, Jun. 1, 2000.
Geneseq Database, Accession No. ABJ05537, Nov. 14, 2002.
Geneseq Database, Accession No. ABT07694, Nov. 14, 2002.
Jiang, Y. et al., "Discovery of differentially expressed genes in human breast cancer using subtracted cDNA libraries and cDNA microarrays," *Oncogene* 21:2270-2282, 2002.
Kaiser, J., "First Pass at Cancer Genome Reveals Complex Landscape," *Science* 313:1370, Sep. 8, 2006.
Kirkin, A.F. et al., "Melanoma-associated antigens recognized by cytotoxic T lymphocytes," *APMIS* 106:665-679, 1998.
Lee, K.-H. et al., "Increased Vaccine-Specific T Cell Frequency After Peptide-Based Vaccination Correlates with Increased Susceptibility to In Vitro Stimulation But Does Not Lead to Tumor Regression," *Journal of Immunology* 163:6292-6300, 1999.
Montesano, R., "Genetic Alteration in Esophageal Cancer and Their Relevance to Etiology and Pathogenesis: A Review," *International Journal of Cancer* 69(3):225-235, 1996.
Smith, R.T., "Cancer and the Immune System," *Clinical Immunology* 41(4):841-849, Aug. 1994.
Xu, J. et al., "Identification of Differentially Expressed Genes in Human Prostate Cancer Using Subtraction and Microarray," *Cancer Research* 60:1677-1682, Mar. 15, 2000.
Xu, J. et al., "Identification of differentially expressed genes in human breast tumor using subtraction and microarray," *Proceedings of the American Association for Cancer Research. Annual Meeting* 40:319, Abstract #2115, 1999.
Zehentner, B.K. et al., "Application of a Multigene Reverse Transcription-PCR Assay for Detection of Mammaglobin and Complementary Transcribed Genes in Breast Cancer Lymph Nodes," *Clinical Chemistry* 48(8):1225-1231, 2002.

* cited by examiner

SYN18C6 Northern Blot

COMPOSITIONS AND METHODS FOR THE THERAPY AND DIAGNOSIS OF BREAST CANCER

CROSS REFERENCE TO RELATED APPLICATIONS

This application is a Continuation-In-Part of U.S. patent application Ser. No. 09/834,759, filed Apr. 13, 2001 now U.S. Pat. No. 6,680,197 which is a Continuation-In-Part of U.S. patent application Ser. No. 09/620,405, filed Jul. 20, 2000, now U.S. Pat. No. 6,528,054 which is a Continuation-In-Part of U.S. patent application Ser. No. 09/604,287, filed Jun. 22, 2000, now U.S. Pat. No. 6,586,572 which is a Continuation-In-Part of U.S. patent application Ser. No. 09/590,751, filed Jun. 8, 2000, which is a Continuation-In-Part of U.S. patent application Ser. No. 09/551,621, filed Apr. 17, 2000, which is a Continuation-In-Part of U.S. patent application Ser. No. 09/433,826, filed on Nov. 3, 1999, now U.S. Pat. No. 6,579,973 which is a Continuation-In-Part of U.S. application Ser. No. 09/389,681, filed on Sep. 2, 1999, now U.S. Pat. No. 6,518,237 which is a Continuation-In-Part of U.S. application Ser. No. 09/339,338, filed on Jun. 23, 1999, now U.S. Pat. No. 6,573,368 which is a Continuation-In-Part of U.S. application Ser. No. 09/285,480, filed on Apr. 2, 1999, now U.S. Pat. No. 6,590,076 which is a Continuation-In-Part of U.S. application Ser. No. 09/222,575, filed Dec. 28, 1998 now U.S. Pat No. 6,387,697.

TECHNICAL FIELD OF THE INVENTION

The present invention relates generally to therapy and diagnosis of cancer, such as breast cancer. The invention is more specifically related to polypeptides, comprising at least a portion of a breast tumor protein, and to polynucleotides encoding such polypeptides. Such polypeptides and polynucleotides are useful in pharmaceutical compositions, e.g., vaccines, and other compositions for the diagnosis and treatment of breast cancer.

BACKGROUND OF THE INVENTION

1. Field of the Invention

Breast cancer is a significant health problem for women in the United States and throughout the world. Although advances have been made in detection and treatment of the disease, breast cancer remains the second leading cause of cancer-related deaths in women, affecting more than 180,000 women in the United States each year. For women in North America, the life-time odds of getting breast cancer are one in eight.

2. Description of the Related Art

No vaccine or other universally successful method for the prevention or treatment of breast cancer is currently available. Management of the disease currently relies on a combination of early diagnosis (through routine breast screening procedures) and aggressive treatment, which may include one or more of a variety of treatments such as surgery, radiotherapy, chemotherapy and hormone therapy. The course of treatment for a particular breast cancer is often selected based on a variety of prognostic parameters, including an analysis of specific tumor markers. See, e.g., Porter-Jordan and Lippman, *Breast Cancer* 8:73-100 (1994). However, the use of established markers often leads to a result that is difficult to interpret, and the high mortality observed in breast cancer patients indicates that improvements are needed in the treatment, diagnosis and prevention of the disease.

Accordingly, there is a need in the art for improved methods for the treatment and diagnosis of breast cancer. The present invention fulfills these needs and further provides other related advantages.

SUMMARY OF THE INVENTION

In one aspect, the present invention provides polynucleotide compositions comprising a sequence selected from the group consisting of:

(a) sequences provided in SEQ ID NO:1-61, 63-175, 178, 180, 182-468, 474, 476, 477, 479, 482, 484, 486, 489-492, 504-506, 510-513, 520-533, 548-550, 564, 566-569, and 576;

(b) complements of the sequences provided in SEQ ID NO:1-61, 63-175, 178, 180, 182-468, 474, 476, 477, 479, 482, 484, 486, 489-492, 504-506, 510-513, 520-533, 548-550, 564, 566-569, and 576;

(c) sequences consisting of at least 20 contiguous residues of a sequence provided in SEQ ID NO:1-61, 63-175, 178, 180, 182-468, 474, 476, 477, 479, 482, 484, 486, 489-492, 504-506, 510-513, 520-533, 548-550, 564, 566-569, and 576;

(d) sequences that hybridize to a sequence provided in SEQ ID NO:1-61, 63-175, 178, 180, 182-468, 474, 476, 477, 479, 482, 484, 486, 489-492, 504-506, 510-513, 520-533, 548-550, 564, 566-569, and 576, under moderately stringent conditions;

(e) sequences having at least 75% identity to a sequence of SEQ ID NO:1-61, 63-175, 178, 180, 182-468, 474, 476, 477, 479, 482, 484, 486, 489-492, 504-506, 510-513, 520-533, 548-550, 564, 566-569, and 576;

(f) sequences having at least 90% identity to a sequence of SEQ ID NO:1-61, 63-175, 178, 180, 182-468, 474, 476, 477, 479, 482, 484, 486, 489-492, 504-506, 510-513, 520-533, 548-550, 564, 566-569, and 576; and (g) degenerate variants of a sequence provided in SEQ ID NO:1-61, 63-175, 178, 180, 182-468, 474, 476, 477, 479, 482, 484, 486, 489-492, 504-506, 510-513, 520-533, 548-550, 564, 566-569, and 576.

In one preferred embodiment, the polynucleotide compositions of the invention are expressed in at least about 20%, more preferably in at least about 30%, and most preferably in at least about 50% of breast tumors samples tested, at a level that is at least about 2-fold, preferably at least about 5-fold, and most preferably at least about 10-fold higher than that for normal tissues.

The present invention, in another aspect, provides polypeptide compositions comprising an amino acid sequence that is encoded by a polynucleotide sequence described above.

The present invention further provides polypeptide compositions comprising an amino acid sequence selected from the group consisting of sequences recited in SEQ ID NO:62, 176, 179, 181, 469-473, 475, 478, 483, 485, 487, 488, 493-503, 507-509, 514-519, 534-547, 551-553, 565, 570-573, and 577-593.

In certain preferred embodiments, the polypeptides and/or polynucleotides of the present invention are immunogenic, i.e., they are capable of eliciting an immune response, particularly a humoral and/or cellular immune response, as further described herein.

The present invention further provides fragments, variants and/or derivatives of the disclosed polypeptide and/or polynucleotide sequences, wherein the fragments, variants and/or derivatives preferably have a level of immunogenic activity of at least about 50%, preferably at least about 70% and more preferably at least about 90% of the level of immunogenic activity of a polypeptide sequence set forth in SEQ ID NOs: 62, 176, 179, 181, 469-473, 475, 478, 483, 485, 487, 488, 493-503, 507-509, 514-519, 534-547, 551-553, 565, 570-573, and 577-593 or a polypeptide sequence encoded by a polynucleotide sequence set forth in SEQ ID NOs: 1-61, 63-175, 178, 180, 182-468, 474, 476, 477, 479, 482, 484, 486, 489-492, 504-506, 510-513, 520-533, 548-550, 564, 566-569, and 576.

The present invention further provides polynucleotides that encode a polypeptide described above, expression vectors comprising such polynucleotides and host cells transformed or transfected with such expression vectors.

Within other aspects, the present invention provides pharmaceutical compositions comprising a polypeptide or polynucleotide as described above and a physiologically acceptable carrier.

Within a related aspect of the present invention, the pharmaceutical compositions, e.g., vaccine compositions, are provided for prophylactic or therapeutic applications. Such compositions generally comprise an immunogenic polypeptide or polynucleotide of the invention and an immunostimulant, such as an adjuvant.

The present invention further provides pharmaceutical compositions that comprise: (a) an antibody or antigen-binding fragment thereof that specifically binds to a polypeptide of the present invention, or a fragment thereof; and (b) a physiologically acceptable carrier.

Within further aspects, the present invention provides pharmaceutical compositions comprising: (a) an antigen presenting cell that expresses a polypeptide as described above and (b) a pharmaceutically acceptable carrier or excipient. Illustrative antigen presenting cells include dendritic cells, macrophages, monocytes, fibroblasts and B cells.

Within related aspects, pharmaceutical compositions are provided that comprise: (a) an antigen presenting cell that expresses a polypeptide as described above and (b) an immunostimulant.

The present invention further provides, in other aspects, fusion proteins that comprise at least one polypeptide as described above, as well as polynucleotides encoding such fusion proteins, typically in the form of pharmaceutical compositions, e.g., vaccine compositions, comprising a physiologically acceptable carrier and/or an immunostimulant. The fusions proteins may comprise multiple immunogenic polypeptides or portions/variants thereof, as described herein, and may further comprise one or more polypeptide segments for facilitating the expression, purification and/or immunogenicity of the polypeptide(s).

The present invention further provides, in other aspects, fusion proteins that comprise at least one polypeptide as described above, as well as polynucleotides encoding such fusion proteins. Exemplary fusion proteins according to the present invention comprise a first amino acid portion and a second amino acid portion wherein the first amino acid portion includes 9 or more contiguous amino acids from mammaglobin as depicted by amino acids 1-93 of SEQ ID NO:493 (SEQ ID NO:503); wherein the second amino acid portion includes 9 or more contiguous amino acids from B726P as depicted by SEQ ID NO:475, SEQ ID NO:469, or SEQ ID NO:176; and wherein the first amino acid portion is connected to either the amino terminal or carboxy-terminal end of the second amino acid portion.

Still further embodiments of the present invention provide fusion proteins wherein said first amino acid portion is selected from the group consisting of: IDELKECFLNQTDE-TLSNVE (SEQ ID NO:496; amino acids 59-78 of SEQ ID NO:493); TTNAIDELKECFLNQ (SEQ ID NO:497; amino acids 55-69 of SEQ ID NO:493); SQHCYAGSGCPLLEN-VISKTI (SEQ ID NO:498; amino acids 13-33 of SEQ ID NO:493); EYKELLQEFIDDNATTNAID (SEQ ID NO:499; amino acids 41-60 of SEQ ID NO:493); KLLMVLMLA (SEQ ID NO:500; amino acids 2-10 of SEQ ID NO:493); QEFIDDNATTNAI (SEQ ID NO:501; amino acids 47-59 of SEQ ID NO:493); LKECFLNQTDETL (SEQ ID NO:502; amino acids 62-74 of SEQ ID NO:493), and any one of the amino acid sequences set forth in SEQ ID NOs:578-593.

Alternative embodiments provide fusion proteins wherein the second amino acid portion includes 9 or more contiguous amino acids encoded by (1) the combined upstream and downstream open reading frame (ORF) of B726P as depicted in SEQ ID NO:475; (2) the upstream ORF of B726P as depicted in SEQ ID NO:469; and (3) the downstream ORF of B726P as depicted in SEQ ID NO:176. Fusion proteins according to the present invention may also comprise a second amino acid portion that includes 9 or more contiguous amino acids from the amino acid sequence depicted by amino acids 1-129 of SEQ ID NO:475. Still additional exemplary fusion proteins are depicted herein by SEQ ID NO:493, SEQ ID NO:494, and SEQ ID NO:495.

Fusion proteins are provided wherein the mammaglobin amino acid portion is connected to the amino-terminus of the B726P amino acid portion while other fusion proteins are provided wherein the mammaglobin amino acid portion is connected to the carboxy-terminus of the B726P amino acid portion. The connection between the mammaglobin amino acid portion and the B726P portion may be a covalent bond. Additionally, a stretch of amino acids either unrelated or related to either mammaglobin and/or B726P may be incorporated between or either amino- or carboxy-terminal to either the mammaglobin and/or B726P amino acid portion.

The present invention also provides isolated polynucleotides that encode any of the fusion proteins that are specifically disclosed herein as well as those fusion proteins that may be accomplished with routine experimentation by the ordinarily skilled artisan.

Within further aspects, the present invention provides methods for stimulating an immune response in a patient, preferably a T cell response in a human patient, comprising administering a pharmaceutical composition described herein. The patient may be afflicted with breast cancer, in which case the methods provide treatment for the disease, or patient considered at risk for such a disease may be treated prophylactically.

Within further aspects, the present invention provides methods for inhibiting the development of a cancer in a patient, comprising administering to a patient a pharmaceutical composition as recited above. The patient may be afflicted with breast cancer, in which case the methods provide treatment for the disease, or patient considered at risk for such a disease may be treated prophylactically.

The present invention further provides, within other aspects, methods for removing tumor cells from a biological sample, comprising contacting a biological sample with T cells that specifically react with a polypeptide of the present invention, wherein the step of contacting is performed under conditions and for a time sufficient to permit the removal of cells expressing the protein from the sample.

Within related aspects, methods are provided for inhibiting the development of a cancer in a patient, comprising administering to a patient a biological sample treated as described above.

Methods are further provided, within other aspects, for stimulating and/or expanding T cells specific for a polypeptide of the present invention, comprising contacting T cells with one or more of: (i) a polypeptide as described above; (ii) a polynucleotide encoding such a polypeptide; and/or (iii) an antigen presenting cell that expresses such a polypeptide; under conditions and for a time sufficient to permit the stimulation and/or expansion of T cells. Isolated T cell populations comprising T cells prepared as described above are also provided.

Within further aspects, the present invention provides methods for inhibiting the development of a cancer in a patient, comprising administering to a patient an effective amount of a T cell population as described above.

The present invention further provides methods for inhibiting the development of a cancer in a patient, comprising the steps of: (a) incubating CD4+ and/or CD8+ T cells isolated from a patient with one or more of: (i) a polypeptide comprising at least an immunogenic portion of polypeptide disclosed herein; (ii) a polynucleotide encoding such a polypeptide; and (iii) an antigen-presenting cell that expressed such a polypeptide; and (b) administering to the patient an effective amount of the proliferated T cells, and thereby inhibiting the development of a cancer in the patient. Proliferated cells may, but need not, be cloned prior to administration to the patient.

Within further aspects, the present invention provides methods for determining the presence or absence of a cancer, preferably a breast cancer, in a patient comprising: (a) contacting a biological sample obtained from a patient with a binding agent that binds to a polypeptide as recited above; (b) detecting in the sample an amount of polypeptide that binds to the binding agent; and (c) comparing the amount of polypeptide with a predetermined cut-off value, and therefrom determining the presence or absence of a cancer in the patient. Within preferred embodiments, the binding agent is an antibody, more preferably a monoclonal antibody.

The present invention also provides, within other aspects, methods for monitoring the progression of a cancer in a patient. Such methods comprise the steps of: (a) contacting a biological sample obtained from a patient at a first point in time with a binding agent that binds to a polypeptide as recited above; (b) detecting in the sample an amount of polypeptide that binds to the binding agent; (c) repeating steps (a) and (b) using a biological sample obtained from the patient at a subsequent point in time; and (d) comparing the amount of polypeptide detected in step (c) with the amount detected in step (b) and therefrom monitoring the progression of the cancer in the patient.

The present invention further provides, within other aspects, methods for determining the presence or absence of a cancer in a patient, comprising the steps of: (a) contacting a biological sample obtained from a patient with an oligonucleotide that hybridizes to a polynucleotide that encodes a polypeptide of the present invention; (b) detecting in the sample a level of a polynucleotide, preferably mRNA, that hybridizes to the oligonucleotide; and (c) comparing the level of polynucleotide that hybridizes to the oligonucleotide with a predetermined cut-off value, and therefrom determining the presence or absence of a cancer in the patient. Within certain embodiments, the amount of mRNA is detected via polymerase chain reaction using, for example, at least one oligonucleotide primer that hybridizes to a polynucleotide encoding a polypeptide as recited above, or a complement of such a polynucleotide. Within other embodiments, the amount of mRNA is detected using a hybridization technique, employing an oligonucleotide probe that hybridizes to a polynucleotide that encodes a polypeptide as recited above, or a complement of such a polynucleotide.

In related aspects, methods are provided for monitoring the progression of a cancer in a patient, comprising the steps of: (a) contacting a biological sample obtained from a patient with an oligonucleotide that hybridizes to a polynucleotide that encodes a polypeptide of the present invention; (b) detecting in the sample an amount of a polynucleotide that hybridizes to the oligonucleotide; (c) repeating steps (a) and (b) using a biological sample obtained from the patient at a subsequent point in time; and (d) comparing the amount of polynucleotide detected in step (c) with the amount detected in step (b) and therefrom monitoring the progression of the cancer in the patient.

Within further aspects, the present invention provides antibodies, such as monoclonal antibodies, that bind to a polypeptide as described above, as well as diagnostic kits comprising such antibodies. Diagnostic kits comprising one or more oligonucleotide probes or primers as described above are also provided.

These and other aspects of the present invention will become apparent upon reference to the following detailed description and attached drawings. All references disclosed herein are hereby incorporated by reference in their entirety as if each was incorporated individually.

BRIEF DESCRIPTION OF THE DRAWINGS AND SEQUENCE IDENTIFIERS

Figure 1:
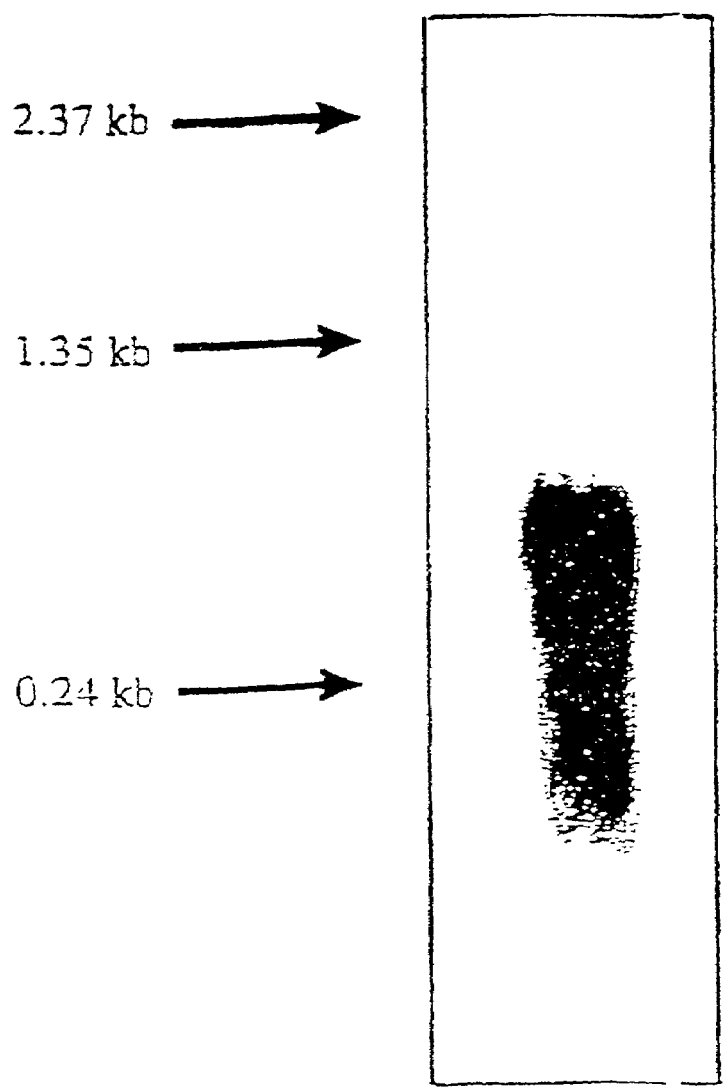
FIG. 1 shows the results of a Northern blot of the clone SYN18C6 (SEQ ID NO:40).

SEQ ID NO:1 is the determined cDNA sequence of JBT2.
SEQ ID NO:2 is the determined cDNA sequence of JBT6.
SEQ ID NO:3 is the determined cDNA sequence of JBT7.
SEQ ID NO:4 is the determined cDNA sequence of JBT10.
SEQ ID NO:5 is the determined cDNA sequence of JBT13.
SEQ ID NO:6 is the determined cDNA sequence of JBT14.
SEQ ID NO:7 is the determined cDNA sequence of JBT15.
SEQ ID NO:8 is the determined cDNA sequence of JBT16.
SEQ ID NO:9 is the determined cDNA sequence of JBT17.
SEQ ID NO:10 is the determined cDNA sequence of JBT22.
SEQ ID NO:11 is the determined cDNA sequence of JBT25.
SEQ ID NO:12 is the determined cDNA sequence of JBT28.
SEQ ID NO:13 is the determined cDNA sequence of JBT32.
SEQ ID NO:14 is the determined cDNA sequence of JBT33.
SEQ ID NO:15 is the determined cDNA sequence of JBT34.
SEQ ID NO:16 is the determined cDNA sequence of JBT36.
SEQ ID NO:17 is the determined cDNA sequence of JBT37.
SEQ ID NO:18 is the determined cDNA sequence of JBT51.
SEQ ID NO:19 is the determined cDNA sequence of JBTT1.
SEQ ID NO:20 is the determined cDNA sequence of JBTT7.
SEQ ID NO:21 is the determined cDNA sequence of JBTT11.
SEQ ID NO:22 is the determined cDNA sequence of JBTT14.
SEQ ID NO:23 is the determined cDNA sequence of JBTT18.
SEQ ID NO:24 is the determined cDNA sequence of JBTT19.

SEQ ID NO:25 is the determined cDNA sequence of JBTT20.

SEQ ID NO:26 is the determined cDNA sequence of JBTT21.

SEQ ID NO:27 is the determined cDNA sequence of JBTT22.

SEQ ID NO:28 is the determined cDNA sequence of JBTT28.

SEQ ID NO:29 is the determined cDNA sequence of JBTT29.

SEQ ID NO:30 is the determined cDNA sequence of JBTT33.

SEQ ID NO:31 is the determined cDNA sequence of JBTT37.

SEQ ID NO:32 is the determined cDNA sequence of JBTT38.

SEQ ID NO:33 is the determined cDNA sequence of JBTT47.

SEQ ID NO:34 is the determined cDNA sequence of JBTT48.

SEQ ID NO:35 is the determined cDNA sequence of JBTT50.

SEQ ID NO:36 is the determined cDNA sequence of JBTT51.

SEQ ID NO:37 is the determined cDNA sequence of JBTT52.

SEQ ID NO:38 is the determined cDNA sequence of JBTT54.

SEQ ID NO:39 is the determined cDNA sequence of SYN17F4.

SEQ ID NO:40 is the determined cDNA sequence of SYN18C6 (also known as B709P).

SEQ ID NO:41 is the determined cDNA sequence of SYN19A2.

SEQ ID NO:42 is the determined cDNA sequence of SYN19C8.

SEQ ID NO:43 is the determined cDNA sequence of SYN20A12.

SEQ ID NO:44 is the determined cDNA sequence of SYN20G6.

SEQ ID NO:45 is the determined cDNA sequence of SYN20G6-2.

SEQ ID NO:46 is the determined cDNA sequence of SYN21B9.

SEQ ID NO:47 is the determined cDNA sequence of SYN21B9-2.

SEQ ID NO:48 is the determined cDNA sequence of SYN21BC9.

SEQ ID NO:49 is the determined cDNA sequence of SYN21G10.

SEQ ID NO:50 is the determined cDNA sequence of SYN21G10-2.

SEQ ID NO:51 is the determined cDNA sequence of SYN21G101.

SEQ ID NO:52 is the determined cDNA sequence of SYN21G11-2.

SEQ ID NO:53 is the determined cDNA sequence of SYN21H8.

SEQ ID NO:54 is the determined cDNA sequence of SYN22A10.

SEQ ID NO:55 is the determined cDNA sequence of SYN22A10-2.

SEQ ID NO:56 is the determined cDNA sequence of SYN22A12.

SEQ ID NO:57 is the determined cDNA sequence of SYN22A2 (also referred to as B718P).

SEQ ID NO:58 is the determined cDNA sequence of SYN22B4.

SEQ ID NO:59 is the determined cDNA sequence of SYN22C2.

SEQ ID NO:60 is the determined cDNA sequence of SYN22E10.

SEQ ID NO:61 is the determined cDNA sequence of SYN22F2.

SEQ ID NO:62 is a predicted amino acid sequence for SYN18C6 (also known as B709P).

SEQ ID NO:63 is the determined cDNA sequence of B723P.

SEQ ID NO:64 is the determined cDNA sequence for B724P.

SEQ ID NO:65 is the determined cDNA sequence of B770P.

SEQ ID NO:66 is the determined cDNA sequence of B716P.

SEQ ID NO:67 is the determined cDNA sequence of B725P.

SEQ ID NO:68 is the determined cDNA sequence of B717P.

SEQ ID NO:69 is the determined cDNA sequence of B771P.

SEQ ID NO:70 is the determined cDNA sequence of B722P.

SEQ ID NO:71 is the determined cDNA sequence of B726P.

SEQ ID NO:72 is the determined cDNA sequence of B727P.

SEQ ID NO:73 is the determined cDNA sequence of B728P.

SEQ ID NO:74-87 are the determined cDNA sequences of isolated clones which show homology to known sequences.

SEQ ID NO:88 is the determined cDNA sequence of 13053.

SEQ ID NO:89 is the determined cDNA sequence of 13057.

SEQ ID NO:90 is the determined cDNA sequence of 13059.

SEQ ID NO:91 is the determined cDNA sequence of 13065.

SEQ ID NO:92 is the determined cDNA sequence of 13067.

SEQ ID NO:93 is the determined cDNA sequence of 13068.

SEQ ID NO:94 is the determined cDNA sequence of 13071.

SEQ ID NO:95 is the determined cDNA sequence of 13072.

SEQ ID NO:96 is the determined cDNA sequence of 13073.

SEQ ID NO:97 is the determined cDNA sequence of 13075.

SEQ ID NO:98 is the determined cDNA sequence of 13078.

SEQ ID NO:99 is the determined cDNA sequence of 13079.

SEQ ID NO:100 is the determined cDNA sequence of 13081.

SEQ ID NO:101 is the determined cDNA sequence of 13082.

SEQ ID NO:102 is the determined cDNA sequence of 13092.

SEQ ID NO:103 is the determined cDNA sequence of 13097.

SEQ ID NO:104 is the determined cDNA sequence of 13101.
SEQ ID NO:105 is the determined cDNA sequence of 13102.
SEQ ID NO:106 is the determined cDNA sequence of 13119.
SEQ ID NO:107 is the determined cDNA sequence of 13131.
SEQ ID NO:108 is the determined cDNA sequence of 13133.
SEQ ID NO:109 is the determined cDNA sequence of 13135.
SEQ ID NO:110 is the determined cDNA sequence of 13139.
SEQ ID NO:111 is the determined cDNA sequence of 13140.
SEQ ID NO:112 is the determined cDNA sequence of 13146.
SEQ ID NO:113 is the determined cDNA sequence of 13147.
SEQ ID NO:114 is the determined cDNA sequence of 13148.
SEQ ID NO:115 is the determined cDNA sequence of 13149.
SEQ ID NO:116 is the determined cDNA sequence of 13151.
SEQ ID NO:117 is the determined cDNA sequence of 13051.
SEQ ID NO:118 is the determined cDNA sequence of 13052.
SEQ ID NO:119 is the determined cDNA sequence of 13055.
SEQ ID NO:120 is the determined cDNA sequence of 13058.
SEQ ID NO:121 is the determined cDNA sequence of 13062.
SEQ ID NO:122 is the determined cDNA sequence of 13064.
SEQ ID NO:123 is the determined cDNA sequence of 13080.
SEQ ID NO:124 is the determined cDNA sequence of 13093.
SEQ ID NO:125 is the determined cDNA sequence of 13094.
SEQ ID NO:126 is the determined cDNA sequence of 13095.
SEQ ID NO:127 is the determined cDNA sequence of 13096.
SEQ ID NO:128 is the determined cDNA sequence of 13099.
SEQ ID NO:129 is the determined cDNA sequence of 13100.
SEQ ID NO:130 is the determined cDNA sequence of 13103.
SEQ ID NO:131 is the determined cDNA sequence of 13106.
SEQ ID NO:132 is the determined cDNA sequence of 13107.
SEQ ID NO:133 is the determined cDNA sequence of 13108.
SEQ ID NO:134 is the determined cDNA sequence of 13121.
SEQ ID NO:135 is the determined cDNA sequence of 13126.
SEQ ID NO:136 is the determined cDNA sequence of 13129.
SEQ ID NO:137 is the determined cDNA sequence of 13130.
SEQ ID NO:138 is the determined cDNA sequence of 13134.
SEQ ID NO:139 is the determined cDNA sequence of 13141.
SEQ ID NO:140 is the determined cDNA sequence of 13142.
SEQ ID NO:141 is the determined cDNA sequence of 14376.
SEQ ID NO:142 is the determined cDNA sequence of 14377.
SEQ ID NO:143 is the determined cDNA sequence of 14383.
SEQ ID NO:144 is the determined cDNA sequence of 14384.
SEQ ID NO:145 is the determined cDNA sequence of 14387.
SEQ ID NO:146 is the determined cDNA sequence of 14392.
SEQ ID NO:147 is the determined cDNA sequence of 14394.
SEQ ID NO:148 is the determined cDNA sequence of 14398.
SEQ ID NO:149 is the determined cDNA sequence of 14401.
SEQ ID NO:150 is the determined cDNA sequence of 14402.
SEQ ID NO:151 is the determined cDNA sequence of 14405.
SEQ ID NO:152 is the determined cDNA sequence of 14409.
SEQ ID NO:153 is the determined cDNA sequence of 14412.
SEQ ID NO:154 is the determined cDNA sequence of 14414.
SEQ ID NO:155 is the determined cDNA sequence of 14415.
SEQ ID NO:156 is the determined cDNA sequence of 14416.
SEQ ID NO:157 is the determined cDNA sequence of 14419
SEQ ID NO:158 is the determined cDNA sequence of 14426.
SEQ ID NO:159 is the determined cDNA sequence of 14427.
SEQ ID NO:160 is the determined cDNA sequence of 14375.
SEQ ID NO:161 is the determined cDNA sequence of 14378.
SEQ ID NO:162 is the determined cDNA sequence of 14379.
SEQ ID NO:163 is the determined cDNA sequence of 14380.
SEQ ID NO:164 is the determined cDNA sequence of 14381.
SEQ ID NO:165 is the determined cDNA sequence of 14382.
SEQ ID NO:166 is the determined cDNA sequence of 14388.
SEQ ID NO:167 is the determined cDNA sequence of 14399.
SEQ ID NO:168 is the determined cDNA sequence of 14406.
SEQ ID NO:169 is the determined cDNA sequence of 14407.

SEQ ID NO:170 is the determined cDNA sequence of 14408.

SEQ ID NO:171 is the determined cDNA sequence of 14417.

SEQ ID NO:172 is the determined cDNA sequence of 14418.

SEQ ID NO:173 is the determined cDNA sequence of 14423.

SEQ ID NO:174 is the determined cDNA sequence of 14424.

SEQ ID NO:175 is the determined cDNA sequence of B726P-20.

SEQ ID NO:176 is the predicted amino acid sequence of B726P-20 (also referred to as B726P downstream ORF).

SEQ ID NO:177 is a PCR primer.

SEQ ID NO:178 is the determined cDNA sequence of B726P-74.

SEQ ID NO:179 is the predicted amino acid sequence of B726P-74.

SEQ ID NO:180 is the determined cDNA sequence of B726P-79.

SEQ ID NO:181 is the predicted amino acid sequence of B726P-79.

SEQ ID NO:182 is the determined cDNA sequence of 19439.1, showing homology to the mammaglobin gene.

SEQ ID NO:183 is the determined cDNA sequence of 19407.1, showing homology to the human keratin gene.

SEQ ID NO:184 is the determined cDNA sequence of 19428.1, showing homology to human chromosome 17 clone.

SEQ ID NO:185 is the determined cDNA sequence of B808P (19408), showing no significant homology to any known gene.

SEQ ID NO:186 is the determined cDNA sequence of 19460.1, showing no significant homology to any known gene.

SEQ ID NO:187 is the determined cDNA sequence of 19419.1, showing homology to Ig kappa light chain.

SEQ ID NO:188 is the determined cDNA sequence of 19411.1, showing homology to human alpha-i collagen.

SEQ ID NO:189 is the determined cDNA sequence of 19420.1, showing homology to mus musculus proteinase-3.

SEQ ID NO:190 is the determined cDNA sequence of 19432.1, showing homology to human high motility group box.

SEQ ID NO:191 is the determined cDNA sequence of 19412.1, showing homology to the human plasminogen activator gene.

SEQ ID NO:192 is the determined cDNA sequence of 19415.1, showing homology to mitogen activated protein kinase.

SEQ ID NO:193 is the determined cDNA sequence of 19409.1, showing homology to the chondroitin sulfate proteoglycan protein.

SEQ ID NO:194 is the determined cDNA sequence of 19406.1, showing no significant homology to any known gene.

SEQ ID NO:195 is the determined cDNA sequence of 19421.1, showing homology to human fibronectin.

SEQ ID NO:196 is the determined cDNA sequence of 19426.1, showing homology to the retinoic acid receptor responder 3.

SEQ ID NO:197 is the determined cDNA sequence of 19425.1, showing homology to MyD88 mRNA SEQ ID NO:198 is the determined cDNA sequence of 19424.1, showing homology to peptide transporter (TAP-1) mRNA.

SEQ ID NO:199 is the determined cDNA sequence of 19429.1, showing no significant homology to any known gene.

SEQ ID NO:200 is the determined cDNA sequence of 19435.1, showing homology to human polymorphic epithelial mucin.

SEQ ID NO:201 is the determined cDNA sequence of B813P (19434.1), showing homology to human GATA-3 transcription factor.

SEQ ID NO:202 is the determined cDNA sequence of 19461.1, showing homology to the human AP-2 gene.

SEQ ID NO:203 is the determined cDNA sequence of 19450.1, showing homology to DNA binding regulatory factor.

SEQ ID NO:204 is the determined cDNA sequence of 19451.1, showing homology to Na/H exchange regulatory co-factor.

SEQ ID NO:205 is the determined cDNA sequence of 19462.1, showing no significant homology to any known gene.

SEQ ID NO:206 is the determined cDNA sequence of 19455.1, showing homology to human mRNA for histone HAS.Z.

SEQ ID NO:207 is the determined cDNA sequence of 19459.1, showing homology to PAC clone 179N16.

SEQ ID NO:208 is the determined cDNA sequence of 19464.1, showing no significant homology to any known gene.

SEQ ID NO:209 is the determined cDNA sequence of 19414.1, showing homology to lipophilin B.

SEQ ID NO:210 is the determined cDNA sequence of 19413.1, showing homology to chromosome 17 clone hRPK.209_J_20.

SEQ ID NO:211 is the determined cDNA sequence of 19416.1, showing no significant homology to any known gene SEQ ID NO:212 is the determined cDNA sequence of 19437.1, showing homology to human clone 24976 mRNA.

SEQ ID NO:213 is the determined cDNA sequence of 19449.1, showing homology to mouse DNA for PG-M core protein.

SEQ ID NO:214 is the determined cDNA sequence of 19446.1, showing no significant homology to any known gene.

SEQ ID NO:215 is the determined cDNA sequence of 19452.1, showing no significant homology to any known gene.

SEQ ID NO:216 is the determined cDNA sequence of 19483.1, showing no significant homology to any known gene.

SEQ ID NO:217 is the determined cDNA sequence of 19526.1, showing homology to human lipophilin C.

SEQ ID NO:218 is the determined cDNA sequence of 19484.1, showing homology to the secreted cement gland protein XAG-2.

SEQ ID NO:219 is the determined cDNA sequence of 19470.1, showing no significant homology to any known gene.

SEQ ID NO:220 is the determined cDNA sequence of 19469.1, showing homology to the human HLA-DM gene.

SEQ ID NO:221 is the determined cDNA sequence of 19482.1, showing homology to the human pS2 protein gene.

SEQ ID NO:222 is the determined cDNA sequence of B805P (19468.1), showing no significant homology to any known gene.

SEQ ID NO:223 is the determined cDNA sequence of 19467.1, showing homology to human thrombospondin mRNA.

SEQ ID NO:224 is the determined cDNA sequence of 19498.1, showing homology to the CDC2 gene involved in cell cycle control.

SEQ ID NO:225 is the determined cDNA sequence of 19506.1, showing homology to human cDNA for TREB protein SEQ ID NO:226 is the determined cDNA sequence of B806P (19505.1), showing no significant homology to any known gene.

SEQ ID NO:227 is the determined cDNA sequence of 19486.1, showing homology to type I epidermal keratin.

SEQ ID NO:228 is the determined cDNA sequence of 19510.1, showing homology to glucose transporter for glycoprotein.

SEQ ID NO:229 is the determined cDNA sequence of 19512.1, showing homology to the human lysyl hydroxylase gene.

SEQ ID NO:230 is the determined cDNA sequence of 19511.1, showing homology to human palimotoyl-protein thioesterase.

SEQ ID NO:231 is the determined cDNA sequence of 19508.1, showing homology to human alpha enolase.

SEQ ID NO:232 is the determined cDNA sequence of B807P (19509.1), showing no significant homology to any known gene.

SEQ ID NO:233 is the determined cDNA sequence of B809P (19520.1), showing homology to clone 102D24 on chromosome 11q13.31.

SEQ ID NO:234 is the determined cDNA sequence of 19507.1, showing homology toprosome beta-subunit.

SEQ ID NO:235 is the determined cDNA sequence of 19525.1, showing homology to human pro-urokinase precursor.

SEQ ID NO:236 is the determined cDNA sequence of 19513.1, showing no significant homology to any known gene.

SEQ ID NO:237 is the determined cDNA sequence of 19517.1, showing homology to human PAC 128M19 clone.

SEQ ID NO:238 is the determined cDNA sequence of 19564.1, showing homology to human cytochrome P450-IIB.

SEQ ID NO:239 is the determined cDNA sequence of 19553.1, showing homology to human GABA-A receptor pi subunit.

SEQ ID NO:240 is the determined cDNA sequence of B811P (19575.1), showing no significant homology to any known gene.

SEQ ID NO:241 is the determined cDNA sequence of B810P (19560.1), showing no significant homology to any known gene.

SEQ ID NO:242 is the determined cDNA sequence of 19588.1, showing homology to aortic carboxypetidase-like protein.

SEQ ID NO:243 is the determined cDNA sequence of 19551.1, showing homology to human BCL-1 gene.

SEQ ID NO:244 is the determined cDNA sequence of 19567.1, showing homology to human proteasome-related mRNA.

SEQ ID NO:245 is the determined cDNA sequence of B803P (19583.1), showing no significant homology to any known gene.

SEQ ID NO:246 is the determined cDNA sequence of B812P (19587.1), showing no significant homology to any known gene.

SEQ ID NO:247 is the determined cDNA sequence of B802P (19392.2), showing homology to human chromosome 17.

SEQ ID NO:248 is the determined cDNA sequence of 19393.2, showing homology to human nicein B2 chain.

SEQ ID NO:249 is the determined cDNA sequence of 19398.2, human MHC class II DQ alpha mRNA.

SEQ ID NO:250 is the determined cDNA sequence of B804P (19399.2), showing homology to human Xp22 BAC GSHB-184P14.

SEQ ID NO:251 is the determined cDNA sequence of 19401.2, showing homology to human ikB kinase-b gene.

SEQ ID NO:252 is the determined cDNA sequence of 20266, showing no significant homology to any known gene.

SEQ ID NO:253 is the determined cDNA sequence of B826P (20270), showing no significant homology to any known gene SEQ ID NO:254 is the determined cDNA sequence of 20274, showing no significant homology to any known gene.

SEQ ID NO:255 is the determined cDNA sequence of 20276, showing no significant homology to any known gene.

SEQ ID NO:256 is the determined cDNA sequence of 20277, showing no significant homology to any known gene.

SEQ ID NO:257 is the determined cDNA sequence of B823P (20280), showing no significant homology to any known gene.

SEQ ID NO:258 is the determined cDNA sequence of B821P (20281), showing no significant homology to any known gene.

SEQ ID NO:259 is the determined cDNA sequence of B824P (20294), showing no significant homology to any known gene.

SEQ ID NO:260 is the determined cDNA sequence of 20303, showing no significant homology to any known gene.

SEQ ID NO:261 is the determined cDNA sequence of B820P (20310), showing no significant homology to any known gene.

SEQ ID NO:262 is the determined cDNA sequence of B825P (20336), showing no significant homology to any known gene.

SEQ ID NO:263 is the determined cDNA sequence of B827P (20341), showing no significant homology to any known gene.

SEQ ID NO:264 is the determined cDNA sequence of 20941, showing no significant homology to any known gene.

SEQ ID NO:265 is the determined cDNA sequence of 20954, showing no significant homology to any known gene.

SEQ ID NO:266 is the determined cDNA sequence of 20961, showing no significant homology to any known gene.

SEQ ID NO:267 is the determined cDNA sequence of 20965, showing no significant homology to any known gene.

SEQ ID NO:268 is the determined cDNA sequence of 20975, showing no significant homology to any known gene.

SEQ ID NO:269 is the determined cDNA sequence of 20261, showing homology to Human p120 catenin.

SEQ ID NO:270 is the determined cDNA sequence of B822P (20262), showing homology to Human membrane glycoprotein 4F2.

SEQ ID NO:271 is the determined cDNA sequence of 20265, showing homology to Human Na, K-ATPase Alpha 1.

SEQ ID NO:272 is the determined cDNA sequence of 20267, showing homology to Human heart HS 90, partial cds.

SEQ ID NO:273 is the determined cDNA sequence of 20268, showing homology to Human mRNA GPI-anchored protein p137.

SEQ ID NO:274 is the determined cDNA sequence of 20271, showing homology to Human cleavage stimulation factor 77 kDa subunit.

SEQ ID NO:275 is the determined cDNA sequence of 20272, showing homology to Human p190-B.

SEQ ID NO:276 is the determined cDNA sequence of 20273, showing homology to Human ribophorin.

SEQ ID NO:277 is the determined cDNA sequence of 20278, showing homology to Human omithine amino transferase.

SEQ ID NO:278 is the determined cDNA sequence of 20279, showing homology to Human S-adenosylmethionine synthetase.

SEQ ID NO:279 is the determined cDNA sequence of 20293, showing homology to Human x inactivation transcript.

SEQ ID NO:280 is the determined cDNA sequence of 20300, showing homology to Human cytochrome p450.

SEQ ID NO:281 is the determined cDNA sequence of 20305, showing homology to Human elongation factor-1 alpha.

SEQ ID NO:282 is the determined cDNA sequence of 20306, showing homology to Human epithelial ets protein.

SEQ ID NO:283 is the determined cDNA sequence of 20307, showing homology to Human signal transducer mRNA.

SEQ ID NO:284 is the determined cDNA sequence of 20313, showing homology to Human GABA-A receptor pi subunit mRNA.

SEQ ID NO:285 is the determined cDNA sequence of 20317, showing homology to Human tyrosine phosphatase.

SEQ ID NO:286 is the determined cDNA sequence of 20318, showing homology to Human cathepsine B proteinase.

SEQ ID NO:287 is the determined cDNA sequence of 20320, showing homology to Human 2-phosphopyruvate-hydratase-alpha-enolase.

SEQ ID NO:288 is the determined cDNA sequence of 20321, showing homology to Human E-cadherin.

SEQ ID NO:289 is the determined cDNA sequence of 20322, showing homology to Human hsp86.

SEQ ID NO:290 is the determined cDNA sequence of B828P (20326), showing homology to Human x inactivation transcript.

SEQ ID NO:291 is the determined cDNA sequence of 20333, showing homology to Human chromatin regulator, SMARCA5.

SEQ ID NO:292 is the determined cDNA sequence of 20335, showing homology to Human sphingolipid activator protein 1.

SEQ ID NO:293 is the determined cDNA sequence of 20337, showing homology to Human hepatocyte growth factor activator inhibitor type 2.

SEQ ID NO:294 is the determined cDNA sequence of 20338, showing homology to Human cell adhesion molecule CD44.

SEQ ID NO:295 is the determined cDNA sequence of 20340, showing homology to Human nuclear factor (erythroid-derived)-like 1.

SEQ ID NO:296 is the determined cDNA sequence of 20938, showing homology to Human vinculin mRNA.

SEQ ID NO:297 is the determined cDNA sequence of 20939, showing homology to Human elongation factor EF-1-alpha.

SEQ ID NO:298 is the determined cDNA sequence of 20940, showing homology to Human nestin gene.

SEQ ID NO:299 is the determined cDNA sequence of 20942, showing homology to Human pancreatic ribonuclease.

SEQ ID NO:300 is the determined cDNA sequence of 20943, showing homology to Human transcobalamin I.

SEQ ID NO:301 is the determined cDNA sequence of 20944, showing homology to Human beta-tubulin.

SEQ ID NO:302 is the determined cDNA sequence of 20946, showing homology to Human HS1 protein.

SEQ ID NO:303 is the determined cDNA sequence of 20947, showing homology to Human cathepsin B.

SEQ ID NO:304 is the determined cDNA sequence of 20948, showing homology to Human testis enhanced gene transcript.

SEQ ID NO:305 is the determined cDNA sequence of 20949, showing homology to Human elongation factor EF-1-alpha.

SEQ ID NO:306 is the determined cDNA sequence of 20950, showing homology to Human ADP-ribosylation factor 3.

SEQ ID NO:307 is the determined cDNA sequence of 20951, showing homology to Human IFP53 or WRS for tryptophanyl-tRNA synthetase.

SEQ ID NO:308 is the determined cDNA sequence of 20952, showing homology to Human cyclin-dependent protein kinase.

SEQ ID NO:309 is the determined cDNA sequence of 20957, showing homology to Human alpha-tubulin isoform 1.

SEQ ID NO:310 is the determined cDNA sequence of 20959, showing homology to Human tyrosine phosphatase-61bp deletion.

SEQ ID NO:311 is the determined cDNA sequence of 20966, showing homology to Human tyrosine phosphatase.

SEQ ID NO:312 is the determined cDNA sequence of B830P (20976), showing homology to Human nuclear factor NF 45.

SEQ ID NO:313 is the determined cDNA sequence of B829P (20977), showing homology to Human delta-6 fatty acid desaturase.

SEQ ID NO:314 is the determined cDNA sequence of 20978, showing homology to Human nuclear aconitase.

SEQ ID NO:315 is the determined cDNA sequence of clone 23176.

SEQ ID NO:316 is the determined cDNA sequence of clone 23140.

SEQ ID NO:317 is the determined cDNA sequence of clone 23166.

SEQ ID NO:318 is the determined cDNA sequence of clone 23167.

SEQ ID NO:319 is the determined cDNA sequence of clone 23177.

SEQ ID NO:320 is the determined cDNA sequence of clone 23217.

SEQ ID NO:321 is the determined cDNA sequence of clone 23169.

SEQ ID NO:322 is the determined cDNA sequence of clone 23160.

SEQ ID NO:323 is the determined cDNA sequence of clone 23182.

SEQ ID NO:324 is the determined cDNA sequence of clone 23232.

SEQ ID NO:325 is the determined cDNA sequence of clone 23203.

SEQ ID NO:326 is the determined cDNA sequence of clone 23198.

SEQ ID NO:327 is the determined cDNA sequence of clone 23224.
SEQ ID NO:328 is the determined cDNA sequence of clone 23142.
SEQ ID NO:329 is the determined cDNA sequence of clone 23138.
SEQ ID NO:330 is the determined cDNA sequence of clone 23147.
SEQ ID NO:331 is the determined cDNA sequence of clone 23148.
SEQ ID NO:332 is the determined cDNA sequence of clone 23149.
SEQ ID NO:333 is the determined cDNA sequence of clone 23172.
SEQ ID NO:334 is the determined cDNA sequence of clone 23158.
SEQ ID NO:335 is the determined cDNA sequence of clone 23156.
SEQ ID NO:336 is the determined cDNA sequence of clone 23221.
SEQ ID NO:337 is the determined cDNA sequence of clone 23223.
SEQ ID NO:338 is the determined cDNA sequence of clone 23155.
SEQ ID NO:339 is the determined cDNA sequence of clone 23225.
SEQ ID NO:340 is the determined cDNA sequence of clone 23226.
SEQ ID NO:341 is the determined cDNA sequence of clone 23228.
SEQ ID NO:342 is the determined cDNA sequence of clone 23229.
SEQ ID NO:343 is the determined cDNA sequence of clone 23231.
SEQ ID NO:344 is the determined cDNA sequence of clone 23154.
SEQ ID NO:345 is the determined cDNA sequence of clone 23157.
SEQ ID NO:346 is the determined cDNA sequence of clone 23153.
SEQ ID NO:347 is the determined cDNA sequence of clone 23159.
SEQ ID NO:348 is the determined cDNA sequence of clone 23152.
SEQ ID NO:349 is the determined cDNA sequence of clone 23161.
SEQ ID NO:350 is the determined cDNA sequence of clone 23162.
SEQ ID NO:351 is the determined cDNA sequence of clone 23163.
SEQ ID NO:352 is the determined cDNA sequence of clone 23164.
SEQ ID NO:353 is the determined cDNA sequence of clone 23165.
SEQ ID NO:354 is the determined cDNA sequence of clone 23151.
SEQ ID NO:355 is the determined cDNA sequence of clone 23150.
SEQ ID NO:356 is the determined cDNA sequence of clone 23168.
SEQ ID NO:357 is the determined cDNA sequence of clone 23146.
SEQ ID NO:358 is the determined cDNA sequence of clone 23170.
SEQ ID NO:359 is the determined cDNA sequence of clone 23171.
SEQ ID NO:360 is the determined cDNA sequence of clone 23145.
SEQ ID NO:361 is the determined cDNA sequence of clone 23174.
SEQ ID NO:362 is the determined cDNA sequence of clone 23175.
SEQ ID NO:363 is the determined cDNA sequence of clone 23144.
SEQ ID NO:364 is the determined cDNA sequence of clone 23178.
SEQ ID NO:365 is the determined cDNA sequence of clone 23179.
SEQ ID NO:366 is the determined cDNA sequence of clone 23180.
SEQ ID NO:367 is the determined cDNA sequence of clone 23181.
SEQ ID NO:368 is the determined cDNA sequence of clone 23143.
SEQ ID NO:369 is the determined cDNA sequence of clone 23183.
SEQ ID NO:370 is the determined cDNA sequence of clone 23184.
SEQ ID NO:371 is the determined cDNA sequence of clone 23185.
SEQ ID NO:372 is the determined cDNA sequence of clone 23186.
SEQ ID NO:373 is the determined cDNA sequence of clone 23187.
SEQ ID NO:374 is the determined cDNA sequence of clone 23190.
SEQ ID NO:375 is the determined cDNA sequence of clone 23189.
SEQ ID NO:376 is the determined cDNA sequence of clone 23202.
SEQ ID NO:378 is the determined cDNA sequence of clone 23191.
SEQ ID NO:379 is the determined cDNA sequence of clone 23188.
SEQ ID NO:380 is the determined cDNA sequence of clone 23194.
SEQ ID NO:381 is the determined cDNA sequence of clone 23196.
SEQ ID NO:382 is the determined cDNA sequence of clone 23195.
SEQ ID NO:383 is the determined cDNA sequence of clone 23193.
SEQ ID NO:384 is the determined cDNA sequence of clone 23199.
SEQ ID NO:385 is the determined cDNA sequence of clone 23200.
SEQ ID NO:386 is the determined cDNA sequence of clone 23192.
SEQ ID NO:387 is the determined cDNA sequence of clone 23201.
SEQ ID NO:388 is the determined cDNA sequence of clone 23141.
SEQ ID NO:389 is the determined cDNA sequence of clone 23139.
SEQ ID NO:390 is the determined cDNA sequence of clone 23204.
SEQ ID NO:391 is the determined cDNA sequence of clone 23205.
SEQ ID NO:392 is the determined cDNA sequence of clone 23206.
SEQ ID NO:393 is the determined cDNA sequence of clone 23207.

SEQ ID NO:394 is the determined cDNA sequence of clone 23208.
SEQ ID NO:395 is the determined cDNA sequence of clone 23209.
SEQ ID NO:396 is the determined cDNA sequence of clone 23210.
SEQ ID NO:397 is the determined cDNA sequence of clone 23211.
SEQ ID NO:398 is the determined cDNA sequence of clone 23212.
SEQ ID NO:399 is the determined cDNA sequence of clone 23214.
SEQ ID NO:400 is the determined cDNA sequence of clone 23215.
SEQ ID NO:401 is the determined cDNA sequence of clone 23216.
SEQ ID NO:402 is the determined cDNA sequence of clone 23137.
SEQ ID NO:403 is the determined cDNA sequence of clone 23218.
SEQ ID NO:404 is the determined cDNA sequence of clone 23220.
SEQ ID NO:405 is the determined cDNA sequence of clone 19462.
SEQ ID NO:406 is the determined cDNA sequence of clone 19430.
SEQ ID NO:407 is the determined cDNA sequence of clone 19407.
SEQ ID NO:408 is the determined cDNA sequence of clone 19448.
SEQ ID NO:409 is the determined cDNA sequence of clone 19447.
SEQ ID NO:410 is the determined cDNA sequence of clone 19426.
SEQ ID NO:411 is the determined cDNA sequence of clone 19441.
SEQ ID NO:412 is the determined cDNA sequence of clone 19454.
SEQ ID NO:413 is the determined cDNA sequence of clone 19463.
SEQ ID NO:414 is the determined cDNA sequence of clone 19419.
SEQ ID NO:415 is the determined cDNA sequence of clone 19434.
SEQ ID NO:416 is the determined extended cDNA sequence of B820P.
SEQ ID NO:417 is the determined extended cDNA sequence of B821P.
SEQ ID NO:418 is the determined extended cDNA sequence of B822P.
SEQ ID NO:419 is the determined extended cDNA sequence of B823P.
SEQ ID NO:420 is the determined extended cDNA sequence of B824P.
SEQ ID NO:421 is the determined extended cDNA sequence of B825P.
SEQ ID NO:422 is the determined extended cDNA sequence of B826P.
SEQ ID NO:423 is the determined extended cDNA sequence of B827P.
SEQ ID NO:424 is the determined extended cDNA sequence of B828P.
SEQ ID NO:425 is the determined extended cDNA sequence of B829P.
SEQ ID NO:426 is the determined extended cDNA sequence of B830P.
SEQ ID NO:427 is the determined cDNA sequence of clone 266B4.
SEQ ID NO:428 is the determined cDNA sequence of clone 22892.
SEQ ID NO:429 is the determined cDNA sequence of clone 266G3.
SEQ ID NO:430 is the determined cDNA sequence of clone 22890.
SEQ ID NO:431 is the determined cDNA sequence of clone 264B4.
SEQ ID NO:432 is the determined cDNA sequence of clone 22883.
SEQ ID NO:433 is the determined cDNA sequence of clone 22882.
SEQ ID NO:434 is the determined cDNA sequence of clone 2880.
SEQ ID NO:435 is the determined cDNA sequence of clone 263G1.
SEQ ID NO:436 is the determined cDNA sequence of clone 263G6.
SEQ ID NO:437 is the determined cDNA sequence of clone 262B2.
SEQ ID NO:438 is the determined cDNA sequence of clone 262B6.
SEQ ID NO:439 is the determined cDNA sequence of clone 22869.
SEQ ID NO:440 is the determined cDNA sequence of clone 21374.
SEQ ID NO:441 is the determined cDNA sequence of clone 21362.
SEQ ID NO:442 is the determined cDNA sequence of clone 21349.
SEQ ID NO:443 is the determined cDNA sequence of clone 21309.
SEQ ID NO:444 is the determined cDNA sequence of clone 21097.
SEQ ID NO:445 is the determined cDNA sequence of clone 21096.
SEQ ID NO:446 is the determined cDNA sequence of clone 21094.
SEQ ID NO:447 is the determined cDNA sequence of clone 21093.
SEQ ID NO:448 is the determined cDNA sequence of clone 21091.
SEQ ID NO:449 is the determined cDNA sequence of clone 21089.
SEQ ID NO:450 is the determined cDNA sequence of clone 21087.
SEQ ID NO:451 is the determined cDNA sequence of clone 21085.
SEQ ID NO:452 is the determined cDNA sequence of clone 21084.
SEQ ID NO:453 is a first partial cDNA sequence of clone 2BT1-40.
SEQ ID NO:454 is a second partial cDNA sequence of clone 2BT1-40.
SEQ ID NO:455 is the determined cDNA sequence of clone 21063.
SEQ ID NO:456 is the determined cDNA sequence of clone 21062.
SEQ ID NO:457 is the determined cDNA sequence of clone 21060.
SEQ ID NO:458 is the determined cDNA sequence of clone 21053.
SEQ ID NO:459 is the determined cDNA sequence of clone 21050.

SEQ ID NO:460 is the determined cDNA sequence of clone 21036.

SEQ ID NO:461 is the determined cDNA sequence of clone 21037.

SEQ ID NO:462 is the determined cDNA sequence of clone 21048.

SEQ ID NO:463 is a consensus DNA sequence of B726P (referred to as B726P-spliced_seq_B726P).

SEQ ID NO:464 is the determined cDNA sequence of a second splice form of B726P (referred to as 27490.seq_B726P).

SEQ ID NO:465 is the determined cDNA sequence of a third splice form of B726P (referred to as 27068.seq_B726P).

SEQ ID NO:466 is the determined cDNA sequence of a second splice form of B726P (referred to as 23113.seq_B726P).

SEQ ID NO:467 is the determined cDNA sequence of a second splice form of B726P (referred to as 23103.seq_B726P).

SEQ ID NO:468 is the determined cDNA sequence of a second splice form of B726P (referred to as 19310.seq_B726P).

SEQ ID NO:469 is the predicted amino acid sequence encoded by the upstream ORF of SEQ ID NO:463.

SEQ ID NO:470 is the predicted amino acid sequence encoded by SEQ ID NO:464.

SEQ ID NO:471 is the predicted amino acid sequence encoded by SEQ ID NO:465.

SEQ ID NO:472 is the predicted amino acid sequence encoded by SEQ ID NO:466.

SEQ ID NO:473 is the predicted amino acid sequence encoded by SEQ ID NO:467.

SEQ ID NO:474 is the determined cDNA sequence for an alternative splice form of B726P.

SEQ ID NO:475 is the amino acid sequence encoded by SEQ ID NO:474.

SEQ ID NO:476 is the isolated cDNA sequence of B720P.

SEQ ID NO:477 is the cDNA sequence of a known keratin gene.

SEQ ID NO:478 is the amino acid sequence encoded by SEQ ID NO:477.

SEQ ID NO:479 is the determined cDNA sequence for clone 19465.

SEQ ID NO:480 and 481 are PCR primers.

SEQ ID NO:482 is the cDNA sequence for the expressed downstream ORF of B726P.

SEQ ID NO:483 is the amino acid sequence for the expressed recombinant downstream ORF of B726P.

SEQ ID NO:484 is the determined full-length cDNA sequence for B720P.

SEQ ID NO:485 is the amino acid sequence encoded by SEQ ID NO:484.

SEQ ID NO:486 is the determined cDNA sequence of a truncated form of B720P, referred to as B720P-tr.

SEQ ID NO:487 is the amino acid sequence of B720P-tr.

SEQ ID NO:488 is the amino acid sequence of a naturally processed epitope of B726P recognized by B726P-specific CTL.

SEQ ID NO:489 is a DNA sequence encoding the B726P epitope set forth in SEQ ID NO:488.

SEQ ID NO:490 is a DNA sequence encoding a fusion protein wherein mammaglobin is fused to the B726P combined upstream and downstream open reading frame (ORF) (the amino acid sequence of the B726P combined ORF is disclosed herein as SEQ ID NO:475 which is encoded by the DNA sequence of SEQ ID NO:474).

SEQ ID NO:491 is a DNA sequence encoding a fusion protein wherein mammaglobin is fused to the B726P upstream ORF (the amino acid sequence of the B726P upstream ORF is disclosed herein as SEQ ID NO:469 which is encoded by the DNA sequence of SEQ ID NO:463).

SEQ ID NO:492 is a DNA sequence encoding a fusion protein wherein mammaglobin is fused to the B726P downstream ORF (the amino acid sequence of the B726P downstream ORF is disclosed herein as SEQ ID NO:176 which is encoded by the DNA sequence of SEQ ID NO:175).

SEQ ID NO:493 is the amino acid sequence encoded by the DNA sequence of SEQ ID NO:490.

SEQ ID NO:494 is the amino acid sequence encoded by the DNA sequence of SEQ ID NO:491.

SEQ ID NO:495 is the amino acid sequence encoded by the DNA sequence of SEQ ID NO:492.

SEQ ID NO:496 is amino acids 59-78 of SEQ ID NO:493.
SEQ ID NO:497 is amino acids 55-69 of SEQ ID NO:493.
SEQ ID NO:498 is amino acids 13-33 of SEQ ID NO:493.
SEQ ID NO:499 is amino acids 41-60 of SEQ ID NO:493.
SEQ ID NO:500 is amino acids 2-10 of SEQ ID NO:493.
SEQ ID NO:501 is amino acids 47-59 of SEQ ID NO:493.
SEQ ID NO:502 is amino acids 62-74 of SEQ ID NO:493.
SEQ ID NO:503 is amino acids 1-93 of SEQ ID NO:493.

SEQ ID NO:504 is the full-length cDNA sequence for B718P.

SEQ ID NO:505 is the cDNA sequence of the open reading frame of B718P including stop codon.

SEQ ID NO:506 is the cDNA sequence of the open reading frame of B718P without stop codon.

SEQ ID NO:507 is the full-length amino acid sequence of B718P.

SEQ ID NO:508 represents amino acids 1-158 of SEQ ID NO:507.

SEQ ID NO:509 represents amino acids 159-243 of SEQ ID NO:509.

SEQ ID NO:510 is the entire cDNA sequence of the open reading frame, including stop codon, of a first variant of B723P, referred to as B723P-short.

SEQ ID NO:511 is the entire cDNA sequence of the open reading frame, without stop codon, of a first variant of B723P, referred to as B723P-short.

SEQ ID NO:512 is the entire cDNA sequence of the open reading frame, including stop codon, of a second variant of B723P, referred to as B723P-long.

SEQ ID NO:513 is the entire cDNA sequence of the open reading frame, without stop codon, of a second variant of B723P, referred to as B723P-long.

SEQ ID NO:514 is the amino acid sequence of B723P-short.

SEQ ID NO:515 is the amino acid sequence of B723P-long.

SEQ ID NO:516 is amino acids 1-197 of B723P-short.
SEQ ID NO:517 is amino acids 1-232 of B723P-long.
SEQ ID NO:518 is amino acids 198-243 of B723P-short.
SEQ ID NO:519 is amino acids 218-243 of B723P-short.
SEQ ID NO:520-533 are the DNA sequences of epitopes of B726P.

SEQ ID NO:534-547 are the amino acid sequences of epitopes of B726P.

SEQ ID NO:548 is the cDNA sequence of B726P Combined ORF coding_region for expression in *E. coli*.

SEQ ID NO:549 is the cDNA sequence of B726P Upstream ORF coding_region for expression in *E. coli*.

SEQ ID NO:550 is the cDNA sequence of B726P Downstream ORF coding_region for expression in *E. coli*.

SEQ ID NO:551 is the amino acid sequence of B726P Downstream ORF encoded by the cDNA set forth in SEQ ID NO:550.

SEQ ID NO:552 is the amino acid sequence of B726P Upstream ORF with HIS, encoded by the cDNA set forth in SEQ ID NO:549.

SEQ ID NO:553 is the amino acid sequence of B726P Combined ORF correct, encoded by the cDNA set forth in SEQ ID NO:548.

SEQ ID NOs: 554-563 are PCR primers as described in Example 8.

SEQ ID NO:564 is the cDNA sequence for NY-BR-1, an extended sequence of B726P.

SEQ ID NO:565 is the amino acid sequence for NY-BR-1, an extended sequence of B726P, and encoded by the nucleotide sequence set forth in SEQ ID NO:564.

SEQ ID NO:566 is the cDNA sequence for B726P XC coding region with changes.

SEQ ID NO:567 is the cDNA sequence for B726P XB clone 83686 with 2 changes from the published NY-BR-1 sequence in SEQ ID NO:564.

SEQ ID NO:568 is the cDNA sequence for B726P XB clone 84330 with 4 changes from the published NY-BR-I sequence in SEQ ID NO:564.

SEQ ID NO:569 is the cDNA sequence for B726P XB clone 84328 with 3 changes from the published NY-BR-1 sequence in SEQ ID NO:564.

SEQ ID NO:570 is the amino acid sequence for B726P XB clone 84328, encoded by the sequence set forth in SEQ ID NO:569.

SEQ ID NO:571 is the amino acid sequence for B726P XB clone 84330, encoded by the sequence set forth in SEQ ID NO:568.

SEQ ID NO:572 is the amino acid sequence for B726P XB clone 83686, encoded by the sequence set forth in SEQ ID NO:567.

SEQ ID NO:573 is the amino acid sequence for B726P XC, encoded by the sequence set forth in SEQ ID NO:566.

SEQ ID NOs:574-575 are PCR primers as described in Example 12.

SEQ ID NO:576 is the full-length cDNA sequence for NY-BR-1.1.

SEQ ID NO:577 is the full-length amino acid sequence for NY-BR-1.1, encoded by the nucleotide sequence set forth in SEQ ID NO:576.

SEQ ID NO:578 is amino acids 289-308 of the B726P downstream ORF and corresponds to the peptide recognized by the 220A2.1 antibody.

SEQ ID NO:579 is amino acids 225-244 of the B726P downstream ORF and corresponds to the peptide recognized by the 220A19.1 antibody.

SEQ ID NO:580 is amino acids 232252 of the B726P downstream ORF and corresponds to the peptide recognized by the 220A19.1 and the 220A43 antibodies.

SEQ ID NO:581 is amino acids 73-92 of the B726P downstream ORF and corresponds to the peptide recognized by the 220A94.1 antibody.

SEQ ID NO:582 is amino acids 145-164 of the B726P downstream ORF and corresponds to the peptide recognized by the 220A151.1 and 220A86 antibodies.

SEQ ID NO:583 is amino acids 153-172 of the B726P downstream ORF and corresponds to the peptide recognized by the 220A151.1 and 220A86 antibodies.

SEQ ID NO:584 is amino acids 1-20 of the B726P downstream ORF and corresponds to the peptide recognized by purified B726 polyclonal antibodies.

SEQ ID NO:585 is amino acids 9-28 of the B726P downstream ORF and corresponds to the peptide recognized by purified B726 polyclonal antibodies.

SEQ ID NO:586 is amino acids 17-36 of the B726P downstream ORF and corresponds to the peptide recognized by purified B726 polyclonal antibodies.

SEQ ID NO:587 is amino acids 24-44 of the B726P downstream ORF and corresponds to the peptide recognized by purified B726 polyclonal antibodies.

SEQ ID NO:588 is amino acids 97-116 of the B726P downstream ORF and corresponds to the peptide recognized by purified B726 polyclonal antibodies.

SEQ ID NO:589 is amino acids 105-124 of the B726P downstream ORF and corresponds to the peptide recognized by purified B726 polyclonal antibodies.

SEQ ID NO:590 is amino acids 113-132 of the B726P downstream ORF and corresponds to the peptide recognized by purified B726 polyclonal antibodies.

SEQ ID NO:591 is amino acids 121-140 of the B726P downstream ORF and corresponds to the peptide recognized by purified B726 polyclonal antibodies.

SEQ ID NO:592 is amino acids 129-148 of the B726P downstream ORF and corresponds to the peptide recognized by purified B726 polyclonal antibodies.

SEQ ID NO:593 is amino acids 137-156 of the B726P downstream ORF and corresponds to the peptide recognized by purified B726 polyclonal antibodies.

DETAILED DESCRIPTION OF THE INVENTION

The present invention is directed generally to compositions and their use in the therapy and diagnosis of cancer, particularly breast cancer. As described further below, illustrative compositions of the present invention include, but are not restricted to, polypeptides, particularly immunogenic polypeptides, polynucleotides encoding such polypeptides, antibodies and other binding agents, antigen presenting cells (APCs) and immune system cells (e.g., T cells).

The practice of the present invention will employ, unless indicated specifically to the contrary, conventional methods of virology, immunology, microbiology, molecular biology and recombinant DNA techniques within the skill of the art, many of which are described below for the purpose of illustration. Such techniques are explained fully in the literature. See, e.g., Sambrook, et al. Molecular Cloning: A Laboratory Manual (2nd Edition, 1989); Maniatis et al. Molecular Cloning: A Laboratory Manual (1982); DNA Cloning: A Practical Approach, vol. I & II (D. Glover, ed.); Oligonucleotide Synthesis (N. Gait, ed., 1984); Nucleic Acid Hybridization (B. Hames & S. Higgins, eds., 1985); Transcription and Translation (B. Hames & S. Higgins, eds., 1984); Animal Cell Culture (R. Freshney, ed., 1986); Perbal, A Practical Guide to Molecular Cloning (1984).

All publications, patents and patent applications cited herein, whether supra or infra, are hereby incorporated by reference in their entirety.

As used in this specification and the appended claims, the singular forms "a," "an" and "the" include plural references unless the content clearly dictates otherwise.

Polypeptide Compositions

As used herein, the term "polypeptide" "is used in its conventional meaning, i.e., as a sequence of amino acids. The polypeptides are not limited to a specific length of the product; thus, peptides, oligopeptides, and proteins are included within the definition of polypeptide, and such terms may be used interchangeably herein unless specifically indicated otherwise. This term also does not refer to or exclude post-expression modifications of the polypeptide, for example, glycosylations, acetylations, phosphorylations and the like, as well as other modifications known in the art, both naturally occurring and non-naturally occurring. A polypeptide may be an entire protein, or a subsequence thereof. Particular polypeptides of interest in the context of this invention are amino acid subsequences comprising epitopes, i.e., antigenic determinants substantially responsible for the immunogenic properties of a polypeptide and being capable of evoking an immune response.

Particularly illustrative polypeptides of the present invention comprise those encoded by a polynucleotide sequence set forth in any one of SEQ ID NOs: 1-61, 63-175, 178, 180, 182-468, 474, 476, 477, 479, 482, 484, 486, 489-492, 504-506, 510-513, 520-533, 548-550, 564, 566-569, and 576, or a sequence that hybridizes under moderately stringent conditions, or, alternatively, under highly stringent conditions, to a polynucleotide sequence set forth in any one of SEQ ID NOs: 1-61, 63-175, 178, 180, 182-468, 474, 476, 477, 479, 482, 484, 486, 489-492, 504-506, 510-513, 520-533, 548-550, 564, 566-569, and 576. Certain other illustrative polypeptides of the invention comprise amino acid sequences as set forth in any one of SEQ ID NOs: 62, 176, 179, 181, 469-473, 475, 478, 483, 485, 487, 488, 493-503, 507-509, 514-519, 534-547, 551-553, 565, 570-573, and 577-593.

The polypeptides of the present invention are sometimes herein referred to as breast tumor proteins or breast tumor polypeptides, as an indication that their identification has been based at least in part upon their increased levels of expression in breast tumor samples. Thus, a "breast tumor polypeptide" or "breast tumor protein," refers generally to a polypeptide sequence of the present invention, or a polynucleotide sequence encoding such a polypeptide, that is expressed in a substantial proportion of breast tumor samples, for example preferably greater than about 20%, more preferably greater than about 30%, and most preferably greater than about 50% or more of breast tumor samples tested, at a level that is at least two fold, and preferably at least five fold, greater than the level of expression in normal tissues, as determined using a representative assay provided herein. A breast tumor polypeptide sequence of the invention, based upon its increased level of expression in tumor cells, has particular utility both as a diagnostic marker as well as a therapeutic target, as further described below.

In certain preferred embodiments, the polypeptides of the invention are immunogenic, i.e., they react detectably within an immunoassay (such as an ELISA or T-cell stimulation assay) with antisera and/or T-cells from a patient with breast cancer. Screening for immunogenic activity can be performed using techniques well known to the skilled artisan. For example, such screens can be performed using methods such as those described in Harlow and Lane, *Antibodies: A Laboratory Manual*, Cold Spring Harbor Laboratory, 1988. In one illustrative example, a polypeptide may be immobilized on a solid support and contacted with patient sera to allow binding of antibodies within the sera to the immobilized polypeptide. Unbound sera may then be removed and bound antibodies detected using, for example, $^{125}$I-labeled Protein A.

As would be recognized by the skilled artisan, immunogenic portions of the polypeptides disclosed herein are also encompassed by the present invention. An "immunogenic portion," as used herein, is a fragment of an immunogenic polypeptide of the invention that itself is immunologically reactive (i.e., specifically binds) with the B-cells and/or T-cell surface antigen receptors that recognize the polypeptide. Immunogenic portions may generally be identified using well known techniques, such as those summarized in Paul, *Fundamental Immunology*, 3rd ed., 243-247 (Raven Press, 1993) and references cited therein. Such techniques include screening polypeptides for the ability to react with antigen-specific antibodies, antisera and/or T-cell lines or clones. As used herein, antisera and antibodies are "antigen-specific" if they specifically bind to an antigen (i.e., they react with the protein in an ELISA or other immunoassay, and do not react detectably with unrelated proteins). Such antisera and antibodies may be prepared as described herein, and using well-known techniques.

In one preferred embodiment. an immunogenic portion of a polypeptide of the present invention is a portion that reacts with antisera and/or T-cells at a level that is not substantially less than the reactivity of the full-length polypeptide (e.g., in an ELISA and/or T-cell reactivity assay). Preferably, the level of immunogenic activity of the immunogenic portion is at least about 50%, preferably at least about 70% and most preferably greater than about 90% of the immunogenicity for the full-length polypeptide. In some instances, preferred immunogenic portions will be identified that have a level of immunogenic activity greater than that of the corresponding full-length polypeptide, e.g., having greater than about 100% or 150% or more immunogenic activity.

In certain other embodiments, illustrative immunogenic portions may include peptides in which an N-terminal leader sequence and/or transmembrane domain have been deleted. Other illustrative immunogenic portions will contain a small N- and/or C-terminal deletion (e.g., 1-30 amino acids, preferably 5-15 amino acids), relative to the mature protein.

In another embodiment, a polypeptide composition of the invention may also comprise one or more polypeptides that are immunologically reactive with T cells and/or antibodies generated against a polypeptide of the invention, particularly a polypeptide having an amino acid sequence disclosed herein, or to an immunogenic fragment or variant thereof.

In another embodiment of the invention, polypeptides are provided that comprise one or more polypeptides that are capable of eliciting T cells and/or antibodies that are immunologically reactive with one or more polypeptides described herein, or one or more polypeptides encoded by contiguous nucleic acid sequences contained in the polynucleotide sequences disclosed herein, or immunogenic fragments or variants thereof, or to one or more nucleic acid sequences which hybridize to one or more of these sequences under conditions of moderate to high stringency.

The present invention, in another aspect, provides polypeptide fragments comprising at least about 5, 10, 15, 20, 25, 50, or 100 contiguous amino acids, or more, including all intermediate lengths, of a polypeptide compositions set forth herein, such as those set forth in SEQ ID NOs: 62, 176, 179, 181, 469-473, 475. 478, 483, 485, 487, 488, 493-503, 507-509, 514-519, 534-547, 551-553, 565, 570-573, and 577-593, or those encoded by a polynucleotide sequence set forth in a sequence of SEQ ID NOs: 1-61, 63-175, 178, 180, 182-468, 474, 476, 477, 479, 482, 484, 486, 489-492, 504-506, 510-513, 520-533, 548-550, 564, 566-569, and 576.

In another aspect, the present invention provides variants of the polypeptide compositions described herein. Polypeptide variants generally encompassed by the present invention will typically exhibit at least about 70%, 75%, 80%, 85%, 90%, 91%, 92%, 93%, 94%, 95%, 96%, 97%, 98%, or 99% or more identity (determined as described below), along its length, to a polypeptide sequences set forth herein.

In one preferred embodiment, the polypeptide fragments and variants provide by the present invention are immunologically reactive with an antibody and/or T-cell that reacts with a full-length polypeptide specifically set for the herein.

In another preferred embodiment, the polypeptide fragments and variants provided by the present invention exhibit a level of immunogenic activity of at least about 50%, preferably at least about 70%, and most preferably at least about 90% or more of that exhibited by a full-length polypeptide sequence specifically set forth herein.

A polypeptide "variant," as the term is used herein, is a polypeptide that typically differs from a polypeptide specifically disclosed herein in one or more substitutions, deletions, additions and/or insertions. Such variants may be naturally occurring or may be synthetically generated, for example, by modifying one or more of the above polypeptide sequences of the invention and evaluating their immunogenic activity as described herein and/or using any of a number of techniques well known in the art.

For example, certain illustrative variants of the polypeptides of the invention include those in which one or more portions, such as an N-terminal leader sequence or transmembrane domain, have been removed. Other illustrative variants include variants in which a small portion (e.g., 1-30 amino acids, preferably 5-15 amino acids) has been removed from the N- and/or C-terminal of the mature protein.

In many instances, a variant will contain conservative substitutions. A "conservative substitution" is one in which an amino acid is substituted for another amino acid that has similar properties, such that one skilled in the art of peptide chemistry would expect the secondary structure and hydropathic nature of the polypeptide to be substantially unchanged. As described above, modifications may be made in the structure of the polynucleotides and polypeptides of the present invention and still obtain a functional molecule that encodes a variant or derivative polypeptide with desirable characteristics, e.g., with immunogenic characteristics. When it is desired to alter the amino acid sequence of a polypeptide to create an equivalent, or even an improved, immunogenic variant or portion of a polypeptide of the invention, one skilled in the art will typically change one or more of the codons of the encoding DNA sequence according to Table 1.

For example, certain amino acids may be substituted for other amino acids in a protein structure without appreciable loss of interactive binding capacity with structures such as, for example, antigen-binding regions of antibodies or binding sites on substrate molecules. Since it is the interactive capacity and nature of a protein that defines that protein's biological functional activity, certain amino acid sequence substitutions can be made in a protein sequence, and, of course, its underlying DNA coding sequence, and nevertheless obtain a protein with like properties. It is thus contemplated that various changes may be made in the peptide sequences of the disclosed compositions, or corresponding DNA sequences which encode said peptides without appreciable loss of their biological utility or activity.

TABLE 1

| Amino Acids | Codons | | |
|---|---|---|---|
| Alanine | Ala | A | GCA GCC GCG GCU |
| Cysteine | Cys | C | UGC UGU |
| Aspartic acid | Asp | D | GAC GAU |
| Glutamic acid | Glu | E | GAA GAG |
| Phenylalanine | Phe | F | UUC UUU |
| Glycine | Gly | G | GGA GGC GGG GGU |
| Histidine | His | H | CAC CAU |
| Isoleucine | Ile | I | AUA AUC AUU |

TABLE 1-continued

| Amino Acids | Codons | | |
|---|---|---|---|
| Lysine | Lys | K | AAA AAG |
| Leucine | Leu | L | UUA UUG CUA CUC CUG CUU |
| Methionine | Met | M | AUG |
| Asparagine | Asn | N | AAC AAU |
| Proline | Pro | P | CCA CCC CCG CCU |
| Glutamine | Gln | Q | CAA CAG |
| Arginine | Arg | R | AGA AGG CGA CGC CGG CGU |
| Serine | Ser | S | AGC AGU UCA UCC UCG UCU |
| Threonine | Thr | T | ACA ACC ACG ACU |
| Valine | Val | V | GUA GUC GUG GUU |
| Tryptophan | Trp | W | UGG |
| Tyrosine | Tyr | Y | UAC UAU |

In making such changes, the hydropathic index of amino acids may be considered. The importance of the hydropathic amino acid index in conferring interactive biologic function on a protein is generally understood in the art (Kyte and Doolittle, 1982, incorporated herein by reference). It is accepted that the relative hydropathic character of the amino acid contributes to the secondary structure of the resultant protein, which in turn defines the interaction of the protein with other molecules, for example, enzymes, substrates, receptors, DNA, antibodies, antigens, and the like. Each amino acid has been assigned a hydropathic index on the basis of its hydrophobicity and charge characteristics (Kyte and Doolittle, 1982). These values are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5) lysine (−3.9); and arginine (−4.5).

It is known in the art that certain amino acids may be substituted by other amino acids having a similar hydropathic index or score and still result in a protein with similar biological activity, i.e. still obtain a biological functionally equivalent protein. In making such changes, the substitution of amino acids whose hydropathic indices are within ±2 is preferred, those within ±1 are particularly preferred, and those within ±0.5 are even more particularly preferred. It is also understood in the art that the substitution of like amino acids can be made effectively on the basis of hydrophilicity. U.S. Pat. No. 4,554,101 (specifically incorporated herein by reference in its entirety), states that the greatest local average hydrophilicity of a protein, as governed by the hydrophilicity of its adjacent amino acids, correlates with a biological property of the protein.

As detailed in U.S. Pat. No. 4,554,101, the following hydrophilicity values have been assigned to amino acid residues: arginine (+3.0); lysine (+3.0); aspartate (+3.0±1); glutamate (+3.0±1); serine (+0.3); asparagine (+0.2); glutamine (+0.2); glycine (0); threonine (−0.4); proline (−0.5±1); alanine (−0.5); histidine (−0.5); cysteine (−1.0); methionine (−1.3); valine (−1.5); leucine (−1.8); isoleucine (−1.8); tyrosine (−2.3); phenylalanine (−2.5); tryptophan (−3.4). It is understood that an amino acid can be substituted for another having a similar hydrophilicity value and still obtain a biologically equivalent, and in particular, an immunologically equivalent protein. In such changes, the substitution of amino acids whose hydrophilicity values are within ±2 is preferred, those within ±1 are particularly preferred, and those within ±0.5 are even more particularly preferred.

As outlined above, amino acid substitutions are generally therefore based on the relative similarity of the amino acid side-chain substituents, for example, their hydrophobicity, hydrophilicity, charge, size, and the like. Exemplary substitutions that take various of the foregoing characteristics into consideration are well known to those of skill in the art and include: arginine and lysine; glutamate and aspartate; serine and threonine; glutamine and asparagine; and valine, leucine and isoleucine.

In addition, any polynucleotide may be further modified to increase stability in vivo. Possible modifications include, but are not limited to, the addition of flanking sequences at the 5' and/or 3' ends; the use of phosphorothioate or 2' O-methyl rather than phosphodiesterase linkages in the backbone; and/or the inclusion of nontraditional bases such as inosine, queosine and wybutosine, as well as acetyl- methyl-, thio- and other modified forms of adenine, cytidine, guanine, thymine and uridine.

Amino acid substitutions may further be made on the basis of similarity in polarity, charge, solubility, hydrophobicity, hydrophilicity and/or the amphipathic nature of the residues. For example, negatively charged amino acids include aspartic acid and glutamic acid; positively charged amino acids include lysine and arginine; and amino acids with uncharged polar head groups having similar hydrophilicity values include leucine, isoleucine and valine; glycine and alanine; asparagine and glutamine; and serine, threonine, phenylalanine and tyrosine. Other groups of amino acids that may represent conservative changes include: (1) ala, pro, gly, glu, asp, gln, asn, ser, thr; (2) cys, ser, tyr, thr; (3) val, ile, leu, met, ala, phe; (4) lys, arg, his; and (5) phe, tyr, trp, his. A variant may also, or alternatively, contain nonconservative changes. In a preferred embodiment, variant polypeptides differ from a native sequence by substitution, deletion or addition of five amino acids or fewer. Variants may also (or alternatively) be modified by, for example, the deletion or addition of amino acids that have minimal influence on the immunogenicity, secondary structure and hydropathic nature of the polypeptide.

As noted above, polypeptides may comprise a signal (or leader) sequence at the N-terminal end of the protein, which co-translationally or post-translationally directs transfer of the protein. The polypeptide may also be conjugated to a linker or other sequence for ease of synthesis, purification or identification of the polypeptide (e.g., poly-His), or to enhance binding of the polypeptide to a solid support. For example, a polypeptide may be conjugated to an immunoglobulin Fc region.

When comparing polypeptide sequences, two sequences are said to be "identical" if the sequence of amino acids in the two sequences is the same when aligned for maximum correspondence, as described below. Comparisons between two sequences are typically performed by comparing the sequences over a comparison window to identify and compare local regions of sequence similarity. A "comparison window" as used herein, refers to a segment of at least about 20 contiguous positions, usually 30 to about 75, 40 to about 50, in which a sequence may be compared to a reference sequence of the same number of contiguous positions after the two sequences are optimally aligned.

Optimal alignment of sequences for comparison may be conducted using the Megalign program in the Lasergene suite of bioinformatics software (DNASTAR, Inc., Madison, Wis.), using default parameters. This program embodies several alignment schemes described in the following references: Dayhoff, M. O. (1978) A model of evolutionary change in proteins—Matrices for detecting distant relationships. In Dayhoff, M. O. (ed.) Atlas of Protein Sequence and Structure, National Biomedical Research Foundation, Washington DC Vol. 5, Suppl. 3, pp. 345-358; Hein J. (1990) Unified Approach to Alignment and Phylogenes pp. 626-645 *Methods in Enzymology* vol. 183, Academic Press, Inc., San Diego, Calif.; Higgins, D. G. and Sharp, P. M. (1989) *CABIOS* 5:151-153; Myers, E. W. and Muller W. (1988) *CABIOS* 4:11-17; Robinson, E. D. (1971) *Comb. Theor* 11:105; Santou, N. Nes, M; (1987) *Mol. Biol. Evol.* 4:406-425; Sneath, P. H. A. and Sokal, R. R. (1973) *Numerical Taxonomy—the Principles and Practice of Numerical Taxonomy*, Freeman Press, San Francisco, Calif.; Wilbur, W. J. and Lipman, D. J. (1983) *Proc. Natl. Acad., Sci. USA* 80:726-730.

Alternatively, optimal alignment of sequences for comparison may be conducted by the local identity algorithm of Smith and Waterman (1981) *Add. APL. Math* 2:482, by the identity alignment algorithm of Needleman and Wunsch (1970) *J. Mol. Biol.* 48:443, by the search for similarity methods of Pearson and Lipman (1988) *Proc. Natl. Acad. Sci. USA* 85: 2444, by computerized implementations of these algorithms (GAP, BESTFIT, BLAST, FASTA, and TFASTA in the Wisconsin Genetics Software Package, Genetics Computer Group (GCG), 575 Science Dr., Madison, Wis.), or by inspection.

One preferred example of algorithms that are suitable for determining percent sequence identity and sequence similarity are the BLAST and BLAST 2.0 algorithms, which are described in Altschul et al. (1977) *Nucl. Acids Res.* 25:3389-3402 and Altschul et al. (1990) *J. Mol. Biol.* 215:403-410, respectively. BLAST and BLAST 2.0 can be used, for example with the parameters described herein, to determine percent sequence identity for the polynucleotides and polypeptides of the invention. Software for performing BLAST analyses is publicly available through the National Center for Biotechnology Information. For amino acid sequences, a scoring matrix can be used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T and X determine the sensitivity and speed of the alignment.

In one preferred approach, the "percentage of sequence identity" is determined by comparing two optimally aligned sequences over a window of comparison of at least 20 positions, wherein the portion of the polypeptide sequence in the comparison window may comprise additions or deletions (i.e., gaps) of 20 percent or less, usually 5 to 15 percent, or 10 to 12 percent, as compared to the reference sequences (which does not comprise additions or deletions) for optimal alignment of the two sequences. The percentage is calculated by determining the number of positions at which the identical amino acid residue occurs in both sequences to yield the number of matched positions, dividing the number of matched positions by the total number of positions in the reference sequence (i.e., the window size) and multiplying the results by 100 to yield the percentage of sequence identity.

Within other illustrative embodiments, a polypeptide may be a fusion polypeptide that comprises multiple polypeptides as described herein, or that comprises at least one polypeptide as described herein and an unrelated sequence. such as a known tumor protein. A fusion partner may, for example, assist in providing T helper epitopes (an immunological fusion partner), preferably T helper epitopes recognized by humans, or may assist in expressing the protein (an expression enhancer) at higher yields than the native recombinant protein. Certain preferred fusion partners are both immunological and expression enhancing fusion partners. Other fusion partners may be selected so as to increase the solubility of the polypeptide or to enable the polypeptide to be targeted to desired intracellular compartments. Still further fusion partners include affinity tags, which facilitate purification of the polypeptide.

Fusion polypeptides may generally be prepared using standard techniques, including chemical conjugation. Preferably, a fusion polypeptide is expressed as a recombinant polypeptide, allowing the production of increased levels, relative to a non-fused polypeptide, in an expression system. Briefly, DNA sequences encoding the polypeptide components may be assembled separately, and ligated into an appropriate expression vector. The 3' end of the DNA sequence encoding one polypeptide component is ligated, with or without a peptide linker, to the 5' end of a DNA sequence encoding the second polypeptide component so that the reading frames of the sequences are in phase. This permits translation into a single fusion polypeptide that retains the biological activity of both component polypeptides.

A peptide linker sequence may be employed to separate the first and second polypeptide components by a distance sufficient to ensure that each polypeptide folds into its secondary and tertiary structures. Such a peptide linker sequence is incorporated into the fusion polypeptide using standard techniques well known in the art. Suitable peptide linker sequences may be chosen based on the following factors: (1) their ability to adopt a flexible extended conformation; (2) their inability to adopt a secondary structure that could interact with functional epitopes on the first and second polypeptides; and (3) the lack of hydrophobic or charged residues that might react with the polypeptide functional epitopes. Preferred peptide linker sequences contain Gly, Asn and Ser residues. Other near neutral amino acids, such as Thr and Ala may also be used in the linker sequence. Amino acid sequences which may be usefully employed as linkers include those disclosed in Maratea et al., *Gene* 40:39-46, 1985; Murphy et al., *Proc. Natl. Acad. Sci. USA* 83:8258-8262, 1986; U.S. Pat. No. 4,935,233 and U.S. Pat. No. 4,751,180. The linker sequence may generally be from 1 to about 50 amino acids in length. Linker sequences are not required when the first and second polypeptides have non-essential N-terminal amino acid regions that can be used to separate the functional domains and prevent steric interference.

The ligated DNA sequences are operably linked to suitable transcriptional or translational regulatory elements. The regulatory elements responsible for expression of DNA are located only 5' to the DNA sequence encoding the first polypeptides. Similarly, stop codons required to end translation and transcription termination signals are only present 3' to the DNA sequence encoding the second polypeptide.

The fusion polypeptide can comprise a polypeptide as described herein together with an unrelated immunogenic protein, such as an immunogenic protein capable of eliciting a recall response. Examples of such proteins include tetanus, tuberculosis and hepatitis proteins (see, for example, Stoute et al. *New Engl. J. Med.*, 336:86-91, 1997).

In one preferred embodiment, the immunological fusion partner is derived from a Mycobacterium sp., such as a Mycobacterium tuberculosis-derived Ra12 fragment. Ra12 compositions and methods for their use in enhancing the expression and/or immunogenicity of heterologous polynucleotide/polypeptide sequences is described in U.S. Patent Application 60/158,585, the disclosure of which is incorporated herein by reference in its entirety. Briefly, Ra12 refers to a polynucleotide region that is a subsequence of a *Mycobacterium tuberculosis* MTB32A nucleic acid. MTB32A is a serine protease of 32 KD molecular weight encoded by a gene in virulent and avirulent strains of *M. tuberculosis*. The nucleotide sequence and amino acid sequence of MTB32A have been described (for example, U.S. Patent Application 60/158, 585; see also, Skeiky et al., *Infection and Immun.* (1999) 67:3998-4007, incorporated herein by reference). C-terminal fragments of the MTB32A coding sequence express at high levels and remain as a soluble polypeptides throughout the purification process. Moreover, Ra12 may enhance the immunogenicity of heterologous immunogenic polypeptides with which it is fused. One preferred Ra12 fusion polypeptide comprises a 14 KD C-terminal fragment corresponding to amino acid residues 192 to 323 of MTB32A. Other preferred Ra12 polynucleotides generally comprise at least about 15 consecutive nucleotides, at least about 30 nucleotides, at least about 60 nucleotides, at least about 100 nucleotides, at least about 200 nucleotides, or at least about 300 nucleotides that encode a portion of a Ra12 polypeptide. Ra12 polynucleotides may comprise a native sequence (i.e., an endogenous sequence that encodes a Ra12 polypeptide or a portion thereof) or may comprise a variant of such a sequence. Ra12 polynucleotide variants may contain one or more substitutions, additions, deletions and/or insertions such that the biological activity of the encoded fusion polypeptide is not substantially diminished, relative to a fusion polypeptide comprising a native Ra12 polypeptide. Variants preferably exhibit at least about 70% identity, more preferably at least about 80% identity and most preferably at least about 90% identity to a polynucleotide sequence that encodes a native Ra12 polypeptide or a portion thereof.

Within other preferred embodiments, an immunological fusion partner is derived from protein D, a surface protein of the gram-negative bacterium Haemophilus influenza B (WO 91/18926). Preferably, a protein D derivative comprises approximately the first third of the protein (e.g., the first N-terminal 100-110 amino acids), and a protein D derivative may be lipidated. Within certain preferred embodiments, the first 109 residues of a Lipoprotein D fusion partner is included on the N-terminus to provide the polypeptide with additional exogenous T-cell epitopes and to increase the expression level in *E. coli* (thus functioning as an expression enhancer). The lipid tail ensures optimal presentation of the antigen to antigen presenting cells. Other fusion partners include the non-structural protein from influenzae virus, NS1 (hemaglutinin). Typically, the N-terminal 81 amino acids are used, although different fragments that include T-helper epitopes may be used.

In another embodiment, the immunological fusion partner is the protein known as LYTA, or a portion thereof (preferably a C-terminal portion). LYTA is derived from *Streptococcus pneumoniae*, which synthesizes an N-acetyl-L-alanine amidase known as amidase LYTA (encoded by the LytA gene; *Gene* 43:265-292, 1986). LYTA is an autolysin that specifically degrades certain bonds in the peptidoglycan backbone. The C-terminal domain of the LYTA protein is responsible for the affinity to the choline or to some choline analogues such as DEAE. This property has been exploited for the development of *E. coli* C-LYTA expressing plasmids useful for expression of fusion proteins. Purification of hybrid proteins containing the C-LYTA fragment at the amino terminus has been described (see *Biotechnology* 10:795-798, 1992). Within a preferred embodiment, a repeat portion of LYTA may be incorporated into a fusion polypeptide. A repeat portion is found in the C-terminal region starting at residue 178. A particularly preferred repeat portion incorporates residues 188-305.

Yet another illustrative embodiment involves fusion polypeptides, and the polynucleotides encoding them, wherein the fusion partner comprises a targeting signal capable of directing a polypeptide to the endosomal/lysosomal compartment, as described in U.S. Pat. No. 5,633,234. An immunogenic polypeptide of the invention, when fused with this targeting signal, will associate more efficiently with MHC class II molecules and thereby provide enhanced in vivo stimulation of CD4+ T-cells specific for the polypeptide.

Polypeptides of the invention are prepared using any of a variety of well known synthetic and/or recombinant techniques, the latter of which are further described below. Polypeptides, portions and other variants generally less than about 150 amino acids can be generated by synthetic means, using techniques well known to those of ordinary skill in the art. In one illustrative example, such polypeptides are synthesized using any of the commercially available solid-phase techniques, such as the Merrifield solid-phase synthesis method, where amino acids are sequentially added to a growing amino acid chain. See Merrifield, *J. Am. Chem. Soc.* 85:2149-2146, 1963. Equipment for automated synthesis of polypeptides is commercially available from suppliers such as Perkin Elmer/Applied BioSystems Division (Foster City, Calif.), and may be operated according to the manufacturer's instructions.

In general, polypeptide compositions (including fusion polypeptides) of the invention are isolated. An "isolated" polypeptide is one that is removed from its original environment. For example, a naturally-occurring protein or polypeptide is isolated if it is separated from some or all of the coexisting materials in the natural system. Preferably, such polypeptides are also purified, e.g., are at least about 90% pure, more preferably at least about 95% pure and most preferably at least about 99% pure.

Polynucleotide Compositions

The present invention in other aspects, provides polynucleotide compositions. The terms "DNA" and "polynucleotide" are used essentially interchangeably herein to refer to a DNA molecule that has been isolated free of total genomic DNA of a particular species. "Isolated," as used herein, means that a polynucleotide is substantially away from other coding sequences, and that the DNA molecule does not contain large portions of unrelated coding DNA, such as large chromosomal fragments or other functional genes or polypeptide coding regions. Of course, this refers to the DNA molecule as originally isolated, and does not exclude genes or coding regions later added to the segment by the hand of man.

As will be understood by those skilled in the art, the polynucleotide compositions of this invention can include genomic sequences, extra-genomic and plasmid-encoded sequences and smaller engineered gene segments that express, or may be adapted to express, proteins, polypeptides, peptides and the like. Such segments may be naturally isolated, or modified synthetically by the hand of man.

As will be also recognized by the skilled artisan, polynucleotides of the invention may be single-stranded (coding or antisense) or double-stranded, and may be DNA (genomic, cDNA or synthetic) or RNA molecules. RNA molecules may include mRNA molecules, which contain introns and correspond to a DNA molecule in a one-to-one manner, and mRNA molecules, which do not contain introns. Additional coding or non-coding sequences may, but need not, be present within a polynucleotide of the present invention, and a polynucleotide may, but need not, be linked to other molecules and/or support materials.

Polynucleotides may comprise a native sequence (i.e., an endogenous sequence that encodes a polypeptide/protein of the invention or a portion thereof) or may comprise a sequence that encodes a variant or derivative, preferably and immunogenic variant or derivative, of such a sequence.

Therefore, according to another aspect of the present invention, polynucleotide compositions are provided that comprise some or all of a polynucleotide sequence set forth in any one of SEQ ID NOs: 1-61, 63-175, 178, 180, 182-468, 474, 476, 477, 479, 482, 484, 486, 489-492, 504-506, 510-513, 520-533, 548-550, 564, 566-569, and 576, complements of a polynucleotide sequence set forth in any one of SEQ ID NOs: 1-61, 63-175, 178, 180, 182-468, 474, 476, 477, 479, 482, 484, 486, 489-492, 504-506, 510-513, 520-533, 548-550, 564, 566-569, and 576, and degenerate variants of a polynucleotide sequence set forth in any one of SEQ ID NOs: 1-61, 63-175, 178, 180, 182-468, 474, 476, 477, 479, 482, 484, 486, 489-492, 504-506, 510-513, 520-533, 548-550, 564, 566-569, and 576. In certain preferred embodiments, the polynucleotide sequences set forth herein encode immunogenic polypeptides, as described above.

In other related embodiments, the present invention provides polynucleotide variants having substantial identity to the sequences disclosed herein in SEQ ID NOs: 1-61, 63-175, 178, 180, 182-468, 474, 476, 477, 479, 482, 484, 486, 489-492, 504-506, 510-513, 520-533, 548-550, 564, 566-569, and 576, for example those comprising at least 70% sequence identity, preferably at least 75%, 80%, 85%, 90%, 95%, 96%, 97%, 98%, or 99% or higher, sequence identity compared to a polynucleotide sequence of this invention using the methods described herein, (e.g., BLAST analysis using standard parameters, as described below). One skilled in this art will recognize that these values can be appropriately adjusted to determine corresponding identity of proteins encoded by two nucleotide sequences by taking into account codon degeneracy, amino acid similarity, reading frame positioning and the like.

Typically, polynucleotide variants will contain one or more substitutions, additions, deletions and/or insertions, preferably such that the immunogenicity of the polypeptide encoded by the variant polynucleotide is not substantially diminished relative to a polypeptide encoded by a polynucleotide sequence specifically set forth herein). The term "variants" should also be understood to encompasses homologous genes of xenogenic origin.

In additional embodiments, the present invention provides polynucleotide fragments comprising various lengths of contiguous stretches of sequence identical to or complementary to one or more of the sequences disclosed herein. For example, polynucleotides are provided by this invention that comprise at least about 10, 15, 20, 30, 40, 50, 75, 100, 150, 200, 300, 400, 500 or 1000 or more contiguous nucleotides of one or more of the sequences disclosed herein as well as all intermediate lengths there between. It will be readily understood that "intermediate lengths", in this context, means any length between the quoted values, such as 16, 17, 18, 19, etc.; 21, 22, 23, etc.; 30, 31, 32, etc.; 50, 51, 52, 53, etc.; 100, 101, 102, 103. etc.; 150, 151, 152, 153, etc.; including all integers through 200-500; 500-1,000, and the like.

In another embodiment of the invention, polynucleotide compositions are provided that are capable of hybridizing under moderate to high stringency conditions to a polynucleotide sequence provided herein, or a fragment thereof, or a complementary sequence thereof. Hybridization techniques are well known in the art of molecular biology. For purposes of illustration, suitable moderately stringent conditions for testing the hybridization of a polynucleotide of this invention with other polynucleotides include prewashing in a solution of 5× SSC, 0.5% SDS, 1.0 mM EDTA (pH 8.0); hybridizing at 50° C.-60° C., 5× SSC, overnight; followed by washing twice at 65° C. for 20 minutes with each of 2×, 0.5× and 0.2× SSC containing 0.1% SDS. One skilled in the art will understand that the stringency of hybridization can be readily manipulated, such as by altering the salt content of the hybridization solution and/or the temperature at which the hybridization is performed. For example, in another embodiment, suitable highly stringent hybridization conditions include those described above, with the exception that the temperature of hybridization is increased, e.g., to 60-65° C. or 65-70° C.

In certain preferred embodiments, the polynucleotides described above, e.g., polynucleotide variants, fragments and hybridizing sequences, encode polypeptides that are immunologically cross-reactive with a polypeptide sequence specifically set forth herein.

In other preferred embodiments, such polynucleotides encode polypeptides that have a level of immunogenic activity of at least about 50%, preferably at least about 70%, and more preferably at least about 90% of that for a polypeptide sequence specifically set forth herein.

The polynucleotides of the present invention, or fragments thereof, regardless of the length of the coding sequence itself, may be combined with other DNA sequences, such as promoters, polyadenylation signals, additional restriction enzyme sites, multiple cloning sites, other coding segments, and the like, such that their overall length may vary considerably. It is therefore contemplated that a nucleic acid fragment of almost any length may be employed, with the total length preferably being limited by the ease of preparation and use in the intended recombinant DNA protocol. For example, illustrative polynucleotide segments with total lengths of about 10,000, about 5000, about 3000, about 2,000, about 1,000, about 500, about 200, about 100, about 50 base pairs in length, and the like, (including all intermediate lengths) are contemplated to be useful in many implementations of this invention.

When comparing polynucleotide sequences, two sequences are said to be "identical" if the sequence of nucleotides in the two sequences is the same when aligned for maximum correspondence, as described below. Comparisons between two sequences are typically performed by comparing the sequences over a comparison window to identify and compare local regions of sequence similarity. A "comparison window" as used herein, refers to a segment of at least about 20 contiguous positions, usually 30 to about 75, 40 to about 50, in which a sequence may be compared to a reference sequence of the same number of contiguous positions after the two sequences are optimally aligned.

Optimal alignment of sequences for comparison may be conducted using the Megalign program in the Lasergene suite of bioinformatics software (DNASTAR, Inc., Madison, Wis.), using default parameters. This program embodies several alignment schemes described in the following references: Dayhoff, M. O. (1978) A model of evolutionary change in proteins—Matrices for detecting distant relationships. In Dayhoff, M. O. (ed.) Atlas of Protein Sequence and Structure, National Biomedical Research Foundation, Washington D.C. Vol. 5, Suppl. 3, pp. 345-358; Hein J. (1990) Unified Approach to Alignment and Phylogenes pp. 626-645 *Methods in Enzymology* vol. 183, Academic Press, Inc., San Diego, Calif.; Higgins, D. G. and Sharp, P. M. (1989) *CABIOS* 5:151-153; Myers, E. W. and Muller W. (1988) *CABIOS* 4:11-17; Robinson, E. D. (1971) *Comb. Theor* 11:105; Santou, N. Nes, M. (1987) *Mol. Biol. Evol.* 4:406-425; Sneath, P. H. A. and Sokal, R. R. (1973) *Numerical Taxonomy—the Principles and Practice of Numerical Taxonomy*, Freeman Press, San Francisco, Calif.; Wilbur, W. J. and Lipman, D. J. (1983) *Proc. Natl. Acad, Sci. USA* 80:726-730.

Alternatively, optimal alignment of sequences for comparison may be conducted by the local identity algorithm of Smith and Waterman (1981) *Add. APL. Math* 2:482, by the identity alignment algorithm of Needieman and Wunsch (1970) *J. Mol. Biol.* 48:443, by the search for similarity methods of Pearson and Lipman (1988) *Proc. Natl. Acad. Sci. USA* 85: 2444, by computerized implementations of these algorithms (GAP, BESTFIT, BLAST, FASTA, and TFASTA in the Wisconsin Genetics Software Package, Genetics Computer Group (GCG), 575 Science Dr., Madison, Wis.), or by inspection.

One preferred example of algorithms that are suitable for determining percent sequence identity and sequence similarity are the BLAST and BLAST 2.0 algorithms, which are described in Altschul et al. (1977) *Nucl. Acids Res.* 25:3389-3402 and Altschul et al. (1990) *J. Mol. Biol.* 215:403-410, respectively. BLAST and BLAST 2.0 can be used, for example with the parameters described herein, to determine percent sequence identity for the polynucleotides of the invention. Software for performing BLAST analyses is publicly available through the National Center for Biotechnology Information. In one illustrative example, cumulative scores can be calculated using, for nucleotide sequences, the parameters M (reward score for a pair of matching residues; always >0) and N (penalty score for mismatching residues; always <0). Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T and X determine the sensitivity and speed of the alignment. The BLASTN program (for nucleotide sequences) uses as defaults a wordlength (W) of 11, and expectation (E) of 10, and the BLOSUM62 scoring matrix (see Henikoff and Henikoff (1989) *Proc. Natl. Acad. Sci. USA* 89:10915) alignments, (B) of 50, expectation (E) of 10, M=5, N=-4 and a comparison of both strands.

Preferably, the "percentage of sequence identity" is determined by comparing two optimally aligned sequences over a window of comparison of at least 20 positions, wherein the portion of the polynucleotide sequence in the comparison window may comprise additions or deletions (i.e., gaps) of 20 percent or less, usually 5 to 15 percent, or 10 to 12 percent, as compared to the reference sequences (which does not comprise additions or deletions) for optimal alignment of the two sequences. The percentage is calculated by determining the number of positions at which the identical nucleic acid bases occurs in both sequences to yield the number of matched positions, dividing the number of matched positions by the total number of positions in the reference sequence (i.e., the window size) and multiplying the results by 100 to yield the percentage of sequence identity.

It will be appreciated by those of ordinary skill in the art that, as a result of the degeneracy of the genetic code, there are many nucleotide sequences that encode a polypeptide as described herein. Some of these polynucleotides bear minimal homology to the nucleotide sequence of any native gene. Nonetheless, polynucleotides that vary due to differences in codon usage are specifically contemplated by the present invention. Further, alleles of the genes comprising the polynucleotide sequences provided herein are within the scope of the present invention. Alleles are endogenous genes that are altered as a result of one or more mutations, such as deletions, additions and/or substitutions of nucleotides. The resulting mRNA and protein may, but need not, have an altered structure or function. Alleles may be identified using standard techniques (such as hybridization, amplification and/or database sequence comparison).

Therefore, in another embodiment of the invention, a mutagenesis approach, such as site-specific mutagenesis, is employed for the preparation of immunogenic variants and/or derivatives of the polypeptides described herein. By this approach, specific modifications in a polypeptide sequence can be made through mutagenesis of the underlying polynucleotides that encode them. These techniques provides a straightforward approach to prepare and test sequence variants, for example, incorporating one or more of the foregoing considerations, by introducing one or more nucleotide sequence changes into the polynucleotide.

Site-specific mutagenesis allows the production of mutants through the use of specific oligonucleotide sequences which encode the DNA sequence of the desired mutation, as well as a sufficient number of adjacent nucleotides, to provide a primer sequence of sufficient size and sequence complexity to form a stable duplex on both sides of the deletion junction being traversed. Mutations may be employed in a selected polynucleotide sequence to improve, alter, decrease, modify, or otherwise change the properties of the polynucleotide itself, and/or alter the properties, activity, composition, stability, or primary sequence of the encoded polypeptide.

In certain embodiments of the present invention, the inventors contemplate the mutagenesis of the disclosed polynucleotide sequences to alter one or more properties of the encoded polypeptide, such as the immunogenicity of a polypeptide vaccine. The techniques of site-specific mutagenesis are well-known in the art, and are widely used to create variants of both polypeptides and polynucleotides. For example, site-specific mutagenesis is often used to alter a specific portion of a DNA molecule. In such embodiments, a primer comprising typically about 14 to about 25 nucleotides or so in length is employed, with about 5 to about 10 residues on both sides of the junction of the sequence being altered.

As will be appreciated by those of skill in the art, site-specific mutagenesis techniques have often employed a phage vector that exists in both a single stranded and double stranded form. Typical vectors useful in site-directed mutagenesis include vectors such as the M13 phage. These phage are readily commercially-available and their use is generally well-known to those skilled in the art. Double-stranded plasmids are also routinely employed in site directed mutagenesis that eliminates the step of transferring the gene of interest from a plasmid to a phage.

In general, site-directed mutagenesis in accordance herewith is performed by first obtaining a single-stranded vector or melting apart of two strands of a double-stranded vector that includes within its sequence a DNA sequence that encodes the desired peptide. An oligonucleotide primer bearing the desired mutated sequence is prepared, generally synthetically. This primer is then annealed with the single-stranded vector, and subjected to DNA polymerizing enzymes such as *E. coli* polymerase I Klenow fragment, in order to complete the synthesis of the mutation-bearing strand. Thus, a heteroduplex is formed wherein one strand encodes the original non-mutated sequence and the second strand bears the desired mutation. This heteroduplex vector is then used to transform appropriate cells, such as *E. coli* cells, and clones are selected which include recombinant vectors bearing the mutated sequence arrangement.

The preparation of sequence variants of the selected peptide-encoding DNA segments using site-directed mutagenesis provides a means of producing potentially useful species and is not meant to be limiting as there are other ways in which sequence variants of peptides and the DNA sequences encoding them may be obtained. For example, recombinant vectors encoding the desired peptide sequence may be treated with mutagenic agents, such as hydroxylamine, to obtain sequence variants. Specific details regarding these methods and protocols are found in the teachings of Maloy et al., 1994; Segal, 1976; Prokop and Bajpai, 1991; Kuby, 1994; and Maniatis et al., 1982, each incorporated herein by reference, for that purpose.

As used herein, the term "oligonucleotide directed mutagenesis procedure" refers to template-dependent processes and vector-mediated propagation which result in an increase in the concentration of a specific nucleic acid molecule relative to its initial concentration, or in an increase in the concentration of a detectable signal, such as amplification. As used herein, the term "oligonucleotide directed mutagenesis procedure" is intended to refer to a process that involves the template-dependent extension of a primer molecule. The term template dependent process refers to nucleic acid synthesis of an RNA or a DNA molecule wherein the sequence of the newly synthesized strand of nucleic acid is dictated by the well-known rules of complementary base pairing (see, for example, Watson, 1987). Typically, vector mediated methodologies involve the introduction of the nucleic acid fragment into a DNA or RNA vector, the clonal amplification of the vector, and the recovery of the amplified nucleic acid fragment. Examples of such methodologies are provided by U.S. Pat. No. 4,237,224, specifically incorporated herein by reference in its entirety.

In another approach for the production of polypeptide variants of the present invention, recursive sequence recombination, as described in U.S. Pat. No. 5,837,458, may be employed. In this approach, iterative cycles of recombination and screening or selection are performed to "evolve" individual polynucleotide variants of the invention having, for example, enhanced immunogenic activity.

In other embodiments of the present invention, the polynucleotide sequences provided herein can be advantageously used as probes or primers for nucleic acid hybridization. As such, it is contemplated that nucleic acid segments that comprise a sequence region of at least about 15 nucleotide long contiguous sequence that has the same sequence as, or is complementary to, a 15 nucleotide long contiguous sequence disclosed herein will find particular utility. Longer contiguous identical or complementary sequences, e.g., those of about 20, 30, 40, 50, 100, 200, 500, 1000 (including all intermediate lengths) and even up to full length sequences will also be of use in certain embodiments.

The ability of such nucleic acid probes to specifically hybridize to a sequence of interest will enable them to be of use in detecting the presence of complementary sequences in a given sample. However, other uses are also envisioned, such as the use of the sequence information for the preparation of mutant species primers, or primers for use in preparing other genetic constructions.

Polynucleotide molecules having sequence regions consisting of contiguous nucleotide stretches of 10-14, 15-20, 30, 50, or even of 100-200 nucleotides or so (including intermediate lengths as well), identical or complementary to a polynucleotide sequence disclosed herein, are particularly contemplated as hybridization probes for use in, e.g., Southern and Northern blotting. This would allow a gene product, or fragment thereof, to be analyzed, both in diverse cell types and also in various bacterial cells. The total size of fragment, as well as the size of the complementary stretch(es), will ultimately depend on the intended use or application of the particular nucleic acid segment. Smaller fragments will generally find use in hybridization embodiments, wherein the length of the contiguous complementary region may be varied, such as between about 15 and about 100 nucleotides, but larger contiguous complementarity stretches may be used, according to the length complementary sequences one wishes to detect.

The use of a hybridization probe of about 15-25 nucleotides in length allows the formation of a duplex molecule that is both stable and selective. Molecules having contiguous complementary sequences over stretches greater than 15 bases in length are generally preferred, though, in order to increase stability and selectivity of the hybrid, and thereby improve the quality and degree of specific hybrid molecules obtained. One will generally prefer to design nucleic acid molecules having gene-complementary stretches of 15 to 25 contiguous nucleotides, or even longer where desired.

Hybridization probes may be selected from any portion of any of the sequences disclosed herein. All that is required is to review the sequences set forth herein, or to any continuous portion of the sequences, from about 15-25 nucleotides in length up to and including the full length sequence, that one wishes to utilize as a probe or primer. The choice of probe and primer sequences may be governed by various factors. For example, one may wish to employ primers from towards the termini of the total sequence.

Small polynucleotide segments or fragments may be readily prepared by, for example, directly synthesizing the fragment by chemical means, as is commonly practiced using an automated oligonucleotide synthesizer. Also, fragments may be obtained by application of nucleic acid reproduction technology, such as the PCR™ technology of U.S. Pat. No. 4,683,202 (incorporated herein by reference), by introducing selected sequences into recombinant vectors for recombinant production, and by other recombinant DNA techniques generally known to those of skill in the art of molecular biology.

The nucleotide sequences of the invention may be used for their ability to selectively form duplex molecules with complementary stretches of the entire gene or gene fragments of interest. Depending on the application envisioned, one will typically desire to employ varying conditions of hybridization to achieve varying degrees of selectivity of probe towards target sequence. For applications requiring high selectivity, one will typically desire to employ relatively stringent conditions to form the hybrids, e.g., one will select relatively low salt and/or high temperature conditions, such as provided by a salt concentration of from about 0.02 M to about 0.15 M salt at temperatures of from about 50° C. to about 70° C. Such selective conditions tolerate little, if any, mismatch between the probe and the template or target strand, and would be particularly suitable for isolating related sequences.

Of course, for some applications, for example, where one desires to prepare mutants employing a mutant primer strand hybridized to an underlying template, less stringent (reduced stringency) hybridization conditions will typically be needed in order to allow formation of the heteroduplex. In these circumstances, one may desire to employ salt conditions such as those of from about 0.15 M to about 0.9 M salt, at temperatures ranging from about 20° C. to about 55° C. Cross-hybridizing species can thereby be readily identified as positively hybridizing signals with respect to control hybridizations. In any case, it is generally appreciated that conditions can be rendered more stringent by the addition of increasing amounts of formamide, which serves to destabilize the hybrid duplex in the same manner as increased temperature. Thus, hybridization conditions can be readily manipulated, and thus will generally be a method of choice depending on the desired results.

According to another embodiment of the present invention, polynucleotide compositions comprising antisense oligonucleotides are provided. Antisense oligonucleotides have been demonstrated to be effective and targeted inhibitors of protein synthesis, and, consequently, provide a therapeutic approach by which a disease can be treated by inhibiting the synthesis of proteins that contribute to the disease. The efficacy of antisense oligonucleotides for inhibiting protein synthesis is well established. For example, the synthesis of polygalactauronase and the muscarine type 2 acetylcholine receptor are inhibited by antisense oligonucleotides directed to their respective mRNA sequences (U.S. Pat. No. 5,739,119 and U.S. Pat. No. 5,759,829). Further, examples of antisense inhibition have been demonstrated with the nuclear protein cyclin, the multiple drug resistance gene (MDG1), ICAM-1, E-selectin, STK-1, striatal $GABA_A$ receptor and human EGF (Jaskulski et al., Science. Jun. 10, 1988;240(4858):1544-6; Vasanthakumar and Ahmed, Cancer Commun. 1989;1(4): 225-32; Peris et al., Brain Res Mol Brain Res. Jun. 15, 1998; 57(2):310-20; U.S. Pat. No. 5,801,154; U.S. Pat. No. 5,789, 573; U.S. Pat. No. 5,718,709 and U.S. Pat. No. 5,610,288). Antisense constructs have also been described that inhibit and can be used to treat a variety of abnormal cellular proliferations, e.g. cancer (U.S. Pat. No. 5,747,470; U.S. Pat. No. 5,591,317 and U.S. Pat. No. 5,783,683).

Therefore, in certain embodiments, the present invention provides oligonucleotide sequences that comprise all, or a portion of, any sequence that is capable of specifically binding to polynucleotide sequence described herein, or a complement thereof. In one embodiment, the antisense oligonucleotides comprise DNA or derivatives thereof. In another embodiment, the oligonucleotides comprise RNA or derivatives thereof. In a third embodiment, the oligonucleotides are modified DNAs comprising a phosphorothioated modified backbone. In a fourth embodiment, the oligonucleotide sequences comprise peptide nucleic acids or derivatives thereof. In each case, preferred compositions comprise a sequence region that is complementary, and more preferably substantially-complementary, and even more preferably, completely complementary to one or more portions of polynucleotides disclosed herein. Selection of antisense compositions specific for a given gene sequence is based upon analysis of the chosen target sequence and determination of secondary structure, $T_m$, binding energy, and relative stability. Antisense compositions may be selected based upon their relative inability to form dimers, hairpins, or other secondary structures that would reduce or prohibit specific binding to the target mRNA in a host cell. Highly preferred target regions of the mRNA, are those which are at or near the AUG translation initiation codon, and those sequences which are substantially complementary to 5' regions of the mRNA. These secondary structure analyses and target site selection considerations can be performed, for example, using v.4 of the OLIGO primer analysis software and/or the BLASTN 2.0.5 algorithm software (Altschul et al., Nucleic Acids Res. 1997, 25(17):3389-402).

The use of an antisense delivery method employing a short peptide vector, termed MPG (27 residues), is also contemplated. The MPG peptide contains a hydrophobic domain derived from the fusion sequence of HIV gp41 and a hydrophilic domain from the nuclear localization sequence of SV40 T-antigen (Morris et al., Nucleic Acids Res. 1997 Jul. 15;25(14):2730-6). It has been demonstrated that several molecules of the MPG peptide coat the antisense oligonucleotides and can be delivered into cultured mammalian cells in less than 1 hour with relatively high efficiency (90%). Further, the interaction with MPG strongly increases both the stability of the oligonucleotide to nuclease and the ability to cross the plasma membrane.

According to another embodiment of the invention, the polynucleotide compositions described herein are used in the design and preparation of ribozyme molecules for inhibiting expression of the tumor polypeptides and proteins of the present invention in tumor cells. Ribozymes are RNA-protein complexes that cleave nucleic acids in a site-specific fashion. Ribozymes have specific catalytic domains that possess endonuclease activity (Kim and Cech, Proc Natl Acad Sci USA. 1987 December;84(24):8788-92; Forster and Symons, Cell. 1987 April 24;49(2):211-20). For example, a large number of ribozymes accelerate phosphoester transfer reactions with a high degree of specificity, often cleaving only one of several phosphoesters in an oligonucleotide substrate (Cech et al., Cell. 1981 December;27(3 Pt 2):487-96; Michel and Westhof, J Mol Biol. 1990 Dec. 5;216(3):585-610; Reinhold-Hurek and Shub, Nature. 1992 May 14;357(6374):173-6). This specificity has been attributed to the requirement that the substrate bind via specific base-pairing interactions to the internal guide sequence ("IGS") of the ribozyme prior to chemical reaction.

Six basic varieties of naturally-occurring enzymatic RNAs are known presently. Each can catalyze the hydrolysis of RNA phosphodiester bonds in trans (and thus can cleave other RNA molecules) under physiological conditions. In general, enzymatic nucleic acids act by first binding to a target RNA. Such binding occurs through the target binding portion of a enzymatic nucleic acid which is held in close proximity to an enzymatic portion of the molecule that acts to cleave the target RNA. Thus, the enzymatic nucleic acid first recognizes and then binds a target RNA through complementary base-pairing, and once bound to the correct site, acts enzymatically to cut the target RNA. Strategic cleavage of such a target RNA will destroy its ability to direct synthesis of an encoded protein. After an enzymatic nucleic acid has bound and cleaved its RNA target, it is released from that RNA to search for another target and can repeatedly bind and cleave new targets.

The enzymatic nature of a ribozyme is advantageous over many technologies, such as antisense technology (where a nucleic acid molecule simply binds to a nucleic acid target to block its translation) since the concentration of ribozyme necessary to affect a therapeutic treatment is lower than that of an antisense oligonucleotide. This advantage reflects the ability of the ribozyme to act enzymatically. Thus, a single ribozyme molecule is able to cleave many molecules of target RNA. In addition, the ribozyme is a highly specific inhibitor, with the specificity of inhibition depending not only on the base pairing mechanism of binding to the target RNA, but also on the mechanism of target RNA cleavage. Single mismatches, or base-substitutions, near the site of cleavage can completely eliminate catalytic activity of a ribozyme. Similar mismatches in antisense molecules do not prevent their action (Woolf et al., Proc Natl Acad Sci USA. 1992 Aug. 15;89(16):7305-9). Thus, the specificity of action of a ribozyme is greater than that of an antisense oligonucleotide binding the same RNA site.

The enzymatic nucleic acid molecule may be formed in a hammerhead, hairpin, a hepatitis δ virus, group I intron or RNaseP RNA (in association with an RNA guide sequence) or Neurospora VS RNA motif. Examples of hammerhead motifs are described by Rossi et al Nucleic Acids Res. 1992 Sep. 11;20(17):4559-65. Examples of hairpin motifs are described by Hampel et al. (Eur. Pat. Appl. Publ. No. EP 0360257), Hampel and Tritz, Biochemistry 1989 Jun. 13;28 (12):4929-33; Hampel et al., Nucleic Acids Res. 1990 Jan. 15;18(2):299-304 and U.S. Pat. No. 5,631,359. An example of the hepatitis δ virus motif is described by Perrotta and Been, Biochemistry. 1992 Dec. 1;31 (47):11843-52; an example of the RNaseP motif is described by Guerrier-Takada et al., Cell. 1983 December;35(3 Pt 2):849-57; Neurospora VS RNA ribozyme motif is described by Collins (Saville and Collins, Cell. 1990 May 18;61(4):685-96; Saville and Collins, Proc Natl Acad Sci USA. 1991 Oct. 1;88(19):8826-30; Collins and Olive, Biochemistry. 1993 Mar. 23;32(11):2795-9); and an example of the Group I intron is described in (U.S. Pat. No. 4,987,071). All that is important in an enzymatic nucleic acid molecule of this invention is that it has a specific substrate binding site which is complementary to one or more of the target gene RNA regions, and that it have nucleotide sequences within or surrounding that substrate binding site which impart an RNA cleaving activity to the molecule. Thus the ribozyme constructs need not be limited to specific motifs mentioned herein.

Ribozymes may be designed as described in Int. Pat. Appl. Publ. No. WO 93/23569 and Int. Pat. Appl. Publ. No. WO 94/02595, each specifically incorporated herein by reference) and synthesized to be tested in vitro and in vivo, as described. Such ribozymes can also be optimized for delivery. While specific examples are provided, those in the art will recognize that equivalent RNA targets in other species can be utilized when necessary.

Ribozyme activity can be optimized by altering the length of the ribozyme binding arms, or chemically synthesizing ribozymes with modifications that prevent their degradation by serum ribonucleases (see e.g., Int. Pat. Appl. Publ. No. WO 92/07065; Int. Pat. Appl. Publ. No. WO 93/15187; Int. Pat. Appl. Publ. No. WO 91/03162; Eur. Pat. Appl. Publ. No. 92110298.4; U.S. Pat. No. 5,334,711; and Int. Pat. Appl. Publ. No. WO 94/13688, which describe various chemical modifications that can be made to the sugar moieties of enzymatic RNA molecules), modifications which enhance their efficacy in cells, and removal of stem II bases to shorten RNA synthesis times and reduce chemical requirements.

Sullivan et al. (Int. Pat. Appl. Publ. No. WO 94/02595) describes the general methods for delivery of enzymatic RNA molecules. Ribozymes may be administered to cells by a variety of methods known to those familiar to the art, including, but not restricted to, encapsulation in liposomes, by iontophoresis, or by incorporation into other vehicles, such as hydrogels, cyclodextrins, biodegradable nanocapsules, and bioadhesive microspheres. For some indications, ribozymes may be directly delivered ex vivo to cells or tissues with or without the aforementioned vehicles. Alternatively, the RNA/vehicle combination may be locally delivered by direct inhalation, by direct injection or by use of a catheter, infusion pump or stent. Other routes of delivery include, but are not limited to, intravascular, intramuscular, subcutaneous or joint injection, aerosol inhalation, oral (tablet or pill form), topical, systemic, ocular, intraperitoneal and/or intrathecal delivery. More detailed descriptions of ribozyme delivery and administration are provided in Int. Pat. Appl. Publ. No. WO 94/02595 and Int. Pat. Appl. Publ. No. WO 93/23569, each specifically incorporated herein by reference.

Another means of accumulating high concentrations of a ribozyme(s) within cells is to incorporate the ribozyme-encoding sequences into a DNA expression vector. Transcription of the ribozyme sequences are driven from a promoter for eukaryotic RNA polymerase I (pol I), RNA polymerase II (pol II), or RNA polymerase III (pol III). Transcripts from pol II or pol III promoters will be expressed at high levels in all cells; the levels of a given pol II promoter in a given cell type will depend on the nature of the gene regulatory sequences (enhancers, silencers, etc.) present nearby. Prokaryotic RNA polymerase promoters may also be used, providing that the prokaryotic RNA polymerase enzyme is expressed in the appropriate cells Ribozymes expressed from such promoters have been shown to function in mammalian cells. Such transcription units can be incorporated into a variety of vectors for introduction into mammalian cells, including but not restricted to, plasmid DNA vectors, viral DNA vectors (such as adenovirus or adeno-associated vectors), or viral RNA vectors (such as retroviral, semliki forest virus, sindbis virus vectors).

In another embodiment of the invention, peptide nucleic acids (PNAs) compositions are provided. PNA is a DNA mimic in which the nucleobases are attached to a pseudopeptide backbone (Good and Nielsen, Antisense Nucleic Acid Drug Dev. 1997 7(4) 431-37). PNA is able to be utilized in a number methods that traditionally have used RNA or DNA. Often PNA sequences perform better in techniques than the corresponding RNA or DNA sequences and have utilities that are not inherent to RNA or DNA. A review of PNA including methods of making, characteristics of, and methods of using, is provided by Corey (*Trends Biotechnol* 1997 June;15(6): 224-9). As such, in certain embodiments, one may prepare PNA sequences that are complementary to one or more portions of the ACE mRNA sequence, and such PNA compositions may be used to regulate, alter, decrease, or reduce the translation of ACE-specific mRNA, and thereby alter the level of ACE activity in a host cell to which such PNA compositions have been administered.

PNAs have 2-aminoethyl-glycine linkages replacing the normal phosphodiester backbone of DNA (Nielsen et al., Science 1991 Dec. 6;254(5037):1497-500; Hanvey et al., Science. 1992 Nov. 27;258(5087):1481-5; Hyrup and Nielsen, Bioorg Med Chem. 1996 January;4(1):5-23). This chemistry has three important consequences: firstly, in contrast to DNA or phosphorothioate oligonucleotides, PNAs are neutral molecules; secondly, PNAs are achiral, which avoids the need to develop a stereoselective synthesis; and thirdly, PNA synthesis uses standard Boc or Fmoc protocols for solid-phase peptide synthesis, although other methods, including a modified Merrifield method, have been used.

PNA monomers or ready-made oligomers are commercially available from PerSeptive Biosystems (Framingham, Mass.). PNA syntheses by either Boc or Fmoc protocols are straightforward using manual or automated protocols (Norton et al., Bioorg Med Chem. 1995 April;3(4):437-45). The manual protocol lends itself to the production of chemically modified PNAs or the simultaneous synthesis of families of closely related PNAs.

As with peptide synthesis, the success of a particular PNA synthesis will depend on the properties of the chosen sequence. For example, while in theory PNAs can incorporate any combination of nucleotide bases, the presence of adjacent purines can lead to deletions of one or more residues in the product. In expectation of this difficulty, it is suggested that, in producing PNAs with adjacent purines, one should repeat the coupling of residues likely to be added inefficiently. This should be followed by the purification of PNAs by reverse-phase high-pressure liquid chromatography, providing yields and purity of product similar to those observed during the synthesis of peptides.

Modifications of PNAs for a given application may be accomplished by coupling amino acids during solid-phase synthesis or by attaching compounds that contain a carboxylic acid group to the exposed N-terminal amine. Alternatively, PNAs can be modified after synthesis by coupling to an introduced lysine or cysteine. The ease with which PNAs can be modified facilitates optimization for better solubility or for specific functional requirements. Once synthesized, the identity of PNAs and their derivatives can be confirmed by mass spectrometry. Several studies have made and utilized modifications of PNAs (for example, Norton et al., Bioorg Med Chem. 1995 April;3(4):437-45; Petersen et al, J Pept Sci. 1995 May-June;1(3):175-83; Orum et al., Biotechniques. 1995 September;19(3):472-80; Footer et al., Biochemistry. 1996 Aug. 20;35(33): 10673-9; Griffith et al., Nucleic Acids Res. 1995 Aug. 11;23(15):3003-8; Pardridge et al., Proc Natl Acad Sci USA. 1995 Jun. 6;92(12):5592-6; Boffa et al., Proc Natl Acad Sci USA. 1995 Mar. 14, 1995;92(6):1901-5; Gambacorti-Passerini et al., Blood. 1996 August 15, 1996;88(4): 1411-7; Armitage et al., Proc Natl Acad Sci USA. 1997 Nov. 11;94(23):12320-5; Seeger et al., Biotechniques. 1997 September;23(3):512-7). U.S. Pat. No. 5,700,922 discusses PNA-DNA-PNA chimeric molecules and their uses in diagnostics, modulating protein in organisms, and treatment of conditions susceptible to therapeutics.

Methods of characterizing the antisense binding properties of PNAs are discussed in Rose (Anal Chem. 1993 Dec. 15;65 (24):3545-9) and Jensen et al. (Biochemistry. 1997 Apr. 22;36 (16):5072-7). Rose uses capillary gel electrophoresis to determine binding of PNAs to their complementary oligonucleotide, measuring the relative binding kinetics and stoichiometry. Similar types of measurements were made by Jensen et al. using BIAcore™ technology.

Other applications of PNAs that have been described and will be apparent to the skilled artisan include use in DNA strand invasion, antisense inhibition, mutational analysis, enhancers of transcription, nucleic acid purification, isolation of transcriptionally active genes, blocking of transcription factor binding, genome cleavage, biosensors, in situ hybridization, and the like.

Polynucleotide Identification, Characterization and Expression

Polynucleotides compositions of the present invention may be identified, prepared and/or manipulated using any of a variety of well established techniques (see generally, Sambrook et al., *Molecular Cloning: A Laboratory Manual*, Cold Spring Harbor Laboratories, Cold Spring Harbor, N.Y., 1989, and other like references). For example, a polynucleotide may be identified, as described in more detail below, by screening a microarray of cDNAs for tumor-associated expression (i.e., expression that is at least two fold greater in a tumor than in normal tissue, as determined using a representative assay provided herein). Such screens may be performed, for example, using the microarray technology of Affymetrix, Inc. (Santa Clara, Calif.) according to the manufacturer's instructions (and essentially as described by Schena et al., *Proc. Natl. Acad. Sci. USA* 93:10614-10619, 1996 and Heller et al., *Proc. Natl. Acad. Sci. USA* 94:2150-2155, 1997). Alternatively, polynucleotides may be amplified from cDNA prepared from cells expressing the proteins described herein, such as tumor cells.

Many template dependent processes are available to amplify a target sequences of interest present in a sample. One of the best known amplification methods is the polymerase chain reaction (PCR™) which is described in detail in U.S. Pat. Nos. 4,683,195, 4,683,202 and 4,800,159, each of which is incorporated herein by reference in its entirety. Briefly, in PCR™, two primer sequences are prepared which are complementary to regions on opposite complementary strands of the target sequence. An excess of deoxynucleoside triphosphates is added to a reaction mixture along with a DNA polymerase (e.g., Taq polymerase). If the target sequence is present in a sample, the primers will bind to the target and the polymerase will cause the primers to be extended along the target sequence by adding on nucleotides. By raising and lowering the temperature of the reaction mixture, the extended primers will dissociate from the target to form reaction products, excess primers will bind to the target and to the reaction product and the process is repeated. Preferably reverse transcription and PCR™ amplification procedure may be performed in order to quantify the amount of mRNA amplified. Polymerase chain reaction methodologies are well known in the art.

Any of a number of other template dependent processes, many of which are variations of the PCR™ amplification technique, are readily known and available in the art. Illustratively, some such methods include the ligase chain reaction (referred to as LCR), described, for example, in Eur. Pat. Appl. Publ. No. 320,308 and U.S. Pat. No. 4,883,750; Qbeta Replicase, described in PCT Intl. Pat. Appl. Publ. No. PCT/US87/00880; Strand Displacement Amplification (SDA) and Repair Chain Reaction (RCR). Still other amplification methods are described in Great Britain Pat. Appl. No. 2 202 328, and in PCT Intl. Pat. Appl. Publ. No. PCT/US89/01025. Other nucleic acid amplification procedures include transcription-based amplification systems (TAS) (PCT Intl. Pat. Appl. Publ. No. WO 88/10315), including nucleic acid sequence based amplification (NASBA) and 3SR. Eur. Pat. Appl. Publ. No. 329,822 describes a nucleic acid amplification process involving cyclically synthesizing single-stranded RNA ("ssRNA"), ssDNA, and double-stranded DNA (dsDNA). PCT Intl. Pat. Appl. Publ. No. WO 89/06700 describes a nucleic acid sequence amplification scheme based on the hybridization of a promoter/primer sequence to a target single-stranded DNA ("ssDNA") followed by transcription of many RNA copies of the sequence. Other amplification methods such as "RACE" (Frohman, 1990), and "one-sided PCR" (Ohara, 1989) are also well-known to those of skill in the art.

An amplified portion of a polynucleotide of the present invention may be used to isolate a full length gene from a suitable library (e.g., a tumor cDNA library) using well known techniques. Within such techniques, a library (cDNA or genomic) is screened using one or more polynucleotide probes or primers suitable for amplification. Preferably, a library is size-selected to include larger molecules. Random primed libraries may also be preferred for identifying 5' and upstream regions of genes. Genomic libraries are preferred for obtaining introns and extending 5' sequences.

For hybridization techniques, a partial sequence may be labeled (e.g., by nick-translation or end-labeling with $^{32}P$) using well known techniques. A bacterial or bacteriophage library is then generally screened by hybridizing filters containing denatured bacterial colonies (or lawns containing phage plaques) with the labeled probe (see Sambrook et al., *Molecular Cloning: A Laboratory Manual*, Cold Spring Harbor Laboratories, Cold Spring Harbor, N.Y., 1989). Hybridizing colonies or plaques are selected and expanded, and the DNA is isolated for further analysis. cDNA clones may be analyzed to determine the amount of additional sequence by, for example, PCR using a primer from the partial sequence and a primer from the vector. Restriction maps and partial sequences may be generated to identify one or more overlapping clones. The complete sequence may then be determined using standard techniques, which may involve generating a series of deletion clones. The resulting overlapping sequences can then assembled into a single contiguous sequence. A full length cDNA molecule can be generated by ligating suitable fragments, using well known techniques.

Alternatively, amplification techniques, such as those described above, can be useful for obtaining a full length coding sequence from a partial cDNA sequence. One such amplification technique is inverse PCR (see Triglia et al., *Nucl. Acids Res.* 16:8186, 1988), which uses restriction enzymes to generate a fragment in the known region of the gene. The fragment is then circularized by intramolecular ligation and used as a template for PCR with divergent primers derived from the known region. Within an alternative approach, sequences adjacent to a partial sequence may be retrieved by amplification with a primer to a linker sequence and a primer specific to a known region. The amplified sequences are typically subjected to a second round of amplification with the same linker primer and a second primer specific to the known region. A variation on this procedure, which employs two primers that initiate extension in opposite directions from the known sequence, is described in WO 96/38591. Another such technique is known as "rapid amplification of cDNA ends" or RACE. This technique involves the use of an internal primer and an external primer, which hybridizes to a polyA region or vector sequence, to identify sequences that are 5' and 3' of a known sequence. Additional techniques include capture PCR (Lagerstrom et al., *PCR Methods Applic.* 1:111-19, 1991) and walking PCR (Parker et al., *Nucl. Acids. Res.* 19:3055-60, 1991). Other methods employing amplification may also be employed to obtain a full length cDNA sequence.

In certain instances, it is possible to obtain a full length cDNA sequence by analysis of sequences provided in an expressed sequence tag (EST) database, such as that available from GenBank. Searches for overlapping ESTs may generally be performed using well known programs (e.g., NCBI BLAST searches), and such ESTs may be used to generate a contiguous full length sequence. Full length DNA sequences may also be obtained by analysis of genomic fragments.

In other embodiments of the invention, polynucleotide sequences or fragments thereof which encode polypeptides of the invention, or fusion proteins or functional equivalents thereof, may be used in recombinant DNA molecules to direct expression of a polypeptide in appropriate host cells. Due to the inherent degeneracy of the genetic code, other DNA sequences that encode substantially the same or a functionally equivalent amino acid sequence may be produced and these sequences may be used to clone and express a given polypeptide.

As will be understood by those of skill in the art, it may be advantageous in some instances to produce polypeptide-encoding nucleotide sequences possessing non-naturally occurring codons. For example, codons preferred by a particular prokaryotic or eukaryotic host can be selected to increase the rate of protein expression or to produce a recombinant RNA transcript having desirable properties, such as a half-life which is longer than that of a transcript generated from the naturally occurring sequence.

Moreover, the polynucleotide sequences of the present invention can be engineered using methods generally known in the art in order to alter polypeptide encoding sequences for a variety of reasons, including but not limited to, alterations which modify the cloning, processing, and/or expression of the gene product. For example, DNA shuffling by random fragmentation and PCR reassembly of gene fragments and synthetic oligonucleotides may be used to engineer the nucleotide sequences. In addition, site-directed mutagenesis may be used to insert new restriction sites, alter glycosylation patterns, change codon preference, produce splice variants, or introduce mutations, and so forth.

In another embodiment of the invention, natural, modified, or recombinant nucleic acid sequences may be ligated to a heterologous sequence to encode a fusion protein. For example, to screen peptide libraries for inhibitors of polypeptide activity, it may be useful to encode a chimeric protein that can be recognized by a commercially available antibody. A fusion protein may also be engineered to contain a cleavage site located between the polypeptide-encoding sequence and the heterologous protein sequence, so that the polypeptide may be cleaved and purified away from the heterologous moiety.

Sequences encoding a desired polypeptide may be synthesized, in whole or in part, using chemical methods well known in the art (see Caruthers, M. H. et al. (1980) Nucl. Acids Res. Symp. Ser. 215-223, Horn, T. et al. (1980) Nucl. Acids Res. Symp. Ser. 225-232). Alternatively, the protein itself may be produced using chemical methods to synthesize the amino acid sequence of a polypeptide, or a portion thereof. For example, peptide synthesis can be performed using various solid-phase techniques (Roberge, J. Y. et al. (1995) Science 269:202-204) and automated synthesis may be achieved, for example, using the ABI 431 A Peptide Synthesizer (Perkin Elmer, Palo Alto, Calif.).

A newly synthesized peptide may be substantially purified by preparative high performance liquid chromatography (e.g., Creighton, T. (1983) Proteins, Structures and Molecular Principles, WH Freeman and Co., New York, N.Y.) or other comparable techniques available in the art. The composition of the synthetic peptides may be confirmed by amino acid analysis or sequencing (e.g., the Edman degradation procedure). Additionally, the amino acid sequence of a polypeptide, or any part thereof, may be altered during direct synthesis and/or combined using chemical methods with sequences from other proteins, or any part thereof, to produce a variant polypeptide.

In order to express a desired polypeptide, the nucleotide sequences encoding the polypeptide, or functional equivalents, may be inserted into appropriate expression vector, i.e., a vector which contains the necessary elements for the transcription and translation of the inserted coding sequence. Methods which are well known to those skilled in the art may be used to construct expression vectors containing sequences encoding a polypeptide of interest and appropriate transcriptional and translational control elements. These methods include in vitro recombinant DNA techniques, synthetic techniques, and in vivo genetic recombination. Such techniques are described, for example, in Sambrook, J. et al. (1989) Molecular Cloning, A Laboratory Manual, Cold Spring Harbor Press, Plainview, N.Y., and Ausubel, F. M. et al. (1989) Current Protocols in Molecular Biology, John Wiley & Sons, New York. N.Y.

A variety of expression vector/host systems may be utilized to contain and express polynucleotide sequences. These include, but are not limited to, microorganisms such as bacteria transformed with recombinant bacteriophage, plasmid, or cosmid DNA expression vectors; yeast transformed with yeast expression vectors; insect cell systems infected with virus expression vectors (e.g., baculovirus); plant cell systems transformed with virus expression vectors (e.g., cauliflower mosaic virus, CaMV; tobacco mosaic virus, TMV) or with bacterial expression vectors (e.g., Ti or pBR322 plasmids); or animal cell systems.

The "control elements" or "regulatory sequences" present in an expression vector are those non-translated regions of the vector—enhancers, promoters, 5' and 3' untranslated regions—which interact with host cellular proteins to carry out transcription and translation. Such elements may vary in their strength and specificity. Depending on the vector system and host utilized, any number of suitable transcription and translation elements, including constitutive and inducible promoters, may be used. For example, when cloning in bacterial systems, inducible promoters such as the hybrid lacZ promoter of the pBLUESCRIPT phagemid (Stratagene, La Jolla, Calif.) or PSPORT1 plasmid (Gibco BRL, Gaithersburg, Md.) and the like may be used. In mammalian cell systems, promoters from mammalian genes or from mammalian viruses are generally preferred. If it is necessary to generate a cell line that contains multiple copies of the sequence encoding a polypeptide, vectors based on SV40 or EBV may be advantageously used with an appropriate selectable marker.

In bacterial systems, any of a number of expression vectors may be selected depending upon the use intended for the expressed polypeptide. For example, when large quantities are needed, for example for the induction of antibodies, vectors which direct high level expression of fusion proteins that are readily purified may be used. Such vectors include, but are not limited to, the multifunctional E. coli cloning and expression vectors such as BLUESCRIPT (Stratagene), in which the sequence encoding the polypeptide of interest may be ligated into the vector in frame with sequences for the amino-terminal Met and the subsequent 7 residues of .beta.-galactosidase so that a hybrid protein is produced; pIN vectors (Van Heeke, G. and S. M. Schuster (1989) J. Biol. Chem. 264:5503-5509); and the like. pGEX Vectors (Promega, Madison, Wis.) may also be used to express foreign polypeptides as fusion proteins with glutathione S-transferase (GST). In general, such fusion proteins are soluble and can easily be purified from lysed cells by adsorption to glutathione-agarose beads followed by elution in the presence of free glutathione. Proteins made in such systems may be designed to include heparin, thrombin, or factor XA protease cleavage sites so that the cloned polypeptide of interest can be released from the GST moiety at will.

In the yeast, Saccharomyces cerevisiae, a number of vectors containing constitutive or inducible promoters such as alpha factor, alcohol oxidase, and PGH may be used. For reviews, see Ausubel et al. (supra) and Grant et al. (1987) Methods Enzymol. 153:516-544.

In cases where plant expression vectors are used, the expression of sequences encoding polypeptides may be driven by any of a number of promoters. For example, viral promoters such as the 35S and 19S promoters of CaMV may be used alone or in combination with the omega leader sequence from TMV (Takamatsu, N. (1987) EMBO J. 6:307-311. Alternatively, plant promoters such as the small subunit of RUBISCO or heat shock promoters may be used (Coruzzi, G. et al. (1984) EMBO J. 3:1671-1680; Broglie, R. et al. (1984) Science 224:838-843; and Winter, J. et al. (1991) Results Probl. Cell Differ. 17:85-105). These constructs can be introduced into plant cells by direct DNA transformation or pathogen-mediated transfection. Such techniques are described in a number of generally available reviews (see, for example, Hobbs, S. or Muny, L. E. in McGraw Hill Yearbook of Science and Technology (1992) McGraw Hill, New York, N.Y.; pp. 191-196).

An insect system may also be used to express a polypeptide of interest. For example, in one such system, Autographa californica nuclear polyhedrosis virus (AcNPV) is used as a vector to express foreign genes in Spodoptera frugiperda cells or in Trichoplusia larvae. The sequences encoding the polypeptide may be cloned into a non-essential region of the virus, such as the polyhedrin gene, and placed under control of the polyhedrin promoter. Successful insertion of the polypeptide-encoding sequence will render the polyhedrin gene inactive and produce recombinant virus lacking coat protein. The recombinant viruses may then be used to infect, for example, *S. frugiperda* cells or *Trichoplusia larvae* in which the polypeptide of interest may be expressed (Engelhard, E. K. et al. (1994) *Proc. Natl. Acad. Sci.* 91:3224-3227).

In mammalian host cells, a number of viral-based expression systems are generally available. For example, in cases where an adenovirus is used as an expression vector, sequences encoding a polypeptide of interest may be ligated into an adenovirus transcription/translation complex consisting of the late promoter and tripartite leader sequence. Insertion in a non-essential E1 or E3 region of the viral genome may be used to obtain a viable virus which is capable of expressing the polypeptide in infected host cells (Logan, J. and Shenk, T. (1984) *Proc. Natl. Acad. Sci.* 81:3655-3659). In addition, transcription enhancers, such as the Rous sarcoma virus (RSV) enhancer, may be used to increase expression in mammalian host cells.

Specific initiation signals may also be used to achieve more efficient translation of sequences encoding a polypeptide of interest. Such signals include the ATG initiation codon and adjacent sequences. In cases where sequences encoding the polypeptide, its initiation codon, and upstream sequences are inserted into the appropriate expression vector, no additional transcriptional or translational control signals may be needed. However, in cases where only coding sequence, or a portion thereof, is inserted, exogenous translational control signals including the ATG initiation codon should be provided. Furthermore, the initiation codon should be in the correct reading frame to ensure translation of the entire insert. Exogenous translational elements and initiation codons may be of various origins, both natural and synthetic. The efficiency of expression may be enhanced by the inclusion of enhancers which are appropriate for the particular cell system which is used, such as those described in the literature (Scharf, D. et al. (1994) *Results Probl. Cell Differ.* 20:125-162).

In addition, a host cell strain may be chosen for its ability to modulate the expression of the inserted sequences or to process the expressed protein in the desired fashion. Such modifications of the polypeptide include, but are not limited to, acetylation, carboxylation. glycosylation, phosphorylation, lipidation, and acylation. Post-translational processing which cleaves a "prepro" form of the protein may also be used to facilitate correct insertion, folding and/or function. Different host cells such as CHO, COS, HeLa, MDCK, HEK293, and WI38, which have specific cellular machinery and characteristic mechanisms for such post-translational activities, may be chosen to ensure the correct modification and processing of the foreign protein.

For long-term, high-yield production of recombinant proteins, stable expression is generally preferred. For example, cell lines which stably express a polynucleotide of interest may be transformed using expression vectors which may contain viral origins of replication and/or endogenous expression elements and a selectable marker gene on the same or on a separate vector. Following the introduction of the vector, cells may be allowed to grow for 1-2 days in an enriched media before they are switched to selective media. The purpose of the selectable marker is to confer resistance to selection, and its presence allows growth and recovery of cells which successfully express the introduced sequences. Resistant clones of stably transformed cells may be proliferated using tissue culture techniques appropriate to the cell type.

Any number of selection systems may be used to recover transformed cell lines. These include, but are not limited to, the herpes simplex virus thymidine kinase (Wigler, M. et al. (1977) *Cell* 11:223-32) and adenine phosphoribosyltransferase (Lowy, I. et al. (1990) *Cell* 22:817-23) genes which can be employed in tk.sup.- or aprt.sup.-cells, respectively. Also, antimetabolite, antibiotic or herbicide resistance can be used as the basis for selection; for example, dhfr which confers resistance to methotrexate (Wigler, M. et al. (1980) *Proc. Natl. Acad. Sci.* 77:3567-70); npt, which confers resistance to the aminoglycosides, neomycin and G-418 (Colbere-Garapin, F. et al (1981) *J. Mol. Biol.* 150:1-14); and als or pat, which confer resistance to chlorsulfuron and phosphinotricin acetyltransferase, respectively (Murry, supra). Additional selectable genes have been described, for example, trpB, which allows cells to utilize indole in place of tryptophan, or hisD, which allows cells to utilize histinol in place of histidine (Hartman, S. C. and R. C. Mulligan (1988) *Proc. Natl. Acad. Sci.* 85:8047-51). The use of visible markers has gained popularity with such markers as anthocyanins, beta-glucuronidase and its substrate GUS, and luciferase and its substrate luciferin, being widely used not only to identify transformants, but also to quantify the amount of transient or stable protein expression attributable to a specific vector system (Rhodes, C. A. et al. (1995) *Methods Mol. Biol.* 55:121-131).

Although the presence/absence of marker gene expression suggests that the gene of interest is also present, its presence and expression may need to be confirmed. For example, if the sequence encoding a polypeptide is inserted within a marker gene sequence, recombinant cells containing sequences can be identified by the absence of marker gene function. Alternatively, a marker gene can be placed in tandem with a polypeptide-encoding sequence under the control of a single promoter. Expression of the marker gene in response to induction or selection usually indicates expression of the tandem gene as well.

Alternatively, host cells that contain and express a desired polynucleotide sequence may be identified by a variety of procedures known to those of skill in the art. These procedures include, but are not limited to, DNA-DNA or DNA-RNA hybridizations and protein bioassay or immunoassay techniques which include, for example, membrane, solution, or chip based technologies for the detection and/or quantification of nucleic acid or protein.

A variety of protocols for detecting and measuring the expression of polynucleotide-encoded products, using either polyclonal or monoclonal antibodies specific for the product are known in the art. Examples include enzyme-linked immunosorbent assay (ELISA), radioimmunoassay (RIA), and fluorescence activated cell sorting (FACS). A two-site, monoclonal-based immunoassay utilizing monoclonal antibodies reactive to two non-interfering epitopes on a given polypeptide may be preferred for some applications, but a competitive binding assay may also be employed. These and other assays are described, among other places, in Hampton, R. et al. (1990; Serological Methods, a Laboratory Manual, APS Press, St Paul. Minn.) and Maddox, D. E. et al. (1983; *J. Exp. Med.* 158:1211-1216).

A wide variety of labels and conjugation techniques are known by those skilled in the art and may be used in various nucleic acid and amino acid assays. Means for producing labeled hybridization or PCR probes for detecting sequences related to polynucleotides include oligolabeling, nick translation, end-labeling or PCR amplification using a labeled nucleotide. Alternatively, the sequences, or any portions thereof may be cloned into a vector for the production of an mRNA probe. Such vectors are known in the art, are commercially available, and may be used to synthesize RNA probes in vitro by addition of an appropriate RNA polymerase such as T7, T3, or SP6 and labeled nucleotides. These procedures may be conducted using a variety of commercially available kits. Suitable reporter molecules or labels, which may be used include radionuclides, enzymes, fluorescent, chemiluminescent, or chromogenic agents as well as substrates, cofactors, inhibitors, magnetic particles, and the like.

Host cells transformed with a polynucleotide sequence of interest may be cultured under conditions suitable for the expression and recovery of the protein from cell culture. The protein produced by a recombinant cell may be secreted or contained intracellularly depending on the sequence and/or the vector used. As will be understood by those of skill in the art, expression vectors containing polynucleotides of the invention may be designed to contain signal sequences which direct secretion of the encoded polypeptide through a prokaryotic or eukaryotic cell membrane. Other recombinant constructions may be used to join sequences encoding a polypeptide of interest to nucleotide sequence encoding a polypeptide domain which will facilitate purification of soluble proteins. Such purification facilitating domains include, but are not limited to, metal chelating peptides such as histidine-tryptophan modules that allow purification on immobilized metals, protein A domains that allow purification on immobilized immunoglobulin, and the domain utilized in the FLAGS extension/affinity purification system (Irununex Corp., Seattle, Wash.). The inclusion of cleavable linker sequences such as those specific for Factor XA or enterokinase (Invitrogen. San Diego, Calif.) between the purification domain and the encoded polypeptide may be used to facilitate purification. One such expression vector provides for expression of a fusion protein containing a polypeptide of interest and a nucleic acid encoding 6 histidine residues preceding a thioredoxin or an enterokinase cleavage site. The histidine residues facilitate purification on IMIAC (immobilized metal ion affinity chromatography) as described in Porath, J. et al. (1992, *Prot. Exp. Purif.* 3:263-281) while the enterokinase cleavage site provides a means for purifying the desired polypeptide from the fusion protein. A discussion of vectors which contain fusion proteins is provided in Kroll, D. J. et al. (1993; *DNA Cell Biol.* 12:441-453).

In addition to recombinant production methods, polypeptides of the invention, and fragments thereof, may be produced by direct peptide synthesis using solid-phase techniques (Merrifield J. (1963) *J. Am. Chem. Soc.* 85:2149-2154). Protein synthesis may be performed using manual techniques or by automation. Automated synthesis may be achieved, for example, using Applied Biosystems 431A Peptide Synthesizer (Perkin Elmer). Alternatively, various fragments may be chemically synthesized separately and combined using chemical methods to produce the full length molecule.

Antibody Compositions, Fragments Thereof and Other Binding Agents

According to another aspect, the present invention further provides binding agents, such as antibodies and antigen-binding fragments thereof, that exhibit immunological binding to a tumor polypeptide disclosed herein, or to a portion, variant or derivative thereof. An antibody, or antigen-binding fragment thereof, is said to "specifically bind," "immunogically bind," and/or is "immunologically reactive" to a polypeptide of the invention if it reacts at a detectable level (within, for example, an ELISA assay) with the polypeptide, and does not react detectably with unrelated polypeptides under similar conditions.

Immunological binding, as used in this context, generally refers to the non-covalent interactions of the type which occur between an immunoglobulin molecule and an antigen for which the immunoglobulin is specific. The strength, or affinity of immunological binding interactions can be expressed in terms of the dissociation constant ($K_d$) of the interaction, wherein a smaller $K_d$ represents a greater affinity. Immunological binding properties of selected polypeptides can be quantified using methods well known in the art. One such method entails measuring the rates of antigen-binding site/antigen complex formation and dissociation, wherein those rates depend on the concentrations of the complex partners, the affinity of the interaction, and on geometric parameters that equally influence the rate in both directions. Thus, both the "on rate constant" ($K_{on}$) and the "off rate constant" ($K_{off}$) can be determined by calculation of the concentrations and the actual rates of association and dissociation. The ratio of $K_{off}/K_{on}$ enables cancellation of all parameters not related to affinity, and is thus equal to the dissociation constant $K_d$. See, generally, Davies et al. (1990) Annual Rev. Biochem. 59:439-473.

An "antigen-binding site," or "binding portion" of an antibody refers to the part of the immunoglobulin molecule that participates in antigen binding. The antigen binding site is formed by amino acid residues of the N-terminal variable ("V") regions of the heavy ("H") and light ("L") chains. Three highly divergent stretches within the V regions of the heavy and light chains are referred to as "hypervariable regions" which are interposed between more conserved flanking stretches known as "framework regions," or "FRs". Thus the term "FR" refers to amino acid sequences which are naturally found between and adjacent to hypervariable regions in immunoglobulins. In an antibody molecule, the three hypervariable regions of a light chain and the three hypervariable regions of a heavy chain are disposed relative to each other in three dimensional space to form an antigen-binding surface. The antigen-binding surface is complementary to the three-dimensional surface of a bound antigen, and the three hypervariable regions of each of the heavy and light chains are referred to as "complementarity-determining regions," or "CDRs."

Binding agents may be further capable of differentiating between patients with and without a cancer, such as breast cancer, using the representative assays provided herein. For example, antibodies or other binding agents that bind to a tumor protein will preferably generate a signal indicating the presence of a cancer in at least about 20% of patients with the disease, more preferably at least about 30% of patients. Alternatively, or in addition, the antibody will generate a negative signal indicating the absence of the disease in at least about 90% of individuals without the cancer. To determine whether a binding agent satisfies this requirement, biological samples (e.g., blood, sera, sputum, urine and/or tumor biopsies) from patients with and without a cancer (as determined using standard clinical tests) may be assayed as described herein for the presence of polypeptides that bind to the binding agent. Preferably, a statistically significant number of samples with and without the disease will be assayed. Each binding agent should satisfy the above criteria; however, those of ordinary skill in the art will recognize that binding agents may be used in combination to improve sensitivity.

Any agent that satisfies the above requirements may be a binding agent. For example, a binding agent may be a ribosome, with or without a peptide component, an RNA molecule or a polypeptide. In a preferred embodiment, a binding agent is an antibody or an antigen-binding fragment thereof. Antibodies may be prepared by any of a variety of techniques known to those of ordinary skill in the art. See, e.g., Harlow and Lane, *Antibodies: A Laboratory Manual*, Cold Spring Harbor Laboratory, 1988. In general, antibodies can be produced by cell culture techniques, including the generation of monoclonal antibodies as described herein, or via transfection of antibody genes into suitable bacterial or mammalian cell hosts, in order to allow for the production of recombinant antibodies. In one technique, an immunogen comprising the polypeptide is initially injected into any of a wide variety of mammals (e.g., mice, rats, rabbits, sheep or goats). In this step, the polypeptides of this invention may serve as the immunogen without modification. Alternatively, particularly for relatively short polypeptides, a superior immune response may be elicited if the polypeptide is joined to a carrier protein, such as bovine serum albumin or keyhole limpet hemocyanin. The immunogen is injected into the animal host, preferably according to a predetermined schedule incorporating one or more booster immunizations, and the animals are bled periodically. Polyclonal antibodies specific for the polypeptide may then be purified from such antisera by, for example, affinity chromatography using the polypeptide coupled to a suitable solid support.

Monoclonal antibodies specific for an antigenic polypeptide of interest may be prepared, for example, using the technique of Kohler and Milstein, *Eur. J. Immunol.* 6:511-519, 1976, and improvements thereto. Briefly, these methods involve the preparation of immortal cell lines capable of producing antibodies having the desired specificity (i.e., reactivity with the polypeptide of interest). Such cell lines may be produced, for example, from spleen cells obtained from an animal immunized as described above. The spleen cells are then immortalized by, for example, fusion with a myeloma cell fusion partner, preferably one that is syngeneic with the immunized animal. A variety of fusion techniques may be employed. For example, the spleen cells and myeloma cells may be combined with a nonionic detergent for a few minutes and then plated at low density on a selective medium that supports the growth of hybrid cells, but not myeloma cells. A preferred selection technique uses HAT (hypoxanthine, aminopterin, thymidine) selection. After a sufficient time, usually about 1 to 2 weeks, colonies of hybrids are observed. Single colonies are selected and their culture supernatants tested for binding activity against the polypeptide. Hybridomas having high reactivity and specificity are preferred.

Monoclonal antibodies may be isolated from the supernatants of growing hybridoma colonies. In addition, various techniques may be employed to enhance the yield, such as injection of the hybridoma cell line into the peritoneal cavity of a suitable vertebrate host, such as a mouse. Monoclonal antibodies may then be harvested from the ascites fluid or the blood. Contaminants may be removed from the antibodies by conventional techniques, such as chromatography, gel filtration, precipitation, and extraction. The polypeptides of this invention may be used in the purification process in, for example, an affinity chromatography step.

A number of therapeutically useful molecules are known in the art which comprise antigen-binding sites that are capable of exhibiting immunological binding properties of an antibody molecule. The proteolytic enzyme papain preferentially cleaves IgG molecules to yield several fragments, two of which (the "F(ab)" fragments) each comprise a covalent heterodimer that includes an intact antigen-binding site. The enzyme pepsin is able to cleave IgG molecules to provide several fragments, including the "F(ab')$_2$" fragment which comprises both antigen-binding sites. An "Fv" fragment can be produced by preferential proteolytic cleavage of an IgM, and on rare occasions IgG or IgA immunoglobulin molecule. Fv fragments are, however, more commonly derived using recombinant techniques known in the art. The Fv fragment includes a non-covalent $V_H::V_L$ heterodimer including an antigen-binding site which retains much of the antigen recognition and binding capabilities of the native antibody molecule. Inbar et al. (1972) Proc. Nat. Acad. Sci. USA 69:2659-2662; Hochman et al. (1976) Biochem 15:2706-2710; and Ehrlich et al. (1980) Biochem 19:4091-4096.

A single chain Fv ("sFv") polypeptide is a covalently linked $V_H::V_L$ heterodimer which is expressed from a gene fusion including $V_H$- and $V_L$-encoding genes linked by a peptide-encoding linker. Huston et al. (1988) Proc. Nat. Acad. Sci. USA 85(16):5879-5883. A number of methods have been described to discern chemical structures for converting the naturally aggregated—but chemically separated—light and heavy polypeptide chains from an antibody V region into an sFv molecule which will fold into a three dimensional structure substantially similar to the structure of an antigen-binding site. See, e.g., U.S. Pat. Nos. 5,091,513 and 5,132,405, to Huston et al.; and U.S. Pat. No. 4,946,778, to Ladner et al.

Each of the above-described molecules includes a heavy chain and a light chain CDR set, respectively interposed between a heavy chain and a light chain FR set which provide support to the CDRs and define the spatial relationship of the CDRs relative to each other. As used herein, the term "CDR set" refers to the three hypervariable regions of a heavy or light chain V region. Proceeding from the N-terminus of a heavy or light chain, these regions are denoted as "CDR1," "CDR2," and "CDR3" respectively. An antigen-binding site, therefore, includes six CDRs, comprising the CDR set from each of a heavy and a light chain V region. A polypeptide comprising a single CDR, (e.g., a CDR1, CDR2 or CDR3) is referred to herein as a "molecular recognition unit." Crystallographic analysis of a number of antigen-antibody complexes has demonstrated that the amino acid residues of CDRs form extensive contact with bound antigen, wherein the most extensive antigen contact is with the heavy chain CDR3. Thus, the molecular recognition units are primarily responsible for the specificity of an antigen-binding site.

As used herein, the term "FR set" refers to the four flanking amino acid sequences which frame the CDRs of a CDR set of a heavy or light chain V region. Some FR residues may contact bound antigen; however, FRs are primarily responsible for folding the V region into the antigen-binding site, particularly the FR residues directly adjacent to the CDRS. Within FRs, certain amino residues and certain structural features are very highly conserved. In this regard, all V region sequences contain an internal disulfide loop of around 90 amino acid residues. When the V regions fold into a binding-site, the CDRs are displayed as projecting loop motifs which form an antigen-binding surface. It is generally recognized that there are conserved structural regions of FRs which influence the folded shape of the CDR loops into certain "canonical" structures—regardless of the precise CDR amino acid sequence. Further, certain FR residues are known to participate in non-covalent interdomain contacts which stabilize the interaction of the antibody heavy and light chains.

A number of "humanized" antibody molecules comprising an antigen-binding site derived from a non-human immunoglobulin have been described, including chimeric antibodies having rodent V regions and their associated CDRs fused to human constant domains (Winter et al. (1991) Nature 349: 293-299; Lobuglio et al. (1989) Proc. Nat. Acad. Sci. USA 86:4220-4224; Shaw et al. (1987) J Immunol. 138:4534-4538; and Brown et al. (1987) Cancer Res. 47:3577-3583), rodent CDRs grafted into a human supporting FR prior to fusion with an appropriate human antibody constant domain (Riechmann et al. (1988) Nature 332:323-327; Verhoeyen et al. (1988) Science 239:1534-1536; and Jones et al. (1986) Nature 321:522-525), and rodent CDRs supported by recombinantly veneered rodent FRs (European Patent Publication No. 519,596, published Dec. 23, 1992). These "humanized" molecules are designed to minimize unwanted immunological response toward rodent antihuman antibody molecules which limits the duration and effectiveness of therapeutic applications of those moieties in human recipients.

As used herein, the terms "veneered FRs" and "recombinantly veneered FRs" refer to the selective replacement of FR residues from, e.g., a rodent heavy or light chain V region, with human FR residues in order to provide a xenogeneic molecule comprising an antigen-binding site which retains substantially all of the native FR polypeptide folding structure. Veneering techniques are based on the understanding that the ligand binding characteristics of an antigen-binding site are determined primarily by the structure and relative disposition of the heavy and light chain CDR sets within the antigen-binding surface. Davies et al. (1990) Ann. Rev. Biochem. 59:439-473. Thus, antigen binding specificity can be preserved in a humanized antibody only wherein the CDR structures, their interaction with each other, and their interaction with the rest of the V region domains are carefully maintained. By using veneering techniques, exterior (e.g., solvent-accessible) FR residues which are readily encountered by the immune system are selectively replaced with human residues to provide a hybrid molecule that comprises either a weakly immunogenic, or substantially non-immunogenic veneered surface.

The process of veneering makes use of the available sequence data for human antibody variable domains compiled by Kabat et al., in Sequences of Proteins of Immunological Interest, 4th ed., (U.S. Dept. of Health and Human Services, U.S. Government Printing Office, 1987), updates to the Kabat database, and other accessible U.S. and foreign databases (both nucleic acid and protein). Solvent accessibilities of V region amino acids can be deduced from the known three-dimensional structure for human and murine antibody fragments. There are two general steps in veneering a murine antigen-binding site. Initially, the FRs of the variable domains of an antibody molecule of interest are compared with corresponding FR sequences of human variable domains obtained from the above-identified sources. The most homologous human V regions are then compared residue by residue to corresponding murine amino acids. The residues in the murine FR which differ from the human counterpart are replaced by the residues present in the human moiety using recombinant techniques well known in the art. Residue switching is only carried out with moieties which are at least partially exposed (solvent accessible), and care is exercised in the replacement of amino acid residues which may have a significant effect on the tertiary structure of V region domains, such as proline, glycine and charged amino acids.

In this manner, the resultant "veneered" murine antigen-binding sites are thus designed to retain the murine CDR residues, the residues substantially adjacent to the CDRs, the residues identified as buried or mostly buried (solvent inaccessible), the residues believed to participate in non-covalent (e.g., electrostatic and hydrophobic) contacts between heavy and light chain domains, and the residues from conserved structural regions of the FRs which are believed to influence the "canonical" tertiary structures of the CDR loops. These design criteria are then used to prepare recombinant nucleotide sequences which combine the CDRs of both the heavy and light chain of a murine antigen-binding site into human-appearing FRs that can be used to transfect mammalian cells for the expression of recombinant human antibodies which exhibit the antigen specificity of the murine antibody molecule.

In another embodiment of the invention, monoclonal antibodies of the present invention may be coupled to one or more therapeutic agents. Suitable agents in this regard include radionuclides, differentiation inducers, drugs, toxins, and derivatives thereof. Preferred radionuclides include $^{90}$Y, $^{123}$I, $^{125}$I, $^{131}$I, $^{186}$Re, $^{188}$Re, $^{211}$At, and $^{212}$Bi. Preferred drugs include methotrexate, and pyrimidine and purine analogs. Preferred differentiation inducers include phorbol esters and butyric acid. Preferred toxins include ricin, abrin, diptheria toxin, cholera toxin, gelonin, Pseudomonas exotoxin, Shigella toxin, and pokeweed antiviral protein.

A therapeutic agent may be coupled (e.g., covalently bonded) to a suitable monoclonal antibody either directly or indirectly (e.g., via a linker group). A direct reaction between an agent and an antibody is possible when each possesses a substituent capable of reacting with the other. For example, a nucleophilic group, such as an amino or sulfhydryl group, on one may be capable of reacting with a carbonyl-containing group, such as an anhydride or an acid halide, or with an alkyl group containing a good leaving group (e.g., a halide) on the other.

Alternatively, it may be desirable to couple a therapeutic agent and an antibody via a linker group. A linker group can function as a spacer to distance an antibody from an agent in order to avoid interference with binding capabilities. A linker group can also serve to increase the chemical reactivity of a substituent on an agent or an antibody, and thus increase the coupling efficiency. An increase in chemical reactivity may also facilitate the use of agents, or functional groups on agents, which otherwise would not be possible.

It will be evident to those skilled in the art that a variety of bifunctional or polyfunctional reagents, both homo- and hetero-functional (such as those described in the catalog of the Pierce Chemical Co., Rockford, Ill.), may be employed as the linker group. Coupling may be effected, for example, through amino groups, carboxyl groups, sulfhydryl groups or oxidized carbohydrate residues. There are numerous references describing such methodology, e.g., U.S. Pat. No. 4,671,958, to Rodwell et al.

Where a therapeutic agent is more potent when free from the antibody portion of the immunoconjugates of the present invention, it may be desirable to use a linker group which is cleavable during or upon internalization into a cell. A number of different cleavable linker groups have been described. The mechanisms for the intracellular release of an agent from these linker groups include cleavage by reduction of a disulfide bond (e.g., U.S. Pat. No. 4,489,710, to Spitler), by irradiation of a photolabile bond (e.g., U.S. Pat. No. 4,625,014, to Senter et al.), by hydrolysis of derivatized amino acid side chains (e.g., U.S. Pat. No. 4,638,045, to Kohn et al.), by serum complement-mediated hydrolysis (e.g., U.S. Pat. No. 4,671,958, to Rodwell et al.), and acid-catalyzed hydrolysis (e.g., U.S. Pat. No. 4,569,789, to Blattler et al.).

It may be desirable to couple more than one agent to an antibody. In one embodiment, multiple molecules of an agent are coupled to one antibody molecule. In another embodiment, more than one type of agent may be coupled to one antibody. Regardless of the particular embodiment, immunoconjugates with more than one agent may be prepared in a variety of ways. For example, more than one agent may be coupled directly to an antibody molecule, or linkers that provide multiple sites for attachment can be used. Alternatively, a carrier can be used.

A carrier may bear the agents in a variety of ways, including covalent bonding either directly or via a linker group. Suitable carriers include proteins such as albumins (e.g., U.S. Pat. No. 4,507,234, to Kato et al.), peptides and polysaccharides such as aminodextran (e.g., U.S. Pat. No. 4,699,784, to Shih et al.). A carrier may also bear an agent by noncovalent bonding or by encapsulation, such as within a liposome vesicle (e.g., U.S. Pat. Nos. 4,429,008 and 4,873,088). Carriers specific for radionuclide agents include radiohalogenated small molecules and chelating compounds. For example, U.S. Pat. No. 4,735,792 discloses representative radiohalogenated small molecules and their synthesis. A radionuclide chelate may be formed from chelating compounds that include those containing nitrogen and sulfur atoms as the donor atoms for binding the metal, or metal oxide, radionuclide. For example, U.S. Pat. No. 4,673,562, to Davison et al. discloses representative chelating compounds and their synthesis.

T Cell Compositions

The present invention, in another aspect, provides T cells specific for a tumor polypeptide disclosed herein, or for a variant or derivative thereof. Such cells may generally be prepared in vitro or ex vivo, using standard procedures. For example, T cells may be isolated from bone marrow, peripheral blood, or a fraction of bone marrow or peripheral blood of a patient, using a commercially available cell separation system, such as the Isolex™ System, available from Nexell Therapeutics, Inc. (Irvine, Calif.; see also U.S. Pat. No. 5,240,856; U.S. Pat. No. 5,215,926; WO 89/06280; WO 91/16116 and WO 92/07243). Alternatively, T cells may be derived from related or unrelated humans, non-human mammals, cell lines or cultures.

T cells may be stimulated with a polypeptide, polynucleotide encoding a polypeptide and/or an antigen presenting cell (APC) that expresses such a polypeptide. Such stimulation is performed under conditions and for a time sufficient to permit the generation of T cells that are specific for the polypeptide of interest. Preferably, a tumor polypeptide or polynucleotide of the invention is present within a delivery vehicle, such as a microsphere, to facilitate the generation of specific T cells.

T cells are considered to be specific for a polypeptide of the present invention if the T cells specifically proliferate, secrete cytokines or kill target cells coated with the polypeptide or expressing a gene encoding the polypeptide. T cell specificity may be evaluated using any of a variety of standard techniques. For example, within a chromium release assay or proliferation assay, a stimulation index of more than two fold increase in lysis and/or proliferation, compared to negative controls, indicates T cell specificity. Such assays may be performed, for example, as described in Chen et al., *Cancer Res.* 54:1065-1070, 1994. Alternatively, detection of the proliferation of T cells may be accomplished by a variety of known techniques. For example, T cell proliferation can be detected by measuring an increased rate of DNA synthesis (e.g., by pulse-labeling cultures of T cells with tritiated thymidine and measuring the amount of tritiated thymidine incorporated into DNA). Contact with a tumor polypeptide (100 ng/ml-100 µg/ml, preferably 200 ng/ml-25 µg/ml) for 3-7 days will typically result in at least a two fold increase in proliferation of the T cells. Contact as described above for 2-3 hours should result in activation of the T cells, as measured using standard cytokine assays in which a two fold increase in the level of cytokine release (e.g., TNF or IFN-γ) is indicative of T cell activation (see Coligan et al., Current Protocols in Immunology, vol. 1, Wiley Interscience (Greene 1998)). T cells that have been activated in response to a tumor polypeptide, polynucleotide or polypeptide-expressing APC may be $CD4^+$ and/or $CD8^+$. Tumor polypeptide-specific T cells may be expanded using standard techniques. Within preferred embodiments, the T cells are derived from a patient, a related donor or an unrelated donor, and are administered to the patient following stimulation and expansion.

For therapeutic purposes, $CD4^+$ or $CD8^+$ T cells that proliferate in response to a tumor polypeptide, polynucleotide or APC can be expanded in number either in vitro or in vivo. Proliferation of such T cells in vitro may be accomplished in a variety of ways. For example, the T cells can be re-exposed to a tumor polypeptide, or a short peptide corresponding to an immunogenic portion of such a polypeptide, with or without the addition of T cell growth factors, such as interleukin-2, and/or stimulator cells that synthesize a tumor polypeptide. Alternatively, one or more T cells that proliferate in the presence of the tumor polypeptide can be expanded in number by cloning. Methods for cloning cells are well known in the art, and include limiting dilution.

Pharmaceutical Compositions

In additional embodiments, the present invention concerns formulation of one or more of the polynucleotide, polypeptide, T-cell and/or antibody compositions disclosed herein in pharmaceutically-acceptable carriers for administration to a cell or an animal, either alone, or in combination with one or more other modalities of therapy.

It will be understood that, if desired, a composition as disclosed herein may be administered in combination with other agents as well, such as, e.g., other proteins or polypeptides or various pharmaceutically-active agents. In fact, there is virtually no limit to other components that may also be included, given that the additional agents do not cause a significant adverse effect upon contact with the target cells or host tissues. The compositions may thus be delivered along with various other agents as required in the particular instance. Such compositions may be purified from host cells or other biological sources, or alternatively may be chemically synthesized as described herein. Likewise, such compositions may further comprise substituted or derivatized RNA or DNA compositions.

Therefore, in another aspect of the present invention, pharmaceutical compositions are provided comprising one or more of the polynucleotide, polypeptide, antibody, and/or T-cell compositions described herein in combination with a physiologically acceptable carrier. In certain preferred embodiments, the pharmaceutical compositions of the invention comprise immunogenic polynucleotide and/or polypeptide compositions of the invention for use in prophylactic and theraputic vaccine applications. Vaccine preparation is generally described in, for example, M. F. Powell and M. J. Newman, eds., "Vaccine Design (the subunit and adjuvant approach)," Plenum Press (NY, 1995). Generally, such compositions will comprise one or more polynucleotide and/or polypeptide compositions of the present invention in combination with one or more immunostimulants.

It will be apparent that any of the pharmaceutical compositions described herein can contain pharmaceutically acceptable salts of the polynucleotides and polypeptides of the invention. Such salts can be prepared, for example, from pharmaceutically acceptable non-toxic bases, including organic bases (e.g. salts of primary, secondary and tertiary amines and basic amino acids) and inorganic bases (e.g., sodium, potassium, lithium, ammonium, calcium and magnesium salts).

In another embodiment, illustrative immunogenic compositions, e.g., vaccine compositions, of the present invention comprise DNA encoding one or more of the polypeptides as described above, such that the polypeptide is generated in situ. As noted above, the polynucleotide may be administered within any of a variety of delivery systems known to those of ordinary skill in the art. Indeed, numerous gene delivery techniques are well known in the art, such as those described by Rolland, Crit. Rev. Therap. Drug Carrier Systems 15:143-198, 1998, and references cited therein. Appropriate polynucleotide expression systems will, of course, contain the necessary regulatory DNA regulatory sequences for expression in a patient (such as a suitable promoter and terminating signal). Alternatively, bacterial delivery systems may involve the administration of a bacterium (such as Bacillus-Calmette-Guerrin) that expresses an immunogenic portion of the polypeptide on its cell surface or secretes such an epitope.

Therefore, in certain embodiments, polynucleotides encoding immunogenic polypeptides described herein are introduced into suitable mammalian host cells for expression using any of a number of known viral-based systems. In one illustrative embodiment, retroviruses provide a convenient and effective platform for gene delivery systems. A selected nucleotide sequence encoding a polypeptide of the present invention can be inserted into a vector and packaged in retroviral particles using techniques known in the art. The recombinant virus can then be isolated and delivered to a subject. A number of illustrative retroviral systems have been described (e.g., U.S. Pat. No. 5,219,740; Miller and Rosman (1989) BioTechniques 7:980-990; Miller, A. D. (1990) Human Gene Therapy 1:5-14; Scarpa et al. (1991) Virology 180:849-852; Burns et al. (1993) Proc. Natl. Acad. Sci. USA 90:8033-8037; and Boris-Lawrie and Temin (1993) Cur. Opin. Genet. Develop. 3:102-109.

In addition, a number of illustrative adenovirus-based systems have also been described. Unlike retroviruses which integrate into the host genome, adenoviruses persist extrachromosomally thus minimizing the risks associated with insertional mutagenesis (Haj-Ahmad and Graham (1986) J. Virol. 57:267-274; Bett et al. (1993) J. Virol. 67:5911-5921; Mittereder et al. (1994) Human Gene Therapy 5:717-729; Seth et al. (1994) J. Virol. 68:933-940; Barr et al. (1994) Gene Therapy 1:51-58; Berkner, K. L. (1988) BioTechniques 6:616-629; and Rich et al. (1993) Human Gene Therapy 4:461-476).

Various adeno-associated virus (AAV) vector systems have also been developed for polynucleotide delivery. AAV vectors can be readily constructed using techniques well known in the art. See, e.g., U.S. Pat. Nos. 5,173,414 and 5,139,941; International Publication Nos. WO 92/01070 and WO 93/03769; Lebkowski et al. (1988) Molec. Cell. Biol. 8:3988-3996; Vincent et al. (1990) Vaccines 90 (Cold Spring Harbor Laboratory Press); Carter, B. J. (1992) Current Opinion in Biotechnology 3:533-539; Muzyczka, N. (1992) Current Topics in Microbiol. and Immunol. 158:97-129; Kotin, R. M. (1994) Human Gene Therapy 5:793-801; Shelling and Smith (1994) Gene Therapy 1:165-169; and Zhou et al. (1994) J. Exp. Med. 179:1867-1875.

Additional viral vectors useful for delivering the polynucleotides encoding polypeptides of the present invention by gene transfer include those derived from the pox family of viruses, such as vaccinia virus and avian poxvirus. By way of example, vaccinia virus recombinants expressing the novel molecules can be constructed as follows. The DNA encoding a polypeptide is first inserted into an appropriate vector so that it is adjacent to a vaccinia promoter and flanking vaccinia DNA sequences, such as the sequence encoding thymidine kinase (TK). This vector is then used to transfect cells which are simultaneously infected with vaccinia. Homologous recombination serves to insert the vaccinia promoter plus the gene encoding the polypeptide of interest into the viral genome. The resulting TK.sup.(−) recombinant can be selected by culturing the cells in the presence of 5-bromodeoxyuridine and picking viral plaques resistant thereto.

A vaccinia-based infection/transfection system can be conveniently used to provide for inducible, transient expression or coexpression of one or more polypeptides described herein in host cells of an organism. In this particular system, cells are first infected in vitro with a vaccinia virus recombinant that encodes the bacteriophage T7 RNA polymerase. This polymerase displays exquisite specificity in that it only transcribes templates bearing T7 promoters. Following infection, cells are transfected with the polynucleotide or polynucleotides of interest, driven by a T7 promoter. The polymerase expressed in the cytoplasm from the vaccinia virus recombinant transcribes the transfected DNA into RNA which is then translated into polypeptide by the host translational machinery. The method provides for high level, transient, cytoplasmic production of large quantities of RNA and its translation products. See, e.g., Elroy-Stein and Moss, Proc. Natl. Acad. Sci. USA (1990) 87:6743-6747; Fuerst et al. Proc. Natl. Acad. Sci. USA (1986) 83:8122-8126.

Alternatively, avipoxviruses, such as the fowlpox and canarypox viruses, can also be used to deliver the coding sequences of interest. Recombinant avipox viruses, expressing immunogens from mammalian pathogens, are known to confer protective immunity when administered to non-avian species. The use of an Avipox vector is particularly desirable in human and other mammalian species since members of the Avipox genus can only productively replicate in susceptible avian species and therefore are not infective in mammalian cells. Methods for producing recombinant Avipoxviruses are known in the art and employ genetic recombination, as described above with respect to the production of vaccinia viruses. See, e.g., WO 91/12882; WO 89/03429; and WO 92/03545.

Any of a number of alphavirus vectors can also be used for delivery of polynucleotide compositions of the present invention, such as those vectors described in U.S. Pat. Nos. 5,843,723; 6,015,686; 6,008,035 and 6,015,694. Certain vectors based on Venezuelan Equine Encephalitis (VEE) can also be used, illustrative examples of which can be found in U.S. Pat. Nos. 5,505,947 and 5,643,576.

Moreover, molecular conjugate vectors, such as the adenovirus chimeric vectors described in Michael et al. J. Biol. Chem. (1993) 268:6866-6869 and Wagner et al. Proc. Natl. Acad. Sci. USA (1992) 89:6099-6103, can also be used for gene delivery under the invention.

Additional illustrative information on these and other known viral-based delivery systems can be found, for example, in Fisher-Hoch et al., Proc. Natl. Acad. Sci. USA 86:317-321, 1989; Flexner et al., Ann. NY. Acad. Sci. 569:86-103, 1989; Flexner et al., Vaccine 8:17-21, 1990; U.S. Pat. Nos. 4,603,112, 4,769,330, and 5,017,487; WO 89/01973; U.S. Pat. No. 4,777,127; GB 2,200,651; EP 0,345,242; WO 91/02805; Berkner, Biotechniques 6:616-627, 1988; Rosenfeld et al., Science 252:431-434, 1991; Kolls et al., Proc. Natl. Acad. Sci. USA 91:215-219, 1994; Kass-Eisler et al., Proc. Natl. Acad. Sci. USA 90:11498-11502, 1993; Guzman et al., Circulation 88:2838-2848, 1993; and Guzman et al., Cir. Res. 73:1202-1207, 1993.

In certain embodiments, a polynucleotide may be integrated into the genome of a target cell. This integration may be in the specific location and orientation via homologous recombination (gene replacement) or it may be integrated in a random, non-specific location (gene augmentation). In yet further embodiments, the polynucleotide may be stably maintained in the cell as a separate, episomal segment of DNA. Such polynucleotide segments or "episomes" encode sequences sufficient to permit maintenance and replication independent of or in synchronization with the host cell cycle. The manner in which the expression construct is delivered to a cell and where in the cell the polynucleotide remains is dependent on the type of expression construct employed.

In another embodiment of the invention, a polynucleotide is administered/delivered as "naked" DNA, for example as described in Ulmer et al., Science 259:1745-1749, 1993 and reviewed by Cohen, Science 259:1691-1692, 1993. The uptake of naked DNA may be increased by coating the DNA onto biodegradable beads, which are efficiently transported into the cells.

In still another embodiment, a composition of the present invention can be delivered via a particle bombardment approach, many of which have been described. In one illustrative example, gas-driven particle acceleration can be achieved with devices such as those manufactured by Powderject Pharmaceuticals PLC (Oxford, UK) and Powderject Vaccines Inc. (Madison, Wis.), some examples of which are described in U.S. Pat. Nos. 5,846,796; 6,010,478; 5,865,796; 5,584,807; and EP Patent No. 0500 799. This approach offers a needle-free delivery approach wherein a dry powder formulation of microscopic particles, such as polynucleotide or polypeptide particles, are accelerated to high speed within a helium gas jet generated by a hand held device, propelling the particles into a target tissue of interest.

In a related embodiment, other devices and methods that may be useful for gas-driven needle-less injection of compositions of the present invention include those provided by Bioject, Inc. (Portland, Oreg.), some examples of which are described in U.S. Pat. Nos. 4,790,824; 5,064,413; 5,312,335; 5,383,851; 5,399,163; 5,520,639 and 5,993,412.

According to another embodiment, the pharmaceutical compositions described herein will comprise one or more immunostimulants in addition to the immunogenic polynucleotide, polypeptide, antibody, T-cell and/or APC compositions of this invention. An immunostimulant refers to essentially any substance that enhances or potentiates an immune response (antibody and/or cell-mediated) to an exogenous antigen. One preferred type of immunostimulant comprises an adjuvant. Many adjuvants contain a substance designed to protect the antigen from rapid catabolism, such as aluminum hydroxide or mineral oil, and a stimulator of immune responses, such as lipid A, Bortadella pertussis or Mycobacterium tuberculosis derived proteins. Certain adjuvants are commercially available as, for example, Freund's Incomplete Adjuvant and Complete Adjuvant (Difco Laboratories, Detroit, Mich.); Merck Adjuvant 65 (Merck and Company, Inc., Rahway, N.J.); AS-2 (SmithKline Beecham, Philadelphia, Pa.); aluminum salts such as aluminum hydroxide gel (alum) or aluminum phosphate; salts of calcium, iron or zinc; an insoluble suspension of acylated tyrosine; acylated sugars; cationically or anionically derivatized polysaccharides; —polyphosphazenes; biodegradable microspheres; monophosphoryl lipid A and quil A. Cytokines, such as GM-CSF, interleukin-2,-7,-12, and other like growth factors, may also be used as adjuvants.

Within certain embodiments of the invention, the adjuvant composition is preferably one that induces an immune response predominantly of the Th1 type. High levels of Th1-type cytokines (e.g., IFN-γ, TNFα, IL-2 and IL-12) tend to favor the induction of cell mediated immune responses to an administered antigen. In contrast, high levels of Th2-type cytokines (e.g., IL-4, IL-5, IL-6 and IL-10) tend to favor the induction of humoral immune responses. Following application of a vaccine as provided herein, a patient will support an immune response that includes Th1- and Th2-type responses. Within a preferred embodiment, in which a response is predominantly Th1-type, the level of Th1-type cytokines will increase to a greater extent than the level of Th2-type cytokines. The levels of these cytokines may be readily assessed using standard assays. For a review of the families of cytokines, see Mosmann and Coffinan, Ann. Rev. Immunol. 7:145-173, 1989.

Certain preferred adjuvants for eliciting a predominantly Th1-type response include, for example, a combination of monophosphoryl lipid A, preferably 3-de-O-acylated monophosphoryl lipid A, together with an aluminum salt. MPL® adjuvants are available from Corixa Corporation (Seattle, Wash.; see, for example, U.S. Pat. Nos. 4,436,727; 4,877,611; 4,866,034 and 4,912,094). CpG-containing oligonucleotides (in which the CpG dinucleotide is unmethylated) also induce a predominantly Th1 response. Such oligonucleotides are well known and are described, for example, in WO 96/02555, WO 99/33488 and U.S. Pat. Nos. 6,008,200 and 5,856,462. Immunostimulatory DNA sequences are also described, for example, by Sato et al., Science 273:352, 1996. Another preferred adjuvant comprises a saponin, such as Quil A, or derivatives thereof, including QS21 and QS7 (Aquila Biopharnaceuticals Inc., Framingham, Mass.); Escin; Digitonin; or Gypsophila or Chenopodium quinoa saponins. Other preferred formulations include more than one saponin in the adjuvant combinations of the present invention, for example combinations of at least two of the following group comprising QS21, QS7, Quil A, β-escin, or digitonin.

Alternatively the saponin formulations may be combined with vaccine vehicles composed of chitosan or other polycationic polymers, polylactide and polylactide-co-glycolide particles, poly-N-acetyl glucosamine-based polymer matrix, particles composed of polysaccharides or chemically modified polysaccharides, liposomes and lipid-based particles, particles composed of glycerol monoesters, etc. The saponins may also be formulated in the presence of cholesterol to form particulate structures such as liposomes or ISCOMs. Furthermore, the saponins may be formulated together with a polyoxyethylene ether or ester, in either a non-particulate solution or suspension, or in a particulate structure such as a paucilamelar liposome or ISCOM. The saponins may also be formulated with excipients such as Carbopol$^R$ to increase viscosity, or may be formulated in a dry powder form with a powder excipient such as lactose.

In one preferred embodiment, the adjuvant system includes the combination of a monophosphoryl lipid A and a saponin derivative, such as the combination of QS21 and 3D-MPL® adjuvant, as described in WO 94/00153, or a less reactogenic composition where the QS21 is quenched with cholesterol, as described in WO 96/33739. Other preferred formulations comprise an oil-in-water emulsion and tocopherol. Another particularly preferred adjuvant formulation employing QS21, 3D-MPL® adjuvant and tocopherol in an oil-in-water emulsion is described in WO 95/17210.

Another enhanced adjuvant system involves the combination of a CpG-containing oligonucleotide and a saponin derivative particularly the combination of CpG and QS21 is disclosed in WO 00/09159. Preferably the formulation additionally comprises an oil in water emulsion and tocopherol.

Additional illustrative adjuvants for use in the pharmaceutical compositions of the invention include Montanide ISA 720 (Seppic, France), SAF (Chiron, Calif., United States), ISCOMS (CSL), MF-59 (Chiron), the SBAS series of adjuvants (e.g., SBAS-2 or SBAS-4, available from SmithKline Beecham, Rixensart, Belgium), Detox (Enhanzyn®) (Corixa, Hamilton, Mont.), RC-529 (Corixa, Hamilton, Mont.) and other aminoalkyl glucosaminide 4-phosphates (AGPs), such as those described in pending U.S. patent application Ser. Nos. 08/853,826 and 09/074,720, the disclosures of which are incorporated herein by reference in their entireties, and polyoxyethylene ether adjuvants such as those described in WO 99/52549A1.

Other preferred adjuvants include adjuvant molecules of the general formula

$$HO(CH_2CH_2O)_n\text{—}A\text{—}R, \qquad (I)$$

wherein, n is 1-50, A is a bond or —C(O)—, R is $C_{1-50}$ alkyl or Phenyl $C_{1-50}$ alkyl.

One embodiment of the present invention consists of a vaccine formulation comprising a polyoxyethylene ether of general formula (I), wherein n is between 1 and 50, preferably 4-24, most preferably 9; the R component is $C_{1-50}$, preferably $C_4$-$C_{20}$ alkyl and most preferably $C_{12}$ alkyl, and A is a bond. The concentration of the polyoxyethylene ethers should be in the range 0.1-20%, preferably from 0.1-10%, and most preferably in the range 0.1-1%. Preferred polyoxyethylene ethers are selected from the following group: polyoxyethylene-9-lauryl ether, polyoxyethylene-9-steoryl ether, polyoxyethylene-8-steoryl ether, polyoxyethylene-4-lauryl ether, polyoxyethylene-35-lauryl ether, and polyoxyethylene-23-lauryl ether. Polyoxyethylene ethers such as polyoxyethylene lauryl ether are described in the Merck index ($12^{th}$ edition: entry 7717). These adjuvant molecules are described in WO 99/52549.

The polyoxyethylene ether according to the general formula (I) above may, if desired, be combined with another adjuvant. For example, a preferred adjuvant combination is preferably with CpG as described in the pending UK patent application GB 9820956.2.

According to another embodiment of this invention, an immunogenic composition described herein is delivered to a host via antigen presenting cells (APCs), such as dendritic cells, macrophages, B cells, monocytes and other cells that may be engineered to be efficient APCs. Such cells may, but need not, be genetically modified to increase the capacity for presenting the antigen, to improve activation and/or maintenance of the T cell response, to have anti-tumor effects per se and/or to be immunologically compatible with the receiver (i.e., matched HLA haplotype). APCs may generally be isolated from any of a variety of biological fluids and organs, including tumor and peritumoral tissues, and may be autologous, allogeneic, syngeneic or xenogeneic cells.

Certain preferred embodiments of the present invention use dendritic cells or progenitors thereof as antigen-presenting cells. Dendritic cells are highly potent APCs (Banchereau and Steinman, Nature 392:245-251, 1998) and have been shown to be effective as a physiological adjuvant for eliciting prophylactic or therapeutic antitumor immunity (see Timmerman and Levy, Ann. Rev. Med. 50:507-529, 1999). In general, dendritic cells may be identified based on their typical shape (stellate in situ, with marked cytoplasmic processes (dendrites) visible in vitro), their ability to take up, process and present antigens with high efficiency and their ability to activate naïve T cell responses. Dendritic cells may, of course, be engineered to express specific cell-surface receptors or ligands that are not commonly found on dendritic cells in vivo or ex vivo, and such modified dendritic cells are contemplated by the present invention. As an alternative to dendritic cells, secreted vesicles antigen-loaded dendritic cells (called exosomes) may be used within a vaccine (see Zitvogel et al., Nature Med. 4:594-600, 1998).

Dendritic cells and progenitors may be obtained from peripheral blood, bone marrow, tumor-infiltrating cells, peritumoral tissues-infiltrating cells, lymph nodes, spleen, skin, umbilical cord blood or any other suitable tissue or fluid. For example, dendritic cells may be differentiated ex vivo by adding a combination of cytokines such as GM-CSF, IL-4, IL-13 and/or TNFα to cultures of monocytes harvested from peripheral blood. Alternatively, CD34 positive cells harvested from peripheral blood, umbilical cord blood or bone marrow may be differentiated into dendritic cells by adding to the culture medium combinations of GM-CSF, IL-3, TNFα, CD40 ligand, LPS, flt3 ligand and/or other compound(s) that induce differentiation, maturation and proliferation of dendritic cells.

Dendritic cells are conveniently categorized as "immature" and "mature" cells, which allows a simple way to discriminate between two well characterized phenotypes. However, this nomenclature should not be construed to exclude all possible intermediate stages of differentiation. Immature dendritic cells are characterized as APC with a high capacity for antigen uptake and processing, which correlates with the high expression of Fcγ receptor and mannose receptor. The mature phenotype is typically characterized by a lower expression of these markers, but a high expression of cell surface molecules responsible for T cell activation such as class I and class II MHC, adhesion molecules (e.g., CD54 and CD11) and costimulatory molecules (e.g., CD40, CD80, CD86 and 4-1BB).

APCs may generally be transfected with a polynucleotide of the invention (or portion or other variant thereof) such that the encoded polypeptide, or an immunogenic portion thereof, is expressed on the cell surface. Such transfection may take place ex vivo, and a pharmaceutical composition comprising such transfected cells may then be used for therapeutic purposes, as described herein. Alternatively, a gene delivery vehicle that targets a dendritic or other antigen presenting cell may be administered to a patient, resulting in transfection that occurs in vivo. In vivo and ex vivo transfection of dendritic cells, for example, may generally be performed using any methods known in the art, such as those described in WO 97/24447, or the gene gun approach described by Mahvi et al., Immunology and cell Biology 75:456-460, 1997. Antigen loading of dendritic cells may be achieved by incubating dendritic cells or progenitor cells with the tumor polypeptide, DNA (naked or within a plasmid vector) or RNA; or with antigen-expressing recombinant bacterium or viruses (e.g., vaccinia, fowlpox, adenovirus or lentivirus vectors). Prior to loading, the polypeptide may be covalently conjugated to an immunological partner that provides T cell help (e.g., a carrier molecule). Alternatively, a dendritic cell may be pulsed with a non-conjugated immunological partner, separately or in the presence of the polypeptide.

While any suitable carrier known to those of ordinary skill in the art may be employed in the pharmaceutical compositions of this invention, the type of carrier will typically vary depending on the mode of administration. Compositions of the present invention may be formulated for any appropriate manner of administration, including for example, topical, oral, nasal, mucosal, intravenous, intracranial, intraperitoneal, subcutaneous and intramuscular administration.

Carriers for use within such pharmaceutical compositions are biocompatible, and may also be biodegradable. In certain embodiments, the formulation preferably provides a relatively constant level of active component release. In other embodiments, however, a more rapid rate of release immediately upon administration may be desired. The formulation of such compositions is well within the level of ordinary skill in the art using known techniques. Illustrative carriers useful in this regard include microparticles of poly(lactide-co-glycolide), polyacrylate, latex, starch, cellulose, dextran and the like. Other illustrative delayed-release carriers include supramolecular biovectors, which comprise a non-liquid hydrophilic core (e.g., a cross-linked polysaccharide or oligosaccharide) and, optionally, an external layer comprising an amphiphilic compound, such as a phospholipid (see e.g., U.S. Pat. No. 5,151,254 and PCT applications WO 94/20078, WO/94/23701 and WO 96/06638). The amount of active compound contained within a sustained release formulation depends upon the site of implantation, the rate and expected duration of release and the nature of the condition to be treated or prevented.

In another illustrative embodiment, biodegradable microspheres (e.g., polylactate polyglycolate) are employed as carriers for the compositions of this invention. Suitable biodegradable microspheres are disclosed, for example, in U.S. Pat. Nos. 4,897,268; 5,075,109; 5,928,647; 5,811,128; 5,820,883; 5,853,763; 5,814,344, 5,407,609 and 5,942,252. Modified hepatitis B core protein carrier systems. such as described in WO/99 40934, and references cited therein, will also be useful for many applications. Another illustrative carrier/delivery system employs a carrier comprising particulate-protein complexes, such as those described in U.S. Pat. No. 5,928,647, which are capable of inducing a class I-restricted cytotoxic T lymphocyte responses in a host.

The pharmaceutical compositions of the invention will often further comprise one or more buffers (e.g., neutral buffered saline or phosphate buffered saline), carbohydrates (e.g., glucose, mannose, sucrose or dextrans), mannitol, proteins, polypeptides or amino acids such as glycine, antioxidants, bacteriostats, chelating agents such as EDTA or glutathione, adjuvants (e.g., aluminum hydroxide), solutes that render the formulation isotonic, hypotonic or weakly hypertonic with the blood of a recipient, suspending agents, thickening agents and/or preservatives. Alternatively, compositions of the present invention may be formulated as a lyophilizate.

The pharmaceutical compositions described herein may be presented in unit-dose or multi-dose containers, such as sealed ampoules or vials. Such containers are typically sealed in such a way to preserve the sterility and stability of the formulation until use. In general, formulations may be stored as suspensions, solutions or emulsions in oily or aqueous vehicles. Alternatively, a pharmaceutical composition may be stored in a freeze-dried condition requiring only the addition of a sterile liquid carrier immediately prior to use.

The development of suitable dosing and treatment regimens for using the particular compositions described herein in a variety of treatment regimens, including e.g., oral, parenteral, intravenous, intranasal, and intramuscular administration and formulation, is well known in the art, some of which are briefly discussed below for general purposes of illustration.

In certain applications, the pharmaceutical compositions disclosed herein may be delivered via oral administration to an animal. As such, these compositions may be formulated with an inert diluent or with an assimilable edible carrier, or they may be enclosed in hard- or soft-shell gelatin capsule, or they may be compressed into tablets, or they may be incorporated directly with the food of the diet.

The active compounds may even be incorporated with excipients and used in the form of ingestible tablets, buccal tables, troches, capsules, elixirs, suspensions, syrups, wafers, and the like (see, for example, Mathiowitz et al., Nature Mar. 27, 1997;386(6623):410-4; Hwang et al., Crit Rev Ther Drug Carrier Syst 1998;15(3):243-84; U.S. Pat. No. 5,641,515; U.S. Pat. No. 5,580,579 and U.S. Pat. No. 5,792,451). Tablets, troches, pills, capsules and the like may also contain any of a variety of additional components, for example, a binder, such as gum tragacanth, acacia, cornstarch, or gelatin; excipients, such as dicalcium phosphate; a disintegrating agent, such as corn starch, potato starch, alginic acid and the like; a lubricant, such as magnesium stearate; and a sweetening agent, such as sucrose, lactose or saccharin may be added or a flavoring agent, such as peppermint, oil of wintergreen, or cherry flavoring. When the dosage unit form is a capsule, it may contain, in addition to materials of the above type, a liquid carrier. Various other materials may be present as coatings or to otherwise modify the physical form of the dosage unit. For instance, tablets, pills, or capsules may be coated with shellac, sugar, or both. Of course, any material used in preparing any dosage unit form should be pharmaceutically pure and substantially non-toxic in the amounts employed. In addition, the active compounds may be incorporated into sustained-release preparation and formulations.

Typically, these formulations will contain at least about 0.1% of the active compound or more, although the percentage of the active ingredient(s) may, of course, be varied and may conveniently be between about 1 or 2% and about 60% or 70% or more of the weight or volume of the total formulation. Naturally, the amount of active compound(s) in each therapeutically useful composition may be prepared is such a way that a suitable dosage will be obtained in any given unit dose of the compound. Factors such as solubility, bioavailability, biological half-life, route of administration, product shelf life, as well as other pharmacological considerations will be contemplated by one skilled in the art of preparing such pharmaceutical formulations, and as such, a variety of dosages and treatment regimens may be desirable.

For oral administration the compositions of the present invention may alternatively be incorporated with one or more excipients in the form of a mouthwash, dentifrice, buccal tablet, oral spray, or sublingual orally-administered formulation. Alternatively, the active ingredient may be incorporated into an oral solution such as one containing sodium borate, glycerin and potassium bicarbonate, or dispersed in a dentifrice, or added in a therapeutically-effective amount to a composition that may include water, binders, abrasives, flavoring agents, foaming agents, and humectants. Alternatively the compositions may be fashioned into a tablet or solution form that may be placed under the tongue or otherwise dissolved in the mouth.

In certain circumstances it will be desirable to deliver the pharmaceutical compositions disclosed herein parenterally, intravenously, intramuscularly, or even intraperitoneally. Such approaches are well known to the skilled artisan, some of which are further described, for example, in U.S. Pat. No. 5,543,158; U.S. Pat. No. 5,641,515 and U.S. Pat. No. 5,399,363. In certain embodiments, solutions of the active compounds as free base or pharmacologically acceptable salts may be prepared in water suitably mixed with a surfactant, such as hydroxypropylcellulose. Dispersions may also be prepared in glycerol, liquid polyethylene glycols, and mixtures thereof and in oils. Under ordinary conditions of storage and use, these preparations generally will contain a preservative to prevent the growth of microorganisms.

Illustrative pharmaceutical forms suitable for injectable use include sterile aqueous solutions or dispersions and sterile powders for the extemporaneous preparation of sterile injectable solutions or dispersions (for example, see U.S. Pat.

No. 5,466,468). In all cases the form must be sterile and must be fluid to the extent that easy syringability exists. It must be stable under the conditions of manufacture and storage and must be preserved against the contaminating action of microorganisms, such as bacteria and fungi. The carrier can be a solvent or dispersion medium containing, for example, water, ethanol, polyol (e.g., glycerol, propylene glycol, and liquid polyethylene glycol, and the like), suitable mixtures thereof, and/or vegetable oils. Proper fluidity may be maintained, for example, by the use of a coating, such as lecithin, by the maintenance of the required particle size in the case of dispersion and/or by the use of surfactants. The prevention of the action of microorganisms can be facilitated by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

In one embodiment, for parenteral administration in an aqueous solution, the solution should be suitably buffered if necessary and the liquid diluent first rendered isotonic with sufficient saline or glucose. These particular aqueous solutions are especially suitable for intravenous, intramuscular, subcutaneous and intraperitoneal administration. In this connection, a sterile aqueous medium that can be employed will be known to those of skill in the art in light of the present disclosure. For example, one dosage may be dissolved in 1 ml of isotonic NaCl solution and either added to 1000 ml of hypodermoclysis fluid or injected at the proposed site of infusion, (see for example, "Remington's Pharmaceutical Sciences" 15th Edition, pages 1035-1038 and 1570-1580). Some variation in dosage will necessarily occur depending on the condition of the subject being treated. Moreover, for human administration, preparations will of course preferably meet sterility, pyrogenicity, and the general safety and purity standards as required by FDA Office of Biologics standards.

In another embodiment of the invention, the compositions disclosed herein may be formulated in a neutral or salt form. Illustrative pharmaceutically-acceptable salts include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like. Upon formulation, solutions will be administered in a manner compatible with the dosage formulation and in such amount as is therapeutically effective.

The carriers can further comprise any and all solvents, dispersion media, vehicles, coatings, diluents, antibacterial and antifungal agents, isotonic and absorption delaying agents, buffers, carrier solutions, suspensions, colloids, and the like. The use of such media and agents for pharmaceutical active substances is well known in the art. Except insofar as any conventional media or agent is incompatible with the active ingredient, its use in the therapeutic compositions is contemplated. Supplementary active ingredients can also be incorporated into the compositions. The phrase "pharmaceutically-acceptable" refers to molecular entities and compositions that do not produce an allergic or similar untoward reaction when administered to a human.

In certain embodiments, the pharmaceutical compositions may be delivered by intranasal sprays, inhalation, and/or other aerosol delivery vehicles. Methods for delivering genes, nucleic acids, and peptide compositions directly to the lungs via nasal aerosol sprays has been described, e.g., in U.S. Pat. No. 5,756,353 and U.S. Pat. No. 5,804,212. Likewise, the delivery of drugs using intranasal microparticle resins (Takenaga et al., J Controlled Release 1998 Mar. 2;52(1-2):81-7) and lysophosphatidyl-glycerol compounds (U.S. Pat. No. 5,725,871) are also well-known in the pharmaceutical arts. Likewise, illustrative transmucosal drug delivery in the form of a polytetrafluoroetheylene support matrix is described in U.S. Pat. No. 5,780,045.

In certain embodiments, liposomes, nanocapsules, microparticles, lipid particles, vesicles, and the like, are used for the introduction of the compositions of the present invention into suitable host cells/organisms. In particular, the compositions of the present invention may be formulated for delivery either encapsulated in a lipid particle, a liposome, a vesicle, a nanosphere, or a nanoparticle or the like. Alternatively, compositions of the present invention can be bound, either covalently or non-covalently, to the surface of such carrier vehicles.

The formation and use of liposome and liposome-like preparations as potential drug carriers is generally known to those of skill in the art (see for example, Lasic, Trends Biotechnol 1998 July;16(7):307-21; Takakura, Nippon Rinsho 1998 March;56(3): 691-5; Chandran et al., Indian J Exp Biol. 1997 August;35(8):801-9; Margalit, Crit Rev Ther Drug Carrier Syst. 1995;12(2-3):233-61; U.S. Pat. No. 5,567,434; U.S. Pat. No. 5,552,157; U.S. Pat. No. 5,565,213; U.S. Pat. No. 5,738,868 and U.S. Pat. No. 5,795,587, each specifically incorporated herein by reference in its entirety).

Liposomes have been used successfully with a number of cell types that are normally difficult to transfect by other procedures, including T cell suspensions, primary hepatocyte cultures and PC 12 cells (Renneisen et al., J Biol Chem. 1990 September 25;265(27):16337-42; Muller et al., DNA Cell Biol. 1990 April;9(3):221-9). In addition, liposomes are free of the DNA length constraints that are typical of viral-based delivery systems. Liposomes have been used effectively to introduce genes, various drugs, radiotherapeutic agents, enzymes, viruses, transcription factors, allosteric effectors and the like, into a variety of cultured cell lines and animals. Furthermore, he use of liposomes does not appear to be associated with autoimmune responses or unacceptable toxicity after systemic delivery In certain embodiments, liposomes are formed from phospholipids that are dispersed in an aqueous medium and spontaneously form multilarnellar concentric bilayer vesicles (also termed multilamellar vesicles (MLVs).

Alternatively, in other embodiments, the invention provides for pharmaceutically-acceptable nanocapsule formulations of the compositions of the present invention. Nanocapsules can generally entrap compounds in a stable and reproducible way (see, for example, Quintanar-Guerrero et al., Drug Dev Ind Pharm. 1998 December;24(12):1113-28). To avoid side effects due to intracellular polymeric overloading, such ultrafine particles (sized around 0.1 μm) may be designed using polymers able to be degraded in vivo. Such particles can be made as described, for example, by Couvreur et al., Crit Rev Ther Drug Carrier Syst. 1988;5(1):1-20; zur Muhlen et al., Eur J Pharm Biopharm. 1998 March;45(2): 149-55; Zambaux et al. J Controlled Release. 1998 Jan. 2;50 (1-3): 31-40; Pat. No. 5,145,684.

Cancer Therapeutic Methods

In farther aspects of the present invention, the pharmaceutical compositions described herein may be used for the treatment of cancer, particularly for the immunotherapy of breast cancer. Within such methods, the pharmaceutical compositions described herein are administered to a patient, typically a warm-blooded animal, preferably a human. A patient may or may not be afflicted with cancer. Accordingly, the above pharmaceutical compositions may be used to prevent the development of a cancer or to treat a patient afflicted with a cancer. Pharmaceutical compositions and vaccines may be administered either prior to or following surgical removal of primary tumors and/or treatment such as administration of radiotherapy or conventional chemotherapeutic drugs. As discussed above, administration of the pharmaceutical compositions may be by any suitable method, including administration by intravenous, intraperitoneal, intramuscular, subcutaneous, intranasal, intradermal, anal, vaginal, topical and oral routes.

Within certain embodiments, immunotherapy may be active immunotherapy, in which treatment relies on the in vivo stimulation of the endogenous host immune system to react against tumors with the administration of immune response-modifying agents (such as polypeptides and polynucleotides as provided herein).

Within other embodiments, immunotherapy may be passive immunotherapy, in which treatment involves the delivery of agents with established tumor-immune reactivity (such as effector cells or antibodies) that can directly or indirectly mediate antitumor effects and does not necessarily depend on an intact host immune system. Examples of effector cells include T cells as discussed above, T lymphocytes (such as CD8+cytotoxic T lymphocytes and CD4+ T-helper tumor-infiltrating lymphocytes), killer cells (such as Natural Killer cells and lymphokine-activated killer cells), B cells and antigen-presenting cells (such as dendritic cells and macrophages) expressing a polypeptide provided herein. T cell receptors and antibody receptors specific for the polypeptides recited herein may be cloned, expressed and transferred into other vectors or effector cells for adoptive immunotherapy. The polypeptides provided herein may also be used to generate antibodies or anti-idiotypic antibodies (as described above and in U.S. Pat. No. 4,918,164) for passive immunotherapy.

Effector cells may generally be obtained in sufficient quantities for adoptive immunotherapy by growth in vitro, as described herein. Culture conditions for expanding single antigen-specific effector cells to several billion in number with retention of antigen recognition in vivo are well known in the art. Such in vitro culture conditions typically use intermittent stimulation with antigen, often in the presence of cytokines (such as IL-2) and non-dividing feeder cells. As noted above, immunoreactive polypeptides as provided herein may be used to rapidly expand antigen-specific T cell cultures in order to generate a sufficient number of cells for immunotherapy. In particular, antigen-presenting cells, such as dendritic, macrophage, monocyte, fibroblast and/or B cells, may be pulsed with immunoreactive polypeptides or transfected with one or more polynucleotides using standard techniques well known in the art. For example, antigen-presenting cells can be transfected with a polynucleotide having a promoter appropriate for increasing expression in a recombinant virus or other expression system. Cultured effector cells for use in therapy must be able to grow and distribute widely, and to survive long term in vivo. Studies have shown that cultured effector cells can be induced to grow in vivo and to survive long term in substantial numbers by repeated stimulation with antigen supplemented with IL-2 (see, for example, Cheever et al., *Immunological Reviews* 157:177, 1997).

Alternatively, a vector expressing a polypeptide recited herein may be introduced into antigen presenting cells taken from a patient and clonally propagated ex vivo for transplant back into the same patient. Transfected cells may be reintroduced into the patient using any means known in the art, preferably in sterile form by intravenous, intracavitary, intraperitoneal or intratumor administration.

Routes and frequency of administration of the therapeutic compositions described herein, as well as dosage, will vary from individual to individual, and may be readily established using standard techniques. In general, the pharmaceutical compositions and vaccines may be administered by injection (e.g., intracutaneous, intramuscular, intravenous or subcutaneous), intranasally (e.g., by aspiration) or orally. Preferably, between 1 and 10 doses may be administered over a 52 week period. Preferably, 6 doses are administered, at intervals of 1 month, and booster vaccinations may be given periodically thereafter. Alternate protocols may be appropriate for individual patients. A suitable dose is an amount of a compound that, when administered as described above, is capable of promoting an anti-tumor immune response, and is at least 10-50% above the basal (i.e., untreated) level. Such response can be monitored by measuring the anti-tumor antibodies in a patient or by vaccine-dependent generation of cytolytic effector cells capable of killing the patient's tumor cells in vitro. Such vaccines should also be capable of causing an immune response that leads to an improved clinical outcome (e.g., more frequent remissions, complete or partial or longer disease-free survival) in vaccinated patients as compared to non-vaccinated patients. In general, for pharmaceutical compositions and vaccines comprising one or more polypeptides, the amount of each polypeptide present in a dose ranges from about 25 μg to 5 mg per kg of host. Suitable dose sizes will vary with the size of the patient, but will typically range from about 0.1 ml, to about 5 mL.

In general, an appropriate dosage and treatment regimen provides the active compound(s) in an amount sufficient to provide therapeutic and/or prophylactic benefit. Such a response can be monitored by establishing an improved clinical outcome (e.g., more frequent remissions, complete or partial, or longer disease-free survival) in treated patients as compared to non-treated patients. Increases in preexisting immune responses to a tumor protein generally correlate with an improved clinical outcome. Such immune responses may generally be evaluated using standard proliferation, cytotoxicity or cytokine assays, which may be performed using samples obtained from a patient before and after treatment.

Cancer Detection and Diagnostic Compositions Methods and Kits

In general, a cancer may be detected in a patient based on the presence of one or more breast tumor proteins and/or polynucleotides encoding such proteins in a biological sample (for example, blood, sera, sputum urine and/or tumor biopsies) obtained from the patient. In other words, such proteins may be used as markers to indicate the presence or absence of a cancer such as breast cancer. In addition, such proteins may be useful for the detection of other cancers. The binding agents provided herein generally permit detection of the level of antigen that binds to the agent in the biological sample. Polynucleotide primers and probes may be used to detect the level of mRNA encoding a tumor protein, which is also indicative of the presence or absence of a cancer. In general, a breast tumor sequence should be present at a level that is at least three fold higher in tumor tissue than in normal tissue.

There are a variety of assay formats known to those of ordinary skill in the art for using a binding agent to detect polypeptide markers in a sample. See, e.g., Harlow and Lane, *Antibodies: A Laboratory Manual*, Cold Spring Harbor Laboratory, 1988. In general, the presence or absence of a cancer in a patient may be determined by (a) contacting a biological sample obtained from a patient with a binding agent; (b) detecting in the sample a level of polypeptide that binds to the binding agent; and (c) comparing the level of polypeptide with a predetermined cut-off value.

In a preferred embodiment, the assay involves the use of binding agent immobilized on a solid support to bind to and remove the polypeptide from the remainder of the sample. The bound polypeptide may then be detected using a detection reagent that contains a reporter group and specifically binds to the binding agent/polypeptide complex. Such detection reagents may comprise, for example, a binding agent that specifically binds to the polypeptide or an antibody or other agent that specifically binds to the binding agent, such as an anti-immunoglobulin, protein G, protein A or a lectin. Alternatively, a competitive assay may be utilized, in which a polypeptide is labeled with a reporter group and allowed to bind to the immobilized binding agent after incubation of the binding agent with the sample. The extent to which components of the sample inhibit the binding of the labeled polypeptide to the binding agent is indicative of the reactivity of the sample with the immobilized binding agent. Suitable polypeptides for use within such assays include full length breast tumor proteins and polypeptide portions thereof to which the binding agent binds, as described above.

The solid support may be any material known to those of ordinary skill in the art to which the tumor protein may be attached. For example, the solid support may be a test well in a microtiter plate or a nitrocellulose or other suitable membrane. Alternatively, the support may be a bead or disc, such as glass, fiberglass, latex or a plastic material such as polystyrene or polyvinylchloride. The support may also be a magnetic particle or a fiber optic sensor, such as those disclosed, for example, in U.S. Pat. No. 5,359,681. The binding agent may be immobilized on the solid support using a variety of techniques known to those of skill in the art, which are amply described in the patent and scientific literature. In the context of the present invention, the term "immobilization" refers to both noncovalent association, such as adsorption, and covalent attachment (which may be a direct linkage between the agent and functional groups on the support or may be a linkage by way of a cross-linking agent). Immobilization by adsorption to a well in a microtiter plate or to a membrane is preferred. In such cases, adsorption may be achieved by contacting the binding agent, in a suitable buffer, with the solid support for a suitable amount of time. The contact time varies with temperature, but is typically between about 1 hour and about 1 day. In general, contacting a well of a plastic microtiter plate (such as polystyrene or polyvinylchloride) with an amount of binding agent ranging from about 10 ng to about 10 µg, and preferably about 100 ng to about 1 µg, is sufficient to immobilize an adequate amount of binding agent.

Covalent attachment of binding agent to a solid support may generally be achieved by first reacting the support with a bifunctional reagent that will react with both the support and a functional group, such as a hydroxyl or amino group, on the binding agent. For example, the binding agent may be covalently attached to supports having an appropriate polymer coating using benzoquinone or by condensation of an aldehyde group on the support with an amine and an active hydrogen on the binding partner (see, e.g., Pierce Immunotechnology Catalog and Handbook, 1991, at A12-A13).

In certain embodiments, the assay is a two-antibody sandwich assay. This assay may be performed by first contacting an antibody that has been immobilized on a solid support, commonly the well of a microtiter plate, with the sample, such that polypeptides within the sample are allowed to bind to the immobilized antibody. Unbound sample is then removed from the immobilized polypeptide-antibody complexes and a detection reagent (preferably a second antibody capable of binding to a different site on the polypeptide) containing a reporter group is added. The amount of detection reagent that remains bound to the solid support is then determined using a method appropriate for the specific reporter group.

More specifically, once the antibody is immobilized on the support as described above, the remaining protein binding sites on the support are typically blocked. Any suitable blocking agent known to those of ordinary skill in the art, such as bovine serum albumin or Tween 20™ (Sigma Chemical Co., St. Louis, Mo.). The immobilized antibody is then incubated with the sample, and polypeptide is allowed to bind to the antibody. The sample may be diluted with a suitable diluent, such as phosphate-buffered saline (PBS) prior to incubation. In general, an appropriate contact time (i.e., incubation time) is a period of time that is sufficient to detect the presence of polypeptide within a sample obtained from an individual with breast cancer. Preferably, the contact time is sufficient to achieve a level of binding that is at least about 95% of that achieved at equilibrium between bound and unbound polypeptide. Those of ordinary skill in the art will recognize that the time necessary to achieve equilibrium may be readily determined by assaying the level of binding that occurs over a period of time. At room temperature, an incubation time of about 30 minutes is generally sufficient.

Unbound sample may then be removed by washing the solid support with an appropriate buffer, such as PBS containing 0.1% Tween 20™. The second antibody, which contains a reporter group, may then be added to the solid support. Preferred reporter groups include those groups recited above.

The detection reagent is then incubated with the immobilized antibody-polypeptide complex for an amount of time sufficient to detect the bound polypeptide. An appropriate amount of time may generally be determined by assaying the level of binding that occurs over a period of time. Unbound detection reagent is then removed and bound detection reagent is detected using the reporter group. The method employed for detecting the reporter group depends upon the nature of the reporter group. For radioactive groups, scintillation counting or autoradiographic methods are generally appropriate. Spectroscopic methods may be used to detect dyes, luminescent groups and fluorescent groups. Biotin may be detected using avidin, coupled to a different reporter group (commonly a radioactive or fluorescent group or an enzyme). Enzyme reporter groups may generally be detected by the addition of substrate (generally for a specific period of time), followed by spectroscopic or other analysis of the reaction products.

To determine the presence or absence of a cancer, such as breast cancer, the signal detected from the reporter group that remains bound to the solid support is generally compared to a signal that corresponds to a predetermined cut-off value. In one preferred embodiment, the cut-off value for the detection of a cancer is the average mean signal obtained when the immobilized antibody is incubated with samples from patients without the cancer. In general, a sample generating a signal that is three standard deviations above the predetermined cut-off value is considered positive for the cancer. In an alternate preferred embodiment, the cut-off value is determined using a Receiver Operator Curve, according to the method of Sackett et al., *Clinical Epidemiology: A Basic Science for Clinical Medicine*, Little Brown and Co., 1985, p. 106-7. Briefly, in this embodiment, the cut-off value may be determined from a plot of pairs of true positive rates (i.e., sensitivity) and false positive rates (100%-specificity) that correspond to each possible cut-off value for the diagnostic test result. The cut-off value on the plot that is the closest to the upper left-hand corner (i.e., the value that encloses the largest area) is the most accurate cut-off value, and a sample generating a signal that is higher than the cut-off value determined by this method may be considered positive. Alternatively, the cut-off value may be shifted to the left along the plot, to minimize the false positive rate, or to the right, to minimize the false negative rate. In general, a sample generating a signal that is higher than the cut-off value determined by this method is considered positive for a cancer.

In a related embodiment, the assay is performed in a flow-through or strip test format, wherein the binding agent is immobilized on a membrane, such as nitrocellulose. In the flow-through test, polypeptides within the sample bind to the immobilized binding agent as the sample passes through the membrane. A second, labeled binding agent then binds to the binding agent-polypeptide complex as a solution containing the second binding agent flows through the membrane. The detection of bound second binding agent may then be performed as described above. In the strip test format, one end of the membrane to which binding agent is bound is immersed in a solution containing the sample. The sample migrates along the membrane through a region containing second binding agent and to the area of immobilized binding agent. Concentration of second binding agent at the area of immobilized antibody indicates the presence of a cancer. Typically, the concentration of second binding agent at that site generates a pattern, such as a line, that can be read visually. The absence of such a pattern indicates a negative result. In general, the amount of binding agent immobilized on the membrane is selected to generate a visually discernible pattern when the biological sample contains a level of polypeptide that would be sufficient to generate a positive signal in the two-antibody sandwich assay, in the format discussed above. Preferred binding agents for use in such assays are antibodies and antigen-binding fragments thereof. Preferably, the amount of antibody immobilized on the membrane ranges from about 25 ng to about 1 µg, and more preferably from about 50 ng to about 500 ng. Such tests can typically be performed with a very small amount of biological sample.

Of course, numerous other assay protocols exist that are suitable for use with the tumor proteins or binding agents of the present invention. The above descriptions are intended to be exemplary only. For example, it will be apparent to those of ordinary skill in the art that the above protocols may be readily modified to use tumor polypeptides to detect antibodies that bind to such polypeptides in a biological sample. The detection of such tumor protein specific antibodies may correlate with the presence of a cancer.

A cancer may also, or alternatively, be detected based on the presence of T cells that specifically react with a tumor protein in a biological sample. Within certain methods, a biological sample comprising $CD4^+$ and/or $CD8^+$ T cells isolated from a patient is incubated with a tumor polypeptide, a polynucleotide encoding such a polypeptide and/or an APC that expresses at least an immunogenic portion of such a polypeptide, and the presence or absence of specific activation of the T cells is detected. Suitable biological samples include, but are not limited to, isolated T cells. For example, T cells may be isolated from a patient by routine techniques (such as by Ficoll/Hypaque density gradient centrifugation of peripheral blood lymphocytes). T cells may be incubated in vitro for 2-9 days (typically 4 days) at 37° C. with polypeptide (e.g., 5-25 µg/ml). It may be desirable to incubate another aliquot of a T cell sample in the absence of tumor polypeptide to serve as a control. For $CD4^+$ T cells, activation is preferably detected by evaluating proliferation of the T cells. For $CD8^+$ T cells, activation is preferably detected by evaluating cytolytic activity. A level of proliferation that is at least two fold greater and/or a level of cytolytic activity that is at least 20% greater than in disease-free patients indicates the presence of a cancer in the patient.

As noted above, a cancer may also, or alternatively, be detected based on the level of mRNA encoding a tumor protein in a biological sample. For example, at least two oligonucleotide primers may be employed in a polymerase chain reaction (PCR) based assay to amplify a portion of a tumor cDNA derived from a biological sample, wherein at least one of the oligonucleotide primers is specific for (i.e., hybridizes to) a polynucleotide encoding the tumor protein. The amplified cDNA is then separated and detected using techniques well known in the art, such as gel electrophoresis. Similarly, oligonucleotide probes that specifically hybridize to a polynucleotide encoding a tumor protein may be used in a hybridization assay to detect the presence of polynucleotide encoding the tumor protein in a biological sample.

To permit hybridization under assay conditions, oligonucleotide primers and probes should comprise an oligonucleotide sequence that has at least about 60%, preferably at least about 75% and more preferably at least about 90%, identity to a portion of a polynucleotide encoding a tumor protein of the invention that is at least 10 nucleotides, and preferably at least 20 nucleotides, in length. Preferably, oligonucleotide primers and/or probes hybridize to a polynucleotide encoding a polypeptide described herein under moderately stringent conditions, as defined above. Oligonucleotide primers and/or probes which may be usefully employed in the diagnostic methods described herein preferably are at least 10-40 nucleotides in length. In a preferred embodiment, the oligonucleotide primers comprise at least 10 contiguous nucleotides, more preferably at least 15 contiguous nucleotides, of a DNA molecule having a sequence as disclosed herein. Techniques for both PCR based assays and hybridization assays are well known in the art (see, for example, Mullis et al., *Cold Spring Harbor Symp. Quant. Biol.*, 51:263, 1987; Erlich ed., *PCR Technology*, Stockton Press, NY, 1989).

One preferred assay employs RT-PCR, in which PCR is applied in conjunction with reverse transcription. Typically, RNA is extracted from a biological sample, such as biopsy tissue, and is reverse transcribed to produce cDNA molecules. PCR amplification using at least one specific primer generates a cDNA molecule, which may be separated and visualized using, for example, gel electrophoresis. Amplification may be performed on biological samples taken from a test patient and from an individual who is not afflicted with a cancer. The amplification reaction may be performed on several dilutions of cDNA spanning two orders of magnitude. A two-fold or greater increase in expression in several dilutions of the test patient sample as compared to the same dilutions of the non-cancerous sample is typically considered positive.

In another embodiment, the compositions described herein may be used as markers for the progression of cancer. In this embodiment, assays as described above for the diagnosis of a cancer may be performed over time, and the change in the level of reactive polypeptide(s) or polynucleotide(s) evaluated. For example, the assays may be performed every 24-72 hours for a period of 6 months to 1 year, and thereafter performed as needed. In general, a cancer is progressing in those patients in whom the level of polypeptide or polynucleotide detected increases over time. In contrast, the cancer is not progressing when the level of reactive polypeptide or polynucleotide either remains constant or decreases with time.

Certain in vivo diagnostic assays may be performed directly on a tumor. One such assay involves contacting tumor cells with a binding agent. The bound binding agent may then be detected directly or indirectly via a reporter group. Such binding agents may also be used in histological applications. Alternatively, polynucleotide probes may be used within such applications.

As noted above, to improve sensitivity, multiple tumor protein markers may be assayed within a given sample. It will be apparent that binding agents specific for different proteins provided herein may be combined within a single assay. Further, multiple primers or probes may be used concurrently. The selection of tumor protein markers may be based on routine experiments to determine combinations that results in optimal sensitivity. In addition, or alternatively, assays for tumor proteins provided herein may be combined with assays for other known tumor antigens.

The present invention further provides kits for use within any of the above diagnostic methods. Such kits typically comprise two or more components necessary for performing a diagnostic assay. Components may be compounds, reagents, containers and/or equipment. For example, one container within a kit may contain a monoclonal antibody or fragment thereof that specifically binds to a tumor protein. Such antibodies or fragments may be provided attached to a support material, as described above. One or more additional containers may enclose elements, such as reagents or buffers, to be used in the assay. Such kits may also, or alternatively, contain a detection reagent as described above that contains a reporter group suitable for direct or indirect detection of antibody binding.

Alternatively, a kit may be designed to detect the level of mRNA encoding a tumor protein in a biological sample. Such kits generally comprise at least one oligonucleotide probe or primer, as described above, that hybridizes to a polynucleotide encoding a tumor protein. Such an oligonucleotide may be used, for example, within a PCR or hybridization assay. Additional components that may be present within such kits include a second oligonucleotide and/or a diagnostic reagent or container to facilitate the detection of a polynucleotide encoding a tumor protein.

The following Examples are offered by way of illustration and not by way of limitation.

EXAMPLE 1

Isolation and Characterization of Breast Tumor Polypeptides

This Example describes the isolation of breast tumor polypeptides from a breast tumor cDNA library.

A cDNA subtraction library containing cDNA from breast tumor subtracted with normal breast cDNA was constructed as follows. Total RNA was extracted from primary tissues using Trizol reagent (Gibco BRL Life Technologies, Gaithersburg, Md.) as described by the manufacturer. The polyA+ RNA was purified using an oligo(dT) cellulose column according to standard protocols. First strand cDNA was synthesized using the primer supplied in a Clontech PCR-Select cDNA Subtraction Kit (Clontech, Palo Alto, Calif.). The driver DNA consisted of cDNAs from two normal breast tissues with the tester cDNA being from three primary breast tumors. Double-stranded cDNA was synthesized for both tester and driver, and digested with a combination of endonucleases (MluI, MscI, PvuII, SalI and StuI) which recognize six base pairs DNA. This modification increased the average cDNA size dramatically compared with cDNAs generated according to the protocol of Clontech (Palo Alto, Calif.). The digested tester cDNAs were ligated to two different adaptors and the subtraction was performed according to Clontech's protocol. The subtracted cDNAs were subjected to two rounds of PCR amplification, following the manufacturer's protocol. The resulting PCR products were subcloned into the TA cloning vector, pCRII (Invitrogen, San Diego, Calif.) and transformed into ElectroMax *E. coli* DH10B cells (Gibco BRL Life, Technologies) by electroporation. DNA was isolated from independent clones and sequenced using a Perkin Elmer/Applied Biosystems Division (Foster City, Calif.) Automated Sequencer Model 373A.

Sixty-three distinct cDNA clones were found in the subtracted breast tumor-specific cDNA library. The determined one strand (5' or 3') cDNA sequences for the clones are provided in SEQ ID NO:1-61, 72 and 73, respectively. Comparison of these cDNA sequences with known sequences in the gene bank using the EMBL and GenBank databases (Release 97) revealed no significant homologies to the sequences provided in SEQ ID NO:14, 21, 22, 27, 29, 30, 32, 38, 44, 45, 53, 57, 72 and 73. The sequences of SEQ ID NO:1, 3, 16, 17, 34, 48, 60 and 61 were found to represent known human genes. The sequences of SEQ ID NO:2, 4, 23, 39 and 50 were found to show some similarity to previously identified non-human genes. The remaining clones (SEQ ID NO:5-13, 15, 18-20, 24-26, 28, 31, 33, 35-37, 40-43, 46, 47, 49, 51, 52, 54-56, 58 and 59) were found to show at least some degree of homology to previously identified expressed sequence tags (ESTs).

Further studies resulted in the isolation of the full-length cDNA sequence for the clone of SEQ ID NO:57 (referred to as B718P). By computer analysis, the full-length sequence was found to contain a putative transmembrane domain at amino acids 137-158. The full-length cDNA sequence of B718P is provided in SEQ ID NO:504, with the cDNA sequence of the open reading frame including stop codon being provided in SEQ ID NO:505 and the cDNA sequence of the open reading frame without stop codon being provided in SEQ ID NO:506. The full-length amino acid sequence of B718P is provided is SEQ ID NO:507. SEQ ID NO:508 represents amino acids 1-158 of B718P, and SEQ ID NO:509 represents amino acids 159-243 of B718P.

To determine mRNA expression levels of the isolated cDNA clones, cDNA clones from the breast subtraction described above were randomly picked and colony PCR amplified. Their mRNA expression levels in breast tumor, normal breast and various other normal tissues were determined using microarray technology (Synteni, Palo Alto, Calif.). Briefly, the PCR amplification products were arrayed onto slides in an array format, with each product occupying a unique location in the array. mRNA was extracted from the tissue sample to be tested, reverse transcribed, and fluorescent-labeled cDNA probes were generated. The microarrays were probed with the labeled cDNA probes, the slides scanned and fluorescence intensity was measured. Data was analyzed using Synteni provided GEMTOOLS Software. Of the seventeen cDNA clones examined, those of SEQ ID NO:40, 46, 59 and 73 were found to be over-expressed in breast tumor and expressed at low levels in all normal tissues tested (breast, PBMC, colon, fetal tissue, salivary gland, bone marrow, lung, pancreas, large intestine, spinal cord, adrenal gland, kidney, pancreas, liver, stomach, skeletal muscle, heart, small intestine, skin, brain and human mammary epithelial cells). The clones of SEQ ID NO:41 and 48 were found to be over-expressed in breast tumor and expressed at low levels in all other tissues tested, with the exception of bone marrow. The clone of SEQ ID NO:42 was found to be over-expressed in breast tumor and expressed at low levels in all other tissues tested except bone marrow and spinal cord. The clone of SEQ ID NO:43 was found to be over-expressed in breast tumor and expressed at low levels in all other tissues tested with the exception of spinal cord, heart and small intestine. The clone of SEQ ID NO:51 was found to be over-expressed in breast tumor and expressed at low levels in all other tissues tested with the exception of large intestine. The clone of SEQ ID NO:54 was found to be over-expressed in breast tumor and expressed at low levels in all other tissues tested with the exception of PBMC, stomach and small intestine. The clone of SEQ ID NO:56 was found to be over-expressed in breast tumor and expressed at low levels in all other tissues tested with the exception of large and small intestine, human mammary epithelia cells and SCID mouse-passaged breast tumor. The clone of SEQ ID NO:60 was found to be over-expressed in breast tumor and expressed at low levels in all other tissues tested with the exception of spinal cord and heart. The clone of SEQ ID NO:61 was found to be over-expressed in breast tumor and expressed at low levels in all other tissues tested with the exception of small intestine. The clone of SEQ ID NO:72 was found to be over-expressed in breast tumor and expressed at low levels in all other tissues tested with the exception of colon and salivary gland.

The results of a Northern blot analysis of the clone SYN18C6 (SEQ ID NO:40) are shown in FIG. 1. A predicted protein sequence encoded by SYN18C6 is provided in SEQ ID NO:62.

Additional cDNA clones that are over-expressed in breast tumor tissue were isolated from breast cDNA subtraction libraries as follows. Breast subtraction libraries were prepared, as described above, by PCR-based subtraction employing pools of breast tumor cDNA as the tester and pools of either normal breast cDNA or cDNA from other normal tissues as the driver. cDNA clones from breast subtraction were randomly picked and colony PCR amplified and their mRNA expression levels in breast tumor, normal breast and various other normal tissues were determined using the microarray technology described above. Twenty-four distinct cDNA clones were found to be over-expressed in breast tumor and expressed at low levels in all normal tissues tested (breast, brain, liver, pancreas, lung, salivary gland, stomach, colon, kidney, bone marrow, skeletal muscle, PBMC, heart, small intestine, adrenal gland, spinal cord, large intestine and skin). The determined cDNA sequences for these clones are provided in SEQ ID NO:63-87. Comparison of the sequences of SEQ ID NO:74-87 with those in the gene bank as described above, revealed homology to previously identified human genes. No significant homologies were found to the sequences of SEQ ID NO:63-73.

Three DNA isoforms for the clone B726P (partial sequence provided in SEQ ID NO:71) were isolated as follows. A radioactive probe was synthesized from B726P by excising B726P DNA from a pT7Blue vector (Novagen) by a BamHI/XbaI restriction digest and using the resulting DNA as the template in a single-stranded PCR in the presence of [α-32P] dCTP. The sequence of the primer employed for this PCR is provided in SEQ ID NO:177. The resulting radioactive probe was used to probe a directional cDNA library and a random-primed cDNA library made using RNA isolated from breast tumors. Eighty-five clones were identified, excised, purified and sequenced. Of these 85 clones, three were found to each contain a significant open reading frame. The determined cDNA sequence of the isoform B726P-20 is provided in SEQ ID NO:175, with the corresponding predicted amino acid sequence being provided in SEQ ID NO:176. The determined cDNA sequence of the isoform B726P-74 is provided in SEQ ID NO:178, with the corresponding predicted amino acid sequence being provided in SEQ ID NO:179. The determined cDNA sequence of the isoform B726P-79 is provided in SEQ ID NO:180, with the corresponding predicted amino acid sequence being provided in SEQ ID NO:181.

Efforts to obtain a full-length clone of B726P using standard techniques led to the isolation of five additional clones that represent additional 5' sequence of B726P. These clones appear to be alternative splice forms of the same gene. The determined cDNA sequences of these clones are provided in SEQ ID NO:464-468, with the predicted amino acid sequences encoded by SEQ ID NO:464-467 being provided in SEQ ID NO:470-473, respectively. Using standard computer techniques, a 3,681 bp consensus DNA sequence (SEQ ID NO:463) was created that contains two large open reading frames. The downstream ORF encodes the amino acid sequence of SEQ ID NO:176. The predicted amino acid sequence encoded by the upstream ORF is provided in SEQ ID NO:469. Subsequent studies led to the isolation of an additional splice form of B726P that has 184 bp insert relative to the other forms. This 184 bp insert causes a frameshift that brings the down stream and upstream ORFs together into a single ORF that is 1002 aa in length. The determined cDNA sequence of this alternative splice form is disclosed in SEQ ID NO:474, with the corresponding amino acid sequence being provided in SEQ ID NO:475.

Comparison of the cDNA sequence of SEQ ID NO:63 (referred to as B723P) with the sequences in the GeneSeq™ DNA database showed matches to 5 DNA sequences (Accession nos. A26456, A37144, A26424, V84525 and T22133), 4 of which appear to represent the full-length sequence of the gene. Three of these sequences encode a 243 amino acid open reading frame (ORF), while one of the DNA sequences (Accession no. A37144) contains an extra C at position 35, resulting in a 278 amino acid ORF. The open reading frame, including stop codon, of the first variant of B723P (referred to as B723P-short) is provided in SEQ ID NO:510, with the open reading frame without stop codon being provided in SEQ ID NO:511. The open reading frame, including stop codon, of the second variant of B723P (referred to as B723P-long) is provided in SEQ ID NO:512, with the open reading frame without stop codon being provided in SEQ ID NO:513. The amino acid sequences of B723P-short and B723P-long are provided in SEQ ID NO:514 and 515, respectively. Computer analysis of these sequences demonstrated the presence of putative transmembrane domains at amino acids 233-252 of the B723P-long ORF and amino acids 198-217 of the B723P-short ORF. SEQ ID NO:516, 518 and 519 represent amino acids 1-197, 198-243 and 218-243, respectively of B723P-short. SEQ ID NO:517 represents amino acids 1-232 of B723P-long.

Further isolation of individual clones that are over-expressed in breast tumor tissue was conducted using cDNA subtraction library techniques described above. In particular, a cDNA subtraction library containing cDNA from breast tumors subtracted with five other normal human tissue cDNAs (brain, liver, PBMC, pancreas and normal breast) was utilized in this screening. From the original subtraction, one hundred seventy seven clones were selected to be further characterized by DNA sequencing and microarray analysis. Microarray analysis demonstrated that the sequences in SEQ ID NO:182-251 and 479 were 2 or more fold over-expressed in human breast tumor tissues over normal human tissues. No significant homologies were found for nineteen of these clones, including, SEQ ID NO:185, 186, 194, 199, 205, 208, 211, 214-216, 219, 222, 226, 232, 236, 240, 241, 245, 246 and 479, with the exception of some previously identified expressed sequence tags (ESTs). The remaining clones share some homology to previously identified genes, specifically SEQ ID NO:181-184, 187-193, 195-198, 200-204, 206, 207, 209, 210, 212, 213, 217, 218, 220, 221, 223-225, 227-231, 233-235, 237-239, 242-244 and 247-251.

One of the cDNA clones isolated by PCR subtraction as described above (SEQ ID NO:476; referred to as B720P) which was shown by microarray to be over-expressed in breast tumor tissues, was found to be identical to a known keratin gene. The full-length cDNA sequence of the known keratin gene is provided in SEQ ID NO:477, with the corresponding amino acid sequence being provided in SEQ ID NO:478. Primers were generated based on the sequence of SEQ ID NO:477 and used to clone full-length cDNA from mRNA which was obtained from total RNA showing high expression of B720P in real-time PCR analysis. Products were then cloned and sequenced. The determined full-length cDNA sequence for B720P is provided in SEQ ID NO:484, with the corresponding amino acid sequence being provided in SEQ ID NO:485.

In further studies, a truncated form of B720P (referred to as B720P-tr) was identified in breast carcinomas. This antigen was cloned from mRNA derived from total breast tumor RNA that showed high expression of B720P-tr in real-time PCR analysis. mRNA was used to generate a pool of cDNA which was then used as a template to amplify the cDNA corresponding to B720P-tr by PCR. The determined cDNA sequence for B720P-tr is provided in SEQ ID NO:486. B720P-tr has an ORF of 708 base pairs which encodes a 236 amino acid protein (SEQ ID NO:487). The size of the transcript was confirmed by northern analysis.

Of the seventy clones showing over-expression in breast tumor tissues, fifteen demonstrated particularly good expression levels in breast tumor over normal human tissues. The following eleven clones did not show any significant homology to any known genes. Clone 19463.1 (SEQ ID NO:185) was over-expressed in the majority of breast tumors and also in the SCID breast tumors tested (refer to Example 2); additionally, over-expression was found in a majority of normal breast tissues. Clone 19483.1 (SEQ ID NO:216) was over-expressed in a few breast tumors, with no over-expression in any normal tissues tested. Clone 19470.1 (SEQ ID NO:219) was found to be slightly over-expressed in some breast tumors. Clone 19468.1 (SEQ ID NO:222) was found to be slightly over-expressed in the majority of breast tumors tested. Clone 19505.1 (SEQ ID NO:226) was found to be slightly over-expressed in 50% of breast tumors, as well as in SCID tumor tissues, with some degree of over-expression in found in normal breast. Clone 1509.1 (SEQ ID NO:232) was found to be over-expressed in very few breast tumors, but with a certain degree of over-expression in metastatic breast tumor tissues, as well as no significant over-expression found in normal tissues. Clone 19513.1 (SEQ ID NO:236) was shown to be slightly over-expressed in few breast tumors, with no significant over-expression levels found in normal tissues. Clone 19575.1 (SEQ ID NO:240) showed low level over-expression in some breast tumors and also in normal breast. Clone 19560.1 (SEQ ID NO:241) was over-expressed in 50% of breast tumors tested, as well as in some normal breast tissues. Clone 19583.1 (SEQ ID NO:245) was slightly over-expressed in some breast tumors, with very low levels of over-expression found in normal tissues. Clone 19587.1 (SEQ ID NO:246) showed low level over-expression in some breast tumors and no significant over-expression in normal tissues.

Clone 19520.1 (SEQ ID NO:233), showing homology to clone 102D24 on chromosome 11q13.31, was found to be over-expressed in breast tumors and in SCID tumors. Clone 19517.1 (SEQ ID NO:237), showing homology to human PAC 128M19 clone, was found to be slightly over-expressed in the majority of breast tumors tested. Clone 19392.2 (SEQ ID NO:247), showing homology to human chromosome 17, was shown to be over-expressed in 50% of breast tumors tested. Clone 19399.2 (SEQ ID NO:250), showing homology to human Xp22 BAC GSHB-184P14, was shown to be slightly over-expressed in a limited number of breast tumors tested.

In subsequent studies, 64 individual clones were isolated from a subtracted cDNA library containing cDNA from a pool of breast tumors subtracted with cDNA from five normal tissues (brain, liver, PBMC, pancreas and normal breast). The subtracted cDNA library was prepared as described above with the following modification. A combination of five six-base cutters (MluI, MscI, PvuII, SalI and StuI) was used to digest the cDNA instead of RsaI. This resulted in an increase in the average insert size from 300 bp to 600 bp. The 64 isolated clones were colony PCR amplified and their mRNA expression levels in breast tumor tissue, normal breast and various other normal tissues were examined by microarray technology as described above. The determined cDNA sequences of 11 clones which were found to be over-expressed in breast tumor tissue are provided in SEQ ID NO:405-415. Comparison of these sequences to those in the public database, as outlined above, revealed homologies between the sequences of SEQ ID NO:408, 411, 413 and 414 and previously isolated ESTs. The sequences of SEQ ID NO:405-407, 409, 410, 412 and 415 were found to show some homology to previously identified sequences.

In further studies, a subtracted cDNA library was prepared from cDNA from metastatic breast tumors subtracted with a pool of cDNA from five normal tissues (breast, brain, lung, pancreas and PBMC) using the PCR-subtraction protocol of Clontech, described above. The determined cDNA sequences of 90 clones isolated from this library are provided in SEQ ID NO:316-404. Comparison of these sequences with those in the public database, as described above, revealed no significant homologies to the sequence of SEQ ID NO:366. The sequences of SEQ ID NO:321-325, 343, 354, 368, 369, 377, 382, 385, 389, 395, 397 and 400 were found to show some homology to previously isolated ESTs. The remaining sequences were found to show homology to previously identified gene sequences.

In yet further studies, a subtracted cDNA library (referred to as 2BT) was prepared from cDNA from breast tumors subtracted with a pool of cDNA from six normal tissues (liver, brain, stomach, small intestine, kidney and heart) using the PCR-subtraction protocol of Clontech, described above. cDNA clones isolated from this subtraction were subjected to DNA microarray analysis as described above and the resulting data subjected to four modified Gemtools analyses. The first analysis compared 28 breast tumors with 28 non-breast normal tissues. A mean over-expression of at least 2.1 fold was used as a selection cut-off. The second analysis compared 6 metastatic breast tumors with 29 non-breast normal tissues.

A mean over-expression of at least 2.5 fold was used as a cut-off. The third and fourth analyses compared 2 early SCID mouse-passaged with 2 late SCID mouse-passaged tumors. A mean over-expression in the early or late passaged tumors of 2.0 fold or greater was used as a cut-off. In addition, a visual analysis was performed on the microarray data for the 2BT clones. The determined cDNA sequences of 13 clones identified in the visual analysis are provided in SEQ ID NO:427-439. The determined cDNA sequences of 22 clones identified using the modified Gemtools analysis are provided in SEQ ID NO:440-462, wherein SEQ ID NO:453 and 454 represent two partial, non-overlapping, sequences of the same clone.

Comparison of the clone sequences of SEQ ID NO:436 and 437 (referred to as 263G6 and 262B2) with those in the public databases, as described above, revealed no significant homologies to previously identified sequences. The sequences of SEQ ID NO:427, 429, 431, 435, 438, 441, 443, 444, 445, 446, 450, 453 and 454 (referred to as 266B4, 266G3, 264B4, 263G1, 262B6, 2BT2-34, 2BT1-77, 2BT1-62, 2BT1-60,61, 2BT1-59, 2BT1-52 and 2BT1-40, respectively) showed some homology to previously isolated expressed sequences tags (ESTs). The sequences of SEQ ID NO:428, 430, 432, 433, 434, 439, 440, 442, 447, 448, 449, 451, 452 and 455-462 (referred to as clones 22892, 22890, 22883, 22882, 22880, 22869, 21374, 21349, 21093, 21091, 21089, 21085, 21084, 21063, 21062, 21060, 21053, 21050, 21036, 21037 and 21048, respectively), showed some homology to gene sequences previously identified in humans.

EXAMPLE 2

Isolation and Characterization of Breast Tumor Polypeptides Obtained by PCR-Based Subtraction Using SCID-Passaged Tumor RNA Human breast tumor antigens were obtained by PCR-based subtraction using SCID mouse passaged breast tumor RNA as follows. Human breast tumor was implanted in SCID mice and harvested on the first or sixth serial passage, as described in patent application Ser. No. 08/556,659 filed Nov. 13, 1995, U.S. Pat. No. 5,986,170. Genes found to be differentially expressed between early and late passage SCID tumor may be stage specific and therefore useful in therapeutic and diagnostic applications. Total RNA was prepared from snap frozen SCID passaged human breast tumor from both the first and sixth passage.

PCR-based subtraction was performed essentially as described above. In the first subtraction (referred to as T9), RNA from first passage tumor was subtracted from sixth passage tumor RNA to identify more aggressive, later passage-specific antigens. Of the 64 clones isolated and sequenced from this subtraction, no significant homologies were found to 30 of these clones, hereinafter referred to as: 13053, 13057, 13059, 13065, 13067, 13068, 13071-13073, 13075, 13078, 13079, 13081, 13082, 13092, 13097, 13101, 13102, 13131, 13133, 13119, 13135, 13139, 13140, 13146-13149, and 13151, with the exception of some previously identified expressed sequence tags (ESTs). The determined cDNA sequences for these clones are provided in SEQ ID NO:88-116, respectively. The isolated cDNA sequences of SEQ ID NO:117-140 showed homology to known genes.

In a second PCR-based subtraction. RNA from sixth passage tumor was subtracted from first passage tumor RNA to identify antigens down-regulated over multiple passages. Of the 36 clones isolated and sequenced, no significant homologies were found to nineteen of these clones, hereinafter referred to as: 14376, 14377, 14383, 14384, 14387, 14392, 14394, 14398, 14401, 14402, 14405, 14409, 14412, 14414-14416, 14419, 14426, and 14427, with the exception of some previously identified expressed sequence tags (ESTs). The determined cDNA sequences for these clones are provided in SEQ ID NO:141-159, respectively. The isolated cDNA sequences of SEQ ID NO:160-174 were found to show homology to previously known genes.

Further analysis of human breast tumor antigens through PCR-based subtraction using first and sixth passage SCID tumor RNA was performed. Sixty three clones were found to be differentially expressed by a two or more fold margin, as determined by microarray analysis, i.e., higher expression in early passage tumor over late passage tumor, or vice versa. Seventeen of these clones showed no significant homology to any known genes, although some degree of homology with previously identified expressed sequence tags (ESTs) was found, hereinafter referred to as 20266, 20270, 20274, 20276, 20277, 20280, 20281, 20294, 20303, 20310, 20336, 20341, 20941, 20954, 20961, 20965 and 20975 (SEQ ID NO:252-268, respectively). The remaining clones were found to share some degree of homology to known genes, which are identified in the Brief Description of the Drawings and Sequence Identifiers section above, hereinafter referred to as 20261, 20262, 20265, 20267, 20268, 20271, 20272, 20273, 20278, 20279, 20293, 20300, 20305, 20306, 20307, 20313, 20317, 20318, 20320, 20321, 20322, 20326, 20333, 20335, 20337, 20338, 20340 20938, 20939, 20940, 20942, 20943, 20944, 20946, 20947, 20948, 20949, 20950, 20951, 20952, 20957, 20959, 20966, 20976, 20977 and 20978. The determined cDNA sequences for these clones are provided in SEQ ID NO:269-314, respectively.

The clones 20310. 20281, 20262, 20280, 20303, 20336, 20270, 20341, 20326 and 20977 (also referred to as B820P, B821P, B822P, B823P, B824P, B825P, B826P, B827P, B828P and B829P, respectively) were selected for further analysis based on the results obtained with microarray analysis. Specifically, microarray data analysis indicated at least two- to three-fold overexpression of these clones in breast tumor RNA compared to normal tissues tested. Subsequent studies led to the determination of the complete insert sequence for the clones B820P, B821P, B822P. B823P, B824P, B825P, B826P, B827P, B828P and B829P. These extended cDNA sequences are provided in SEQ ID NO:416-426, respectively.

EXAMPLE 3

Synthesis of Polypeptides

Polypeptides may be synthesized on an Perkin Elmer/Applied Biosystems Division 430A peptide synthesizer using FMOC chemistry with HPTU (O-Benzotriazole-N,N,N',N'-tetramethyluronium hexafluorophosphate) activation. A Gly-Cys-Gly sequence may be attached to the amino terminus of the peptide to provide a method of conjugation, binding to an immobilized surface, or labeling of the peptide. Cleavage of the peptides from the solid support may be carried out using the following cleavage mixture: trifluoroacetic acid:ethanedithiol:thioanisole:water:phenol (40:1:2:2:3). After cleaving for 2 hours, the peptides may be precipitated in cold methyl-t-butyl-ether. The peptide pellets may then be dissolved in water containing 0.1% trifluoroacetic acid (TFA) and lyophilized prior to purification by C18 reverse phase HPLC. A gradient of 0%-60% acetonitrile (containing 0.1% TFA) in water (containing 0.1% TFA) may be used to elute the peptides. Following lyophilization of the pure fractions, the peptides may be characterized using electrospray or other types of mass spectrometry and by amino acid analysis.

EXAMPLE 4

Elicitation of Breast Antigen-Specific CTL Responses in Human Blood

This Example illustrates the ability of the breast-specific antigen B726P to elicit a cytotoxic T lymphocyte (CTL) response in peripheral blood lymphocytes from normal humans.

Autologous dendritic cells (DC) were differentiated from monocyte cultures derived from PBMC of a normal donor by growth for five days in RPMI medium containing 10% human serum, 30 ng/ml GM-CSF and 30 ng/ml IL-4. Following five days of culture, DC were infected overnight with adenovirus expressing recombinant B726P (downstream ORF; SEQ ID NO:176) at an M.O.I. of 2.5 and matured for 8 hours by the addition of 2 micrograms/ml CD40 ligand. CD8 positive cells were enriched for by the depletion of CD4 and CD14-positive cells. Priming cultures were initiated in individual wells of several 96-well plates with the cytokines IL-6 and IL-12. These cultures were restimulated in the presence of IL-2 using autologous fibroblasts treated with IFN-gamma and transduced with B726P and CD80. Following three stimulation cycles, the presence of B726P-specific CTL activity was assessed in IFN-gamma Elispot assays (Lalvani et al., *J. Exp. Med.* 186:859-865, 1997) using IFN-gamma treated autologous fibroblasts transduced to express either B726P or an irrelevant, control, antigen as antigen presenting cells (APC). Of approximately 96 lines, one line (referred to as 6-2B) was identified that appeared to specifically recognize B726P-transduced APC but not control antigen-transduced APC. This microculture was cloned using standard protocols. B726P-specific CTL were identified by Elispot analysis and expanded for further analysis. These CTL clones were demonstrated to recognize B726P-expressing fibroblasts, but not the control antigen MART-1, using chromium-51 release assays. Furthermore, using a panel of allogeneic fibroblasts transduced with B726P in antibody blocking assays, the HLA restriction element for these B726P-specific CTL was identified as HLA-B* 1501.

In order to define more accurately the location of the epitope recognized by the B726P-specific CTL clones, a deletion construct comprising only the N-terminal half (a.a. 1-129) of B726P (referred to as B726Pdelta3') was constructed in the pBIB retroviral expression plasmid. This plasmid, as well as other plasmids containing B726P, were transfected into COS-7 cells either alone or in combination with a plasmid expressing HLA-B*1501. Aproximately 48 hours after transfection, a B726P-specific CTL clone (1-9B) was added at approximately $10^4$ cells per well. The cells were harvested the next day and the amount of IFN-gamma released was measured by ELISA. The CTL responded above background (EGFP) to COS-7 cells that had been transfected with both B726P and HLA-B*1501. There was no response above background to COS-7 cells that had been transfected with either B726P or HLA-B*1501 alone. Importantly, a higher response was seen with COS-7 cells that had been transfected with both HLA-B* 1501 and B726Pdelta3'. This result indicated that the epitope was likely to be located in the N-terminal region (a.a. 1-129) of B726P. This region was examined and amino acid sequences that corresponded to the HLA-B* 1501 peptide binding motif (*J. Immunol.*1999,162: 7277-84) were identified and synthesized. These peptides were pulsed at 10 ug/ml onto autologous B-LCL overnight. The next day, the cells were washed and the ability of the cells to stimulate the B726P-specific CTL clone 1-9B was assayed in a IFN-gamma ELISPOT assay. Of the eleven peptides tested, only one peptide, having the amino acid sequence SLTKRASQY (a.a. 76-84 of B726P; SEQ ID NO:488) was recognized by the CTL clone. This result identifies this peptide as being a naturally-processed epitope recognized by this B726P-specific CTL clone.

Figure 2:
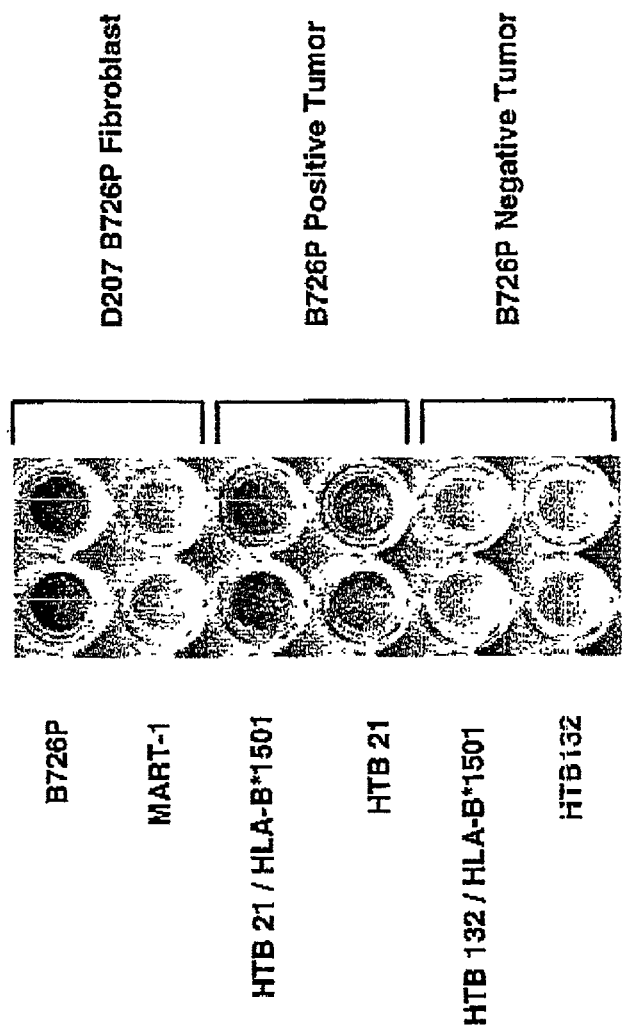
FIG. 2 shows the results of an IFN-gamma ELISPOT assay demonstrating that the B726P-specific CTL clone recognizes and lyses breast tumor cell lines expressing B726P.

In further studies, a panel of breast tumor cell lines obtained from the American Type Culture Collection (Manassas, Va.), was analyzed using real time PCR to determine their B726P message level. The cell line that expressed the highest level of B726P (referred to as HTB21) and a line that expressed no B726P (referred to as HTB132) were transduced with HLA-B*1501. These cell lines were grown up and analyzed using FACS to determine their B1501 expression. The line HTB 21 was found to endogenously express B1501. To determine if clone 1-9A would recognize the tumor cell line HTB21, an IFN-gamma ELISPOT assay was performed using 20,000 T cells, low dose IL-2 (5 ug/ml), and 20,000 of the following targets: autologous B726P or Mart-1 fibroblasts, untransduced or B1501-transduced HTB21; or untransduced or B1501-transduced HTB132. These were incubated overnight and the assay was developed the next day. The results of this assay are shown in FIG. 2. These studies demonstrate that B726P-specific CTL can recognize and lyse breast tumor cells expressing B726P.

EXAMPLE 5

Identification of Immunogenic CD4 T Cell Epitopes in Breast Antigens

Immunogenic CD4 T cell epitopes derived from the breast antigen B726P were identified as follows.

A total of thirty-five 20-mer peptides overlapping by 12 amino acids and derived from the downstream ORF of B726P (corresponding to amino acids 1-317 of SEQ ID NO:176) were generated by standard procedure. Dendritic cells (DC) were derived from PBMC of a normal male donor using GMCSF and IL-4 by standard protocol. Purified CD4 T cells were generated from the same donor as the DC using MACS beads and negative selection of PBMCs. DC were pulsed overnight with pools of the 20-mer peptides, with each peptide at an individual concentration of 0.5 micrograms/mL. Pulsed DC were washed and plated at 10,000 cells/well of 96-well U bottom plates, and purified CD4 T cells were added at 100,000 cells/well. Cultures were supplemented with 10 ng/mL IL-6 and 5 ng/mL IL-12 and incubated at 37° C. Cultures were restimulated as above on a weekly basis using DC made and pulsed as above as the antigen presenting cell, supplemented with 10 u/mL IL-2 and 5 ng/mL IL-7. Following three in vitro stimulation cycles (the initial priming+two restimulations), cell lines (each corresponding to one well) were tested for specific proliferation and cytokine production in response to the stimulating pool versus an irrelevant pool of peptides derived from unrelated antigens. A number of individual CD4 T cell lines (36/672 by IFN-gamma and 64/672 by proliferation) demonstrated significant cytokine release (IFN-gamma) and proliferation in response to the B726P peptide pools but not to the control peptide pool. Twenty-five of these T cell lines were restimulated on the appropriate pool of B726P peptides and reassayed on autologous DC pulsed with either the individual peptides or recombinant B726P protein made in *E. coli*. Approximately 14 immunogenic peptides were recognized by the T cells from the entire set of peptide antigens tested. The amino acid sequences of these 14 peptides are provided in SEQ ID NO:534-547, with the corresponding DNA sequences being provided in SEQ ID NO:520-533, respectively. In some cases the peptide reactivity of the T cell line could be mapped to a single peptide but some could be mapped to more than one peptide in each pool. Thirteen of the fifteen T cell lines recognized the recombinant B726P protein. These results demonstrate that 13 of the 14 peptide sequences (SEQ ID NO:534-542 and 544-547) may be naturally processed CD4 epitopes of the B726P protein.

EXAMPLE 6

Preparation and Characterization of Antibodies Against Breast Tumor Antigen B726P Polyclonal antibodies against both the downstream (SEQ ID NO:176) and upstream (SEQ ID NO:469) ORF of the breast tumor antigen B726P were prepared as follows.

The downstream or upstream ORF of B726P expressed in an *E. coli* recombinant expression system was grown overnight in LB broth with the appropriate antibiotics at 37° C. in a shaking incubator. The next morning, 10 ml of the overnight culture was added to 500 ml to 2×YT plus appropriate antibiotics in a 2L-baffled Erlenmeyer flask. When the Optical Density (at 560 nm) of the culture reached 0.4-0.6, the cells were induced with IPTG (1 mM). Four hours after induction with IPTG, the cells were harvested by centrifugation. The cells were then washed with phosphate buffered saline and centrifuged again. The supernatant was discarded and the cells were either frozen for future use or immediately processed. Twenty ml of lysis buffer was added to the cell pellets and vortexed. To break open the *E. coli* cells, this mixture was then run through the French Press at a pressure of 16,000 psi. The cells were then centrifuged again and the supernatant and pellet were checked by SDS-PAGE for the partitioning of the recombinant protein. For proteins that localized to the cell pellet, the pellet was resuspended in 10 mM Tris pH 8.0, 1% CHAPS and the inclusion body pellet was washed and centrifuged again. This procedure was repeated twice more. The washed inclusion body pellet was solubilized with either 8 M urea or 6 M guanidine HCl containing 10 mM Tris pH 8.0 plus 10 mM imidazole. The solubilized protein was added to 5 ml of nickel-chelate resin (Qiagen) and incubated for 45 min to 1 hour at room temperature with continuous agitation. After incubation, the resin and protein mixture were poured through a disposable column and the flow through was collected. The column was then washed with 10-20 column volumes of the solubilization buffer. The antigen was then eluted from the column using 8M urea, 10 mM Tris pH 8.0 and 300 mM imidazole and collected in 3 ml fractions. A SDS-PAGE gel was run to determine which fractions to pool for further purification.

As a final purification step, a strong anion exchange resin, such as HiPrepQ (Biorad), was equilibrated with the appropriate buffer and the pooled fractions from above were loaded onto the column. Antigen was eluted off the column with a increasing salt gradient. Fractions were collected as the column was run and another SDS-PAGE gel was run to determine which fractions from the column to pool. The pooled fractions were dialyzed against 10 mM Tris pH 8.0. The protein was then vialed after filtration through a 0.22 micron filter and the antigens were frozen until needed for immunization.

Four hundred micrograms of the B726P antigen was combined with 100 micrograms of muramyldipeptide (MDP). Every four weeks rabbits were boosted with 100 micrograms mixed with an equal volume of Incomplete Freund's Adjuvant (IFA). Seven days following each boost, the animal was bled. Sera was generated by incubating the blood at 4° C. for 12-24 hours followed by centrifugation.

Ninety-six well plates were coated with B726P antigen by incubating with 50 microliters (typically 1 microgram) of recombinant protein at 4° C. for 20 hours. 250 Microliters of BSA blocking buffer was added to the wells and incubated at room temperature for 2 hours. Plates were washed 6 times with PBS/0.01% Tween. Rabbit sera was diluted in PBS. Fifty microliters of diluted sera was added to each well and incubated at room temperature for 30 min. Plates were washed as described above before 50 microliters of goat anti-rabbit horse radish peroxidase (HRP) at a 1:10000 dilution was added and incubated at room temperature for 30 min. Plates were again washed as described above and 100 microliters of TMB microwell peroxidase substrate was added to each well. Following a 15 min incubation in the dark at room temperature, the calorimetric reaction was stopped with 100 microliters of IN $H_2SO_4$ and read immediately at 450 nm. All the polyclonal antibodies showed inmmunoreactivity to the appropriate B726P antigen.

B) Preparation of Polyclonal Antibodies Against B709P and B720P

The breast antigens B709P (SEQ ID NO:62) and B720P (SEQ ID NO:485) expressed in an *E. coli* recombinant expression system were grown overnight in LB Broth with the appropriate antibiotics at 37° C. in a shaking incubator. Ten ml of the overnight culture was added to 500 ml of 2×YT plus appropriate antibiotics in a 2L-baffied Erlenmeyer flask. When the optical density (at 560 nanometers) of the culture reached 0.4-0.6, the cells were induced with IPTG (1 mM). Four hours after induction with IPTG, the cells were harvested by centrifugation. The cells were washed with phosphate buffered saline and centrifuged again. The supernatant was discarded and the cells were either frozen for future use or immediately processed. Twenty milliliters of lysis buffer was added to the cell pellets and vortexed. To break open the *E. coli* cells, the mixture was run through a French Press at a pressure of 16,000 psi. The cells were centrifuged again and the supernatant and pellet were checked by SDS-PAGE for the partitioning of the recombinant protein. For proteins that localized to the cell pellet, the pellet was resuspended in 10 mM Tris pH 8.0, 1% CHAPS and the inclusion body pellet was washed and centrifuged again. This procedure was repeated twice more. The washed inclusion body pellet was solubilized with either 8 M urea or 6 M guanidine HCl containing 10 mM Tris pH 8.0 plus 10 mM imidazole. The solubilized protein was added to 5 ml of nickel-chelate resin (Qiagen) and incubated for 45 min to 1 hour at room temperature (RT) with continuous agitation. After incubation, the resin and protein mixture were poured through a disposable column and the flow through was collected. The column was then washed with 10-20 column volumes of the solubilization buffer. The antigen was then eluted from the column using 8M urea, 10 mM Tris pH 8.0 and 300 mM imidazole and collected in 3 ml fractions. A SDS-PAGE gel was run to determine which fractions to pool for further purification. As a final purification step, a strong anion exchange resin such as Hi-Prep Q (Biorad) was equilibrated with the appropriate buffer and the pooled fractions from above were loaded onto the column. Each antigen was eluted off of the column with an increasing salt gradient. Fractions were collected as the column was run and another SDS-PAGE gel was run to determine which fractions from the column to pool. The pooled fractions were dialyzed against 10 mM Tris pH 8.0. The proteins were then vialed after filtration through a 0.22-micron filter and frozen until needed for immunization.

Four hundred micrograms of antigen was combined with 100 micrograms of muramyldipeptide (MDP). An equal volume of Incomplete Freund's Adjuvant (IFA) was added and mixed, and the mixture was injected into a rabbit. The rabbit was boosted with 100 micrograms of antigen mixed with an equal volume of IFA every four weeks. The animal was bled seven days following each boost. Sera was generated by incubating the blood at 4° C. for 12-24 hours followed by centrifugation.

The reactivity of the polyclonal antibodies to recombinant antigen (B709P or B720P) was determined by ELISA as follows. Ninety-six well plates were coated with antigen by incubating with 50 microliters (typically 1 microgram) at 4° C. for 20 hrs. 250 microliters of BSA blocking buffer was added to the wells and incubated at RT for 2 hrs. Plates were washed 6 times with PBS/0.01% Tween. Rabbit sera were diluted in PBS. Fifty microliters of diluted sera was added to each well and incubated at RT for 30 min. Plates were washed as described above before 50 microliters of goat anti-rabbit horse radish peroxidase (HRP) at a 1:10000 dilution was added and incubated at RT for 30 min. Plates were washed as described above and 100 microliters of TMB Microwell Peroxidase Substrate was added to each well. Following a 15-minute incubation in the dark at RT, the calorimetric reaction was stopped with 100 microliters of IN $H_2SO_4$ and read immediately at 450 nm. The polyclonal antibodies showed immunoreactivity to the appropriate antigen.

EXAMPLE 7

Protein Expression of Breast Tumor Antigens

The downstream ORF of B726P (SEQ ID NO:176), together with a C-terminal 6× His Tag, was expressed in insect cells using the baculovirus expression system as follows.

The cDNA for the full-length downstream ORF of B726P was PCR amplified using the primers of SEQ ID NO:480 and 481. The PCR product with the expected size was recovered from agarose gel, restriction digested with EcoRI and Hind II, and ligated into the transfer plasmid pFastBacI, which was digested with the same restriction enzymes. The sequence of the insert was confirmed by DNA sequencing. The recombinant transfer plasmid pFBB726P was used to make recombinant bacmid DNA and virus using the Bac-To-Bac Baculovirus expression system (BRL Life Technologies, Gaithersburg, Md.). High Five cells were infected with the recombinant virus BVB726P to produce protein. The cDNA and amino acid sequences of the expressed B726P recombinant protein are provided in SEQ ID NO:482 and 483, respectively.

EXAMPLE 8

Generation of Constructs for Protein Expression of B726P in E. coli

Three different open reading frames (ORFs) of B726P were subcloned into pPDM, a modified pET28 vector for exression in E. coli.

Construct for the expression of B726P Upstream ORF in E. coli (cDNA: SEQ ID NO:549; amino acid: SEQ ID NO:552):

The partial B726P upstream ORF (A) from clone 23113 was PCR amplified with the following primers:

PDM-416 (SEQ ID NO:554) 5' gtcggctccatgagtcccg-caaaag 3' Tm 63° C.

PDM-431 (SEQ ID NO:555) 5' cgagaattcaatacttaagaagac-catctttaccag 3' Tm 61° C.

The amplification conditions were as follows 10 µl 10× Pfu buffer, 1 µl 10 µM dNTPs, 2 µl 10 µM each oligo, 83 µl sterile water, 1.5 µl Pfu DNA polymerase (Stratagene, La Jolla, Calif.), 1 µl PCR 23113. The reaction was first denatured for 2 minutes at 96° C., followed by 40 cylces of 96° C. for 20 seconds, 62° C. for 15 seconds, and extension at 72° C. for 2 minutes. This was followed by a final extension of 72° C. for 4 minutes.

The second partial B726P upstream ORF (B) from clone 19310 was PCR amplified with the following primers:

PDM-432 (SEQ ID NO:556) 5' cataagcttaaggctaactgcg-gaatgaaag 3' Tm 63° C.

PDM-427 (SEQ ID NO:557) 5' cccgcagaattcaacatg-caattttcatgtaagag 3' Tm 62° C.

The amplification and cycling conditions were as described above. The first PCR product was digested with EcoRI and cloned into pPDM His (a modified pET28 vector) that had been digested with EcoRI and Eco72I. The second PCR product was digested with BfrI and EcoRI and cloned into the resulting construct: pPDM B726P UP-A-5 at the EcoRI and BfrI sites. The construct (pPDM B726P Up-4) was confirmed to be correct through sequence analysis and transformed into BL21 (DE3) pLys S and BL21 CodonPlus RIL (DE3) cells. Protein expression was confirmed by Coomassie stained SDS-PAGE and N-terminal protein sequence analysis.

Construct for B726P D-ORF expression in E. coli (cDNA: SEQ ID NO:550; amino acid: SEQ ID NO:551):

The B726P D-ORF was PCR amplified with the following primers:

PDM-290 (SEQ ID NO:558) 5' ctaaatgccggcacaa-gagctctgc 3' Tm 61° C.

PDM-291 (SEQ ID NO:559) 5' cgcgcagaattctattatataact-tctgtttctgc 3' Tm61° C.

The reaction conditions were as described. The cycling conditions were altered slightly in that the annealing temperature was lowered to 61° C. from 62° C. and was held for 15 seconds. The extension time was also increased to 2 minutes and 15 seconds. The PCR product was digested with NaeI and EcoRI and cloned into pPDM His which has been digested with Eco72I and EcoRI. Construct was confirmed by sequencing and then transformed into BL21 (DE3) pLys S cells (Novagen, Madison, Wis.). Protein expression was confirmed by Coomassie stained SDS-PAGE and N-terminal protein sequence analysis.

Construct for B726P Combined ORF expression in E. coli (cDNA: SEQ ID NO:548; amino acid: SEQ ID NO:553):

The B726P C-1 coding region was PCR amplified including the 183bp insert, with the following primers:

PDM-750 (SEQ ID NO:560) 5' ggggaattgtgagcggataa-caattc 3' Tm 58° C.

PDM-752 (SEQ ID NO:561) 5' cgtagaattcaacctgatttaaat-tactttctacac 3' Tm 59° C.

The B726P Downstream ORF was PCR amplified with the following primers:

PDM-753 (SEQ ID NO:562) 5' gaaagtaatttaaatcaggtttctca-cactc 3' Tm 59° C.

PDM-751 (SEQ ID NO:563) 5' gaggccccaaggggttatgctag 3' Tm 61° C. The reaction conditions for these PCR reactions were the same as described above. The cycling conditions were as follows: $1^{st}$ PCR: The reaction was first denatured for 2 minutes at 96° C., followed by 40 cylces of 96° C. for 20 seconds, 58° C. for 15 seconds and extension at 72° C. for 4 minutes. This was followed by a final extension of 72° C. for 4 minutes; $2^{nd}$ PCR: . The reaction was first denatured for 2 minutes at 96° C., followed by 40 cylces of 96° C. for 20 seconds, 59° C. for 15 seconds, and extension at 72° C. for 2 minutes. This was followed by a final extension of 72° C. for 4 minutes. The first PCR product was digested with EcoRI and cloned into pPDM His (a modified pET28 vector) at the Eco 72I and EcoRI sites. The construct was confirmed to be correct through sequence analysis. The second PCR product was digested with EcoRI and cloned into pPDM His at the same sites. The resulting constructs pPDM B726P UA-8 and pPDM B726P DA-7 respectively were digested with SwaI and EcoRI. The pPDM B726P UA-8 construct was used as vector and the insert from the pPDM B726P DA-7 was cloned into this construct successfully. The construct was confirmed to be correct through sequence analysis and then transformed into BLR (DE3) pLys S and HMS 174 (DE3) pLys S cells (Novagen, Madison, Wis.). Protein expression was confirmed by Coomassie stained SDS-PAGE and N-terminal protein sequence analysis.

EXAMPLE 9

Additional Sequence Identified for Breast Tumor Antigen B726P by Bioinformatic Analysis The combined ORF of the breast tumor antigen, B726P (amino acid sequence set forth in SEQ ID NO:475), was used to search public databases. A sequence essentially identical to the combined ORF with additional N-terminal sequence was identified in the GenBank nonredundant protein database and the cDNA and predicted amino acid sequences are set forth in SEQ ID NOs:564 and 565, respectively. The gene is also referred to as NY-BR-1 and was described in described in Cancer Research 61(5):2055-2061, Mar. 1, 2001.

EXAMPLE 10

Analysis of B726P Expression Using Immunohistochemistry

Affinity purified polyclonal antibodies anti-B726Pup (generated against the B726P upstream ORF protein) and anti-B726Pdown (generated against the B726P downstream ORF) were used to assess B726P protein expression in breast cancer and in a variety of normal tissue sections.

In order to determine which tissues express the breast cancer antigen protein B726P immunohistochemistry (IHC) analysis was performed on a diverse range of tissue sections. Tissue samples were fixed in formalin solution for 12-24 hrs and embedded in paraffin before being sliced into 8 micron sections. Steam heat induced epitope retrieval (SHIER) in 0.1 M sodium citrate buffer (pH 6.0) was used for optimal staining conditions. Sections were incubated with 10% serum/PBS for 5 minutes. Primary antibody (either rabbit affinity purified anti-B726Pdown or anti-B726Pup) was added to each section for 25 minutes followed by 25 minute incubation with anti-rabbit biotinylated antibody. Endogenous peroxidase activity was blocked by three 1.5 minute incubations with hydrogen peroxidase. The avidin biotin complex/horse radish peroxidase (ABC/HRP) system was used along with DAB chromogen to visualize antigen expression. Slides were counterstainied with hematoxylin to visualize cell nuclei. Anti-B726Pup and anti-B726Pdown immunoreactivity was observed in about 30-40% of breast cancer samples analyzed but not observed in a majority of various normal tissues. Anti-B726Pdown and anti-b726Pup also stained roughly the same breast cancer samples. Thus, these data confirm earlier microarray analysis (see Example 1) showing that B726P is overexpressed in breast tumor tissue as compared to normal tissue. Therefore, this antigen may be used in diagnostic and immunotherapeutic applications for breast cancer.

EXAMPLE 11

Generation of Monoclonal Antibodies to B726P Downstream and Upstream ORFs

Production and purification of protein used for antibody generation. B726 upstream ORF and B726 downstream ORF proteins were expressed in an *E. coli* recombinant expression system (see Example 8). Cells were grown overnight in LB Broth with the appropriate antibiotics at 37° C. in a shaking incubator. The next morning, 10 ml of the overnight culture was added to 500 ml of 2×YT plus appropriate antibiotics in a 2L-baffled Erlenmeyer flask. When the optical density (at 560 nanometers) of the culture reached 0.4-0.6 the cells were induced with IPTG (1 mM). Four hours after induction with IPTG the cells were harvested by centrifugation. The cells were then washed with phosphate buffered saline and centrifuged again. The supernatant was discarded and the cells were either frozen for future use or immediately processed. Twenty milliliters of lysis buffer was added to the cell pellets and vortexed. To break open the *E. coli* cells, this mixture was then run through the French Press at a pressure of 16,000 psi. The cells were then centrifuged again and the supernatant and pellet were checked by SDS-PAGE for the partitioning of the recombinant protein. For proteins that localized to the cell pellet, the pellet was resuspended in 10 mM Tris pH 8.0, 1% CHAPS and the inclusion body pellet was washed and centrifuged again. This procedure was repeated twice more. The washed inclusion body pellet was solubilized with either 8 M urea or 6 M guanidine HCl containing 10 mM Tris pH 8.0 plus 10 mM imidazole.

The solubilized protein was added to 5 ml of nickel-chelate resin (Qiagen, Valencia, Calif.) and incubated for 45 min to 1 hour at room temperature with continuous agitation. After incubation, the resin and protein mixture were poured through a disposable column and the flow through was collected. The column was then washed with 10-20 column volumes of the solubilization buffer. The antigen was then eluted from the column using 8M urea, 10 mM Tris pH 8.0 and 300 mM imidazole and collected in 3 ml fractions. A SDS-PAGE gel was run to determine which fractions to pool for further purification. As a final purification step, a strong anion exchange resin such as Hi-Prep Q (Biorad) was equilibrated with the appropriate buffer and the pooled fractions from above were loaded onto the column. Each antigen was eluted off of the column with an increasing salt gradient. Fractions were collected as the column was run and another SDS-PAGE gel was run to determine which fractions from the column to pool. The pooled fractions were dialyzed against 10 mM Tris pH 8.0. This material was then submitted to Quality Control for final release. The release criteria were purity as determined by SDS-PAGE or HPLC, concentration as determined by Lowry assay or Amino Acid Analysis, identity as determined by amino terminal protein sequence, and endotoxin level as determined by the Limulus (LAL) assay. The proteins were then vialed after filtration through a 0.22-micron filter and the antigens were frozen until needed for immunization.

To generate anti-B726P mouse monoclonal antibodies, mice were immunized IP with 50 micrograms of recombinant B726P upstream ORF and B726P downstream ORF proteins that had been mixed to form an emulsion with an equal volume of Complete Freund's Adjuvant (CFA). Every three weeks animals were injected IP with 50 micrograms of recombinant B726P upstream ORF and B726P downstream ORF that had been mixed with an equal volume of IFA to form an emulsion. After the fourth injection, spleens were isolated and standard hybridoma fusion procedures were used to generate anti-B726P mouse monoclonal antibody hybridomas. Anti-B726P monoclonal antibodies were screened using the ELISA analysis using the bacterially expressed recombinant B726P upstream ORF and B726P downstream ORF proteins.

A list of the mouse anti-B726P monoclonal antibodies that were generated, as well as their anti-B726P reactivity in an ELISA assay and Western blot are shown in Table 2. The hybridomas were then subcloned and the subclones further tested for reactivity with B726P upstream ORF and B726P downstream ORF proteins. Several monoclonal antibodies showed particularly favorable reactivity: 220A2-21, 220A19-25, 220A94-29, 220A151-33.

For Western blot analysis, recombinant B726P upstream ORF and B726P downstream ORF protein was diluted with SDS-PAGE loading buffer containing beta-mercaptoethanol, then boiled for 10 minutes prior to loading the SDS-PAGE gel. Protein was transferred to nitrocellulose and probed with each of the anti-B726P hybridoma supernatants. Protein A-HRP was used to visualize the anti-B726P reactive bands by incubation in ECL substrate.

TABLE 2

B726PUP AND B726PDOWN MONOCLONAL ANTIBODY REACTIVITY

| Anti-B726P mAbs | ELISA | | | Western Blots | |
|---|---|---|---|---|---|
| | B726PDown | B726PUp | L523S | B726Pdown | B726Pup |
| 220A2   | +++ | +   | −   | +++ | ++  |
| 220A10  | −   | −   | −   | N/A | N/A |
| 220A14  | +++ | +++ | +++ | +++ | ++  |
| 220A19  | ++  | −   | −   | ++  | +   |
| 220A43  | +++ | +   | −   | +++ | ++  |
| 220A86  | +++ | +   | −   | +++ | ++  |
| 220A94  | +++ | −   | −   | ++  | +/− |
| 220A123 | ++  | −   | −   | +   | −   |
| 220A139 | +/− | −   | −   | +   | −   |
| 220A140 | −   | −   | −   | N/A | N/A |
| 220A141 | −   | −   | −   | N/A | N/A |
| 220A143 | −   | −   | −   | N/A | N/A |
| 220A151 | ++  | −   | −   | ++  | −   |
| 220A176 | +/− | −   | −   | +   | −   |

EXAMPLE 12

Identification of Additional Sequences for B726P

Additional 5' sequence was obtained for B726P—this sequence was obtained by PCR from 1st strand cDNA prepared from three separate mRNA sources (metastatic breast tumor, breast tumor, normal testis). Disclosed herein are clones that were isolated, each with differences from the expected published sequence of NY-BR-1.

A 1300 bp fragment of B726P otherwise known as NY-BR-1 was PCR amplified from 1st strand cDNA and cloned into pPDM, a modified pET28 vector as follows:

The B726P XB coding region (NY-BR-1) was PCR amplified with the following primers PDM-784 5' (SEQ ID NO: 574) cacacaaagaggaagaagac-catc 3' Tm56° C.

PDM-814 5' (SEQ ID NO: 575) gattcttttgtaggacatgcaat-catc 3' Tm55° C.

The following PCR conditions were used: 10 µl 10 × Herculase buffer, 1 µl 10 mM dNTPs, 2 µl 10 µM each oligo, 83 µl sterile water, 1.5 µl Herculase DNA polymerase (Stratagene, La Jolla, Calif.), 50 ng DNA. The thermalcycling conditions were as follows:

98° C. 3 minutes
98° C. 40 seconds, 51° C. 15 seconds, 72° C. 4 minutes, X 10 cycles
98° C. 40 seconds, 51° C. 15 seconds, 72° C. 5 minutes, X 10 cycles
98° C. 40 seconds, 51° C. 15 seconds, 72° C. 6 minutes, X 10 cycles
98° C. 40 seconds, 51° C. 15 seconds, 72° C. 7 minutes, X 10 cycles
72° C. 10 minutes The PCR product was ligated into the pPDM vector (a modified pET28) that had been digested with Eco72I and de-phosphorylated. PCR amplification of this gene proved very difficult and required the use of a polymerase lacking proofreading capabilities. However, use of such an enzyme, in this case, Herculase from Stratagene (La Jolla, Calif.), led to what is likely PCR errors in the resulting clones. The cDNA sequence of three of the isolated clones containing mutations are disclosed in SEQ ID NOs:567-569 with the corresponding amino acid sequences disclosed in SEQ ID NOs:572, 571, and 570, respectively.

The resulting construct, pPDM B726P XB (clone 83686), was then digested with BglII and the insert which dropped out from the 5' vector BglII site and the internal BglII site at amino acids 390-391 was cloned into the pPDM B726P C-ORF (SEQ ID NO:548) that had been digested with BglII and was de-phosphorylated. This construct, pPDM B726P XC, was then DNA sequenced and showed two nucleotide changes, which result in two amino acid changes. The cDNA of the full-length clone containing these 2 mutations is disclosed in SEQ ID NO:566 with the corresponding amino acid sequence in SEQ ID NO:573. The full-length expected, published NY-BR-1 is disclosed in SEQ ID NO:564 (cDNA); amino acid SEQ ID NO:565.

EXAMPLE 13

Isolation of Additional 3' Sequence and Real-Time PCR Analysis of B726P Homolog NY-BR1.1

A sequence homolog to the breast candidate B726P, called NY-BR-1.1, was identified and published in Cancer Research 61(5):2055-2061; Mar. 1, 2001. The NY-BR-1.1 gene, thought to be located on chromosome 9 based on 100% sequence identity to genomic sequence from chromosome 9, was shown to be expressed as mRNA in breast tumors as well as in normal brain. However, the published sequence was lacking 3' sequence. Published incomplete sequence for NY-BR-1.1, is represented by GenBank accession number AF269088. A recent BlastN search of the GenBank High Throughput Genomic Sequence database using Ny-Br-1.1 as a query sequence showed a 100% match to the working draft sequence of chromosome 9 (GenBank accession number AL359312), yielding further 3' DNA sequence for Ny-Br-1.1. The compilation of the Ny-Br-1.1 sequence with the additional 3' sequence from chromosome 9 yielded a 3720 bp ORF sequence (SEQ ID NO:576) which encodes a 1240 amino acid protein sequence (SEQ ID NO:577).

Real time PCR primers were designed to a unique region of NY-BR-1.1 to distinguish its mRNA expression profile from B726P. This experiment represents relative values, as it was done without template. The first-strand cDNA used in the quantitative real-time PCR was synthesized from 20 µg of total RNA that was treated with DNase I (Amplification Grade, Gibco BRL Life Technology, Gaithersburg, Md.), using Superscript Reverse Transcriptase (RT) (Gibco BRL Life Technology, Gaithersburg, Md.). Real-time PCR was performed with a GeneAmp™ 5700 sequence detection system (PE Biosystems, Foster City, Calif.). The 5700 system uses SYBR™ green, a fluorescent dye that only intercalates into double stranded DNA, and a set of gene-specific forward and reverse primers. The increase in fluorescence was monitored during the whole amplification process. The optimal concentration of primers was determined using a checkerboard approach and a pool of cDNAs from tumors was used in this process. The PCR reaction was performed in 25 µl volumes that included 2.5 µl of SYBR green buffer, 2 µl of cDNA template and 2.5 µl each of the forward and reverse primers for the gene of interest. The cDNAs used for quantitative real time PCR reactions were diluted 1:10 for each gene of interest and 1:100 for the β-actin control. Levels of mRNA were expressed relative to ureter where NY-BR-1.1 expression was not observed when compared to the β-actin control.

The real time PCR results show that mRNA expression for NY-BR-1.1 is present in breast tumors as well as in normal adrenal gland, brain, retina and testis.

EXAMPLE 14

Characterization of B726P Monoclonal and Purified Polyclonal Antibody Epitopes Mouse monoclonal antibodies and rabbit polyclonal sera were raised against *E. coli* derived B726P recombinant protein and tested by ELISA as described in further detail below, for antibody epitope recognition against overlapping 20 mer peptides that correspond to the amino acid sequence of the downstream ORF of B726P (B726P dORF, set forth in SEQ ID NO:176, encoded by SEQ ID NO:175). Numerous peptides were recognized by the monoclonal and polyclonal antibodies. The corresponding amino acid sequences of these peptide antibody epitopes are summarized in Table 3 and are set forth in SEQ ID NOs: 578-593.

Elisa Analysis:

B726P recombinant protein and peptides were coated onto 96 well ELISA plate: 50 ul/well at 2 ug/ml for 20 hrs at 4° C. Plates were then washed 5 times with PBS+0.1% Tween 20 and blocked with PBS+1% BSA for 2 hr. Affinity purified B726P polyclonal antibodies were then added to the wells at 1ug/ml and B726P monoclonal supernatants were added neat (220A43 and 220A86 were diluted 1/60 and 1/20 respectively). Plates were incubated at room temperature for 30 minutes and then washed again as above, followed by the addition of 50 ul/well donkey anti-mouse-Ig-HRP antibody for 30 minutes at room temperature. Plates were washed, then developed by the addition of 100 ul/well of TMB substrate. The reaction was incubated 15 minutes in the dark at room temperature and then stopped by the addition of 100 ul/well of 1N H2SO4. Plates were read at OD450 in an automated plate reader. Peptides with OD450 readings three times background or above were considered to be positively recognized by the corresponding antibody.

TABLE 3

| | Peptides recognized by B726P Antibodies | | | | | | |
|---|---|---|---|---|---|---|---|
| | B726P Monoclonal Supernatant | | | | | | B726P Purified Polyclonal |
| | 220A2.1 | 220A19.1 | 220A94.1 | 220A151.1 | 220A43 | 220A86 | (1 ug/ml) |
| B726P peptides (amino acids) | 289-308 | 225-244, 232-252 | 73-252 | 145-164, 153-172 | 232-252 | 145-164, 153-172 | 1-20, 9-28, 17-36, 24-44, 97-116, 105-124, 113-132, 121-140, 129-148, 137-156 |

From the foregoing it will be appreciated that, although specific embodiments of the invention have been described herein for purposes of illustration, various modifications may be made without deviating from the spirit and scope of the invention. Accordingly, the invention is not limited except as by the appended claims.

What is claimed:

1. An isolated polynucleotide comprising a sequence selected from the group consisting of:

(a) the sequence provided in SEQ ID NO:467;

(b) the complement of the full-length sequence provided in SEQ ID NO:467;

(c) a variant of the sequence provided in SEQ ID NO: 467, wherein said variant is a degenerate variant of SEQ ID NO: 467 which differs from SEQ ID No: 467 only by codon usage, and which encodes the amino acid sequence set forth in SEQ ID NO: 473.

2. An expression vector comprising the isolated polynucleotide of claim 1 operably linked to an expression control sequence.

3. An isolated host cell transformed or transfected with the expression vector according to claim 2.

4. A composition comprising a physiologically acceptable carrier and the polynucleotide according to claim 1.

* * * * *

UNITED STATES PATENT AND TRADEMARK OFFICE
CERTIFICATE OF CORRECTION

PATENT NO. : 7,598,226 B2
APPLICATION NO. : 10/007805
DATED : October 6, 2009
INVENTOR(S) : Jiang et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1095 days.

Signed and Sealed this

Twenty-eighth Day of September, 2010

David J. Kappos
*Director of the United States Patent and Trademark Office*

SEQUENCE LISTING

<160> NUMBER OF SEQ ID NOS: 593

<210> SEQ ID NO 1
<211> LENGTH: 281
<212> TYPE: DNA
<213> ORGANISM: Homo sapien

<400> SEQUENCE: 1
caatgacagt caatctctat cgacagcctg cttcatattt agctattgtt cgtattgcct      60
tctgtcctag gaacagtcat atctcaagtt caaatgccac aacctgagaa gcggtgggct     120
aagataggtc ctactgcaaa ccaccctcc atatttccgt acgcaattac aattcagttt     180

```
ctgtgacatc tctttacacc actggaggaa aaatgagata ttctctgatt tattctacta    240
taacactcta catagagcta tggtgagtgc taaccacatc g                        281

<210> SEQ ID NO 2
<211> LENGTH: 300
<212> TYPE: DNA
<213> ORGANISM: Homo sapien

<400> SEQUENCE: 2
gaggtcctgg gctaacctaa tggtttatta ttggtggaga gaaagatctg gaaatacttg     60
aggttattac atactagatt agcttctaat gtgaaccatt tttcttttaa cagtgataaa    120
ttattatttc cgaagttaac tgttcccttg gtcgtgatac acactcgatt aacaaacata    180
ctgttgtatt ttttccagtt tgtttggct atgccaccac agtcatcccc agggtctata     240
catactatgt ctcaactgta ttatttgcca ttttggcat agaatgctt cgggaaggct      300

<210> SEQ ID NO 3
<211> LENGTH: 302
<212> TYPE: DNA
<213> ORGANISM: Homo sapien

<400> SEQUENCE: 3
ggccgaggta attggttaag tctaaagaga ttattattcc ttgatgtttg ctttgtattg     60
gctacaaatg tgcagaggta atacatatgt gatgtcgatg tctctgtctt tttttttgtc   120
tttaaaaaat aattggcagc aactgtattt gaataaaatg atttcttagt atgattgtac   180
agtaatgaat gaaagtggaa catgtttctt tttgaaaggg agagaattga ccatttattg   240
ttgtgatgtt taagttataa cttatcgagc acttttagta gtgataactg ttttttaaact  300 tg                                                                  302

<210> SEQ ID NO 4
<211> LENGTH: 293
<212> TYPE: DNA
<213> ORGANISM: Homo sapien

<400> SEQUENCE: 4
tgtaccaatc ctttggcaca agaatatgta agaactatag ttgtttttat tggttttgt    60 tcttgagatt gttttcattc tgttttgac tgtatctctt taggaggctg aggatggcat   120
tattgcttat gatgactgtg gggtgaaact gactattgct tttcaagcca aggatgtgga   180
aggatctact tctcctcaaa tacgagataa ggcaagataa ttctgctcat tcgagagagg   240
gttaagagtt gtcatcttaa tcataaatcc tgcaggatgg gttcttcaaa ttt          293

<210> SEQ ID NO 5
<211> LENGTH: 275
<212> TYPE: DNA
<213> ORGANISM: Homo sapien

<400> SEQUENCE: 5
cgaggtttgg aatcagactt ctgtgtccag taaaaaactc ctgcactgaa gtcattgtga     60
cttgagtagt tacagactga ttccagtgaa cttgatctaa tttcttttga tctaatgaat   120
gtgtctgctt accttgtctc cttttaattg ataagctcca agtagttgct aatttttga    180 caactttaaa tgagtttcat tcacttcttt tacttaatgt tttaagtata gtaccaataa   240
tttcattaac ctgttctcaa gtggtttagc tacca                              275
```

<210> SEQ ID NO 6
<211> LENGTH: 301
<212> TYPE: DNA
<213> ORGANISM: Homo sapien

<400> SEQUENCE: 6

```
gaggtctggt tcctgggta tgcctggact gttgcccagt gtaagatctg tgcaagccat      60
attggatgga agtttacggc caccaaaaaa gacatgtcac ctcaaaaatt ttggggctta     120
acgcgatctg ctctgttgcc cacgatccca gacactgaag atgaaataag tccagacaaa    180
gtaatacttt gcttgtaaac agatgtgata gagataaagt tatctaacaa attggttata    240
ttctaagatc tgctttggaa attattgcct ctgatacata cctaagtaaa cataacatta    300
a                                                                    301
```

<210> SEQ ID NO 7
<211> LENGTH: 301
<212> TYPE: DNA
<213> ORGANISM: Homo sapien

<400> SEQUENCE: 7

```
gtccagtttg tacacagtga ttccttatgc acgccgaaag ggtttccgta aaatgacat      60
tatatacaaa tctgtacacc catccaccag agcgattctc cagctcccag agggagttat    120
caacttaaag caggatacct gaggtttcat gtctttagtt gccttatcat aatcccaaat    180
atacatttca gggtttgttt ttgtttttaa agacactttc ctggaatatg tgcactatgg    240
ttaaaattaa aaacaaaagt aataaaataa aatgatcgct ggaaggactg acctccccac    300
c                                                                    301
```

<210> SEQ ID NO 8
<211> LENGTH: 301
<212> TYPE: DNA
<213> ORGANISM: Homo sapien

<400> SEQUENCE: 8

```
ctgtcctcat ctctgcaaag ttcagcttcc ttccccaggt ctctgtgcac tctgtcttgg      60
atgctctggg gagctcatgg gtggaggagt ctccaccaga gggaggctca ggggactggt    120
tgggccaggg atgaatattt gagggataaa aattgtgtaa gagccaaaga attggtagta    180
ggggagaac agagaggagc tgggctatgg gaaatgattt gaataatgga gctgggaata     240
tggctggata tctggtacta aaaagggtc tttaagaacc tacttcctaa tctcttcccc     300
a                                                                    301
```

<210> SEQ ID NO 9
<211> LENGTH: 301
<212> TYPE: DNA
<213> ORGANISM: Homo sapien

<400> SEQUENCE: 9

```
gaggtctgcc taagtagagg acaaagactt cctcctttca aaggagaact gagcccagga     60
ttggtaagtt taaggcactt aaccttgacc agctctgtag gtctggagca ttctggtccc    120
tggccgcttt caccaccagg cccttctcac ttatccacct cacatactgc cccagcattc    180
ctttggcatt gcgagctgtg acttgacaca ttttaatgac aagattgaag tagctacctt    240
gcaggataga ttttctgggg tataggggac aaaccaacag tgccatcagg tgtcttaaca    300
c                                                                    301
```

<210> SEQ ID NO 10
<211> LENGTH: 301
<212> TYPE: DNA
<213> ORGANISM: Homo sapien

<400> SEQUENCE: 10

```
ggcaggtcca acagttcttc cagttctggt cgagctttga atcgtccctt gaagtcttct      60
tcagtgtgct ccttcactga cagtctgact ccttcaggaa gactgctttg gattatttcc     120
aagaaaattt ctgcaaacgt agcactcaaa ccgctgatct gaaccactcg ctcatgggtg     180
gtaagcactg agtccaggag cattttgctg ccttggtcct gcaactgcaa cacttctatg     240
gttttggttg gcattgcata actttcctcg actttaatgg agagagattg cagaggttgt     300
g                                                                    301
```

<210> SEQ ID NO 11
<211> LENGTH: 301
<212> TYPE: DNA
<213> ORGANISM: Homo sapien

<400> SEQUENCE: 11

```
aggtctgtga ctttcaccca ggacccagga cgcagccctc cgtgggcact gccggcgcct      60
tgtctgcaca ctggaggtcc tccattacag aggcccagcg cacatcgctg ccccacaaa     120
cgttcagggg tacagccatg gcagctcctt cctctgccgt gagaaaagtg cttggagtac     180
ggtttgccac acacgtgact ggacagtgtc caattcaaat ctttcagggc agagtccgag     240
cagcgcttgg tgacagcctg tcctctcctg ctctccaaag gccctgctcc ctgtcctctc     300
t                                                                    301
```

<210> SEQ ID NO 12
<211> LENGTH: 301
<212> TYPE: DNA
<213> ORGANISM: Homo sapien

<400> SEQUENCE: 12

```
gaggtctggg attacaggca cgtgccacca cacctagcta attttttgagc atggggctca     60
aaggaactgc tctctggggc atgtcagatt tcggatttgg ggctgcacac tgatactctc     120
taagtggtgg aggaacttca tcccactgaa attcctttgg catttggggt tttgttttc      180
ttttttcct tcttcatcct cctccttttt taaaagtcaa cgagagcctt cgctgactcc     240
accgaagaag tgcaccactg ggagccaccc cagtgccagg cgcccgtcca gggacacaca     300
c                                                                    301
```

<210> SEQ ID NO 13
<211> LENGTH: 256
<212> TYPE: DNA
<213> ORGANISM: Homo sapien

<400> SEQUENCE: 13

```
tttttttggca taaaaacac aatgatttaa tttctaaagc acttatatta ttatggcatg      60
gtttgggaaa caggttatta tattccacat aggtaattat gcagtgcttc tcatggaaaa    120
aatgcttagg tattggcctt ttctctggaa accatatttt tcctttttta ataatcaact    180
aaaatgtata tgttaaaaag cctcatcttt tgattttcaa tatacaaaat gctttcttta    240
aaagaacaag attcaa                                                    256
```

<210> SEQ ID NO 14
<211> LENGTH: 301
<212> TYPE: DNA
<213> ORGANISM: Homo sapien

<400> SEQUENCE: 14

```
ggtccttgat agaggaagag gaatatccaa ggcaaagcca ccaccacgtc caacctcctc      60
atcctctacc tttcctgtcc ccagaggtat gagatagacc ccctggcctg gttcctgcac     120
tgtgctaggc ccacagtgga cattccacc ttaatggaga ataggcccca tggagtggag      180
gtccctcctc catggcctgc aacccaatga ctatgggggt gacacaagtg acctctgccc     240
tgtgatggct caacaccatc acacgcaact gtccagacaa gcccctcaa cgggctgctg      300
t                                                                    301
```

<210> SEQ ID NO 15
<211> LENGTH: 259
<212> TYPE: DNA
<213> ORGANISM: Homo sapien

<400> SEQUENCE: 15

```
gtcttgaaag tatttattgt ttaataattc tttctcccct cagccccatc cggccactct      60
ctctttctgc ttttctgatc atcctaaagg ctgaatacat cctcctcctg tgtggaggac     120
acgaagcaat actaaaatca atacactcga tcaggtcttc atcagatacc acgtcactgt     180
gggtagagtg ctaattttca acaaatgtgg tgttcttagg gccccacaag gtagtccttt     240
ctcaaggtcg ctgggccac                                                 259
```

<210> SEQ ID NO 16
<211> LENGTH: 301
<212> TYPE: DNA
<213> ORGANISM: Homo sapien

<400> SEQUENCE: 16

```
cgaggttgtt cacattttca aataaataat actccccgta agtaataact gcaaccaatc      60
agtgttattc agtgctatgc ctccttgtaa tgggtagtta ttaattattt tcagagcttt     120
ctggaaatac tgtcctaact ggctatgttt aggatctttg ttatctctga agacaaagaa     180
agaactagga ctcttaattt tggggtgctt cttgactctt agttgggaaa ctgaaaatat     240
ttccaacctt ttacccacgt caatggcata ttctgggaat caccaccacc accaccacta     300
c                                                                    301
```

<210> SEQ ID NO 17
<211> LENGTH: 301
<212> TYPE: DNA
<213> ORGANISM: Homo sapien

<400> SEQUENCE: 17

```
gcccgggcag gtctggggcc tagggtggct ctttgcaaag ctgaggggca agctaaggaa      60
gccaggcagg tcaggggccc tttcggcctt ctcaagcctc cacctgagtt ctcgtcaatg     120
ccagtctccc tggtatgatt ggggacatta tcagagaaac atctaatagc gcacatctgg     180
gcacccacac tctgcttcag ttgcatccat cctcccaccc caaattcaac tcctgaccca     240
atacaaaaga cttttttaac caggatttct tcttgcagga aagctgactt ggaaacacgg     300
g                                                                    301
```

<210> SEQ ID NO 18
<211> LENGTH: 301
<212> TYPE: DNA
<213> ORGANISM: Homo sapien

<400> SEQUENCE: 18

```
attacaggca cgtgccacca cacctagcta attttttgagc atggggctca aaggaactgc    60
tctctgggc atgtcagatt tcggatttgg ggctgcacac tgatactctc taagtggtgg    120
aggaacttca tcccactgaa attcctttgg catttggggt tttgttttc ttttttttcct    180
tcttcatcct cctccttttt taaaagtcaa cgagagcctt cgctgactcc accgaagaag    240
tgcaccactg gggaccaccc agtgccaggc gcccgtccag ggacacacac agtcttcact    300
g                                                                   301
```

<210> SEQ ID NO 19
<211> LENGTH: 301
<212> TYPE: DNA
<213> ORGANISM: Homo sapien

<400> SEQUENCE: 19

```
agaatctctg cactgtcatc aggtacaaca aaagatcaaa ccctgtccc gatgttaact    60
ttttaactta aaagaatgcc agaaaaccca gatcaacact ttccagctac gagccgtcca    120
caaaggccac ccaaaggcca gtcagactcg tgcagatctt attttttaat agtagtaacc    180
acaatacaca gctctttaaa gctgttcata ttcttccccc attaaacacc tgccccgggc    240
ggccaagggc gaattctgca gatatccatc acactggcgg ccgctcgagc atgcatctag    300
a                                                                   301
```

<210> SEQ ID NO 20
<211> LENGTH: 290
<212> TYPE: DNA
<213> ORGANISM: Homo sapien

<400> SEQUENCE: 20

```
aggtttttt ttttttttt ttttttttt ttttccctt tcaattcatt taatttcaac    60
aatctgtcaa aaacagcca ataaacaaat actgaattac attctgctgg gttttttaaa    120
ggctctaaac tataaaaaca tcttgtgtct cccaccctga ccaccctgct acttttccat    180
ataccacagg ccacccataa acacaaagcc aggggtgaa gctgacatgg tctatttgga    240
gccagtaaac aggagggcga taagtcctga taagcactta tggacaatat                290
```

<210> SEQ ID NO 21
<211> LENGTH: 301
<212> TYPE: DNA
<213> ORGANISM: Homo sapien

<400> SEQUENCE: 21

```
agaaaggtaa ctgccagcca ggcttgcatt gtttagccag aaattgctgc ttggttctag    60
actcttaaa aaaaaaaaat acccaggggt tgtcatcatt tcagaggca gagtgccaaa    120
tatcacccaa agctcttgtg tcttttttttt accccttat tttattttta tttattaatt    180
ttttgtgcaa acatcaaatg tcactggtgt tcacagaagg cttttttgac tagccttaaa    240
ttcctgagtc aaaagattaa tcagatttc aggcagtgtt taatcaggtg ctttgtcctg    300
t                                                                   301
```

<210> SEQ ID NO 22

<211> LENGTH: 301
<212> TYPE: DNA
<213> ORGANISM: Homo sapien

<400> SEQUENCE: 22

```
gacgccatgc accctccggt aaccagcagc cgcctgtcca tcccccaaga ccggaaaggc     60
agcagcagcc cccgggagcc cagggctgtc ctcggtgcat ctggctgcag agggaaattg    120
atgaccttac acagcaacta gcggccatgc agtcctcac tgacaagttc caggaccttt    180
gaagttggag ccagcgtccg gagctgcagc caagcgagtt cctccttat cctccttagc    240
cagggctttt tctcttccgc tgcatttgcc cccttcccaa cgcaattcaa agcagttgtg    300
a                                                                     301
```

<210> SEQ ID NO 23
<211> LENGTH: 381
<212> TYPE: DNA
<213> ORGANISM: Homo sapien

<400> SEQUENCE: 23

```
cgaggtccag acagtggacc aagagatacg ctacataaat tggggtttca caattcttac     60
attatttgtc tgtcacagaa gagagctgct tatgattttg aaggggtcag ggagggtggg    120
agttggtaaa gagtagggta tttctataac agatattatt cagtcttatt tcctaagatt    180
ttgttgtaac ttaaggtatc ttgctacagt agacagaatt ggtaatagca acttttaaaa    240
ttgtcattag ttctgcaata ttagctgaaa tgtagtacag aaaagaatgt acatttagac    300
atttgggttc agttgcttgt agtctgtaaa tttaaaacag cttaatttgg tacaggttac    360
acatatggac ctcccgggcg g                                               381
```

<210> SEQ ID NO 24
<211> LENGTH: 214
<212> TYPE: DNA
<213> ORGANISM: Homo sapien

<400> SEQUENCE: 24

```
aatgatgtaa aaattaatca acagggctgc cacttgcgaa tcccctccaa ggatgctgtg     60
caaagggtct cattggtcct gatgaataat cttgtgactg tacatattcc tgggtgcatg    120
tccacaaata ctgaggtata gcctgcatgc cactaaaaat aacaaggtt tcaggggtgg     180
aaacattgtc caccacactg tcatgaccat cttt                                 214
```

<210> SEQ ID NO 25
<211> LENGTH: 302
<212> TYPE: DNA
<213> ORGANISM: Homo sapien

<400> SEQUENCE: 25

```
gggggcactg agaactccct ctggaattct tgggggtgt tggggagaga ctgtgggcct      60
ggagataaaa cttgtctcct ctaccaccac cctgtaccct agcctgcacc tgtcctcatc    120
tctgcaaagt tcagcttcct tccccaggtc tctgtgcact ctgtcttgga tgctctgggg    180
agctcatggg tggaggagtc tccaccagag ggaggctcag gggactggtt gggccaggga    240
tgaatatttg agggataaaa attgtgtaag aagccaaaga aattggtagt aggggggaga    300
ac                                                                    302
```

<210> SEQ ID NO 26
<211> LENGTH: 301

```
<212> TYPE: DNA
<213> ORGANISM: Homo sapien

<400> SEQUENCE: 26
ttggagaacg cgctgacata ctgctcggcc acagtcagtg aagctgctgc atctccatta      60
tgttgtgtca gagctgcagc caggattcga atagcttcag ctttagcctt ggccttcgcc     120
agaactgcac tggcctctcc tgctgcctga tttatctgtg cagccttttc tgcttcggag     180
gccaggatct gggcctgttt cttcccttct gccacattga tggccgactc tcgggtcccc     240
tcagactcta gaactgtggc ccgtttccgc cgctctgcct ccacctgcat ctgcatagac     300
t                                                                     301

<210> SEQ ID NO 27
<211> LENGTH: 301
<212> TYPE: DNA
<213> ORGANISM: Homo sapien

<400> SEQUENCE: 27
aaatcagtca tcacatctgt gaaaagagtg ctagttataa caaatgagat cacaaatttg      60
accattttat tagacaccct ctattagtgt taacagacaa agatgaaggt taagttgaaa     120
tcaaattgaa atcatcttcc ctctgtacag attgcaatat ctgataatac cctcaacttt     180
cttggtgcaa attaattgcc tggtactcac agtccagtgt taacaggcaa taatggtgtg     240
attccagagg agaggactag gtggcaggaa aataaatgag attagcagta tttgacttgg     300
a                                                                     301

<210> SEQ ID NO 28
<211> LENGTH: 286
<212> TYPE: DNA
<213> ORGANISM: Homo sapien

<400> SEQUENCE: 28 ttttttttg cacaggatgc acttattcta ttcattctcc cccacccttc ccatatttac       60
atccttagag gaagagaggg gtaaggtgat aaagtaactg aaggaccgca agacgggtat     120
gtcccttgtt caccaaatgg tcaaagggtc aaagatcgga ggaggtcagg gggtaacgca     180
ggaacaggtg agggcgtttc gccctctctc cctctcccct tttcaacctc ttaatcactg     240
gctaactcgc gacctcatgg gttaattcgt aagcttacac gcgttg                    286

<210> SEQ ID NO 29
<211> LENGTH: 301
<212> TYPE: DNA
<213> ORGANISM: Homo sapien

<400> SEQUENCE: 29
gtcatgttct tgctcttcct tctttacaca tttgagttgt gccttctgtt cttaaagaga      60
ttttcctttg ttcaaaggat ttattcctac catttcacaa atccgaaaat aattgaggaa     120
acaggttaca tcattccaat tttgccttgg gtttgaagag tctctcatgg tggcacagtc     180
ctccagggta gctatgttgt tgggctcccc tacatcccag aagctcagag actttgtcaa     240
aggtgtgccg tccacccatt gccactgacc ctcgacaacc tggtctgaca gtccaataaa     300
a                                                                     301

<210> SEQ ID NO 30
<211> LENGTH: 332
<212> TYPE: DNA
```

<213> ORGANISM: Homo sapien

<400> SEQUENCE: 30

```
gagcagaatt gatgcctatg gctccaagtc aaatactgct aatctcattt attttcctgc    60
cacctagtcc tctcctctgg aatcacacca ttattgcctg ttaacactgg actgtgagta   120
ccaggcaatt aatttgcacc aagaaagttg agggtattat cagatattgc aatctgtaca   180
gagggaagat gatttcaatt tgatttcaac ttaaccttca tctttgtctg ttaacactaa   240
tagagggtgt ctaataaaat ggtcaaattt gtgatctcat ttgttataac tagcactctt   300
ttcacagatg tgatgactga tttccagcag ac                                  332
```

<210> SEQ ID NO 31
<211> LENGTH: 141
<212> TYPE: DNA
<213> ORGANISM: Homo sapien

<400> SEQUENCE: 31

```
aaaggctatc aagtactttg aaggacagga aggaatgaac acacccaggt ggacgtttgg    60
tttcatttgc aggggttcag ggaggggttgc aggggttcag ggagggctct tgtcccacaa   120
ccgggggaag ggagagggca c                                             141
```

<210> SEQ ID NO 32
<211> LENGTH: 201
<212> TYPE: DNA
<213> ORGANISM: Homo sapien

<400> SEQUENCE: 32

```
gagctgatct cacagcacat acagaatgat gctactatgt agaccctcac tcccttggga    60
aatctgtcat ctaccttaaa gagagaaaaa agatggaaca taggcccacc tagtttcatc   120
catccaccta cataaccaac atagatgtga ggtccactgc actgatagcc agactgcctg   180
gggtaaacct tttcagggag g                                             201
```

<210> SEQ ID NO 33
<211> LENGTH: 181
<212> TYPE: DNA
<213> ORGANISM: Homo sapien

<400> SEQUENCE: 33

```
tttcaaaaca ctcatatgtt gcaaaaaaca catagaaaaa taaagtttgg tgggggtgct    60
gactaaactt caagtcacag acttttatgt gacagattgg agcagggttt gttatgcatg   120
tagagaaccc aaactaattt attaaacagg atagaaacag gctgtctggg tgaaatggtt   180
c                                                                   181
```

<210> SEQ ID NO 34
<211> LENGTH: 151
<212> TYPE: DNA
<213> ORGANISM: Homo sapien

<400> SEQUENCE: 34

```
atgtcctgca cagtatagct tggacctctg ggcctgaacc agggtgagca tcaaggcccc    60
catttctcct caccacgggg tcgcttgtca gctccaagaa ccagtctggc cccactgaga   120
acttttcagt cgagggcctg atgaatcttg g                                  151
```

<210> SEQ ID NO 35
<211> LENGTH: 291

```
<212> TYPE: DNA
<213> ORGANISM: Homo sapien

<400> SEQUENCE: 35
tctttagggc aaaatcatgt ttctgtgtac ctagcaatgt gttcccattt tattaagaaa      60
agctttaaca cgtgtaatct gcagtccta acagtggcgt aattgtacgt acctgttgtg     120
tttcagtttg tttttcacct ataatgaatt gtaaaaacaa acatacttgt ggggtctgat     180
agcaaacata gaaatgatgt atattgtttt ttgttatcta tttattttca tcaatacagt     240
attttgatgt attgcaaaaa tagataataa tttatataac aggttttctg t               291

<210> SEQ ID NO 36
<211> LENGTH: 201
<212> TYPE: DNA
<213> ORGANISM: Homo sapien

<400> SEQUENCE: 36
ctgatacaat tataataacg gttccctgaa ccttttagag tgcaattaag aacaaaaact      60 aaatttttgtt tacatgaata tggaataaat acaataatca aaatatgact ctccctaaaa    120
gtgaaacaca caagccaatc cggaactgct gtgcgaaaga taaaatcgag aaaggcaagg     180
tttcggtagg aggacgcgat g                                                 201

<210> SEQ ID NO 37
<211> LENGTH: 121
<212> TYPE: DNA
<213> ORGANISM: Homo sapien

<400> SEQUENCE: 37
catcacactg gcggccgctc gagcatgcat ctagagggcc caattcgccc tataatgagt      60
cgtattacaa ttcactggcc gtcgttttac aacgtcgtga ctgggaaaac cctggcgtta    120
c                                                                       121

<210> SEQ ID NO 38
<211> LENGTH: 200
<212> TYPE: DNA
<213> ORGANISM: Homo sapien

<400> SEQUENCE: 38
aaacatgtat tactctatat ccccaagtcc tagagcatga cctgcatgtt ggagatgttg      60
tacagcaatg tatttatcca gacatacata tgatatttt agagacacag tgattctttt     120
gataacacca cacatagaac attataatta cacacaaatt tatggtaaaa gaattaatat    180
gctgtctggt gctgctgtta                                                   200

<210> SEQ ID NO 39
<211> LENGTH: 760
<212> TYPE: DNA
<213> ORGANISM: Homo sapien

<400> SEQUENCE: 39
gcgtggtcgt cggccgaggt cctgggctag acctaatggt ttattattgg tggagagaaa      60
gatctggaaa tacttgaggt tattacatac tagattagct tctaatgtga accattttc     120 tttttaacagt gatcaaatta ttatttcgaa gttaatcgtt cccttggtgg ctgcatacac    180
atcgcattaa caaacatact gttgtatttt ttcccagttt tgtttggcta tgccaccaca    240
gtcatcccca gggtctatac atactatgtt tcaactgtat tatttgccat ttttggcatt    300
```

```
agaatgcttc gggaaggctt aaagatgagc cctgatgagg gtcaagagga actggaagaa    360
gttcaagctg aattaaagaa gaaagatgaa gaagtaagcc atggcactgt tgatctggac    420
caaaaaggca ctcaactagg aataaacact ctacagaggt ttctcagtgg ccccatctgt    480
gtgatatgcg gggctacaca aaaatagctt cttttgcttt gttctgttct tatacctgtc    540
tgtgatctga cttggggttg gtgtgaatgt agtagagaaa ggaagctgac agatgaatac    600
tgaacacagg taatcagttt ccttaattag gttgattata agctcctgaa aagcaggaac    660
tgtattttat aatttttacct gtttctcccg tggtgtctag gatagtaagt gagcagagca    720
gtaaatactg tttggtttgt tcagacctgc ccgggcggcc                          760

<210> SEQ ID NO 40
<211> LENGTH: 452
<212> TYPE: DNA
<213> ORGANISM: Homo sapien

<400> SEQUENCE: 40
aatcactaaa gatattgact agagaatgct gtgtgctatt tcaattacat ttgttttttct   60 tttattaaca ggaattttga ttcttcaagg aagtggctca atttcaattt caggtgacca    120
ggtttatcgt gacttttcct tcttgtttac ttttcgctag aaggggagt tgtaggggca     180 gattcaggta ttggaatagg aaaattacgt ctaaaccatg gaaatcttgg aaatggaatt    240
ggtggaagtg ggcgaaatgg atatgggtaa gggaacacaa aaaccctga agctaattca     300 tcgctgtcac tgatacttct tttttctcgt tcctggtctt gagagactgg gaaaccaaca    360
gccactgcca agatggctgt gatcaggagg agaactttct tcatctcaaa cgtttcagtc    420
agttctttct ctcacctcgg ccgcgaccac gc                                  452

<210> SEQ ID NO 41
<211> LENGTH: 676
<212> TYPE: DNA
<213> ORGANISM: Homo sapien

<400> SEQUENCE: 41
aatctttgaa tgccaagtct cttctgtact ttcttttatt aacatcatag tctttgcatc    60
aagatacata gcaatgatag caggtttctt tttaaagctt agtattaata ttaaatattt    120
ttccccattt aaattttaca ttacttgcca agaaaaaaaa aaaattaaaa ctcaagttac    180
ttgaagcctg gacacacttc catgattagc cgggctaggt aaaagttggt ggctttattc    240
ttcctgctct ataagcagat ccaggcccta gaaagatggg accagggtat ataattgttt    300
ttgaaaagtg tgctacaaaa atggatggcc tgttataagc caggatacaa agttaaggat    360
gggggtaagg gagggacatt ttcttccaga agaaaagaca gaatttctga agagtcccag    420
tccataattt tcccaaaatg gttggaggag agggtaaaat ctcaacatga gtttcaaagt    480
actgtctctg tgaggggccg gtagatgcct tgctgaggag ggatggctaa tttggaccat    540
gccccatccc cagctaggag aatggaaatg gaaactttaa ttgcccagtg ggtgtgaaag    600
tgggctgaag cttggttggt actgaattct ctaagaggtt tcttctagaa acagacaact    660
cagacctgcc cgggcg                                                    676

<210> SEQ ID NO 42
<211> LENGTH: 468
<212> TYPE: DNA
<213> ORGANISM: Homo sapien

<400> SEQUENCE: 42
```

```
agcgtggtcg cggccgaggt ttggccggga gcctgatcac ctgccctgct gagtcccagg     60
ctgagcctca gtctccctcc cttggggcct atgcagaggt ccacaacaca cagatttgag    120
ctcagccctg gtgggcagag aggtagggat ggggctgtgg ggatagtgag gcatcgcaat    180
gtaagactcg ggattagtac acacttgttg attaatggaa atgtttacag atccccaagc    240
ctggcaaggg aatttcttca actccctgcc cccagcccct ccttatcaaa ggacaccatt    300
ttggcaagct ctatgaccaa ggagccaaac atcctacaag acacagtgac catactaatt    360
aaaaccccct gcaaagccca gcttgaaacc ttcacttagg aacgtaatcg tgtccccctat   420 cctacttccc cttcctaatt ccacagacct gcccgggcgg ccgctcga                468

<210> SEQ ID NO 43
<211> LENGTH: 408
<212> TYPE: DNA
<213> ORGANISM: Homo sapien

<400> SEQUENCE: 43
atcatatcaa acactatct tcccatctgt ttctcaatgc ctgctacttc ttgtagatat     60
ttcatttcag gagagcagca gttaaacccg tggattttgt agttaggaac ctgggttcaa   120
acctctttcc actaattggc tatgtctctg gacagttttt ttttttttt tttttttttaa   180 acccctttctg aactttcact ttctatggct acctcaaaga attgttgtga ggcttgagat   240
aatgcatttg taaagggtct gccagatagg aagatgctag ttatggattt acaaggttgt   300
taaggctgta agagtctaaa acctacagtg aatcacaatg catttacccc cactgacttg   360
gacataagtg aaaactagcc cgaagtctct ttttcaaatt acttacag               408

<210> SEQ ID NO 44
<211> LENGTH: 160
<212> TYPE: DNA
<213> ORGANISM: Homo sapien

<400> SEQUENCE: 44
tggtcgcggc cgaggtcttg tgtgccctgt ggtccagggg accaagaaca acaagatcca    60
ctctctgtgc tacaatgatt gcaccttctc acgcaacact ccaaccagga ctttcaacta   120
caacttctcc gctttggcaa acaccgtcac tcttgctgga                         160

<210> SEQ ID NO 45
<211> LENGTH: 231
<212> TYPE: DNA
<213> ORGANISM: Homo sapien

<400> SEQUENCE: 45
cgagcggccg cccgggcagg tctggggagg tgattccatc cagagtcata tctgttgtca    60
ccccaataag tcgatcagca aggctgacag gctgtgagga aaccccggcc ttgtagcctg   120
tcacctctgg ggggatgatg actgcctggc agacgtaggc tgtgatagat ttgggagaaa   180
acctgactca ccctcaggaa tccggaggtc ggtgacattg tcggtgcaca c            231

<210> SEQ ID NO 46
<211> LENGTH: 371
<212> TYPE: DNA
<213> ORGANISM: Homo sapien

<400> SEQUENCE: 46
cccgggcagg tctgtgtaac atgccaaggc tttgcacttt ctgcagagca gttttttatt    60
```

```
ttccttatca ggtacaggtt ttggttttc ttgactatct ctgatgaatt tttcatgagt    120
ctgtatatgc agaatctttt ccctaaatac tgcttcgtcc catgtctgaa ggcgtaaaat    180
aaagtcattc atcattttt ctttgtacat gtttatttgt tcttttcaa ttacaccaag     240 cattactagt cagaaggaag cacttgctac ctcttgctct tcctctgcct ctggtttgga    300
tcattttgat gacattgccc acattactca tgaaggatga caagattgca ctgtgcaatg    360
tcaattgcct t                                                          371
```

<210> SEQ ID NO 47
<211> LENGTH: 261
<212> TYPE: DNA
<213> ORGANISM: Homo sapien

<400> SEQUENCE: 47

```
gccctgtttt tatacacttc acatttgcag aaatataatg atgccctcat tatcagtgag     60
catgcacgaa tgaaagatgc tctggattac ttgaaagact tcttcagcaa tgtccgagca    120
gcaggattcg atgagattga gcaagatctt actcagagat ttgaagaaaa gctgcaggaa    180
ctagaaagtg tttccaggga tcccagcaat gagaatccta aacttgaaga cctctgcttc    240
atcttacaag aagagtacca c                                               261
```

<210> SEQ ID NO 48
<211> LENGTH: 701
<212> TYPE: DNA
<213> ORGANISM: Homo sapien

<400> SEQUENCE: 48

```
cgagcggccc ccgggcaggt ccaattagta caagtctcat gatataatca ctgcctgcat     60
acatatgcac agatccagtt agtgagtttg tcaagcttaa tctaattggt taagtctcaa    120
agagattatt attcttgatg tttgctttgt attggctaac aaatgtgcag aggtaataca    180
tatgtgatgt ccgatgtctc tgtctttttt tttgtcttta aaaaataatt ggcagcaact    240
gtatttgaat aaaatgattt cttagtatga ttgtaccgta atgaatgaaa gtggaacatg    300
tttctttttg aaagggagag aattgaccat ttattattgt gatgtttaag ttataactta    360
ttgagcactt ttagtagtga taactgtttt taaacttgcc taatacctt cttgggtatt     420 gtttgtaatg tgacttattt aaccccctt tttgtttgtt taagttgctg ctttaggtta     480
acagcgtgtt ttagaagatt taaattttt tcctgtctgc acaattagtt attcagagca     540
agagggcctg attttataga agccccttga aaagaggtcc agatgagagc agagatacag    600
tgagaaatta tgtgatctgt gtgttgtggg aagagaattt tcaatatgta actacggagc    660
tgtagtgcca ttagaaactg tgaatttcca ataaatttg a                          701
```

<210> SEQ ID NO 49
<211> LENGTH: 270
<212> TYPE: DNA
<213> ORGANISM: Homo sapien

<400> SEQUENCE: 49

```
agcggccgcc cgggcaggtc tgatattagt agctttgcaa ccctgataga gtaaataaat     60
tttatgggcg ggtgccaaat actgctgtga atctatttgt atagtatcca tgaatgaatt    120
tatggaaata gatatttgtg cagctcaatt tatgcagaga ttaaatgaca tcataatact    180
ggatgaaaac ttgcatagaa ttctgattaa atagtgggtc tgtttcacat gtgcagtttg    240
aagtatttaa attaaccact cctttcacag                                      270
```

<210> SEQ ID NO 50
<211> LENGTH: 271
<212> TYPE: DNA
<213> ORGANISM: Homo sapien

<400> SEQUENCE: 50

```
atgcatttat ccatatgaac ttgattattc tgaattactg actataaaaa ggctattgtg      60
aaagatatca cactttgaaa cagcaaatga attttcaatt ttacatttaa ttataagacc     120
acaataaaaa gttgaacatg cgcatatcta tgcatttcac agaagattag taaaactgat     180
ggcaacttca gaattatttc atgaagggta caaacagtct ttaccacaat tttcccatgg     240
tcttatcctt caaaataaaa ttccacacac t                                    271
```

<210> SEQ ID NO 51
<211> LENGTH: 241
<212> TYPE: DNA
<213> ORGANISM: Homo sapien

<400> SEQUENCE: 51

```
tggtcgcggc cgaggtgtga ggagatgaac tttgtgttaa tgggggcac tttaaatcga       60
aatggcttat ccccaccgcc atgtaagtta ccatgcctgt ctcctccctc ctacacattt     120
ccagctcctg ctgcagttat cctacagaa gctgccattt accagccctc tgtgattttg      180
aatccacgag cactgcaggc cctccacagc gttactaccc agcaggcact cagctcttca     240
t                                                                     241
```

<210> SEQ ID NO 52
<211> LENGTH: 271
<212> TYPE: DNA
<213> ORGANISM: Homo sapien

<400> SEQUENCE: 52

```
tccaagactt aaaacttagg aaacacctat gatgccactt taactggaag taatggagac      60
atctgattcc aaattcacat tttaaatgcc tatttgcaat cagcaaagag ccaggtatgc     120
tgcatgctgc ttgctgtaag ttacgatttg cttcactag ctcaaatttt ttcactccac      180
caaaagataa ggcacaggcc cgtttgtcca atcaagtttg ctgaaaatac tgcagcctga     240
gtgtagacaa acttcccctg aatttgctag a                                    271
```

<210> SEQ ID NO 53
<211> LENGTH: 493
<212> TYPE: DNA
<213> ORGANISM: Homo sapien

<400> SEQUENCE: 53

```
ttagcgtggt cgcggtccga ggtctggcct gactagctca ctctgaagag tgtctttcac      60
atggattaac caaaaaatgc attactgcct ttggcacact gtcttgaata ttctttctga     120
caatgagaaa atatgattta atggagtcgt tcaataacct cacaatctcg ctgttccgag     180
cagatagttt tcgtgccaac aggaactggc acatctagca ggttcacggc atgacctttt     240
tgtggactgg ctggcataat tggaatgggt tttgatttt cttctgctaa taactcttca      300
agcttttgaa gttttcaagc attcctctcc agttgcctgt ggttggttct tgaacaccat     360
ctccaacccc accacctcca gatgcaacct tgtctcgtga tacagacctg cccgggcggc     420
cctcaagggc gaattctgca gatatccatc acactggcgg ccgctcgagc atgcatctag     480
```

<210> SEQ ID NO 54
<211> LENGTH: 321
<212> TYPE: DNA
<213> ORGANISM: Homo sapien

<400> SEQUENCE: 54

| | |
|---|---|
| cgtggtcgcg gccgaggtct gtttgcttgt tggtgtgagt ttttcttctg gagactttgt | 60 |
| actgaatgtc aataaactct gtgattttgt taggaagtaa aactgggatc tatttagcca | 120 |
| ctggtaagct tctgaggtga aggattcagg gacatctcgt ggaacaaaca ctccccactg | 180 |
| gactttctct ctggagatac ccttttgaat atacaatggc cttggctcac taggtttaaa | 240 |
| tacaaacaag tctgaaaccc actgaagact gagagattgc agcaatattc tctgaattag | 300 |
| gatcgggttc cataactcta a | 321 |

<210> SEQ ID NO 55
<211> LENGTH: 281
<212> TYPE: DNA
<213> ORGANISM: Homo sapien

<400> SEQUENCE: 55

| | |
|---|---|
| ttgcaaatga aactgtggat gtataataag aaaacacaag ggtttattct taacactaaa | 60 |
| attaacatgc cacacgaaga ctgcattaca gctctctgtt tctgtaatgc agaaaaatct | 120 |
| gaacagccca ccttggttac agctagcaaa gatggttact tcaaagtatg gatattaaca | 180 |
| gatgactctg acatatacaa aaaagctgtt ggctggacct gtgactttgt tggtagttat | 240 |
| cacaagtatc aagcaactaa ctgttgtttc tccgaagatg g | 281 |

<210> SEQ ID NO 56
<211> LENGTH: 612
<212> TYPE: DNA
<213> ORGANISM: Homo sapien

<400> SEQUENCE: 56

| | |
|---|---|
| gcgtggtcgc ggccgaggtc ctgtccgggg gcactgagaa ctccctctgg aattcttggg | 60 |
| gggtgttggg gagagactgt gggcctggag ataaaacttg tctcctctac caccaccctg | 120 |
| taccctagcc tgcacctgtc ctcatctctg caaagttcag cttccttccc caggtctctg | 180 |
| tgccactctg tcttggatgc tctggggagc tcatgggtgg aggagtctcc accagaggga | 240 |
| ggctcagggg actggttggg ccagggatga atatttgagg gataaaaatt gtgtaagagc | 300 |
| caaagaattg gtagtagggg gagaacagag aggagctggg ctatgggaaa tgatttgaat | 360 |
| aatggagctg ggaatatggc tggatatctg gtactaaaaa agggtctta agaacctact | 420 |
| tcctaatctc ttccccaatc caaaccatag ctgtctgtcc agtgctctct tcctgcctcc | 480 |
| agctctgccc caggctcctc ctagactctg tccctgggct agggcagggg aggagggaga | 540 |
| gcagggttgg gggagaggct gaggagagtg tgacatgtgg ggagaggacc agacctgccc | 600 |
| gggcggccgt cg | 612 |

<210> SEQ ID NO 57
<211> LENGTH: 363
<212> TYPE: DNA
<213> ORGANISM: Homo sapien

<400> SEQUENCE: 57

| | |
|---|---|
| gtcgcggccg aggtcctgag cgtcacccta gttctgcccc tttttagctg tgtagacttg | 60 |

```
gacaagacat tgacttccc tttctccttg tctataaaat gtggacagtg gacgtctgtc    120
acccaagaga gttgtgggag acaagatcac agctatgagc acctcgcacg gtgtccagga   180
tgcacagcac aatccatgat gcgttttctc cccttacgca ctttgaaacc catgctagaa   240
aagtgaatac atctgactgt gctccactcc aacctccagc gtggatgtcc ctgtctgggc   300 ccttttctg tttttattc tatgttcagc accactggca ccaaatacat tttaattcac    360
cga                                                                 363

<210> SEQ ID NO 58
<211> LENGTH: 750
<212> TYPE: DNA
<213> ORGANISM: Homo sapien

<400> SEQUENCE: 58
cgtggtcgcg gccgaggtct aattccacct gactggcaga acctgcgccc ctcgcctaac    60
ctgcgccctt ctcccaactc gcgtgcctca cagaacccag gtgctgcaca gccccgagat   120
gtggcccttc ttcaggaaag agcaaataag ttggtccaag tacttgatgc ttaaggaata   180
cacaaaggtg cccatcaagc gctcagaaat gctgagagat atcatccgtg aatacactga   240
tgtttatcca gaaatcattg aacgtgcatg ctttgtccta gagaagaaat ttgggattca   300
actgaaagaa attgacaaag aagaacacct gtatattctc atcagtaccc ccgagtccct   360
ggctggcata ctgggaacga ccaaagacac acccaagctc ggtctcttct tggtgattct   420
gggtgtcatc ttcatgaatg caaccgtgc cagtgaggct gtcttttggg aggcactacg    480
caagatggga ctgcgtcctg ggtgagaca tcccctccct tggagatcta aggaaacttc    540
tcacctatga gtttgtaaag cagaaatacc tggactacag acgagtgccc aacagcaacc   600
ccccggagta tgagttcctc tgggcctcc gtccctacca tgagactagc aagatgaaaa    660
tgctgagatt cattgcagag gttcagaaaa gagaccctcg tgactggact gcacagttca   720
tggaggctgc agatgaggac ctgcccgggc                                    750

<210> SEQ ID NO 59
<211> LENGTH: 505
<212> TYPE: DNA
<213> ORGANISM: Homo sapien

<400> SEQUENCE: 59
tggccgcccg ggcaggtcca gtctacaagc agagcactct catggggagc accagatgag    60
ttccagccgc agttcttta taagctttaa gtgcctcatg aagacgcgag gatctcttcc    120
aagtgcaacc tggtcacatc agggcacatt cagcagcaga agtctgtttc cagtatagtc   180
cttggtatgg ctaaattcca ctgtcccttt ctcagcagtc aataatccat gataaattct   240
gtacaacact gtagtcaata acagcagcac cagacagcat attaattctt ttaccataaa   300
tttgtgtgta attataatgt tctatgtgtg gtgttatcaa aagaatcact gtgtctctaa   360
atatcatata tgtatgtctg gataaataca ttgctgtaca acatctccaa catgcaggtc   420
atgctctaag acttggggat atagagtaat acatgtttcg tggacctcgg ccgcgaccac   480
gctaagggcg aattctgcag atatc                                        505

<210> SEQ ID NO 60
<211> LENGTH: 520
<212> TYPE: DNA
<213> ORGANISM: Homo sapien
```

```
<400> SEQUENCE: 60
cgtggtcgcg gccgaggtcc tcaggacaag gaaacaggta tcagcatgat ggtagcagaa      60
accttatcac caaggtgcag gagctgactt cttccaaaga gttgtggttc cgggcagcgg     120
tcattgcctg cccttgctgg agggctgatt ttagtgttgc ttattatgtt ggccctgagg     180
atgcttcgaa gtgaaaataa gaggctgcag gatcagcggc aacagatgct ctcccgtttg     240
cactacagct ttcacggaca ccattccaaa aaggggcagg ttgcaaagtt agacttggaa     300
tgcatggtgc cggtcagtgg gcacgagaac tgctgtctga cctgtgataa aatgagacaa     360
gcagacctca gcaacgataa gatcctctcg cttgttcact ggggcatgta cagtgggcac     420
gggaagctgg aattcgtatg acggagtctt atctgaacta cacttactga acagcttgaa     480
ggacctgccc gggcggccgc tcgaaagggg cgaattctgc                           520

<210> SEQ ID NO 61
<211> LENGTH: 447
<212> TYPE: DNA
<213> ORGANISM: Homo sapien

<400> SEQUENCE: 61
agagaggtgt ttttattctt tgggacaaa gccgggttct gtgggtgtag gattctccag       60
gttctccagg ctgtagggcc cagaggctta atcagaattt tcagacaaaa ctggaacctt     120 tctttttcc cgttggttta tttgtagtcc ttgggcaaac caatgtcttt gttcgaaaga     180
gggaaaataa tccaaacgtt tttctttaa cttttttttt aggttcaggg gcacatgtgt     240
aggcttgcta tataggtaaa ttgcatgtca ccagggtttg ttgtacagat tatttcatca     300
tccagataaa aagcatagta ccagataggt agttttttga tcctcacct ccttccatgc     360 tccgacctca ggtaggcccc agtgtctgac ctgcccggcg gcccgctcga aagggccaat     420
tctgcagata tccatcacac tggccgg                                         447

<210> SEQ ID NO 62
<211> LENGTH: 83
<212> TYPE: PRT
<213> ORGANISM: Homo sapien

<400> SEQUENCE: 62

Lys Lys Val Leu Leu Ile Thr Ala Ile Leu Ala Val Ala Val Gly
 1               5                  10                  15

Phe Pro Val Ser Gln Asp Gln Glu Arg Glu Lys Arg Ser Ile Ser Asp
                20                  25                  30

Ser Asp Glu Leu Ala Ser Gly Phe Phe Val Phe Pro Tyr Pro Tyr Pro
            35                  40                  45

Phe Arg Pro Leu Pro Pro Ile Pro Phe Pro Arg Phe Pro Trp Phe Arg
        50                  55                  60

Arg Asn Phe Pro Ile Pro Ile Pro Ser Ala Pro Thr Thr Pro Leu Pro
65                  70                  75                  80

Ser Glu Lys

<210> SEQ ID NO 63
<211> LENGTH: 683
<212> TYPE: DNA
<213> ORGANISM: Homo sapien

<400> SEQUENCE: 63
acaaagattg gtagctttta tatttttta aaatgctat actaagagaa aaacaaaag         60
```

-continued

```
accacaacaa tattccaaat tataggttga gagaatgtga ctatgaagaa agtattctaa    120
ccaactaaaa aaatattga accactttt gattgaagca aaatgaataa tgctagattt     180
aaaaacagtg tgaaatcaca ctttggtctg taaacatatt tagctttgct tttcattcag   240
atgtatacat aaacttattt aaaatgtcat ttaagtgaac cattccaagg cataataaaa   300
aaagwggtag caaatgaaaa ttaaagcatt tattttggta gttcttcaat aatgatrcga   360
gaaactgaat tccatccagt agaagcatct ccttttgggt aatctgaaca agtrccaacc   420
cagatagcaa catccactaa tccagcacca attccttcac aaagtccttc cacagaagaa   480
gtgcgatgaa tattaattgt tgaattcatt tcagggcttc cttggtccaa ataaattata   540
gcttcaatgg gaagaggtcc tgaacattca gctccattga atgtgaaata ccaacgctga   600
cagcatgcat ttctgcattt tagccgaagt gagccactga acaaaactct tagagcacta   660
tttgaacgca tctttgtaaa tgt                                           683
```

<210> SEQ ID NO 64
<211> LENGTH: 749
<212> TYPE: DNA
<213> ORGANISM: Homo sapiens
<220> FEATURE:
<221> NAME/KEY: misc_feature
<222> LOCATION: 534
<223> OTHER INFORMATION: n = A,T,C or G

<400> SEQUENCE: 64

```
ctgttcattt gtccgccagc tcctggactg gatgtgtgaa aggcatcaca tttccatttt    60
cctccgtgta aatgttttat gtgttcgcct actgatccca ttcgttgctt ctattgtaaa   120
tatttgtcat ttgtatttat tatctctgtg ttttccccct aaggcataaa atggtttact   180
gtgttcattt gaacccattt actgatctct gttgtatatt tttcatgcca ctgctttgtt   240
ttctcctcag aagtcgggta gatagcattt ctatcccatc cctcacgtta ttggaagcat   300
gcaacagtat ttattgctca gggtcttctg cttaaaactg aggaaggtcc acattcctgc   360
aagcattgat tgagacattt gcacaatcta aatgtaagc aaagtaagtc attaaaaata    420
caccctctac ttgggcttta tactgcatac aaatttactc atgagccttc ctttgaggaa   480
ggatgtggat ctccaaataa agatttagtg tttattttga gctctgcatc ttancaagat   540
gatctgaaca cctctccttt gtatcaataa atagccctgt tattctgaag tgagaggacc   600
aagtatagta aatgctgac atctaaaact aaataaatag aaaacaccag gccagaacta   660
tagtcatact cacacaaagg gagaaattta aactcgaacc aagcaaaagg cttcacggaa   720
atagcatgga aaaacaatgc ttccagtgg                                     749
```

<210> SEQ ID NO 65
<211> LENGTH: 612
<212> TYPE: DNA
<213> ORGANISM: Homo sapiens

<400> SEQUENCE: 65

```
acagcagcag tagatggctg caacaacctt cctcctaccc cagcccagaa aatatttctg    60
ccccacccca ggatccggga ccaaaataaa gagcaagcag ccccccttca ctgaggtgct   120
gggtagggct cagtgccaca ttactgtgct ttgagaaaga ggaaggggat tgtttggca    180 cttaaaaat agaggagtaa gcaggactgg agaggccaga gaagatacca aaattggcag    240
ggagagacca tttggcgcca gtcccctagg agatgggagg agggagatag gtatgagggt   300
aggcgctaag aagagtagga ggggtccact ccaagtggca gggtgctgaa atgggctagg   360
```

```
accaacagga cactgactct aggtttatga cctgtccata cccgttccac agcagctggg    420
tgggagaaat caccattttg tgacttctaa taaaataatg ggtctaggca acagttttca    480
atggatgcta aaacgattag gtgaaaagtt gatggagaat tttaattcag gggaattagg    540
ctgataccat ctgaaaccat ttggcatcat taaaaatgtg acaacctggt ggctgccagg    600
gaggaagggg ag                                                        612
```

<210> SEQ ID NO 66
<211> LENGTH: 703
<212> TYPE: DNA
<213> ORGANISM: Homo sapiens

<400> SEQUENCE: 66

```
tagcgtggtc gcggccgagg tacattgatg ggctggagag cagggttggc agcctgttct     60
gcacagaacc aagaattaca gaaaaaagtc caggagctgg agaggcacaa catctccttg    120
gtagctcagc tccgccagct gcagacgcta attgctcaaa cttccaacaa agctgcccag    180
accagcactt gtgttttgat tcttcttttt tccctggctc tcatcatcct gcccagcttc    240
agtccattcc agagtcgacc agaagctggg tctgaggatt accagcctca cggagtgact    300
tccagaaata tcctgaccca caaggacgta acagaaaatc tggagaccca agtggtagag    360
tccagactga gggagccacc tggagccaag gatgcaaatg gctcaacaag gacactgctt    420
gagaagatgg gagggaagcc aagacccagt gggcgcatcc ggtccgtgct gcatgcagat    480
gagatgtgag ctggaacaga ccttcctggc ccacttcctg atcacaagga atcctgggct    540
tccttatggc tttgcttccc actgggattc ctactaggt gtctgccctc aggggtccaa    600
atcacttcag gacaccccaa gagatgtcct ttagtctctg cctgaggcct agtctgcatt    660
tgtttgcata tatgagaggg tacctgcccg ggcggccgct cga                      703
```

<210> SEQ ID NO 67
<211> LENGTH: 1022
<212> TYPE: DNA
<213> ORGANISM: Homo sapiens

<400> SEQUENCE: 67

```
cttgagaaag caggattgtt ttaagttcca agatttaaca aacttactgt tcagcatcat     60
attcaagcct aaaaggaaga taggatttttc aagatatatt tccaacttct ttaacatggc    120
accatggatg aactgtttct cagcactgtg ctgcttcact tggaattaag gatgaattgg    180
gaggagacag tatgacatag gtgggtaggt tgggtggtga ggggaaccag ttctaatagt    240
cctcaactcc actccagctg ttcctgttcc acacggtcca ctgagctggc ccagtccctt    300
tcactcagtg tgtcaccaaa ggcagcttca aggctcaatg gcaagagacc acctataacc    360
tcttcacctt ctgctgcctc tttctgctgc cactgactgc catggccatc tgctatagcc    420
gcattgtcct cagtgtgtcc aggccccaga caaggaaggg gagccatggt gagactccaa    480
ttcccaggcc ttaatcctta ccctagacc tgttgcctct agcatcattt atttatctac    540
ctacctaata gctatctacc agtcattaaa ccatggtgag attctaacca tgtctagcac    600
ctgatgctag agataatttt gttgaatccc ttcaattata aacagctgag ttagctggac    660
aaggactagg gaggcaatca gtattattta ttcttgaaca ccatcaagtc tagacttggt    720
ggcttcatat ttctatcata atccctgggg gtaagaaatc atatagcccc aggttgggaa    780
ggggaaaacg gtttgcaaca ttctcctcct tgtaggaggc gagctctgtc tcactagcta    840
```

```
tgcccctcca tcaattcacc ctatactcag atcagaagct gagtgtctga attacagtat    900
attttctaaa ttcctagccc ctgctggtga atttgccctc ccccgctcct ttgacaattg    960
tccccgtgtt cgtctccggg ccctgagact ggccctgctt atcttgctga ccttcatcct   1020
ct                                                                   1022
```

```
<210> SEQ ID NO 68
<211> LENGTH: 449
<212> TYPE: DNA
<213> ORGANISM: Homo sapiens

<400> SEQUENCE: 68
ccagatccat tttcagtggt ctggatttct ttttattttc ttttcaactt gaaagaaact     60
ggacattagg ccactatgtg ttgttactgc cactagtgtt caagtgcctc ttgttttccc    120
agagatttcc tgggtctgcc agaggcccag acaggctcac tcaagctctt taactgaaaa    180
gcaacaagcc actccaggac aaggttcaaa atggttacaa cagcctctac ctgtcgcccc    240
agggagaaag gggtagtgat acaagtctca tagccagaga tggttttcca ctccttctag    300
atattcccaa aaagaggctg agacaggagg ttatttttcaa ttttattttg gaattaaata   360
cttttttccc tttattactg ttgtagtccc tcacttggat atacctctgt tttcacgata    420
gaaataaggg aggtctagag cttctattc                                      449
```

```
<210> SEQ ID NO 69
<211> LENGTH: 387
<212> TYPE: DNA
<213> ORGANISM: Homo sapiens
<220> FEATURE:
<221> NAME/KEY: misc_feature
<222> LOCATION: 22, 26, 36, 45, 54, 56, 62, 63, 73, 92, 98, 105, 155,
      174, 194, 302, 312, 358, 375, 378, 381
<223> OTHER INFORMATION: n = A,T,C or G

<400> SEQUENCE: 69
gcccttagcg tgggtcgcgg cncgangtct ggagcntatg tgatncctat ggtncncagg     60
cnnatactgc tantctcatt tattctcctg cnacctantc ctctnctctg gaatcacacc    120
attattgcct gttaacactg gactgtgagt accangcaat taatttgcac caanaaagtt    180
gagggtatta tcanatattg caatctgtac agagggaaga tgatttcaat ttgatttcaa    240
cttaaccttc atctttgtct gttaacacta atagagggtg tctaataaaa tggcaaattt    300
gngatctcat tnggtataac tacactcttt ttcacagatg tgatgactga atttccanca    360
acctgcccgg gcggncgntc naagggc                                        387
```

```
<210> SEQ ID NO 70
<211> LENGTH: 836
<212> TYPE: DNA
<213> ORGANISM: Homo sapiens

<400> SEQUENCE: 70
tattccattt acaaaataaa ttcagccctg cactttcttt agatgccttg atttccagaa     60
tggagcttag tgctactgaa taccctggcc acagagccac ctcaggatat tcttttctcc    120
accctagttt atttatttat agatatctgt ttacaaagtc tgtagtaaat cctgatgctg    180
accatctgaa atgtactttt tttctgaatg ctgtttcaat ctaaaatagc agcttttgag    240
aaaacaatga tgtaaattcc ttatgataaa aggatgattc tatatattct ttaatgatat    300
taaatatgcc gaagccaagc acacagtctt tctaaagtgt gtgtatgttt gtgtgaatgt    360
```

| | | | |
|---|---|---|---|
| gaatgatact | gatcttatat | ctgttaaaag | ttgttttaaa | aagctgtggc | atcccattgt | 420 |
| tcatatttgc | caagtcttct | gtaaagatgt | ctaggacgaa | atattttatg | tgctaatgca | 480 |
| tgtatttgta | aaccagattt | gtttaccact | caaaattaac | ttgttttctt | catccaaaaa | 540 |
| agtttatttc | ttccacgtac | ttaaattttc | tgtgtgggta | taatatagct | ttctaatttt | 600 |
| tttctttcac | aaaggcaggt | tcaaaattct | gttgaaagaa | aaatgctttc | tgaaactgag | 660 |
| gtataacacc | agagcttgct | gtttaaagga | ttatatgatg | tacatcagtt | ctataaatgt | 720 |
| gctcagcagt | ttaacatgtg | aatcctgttt | taaagtgctc | agatttcaac | tgtgtaagcc | 780 |
| attgatataa | cgctgtaatt | aaaaatgttt | atatgaaaaa | aaaaaaaaa | aaaaaa | 836 |

<210> SEQ ID NO 71
<211> LENGTH: 618
<212> TYPE: DNA
<213> ORGANISM: Homo sapiens

<400> SEQUENCE: 71

| | | | | | | |
|---|---|---|---|---|---|---|
| gttgcagtga | gctcaagtgt | tgggtgtatc | agctcaaaac | accatgtgat | gccaatcatc | 60 |
| tccacaggag | caatttgttt | acctttttt | tctgatgctt | tactaacttc | atcttttaga | 120 |
| tttaaatcat | tagtagatcc | tagaggagcc | agtttcagaa | aatatagatt | ctagttcagc | 180 |
| accaccgta | gttgtgcatt | gaaataatta | tcattatgat | tatgtatcag | agcttctggt | 240 |
| tttctcattc | tttattcatt | tattcaacaa | ccacgtgaca | aacactggaa | ttacaggatg | 300 |
| aagatgagat | aatccgctcc | ttggcagtgt | tatactatta | taacctga | aaaacaaac | 360 |
| aggtaatttt | cacacaaagt | aatagatatc | atgacacatt | taaaataggg | cactactgga | 420 |
| acacacagat | aggacatcca | ggttttgggt | caatattgta | gacttttgg | tggatgagat | 480 |
| atgcaggttg | atrccagaag | gacaacaaaa | acatatgtca | gatagaaggg | aggagcaaat | 540 |
| gccaagagct | ggagctgagg | aagatcactg | tgaaattcta | tgtagtctag | ttggctggat | 600 |
| gctagagcaa | agaggtgg | | | | | 618 |

<210> SEQ ID NO 72
<211> LENGTH: 806
<212> TYPE: DNA
<213> ORGANISM: Homo sapiens

<400> SEQUENCE: 72

| | | | | | | |
|---|---|---|---|---|---|---|
| tctacgatgg | ccatttgctc | attgtctttc | ctctgtgtgt | agtgagtgac | cctggcagtg | 60 |
| tttgcctgct | cagagtggcc | cctcagaaca | acagggctgg | ccttggaaaa | accccaaaac | 120 |
| aggactgtgg | tgacaactct | ggtcaggtgt | gatttgacat | gagggccgga | ggcggttgct | 180 |
| gacggcagga | ctgagaggc | tgcgtgcccg | gcactggcag | cgaggctcgt | gtgtccccca | 240 |
| ggcagatctg | ggcactttcc | caacccaggt | ttatgccgtc | tccagggaag | cctcggtgcc | 300 |
| agagtggtgg | gcagatctga | ccatccccac | agaccagaaa | caaggaattt | ctgggattac | 360 |
| ccagtccccc | ttcaacccag | ttgatgtaac | cacctcattt | tttacaaata | cagaatctat | 420 |
| tctactcagg | ctatgggcct | cgtcctcact | cagttattgc | gagtgttgct | gtccgcatgc | 480 |
| tccgggcccc | acgtggctcc | tgtgctctag | atcatggtga | ctccccgcc | ctgtggttgg | 540 |
| aatcgatgcc | acggattgca | ggccaaattt | cagatcgtgt | ttccaaacac | ccttgctgtg | 600 |
| cccttttaatg | ggattgaaag | cacttttacc | acatggagaa | atatatttt | aatttgtgat | 660 |
| gcttttctac | aaggtccact | atttctgagt | ttaatgtgtt | tccaacactt | aaggagactc | 720 |
| taatgaaagc | tgatgaattt | tcttttctgt | ccaaacaagt | aaaataaaaa | taaagtcta | 780 |

```
tttagatgtt gaaaaaaaaa aaaaaa                                           806

<210> SEQ ID NO 73
<211> LENGTH: 301
<212> TYPE: DNA
<213> ORGANISM: Homo sapiens
<220> FEATURE:
<221> NAME/KEY: misc_feature
<222> LOCATION: 59
<223> OTHER INFORMATION: n = A,T,C or G

<400> SEQUENCE: 73
actctggtaa gcttgttgtt gtccaagtga agctccctca gatgaggcgt gttggccana     60
gagccattgt caacagcaga gatgctgttg aaactcaatc ccaacttagc caaattattc    120
agtcctttca ggctagctgc atcaactctg ctgattttgt tgccatcaag atgtaattcc    180
gtaagggaag gaggaagacc ttgaggaatg ctggygatat tggyatcagc aatgcggatg    240
tasgaagagc ttcttcmttc cctggaaagc cccatttcca atyccttgag ctcttcakcg    300
g                                                                   301

<210> SEQ ID NO 74
<211> LENGTH: 401
<212> TYPE: DNA
<213> ORGANISM: Homo sapiens

<400> SEQUENCE: 74
agtttacatg atccctgtaa cagccatggt ctcaaactca gatgcttcct ccatctgcca     60
agtgtgttct ggatacagag cacatcgtgg cttctggggt cacactcagc ttaggctgtg    120
ggtccacaga gcactcatct ggctgggcta tggtggtggt ggctctactc aagaagcaaa    180
gcagttacca gcacattcaa acagtgtatt gaacatcttt taaatatcaa agtgagaaac    240
aagaaggcaa cataataatg ttatcagaaa gatgttagga agtaaggaca gctgtgtaaa    300
gcttgaggct gaaaagtagc ttgccagctt catttctttg gtttcttggg tagtgggccg    360
ccggaacagc aagatgtgag gttctggttc atggatcata t                       401

<210> SEQ ID NO 75
<211> LENGTH: 612
<212> TYPE: DNA
<213> ORGANISM: Homo sapiens

<400> SEQUENCE: 75
ttatttttca atttttattt tggttttctt acaaaggttg acatttttcca taacaggtgt     60 aagagtgttg aaaaaaaaat tcaaattttt ggggagcgag ggaaggagtt aatgaaactg    120
tattgcacaa tgctctgatc aatccttctt tttctctttt gcccacaatt taagcaagta    180
gatgtgcaga agaaatggaa ggattcagct ttcagttaaa aaagaagaag aagaaatggc    240
aaagagaaag ttttttcaaa tttctttctt ttttaattta gattgagttc atttatttga    300
aacagactgg gccaatgtcc acaaagaatt cctggtcagc accaccgatg tccaaaggtg    360
caatatcaag gaagggcagg cgtgatggct tatttgtttt gtattcaatg attgtctttc    420
cccattcatt tgtcttttta gagcagccat ctacaagaac agtgtaagtg aacctgctgt    480
tgccctcagc aacaagttca acatcattag agccctgtag aatgacagcc tttttcaggt    540
tgccagtctc ctcatccatg tatgcaatgc tgttcttgca gtggtaggtg atgttctgag    600
aggcatagtt gg                                                       612
```

<210> SEQ ID NO 76
<211> LENGTH: 844
<212> TYPE: DNA
<213> ORGANISM: Homo sapiens

<400> SEQUENCE: 76

| | | | | | |
|---|---|---|---|---|---|
| ggctttcgag | cggccgcccg | ggcaggtctg | atggttctcg | taaaaacccc | gctagaaact | 60 |
| gcagagacct | gaaattctgc | catcctgaac | tcaagagtgg | agaatactgg | gttgaccta | 120 |
| accaaggatg | caaattggat | gctatcaagg | tattctgtaa | tatggaaact | ggggaaacat | 180 |
| gcataagtgc | caatcctttg | aatgttccac | ggaaacactg | gtggacagat | tctagtgctg | 240 |
| agaagaaaca | cgtttggttt | ggagagtcca | tggatggtgg | ttttcagttt | agctacggca | 300 |
| atcctgaact | tcctgaagat | gtccttgatg | tgcagcykgc | attccttcga | cttctctcca | 360 |
| gccgagcttc | ccagaacatc | acatatcact | gcaaaaatag | cattgcatac | atggatcagg | 420 |
| ccagtggaaa | tgtaaagaag | gccctgaagc | tgatggggtc | aaatgaaggt | gaattcaagg | 480 |
| ctgaaggaaa | tagcaaattc | acctacacag | ttctggagga | tggttgcacg | aaacacactg | 540 |
| gggaatggag | caaaacagtc | tttgaatatc | gaacacgcaa | tgctgttcct | tgacattgca | 600 |
| ccaccaatgt | ccagaggtgc | aatgtcaagg | aacggcaggc | gagatggctt | atttgttttg | 660 |
| tattcaatga | ttgtcttgcc | ccattcattt | gtctttttgg | agcagccatc | gactaggaca | 720 |
| gagtaggtga | acctgctgtt | gccctcagca | acaagttcca | catcgttgga | accctgcaga | 780 |
| agcacagcct | tgttcaarct | gcccgtctcc | tcatccagat | acctcggccg | cgaccacgct | 840 |
| aatc | | | | | 844 |

<210> SEQ ID NO 77
<211> LENGTH: 314
<212> TYPE: DNA
<213> ORGANISM: Homo sapiens

<400> SEQUENCE: 77

| | | | | | |
|---|---|---|---|---|---|
| ccagtcctcc | acttggcctg | atgagagtgg | ggagtggcaa | gggacgtttc | tcctgcaata | 60 |
| gacacttaga | tttctctctt | gtgggaagaa | accacctgtc | catccactga | ctcttctaca | 120 |
| ttgatgtgga | aattgctgct | gctaccacca | cctcctgaag | aggcttccct | gatgccaatg | 180 |
| ccagccatcc | tggcatcctg | gccctcgagc | aggctgcggt | aagtagcgat | ctcctgctcc | 240 |
| agccgtgtct | ttatgtcaag | cagcatcttg | tactcctggt | tctgagcctc | catctcgcat | 300 |
| cggagctcac | tcag | | | | 314 |

<210> SEQ ID NO 78
<211> LENGTH: 548
<212> TYPE: DNA
<213> ORGANISM: Homo sapiens

<400> SEQUENCE: 78

| | | | | | |
|---|---|---|---|---|---|
| accaagagcc | aagtgttaca | caggatatt | taaaaataaa | atgtttttgg | aatcctcacc | 60 |
| tcccatgcta | tcttctaaga | taactacaaa | tattcttcaa | agatttaact | gagttctgcc | 120 |
| aaggacctcc | caggactcta | tccagaatga | ttattgtaaa | gctttacaaa | tcccaccttg | 180 |
| gccctagcga | taattaggaa | atcacaggca | aacctcctct | tcggagacc | aatgaccagg | 240 |
| ccaatcagtc | tgcacattgg | ttttgttaga | tactttgtgg | agaaaaacaa | aggctcgtga | 300 |
| tagtgcagct | ctgtgcctac | agagagcctc | ccttttggtt | ctgaaattgc | tgatgtgaca | 360 |
| gagacaaagc | tgctatgggt | ctaaaacctt | caataaagta | actaatgaca | ctcaaggtcc | 420 |

```
tgggactctg agacagacgg tggtaaaacc cacagctgcg attcacattt ccaatttatt      480
ttgagctctt tctgaagctg ttgcttccta cctgagaatt cccatttaga gagctgcaca      540
gcacagtc                                                              548

<210> SEQ ID NO 79
<211> LENGTH: 646
<212> TYPE: DNA
<213> ORGANISM: Homo sapiens

<400> SEQUENCE: 79
accccgtcac tatgtgaata aaggcagcta gaaaatggac tcaattctgc aagccttcat       60
ggcaacagcc catattaaga cttctagaac aagttaaaaa aaatcttcca tttccatcca      120
tgcatgggaa aagggcttta gtatagttta ggatggatgt gtgtataata ataaaatgat      180
aagatatgca tagtggggga ataaagcctc agagtccttc cagtatgggg aatccattgt      240
atcttagaac cgagggattt gtttagattg ttgatctact aattttttc ttcacttata       300 tttgaatttt caatgatagg acttattgga aattggggat aattctgttg tggtattaaa      360
taatattcat tttttaaaaa ctcatcttgg tattgagtta gtgcattgac ttccaatgaa      420
ttgacataag cccatatttc attttaacca gaaacaaaaa ctagaaaatg ttactcccta      480
aataggcaac aatgtatttt ataagcactg cagagattta gtaaaaaaca tgtatagtta      540
ctttagaaac aacttctgac acttgagggt tacccaatgg tctccttccc attctttata      600
tgaggtaaat gcaaaccagg gagccaccga ataaacagcc ctgagt                     646

<210> SEQ ID NO 80
<211> LENGTH: 276
<212> TYPE: DNA
<213> ORGANISM: Homo sapiens
<220> FEATURE:
<221> NAME/KEY: misc_feature
<222> LOCATION: 16, 29, 32, 45, 53, 55, 58, 59, 65, 66, 75, 77, 85, 90,
      97, 109, 112, 163, 170
<223> OTHER INFORMATION: n = A,T,C or G

<400> SEQUENCE: 80
gtctgaatga gcttcnctgc gagatggganc ancataaccc agaantccaa aancntanng      60
aacgnnaaaa cccgntngaa caagnaaacn gcaactnacg gccgcctgnt gnagggcgag      120
gacgcccacc tctcctcctc ccagttctcc tctggatcgc agncatccan agatgtgacc      180
tcttccagcc gccaaatccg caccaaggtc atggatgtgc acgatggcaa ggtgggtgtc      240
cacccacgaa caggtccttc gcaccaagaa ctgagg                                276

<210> SEQ ID NO 81
<211> LENGTH: 647
<212> TYPE: DNA
<213> ORGANISM: Homo sapiens

<400> SEQUENCE: 81
gtcctgcctt tcatctttc tttaaaaaaa ataaatgttt acaaaacatt tccctcagat        60
tttaaaattc atggaagtaa taaacagtaa taaatatgg atactatgaa aactgacaca       120
cagaaaaaca taaccataaa atattgttcc aggatacaga tattaattaa gagtgacttc      180
gttagcaaca cgtagacatt catacatatc cggtggaaga ctggtttctg agatgcgatt      240
gccatccaaa cgcaaatgct tgatcttgga gtaggrtaat ggccccagga tcttgcagaa      300
gctctttatg tcaaacttct caagttgatt gacctccagg taatagtttt caaggttttc      360
```

```
attgacagtt ggtatgtttt taagcttgtt ataggacaga tccagctcaa ccagggatga    420
cacattgaaa gaatttccag gtattccact atcagccagt tcgttgtgag ataaacgcag    480
atactgcaat gcattaaaac gcttgaaata ctcatcaggg atgttgctga tcttattgtt    540
gtctaagtag agagttagaa gagagacagg gagaccagaa ggcagtctgg ctatctgatt    600
gaagctcaag tcaaggtatt cgagtgattt aagacccttta aaagcag                647
```

<210> SEQ ID NO 82
<211> LENGTH: 878
<212> TYPE: DNA
<213> ORGANISM: Homo sapiens

<400> SEQUENCE: 82

```
ccttctttcc ccactcaatt cttcctgccc tgttattaat taagatatct tcagcttgta     60
gtcagacaca atcagaatya cagaaaaatc ctgcctaagg caaagaaata taagacaaga    120
ctatgatatc aatgaatgtg ggttaagtaa tagatttcca gctaaattgg tctaaaaaag    180
aatattaagt gtggacagac ctatttcaaa ggagcttaat tgatctcact tgttttagtt    240
ctgatccagg gagatcaccc ctctaattat ttctgaactt ggttaataaa agtttataag    300
atttttatga agcagccact gtatgatatt ttaagcaaat atgttattta aaatattgat    360
ccttcccttg gaccaccttc atgttagttg ggtattataa ataagagata caaccatgaa    420
tatattatgt ttatacaaaa tcaatctgaa cacaattcat aaagatttct cttttatacc    480
ttcctcactg gcccctcca cctgcccata gtcaccaaat tctgttttaa atcaatgacc     540
taagatcaac aatgaagtat tttataaatg tatttatgct gctagactgt gggtcaaatg    600 tttccattt caaattattt agaattctta tgagtttaaa atttgtaaat ttctaaatcc    660
aatcatgtaa aatgaaactg ttgctccatt ggagtagtct cccacctaaa tatcaagatg    720
gctatatgct aaaagagaa aatatggtca agtctaaaat ggctaattgt cctatgatgc    780
tattatcata gactaatgac atttatcttc aaaacaccaa attgtcttta gaaaaattaa    840
tgtgattaca ggtagagaac ctcggccgcg accacgct                            878
```

<210> SEQ ID NO 83
<211> LENGTH: 645
<212> TYPE: DNA
<213> ORGANISM: Homo sapiens

<400> SEQUENCE: 83

```
acaaacattt tacaaaaaag aacattacca atatcagtgg cagtaagggc aagctgaaga     60
ataaatagac tgagtttccg ggcaatgtct gtcctcaaag acatccaaac tgcgttcagg    120
cagctgaaac aggcttcttt cccagtgaca agcatatgtg gtcagtaata caaacgatgg    180
taaatgaggc tactacatag gcccagttaa caaactcctc ttctcctcgg gtaggccatg    240
atacaagtgg aactcatcaa ataatttaaa cccaaggcga taacaacgct atttcccatc    300
taaactcatt taagccttca caatgtcgca atggattcag ttacttgcaa acgatcccgg    360
gttgtcatac agatacttgt ttttacacat aacgctgtgc catcccttcc ttcactgccc    420
cagtcaggtt tcctgttgtt ggaccgaaag gggatacatt ttagaaatgc ttccctcaag    480
acagaagtga gaaagaaagg agaccctgag gccaggatct attaaacctg gtgtgtgcgc    540
aaaagggagg gggaaggcag gaatttgaaa ggataaacgt ctcctttgcg ccgaggaatc    600
aggaagcgtg actcacttgg gtctgggacg ataccgaaat ccggt                    645
```

<210> SEQ ID NO 84
<211> LENGTH: 301
<212> TYPE: DNA
<213> ORGANISM: Homo sapiens
<220> FEATURE:
<221> NAME/KEY: misc_feature
<222> LOCATION: 270, 284
<223> OTHER INFORMATION: n = A,T,C or G

<400> SEQUENCE: 84

```
tctgatgtca atcacaactt gaaggatgcc aatgatgtac caatccaatg tgaaatctct      60
cctcttatct cctatgctgg agaaggatta gaaggttatg tggcagataa agaattccat     120
gcacctctaa tcatcgatga gaatggagtt catgggctgg tgaaaaatgg tatttgaacc     180
agataccaag ttttgtttgc cacgatagga atagctttta ttttttgatag accaactgtg    240
aacctacaag acgtcttgga caactgaagn ttaaatatcc acangggttt attttgcttg     300
g                                                                     301
```

<210> SEQ ID NO 85
<211> LENGTH: 296
<212> TYPE: DNA
<213> ORGANISM: Homo sapiens
<220> FEATURE:
<221> NAME/KEY: misc_feature
<222> LOCATION: 16, 20, 240
<223> OTHER INFORMATION: n = A,T,C or G

<400> SEQUENCE: 85

```
agcgtgggtc gcggcncgan gtagagaacc gactgaaacg tttgagatga agaaagttct      60
cctcctgatc acagccatct ggcagtggc tgttggtttc ccagtctctc aagaccagga     120
acgagaaaaa agaagtatca gtgacagcga tgaattagct tcagggtttt ttgtgttccc    180
ttacccatat ccatttcgcc cacttccacc aattccattt ccaagatttc catggtttan    240
acgtaatttt cctattccaa tacctgaatc tgcccctaca actccccttc ctagcg         296
```

<210> SEQ ID NO 86
<211> LENGTH: 806
<212> TYPE: DNA
<213> ORGANISM: Homo sapiens

<400> SEQUENCE: 86

```
tctacgatgg ccatttgctc attgtctttc ctctgtgtgt agtgagtgac cctggcagtg      60
tttgcctgct cagagtggcc cctcagaaca acagggctgg ccttggaaaa accccaaaac    120
aggactgtgg tgacaactct ggtcaggtgt gatttgacat gagggccgga ggcggttgct    180
gacggcagga ctggagaggc tgcgtgcccg gcactggcag cgaggctcgt gtgtccccca    240
ggcagatctg ggcactttcc caacccaggt ttatgccgtc tccagggaag cctcggtgcc    300
agagtggtgg gcagatctga ccatccccac agaccagaaa caaggaattt ctgggattac    360
ccagtcccc ttcaacccag ttgatgtaac cacctcattt tttacaaata cagaatctat    420
tctactcagg ctatgggcct cgtcctcact cagttattgc gagtgttgct gtccgcatgc    480
tccgggcccc acgtggctcc tgtgctctag atcatggtga ctccccgcc ctgtggttgg     540
aatcgatgcc acgattgca ggccaaattt cagatcgtgt ttccaaacac ccttgctgtg     600
ccctttaatg ggattgaaag cacttttacc acatggagaa atatattttt aatttgtgat    660
gcttttctac aaggtccact atttctgagt ttaatgtgtt tccaacactt aaggagactc    720
taatgaaagc tgatgaattt tcttttctgt ccaaacaagt aaaataaaaa taaaagtcta    780
```
tttagatgtt gaaaaaaaaa aaaaaa                                            806

<210> SEQ ID NO 87
<211> LENGTH: 620
<212> TYPE: DNA
<213> ORGANISM: Homo sapiens

<400> SEQUENCE: 87 ttttttgcatc agatctgaaa tgtctgagag taatagtttc tgttgaattt ttttttgttc      60 attttttctgc acagtccatt ctgtttttat tactatctag cttgaaaata tatagtttga    120
aattatgaca tccttcctct tgttattttt cctcatgatt gctttggcta ttcaaagttt     180
attttagttt catgtaaatt tttgaattgt attttccatt attgtgaaaa tagtaccact     240
gcaattttaa taggaagttt attgaatcta tagattactt tggataatat ggcacttcaa    300
taatattcat gttttcaatt catagacaaa atattttaaa atttatttgt atcttttcta     360 attttttcctt tttttattgt aaagatttac ctccttggtt aatattttcc tcagaaattt   420
attatttaag gtatagtcaa taaaattttc ttcctctatt ttgtcagata gtttaagtgt    480
atgaaaccat agatatactt gtatgttaat tttatatttt gctaatttac tgagtgtatt   540
tattagttta gagaggtttt aatgtactgt ttatggtttt ttaaatataa gattacttat    600
tttttaaaaa aaaaaaaaaa                                                 620

<210> SEQ ID NO 88
<211> LENGTH: 308
<212> TYPE: DNA
<213> ORGANISM: Homo sapiens
<220> FEATURE:
<221> NAME/KEY: misc_feature
<222> LOCATION: 9, 189, 194, 206, 238, 296
<223> OTHER INFORMATION: n = A,T,C or G

<400> SEQUENCE: 88
tagctgtgnt cagcaggccg aggttttttt tttttttgag atggagtctc gccctgtcac      60
ccaggctgga gtgcagtggc ctgatctcag ctcactgcaa gctccacctc ctggattcac    120
gctattctcc tgcctcagcc tcccaagtag ctgggactac aggcgcccgc caccacgccc    180
agctaattnt ttgnattttt agtacnagat gcggtttcat cgtgttagcc agcatggnct    240
cgatctcctg acctcgtgaa ctgcccgcct cggcctccca agacctgcc cgggcnggcc    300 gctcgaaa                                                              308

<210> SEQ ID NO 89
<211> LENGTH: 492
<212> TYPE: DNA
<213> ORGANISM: Homo sapiens
<220> FEATURE:
<221> NAME/KEY: misc_feature
<222> LOCATION: 448
<223> OTHER INFORMATION: n = A,T,C or G

<400> SEQUENCE: 89
agcggccgcc cgggcaggtc tgttaagtaa catacatatc accttaataa aaatcaagat      60
gaaatgtttt agaaactatt ttatcaaaag tggctctgat acaaagactt gtacatgatt    120
gttcacagca gcactattaa tgccaaaaag tagacaaaac ctaaatgtcc attaactgat    180
aagcaaaatg tggtatatcc atacaatgga atattatgta gcccacaaca tggcatggag   240
tactacaaca tggatgagcc tcaaaaacgt tatgctaaat gaaaaaagtc agatatagga   300

```
aaccacatgt catatgatcc catttatatg aaatagccag aaaaggcaag tcatagaaac    360
aagatagatc ggaaaatggg ttggaggact acaaatggca ccaggatct ttgaagttga     420 tggaaatggt ctaaaatcag actgtggntg tggttgaaca agtctgtaaa tttaccaaaa    480
tgcgttaata ca                                                       492

<210> SEQ ID NO 90
<211> LENGTH: 390
<212> TYPE: DNA
<213> ORGANISM: Homo sapiens
<220> FEATURE:
<221> NAME/KEY: misc_feature
<222> LOCATION: 106, 184, 206, 209, 234, 314
<223> OTHER INFORMATION: n = A,T,C or G

<400> SEQUENCE: 90
tcgagcggcc gcccgggcag gtacaagctt tttttttttt tttttttttt ttttctaaca    60
gttctctgtt ttattgcaat acagcaaagt ctggttaata ttaagngata tcaacataaa   120
gtattggtga ggagtctttt gtgacatttt ttaccatccc accttaaata tttctgtgca   180
aaanaatcca catcattgtt tggtancana ggatctctta aaaagttccc taanacactg   240
agggcataaa accaaacaaa ataaaataag gagtgatagg ctaaagcagt atcttcccct   300
ccatccacat ttgncaagca ttatattcta accaaaaaat gatcacacca ggccatgcaa   360
aactgtccaa tattaccgag aaaaaaccct                                    390

<210> SEQ ID NO 91
<211> LENGTH: 192
<212> TYPE: DNA
<213> ORGANISM: Homo sapiens

<400> SEQUENCE: 91
agcgtggtcg cggccgaggt ctgtcaatta atgctagtcc tcaggattta aaaaataatc    60
ttaactcaaa gtccaatgca aaaacattaa gttggtaatt actcttgatc ttgaattact   120
tccgttacga aagtccttca cattttcaa actaagctac tatatttaag gcctgcccgg    180
gcggccgctc ga                                                       192

<210> SEQ ID NO 92
<211> LENGTH: 570
<212> TYPE: DNA
<213> ORGANISM: Homo sapiens
<220> FEATURE:
<221> NAME/KEY: misc_feature
<222> LOCATION: 519, 559
<223> OTHER INFORMATION: n = A,T,C or G

<400> SEQUENCE: 92
agcgtggtcg cggccgaggt ctgacaacta acaaagaagc aaaaactggc atcttggaca    60
tcctagtatt acacttgcaa gcaattagaa cacaaggagg gccaaggaaa aagtttagct   120
ttgaatcact tccaaatcta ctgattttga ggttccgcag tagttctaac aaaacttttc   180
agacaatgtt aactttcgat taagaaagaa aaaaacccca aacatcttca ggaattccat   240
gccaggttca gtctcttcca gtgagcccgc ttgctaaaag tccacgtgca ccattaatta   300
gctgggctgg cagcaccatg taaaagaag cctattcacc accaaccaca cagactagac    360
atgtaaagta ggatcaagta atggatgaca accatggtcg tggaatatgg tcaatgagag   420
tcagaaaagt acaggcacca gtacaagcag cagataacag aattgacggg ccaaggata    480 aaaataggct tatttaaata ggatgctaca gaacacatnc acttctaatt ggaagctgct   540
```

```
ttacactggg tggcattgna ccatatgcat                                      570
```

```
<210> SEQ ID NO 93
<211> LENGTH: 446
<212> TYPE: DNA
<213> ORGANISM: Homo sapiens
<220> FEATURE:
<221> NAME/KEY: misc_feature
<222> LOCATION: 328, 389
<223> OTHER INFORMATION: n = A,T,C or G

<400> SEQUENCE: 93
tcgagcggcc gcccgggcag gtccaggttt ttatttagtt gtgtaatctt ggacaagtta     60
cctaactttt ttgagtctga atatatttaa tctgcaaaat gagaatcatg ataatacgtc    120
ataggcttaa ttaggaggat taaatgaaat aatttatagg tggtgccatg gttacataca    180
agtattagta gttaattctt ttcctttgtt tactttttata gtataggttg gatgaaggtt   240
ccagtatagg caaaaatact acttgggggt aaagtagagt gtgatacttt atttgaaatg    300
ttccctgaat ctgatcttta cttttttgnta ctgctgcact acccaaatcc aaattttcat   360
cccaacattc ttggatttgt gggacagcng tagcagcttt ccaatataaa tctatactac    420
atcttttctt actttggtgc tttttg                                          446

<210> SEQ ID NO 94
<211> LENGTH: 409
<212> TYPE: DNA
<213> ORGANISM: Homo sapiens

<400> SEQUENCE: 94
cgagcggccg cccgggcagg tccatcagct cttctgctta gaatacgagg cagacagtgg     60
agaggtcaca tcagttatcg tctatcaggg tgatgaccca agaaaggtga gtgagaaggt    120
gtcggcacac acgcctctgg atccacccat gcgagaagcc ctcaagttgc gtatccagga    180
ggagattgca aagcgccaga gccaacactg accatgttga aggcgttctc tccaggctgg    240
attcactgca ctcggaagaa ttctgcccag ggaatttagt gtgggggtac caggaccagt    300
ttgtcttgat cttgagaccc ccagagctgc tgcatccata gggtgttgca ggactacacc    360
tggcctgcct tgcagtcatt ctttcttata tgttgaccca tttgcccaa                 409

<210> SEQ ID NO 95
<211> LENGTH: 490
<212> TYPE: DNA
<213> ORGANISM: Homo sapiens
<220> FEATURE:
<221> NAME/KEY: misc_feature
<222> LOCATION: 486
<223> OTHER INFORMATION: n = A,T,C or G

<400> SEQUENCE: 95
tcgagcggcc gcccgggcag gtcctacttg tttgcagctt ccacacactg cacctaccta     60
ctacctctct tccatgctta actgggttta gaaaggtgag ctatgcgtag aagaactact    120
tgggatattc aagtgctgta tttgaacgat aagcctatag ataacagtct gaagctgcaa    180
gggagacttt gttagtacac tactataaac aggtaaacta cctgtttgta cttgatatag    240
tgcatatgaa atgactgatt taatacaaaa ctacagaaca tgcaaaattt tttctgagat    300
gttaagtatt acttcagtgg agaacaaaac ttacttaacc tttcgctaat gcatgtagta    360
ccagaaagca aacatggttt tagcttccctt tactcaaaat atgaacatta agtggttgtg    420
```

```
aattttgtct gccaagtggt tcagaaaata cattataaat aacctaagtt aaaaaaaga      480 aactgngaac                                                            490

<210> SEQ ID NO 96
<211> LENGTH: 223
<212> TYPE: DNA
<213> ORGANISM: Homo sapiens

<400> SEQUENCE: 96
agcgtggtcg cggccgaggt ctggaagccc accctaggac ttgaatggca ccttgtcctt      60
tctctgccag taatgcaatc caacacaata tgctacaggg aaaacagaat ttccacggtg     120
ccgccctctg gtacaaggga acagcacgc aaagcaaaag ccacagagg gctccctgag      180 aatccagtac aactaagcga ggacctgccc gggcggccgc tcg                        223

<210> SEQ ID NO 97
<211> LENGTH: 527
<212> TYPE: DNA
<213> ORGANISM: Homo sapiens
<220> FEATURE:
<221> NAME/KEY: misc_feature
<222> LOCATION: 404, 436, 451, 476
<223> OTHER INFORMATION: n = A,T,C or G

<400> SEQUENCE: 97
tcgagcggcc gcccgggcag gtctgtgcag gagacactga agtgggtagt gtccataatc      60
tttttagcct gttgctgaaa ttccagttgt actccttcaa accaaaatgc ttacaggatc     120
atgggaaagc ctcggttgca gaaatcaaga caggcaagtg ggaagataac tcggctttga     180
ggttaaacag atctgggttc aaagcatagt ttcactctct gtcttgtgaa gtgtcctggg     240
tgaagtcatt tcctctcttg aatttcagag aggatgaaaa tataaaaagt ataataacta     300
tcttcataat ctttgtgagg attaaagaag acgaagtgtg tgaaaagcta agcacagagc     360
aggcattcta caataagtag ttattatttt tggaaccatc ccgncccctag ccccagccca     420 attaccttct cttagnctct tcatatcgaa ngccgtaatc ttgaccttct cttgcnactg     480
gattggtgct ggttgatgcc caaacttccc gagatgctgt ctgggaa                    527

<210> SEQ ID NO 98
<211> LENGTH: 514
<212> TYPE: DNA
<213> ORGANISM: Homo sapiens
<220> FEATURE:
<221> NAME/KEY: misc_feature
<222> LOCATION: 455
<223> OTHER INFORMATION: n = A,T,C or G

<400> SEQUENCE: 98
tcgagcggcc gcccgggcag gtctggctcc catggccctt ggggtggcct gactctgtca      60
ctattcctaa aaccttctag gacatctgct ccaggaagaa ctttcaacac caaaattcat     120 ctcaattta cagatgggaa aagtgattct gagaccagac cagggtcagg ccaaggtcat     180
ccagcatcag tggctgggct gagactgggc ccagggaacc ctgtctgctc ctcttttcc     240 cagagctgtg agttctctag ccaaggctgc actcttgagg gagagccagg aagcatagct     300
gaggccatga caacctcact cttcacctga aaatttaacc cgtggcagag gatccaggca     360
catataggct tcggagccaa acaggacctc ggccgcgacc acgctaagcc gaattccagc     420
acactggcgg ccgttactag tggatcccga gcttngtac caagcttggc gtaatcatgg     480
gcatagctgg ttcctggggt gaaaatggta tccg                                  514
```

<210> SEQ ID NO 99
<211> LENGTH: 530
<212> TYPE: DNA
<213> ORGANISM: Homo sapiens
<220> FEATURE:
<221> NAME/KEY: misc_feature
<222> LOCATION: 430, 522
<223> OTHER INFORMATION: n = A,T,C or G

<400> SEQUENCE: 99
tcgagcggcc gcccgggcag gtctgaagaa acaggtataa atttggcagc cagtaatttt      60
gacagggaag ttacagcttg catgacttta aatatgtaaa tttgaaaata ctgaatttcg     120
agtaatcatt gtgctttgtg ttgatctgaa aaatataaca ctggctgtcg aagaagcatg     180
ttcaaaaata tttaattcac ttcaaaatgt catacaaatt atggtggttt ctatgcaccc     240
ctaaagcttc aagtcattta gctcaggtac atactaaagt aatatattaa ttcttccagt     300
acagtggtgt ttcataccat tgacatttgc atacccctaga ataatttaag aaagacatgt    360
gtaatattca caatgttcag aaaagcaagc aaaaggtcaa ggaacctgct ttggttcttc     420
tggagatggn ctcatatcag cttcataaac attcattcta caaaatagta agctaaccat     480 ttgaaccccca atttccagat taagcatatt ttctcataaa tnatgaagcc               530

<210> SEQ ID NO 100
<211> LENGTH: 529
<212> TYPE: DNA
<213> ORGANISM: Homo sapiens

<400> SEQUENCE: 100
agcgtggtcg cggccgaggt ccaggcacgg tggcttatgt gtgtaatccc agcacttggg      60
gaggctgagg gaggtggatc acttgagtcc aggagtttga gaccagtctg ggcaacatgg     120
cgaaacttca tcactaccaa agaagaaaaa aattagccag gtgtggtggt gtatgcctgt     180
agtcccagat actctggtgg ctgaggtgag aggatagctt gagcccagga aattgaggct     240
gcagtgaact atgattgcac tactgtgctc cagcttgggc aacagagtga gatcttgtct     300
ccaaaagtcc ttgaaggatt ttaggaagtt gttaaaagtc ttgaaacgat gtttgggggc     360
atgttagggt tcttgaatgt ttaattcctc taataactgc ttattcaaga gaagcatttc     420
tgactgggtg cggggcagtg gcttcatgcc ccataatccc agtactttgg gaggctgaag     480
caggaacatt gcttgagccc aggacttcaa gaacagcctg ggtaacata                 529

<210> SEQ ID NO 101
<211> LENGTH: 277
<212> TYPE: DNA
<213> ORGANISM: Homo sapiens

<400> SEQUENCE: 101
tcgagcggcc gcccgggcag gtcgcaggaa gaggatggaa actgaggagt ccaggaagaa      60
gagggaacga gatcttgagc tggaaatggg agatgattat attttggatc ttcagaagta     120 ctgggatttta atgaatttgt ctgaaaaaca tgataagata ccagaaatct gggaaggcca    180
taatatagct gattatattg atccagccat catgaagaaa ttggaagaat tagaaaaaga    240
agaagagctg agaacagacc tcggccgcga ccacgct                               277

<210> SEQ ID NO 102
<211> LENGTH: 490
<212> TYPE: DNA

<213> ORGANISM: Homo sapiens

<400> SEQUENCE: 102

```
gcgtggtcgc ggccgaggtc tgacggcttt gctgtcccag agccgcctaa acgcaagaaa      60
agtcgatggg acagttagag gggatgtgct aaagcgtgaa atcagttgtc cttaattttt     120
agaaagattt tggtaactag gtgtctcagg gctgggttgg ggtccaaagt gtaaggaccc     180
cctgccctta gtggagagct ggagcttgga gacattaccc cttcatcaga aggaattttc     240
ggatgttttc ttgggaagct gttttggtcc ttggaagcag tgagagctgg gaagcttctt     300
ttggctctag gtgagttgtc atgtgggtaa gttgaggtta tcttgggata aagggtcttc     360
tagggcacaa aactcactct aggtttatat tgtatgtagc ttatattttt tactaaggtg     420
tcaccttata agcatctata aattgacttc ttttcttag ttgtatgacc tgccccgggc      480
ggccgctcga                                                             490
```

<210> SEQ ID NO 103
<211> LENGTH: 490
<212> TYPE: DNA
<213> ORGANISM: Homo sapiens

<400> SEQUENCE: 103

```
gagcggccgc ccgggcaggt ccaaaccagc ttgctcataa gtcattaacc aaatccatta      60
taggtaattt gttcagttca atgtttacaa ttcttatgga aaaaattagc aacacacaca     120
tttaaaacgt gtgcatttac ctttgcgtga gtgcttaaaa tacatatttc tatttcaaga     180
tgacatttaa aaattattct aatatatcag cagcaaaaat ataatttgca attacaaaaa     240
actaaactag aatccttaag ttattctcat gtttacagtt gtgattcttt aataaatact     300
attatgcagc tctattgttt aagctttctg gatttggttt aaacacatgc atatatattg     360
tcaattgtgg gaagctttac aagttatatt ccatgcactt tttggacaga gttctaacag     420
agccagccag tccacaaaac aggcaagaca aaagttgaat taactggggc aaaataggac     480
tcttatgcaa                                                             490
```

<210> SEQ ID NO 104
<211> LENGTH: 489
<212> TYPE: DNA
<213> ORGANISM: Homo sapiens

<400> SEQUENCE: 104

```
cgtggtcgcg gccgaggtcc aggctggtct cgaactcctg accttgtgat ctgcccgcct      60
cggcctccca agtgttggg attacaggca tgagccactg cgcccgaccg agttgaacat      120
ttaatgtcag actaggccag agtttctcaa tcttttttatt ctcacttccc aaaggagccg    180
ttggagattt tcccctcaat ctctctcctt catgaaattt cataccacaa atatagtatg     240
ttttattttat gtactgtgac cctttgaagg atcacaaacc aatataatag tttttctttt    300
taacccgtca aggaccaagt ttttgcccct gttggaaatg cataaactgg actgatgaat     360
tggtatagat ggcttttatc atgaggatca gaaaaacttg aaattccttg gctacgacac     420
tccatattta tcaccgtata gggaggacct tggtatgggg aagtagaaac acttctacac     480
tttacagca                                                              489
```

<210> SEQ ID NO 105
<211> LENGTH: 479
<212> TYPE: DNA
<213> ORGANISM: Homo sapiens
<220> FEATURE:
<221> NAME/KEY: misc_feature
<222> LOCATION: 142, 453
<223> OTHER INFORMATION: n = A,T,C or G

<400> SEQUENCE: 105

```
gcgtggtcgc ggccgaggtc tgactggctt cagccccaga agttgagctg gcctttagac    60
aaaataattg cacctccctc tgctgcttat tcccttccgt ttttcatttg agtgtgaaca   120
gttagataaa atctgtggct gnctcttcca ccttgctcta gtttccattg ctgtgagcag   180
gccctcctat gccccgcatt tagctacaat gctgtggact cacttgattc ttttttctccg  240
agctttgtct agaaatatgt gaaggtgagg ttaagtgctt ctctgtgtag atccacttag   300
ccctgtctgc tgtctcgatg ggcgttgctt cgtctctcct ctcttccatc ctttccattt   360
gcttctcacc accttctggc ttcttttctt aatgcaataa aggcagtttc taacaaagaa   420
agaatgtggg ctttggagtt agacagacct ggntttaaat tctgcttctg gctctccaa    479
```

<210> SEQ ID NO 106
<211> LENGTH: 511
<212> TYPE: DNA
<213> ORGANISM: Homo sapiens

<400> SEQUENCE: 106

```
tcgcggccga ggtccaaaac gtggattcca atgacctgcc ttgagcccgc ggttgccagg    60
agttggacct gcagtagtat gggaagctca cggcctaaat accgactgcc ctctgacccc   120
accgtccagc gattctagaa catttctagt aggaaagaca tagcaaggga ttttcatgat   180
tgggaaatac tgggagacaa gctgaagatt tgttaagggc tatgcttctg tcatcttta    240
ggtatttaag gctactcctt tagctagcta ctttgagctg tttaaagtga ctatctccct   300
acacagagtt acacaatgag catctctgaa agagaatatt accctggatt tccaaagatg   360
tactctaaca ggatgaccag gcaaaaggtg accggggga ggagtctgtt ataacactcg    420
gacccacatg ttctcaaggc acttcagaac tttgggaaat cattttgtac cggatcctca   480
gaaagcattt atggaaatac acatccttta g                                   511
```

<210> SEQ ID NO 107
<211> LENGTH: 451
<212> TYPE: DNA
<213> ORGANISM: Homo sapiens

<400> SEQUENCE: 107

```
ggccgcccgg gcaggtccag aatatcaaat caaaaggtca caaatgttca cttcctcctc    60
caccctctta catattggat cttcaattgc aataggagt gtaagatggg cattttagag    120
acgtagttgc atcagcagaa gcaaacccat cttatacaaa tgggttttgg ggataggaaa   180
aggctgctaa aaattcacaa gtcaccattc cccagaagca atgaatagcc gtagaagacc   240
aaggaagatc aacaagtttc caaagtgcta aagccagaga tttggcccctt ccaaaatacc   300
accaggacgc ctggacccgt gggctctccg catgtcacca ctgactgcca ggatgctgct   360
gcacctccct tccttgagac acaacagaga gacagtgaag tcacccaaga ctgggatcat   420
cagaggctcc tcatgcttgc tacagagaag c                                   451
```

<210> SEQ ID NO 108
<211> LENGTH: 461
<212> TYPE: DNA
<213> ORGANISM: Homo sapiens

```
<400> SEQUENCE: 108
ccgcccgggc aggtcctgaa acattcaga  ctaatcaaaa tggtactact gtaacttctt      60
ataatacata atataaaagt ttttgaaaga tatagacaca attaacccct aaacaacaca     120
ctatctgatt ctcaaaagca atggctattt aacaagatgt aaaaggacaa taacatatca     180
aagaactttc acacacctaa agatagcatt tagcagcaag ttagtcagac aaaacaaaca     240
caaatatttt cacatttcct atgtttgttt ttaactttac ttcataaagc cactgataat     300
tgaggtttct ttcaagtata agatttctaa aattaaaaac tgttttgac  atattttat     360 aaagaaataa aaagcaaaac gcaatccaac tatttatatg agtccctctt ctccaacagc     420
tttagatggt tttctgagta ctttttaca  cagaatattt t                         461

<210> SEQ ID NO 109
<211> LENGTH: 441
<212> TYPE: DNA
<213> ORGANISM: Homo sapiens

<400> SEQUENCE: 109
ggccgcccgg gcaggtctga ttataagaga aagaaatcca gtgacacgag ggcaggcagg      60
ccccgctctg ctctgatcga gaaaagcttc ctgatgtcag ggagatggaa ctgccaccat     120
cagaaccatg gcactttggg tgaaggtgtg tcagcgacca aggggcagg  aaatgggcag     180 tgactaaggg ggcaggaaac aggcaggcac atggcaaggt tctcccagcc catcagccca     240
gtgatggcct cgattttgaa gctgcactac tgtctgaaaa gcacaattac tggtgactct     300
taacaaactt cagcatactg gggaaggaga ctgtcaagta actgaattgg aaagatgaaa     360 agaaccatc  tctaaaagtt gatgcttgtc agaagaataa cctcctttgt gcaagtcttg     420
caacatcttc attcaaccac a                                               441

<210> SEQ ID NO 110
<211> LENGTH: 451
<212> TYPE: DNA
<213> ORGANISM: Homo sapiens
<220> FEATURE:
<221> NAME/KEY: misc_feature
<222> LOCATION: 260, 361
<223> OTHER INFORMATION: n = A,T,C or G

<400> SEQUENCE: 110
ggtcgcggcc gaggtctggg gaaggggtga gaatccctgg gccttgccca gtcctgagct      60
ctgggtgtct gcagggaagc acagtggtga gttagtgtta aagaaagcat ccagagaggt     120
aagaggggct tgggtagcac cctttgcctc tgtcacttcc gcaaaaactt cttgttgagg     180
aggaagatga gaaggttgac attgactttg gccttgttga agagtttcat gacagccaca     240
ccctcatact ggagctgcan gagatcctga tagtgaagct tgaaatcgct ccatgtccac     300
acccaggaac ttggcattta cttcaaactt tcctgcctca tctcccggcg tgatgtcaaa     360
natgacgttt cttgaagtga gaggcgggaa agatcttcaa tttccaccaa agacacccectt   420 tttccaggaa gcttgagcaa caagtgtaat g                                    451

<210> SEQ ID NO 111
<211> LENGTH: 407
<212> TYPE: DNA
<213> ORGANISM: Homo sapiens
<220> FEATURE:
<221> NAME/KEY: misc_feature
<222> LOCATION: 26, 33, 36, 79, 105, 111, 133, 149, 186, 206, 220, 239,
      245, 259, 336, 375, 383, 393
```

```
<223> OTHER INFORMATION: n = A,T,C or G

<400> SEQUENCE: 111
ggccgacgtt cgacctgact tctttngagc agntgncact acccgtcttg aggaatgccg      60
actgcagaca gtggcccang gcaaagagtg tgcgtcatcg atganattgg naagatggag     120
ctcttcagtc agnttttcat tcaagctgnt cgtcagacgc tgtctacccc agggactata    180
atcctnggca caatcccagt tcctanagga aagccactgn ctcttgtaga agaaatcana    240
cacanaaagg atgtgaacng tgtttaatgt caccaaggga aaacatgaaa ccaccttctg    300
ccagatatcg ggacgttgcg tgcagatcaa gcacgnaagt gaagacgcgt gcattccttg    360
ccttccgtga acgantgccc agntcaagaa gancctgatg gaaccct                  407

<210> SEQ ID NO 112
<211> LENGTH: 401
<212> TYPE: DNA
<213> ORGANISM: Homo sapiens
<220> FEATURE:
<221> NAME/KEY: misc_feature
<222> LOCATION: 363
<223> OTHER INFORMATION: n = A,T,C or G

<400> SEQUENCE: 112
tcgcggccga ggtcggccga ggtctgacat ctgttgtctg tgataaccac ttctgtattg      60
cgtcttaacc acttctgtat tgtgtggttt taactgccta aggcggcaat gggcagtggg    120
cccctttccc ttaggatggg tatcaattca acaatattta taaggcattt actgtgtgct    180
aagcatttgg aagacccagg ctacaaaata agacatagtt cctgccctcc aggccagcag    240
agggaggcac aaatacccag gaatctctga tgggtgtgaa gtgcggtcgt gggccacaga    300
aaatgaccgt catggagacc ctgctaaagg tcggaccctg agcccaaagg ggtattcaga    360
agnggagatg attttggccc cactcataga tgggtggcaa a                       401

<210> SEQ ID NO 113
<211> LENGTH: 451
<212> TYPE: DNA
<213> ORGANISM: Homo sapiens

<400> SEQUENCE: 113
gtcgcggccg aggtccatat taaaaagtcc atcataaaca aagactcctc ctcatggtat      60
gaatatgctc catatgccca taatggtgca taacggactt agaaattcca atgagtctta    120
gggttgaaat ttccaatgac ctgagcaagg cagctcccta tagcttctgg ataacatttt    180
acacccagag ttcaggctta aacagaccta tcaacacaat tattttcgga ttgtctgtct    240
agaaaacggc aatgctcaaa ggaatataaa taagggtggg gggacatatg cttccagcct    300
ggcctttctc catgtggtaa aaaacaatgg aatggctgtg ttaatttttt tttaatcttt    360
tctgaccttt actatgtttg gtaatggaaa taagtcaggg aaaacaaaat gaacaggtct    420
catcacttaa ttaatactgg gttttcttct t                                   451

<210> SEQ ID NO 114
<211> LENGTH: 441
<212> TYPE: DNA
<213> ORGANISM: Homo sapiens

<400> SEQUENCE: 114
ggccgcccgg gcaggtccat cctgtcagag atggagaag tcacagacgg aatgatggat      60
acaaagatgg ttcactttct tacacactat gctgacaaga ttgaatctgt tcatttttca    120
```

```
gaccagttct ctggtccaaa aattatgcaa gaggaaggtc agcctttaaa gctacctgac      180
actaagagga cactgttgtt tacatttaat gtgcctggct caggtaacac ttacccaaag      240
gatatggagg cactgctacc cctgatgaac atggtgattt attctattga taaagccaaa      300
aagttccgac tcaacagaga aggcaaacaa aaagcagata agaaccgtgc ccgagtagaa      360
gagaacttct tgaaacttga cacatgtgca agacaggaa gcagcacagt ctcggcggga      420
ggaagaaaaa aagaacagag a                                                441

<210> SEQ ID NO 115
<211> LENGTH: 431
<212> TYPE: DNA
<213> ORGANISM: Homo sapiens
<220> FEATURE:
<221> NAME/KEY: misc_feature
<222> LOCATION: 317
<223> OTHER INFORMATION: n = A,T,C or G

<400> SEQUENCE: 115
gccgcccggg caggtccatt ggcggtgaca aaaggaaaag aagcaaagag actcagtcca      60
taatgctgat tagttagaag aaagggctag gattgagaaa gtaccaggaa cttttaatta      120
tttaaaagag aatgctgact gttaatgttt taaatcttac tgttcaaatg tactaatatg      180
aatttttacc ctttgtgcat gaatattcta acaactaga gacctccac aatttagcag        240 ttatgaaagt taaactttt attataaaaa ttctaaacct tactgctcct ttaccaggaa      300
catgacacac tatttancat cagttgcata cctcgccaat agtataattc aactgtcttg      360
cccgaacaat catctccatc tggaagacgt aagcctttag aaacacattt ttctattaat      420
ttctctagaa c                                                           431

<210> SEQ ID NO 116
<211> LENGTH: 421
<212> TYPE: DNA
<213> ORGANISM: Homo sapiens

<400> SEQUENCE: 116
gtcgcggccg aggtccagaa atgaagaaga agtttgcaga tgtatttgca agaagacga       60 aggcagagtg gtgtcaaatc tttgacggca cagatgcctg tgtgactccg gttctgactt      120
ttgaggaggt tgttcatcat gatcacaaca aggaaccggg gctcgtttat caccagtgag      180
gagcaggacg tgagcccccg ccctgcacct ctgctgttaa acaccccagc catcccttct      240
ttcaaaaggg atcctttcat aggagaacac actgaggaga tacttgaaga atttggattc      300
agcccgcgaa gagatttatc aagcttaact cagataaaat cattgaaagt aataaggtaa      360
aagctaagtc tctaacttcc aggcccacgg ctcaagtgaa tttcgaatac tgcatttaca      420
g                                                                      421

<210> SEQ ID NO 117
<211> LENGTH: 489
<212> TYPE: DNA
<213> ORGANISM: Homo sapiens

<400> SEQUENCE: 117
agcgtggtcg cggccgaggt aaggctgcga ggttgtggtg tctgggaaac tccgaggaca      60
gagggctaaa tccatgaagt ttgtggatgg cctgatgatc cacagcggag accctgttaa      120
ctactacgtt gacactgctg tgcgccacgt gttgctcaga cagggtgtgc tgggcatcaa      180
```

```
ggtgaagatc atgctgccct gggacccaac tggtaagatt ggccctaaga agcccctgcc      240
tgaccacgtg agcattgtgg aacccaaaga tgagatactg cccaccaccc ccatctcaga      300
acagaagggt gggaagccag agccgcctgc catgccccag ccagtcccca cagcataaca      360
gggtctcctt ggcagacctg cccgggcggc cgctcgaaag cccgaattcc agcacactgg      420
cggccgttac tagtggatcc cagctcggta ccaagcttgg cgtaatcatg gtcatagctg      480
gtttcctgt                                                              489

<210> SEQ ID NO 118
<211> LENGTH: 489
<212> TYPE: DNA
<213> ORGANISM: Homo sapiens

<400> SEQUENCE: 118
tcgagcggcc gcccgggcag gtattgaata cagcaaaatt ctatatacaa agtgacctgg       60
acctgctgct tcaaaacatg atcctttctt actaatatct tgatagtcgg tccatagagc      120
attagaaagc aattgactct taaataaaca gaaaagtgcc taatgcacat taaatgaatg      180
gcctaactac tggaacttta gtagttctat aaggtgatta acataggtag gatccagttc      240
ctatgacagg ctgctgaaga acagatatga gcatcaagag gccattttgt gcactgccac      300
cgtgatgcca tcgtgtttct ggatcataat gttcccatta tctgattcta gacacaccac      360
aggaatatca gtggggtcag aggttagctt agctgcttgc tgggctagaa cagatatcac      420
tccagcatgc tcatctgaca gggtcccgcg gcaacccaga ttaagtcctt gtgaatctgt      480
gcacaggga                                                              489

<210> SEQ ID NO 119
<211> LENGTH: 181
<212> TYPE: DNA
<213> ORGANISM: Homo sapiens

<400> SEQUENCE: 119
taggttccag agactttgg cccaggagga atatttactt ttagctctgg acatcattac        60
aaaaaggaat atttcccaaa cctcttcaga ccgagaatac atgggtaaaa ttattaaata      120
gttgtataat aaaaataatt ttttccttaa aaaaaaaaa aacctcggcc gcgaccacgc       180
t                                                                      181

<210> SEQ ID NO 120
<211> LENGTH: 489
<212> TYPE: DNA
<213> ORGANISM: Homo sapiens
<220> FEATURE:
<221> NAME/KEY: misc_feature
<222> LOCATION: 422, 487
<223> OTHER INFORMATION: n = A,T,C or G

<400> SEQUENCE: 120
gcgtggtcgc ggccgaggtc catttaaaac aaagaaaaat actaaagcca ctagtaaaca       60
tctgatgtgc aaaatacaac atcctctagt tggctttatg ccattattac ataagctcca      120
aatagctcat cttaaattaa aaagaaaaag tggctgtccc atctctgctg cataaatcag      180 atttttttt aaaggtttag agtacttaa ggaagggaag ttcaaaactg ccagtgaaat       240
tcacagagaa tacaaattta gcaatttaat ttcccaaagc tctttgaaga agcaagagag      300
tctctcttct taatgcagtg ttctcccaag aggaactgta attttgcttg gtacttatgc      360
tgggagatat gcaaaatgtg ttttcaatg tttgctagaa tataatggtt cctcttcagt      420
```

```
gnctggttca tcctggaact catgggttaa gaaggacttc ttggagccga actgcccggg      480 cgggccntt                                                              489

<210> SEQ ID NO 121
<211> LENGTH: 531
<212> TYPE: DNA
<213> ORGANISM: Homo sapiens

<400> SEQUENCE: 121
cgagcggccg cccgggcagg tggccagcgc tggtcccgca gacgccgaga tggaggaaat       60
atttgatgat gcgtcacctg gaaagcaaaa ggaaatccaa gaaccagatc ctacctatga      120
agaaaaaatg caaactgacc gggcaaatag attcgagtat ttattaaagc agacagaact      180
ttttgcacat ttcattcaac ctgctgctca gaagactcca acttcacctt tgaagatgaa      240
accagggcgc ccacgaataa aaaagatgaa gaagcagaac ttactatccg ttggcgatta      300
ccgacaccgt agaacagagc aagaggagga tgaagagcta ttaacagaaa gctccaaagc      360
aaccaatgtt tgcactcgat ttgaagactc tccatcgtat gtaaaatggg gtaaactgag      420
agattatcag gtcccgagga ttaaactggc tcatttcttt gtatgagaat ggcatcaatg      480
gtatccttgc agatgaaatg ggcctaggaa agactcttca acaatttctc t              531

<210> SEQ ID NO 122
<211> LENGTH: 174
<212> TYPE: DNA
<213> ORGANISM: Homo sapiens

<400> SEQUENCE: 122
tcgagcggcc gccgggcag gtctgccaac agcagaggcg gggcctccgg catcttcaaa        60
gcacctctga gcaggctcca gccctctggc tgcgggaggg gtctggggtc tcctctgagc      120
tcggcagcaa agcagatgtt atttctctcc cgcgacctcg ccgcgaccac gct             174

<210> SEQ ID NO 123
<211> LENGTH: 531
<212> TYPE: DNA
<213> ORGANISM: Homo sapiens
<220> FEATURE:
<221> NAME/KEY: misc_feature
<222> LOCATION: 152, 373, 482, 494, 496, 502
<223> OTHER INFORMATION: n = A,T,C or G

<400> SEQUENCE: 123
agcgtggtcg cggccgaggt cctcaaccaa gagggttgat ggcctccagt caagaaactg       60
tggctcatgc cagcagagct ctctcctcgt ccagcaggcg ccatgcaagg gcaggctaaa      120
agacctccag tgcatcaaca tccatctagc anagagaaaa ggggcactga agcagctatg      180
tctgccaggg ctaggggct cccttgcaga cagcaatgct acaataaagg acacagaaat      240
gggggaggtg ggggaagccc tatttttata acaaagtcaa acagatctgt gccgttcatt      300
cccccagaca cacaagtaga aaaaaaccaa tgcttgtggt ttctgccaag atggaatatt      360
cctccttcct aanttccaca catggccgtt tgcaatgctc gacagcattg cactgggctg      420
cttgtctctg tggtctgggc accagtagct tgggcccat atacacttct cagttcccac      480
anggcttatg gccnangggc angctccaat tttcaagcac cacgaaggaa g              531

<210> SEQ ID NO 124
<211> LENGTH: 416
<212> TYPE: DNA
```

<213> ORGANISM: Homo sapiens

<400> SEQUENCE: 124

```
tcgagcggcc gcccgggcag gtccatctat actttctaga gcagtaaatc tcataaattc    60
acttaccaag cccaggaata atgacttta aagccttgaa tatcaactaa gacaaattat    120
gccaattctg atttctcaca tatacttaga ttacacaaag ataaagcttt agatgtgatc    180
attgtttaat gtagacttat ctttaaagtt tttaattaaa aactcagaa gggagtaaac    240
agcaagccaa atgatttaac caaatgattt aagagtaaaa ctcactcaga aagcattata    300
cgtaactaaa tatacatgag catgattata tacatacatg aaactgcaat tttatggcat    360
tctaagtaac tcatttaagt acatttttgg catttaaaca aagatcaaat caagct       416
```

<210> SEQ ID NO 125
<211> LENGTH: 199
<212> TYPE: DNA
<213> ORGANISM: Homo sapiens
<220> FEATURE:
<221> NAME/KEY: misc_feature
<222> LOCATION: 112, 160, 195
<223> OTHER INFORMATION: n = A,T,C or G

<400> SEQUENCE: 125

```
agcgtggtcg cggccgaggt gcttttttt ttttttttt tttttttttt gctattctaa    60
aggggaaggc ccctttttat taaacttgta cattttactt tccttctttc anaatgctaa    120
taaaaaactt ttgtttatac ttaaaaaaac cataaatcan acaaacaaaa gaaacgattc    180
caacatcact tctgngatg                                                199
```

<210> SEQ ID NO 126
<211> LENGTH: 490
<212> TYPE: DNA
<213> ORGANISM: Homo sapiens

<400> SEQUENCE: 126

```
cgtggtcgcg gccgaggtcc agttgctcta agtggattgg atatggttgg agtggcacag    60
actggatctg ggaaaacatt gtcttatttg cttcctgcca ttgtccacat caatcatcag    120
ccattcctag agagaggcga tgggcctatt tgtttggtgc tggcaccaac tcggaactg     180
gcccaacagg tgcagcaagt agctgctgaa tattgtagag catgtcgctt gaagtctact    240
tgtatctacg gtggtgctcc taagggacca caaatacgtg atttggagag aggtgtggaa    300
atctgtattg caacacctgg aagactgatt gacttttag agtgtggaaa accaatctg     360
agaagaacaa cctaccttgt ccttgatgaa gcagatagaa tgcttgatat gggctttgaa    420
ccccaaataa ggaagattgt ggatcaaata agacctgata ggcaaactct aatgtggagt    480
gcgacttggc                                                          490
```

<210> SEQ ID NO 127
<211> LENGTH: 490
<212> TYPE: DNA
<213> ORGANISM: Homo sapiens

<400> SEQUENCE: 127

```
cgtggtcgcg gccgaggtcg gccgaggtct ggagatctga gaacgggcag actgcctcct    60
caagtgggtc cctgacccct gaccccgag cagcctaact gggaggcacc cccagcagg     120
ggcacactga cacctcacac ggcagggtat tccaacagac ctgaagctga gggtcctgtc    180
tgttagaagg aaaactaaca agcagaaagg acagccacat caaaaaccca tctgtacatc    240
```

```
accatcatca aagaccaaaa gtaaataaaa ccacaaagat gggaaaaaaa cagaacagaa      300
aaactggaaa ctctaaaaag cagagcacct ctcctcttcc aaaggaacgc agttcctcac      360
cagcaatgga acaaagctgg atggagaatg actttgacga gctgagaaaa gaacgcttca      420
gacgatcaaa ttactctgag ctacgggagg acattcaaac caaaggcaaa gaagttgaaa      480
actttgaaaa                                                             490

<210> SEQ ID NO 128
<211> LENGTH: 469
<212> TYPE: DNA
<213> ORGANISM: Homo sapiens
<220> FEATURE:
<221> NAME/KEY: misc_feature
<222> LOCATION: 69, 106, 140, 152, 165, 196, 224, 233, 241, 258, 260,
      267, 291, 347, 395
<223> OTHER INFORMATION: n = A,T,C or G

<400> SEQUENCE: 128
cgtggtcgcg gccgaggtgc ttttttttt tttttttttt tttttttttt tgctgattta       60 tttttctnt ttattgttac atacaatgta taaacacata aaacanaaaa cagtagggat      120
cctctaggat ctctagggan acagtaaagt anaagaggt ctcanaaaca tttttttaaa      180
gtacaagaca ttcagngctc ggcccaaagg cgtaaaaggt ttanagccag canatagctg     240
nactaaaggc tccgtctntn tccccanagc caggacaacc ccagggagct ntccattagc     300
agccagtcca cgcaggcagg atgctgcgga aaaagctcta tgctganaac attcccttg      360 atggaaagaa gggcaacaca aaaggggtaa ctaanagctc cttcctctcg tgagggcgac     420
aactgaggaa cagaaaagga gtgtcccatg tcacttttga cccccctccc                 469

<210> SEQ ID NO 129
<211> LENGTH: 419
<212> TYPE: DNA
<213> ORGANISM: Homo sapiens

<400> SEQUENCE: 129
gcgtggtcgc ggccgaggtc tgattttcat ttaaatattt cagagctata gcatttgcct      60
ccatgctcaa atccacacca ttggggctta agccgctcat gccaacatta gcaaatgaca     120
tgcagtttaa tccagagatc actgcttctg ggctgatgca tgccaacaca ctggcgtgat     180
ccacgttatg tgcattttc ttcactttag tgggagaatc aattttact ccaaggcttc       240 ttagttgctt aagagttgca ttaaggacac aatcttgtc caccagtctt gaatgatgtg      300
tttttttctt tgtatggtaa acgttttggg ttctggtgca ttcatgactg ataattactg    360
ctttggtaga cggctgctca gtttccttg gaggaactat ttaataggtg ggttacttg       419

<210> SEQ ID NO 130
<211> LENGTH: 354
<212> TYPE: DNA
<213> ORGANISM: Homo sapiens

<400> SEQUENCE: 130
agcgtggtcg cggccgaggt ccatctgagg agataaccac atcactaaca aagtgggagt      60
gaccccgcag agcacgctgt ggaattccat agttggtctc atccctggtc agtttccaca     120
tgatgatggt cttatctcga gaggcggaga ggatcatgtc cgggaactgc ggggtagtag     180
cgatctgggt tacccagccg ttgtggccct tgagggtgcc acgaagggtc atctgctcag     240
tcatggcggc ggcgagagcg tgtgtcgctg cagcgacgag gatggcactg gatggcttag    300
```

```
agaaactagc accacaacct ctcctgccgc acctgcccgg gcggcccgct cgaa        354
```

```
<210> SEQ ID NO 131
<211> LENGTH: 474
<212> TYPE: DNA
<213> ORGANISM: Homo sapiens
<220> FEATURE:
<221> NAME/KEY: misc_feature
<222> LOCATION: 421
<223> OTHER INFORMATION: n = A,T,C or G

<400> SEQUENCE: 131
cgagcggccg cccgggcagg tctggcagca gcttcctctg gaataattga cagctttgtg    60
ctgcctgact aaaatttgaa atgacaaccg ctgaatgtaa aatgatgtac ctacaatgag   120
agagatttag gaatactatc tgtcaatcca tagatgtaga aacaaaacaa actacagaat   180
gaaaacaaac ttattttaaa ccaaagaaac aaatgtatcc aaaatatagt ccatgatata   240
tttgattact agtataacca cagttgaaaa cttaaaaaaa aaaattgaca tttttttgtaa  300
tgggtactaa tggatttata aaaggtttct gtttccaaag atgttattgg ggtccacata   360
ttccttgaag acttcagcat cccaaagccc gacatcagag atactttcct ttagccattg   420
nttcccgtaa cttgcccact ccatggtgat gtgacaggct tcccttcatt agca         474
```

```
<210> SEQ ID NO 132
<211> LENGTH: 474
<212> TYPE: DNA
<213> ORGANISM: Homo sapiens
<220> FEATURE:
<221> NAME/KEY: misc_feature
<222> LOCATION: 403
<223> OTHER INFORMATION: n = A,T,C or G

<400> SEQUENCE: 132
ggccgaggtg gggaattcat gtggaggtca gagtggaagc aggtgtgaga gggtccagca    60
gaaggaaaca tggctgccaa agtgtttgag tccattggca agtttggcct ggccttagct   120
gttgcaggag gcgtggtgaa ctctgcctta tataatgtgg atgctgggca cagagctgtc   180
atctttgacc gattccgtgg agtgcaggac attgtggtag gggaagggac tcattttctc   240
atcccgtggg tacagaaacc aattatcttt gactgccgtt ctcgaccacg taatgtgcca   300
gtcatcactg gtagcaaaga tttacagaat gtcaacatca cactgcgcat cctcttccgg   360
cctgtcgcca gccagcttcc tcgcatcttc accagcatcg ganaggacta tgatgaaccg   420
tgtgctgccg tccatcacaa ctgagatcct caagtcagtg gtggctcgct ttga         474
```

```
<210> SEQ ID NO 133
<211> LENGTH: 387
<212> TYPE: DNA
<213> ORGANISM: Homo sapiens

<400> SEQUENCE: 133
tgctcgagcg gccgccagtg tgatggatat ctgcagaatt cggcttagcg tggtcgcggc    60
cgaggtctgc gggccccta gcctgccctg cttccaagcg acggccatcc cagtagggga   120
ctttcccaca ctgtgccttt acgatcagcg tgacagagta aagctggag tgcctcacca   180
cacggcccgg aaacagcggg aagtaactgg aaagagcttt aggacagctt agatgccgag   240
tgggcgaatg ccagaccaat gatacccaga gctacctgcc gccaacttgt tgagatgtgt   300
gtttgactgt gagagagtgt gtgtttgtgt gtgtgttttg ccatgaactg tggccccagt   360
```

```
gtatagtgtt tcagtggggg agaactg                                         387

<210> SEQ ID NO 134
<211> LENGTH: 401
<212> TYPE: DNA
<213> ORGANISM: Homo sapiens

<400> SEQUENCE: 134
ggccgcccgg gcaggtctga tgaagaacac gggtgtgatc cttgccaatg acgccaatgc     60
tgagcggctc aagagtgttg tgggcaactt gcatcggctg ggagtcacca acaccattat    120
cagccactat gatgggcgcc agttccccaa ggtggtgggg ggcttttgacc gagtactgct   180 ggatgctccc tgcagtggca ctggggtcat ctccaaggat ccagccgtga agactaacaa    240
ggatgagaag gacatcctgc gcttgtgctc acctccagaa ggaagttgct cctgagtgct    300
attgactctt gtcaatgcga ccttcaagac aggaggctac ctggtttact gcacctgttc    360
tatcacagtg agacctctgc catggcagaa caggggaagc t                        401

<210> SEQ ID NO 135
<211> LENGTH: 451
<212> TYPE: DNA
<213> ORGANISM: Homo sapiens

<400> SEQUENCE: 135
ggtcgcggcc gaggtctgtt cctgagaaca gcctgcattg gaatctacag agaggacaac     60
taatgtgagt gaggaagtga ctgtatgtgg actgtggaga agtaagtca cgtgggccct     120 tgaggacctg gactgggtta ggaacagttg tactttcaga ggtgaggtgt cgagaaggga    180
aagtgaatgt ggtctggagt gtgtccttgg ccttggctcc acagggtgtg ctttcctctg    240
gggccgtcag ggagctcatc ccttgtgttc tgccagggtg gggtaccggg gtttgacact    300
gaggagggta acctgctggc tggagcggca gaacagtggc cttgatttgt cttttggaag    360
attttaaaaa ccaaaaagca taaacattct ggtccttcac aatgctttct ctgaagaaat    420
acttaacgga aggacttctc cattcaccat t                                   451

<210> SEQ ID NO 136
<211> LENGTH: 411
<212> TYPE: DNA
<213> ORGANISM: Homo sapiens

<400> SEQUENCE: 136
ggccgcccgg gcaggtctga atcacgtaga atttgaagat caagatgatg aagccagagt     60
tcagtatgag ggttttcgac ctgggatgta tgtccgcgtt gagattgaaa atgttccctg    120
tgaatttgtg cagaactttg accccctta ccccattatc ctgggtggct tgggcaacag     180
tgagggaaat gttggacatg tgcaggtggg tcccttttgct gcgtatttgg tgcctgaggc   240
tctgtggatt tccctccat caatcatctt acctctcat cccctcaga tgcgtctgaa       300 gaaacatctc tggtataaga aaatcctcaa gtcccaagat ccaatcatat tttctgtagg    360
gtggaggaag tttcagacca tcctgctcta ttatatccga agaccacaat g             411

<210> SEQ ID NO 137
<211> LENGTH: 211
<212> TYPE: DNA
<213> ORGANISM: Homo sapiens
<220> FEATURE:
<221> NAME/KEY: misc_feature
<222> LOCATION: 186
<223> OTHER INFORMATION: n = A,T,C or G
```

<400> SEQUENCE: 137

```
cggccgcccg ggcaggtcgg ttggtgcggc ctccattgtt cgtgttttaa ggcgccatga      60
ggggtgacag aggccgtggt cgtggtgggc gctttggttc cagaggaggc ccaggaggag     120
ggttcaggcc ctttgcacca catatcccat ttgacttcta tttgtgtgaa atggcctttc     180
cccggntcaa gccagcacct cgatgaaact t                                   211
```

<210> SEQ ID NO 138
<211> LENGTH: 471
<212> TYPE: DNA
<213> ORGANISM: Homo sapiens

<400> SEQUENCE: 138

```
gccgcccggg caggtctggg ctggcgactg gcatccaggc cgtaactgca aatctatgct      60
aggcggggtc tcccttctgt gtgttcaagt gttctcgact tggattctta actatttaa     120
aaaatgcact gagtttgggt taaaaaccaa ccaccaaaat ggatttcaac acagctctaa    180
agccaagggc gtggccggct ctcccaacac agcgactcct ggaggccagg tgcccatggg    240
cctacatccc ctctcagcac tgaacagtga gttgattttt cttttacaa taaaaaagc     300
tgagtaatat tgcataggag taccaagaaa ctgcctcatt ggaacaaaa actatttaca    360
ttaaataaaa agcctggccg caggctgcgt ctgccacatt tacagcacgg tgcgatgcac    420
acggtgacca aaccacggag gcaagcttct ggcactcaca ccacgacccg c             471
```

<210> SEQ ID NO 139
<211> LENGTH: 481
<212> TYPE: DNA
<213> ORGANISM: Homo sapiens
<220> FEATURE:
<221> NAME/KEY: misc_feature
<222> LOCATION: 384
<223> OTHER INFORMATION: n = A,T,C or G

<400> SEQUENCE: 139

```
gtcgcggccg aggtctgttc tttagctcag atttaaacct gctgtctctt ctttatttgc      60
agaatgaatt cccagttcct gagcagttca agaccctatg gaacgggcag aagttggtca    120
ccacagtgac agaaattgct ggataagcga agtgccactg ggttctttgc cctcccttca    180
caccatggga taaatctgta tcaagacggt tcttttctag atttcctcta ccttttttgct   240
cttaaaactg cttctctgct ctgagaagca cagctacctg ccttcactga atatacctc    300
aggctgaaat ttggggtggg atagcaggtc agttgatctt ctgcaggaag gtgcagcttt    360
tccatatcag ctcaaccacg ccgncagtcc attcttaagg aactgccgac taggactgat    420
gatgcatttt agcttttgag cttttggggg gtattctacc aaccaacagt ccatttggaa    480
a                                                                    481
```

<210> SEQ ID NO 140
<211> LENGTH: 421
<212> TYPE: DNA
<213> ORGANISM: Homo sapiens
<220> FEATURE:
<221> NAME/KEY: misc_feature
<222> LOCATION: 372
<223> OTHER INFORMATION: n = A,T,C or G

<400> SEQUENCE: 140

```
gtcgcggccg aggtttccca tttaagaaaa atagatcttg agattctgat tcttttccaa      60
```

```
acagtcccct gctttcatgt acagcttttt ctttacctta cccaaaattc tggccttgaa      120
gcagttttcc tctatggctt tgcctttctg attttctcag aggctcgagt ctttaatata      180
accccaaatg aaagaaccaa ggggaggggt gggatggcac ttttttttgt tggtcttgtt      240
ttgttttgtt ttttggttgg ttgggttccg ttatttttta agattagcca ttctctgctg      300
ctatttccct acataatgtc aattttaac cataattttg acatgattga gatgtacttg       360
aggctttttt gntttaattg agaaaagact ttgcaatttt ttttttagga tgagcctctc      420
c                                                                     421
```

<210> SEQ ID NO 141
<211> LENGTH: 242
<212> TYPE: DNA
<213> ORGANISM: Homo sapiens
<220> FEATURE:
<221> NAME/KEY: misc_feature
<222> LOCATION: 4, 6, 20, 31, 35, 39, 72, 94, 141, 142, 211, 222
<223> OTHER INFORMATION: n = A,T,C or G

<400> SEQUENCE: 141

```
cgantngccc gcccgggcan gtctgtctaa ntttntcang gaccacgaac agaaactcgt      60
gcttcaccga anaacaatat cttaaacatc gaanaattta aatattatga aaaaaaacat     120
tgcaaaatat aaaataaata nnaaaaggaa aggaaacttt gaaccttatg taccgagcaa     180
atccaggtct agcaaacagt gctagtccta nattacttga tntacaacaa cacatgaata     240
ca                                                                   242
```

<210> SEQ ID NO 142
<211> LENGTH: 551
<212> TYPE: DNA
<213> ORGANISM: Homo sapiens
<220> FEATURE:
<221> NAME/KEY: misc_feature
<222> LOCATION: 15, 19, 32, 73, 110, 278, 405, 436, 473, 510
<223> OTHER INFORMATION: n = A,T,C or G

<400> SEQUENCE: 142

```
agcgtggtcg cggcncgang tccacagggc anatattctt ttagtgtctg gaattaaaat      60
gtttgaggtt tangttttgcc attgtctttc caaaaggcca aataattcan atgtaaccac    120
accaagtgca aacctgtgct ttctatttca cgtactgttg tccatacagt tctaaataca    180
tgtgcagggg attgtagcta atgcattaca cagtcgttca gtcttctctg cagacacact    240
aagtgatcat accaacgtgt tatacactca actagaanat aataagcttt aatctgaggg    300
caagtacagt cctgacaaaa gggcaagttt gcataataga tcttcgatca attctctctc    360
caaggggccc gcaactaggc tattattcat aaaacacaac tgaanagggg attggtttta    420
ctggtaaatc atgtgntgct aaatcatttt ctgaacagtg gggtctaaat cantcattga    480
tttagtggca gccacctgcc cggcggccgn tcgaagccca attctgcaga tatccatcac    540
actggcggcc g                                                         551
```

<210> SEQ ID NO 143
<211> LENGTH: 515
<212> TYPE: DNA
<213> ORGANISM: Homo sapiens
<220> FEATURE:
<221> NAME/KEY: misc_feature
<222> LOCATION: 5, 286, 498
<223> OTHER INFORMATION: n = A,T,C or G

<400> SEQUENCE: 143

```
cgagnggccc gcccgggcag gtatcttcac aaactcaaca aaggcactac atgagacttc    60
acattcccct agtccaatag ctgacaaatt tttgcaacgt tctgcaatgc gaattaactc   120
ttcatcaagt ggccgtaatc catttgcaca cactactagt tcaaccagtc tagggcatgt   180
cattcccaca cggccaagca catctttgct tactgatctc ccaaagtaca gatgggtggc   240
aggtatttca tagcgaaaga aggggtcaaa ttcttcttca tataanaaaa aatacatcac   300
taagttcact ttgggtgaat gtctgatgaa agcatcccag ctactcttct gaatagtatg   360
gaagtgtgtc tgtccaggat tctcactgac tacatcaatg cgcaaatgtt ctaatcgaac   420 atgttttca gaagacaatg caagtaacaa ctcatcactc aataagtggt aagttcaggg   480
ctagttctct taagccgnga cactgatcag cacac                              515

<210> SEQ ID NO 144
<211> LENGTH: 247
<212> TYPE: DNA
<213> ORGANISM: Homo sapiens
<220> FEATURE:
<221> NAME/KEY: misc_feature
<222> LOCATION: 11, 20, 42, 115, 152, 165, 181, 195, 208, 221
<223> OTHER INFORMATION: n = A,T,C or G

<400> SEQUENCE: 144
tgcattctct ntggatgcan acctgcccgt tggtagggac tntgctcaca cggaacatgg    60
acggttacac ctgtgccgtg ggtgacgtcc accagcttct ggatcatctc ggcgngggtg   120
ttgtggaagg gcagactatc cacctccatg cncacgatgc ccganacgcc actccggact   180
ntgtgctgca ccaanatgcc cagcattnta tcttcaagca nagcacttat cagggtcctt   240
ggcacac                                                             247

<210> SEQ ID NO 145
<211> LENGTH: 309
<212> TYPE: DNA
<213> ORGANISM: Homo sapiens
<220> FEATURE:
<221> NAME/KEY: misc_feature
<222> LOCATION: 18, 155, 247
<223> OTHER INFORMATION: n = A,T,C or G

<400> SEQUENCE: 145
cgtgggtcgc ggcccgangt ctgctgtaac aaaacaccat agtctgggca gctcatagac    60
aatggaattt tatttctcac gcttctggag gctggattcc aagatcaagg ttccaggaga   120
ctcagtgtct ggcaaggtct cggtttctgc ctcanagatg gtgccatctg ctgtgtcct   180 cacaagtagg aaggtgcaag aagctcccct caggctctgt ctgtaagaca ctgatcccat   240
tcatganggg gaaacgtaat gacctaatca gcccccagag accccacttc taacaccatc   300
accttgggg                                                           309

<210> SEQ ID NO 146
<211> LENGTH: 486
<212> TYPE: DNA
<213> ORGANISM: Homo sapiens
<220> FEATURE:
<221> NAME/KEY: misc_feature
<222> LOCATION: 16, 97, 154, 244, 275, 322, 347, 349, 352, 357, 449,
       460, 472
<223> OTHER INFORMATION: n = A,T,C or G

<400> SEQUENCE: 146
agcgtgggtc gcggcncgac gtcctgtcca tatttcacag cccgagaact aatacaagat    60
```

```
gctgacatca tattttgtcc ctacaactat cttctanatg cacaaataag ggaaagtatg    120
gatttaaatc tgaaagaaca ggttgtcatt ttanatgaag ctcataacat cgaggactgt    180
gctcgggaat cagcaagtta cagtgtaaca gaagttcagc ttcggtttgc tcgggatgaa    240
ctanatagta tggtcaacaa taatataagg aaganagatc atgaacccct acgagctgtg    300
tgctgtagcc tcattaattg gntagaagca aacgctgaat atcttgnana angagantat    360
gaatcagctt gtaaaatatg gagtggaaat gaaatgctct taactttaca caaaatgggt    420
atcaccactg ctacttttcc cattttgcng gtaagatatn ttttctacct gngaaacgta    480
tttaag                                                               486
```

<210> SEQ ID NO 147
<211> LENGTH: 430
<212> TYPE: DNA
<213> ORGANISM: Homo sapiens
<220> FEATURE:
<221> NAME/KEY: misc_feature
<222> LOCATION: 13, 26, 28, 289, 299, 352, 390, 399
<223> OTHER INFORMATION: n = A,T,C or G

<400> SEQUENCE: 147

```
gccgcccggg cangttcgac attacntnga gttccatgat gtacaattct ttcacgaaaa    60
acaatgaatg caagaatttg aggatctcct tactcctccc ttttacagat ggtctctcaa    120
tcccttcttc ttcctcttca tcttcatctt cttctgaacg cgctgccggg taccacggct    180
ttctttgtct ttatcgtgag atgaaggtga tgcttctgtt tcttctacca taactgaaga    240
aatttcgctg caagtctctt gactggctgt ttctccgact tcgcctttnt gtcaaacgng    300
agtcttttta cctcatgccc ctcagcttca cagcatcttc atctggatgt tnatttctca    360
aagggctcac tgaggaaact tctgattcan atgtcgaana gcactgtgaa gttttctctt    420
cattttgctg                                                           430
```

<210> SEQ ID NO 148
<211> LENGTH: 483
<212> TYPE: DNA
<213> ORGANISM: Homo sapiens
<220> FEATURE:
<221> NAME/KEY: misc_feature
<222> LOCATION: 20, 24, 53, 55, 374, 381, 423, 431, 459
<223> OTHER INFORMATION: n = A,T,C or G

<400> SEQUENCE: 148

```
cccgggcagg tctgtgttgn tttncaaccg gtgtcctccc cagcgtccag aanangggaaa    60 tgtggagcgg gtgatgatga cccctcgctg tcctgtcacc tcctgcacag cttcgtatgt    120
gggtctggtc tgggaccacc cgtacaggtt gtgcacgttg tagtgctcca cgggggagct    180
gtccggcagg atctgctgac tctccatgca cagagtcttg ctgctcaggc ccttgtccct    240
agattccaaa tatggcatat agggtgggt tatttagcat tcattgctg cagcccctga     300 cagatccatc cacaaaattt gatggctcat tcatatcaat ccacaatcca tcaaacttca    360
agctcttctc tggntctcga nggtttgcat agaactcttc tatctctttc ttccaccacg    420
canacctcgg ncgcgaccac gctaagccga attctgcana tatccatcac actggcggcc    480
gct                                                                  483
```

<210> SEQ ID NO 149
<211> LENGTH: 439
<212> TYPE: DNA

```
<213> ORGANISM: Homo sapiens
<220> FEATURE:
<221> NAME/KEY: misc_feature
<222> LOCATION: 11, 359, 384, 402
<223> OTHER INFORMATION: n = A,T,C or G

<400> SEQUENCE: 149
ctttcacgaa nacaatgaat gcaagaattt gaggatctcc ttactcctcc cttttacaga      60
tggtctctca atcccttctt cttcctcttc atcttcatct tcttctgaac gcgctgccgg     120
gtaccacggc tttctttgtc tttatcgtga gatgaaggtg atgcttctgt tcttctacc     180 ataactgaag aaatttcgct gcaagtctct tgactggctg tttctccgac ttcgccttt     240 tgcaaacgtg agtctttta cctcatgccc ctcagcttcc acagcatctt catctggatg     300
ttcatttctc aaagggctca ctgaggaaac ttctgactca catgtcgaag aagcactgng     360
agtttctctt catttgctgc aaanttgctc tttgctggct gngctctcag accacccatt     420
tggctgcatg ggggctgac                                                   439

<210> SEQ ID NO 150
<211> LENGTH: 578
<212> TYPE: DNA
<213> ORGANISM: Homo sapiens
<220> FEATURE:
<221> NAME/KEY: misc_feature
<222> LOCATION: 4, 15, 260, 336, 371, 430, 461, 535, 572
<223> OTHER INFORMATION: n = A,T,C or G

<400> SEQUENCE: 150
ggcncgcccg ggcangtcca ctccactttt gagctctgag gaatacctt caggagggac       60 agggtcaggg agtcctggca gctccgcagc agagattcac attcattcag agacttgttg     120
tccagtgcaa tgccattgat cgcaacgatc ctgtctccca cagcaaggga cccttcttta    180
gcggcagggc ttccaggcag cacagcggca gcatacactc cattctccag actgatgcca    240 ctgtcttttct gtccactgan gttgatgtgc agcggcgtga ccacttccc acccagggac    300 ttcctccgcc gcacgaccat gttgatgggc cccctnccca ttgaggagcg ccttgatggc    360
ctgcttcttg nccttggtga tgaagtccac atcggtgatt ctcacagcca gtcattgacc    420
cttaagcggn catcagcaat gcttcctttg gccactttag ngacaaatat gccacagtcc    480
ccgggaaaca agggtcattc acaccttctg gcatatcaaa cacctcggcc gggancacta    540
agccgaattc tgcagatatc catcacactg gnggccg                              578

<210> SEQ ID NO 151
<211> LENGTH: 503
<212> TYPE: DNA
<213> ORGANISM: Homo sapiens
<220> FEATURE:
<221> NAME/KEY: misc_feature
<222> LOCATION: 392, 464
<223> OTHER INFORMATION: n = A,T,C or G

<400> SEQUENCE: 151
cgagcggccc gcccgggcag gtctgggaga tcagcgactg ctgccacgtg cccagaaatg       60
gctcgtcctt tcactacagc ggaatgcaat gagggtgggt gagaagatga tgggtcggtt     120
atttcattcc ttttctttt acaacttcac tttcagagac ttcagcgttc catgtctgct     180
gtgctgtgga acccagagtg ctcttgcctg gatggctgag aatcccttgg accctggaag    240
cacctactcc atgatggccc ggtatagtgc aggctcaata taatcttccc ggtatcttga    300
gttgataact cgttgccgtt tcttttcttg cttaacctct ttctctgtga aaatctcatt     360
```

```
gaagcgcatg tctgaagcta ctgacagtct anatttgact ctcttgggaa gctcttcatc    420
cagtgtgtat acatcatctc tcttaaccac aagttggagc catncttaaa cttcacctgg    480
tacatttgga tagggtggga ggc                                            503

<210> SEQ ID NO 152
<211> LENGTH: 553
<212> TYPE: DNA
<213> ORGANISM: Homo sapiens
<220> FEATURE:
<221> NAME/KEY: misc_feature
<222> LOCATION: 293, 432, 459, 481, 536
<223> OTHER INFORMATION: n = A,T,C or G

<400> SEQUENCE: 152
agcgtggtcg cggcccgagg tccactgagc tccgccttcc ccgggctccc tgaggaagca     60
gagtcctgac ttccaggaag gacaggacac agaggcaaga actcagcctg tgaggctctg    120
ggtggctcct gaggccagag gacgccttcc gcgatccatg gctcagcatc gtccttctgg    180
cttcccagcc ccggggccgaa cgttcgggtt aataagcaga gcagttattc ggctcctggc    240
aggagctccc ccgttagttt ccacgttgtg agcacattca tacttaagac tgnttctctt    300
tgtgttttaa gcgtctgtct ctgtagtaaa ctgaaatgtt aacagaaatg cagacctgcc    360
cgggcggccg ctcgaaagcc gaattctgca gatatccatc acactggcgg ccgctcgagc    420
atgcatctag anggcccaat cgccctata gtgagtcgna ttacaattca ctgggccgcg    480
ntttacaacg tcgtgactgg gaaaaccctg cggtacccac ttaatcgcct tgcagnacat    540
ccccctttcg cca                                                       553

<210> SEQ ID NO 153
<211> LENGTH: 454
<212> TYPE: DNA
<213> ORGANISM: Homo sapiens
<220> FEATURE:
<221> NAME/KEY: misc_feature
<222> LOCATION: 198, 307, 325, 347, 386, 389, 392, 415, 425
<223> OTHER INFORMATION: n = A,T,C or G

<400> SEQUENCE: 153
tcgagcggct cgcccgggca ggtccaccta gcatggctcc tctaaacacg caactcagcg     60
aggggacccc cttcacctct ggcaagagag ctgggtagat cagaaacttg gtgacacctg    120
gctagcacag agcaggctca cttgtcttgg tcccactacc cagattcctg cagacattgc    180
aaaccaaatg aaggttgntg aatgacccct gtccccagcc acttgttttg gtatcatctg    240
ctctgcagtg gaatgcctgt gtgtttgagt tcactctgca tctgtatatt tgagtataga    300
aaccgantca agtgatctgt gcatncagac acactggggc acctgancac agaacaaatc    360
accttaacga tctggaatga aactgnganc antgcccgcc tgggtgggtc tgganaaact    420
gccgncttct tgttggacct tggccgcacc acct                                454

<210> SEQ ID NO 154
<211> LENGTH: 596
<212> TYPE: DNA
<213> ORGANISM: Homo sapiens
<220> FEATURE:
<221> NAME/KEY: misc_feature
<222> LOCATION: 19, 33, 37, 131, 377, 425, 439, 505
<223> OTHER INFORMATION: n = A,T,C or G

<400> SEQUENCE: 154
```

```
agcgtggtcg cggcccgang gcggcctcct gantganggg aagggacgtg ggggcggcca      60
cggcaggatt aacctccatt tcagctaatc atgggagaga ttaaagtctc tcctgattat     120
aactggttta naggtacagt tccccttaaa aagattattg tggatgatga tgacagtaag     180
atatggtcgc tctatgacgc gggcccccga agtatcaggt gtcctctcat attcctgccc     240
cctgtcagtg gaactgcaga tgtctttttc cggcagattt tggctctgac tggatggggt     300
taccgggtta tcgctttgca gtatccagtt tattgggacc atctcgagtt cttgtgatgg     360
attcacaaaa cttttanacc atttacaatt ggataaagtt catcttttg gcgcttcttt     420 gggangcttt ttggcccana aatttgctga atacactcac aaatctccta gaagccattc     480
cctaatcctc tgcaattcct tcagngacac ctctatcttc aaccaacttg gactggaaac     540
agctttggct gatgcctgca tttatgctca aaaaatagtt cttggaaatt ttcatc        596
```

<210> SEQ ID NO 155
<211> LENGTH: 343
<212> TYPE: DNA
<213> ORGANISM: Homo sapiens
<220> FEATURE:
<221> NAME/KEY: misc_feature
<222> LOCATION: 6, 12, 23, 44, 58, 86, 99, 279, 310, 319
<223> OTHER INFORMATION: n = A,T,C or G

<400> SEQUENCE: 155

```
ctcganttgg cncgcccggg cangtctgcc tggttttga ccgngcgagc tatttagnct      60
ctggctctgt ttccggagct caaggnaaaa atcttgaana actcgagcag cttctgtgga    120
tagccttggg tacacatact gccgagcata gccaatgtac tttctcaata gctggtgggg    180
aatgggatct attgtttctc caggaaccac ctttagtctt tctgataatg gcttctcaga    240
aactacttca agtacggaag tatttgaatc ttgactatnc atacgagcta ctgtggcact    300
gctaatgggn tctctgctnt ccagctctta ttgcaatcac atg                      343
```

<210> SEQ ID NO 156
<211> LENGTH: 556
<212> TYPE: DNA
<213> ORGANISM: Homo sapiens
<220> FEATURE:
<221> NAME/KEY: misc_feature
<222> LOCATION: 34, 375, 530
<223> OTHER INFORMATION: n = A,T,C or G

<400> SEQUENCE: 156

```
tcgagcggcc cgcccgggca ggtctggcac cacncagatc gattaactgg ctcatctgat      60
ctcgtggccc ccaccctgga actgacttag cacaaaagga cacctcaatt ccttatgatt    120
tcatctccga cccaaccaat caacacccctt gactcactgg ccttccccct cccaccaaat    180
tatccttaaa aactctgatc cccgaatgct cagggagatc gatttgagta ctaataagac    240
tccagtctcc tgcacaagca gctctgtgta ctcttcctct attgcaattc ctgtcttgat    300
aaatcggctc tgtgtaggcg gcggaagaag tgaacctgtt gggcggttac cacctctgtc    360
gtgtgtgaca gttgntttga atctctaatt gctcagtaca gatccacatg caggttaagt    420
aagaagcttt tgaagaaaat ggaaagtctt aagtgatggc ttccaagaaa tcaaacctac    480
attaattagg gaacaacgga ctttacgtat cacaaatgaa gagactgacn aagtaaatca    540
acttggcctt ttctta                                                     556
```

<210> SEQ ID NO 157
<211> LENGTH: 333

<212> TYPE: DNA
<213> ORGANISM: Homo sapiens
<220> FEATURE:
<221> NAME/KEY: misc_feature
<222> LOCATION: 18, 40, 55, 57, 60, 91, 97, 103, 110, 161, 173, 193,
      195, 196, 214, 231, 233, 238, 263, 264, 266, 283, 284, 287, 297,
      298, 323, 331
<223> OTHER INFORMATION: n = A,T,C or G

<400> SEQUENCE: 157

```
ggtccacaaa aatatatnaa ataagctgga tatataaaan caaacactta acatngncan      60
cattccttca gttattcaaa ctcactgata nctaacnggg agnagttggn attctggaag     120
acttcctaag ctaaaagtat atttacatat ttacaacaca ngtaaatata acngaagaac     180
tacttcaaat aangnngaaa ttccagaatt ctanagattt atagctatag ntnacaanta     240
tcaccaattg gtttgcaatc aanngnccag cactacttat gannaangtt taactannaa     300
accaaaaggg gagaaaacct ggnagggaaa nat                                   333
```

<210> SEQ ID NO 158
<211> LENGTH: 629
<212> TYPE: DNA
<213> ORGANISM: Homo sapiens
<220> FEATURE:
<221> NAME/KEY: misc_feature
<222> LOCATION: 345, 565
<223> OTHER INFORMATION: n = A,T,C or G

<400> SEQUENCE: 158

```
tcgagcggcc gcccgggcag gtctggtaca tttgtgcgag gtccggcact ctgttctcat      60
ccagtaagtg gtcgagccct ttctgcagaa ttgctgttaa atgttctcct aatagctgtt     120
tctccacaca agcaatcagt ggtttctgtg tgctgtggtc caagtaagtg attactctgt     180
ctccctcttc ttctaagcgt ttacttacat ggttaagata ttctggaacc tctctttcct     240
gcattaacct ttggccttcg gcagcatata agcaattagt ctcttccaaa aatttcagtt     300
caaatgaatc tttatacacc tgcaggtcag acagcatgcc caggnaggct ccgcaacagg     360
ctccggtcca cggcctcgcc gctcctctcg cgctcgatca gcagtaggat tccatcaatg     420
gttttactct gaaccatttt atcactaata atatgggttc taaacagttc taatcccata     480
tcccagatgg agggcagcgt ggagttctgc agcacatagg tgcggtccaa gaacaggaag     540
atgcttctga tcatgaatca tttgnctggc aatggtcctg ccagcacgtg gtaatctttc     600
ttttaaaaat aaacccttat ctaaacgtc                                       629
```

<210> SEQ ID NO 159
<211> LENGTH: 629
<212> TYPE: DNA
<213> ORGANISM: Homo sapiens
<220> FEATURE:
<221> NAME/KEY: misc_feature
<222> LOCATION: 33, 546, 576
<223> OTHER INFORMATION: n = A,T,C or G

<400> SEQUENCE: 159

```
tcgagcggcc gcccgggcag gttctagagg ganaatctgg ctgatttggg aataaaatat      60
aatcgaatat tcaacaccat gaagataaat cttattttgg aaatctactg accttaatac     120
cccaagcttg ccctgaatac tttgattgga attggaatat atcaaaaaag gttagtattt     180
ttgttgtagt taggatacta aaaggatatt agttacccaa gagatccaat ttgttttttct     240 gatgaatagt gttcagtaaa atgaagcagt cttaagagtg actaataatt tcaaagtgat     300
```

| | |
|---|---|
| ttttcgtcta ttcttaatat tttttaatta tttattttta agagttttat accttgagca | 360 |
| gatacaatga tccgctttag tgagaggaca atttctgatt gattgttttc tcttcaggcc | 420 |
| atctcacctc ttcattctct tgttacattt gaagcagttg atataatggg tttatacttt | 480 |
| aaaagataga catggtgcca tgaagtttgg ggaagttggg tgaattatcc cattctagtt | 540 |
| acagangagc tttccttaaa tgcccttac ttctangttt ggtcaagaag tcattttctg | 600 |
| agtaaaagtt attttcatat atgttgggg | 629 |

<210> SEQ ID NO 160
<211> LENGTH: 519
<212> TYPE: DNA
<213> ORGANISM: Homo sapiens
<220> FEATURE:
<221> NAME/KEY: misc_feature
<222> LOCATION: 46, 309, 397, 430, 434, 471, 497
<223> OTHER INFORMATION: n = A,T,C or G

<400> SEQUENCE: 160

| | |
|---|---|
| tcgagcggcg cgcccgggca ggtctgctgg gattaatgcc aagttnttca gccataaggt | 60 |
| agcgaaatct agcagaatcc agattacatc cacttccaat cacgcggtgt ttgggtaatc | 120 |
| cacttagttt ccagataaca tacgtaagaa tgtccactgg gttggaaacc acaattatga | 180 |
| tgcaatcagg actgtacttg acgatctgag gaataatgaa tttgaagaca ttaacatttc | 240 |
| tctgcaccag attgagccga ctctcccctt cttgctgacg gactcctgca gttaccacta | 300 |
| caatcttana attgggcggg tcacagaata atctttatct gccacaattt taggtgctga | 360 |
| agaaataagc tcccatgctg cagatccatc atttctnctt taagcttatc ttccaaaaca | 420 |
| tccacaagan caangttcat cagccagaga cttccccaga atgctgatag nacacgccat | 480 |
| accaacttgt ccaacancca ctacagcgat cttattggt | 519 |

<210> SEQ ID NO 161
<211> LENGTH: 446
<212> TYPE: DNA
<213> ORGANISM: Homo sapiens
<220> FEATURE:
<221> NAME/KEY: misc_feature
<222> LOCATION: 5, 32, 36, 269, 354, 381
<223> OTHER INFORMATION: n = A,T,C or G

<400> SEQUENCE: 161

| | |
|---|---|
| cgagnggccc gcccgggcag gtccagtaag cntttnacga tgatgggaaa ggttatgcaa | 60 |
| ggtcccagcg gtacaacgag ctgtttctac atcatttgta ttctgcatgg tacgtacaat | 120 |
| agcagacacc atctgaggag aacgcatgat agcgtgtctg gaagcttcct ttttagaaag | 180 |
| ctgatggacc ataactgcag ccttattaac caccacctgg tcctcgtcat ttagcagttt | 240 |
| tgtcagttca gggattgcac gtgtggcang ttctgcatca tcttgatagt taatcaagtt | 300 |
| tacaactggc atgtttcagc atctgcgatg ggctcagcaa acgctggaca ttantgggat | 360 |
| gagcagcatc aaactgtgta natgggatct gcatgccctc atctaatgtc tcagggaaca | 420 |
| tagcagctcg taccctctga gctcga | 446 |

<210> SEQ ID NO 162
<211> LENGTH: 354
<212> TYPE: DNA
<213> ORGANISM: Homo sapiens
<220> FEATURE:
<221> NAME/KEY: misc_feature
<222> LOCATION: 6, 19, 36, 116, 152, 174, 186, 196, 223, 249
<223> OTHER INFORMATION: n = A,T,C or G

<400> SEQUENCE: 162

```
agcgtngtcg cggcccgang tcctgggaag cctttnttgc tgagcctcac agcctctgtc    60
aggcggctgc ggatccagcg gtccaccagg ctctcatggc ctccgggctg ggaggngggt   120
gagggcacaa aaccctcccc aaggccacga anggcaaact tggtggcatt ccanagcttg   180
ttgcanaagt ggcggnaacc cagtatccgg ttcacatcca ggntgatgtc acgaccctgg   240
gacatgtang cacataatcc aaaccggaga gcatcggtgc cacattcacg aatcccgct    300
gggaagtcag ctttctgccc ttctttggcc ttctccacct cgctgggatc cagg          354
```

<210> SEQ ID NO 163
<211> LENGTH: 258
<212> TYPE: DNA
<213> ORGANISM: Homo sapiens
<220> FEATURE:
<221> NAME/KEY: misc_feature
<222> LOCATION: 7, 24, 32, 153, 198, 205
<223> OTHER INFORMATION: n = A,T,C or G

<400> SEQUENCE: 163

```
tttttcncca agtcctcttg ccgngggatc tngactgcaa tttaagacac ttctaattag    60
ttatacccag gccctgcaaa attgctgggt ttatataata tattcttgct gcacgaagat   120
ttattattct gttggatgat tctattttaa ttntatttat tctggccaaa aaagaacctt   180
ctccgctcgt caagagangc caatngtgtct tgaaggacaa gagaaagatg ctaacacaca   240
ctttcttctt cttgagga                                                 258
```

<210> SEQ ID NO 164
<211> LENGTH: 282
<212> TYPE: DNA
<213> ORGANISM: Homo sapiens
<220> FEATURE:
<221> NAME/KEY: misc_feature
<222> LOCATION: 97, 130, 163, 178, 203, 204
<223> OTHER INFORMATION: n = A,T,C or G

<400> SEQUENCE: 164

```
ggaacatatt acttttaaat tacttgggtc aatgaaacat ttaataaaaa catttgcttc    60
tctatataat acgtatgtat aaaataagcc ttttcanaaa ctctggttct cataatcctc   120
tataaatcan atgatctgac ttctaagagg aacaaattac agnaaggggt atacattnat   180
gaatactggt agtactagag ganngacgct aaaccactct actaccactt gcggaactct   240
cacagggtaa atgacaaagc caatgactga ctctaaaaac aa                      282
```

<210> SEQ ID NO 165
<211> LENGTH: 462
<212> TYPE: DNA
<213> ORGANISM: Homo sapiens
<220> FEATURE:
<221> NAME/KEY: misc_feature
<222> LOCATION: 10, 33, 36, 49, 198, 222, 243, 278, 357, 385, 399, 405,
      437
<223> OTHER INFORMATION: n = A,T,C or G

<400> SEQUENCE: 165

```
gcccgggcan gtcctgtaat cccagctact cangangctg agtcatgana atcgcctgaa    60
tccgggaggt agaggccgca gcgagcaaag attaagccac tgcactccag tctgggtgac   120
agagtgagaa tctgtctgtt gctcctctgg cattggtctg aaatgggttt gtagaacatg   180
ccacagaagg accagcanca gcaacaaatg gatttgtgga angcgtagct ccaaatggag   240
```

```
cangcacact tgatgaagca cgctgtgtct gtgcagangc aaccactggc actgttccaa    300
aaacattgct gctagcatta cttgtggaag tatacgcatt actggaggtg gctgcanaac    360
tgaaaacgct gtctagttct gccanagctg catacttgnc tgaanatgca cttgactgac    420
tgggaactga accacanaac caacaggacc tttacctgtg ga                       462
```

<210> SEQ ID NO 166
<211> LENGTH: 365
<212> TYPE: DNA
<213> ORGANISM: Homo sapiens
<220> FEATURE:
<221> NAME/KEY: misc_feature
<222> LOCATION: 14, 18
<223> OTHER INFORMATION: n = A,T,C or G

<400> SEQUENCE: 166

```
cgtgggtcgc ggcncgangt ctgaaaccaa tccagaacta acatcagca cacaaaaaat     60 accaggatag atggaatcaa aagactctga agccaaaagg aggctaggga gagcaactga   120
acttagcaag ctgaggactt cagtgtccat catccgatcc tgccctgtaa caacaggtct   180
atatgataga gatattccat ctgagctgga ggccattatc cttagcaaac taacacagaa   240
cagaaaacca aatacatgtt ctcatttaga agtaggagct aaatgatgag aactcaagga   300
cacaaagaaa ggaacaacag acactggggc ctacttgagg gtggagggtg ggaggaggga   360
gaaga                                                                365
```

<210> SEQ ID NO 167
<211> LENGTH: 364
<212> TYPE: DNA
<213> ORGANISM: Homo sapiens
<220> FEATURE:
<221> NAME/KEY: misc_feature
<222> LOCATION: 19, 342, 361
<223> OTHER INFORMATION: n = A,T,C or G

<400> SEQUENCE: 167

```
agcgtggtcg cggcgcgang tccagcccta gcttgcctgt gactccgcct tcactgggtg     60
ctctctctaa aagttgctga ctctttactg tatctcccaa ttcccactcc attggttcca   120
taaggggagg ggtgtctcac tcaacatggt gttcctggta ccaagaactg gctgacgaag   180
ctgggtgccg tggctcatgc ctgtaatccc agcacttttg ggaggccaag aagggcggat   240
cacctgaggt ctggagttca agatcagcct gaccaacatg atgaaaccaa gtctccacta   300
aaaatataaa acaattagcc aggcatggtg gtgggtgcct gnaatcccag ctactgggga   360 ngct                                                                 364
```

<210> SEQ ID NO 168
<211> LENGTH: 447
<212> TYPE: DNA
<213> ORGANISM: Homo sapiens
<220> FEATURE:
<221> NAME/KEY: misc_feature
<222> LOCATION: 407, 414, 437
<223> OTHER INFORMATION: n = A,T,C or G

<400> SEQUENCE: 168

```
cccgggcagg tcaaaaccca aaacctttca ttttagccca aaccagctca tgattaggta     60
tacaaggata acagaaccag ttgtcaggac gagcatttga caagtaaaag caattcttgc   120
aaagctgcag ttcatccagc tcatggcatg tgtctttata tagcatcctc gcaatgtcag   180
```

```
cttgctcact gtctgctcca tagaaaatca cggtattgtg gagaagcaat tgggcatcag    240
ctttgaactc ttcataactt cggtatttcc cttcattcac tttctcttga atggtgggaa    300
cgtccacaga cctcggccgc gaccacgcta agcccgaatt ctgcagatat ccatcacact    360
ggcggccgtt cgagcatggc atctagaagg cccaattcgc ctatagngag tcgnattacc    420
aattcactgg ccgtcgnttt acaacgc                                         447
```

<210> SEQ ID NO 169
<211> LENGTH: 524
<212> TYPE: DNA
<213> ORGANISM: Homo sapiens
<220> FEATURE:
<221> NAME/KEY: misc_feature
<222> LOCATION: 4, 6, 39, 40, 235, 248, 313, 340, 359, 382, 389, 420,
      434, 442, 453, 496
<223> OTHER INFORMATION: n = A,T,C or G

<400> SEQUENCE: 169

```
cgantngcgc gcccgggcag gtctgagcag cctttctgnn tgctggacta ttgggattgg     60
gttcatccaa cagagactgt atggatgtta aatggaaga cacatcatag gttggactcc    120
aacggttctg aagtatgtcc agacatatac taccatctgc atagactaag aacaaagaag    180
taggtacatt aaacgtaaca agaccactaa ggttttaaca ttatagacaa acanaaata    240 gtcaaganta ctttgctttt gaagtttaaa gattcctatg ttgcttccca gttaactgcc    300 taaaagata agncataacc accactagtg aaataatcan gatgatcaga gaatgtcana    360
tgtgatcagt ataaaactgg angatattna gtgtcatcct ttggaaaagg ctgccctatn    420
atccaggaaa tcanaaacat tnttgaacag ggnccctagc tatccacaga catgtgggaa    480
attcattccc caaatngtag gctggatccc ctatctgaaa taac                      524
```

<210> SEQ ID NO 170
<211> LENGTH: 332
<212> TYPE: DNA
<213> ORGANISM: Homo sapiens
<220> FEATURE:
<221> NAME/KEY: misc_feature
<222> LOCATION: 5, 10, 63, 66, 90, 93, 96, 186, 207, 261, 290, 324, 326
<223> OTHER INFORMATION: n = A,T,C or G

<400> SEQUENCE: 170

```
tcgancggcn cgcccgggca ggtgacaaac ctgttattga agatgttggt tctgatgagg     60
aanaanatca gaagggatgg tgacaagaan aanaanaaga agattaagga aaagtacatc    120
gatcaagaag agctcaacaa aacaaagccc atctggacca gaaatcccga cgatattact    180
aatgangagt acggagaatt ctataanagc ttgaccaatg actgggaaga tcacttggca    240
gtgaagcatt tttcagttga nggacagttg gaattcagag cccttctatn tgtcccacga    300
cgtgctcctt tgatctgtt tganancaga aa                                    332
```

<210> SEQ ID NO 171
<211> LENGTH: 334
<212> TYPE: DNA
<213> ORGANISM: Homo sapiens
<220> FEATURE:
<221> NAME/KEY: misc_feature
<222> LOCATION: 5, 9, 200, 228, 232
<223> OTHER INFORMATION: n = A,T,C or G

<400> SEQUENCE: 171

```
cgagnggcnc gcccgggcag gtctgttgat agcgacttaa cagaaaagtc tagacaaaca     60
```

```
taagcataaa aaattacagt ctttctaccc ttgggaatgg ggagaaaaag gaatctctac    120
cccaagacca gaaataataa gtcctgtttc tggtcctgaa catccagaat tatggaggct    180
ttggcctgac accacattan aatttggtct ggaaatcaaa ctttagaaac angagatcgt    240
aagccatttt atactatcga cctaaattcc agtctaacgg ttcctttaca aagttgcgga    300
aagccctctt atatgctagc tgtaggaaat atag                                334
```

<210> SEQ ID NO 172
<211> LENGTH: 439
<212> TYPE: DNA
<213> ORGANISM: Homo sapiens
<220> FEATURE:
<221> NAME/KEY: misc_feature
<222> LOCATION: 19, 375, 388, 390, 395, 409, 426, 434
<223> OTHER INFORMATION: n = A,T,C or G

<400> SEQUENCE: 172

```
agcgtggtcg cggcccgang tctgcctata aaactagact tctgacgctg ggctccagct    60
tcattctcac aggtcatcat cctcatccgg gagagcagtt gtctgagcaa cctctaagtc    120
gtgctcatac tgtgctgcca aagctgggtc catgacaact tctggtgggg cgagagcagg    180
catggcaaca aattccaagt tagggtctcc aatgagcttc ctagcaagcc agaggaaggg    240
cttttcaaag ttgtagttac ttttggcaga atgtcgtag tactgaagat tcttctttcg    300
gtggaagaca atggatttcg ccttcacttt ctgccttaat atccactttg gtgccacaca    360
acacaatggg gatgntttca cacacttngn accanatctc tatgccagnt aggccatttt    420
ggaagnactt cganggtac                                                  439
```

<210> SEQ ID NO 173
<211> LENGTH: 599
<212> TYPE: DNA
<213> ORGANISM: Homo sapiens
<220> FEATURE:
<221> NAME/KEY: misc_feature
<222> LOCATION: 5, 31
<223> OTHER INFORMATION: n = A,T,C or G

<400> SEQUENCE: 173

```
cgatnggccg cccgggcagg tcctgtaaaa naggaaattc agacatcgta cgactcgtaa    60
ttgaatgtgg agctgactgc aatattttgt caaagcacca gaatagtgcc ctgcactttg    120
cgaagcagtc taacaatgtg cttgtgtacg acttgctgaa gaaccattta gagacactttt  180 caagagtagc agaagagaca ataaaggatt actttgaagc tcgccttgct ctgctagaac    240 cagttttttcc aatcgcatgt catcgactct gtgagggtcc agattttttca acagatttca    300 attaccaacc cccacagaac ataccagaag gctctggcat cctgctgttt atcttccatg    360 caaactttttt gggtaaagaa gttattgctc ggctctgtgg accgtgtagt gtacaagctg    420
tagttctgaa tgataaattt cagcttcctg tttttctggg tctcgctctg ttgtccaggc    480
tggagtgcag tggcgcggat tacagctcac tggagtcttg acttcccagg cacaagcaat    540
cctcccacct cagcctccta actacctggg actaaaaatg caccgccacc acattccgg    599
```

<210> SEQ ID NO 174
<211> LENGTH: 458
<212> TYPE: DNA
<213> ORGANISM: Homo sapiens
<220> FEATURE:
<221> NAME/KEY: misc_feature
<222> LOCATION: 30, 32, 35, 51, 61, 213, 261, 327, 347, 359, 377, 418
<223> OTHER INFORMATION: n = A,T,C or G

<400> SEQUENCE: 174

```
tcgatttggc cgcccgggca ggtccatgcn gnttntgccc attcccatgg ngcccgacaa      60
ncccatcccc gaggccgaca tccccatgtt catgttcatg cccaccatgc cctggctcat     120
ccctgcgctg ttccccagag gggccattcc catggtgccc gtcattacac cgggcatgtt     180
cataggcatg gtccccccca ggagagggtt agnttgaggc cggacaggaa gcatgtttga     240
tggagaactg aggttcacag nctccaaaac tttgagtcat cacattcata ggctgctgca     300
tattctgtct gctgaatcca ttgtatncag tgatggcctg ctggggnttt ggaaggctng     360
cataccaggt agtaagntcg tctaggctga tgtttacacc tggggtcaga ccaagtanga     420
gggcaaggtt ttgctgactg attttctgga cccatatc                             458
```

<210> SEQ ID NO 175
<211> LENGTH: 1206
<212> TYPE: DNA
<213> ORGANISM: Homo sapiens

<400> SEQUENCE: 175

```
ggcacgagga agttttgtgt actgaaaaag aaactgtcag aagcaaaaga aataaaatca      60
cagttagaga accaaaaagt taaatgggaa caagagctct gcagtgtgag gtttctcaca     120
ctcatgaaaa tgaaaattat ctcttacatg aaaattgcat gttgaaaaag gaaattgcca     180
tgctaaaact ggaaatagcc acactgaaac accaatacca ggaaaaggaa ataaatact      240
ttgaggacat taagatttta aaagaaaaga atgctgaact tcagatgacc ctaaaactga     300
aagaggaatc attaactaaa agggcatctc aatatagtgg gcagcttaaa gttctgatag     360
ctgagaacac aatgctcact tctaaattga aggaaaaaca agacaaagaa atactagagg     420
cagaaattga atcacaccat cctagactgg cttctgctgt acaagaccat gatcaaattg     480
tgacatcaag aaaaagtcaa gaacctgctt tccacattgc aggagatgct tgtttgcaaa     540
gaaaaatgaa tgttgatgtg agtagtacga tatataacaa tgaggtgctc catcaaccac     600
tttctgaagc tcaaggaaa tccaaaagcc taaaaattaa tctcaattat gccggagatg     660
ctctaagaga aaatacattg gtttcagaac atgcacaaag agaccaacgt gaaacacagt     720
gtcaaatgaa ggaagctgaa cacatgtatc aaaacgaaca agataatgtg aacaaacaca     780
ctgaacagca ggagtctcta gatcagaaat tatttcaact acaaagcaaa aatatgtggc     840
ttcaacagca attagttcat gcacataaga agctgacaa caaaagcaag ataacaattg     900
atattcattt tcttgagagg aaaatgcaac atcatctcct aaaagagaaa atgaggaga     960
tatttaatta caataaccat ttaaaaaacc gtatatatca atatgaaaaa gagaaagcag    1020
aaacagaagt tatataatag tataacactg ccaaggagcg gattatctca tcttcatcct    1080
gtaattccag tgtttgtcac gtggttgttg aataaatgaa taaagaatga gaaaaccaga    1140
agctctgata cataatcata atgataatta tttcaatgca caactacggg tggtgctgct    1200
cgtgcc                                                              1206
```

<210> SEQ ID NO 176
<211> LENGTH: 317
<212> TYPE: PRT
<213> ORGANISM: Homo sapiens

<400> SEQUENCE: 176

```
Met Gly Thr Arg Ala Leu Gln Cys Glu Val Ser His Thr His Glu Asn
  1               5                  10                  15
```

Glu Asn Tyr Leu Leu His Glu Asn Cys Met Leu Lys Lys Glu Ile Ala
            20                  25                  30

Met Leu Lys Leu Glu Ile Ala Thr Leu Lys His Gln Tyr Gln Glu Lys
        35                  40                  45

Glu Asn Lys Tyr Phe Glu Asp Ile Lys Ile Leu Lys Glu Lys Asn Ala
    50                  55                  60

Glu Leu Gln Met Thr Leu Lys Leu Lys Glu Glu Ser Leu Thr Lys Arg
65                  70                  75                  80

Ala Ser Gln Tyr Ser Gly Gln Leu Lys Val Leu Ile Ala Glu Asn Thr
                85                  90                  95

Met Leu Thr Ser Lys Leu Lys Glu Lys Gln Asp Lys Glu Ile Leu Glu
            100                 105                 110

Ala Glu Ile Glu Ser His His Pro Arg Leu Ala Ser Ala Val Gln Asp
        115                 120                 125

His Asp Gln Ile Val Thr Ser Arg Lys Ser Gln Glu Pro Ala Phe His
130                 135                 140

Ile Ala Gly Asp Ala Cys Leu Gln Arg Lys Met Asn Val Asp Val Ser
145                 150                 155                 160

Ser Thr Ile Tyr Asn Asn Glu Val Leu His Gln Pro Leu Ser Glu Ala
                165                 170                 175

Gln Arg Lys Ser Lys Ser Leu Lys Ile Asn Leu Asn Tyr Ala Gly Asp
            180                 185                 190

Ala Leu Arg Glu Asn Thr Leu Val Ser Glu His Ala Gln Arg Asp Gln
        195                 200                 205

Arg Glu Thr Gln Cys Gln Met Lys Glu Ala Glu His Met Tyr Gln Asn
210                 215                 220

Glu Gln Asp Asn Val Asn Lys His Thr Glu Gln Glu Ser Leu Asp
225                 230                 235                 240

Gln Lys Leu Phe Gln Leu Gln Ser Lys Asn Met Trp Leu Gln Gln Gln
            245                 250                 255

Leu Val His Ala His Lys Lys Ala Asp Asn Lys Ser Lys Ile Thr Ile
        260                 265                 270

Asp Ile His Phe Leu Glu Arg Lys Met Gln His His Leu Leu Lys Glu
    275                 280                 285

Lys Asn Glu Glu Ile Phe Asn Tyr Asn Asn His Leu Lys Asn Arg Ile
        290                 295                 300

Tyr Gln Tyr Glu Lys Glu Lys Ala Glu Thr Glu Val Ile
305                 310                 315

<210> SEQ ID NO 177
<211> LENGTH: 20
<212> TYPE: DNA
<213> ORGANISM: Artificial Sequence
<220> FEATURE:
<223> OTHER INFORMATION: Made in the lab

<400> SEQUENCE: 177
ccaatcatct ccacaggagc                                           20

<210> SEQ ID NO 178
<211> LENGTH: 1665
<212> TYPE: DNA
<213> ORGANISM: Homo sapiens

<400> SEQUENCE: 178
gcaaactttc aagcagagcc tcccgagaag ccatctgcct tcgagcctgc cattgaaatg    60

```
caaaagtctg ttccaaataa agccttggaa ttgaagaatg aacaaacatt gagagcagat      120
cagatgttcc cttcagaatc aaaacaaaag aaggttgaag aaaattcttg ggattctgag      180
agtctccgtg agactgtttc acagaaggat gtgtgtgtac ccaaggctac acatcaaaaa      240
gaaatggata aataagtgg aaaattagaa gattcaacta gcctatcaaa aatcttggat       300
acagttcatt cttgtgaaag agcaaggaa cttcaaaaag atcactgtga acaacgtaca       360 ggaaaatgg aacaaatgaa aaagaagttt tgtgtactga aaagaaact gtcagaagca        420 aaagaaataa aatcacagtt agagaaccaa aaagttaaat gggaacaaga gctctgcagt     480
gtgaggtttc tcacactcat gaaatgaaa attatctctt acatgaaaat tgcatgttga      540
aaaaggaaat tgccatgcta aaactggaaa tagccacact gaaacaccaa taccaggaaa     600
aggaaaataa atactttgag gacattaaga ttttaaaaga aaagaatgct gaacttcaga     660
tgaccctaaa actgaaagag gaatcattaa ctaaaagggc atctcaatat agtgggcagc    720
ttaaagttct gatagctgag aacacaatgc tcacttctaa attgaaggaa aaacaagaca     780
aagaaatact agaggcagaa attgaatcac accatcctag actggcttct gctgtacaag     840
accatgatca aattgtgaca tcaagaaaaa gtcaagaacc tgcttttccac attgcaggag    900 atgcttgttt gcaaagaaaa atgaatgttg atgtgagtag tacgatatat aacaatgagg    960
tgctccatca accactttct gaagctcaaa ggaaatccaa aagcctaaaa attaatctca    1020
attatgccgg agatgctcta agagaaaata cattggtttc agaacatgca caaagagacc    1080
aacgtgaaac acagtgtcaa atgaaggaag ctgaacacat gtatcaaaac gaacaagata    1140
atgtgaacaa acacactgaa cagcaggagt ctctagatca gaaattattt caactacaaa   1200
gcaaaaatat gtggcttcaa cagcaattag ttcatgcaca taagaaagct gacaacaaaa   1260
gcaagataac aattgatatt cattttcttg agaggaaaat gcaacatcat ctcctaaaag    1320
agaaaaatga ggagatattt aattacaata accatttaaa aaaccgtata tatcaatatg    1380
aaaaagagaa agcagaaaca gaaaactcat gagagacaag cagtaagaaa cttcttttgg   1440
agaaacaaca gaccagatct ttactcacaa ctcatgctag gaggccagtc ctagcattac   1500
cttatgttga aaatcttacc aatagtctgt gtcaacagaa tacttatttt agaagaaaaa   1560
ttcatgattt cttcctgaag cctgggcgac agagcgagc tctgtctcaa aaaaaaaaa    1620 aaaaaagaa agaaagaaat gcctgtgctt acttcgcttc ccagg                    1665
```

<210> SEQ ID NO 179
<211> LENGTH: 179
<212> TYPE: PRT
<213> ORGANISM: Homo sapiens

<400> SEQUENCE: 179

```
Ala Asn Phe Gln Ala Glu Pro Pro Glu Lys Pro Ser Ala Phe Glu Pro
 1               5                  10                  15

Ala Ile Glu Met Gln Lys Ser Val Pro Asn Lys Ala Leu Glu Leu Lys
            20                  25                  30

Asn Glu Gln Thr Leu Arg Ala Asp Gln Met Phe Pro Ser Glu Ser Lys
        35                  40                  45

Gln Lys Lys Val Glu Glu Asn Ser Trp Asp Ser Glu Ser Leu Arg Glu
    50                  55                  60

Thr Val Ser Gln Lys Asp Val Cys Val Pro Lys Ala Thr His Gln Lys
65                  70                  75                  80

Glu Met Asp Lys Ile Ser Gly Lys Leu Glu Asp Ser Thr Ser Leu Ser
```

```
                 85                  90                  95
Lys Ile Leu Asp Thr Val His Ser Cys Glu Arg Ala Arg Glu Leu Gln
            100                 105                 110

Lys Asp His Cys Glu Gln Arg Thr Gly Lys Met Glu Gln Met Lys Lys
        115                 120                 125

Lys Phe Cys Val Leu Lys Lys Leu Ser Glu Ala Lys Glu Ile Lys
    130                 135                 140

Ser Gln Leu Glu Asn Gln Lys Val Lys Trp Glu Gln Glu Leu Cys Ser
145                 150                 155                 160

Val Arg Phe Leu Thr Leu Met Lys Met Lys Ile Ile Ser Tyr Met Lys
                165                 170                 175

Ile Ala Cys

<210> SEQ ID NO 180
<211> LENGTH: 1681
<212> TYPE: DNA
<213> ORGANISM: Homo sapiens

<400> SEQUENCE: 180
```

| | | | | | |
|---|---|---|---|---|---|
| gatacagtca | ttcttgtgaa | agagcaaggg | aacttcaaaa | agatcactgt | gaacaacgta | 60 |
| caggaaaaat | ggaacaaatg | aaaaagaagt | tttgtgtact | gaaaaagaaa | ctgtcagaag | 120 |
| caaaagaaat | aaaatcacag | ttagagaacc | aaaaagttaa | atgggaacaa | gagctctgca | 180 |
| gtgtgagatt | gactttaaac | caagaagaag | agaagagaag | aaatgccgat | atattaaatg | 240 |
| aaaaaattag | ggaagaatta | ggaagaatcg | aagagcagca | taggaaagag | ttagaagtga | 300 |
| aacaacaact | tgaacaggct | ctcagaatac | aagatataga | attgaagagt | gtagaaagta | 360 |
| atttgaatca | ggtttctcac | actcatgaaa | atgaaaatta | tctcttacat | gaaaattgca | 420 |
| tgttgaaaaa | ggaaattgcc | atgctaaaac | tggaaatagc | cacactgaaa | caccaatacc | 480 |
| aggaaaagga | aaataaatac | tttgaggaca | ttaagatttt | aaaagaaaag | aatgctgaac | 540 |
| ttcagatgac | cctaaaactg | aaagaggaat | cattaactaa | aagggcatct | caatatagtg | 600 |
| ggcagcttaa | agttctgata | gctgagaaca | caatgctcac | ttctaaattg | aaggaaaaac | 660 |
| aagacaaaga | aatactagag | gcagaaattg | aatcacacca | tcctagactg | gcttctgctg | 720 |
| tacaagacca | tgatcaaatt | gtgacatcaa | gaaaagtca | agaacctgct | ttccacattg | 780 |
| caggagatgc | ttgtttgcaa | agaaaaatga | atgttgatgt | gagtagtacg | atatataaca | 840 |
| atgaggtgct | ccatcaacca | ctttctgaag | ctcaaaggaa | atccaaaagc | ctaaaaatta | 900 |
| atctcaatta | tgccggagat | gctctaagag | aaaatacatt | ggtttcagaa | catgcacaaa | 960 |
| gagaccaacg | tgaaacacag | tgtcaaatga | aggaagctga | acacatgtat | caaaacgaac | 1020 |
| aagataatgt | gaacaaacac | actgaacagc | aggagtctct | agatcagaaa | ttatttcaac | 1080 |
| tacaaagcaa | aaatatgtgg | cttcaacagc | aattagttca | tgcacataag | aaagctgaca | 1140 |
| acaaaagcaa | gataacaatt | gatattcatt | ttcttgagag | gaaaatgcaa | catcatctcc | 1200 |
| taaaagagaa | aaatgaggag | atatttaatt | acaataacca | tttaaaaaac | cgtatatatc | 1260 |
| aatatgaaaa | agagaaagca | gaaacagaaa | actcatgaga | gacaagcagt | aagaaacttc | 1320 |
| ttttggagaa | acaacagacc | agatctttac | tcacaactca | tgctaggagg | ccagtcctag | 1380 |
| cattacctta | tgttgaaaaa | tcttaccaat | agtctgtgtc | aacagaatac | ttattttaga | 1440 |
| agaaaaattc | atgatttctt | cctgaagcct | acagacataa | aataacgtg | tgaagaatta | 1500 |
| cttgttcacg | aattgcataa | aagctgccca | ggatttccat | ctaccctgga | tgatgccgga | 1560 |

```
gacatcattc aatccaacca gaatctcgct ctgtcactca ggctggagtg cagtgggcgc    1620
aatctcggct cactgcaact ctgcctccca ggttcacgcc attctctggc acagcctccc    1680
g                                                                    1681
```

<210> SEQ ID NO 181
<211> LENGTH: 432
<212> TYPE: PRT
<213> ORGANISM: Homo sapiens

<400> SEQUENCE: 181

```
Asp Thr Val His Ser Cys Glu Arg Ala Arg Glu Leu Gln Lys Asp His
 1               5                  10                  15

Cys Glu Gln Arg Thr Gly Lys Met Glu Gln Met Lys Lys Lys Phe Cys
            20                  25                  30

Val Leu Lys Lys Lys Leu Ser Glu Ala Lys Glu Ile Lys Ser Gln Leu
        35                  40                  45

Glu Asn Gln Lys Val Lys Trp Glu Gln Glu Leu Cys Ser Val Arg Leu
    50                  55                  60

Thr Leu Asn Gln Glu Glu Lys Arg Arg Asn Ala Asp Ile Leu Asn
65                  70                  75                  80

Glu Lys Ile Arg Glu Glu Leu Gly Arg Ile Glu Glu Gln His Arg Lys
                85                  90                  95

Glu Leu Glu Val Lys Gln Gln Leu Glu Gln Ala Leu Arg Ile Gln Asp
            100                 105                 110

Ile Glu Leu Lys Ser Val Glu Ser Asn Leu Asn Gln Val Ser His Thr
        115                 120                 125

His Glu Asn Glu Asn Tyr Leu Leu His Glu Asn Cys Met Leu Lys Lys
    130                 135                 140

Glu Ile Ala Met Leu Lys Leu Glu Ile Ala Thr Leu Lys His Gln Tyr
145                 150                 155                 160

Gln Glu Lys Glu Asn Lys Tyr Phe Glu Asp Ile Lys Ile Leu Lys Glu
                165                 170                 175

Lys Asn Ala Glu Leu Gln Met Thr Leu Lys Leu Lys Glu Glu Ser Leu
            180                 185                 190

Thr Lys Arg Ala Ser Gln Tyr Ser Gly Gln Leu Lys Val Leu Ile Ala
        195                 200                 205

Glu Asn Thr Met Leu Thr Ser Lys Leu Lys Glu Lys Gln Asp Lys Glu
    210                 215                 220

Ile Leu Glu Ala Glu Ile Glu Ser His His Pro Arg Leu Ala Ser Ala
225                 230                 235                 240

Val Gln Asp His Asp Gln Ile Val Thr Ser Arg Lys Ser Gln Glu Pro
                245                 250                 255

Ala Phe His Ile Ala Gly Asp Ala Cys Leu Gln Arg Lys Met Asn Val
            260                 265                 270

Asp Val Ser Ser Thr Ile Tyr Asn Asn Glu Val Leu His Gln Pro Leu
        275                 280                 285

Ser Glu Ala Gln Arg Lys Ser Lys Ser Leu Lys Ile Asn Leu Asn Tyr
    290                 295                 300

Ala Gly Asp Ala Leu Arg Glu Asn Thr Leu Val Ser Glu His Ala Gln
305                 310                 315                 320

Arg Asp Gln Arg Glu Thr Gln Cys Gln Met Lys Glu Ala Glu His Met
                325                 330                 335

Tyr Gln Asn Glu Gln Asp Asn Val Asn Lys His Thr Glu Gln Gln Glu
            340                 345                 350
```

```
Ser Leu Asp Gln Lys Leu Phe Gln Leu Gln Ser Lys Asn Met Trp Leu
        355                 360                 365
Gln Gln Gln Leu Val His Ala His Lys Lys Ala Asp Asn Lys Ser Lys
    370                 375                 380
Ile Thr Ile Asp Ile His Phe Leu Glu Arg Lys Met Gln His His Leu
385                 390                 395                 400
Leu Lys Glu Lys Asn Glu Glu Ile Phe Asn Tyr Asn Asn His Leu Lys
                405                 410                 415
Asn Arg Ile Tyr Gln Tyr Glu Lys Glu Lys Ala Glu Thr Glu Asn Ser
            420                 425                 430

<210> SEQ ID NO 182
<211> LENGTH: 511
<212> TYPE: DNA
<213> ORGANISM: Homo sapiens

<400> SEQUENCE: 182
gaagtttcat gaggtttagc ttttctgggc tggggagtgg agagaaagaa gttgcagggc      60
ttacaggaaa tcccagagcc tgaggttttc tcccagattt gagaactcta gattctgcat     120
cattatcttt gagtctatat tctcttgggc tgtaagaaga tgaggaatgt aataggtctg     180
ccccaagcct tcatgccttt ctgtaccaag cttgtttcct tgtgcatcct tcccaggctc     240
tggctgcccc ttattggaga atgtgatttc caagacaatc aatccacaag tgtctaagac     300
tgaatacaaa gaacttcttc aagagttcat agacgacaat gccactacaa atgccataga     360
tgaattgaag gaatgttttc ttaaccaaac ggatgaaact ctgagcaatg ttgaggtgtt     420
tatgcaatta atatatgaca gcagtctttg tgatttattt taactttctg caagaccttt     480
ggctcacaga actgcagggt atggtgagaa a                                    511

<210> SEQ ID NO 183
<211> LENGTH: 260
<212> TYPE: DNA
<213> ORGANISM: Homo sapiens

<400> SEQUENCE: 183
cacctcgcgg ttcagctcct ctgtcttggt gaagaaccat tcctcggcat ccttgcggtt      60
cttctctgcc atcttctcat actggtcacg catctcgttc agaatgcggc tcaggtccac     120
gccaggtgca gcgtccatct ccacattgac atctccaccc acctggcctc tcagggcatt     180
catctcctcc tcgtggttct tcttcaggta ggccagctcc tccttcaggc tctcaatctg     240
catctccagg tcagctctgg                                                 260

<210> SEQ ID NO 184
<211> LENGTH: 461
<212> TYPE: DNA
<213> ORGANISM: Homo sapiens

<400> SEQUENCE: 184
gtctgatggg agaccaaaga atttgcaagt ggatggtttg gtatcactgt aaataaaaag      60
agggcctttt ctagctgtat gactgttact tgaccttctt tgaaaagcat tcccaaaatg     120
ctctatttta gatagattaa cattaaccaa cataattttt tttagatcga gtcagcataa     180
atttctaagt cagcctctag tcgtggttca tctctttcac ctgcatttta tttggtgttt     240
gtctgaagaa aggaaagagg aaagcaaata cgaattgtac tatttgtacc aaatctttgg     300
gattcattgg caaataattt cagtgtggtg tattattaaa tagaaaaaaa aaattttgtt     360
```

```
tcctaggttg aaggtctaat tgataccgtt tgacttatga tgaccattta tgcactttca     420
aatgaatttg ctttcaaaat aaatgaagag cagacctcgg c                        461
```

<210> SEQ ID NO 185
<211> LENGTH: 531
<212> TYPE: DNA
<213> ORGANISM: Homo sapiens

<400> SEQUENCE: 185

```
tctgatttta tttccttctc aaaaaaagtt atttacagaa ggtatatatc aacaatctga     60
caggcagtga acttgacatg attagctggc atgatttttt ctttttttc ccccaaacat     120 tgttttgtg gccttgaatt ttaagacaaa tattctacac ggcatattgc acaggatgga     180
tggcaaaaaa aagtttaaaa acaaaaccc ttaacggaac tgccttaaaa aggcagacgt     240
cctagtgcct gtcatgttat attaaacata catacacaca atcttttgc ttattataat     300 acagacttaa atgtacaaag atgttttcca ctttttcaa tttttaaaca caacagctat     360
aaacctgaac acatatgcta tcatcatgcc ataagactaa aacaattata tttagcgaca     420
agtagaaagg attaaatagt caaatacaag aatgaaaaac gcagtacata gtgtcgcgaa     480
ctcaaatcgg catttagata gatccagtgg tttaaacggc acgttttgc t              531
```

<210> SEQ ID NO 186
<211> LENGTH: 441
<212> TYPE: DNA
<213> ORGANISM: Homo sapiens

<400> SEQUENCE: 186

```
cattcctttc ctcgcgttgg ggtttctctg tgtcagcgag cctcggtaca ctgatttccg     60
atcaaaagaa tcatcatctt taccttgact tttcagggaa ttactgaact ttcttctcag     120
aagatagggc acagccattg ccttggcctc acttgaaggg tctgcatttg ggtcctctgg     180
tctcttgcca agtttcccaa ccactcgagg gagaaatatc gggaggtttg acttcctccg     240
gggctttccc gagggcttca ccgtgagccc tgcggcctc agggctgcaa tcctggattc     300
aatgtctgaa acctcgctct ctgcctgctg gacttctgag gccgtcactg ccactctgtc     360
ctccagctct gacagctcct catctgtggt cctgttgtac tggacggggt ccccagggtc     420
ctgggggctt ttttcctgtc t                                              441
```

<210> SEQ ID NO 187
<211> LENGTH: 371
<212> TYPE: DNA
<213> ORGANISM: Homo sapiens

<400> SEQUENCE: 187

```
aaaagtgaat gagtaactat tatattgttg gcaataataa gttgcaaaat catcaggctg     60
caggctgctg atggtgagag tgaactctgt cccagatcca ctgccgctga accttgatgg     120
gaccccagat tctaaactag acgccttatg gatcaggagc tttggggctt ccctggtttt     180
ctgttgatac caggccaacc aactactaac actctgactg gcccggcaag tgatggtgac     240
tctgtctcct acagttgcag acagggtgga aggagactgg gtcatctgga tgtcacatttt    300 ggcacctggg agccagagca gcaggagccc caggagctga gcggggaccc tcatgtccat     360
gctgagtcct g                                                         371
```

<210> SEQ ID NO 188

```
<211> LENGTH: 226
<212> TYPE: DNA
<213> ORGANISM: Homo sapiens

<400> SEQUENCE: 188
ggtatataaa ttgagatgcc cccccaggcc agcaaatgtt cctttttgtt caaagtctat    60
ttttattcct tgatattttt cttttttttt tttttgtgga tggggacttg tgaattttc    120 taaaggtgct atttaacatg ggaggagagc gtgtgcggct ccagcccagc ccgctgctca   180
ctttccaccc tctctccacc tgcctctggc ttctcaggac ctgccc                  226

<210> SEQ ID NO 189
<211> LENGTH: 391
<212> TYPE: DNA
<213> ORGANISM: Homo sapiens
<220> FEATURE:
<221> NAME/KEY: misc_feature
<222> LOCATION: 43, 112, 131, 156, 195, 208, 221, 317, 333, 367
<223> OTHER INFORMATION: n = A,T,C or G

<400> SEQUENCE: 189
tgggtgaagt ttattctgtt ttcacatcta ggttgttggg ganagtgata gacaaagttc    60
tggattctgg gcatcgtcgg cgcatgcttg taatcctact tgggaggttg anacaggaga   120
cctcggccgc naccacgcta agggcgaatt ctgcanatat ccatcacact ggcggccgct   180
cgagcatgca tctanagggc ccaattcncc ctatagtgag ncgtattaca attcactggc   240
cgtcgtttta caacgtcgtg actgggaaaa ccctggcgtt acccaactta atcgccttgc   300
agcacatccc cctttcncca gctggcttaa tancgaagag gcccgcaccg atcgcccttc   360
ccaacanttg cgcagcctga atggcgaatg g                                  391

<210> SEQ ID NO 190
<211> LENGTH: 501
<212> TYPE: DNA
<213> ORGANISM: Homo sapiens

<400> SEQUENCE: 190
catcttggcc ttttttgagct gtttccgctt cttctcatcc cggtcactgt caccctcatt    60
actggaggag ctggcagagg cgttgctgtc aaactcctct gccacatctt cctcctcttc   120
acctgggttg aatgactcat cggtttcttc tcctgagtca tcgctgctgt cattggcatt   180
ctcctcccgg atcttgcctt cctccttcat cctctccaag taggcatcat gctggtcctc   240
atcagagtca gcatattcat cgtagcttgg gttcatgccc tctttcaatc ctcggttttt   300
gatgttgagc tttttcgcgt tgacaaaatc aaacagtttc ccgtactcct ccctctcaat   360
gctgctgaag gtatactgag tgccctgctt ggtctcaatt tcaaagtcaa aggaacgagt   420
agtagtggta ccacgagcaa agttgacaaa ggagatctca tcgaagcgga tgtgcacagg   480
tggcttgtgg acgtagatga a                                            501

<210> SEQ ID NO 191
<211> LENGTH: 241
<212> TYPE: DNA
<213> ORGANISM: Homo sapiens
<220> FEATURE:
<221> NAME/KEY: misc_feature
<222> LOCATION: 49
<223> OTHER INFORMATION: n = A,T,C or G

<400> SEQUENCE: 191
ggaaaaactg tgaaaaatat atctgaattt attaagtaca gtataaaana ggggttgtggc    60
```

```
aacagaaagt aaaaactaac atggattgct ataaatatgc tgaagcctag ttgttcaaat    120
gatacaattc tctcatgcta ctctaaagtt tataaagaaa aaggatttac actttacaca    180
ctgtacacaa aaggaatacc ttctgagagc caggggagtgg ggaaagggga aggagacttg    240
a                                                                    241

<210> SEQ ID NO 192
<211> LENGTH: 271
<212> TYPE: DNA
<213> ORGANISM: Homo sapiens
<220> FEATURE:
<221> NAME/KEY: misc_feature
<222> LOCATION: 6, 17, 23, 26, 70, 227, 245
<223> OTHER INFORMATION: n = A,T,C or G

<400> SEQUENCE: 192
tggtcntgga ttcacanata aantanatcg actaaaactg gcagaaattg tgaagcaggt    60
gatagaagan caaaccacgt cccacgaatc ccaataatga cagcttcaga ctttgctttt    120
ttaacaattt gaaaaattat tctttaatgt ataaagtaat tttatgtaaa ttaataaatc    180
ataatttcat ttccacattg attaaagctg ctgtatagat ttagggngca ggacttaata    240
atagnggaaa tgaaattatg atttattaat c                                  271

<210> SEQ ID NO 193
<211> LENGTH: 351
<212> TYPE: DNA
<213> ORGANISM: Homo sapiens

<400> SEQUENCE: 193
agtcgaggcg ctgatcccta aaatggcgaa catgtgtttt catcatttca gccaaagtcc    60
taacttcctg tgcctttcct atcacctcga gaagtaatta tcagttggtt tggattttg    120 gaccaccgtt cagtcatttt gggttgccgt gctcccaaaa catttaaaat gaaagtattg    180
gcattcaaaa agacagcaga caaaatgaaa gaaaatgaga gcagaaagta agcatttcca    240
gcctatctaa tttctttagt tttctatttg cctccagtgc agtccatttc ctaatgtata    300
ccagcctact gtactattta aaatgctcaa tttcagcacc gatggacctg c              351

<210> SEQ ID NO 194
<211> LENGTH: 311
<212> TYPE: DNA
<213> ORGANISM: Homo sapiens

<400> SEQUENCE: 194
ctgagacaca gaggcccact gcgagggga cagtggcggt gggactgacc tgctgacagt    60
caccctccct ctgctgggat gaggtccagg agccaactaa acaatggca gaggagacat    120 ctctggtgtt cccaccaccc tagatgaaaa tccacagcac agacctctac cgtgtttctc    180
ttccatccct aaaccacttc cttaaaatgt ttggatttgc aaagccaatt tggggcctgt    240
ggagcctggg gttggatagg gccatggctg gtcccccacc atacctcccc tccacatcac    300
tgacacagac c                                                        311

<210> SEQ ID NO 195
<211> LENGTH: 381
<212> TYPE: DNA
<213> ORGANISM: Homo sapiens

<400> SEQUENCE: 195
```

```
tgtcagagtg gcactggtag aagttccagg aaccctgaac tgtaagggtt cttcatcagt      60
gccaacagga tgacatgaaa tgatgtactc agaagtgtcc tggaatgggg cccatgagat     120
ggttgtctga gagagagctt cttgtcctgt ctttttcctt ccaatcaggg gctcgctctt     180
ctgattattc ttcagggcaa tgacataaat tgtatattcg gttcccggtt ccaggccagt     240
aatagtagcc tctgtgacac cagggcgggg ccgagggacc acttctctgg gaggagaccc     300
aggcttctca tacttgatga tgtagccggt aatcctggca cgtggcggct gccatgatac     360
cagcagggaa ttgggtgtgg t                                               381
```

<210> SEQ ID NO 196
<211> LENGTH: 401
<212> TYPE: DNA
<213> ORGANISM: Homo sapiens

<400> SEQUENCE: 196

```
cacaaacaag aggagcacca gacctcctct tggcttcgag atggcttcgc cacaccaaga      60
gcccaaacct ggagacctga ttgagatttt ccgccttggc tatgagcact gggccctgta     120
tataggagat ggctacgtga tccatctggc tcctccaagt gagtaccccg gggctggctc     180
ctccagtgtc ttctcagtcc tgagcaacag tgcagaggtg aaacgggagc gcctggaaga     240
tgtggtggga ggctgttgct atcgggtcaa caacagcttg gaccatgagt accaaccacg     300
gcccgtggag gtgatcacca gttctgcgaa ggagatggtt ggtcagaaga tgaagtacag     360
tattgtgagc aggaactgtg agcactttgt cacccagacc t                         401
```

<210> SEQ ID NO 197
<211> LENGTH: 471
<212> TYPE: DNA
<213> ORGANISM: Homo sapiens

<400> SEQUENCE: 197

```
ctgtaatgat gtgagcaggg agccttcctc cctgggccac ctgcagagag ctttcccacc      60
aactttgtac cttgattgcc ttacaaagtt atttgtttac aaacagcgac catataaaag     120
cctcctgccc caaagcttgt gggcacatgg gcacatacag actcacatac agacacacac     180
atatatgtac agacatgtac tctcacacac acaggcacca gcatacacac gttttttctag     240 gtacagctcc caggaacagc taggtgggaa agtcccatca ctgagggagc ctaaccatgt     300
ccctgaacaa aaattgggca ctcatctatt ccttttctct tgtgtcccta ctcattgaaa     360
ccaaactctg gaaaggaccc aatgtaccag tatttatacc tctagtgaag cacagagaga     420
ggaagagagc tgcttaaact cacacaacaa tgaactgcag acacagacct g              471
```

<210> SEQ ID NO 198
<211> LENGTH: 201
<212> TYPE: DNA
<213> ORGANISM: Homo sapiens

<400> SEQUENCE: 198

```
ggtccattga ggctctgtcg gccatgccca cagttcgaag ctttgccaac gaggagggcg      60
aagcccagaa gtttagggaa aagctgcaag aaataaagac actcaaccag aaggaggctg     120
tggcctatgc agtcaactcc tggaccacta gtatttcagg tatgctgctg aaagtgggaa     180
tcctctacat tggtgggcag a                                               201
```

<210> SEQ ID NO 199
<211> LENGTH: 551

```
<212> TYPE: DNA
<213> ORGANISM: Homo sapiens

<400> SEQUENCE: 199
tctggcacag atcttcaccc acacggcggt ccacgtgctg atcatcttcc gggtctcacc      60
gggcctggaa cacaccatct tccccatgag cccggtgccc agtctggtga cttccatctt     120
ggccctggc cttatgtccc agttatgacc cctgacttca actctggctc ttaccctgta     180
actccagtcc atctctgaca ttttaacac ccggccttgt gaccgtggac atagctcctg     240
acctcgattc ccatcttgag cccagtgtta gtccatgaga tcatgacctg actcctggtc     300
tccaaccttg tgatcctaat tctgggacct caatcctagc ctctgaactt gggaccctgg     360
agctcctgac cttagtcctg accgctaccc ttgattctga cctttgatcc tgtaacttag     420
gggtggcccc tgaccttatt actgtcattt agctccttga ccttgccact tcaatcctgg     480
ctttatgacc tcctactctc aattttaact ttaaccaaat gaccaaattt gtgacactaa     540
atgaccacaa t                                                          551

<210> SEQ ID NO 200
<211> LENGTH: 211
<212> TYPE: DNA
<213> ORGANISM: Homo sapiens
<220> FEATURE:
<221> NAME/KEY: misc_feature
<222> LOCATION: 8, 36, 40, 78, 165, 170, 171, 173, 203, 207, 208
<223> OTHER INFORMATION: n = A,T,C or G

<400> SEQUENCE: 200
cagctcancg ggcgacatgc ccctacaagt tggcanaagn ggctgccact gctgggtttg      60
tgtaagagag gctgctgnca ccattacctg cagaaacctt ctcataggg ctacgatcgg     120
tactgctagg gggcacatag cgcccatggg tgtggtaggt ggggnactcn ntnataggat     180
ggtaggtatc ccgggctgga aanatgnnca g                                    211

<210> SEQ ID NO 201
<211> LENGTH: 111
<212> TYPE: DNA
<213> ORGANISM: Homo sapiens

<400> SEQUENCE: 201
ccagtgaaag gaaacaaaac tggcagtttg tccatttgaa tatcagacct agtttcttct      60
taatttccac actatttctc ccatattcct taaacttctt ggcatccacc t              111

<210> SEQ ID NO 202
<211> LENGTH: 331
<212> TYPE: DNA
<213> ORGANISM: Homo sapiens

<400> SEQUENCE: 202
tgaaaataca gaataccagg tggtcccaaa tgtttgaagt tctttgaaca gaaagagaga      60
ggagagagag agagaggaaa attccctaac ccttggttta aagacaatat tcatttattg     120
ctcaaatgat gcttttaagg gaggacagtg gaataaaata aactttttt ttctccctac     180
aatacataga agggttatca aaccactcaa gtttcaaaat ctttccaggg tccaatatca     240
cttttttct ttcggttcaa tgaaaagcta aatgtaataa tactaattat agataaaatt     300
ttattttact ttttaaaaat ttgtccagac c                                    331

<210> SEQ ID NO 203
```

```
<211> LENGTH: 491
<212> TYPE: DNA
<213> ORGANISM: Homo sapiens

<400> SEQUENCE: 203
agtcacccag tctacttagt acctggttgc tgcctctgac cttttcagct tgatacctg        60 ggctttagtg taaccaataa atctgtagtg accttacctg tattcccgtg gctatcctgt      120
gggaaggtag gaatgggcta agtatgatga atgtataggt tagggatctt ttggttttaa      180
atcacagaaa acctaattca aactggctta aaataaaaag gatttattgg ttcatgtaac      240
tagaaagtcc ataggtagtg ctggctccag gtgaagactt gacccagtag ttcagtatgt      300
ctctaaatac cggactgact ttttctcac tgttgcatct tctgtaggac catttaagtc       360
tgggccactt aatggctgcc agcattccta agattacact tttccccatt tatgtccaat      420 cagaaaaga aggcatcttt gtaccagaaa tctcagcaaa agccctaata ttcacactga       480
ttaggacctg c                                                           491

<210> SEQ ID NO 204
<211> LENGTH: 361
<212> TYPE: DNA
<213> ORGANISM: Homo sapiens

<400> SEQUENCE: 204
tcccttcctc ccccatgtga taaatgggtc cagggctgat caaagaactc tgactgcaga      60
actgccgctc tcagtggaca gggcatctgt tatcctgaga cctgtggcag acacgtcttg      120
ttttcatttg attttgtta agagtgcagt attgcagagt ctagaggaat ttttgtttcc       180
ttgattaaca tgattttcct ggttgttaca tccaggcat ggcagtggcc tcagccttaa       240
acttttgttc ctactcccac cctcagcgaa ctgggcagca cggggagggt ttggctaccc      300
ctgcccatcc ctgagccagg taccaccatt gtaaggaaac actttcagaa attcagacct      360
c                                                                     361

<210> SEQ ID NO 205
<211> LENGTH: 471
<212> TYPE: DNA
<213> ORGANISM: Homo sapiens
<220> FEATURE:
<221> NAME/KEY: misc_feature
<222> LOCATION: 2, 3
<223> OTHER INFORMATION: n = A,T,C or G

<400> SEQUENCE: 205
cnngtacagt tcttcctgga tggccgacac agatcctggg gaaaggcaat cctggcactg      60
ctctgaaacc agagctcctc ctccctcccc gggcagggtg gagctgagaa gggctgctct      120
agcgttggga ctccacctcc atacacctga tattttgata gggcaggtcc ctgctatggg      180
ccactgttct gggcagtata gtatgcttga cagcatcctt ggcatctatc caccagatcc      240
cagagcaccc gctactagct gtgacaacat cctccaaaca ttgcaaaatt tcccctggga      300
ggcaagattg cctcagatgg gagaatcacg ctctaggaa atctgctggt atgagaaccc       360
caactcccca ctccactgag cctccagatg gcgagcaggc tgcagctcca gcacagacac      420
gaagctccct ccagccactg acggtccatg gctggggtta cccaggacct c               471

<210> SEQ ID NO 206
<211> LENGTH: 261
<212> TYPE: DNA
<213> ORGANISM: Homo sapiens
```

<400> SEQUENCE: 206

```
tagagtattt agagtcctga gataacaagg aatccaggca tcctttagac agtcttctgt    60
tgtcctttct tcccaatcag agatttgtgg atgtgtggaa tgacaccacc accagcaatt   120
gtagccttga tgagagaatc caattcttca tctccacgaa tagcaagttg caagtgacga   180
ggggtaatac gctttacctt taagtctttt gatgcatttc ctgccagttc aagtacctct   240
gcggtgaggt actccaggat g                                             261
```

<210> SEQ ID NO 207
<211> LENGTH: 361
<212> TYPE: DNA
<213> ORGANISM: Homo sapiens

<400> SEQUENCE: 207

```
gctctccggg agcttgaaga agaaactggc tacaaagggg acattgccga atgttctcca    60
gcggtctgta tggacccagg cttgtcaaac tgtactatac acatcgtgac agtcaccatt   120
aacggagatg atgccgaaaa cgcaaggccg aagccaaagc caggggatgg agagtttgtg   180
gaagtcattt ctttacccaa gaatgacctg ctgcagagac ttgatgctct ggtagctgaa   240
gaacatctca cagtggacgc cagggtctat tcctacgctc tagcactgaa acatgcaaat   300
gcaaagccat tgaagtgcc cttcttgaaa ttttaagccc aaatatgaca ctggacctgc   360
c                                                                   361
```

<210> SEQ ID NO 208
<211> LENGTH: 381
<212> TYPE: DNA
<213> ORGANISM: Homo sapiens
<220> FEATURE:
<221> NAME/KEY: misc_feature
<222> LOCATION: 10, 27, 37, 46, 75, 95, 102, 137, 143, 202, 234, 278, 310, 351
<223> OTHER INFORMATION: n = A,T,C or G

<400> SEQUENCE: 208

```
agaggagatn tttgccatgc ctgaatnctt tcctatncca ccctancact taacatatta    60
cttagtctgc tttgntaaaa gcaagtatta ccttnaactt gnctcttact ctttgccctt   120
tagctaacta ataaagnttg atntaggcat tattatataa ttctgagtca ttcatggtat   180
ctctcatgtt tgatgtattt tncaaactaa gatctatgat agttttttt ccanagttcc    240
attaaatcat ttatttcctt tactttctca cctctgtnga acatttagaa aactggattt   300
gggaacccan ttttggaaaa ccagattcat agtcatgaaa atggaaactt ncatattctg   360
tttttgaaaa gatgtggacc t                                             381
```

<210> SEQ ID NO 209
<211> LENGTH: 231
<212> TYPE: DNA
<213> ORGANISM: Homo sapiens
<220> FEATURE:
<221> NAME/KEY: misc_feature
<222> LOCATION: 83
<223> OTHER INFORMATION: n = A,T,C or G

<400> SEQUENCE: 209

```
gtggagagca agtgatttat taaagcaaga cgttgaaacc tttacattct gcagtgaaga    60
tcagggtgtc attgaaagac agnggaaacc aggatgaaag ttttacatg tcacacacta   120
catttcttca atattttcac caggacttcc gcaatgaggc ttcgtttctg aagggacatc   180
```

```
tgatccgtgc atctcttcac tcctaacttg gctgcaacag cttccacctg c            231
```

<210> SEQ ID NO 210
<211> LENGTH: 371
<212> TYPE: DNA
<213> ORGANISM: Homo sapiens

<400> SEQUENCE: 210

```
tccatcctgg ttttgcagag atcaggttgt tgacagttcc tggttgaccc acagctaccc    60
atgtcagtta tctccactaa catatccaag aatctttgta ggacaatttc tccacctgca   120
aggttttta ggtagaactc ttcttttaag gcaattagcc cattgccaaa aggttttact   180
gtcttaaagc tgtctttctg agatctaatt ccaaggactt ctccacagct aagtgagatg   240
cctcacacca ttaggtgatg ctttggacag aacagagtat tttcatcttg tgtttaaagc   300
aattccttgg cttcggctcc tcaccacttt ctatgccagt ctcccattta tgtccctagt   360
aatgcctatg c                                                        371
```

<210> SEQ ID NO 211
<211> LENGTH: 471
<212> TYPE: DNA
<213> ORGANISM: Homo sapiens

<400> SEQUENCE: 211

```
tttattttaa aagaaaaaaa ttaaaataga gccaacaaat gcaattaaga aaaaaaaagt    60
attgagacac aaggggacct acatgttctg gtctaagaag catgcaagta ttacaaagca   120
ttccagatac agtatgacag aggaacagtg aacaagcatt ggaacgatgc tctttctttc   180
agaaacggga gtctaacag ttatgttttc acaatggtag tgattaaacc atctttattt   240
ttaaggaatt ttataggaag aattttagca ccatcattaa aggaaaaata ataataccttt  300
tttagccctg cctatctcca gtcttggaat aataacagaa gcatagcacc tttcagtatc   360
taaaatataa acaagaatag taagtccatc ccagcttcta gagatgaggt agctcatgct   420
aagaaatgtt gggtcatttt tcctatgaaa gttcaaaggc caaatggtca c            471
```

<210> SEQ ID NO 212
<211> LENGTH: 401
<212> TYPE: DNA
<213> ORGANISM: Homo sapiens

<400> SEQUENCE: 212

```
tggcctgtct ccttcacata gtccatatca ccacaaatca cacaacaaaa gggagaggat    60
atattttggg ttcaaaaaaa gtaaaaagat aatgtagctg catttctttg gttattttgg   120
gccccaaata tttcctcatc ttttgttgt tgtcatggat ggtggtgaca tggacttgtt   180
tatagaggac aggtcagctc tctggctcgg tgatctacat tctgaagttg tctgaaaatg   240
tcttcatgat taaattcagc ctaaacgttt tgccgggaac actgcagaga caatgctgtg   300
agtttccaac ctcagcccat ctgcgggcag agaaggtcta gtttgtccat caccattatg   360
atatcaggac tggttacttg gttaaggagg ggtctacctc g                       401
```

<210> SEQ ID NO 213
<211> LENGTH: 461
<212> TYPE: DNA
<213> ORGANISM: Homo sapiens
<220> FEATURE:
<221> NAME/KEY: misc_feature
<222> LOCATION: 239, 290, 358, 359, 391, 393

<223> OTHER INFORMATION: n = A,T,C or G

<400> SEQUENCE: 213

```
tgtgaagcat acataaataa atgaagtaag ccatactgat ttaatttatt ggatgttatt      60
ttccctaaga cctgaaaatg aacatagtat gctagttatt tttcagtgtt agccttttac     120
tttcctcaca caatttggaa tcatataata taggtacttt gtccctgatt aaataatgtg     180
acggatagaa tgcatcaagt gtttattatg aaaagagtgg aaaagtatat agcttttanc     240
aaaaggtgtt tgcccattct aagaaatgag cgaatatata gaaatagtgn gggcatttct     300
tcctgttagg tggagtgtat gtgttgacat ttctccccat ctcttcccac tctgttttnnt    360
ccccattatt tgaataaagt gactgctgaa nangactttg aatccttatc cacttaatttt   420
aatgtttaaa gaaaaaccta taatggaaag tgagactcct t                          461
```

<210> SEQ ID NO 214
<211> LENGTH: 181
<212> TYPE: DNA
<213> ORGANISM: Homo sapiens

<400> SEQUENCE: 214

```
cctgagcttc tactcctttc ccttaagatt cctccaaagc accagctcca taaaatcctt      60
cagctcccca gacccacacc aagaacccca catgttaatt ggatcagcca aatctacaag    120
cagataagtc ctaaggagaa tgccgaagcg ttttttcttct tcctcaagcc tagcatgaga    180
c                                                                     181
```

<210> SEQ ID NO 215
<211> LENGTH: 581
<212> TYPE: DNA
<213> ORGANISM: Homo sapiens

<400> SEQUENCE: 215

```
ctgctttaag aatggttttc cacctttcc ccctaatctc taccaatcag acacatttta       60
ttatttaaat ctgcacctct ctctatttta tttgccaggg gcacgatgtg acatatctgc    120
agtcccagca cagtgggaca aaaagaattt agaccccaaa agtgtcctcg gcatggatct    180
tgaacagaac cagtatctgt catggaactg aacattcatc gatggtctcc atgtattcat    240
ttattcactt gttcattcaa gtatttattg aatacctgcc tcaagctaga gagaaaagag    300
agtgcgcttt ggaaatttat tccagttttc agcctacagc agattatcag ctcggtgact    360
tttctttctg ccaccattta ggtgatggtg tttgattcag agatggctga atttctattc    420
ttagcttatt gtgactgttt cagatctagt ttgggaacag attagaggcc attgtcctct    480
gtcctgatca ggtggcctgg ctgtttcttt ggatccctct gtcccagagc cacccagaac    540
cctgactctt gagaatcaag aaaacaccca gaaaggacct c                          581
```

<210> SEQ ID NO 216
<211> LENGTH: 281
<212> TYPE: DNA
<213> ORGANISM: Homo sapiens
<220> FEATURE:
<221> NAME/KEY: misc_feature
<222> LOCATION: 37, 38, 164, 176, 254
<223> OTHER INFORMATION: n = A,T,C or G

<400> SEQUENCE: 216

```
ccgatgtcct gcttctgtgg accagggggct cctctgnngg tggcctcaac cacggctgag    60
atccctagaa gtccaggagc tgtggggaag agaagcactt agggccagcc agccgggcac   120
```

```
cccacttgc gccccgaccc acgctcacgc accagacctg cccnggcggt cgctcnaaag      180
ggcgaattct gcagatatcc atcacactgg cggacgctcg agcatgcatc tagagggccc      240
aattcaccct atantgagtc gtattacaat tcactggccg t                         281
```

<210> SEQ ID NO 217
<211> LENGTH: 356
<212> TYPE: DNA
<213> ORGANISM: Homo sapiens
<220> FEATURE:
<221> NAME/KEY: misc_feature
<222> LOCATION: 33, 322
<223> OTHER INFORMATION: n = A,T,C or G

<400> SEQUENCE: 217

```
atagcaggtt tcaacaattg tcttgtagtt tgnagtaaaa agacataaga aagagaaggt      60
gtggtttgca gcaatccgta gttggtttct caccataccc tgcagttctg tgagccaaag     120
gtcttgcaga aagttaaaat aaatcacaaa gactgctgtc atatattaat tgcataaaca     180
cctcaacatt gctcagagtt tcatccgttt ggttaagaaa acattccttc aattcatcta     240
tggcatttgt agtggcattg tcgtctatga actcttgaag aagttctttg tattcagtct     300
tagacacttg tggattgatt gncttggaaa tcacattctc caataaggga cctcgg         356
```

<210> SEQ ID NO 218
<211> LENGTH: 321
<212> TYPE: DNA
<213> ORGANISM: Homo sapiens

<400> SEQUENCE: 218

```
ttgtccatcg ggagaaaggt gtttgtcagt tgtttcataa accagattga ggaggacaaa     60
ctgctctgcc aatttctgga tttctttatt ttcagcaaac actttcttta aagcttgact    120
gtgtgggcac tcatccaagt gatgaataat catcaagggt tgttgcttg tcttggattt     180 atatagagct tcttcatatg tctgagtcca gatgagttgg tcaccccaac ctctggagag    240
ggtctggggc agtttgggtc gagagtcctt tgtgtccttt ttggctccag gtttgactgt    300
ggtatctctg gacctgcctg g                                              321
```

<210> SEQ ID NO 219
<211> LENGTH: 271
<212> TYPE: DNA
<213> ORGANISM: Homo sapiens
<220> FEATURE:
<221> NAME/KEY: misc_feature
<222> LOCATION: 41
<223> OTHER INFORMATION: n = A,T,C or G

<400> SEQUENCE: 219

```
ccggttaggt ccacgcgggg gcagtggagg cacaggctca ngtggccgg gctacctggc      60 accctatggc ttacaaagta gagttggccc agtttccttc cacctgaggg gagcactctg    120
actcctaaca gtcttccttg ccctgccatc atctggggtg gctggctgtc aagaaaggcc    180
gggcatgctt tctaaacaca gccacaggag gcttgtaggg catcttccag gtggggaaac    240
agtcttagat aagtaaggtg acttgtctaa g                                   271
```

<210> SEQ ID NO 220
<211> LENGTH: 351
<212> TYPE: DNA
<213> ORGANISM: Homo sapiens
<220> FEATURE:

<221> NAME/KEY: misc_feature
<222> LOCATION: 32, 43
<223> OTHER INFORMATION: n = A,T,C or G

<400> SEQUENCE: 220
gtcctacgac gaggaccagc tttctttctt cnacttttcc canaacactc gggtgcctcg      60
cctgcccgaa tttgctgact gggctcagga acagggagat gctcctgcca ttttatttga     120
caaagagttc tgcgagtgga tgatccagca aatagggcca aaacttgatg ggaaaatccc     180
ggtgtccaga gggtttccta tcgctgaagt gttcacgctg aagcccctgg agtttggcaa     240
gcccaacact ttggtctgtt ttgtcagtaa tctcttccca cccatgctga cagtgaactg     300
gtagcatcat tccgtccctg tggaaggatt tgggcctact tttgtctcag a              351

<210> SEQ ID NO 221
<211> LENGTH: 371
<212> TYPE: DNA
<213> ORGANISM: Homo sapiens

<400> SEQUENCE: 221
gtctgcagaa gcgtgtctga ggtgtccggt ggaggtggca gccgagctct gggactaatc      60
accgtgctgg ggacggcacc gcgtcaggat gcaggcagat ccctgcagaa gtgtctaaaa     120
ttcacactcc tcttctggag ggacgtcgat ggtattagga tagaagcacc aggggacccc     180
acgaacggtg tcgtcgaaac agcagccctt atttgcacac tgggagggcg tgacaccagg     240
aaaaccacaa ttctgtcttt cacgggggc cactgtacac gtctctgtct gggcctcggc      300
cagggtgccg agggccagca tggacaccag gaccagggcg cagatcacct tgttctccat     360
ggtggacctc g                                                          371

<210> SEQ ID NO 222
<211> LENGTH: 471
<212> TYPE: DNA
<213> ORGANISM: Homo sapiens

<400> SEQUENCE: 222
gtccatgttc catcattaat gttccaacat caccagggac acaaagctgc aaaaatgaga      60
agggaaataa ggttagagaa aggatccggg caatcttaag gactgaggaa gacatgttcc     120
ccaacccttg aactcacaaa ccctgaagct caaggattgc atccttcctc caaatctcac     180
tcaacataat aagtgcagaa caacatgcca aagcactgta tgaagcacta gggacaaaga     240
caaggtcaaa atccttgtaa ccaaatttaa tggtattgta atgcagtgtt aacacaggac     300
agtaacagaa cacccaagaa ccaaacagaa gagggtaggg ataagcataa atgaagtaac     360
atgaaataaa cttccaaatg gaaaacttgt ccataccccc agggcaagtc aactacagtc     420
tcccaaagga cataaattcc acttagggca cactagacag aaaacaatat t              471

<210> SEQ ID NO 223
<211> LENGTH: 411
<212> TYPE: DNA
<213> ORGANISM: Homo sapiens

<400> SEQUENCE: 223
agttgctcta caatgacaca caaatcccgt taaataaatt ataaacaagg gtcaattcaa      60
atttgaagta atgttttagt aaggagagat tagaagacaa caggcatagc aaatgacata     120
agctaccgat taactaatcg gaacatgtaa aacagttaca aaaataaacg aactctcctc     180
ttgtcctaca atgaaagccc tcatgtgcag tagagatgca gtttcatcaa agaacaaaca     240

```
tccttgcaaa tgggtgtgac gcggttccag atgtggattt ggcaaaacct catttaagta    300
aaaggttagc agagcaaagt gcggtgcttt agctgctgct tgtgccgctg tggcgtcggg    360
gaggctcctg cctgagcttc cttccccagc tttgctgcct gagaggaacc a             411
```

<210> SEQ ID NO 224
<211> LENGTH: 321
<212> TYPE: DNA
<213> ORGANISM: Homo sapiens
<220> FEATURE:
<221> NAME/KEY: misc_feature
<222> LOCATION: 31
<223> OTHER INFORMATION: n = A,T,C or G

<400> SEQUENCE: 224

```
ggtctgaagt ttgataacaa agaaatatat ntaagacaaa aatagacaag agttaacaat     60
aaaaacacaa ctatctgttg acataacata tggaaacttt ttgtcagaaa gctacatctt    120
cttaatctga ttgtccaaat cattaaaata tggatgattc agtgccattt tgccagaaat    180
tcgtttggct ggatcataga ttaacatttt cgagagcaaa tccaagccat tttcatccaa    240
gtttttgaca tgggatgcta ggcttcctgg tttccatttg ggaaatgtat tcttatagtc    300
ctgtaaagat tccacttctg g                                              321
```

<210> SEQ ID NO 225
<211> LENGTH: 251
<212> TYPE: DNA
<213> ORGANISM: Homo sapiens
<220> FEATURE:
<221> NAME/KEY: misc_feature
<222> LOCATION: 34
<223> OTHER INFORMATION: n = A,T,C or G

<400> SEQUENCE: 225

```
atgtctgggg aaagagttca ttggcaaaag tgtnctccca agaatggttt acaccaagca     60
gagaggacat gtcactgaat ggggaaaggg aaccccgta tccacagtca ctgtaagcat    120
ccagtaggca ggaagatggc tttgggcagt ggctggatga agcagatttt gagatacccca  180 gctccggaac gaggtcatct tctacaggtt cttccttcac tgagacaatg aattcagggt    240
gatcattctc t                                                         251
```

<210> SEQ ID NO 226
<211> LENGTH: 331
<212> TYPE: DNA
<213> ORGANISM: Homo sapiens
<220> FEATURE:
<221> NAME/KEY: misc_feature
<222> LOCATION: 26, 34, 35, 36, 37, 39
<223> OTHER INFORMATION: n = A,T,C or G

<400> SEQUENCE: 226

```
gttaggtccc aggccccccg ccaagnggtt accnnnntna ccactcctga cccaaaaatc     60
aggcatggca ttaaaacgtt gcaaattcct ttactgttat ccccccacc accaggacca    120 tgtagggtgc agtctttact ccctaacccg tttcccgaaa aaggtgctac ctcctttcca    180
gacagatgag agagggcagg acttcaggct ggatccacca ctgggctctc cctcccccag    240
cctggagcac gggaggggag gtgacggctg gtgactgatg gatgggtagt gggctgagaa    300
gaggggacta ggaagggcta ttccaggctc a                                   331
```

<210> SEQ ID NO 227

<211> LENGTH: 391
<212> TYPE: DNA
<213> ORGANISM: Homo sapiens

<400> SEQUENCE: 227
aggtctgccc ttgaagtata ggaaggaatc atagttggag gacttctgca ttatttgttg    60
gctgaagcta aagtgcaac cccctcctga tttctgcagc aagatgaact gccttatccc    120
cagcccgcag gaatgttcat atctgagcaa tcaatgggca ctgtgttcaa ccacgccatt    180
ttcaagattg gctccttaaa ccacccacaa ggcaccagct ctgggagaag ctgcagggag    240
aagagaacaa agccctcgct gtgatcagga tgggtgtctc atacctttc tctggggtca    300 ttccaggtat gagacagagt tgaacctgcg catgagcgtg gaggccgaca tcaacggcct    360
gcgcagggtg ctggatgagc tgaccctgga c    391

<210> SEQ ID NO 228
<211> LENGTH: 391
<212> TYPE: DNA
<213> ORGANISM: Homo sapiens
<220> FEATURE:
<221> NAME/KEY: misc_feature
<222> LOCATION: 35
<223> OTHER INFORMATION: n = A,T,C or G

<400> SEQUENCE: 228
gttgtccata gccacctcct gggatagaag ctttntagtt catagttcga ttagtgtgtc    60
cttaggacat aggtccagcc ctacagatta gctgggtgaa gaaggcaagt gtctcgacag    120
ggcttagtct ccaccctcag gcatggaacc attcagggtg aagcctggga tgtgggcaca    180
ggagactcag gctgatataa aaataacaaa atcagtaata aaaaaattat aaaacctgtt    240
gcttgtctga atagatttga gcaacagtct tgcttttgtt aaaatcctgg agccgttaag    300
tcctgaatat tcttctggac atcattgctg gctggagaaa ggagcccag gcccggctcg    360 gctgacatct gtcaggtttg gaagtctcat c    391

<210> SEQ ID NO 229
<211> LENGTH: 341
<212> TYPE: DNA
<213> ORGANISM: Homo sapiens
<220> FEATURE:
<221> NAME/KEY: misc_feature
<222> LOCATION: 202
<223> OTHER INFORMATION: n = A,T,C or G

<400> SEQUENCE: 229
gtccatggct tctcacccag acagtctttc tgggcaactt ggggaagccc ctgttctgct    60
caagtctcac cccatggaag aggtgggga aggggcctt ggttttcag gaagacgggt    120 tggagagcac gagtcactac aaagcagtaa aagtgaatgg tgtctccagg ggctgggtcc    180
agaacaccgc ggagagcccc anccataaag gtgtgttccg cctctggcct gcaggaatct    240
ctttgaatct ctttgattgg tggctccaag agcaatggga agtcaacagc caggaggctg    300
gactgggttc cctgggaccc cgaggtccca gaggctgctg g    341

<210> SEQ ID NO 230
<211> LENGTH: 511
<212> TYPE: DNA
<213> ORGANISM: Homo sapiens

<400> SEQUENCE: 230
gtccaagcca aggaaaccat tcccttacag gagacctccc tgtacacaca ggaccgcctg    60

```
gggctaaagg aaatggacaa tgcaggacag ctagtgtttc tggctacaga aggggaccat    120
cttcagttgt ctgaagaatg gttttatgcc cacatcatac cattccttgg atgaaacccg    180
tatagttcac aatagagctc agggagcccc taactcttcc aaaccacatg ggagacagtt    240
tccttcatgc ccaagcctga gctcagatcc agcttgcaac taatccttct atcatctaac    300 atgcccctact tggaaagatc taagatctga atcttatcct ttgccatctt ctgttaccat    360
atggtgttga atgcaagttt aattaccatg agattgttt tacaaacttt tgatgtggtc      420
aagttcagtt ttagaaaagg gagtctgttc cagatcagtg ccagaactgt gcccaggccc    480
aaaggagaca actaactaaa gtagtgagat a                                   511

<210> SEQ ID NO 231
<211> LENGTH: 311
<212> TYPE: DNA
<213> ORGANISM: Homo sapiens

<400> SEQUENCE: 231
ggtccaagta agctgtgggc aggcaagccc ttcggtcacc tgttggctac acagacccct     60
cccctcgtgt cagctcaggc agctcgaggc ccccgaccaa cacttgcagg ggtccctgct    120
agttagcgcc ccaccgccgt ggagttcgta ccgcttcctt agaacttcta cagaagccaa    180
gctccctgga gccctgttgg cagctctagc tttgcagtcg tgtaattggc ccaagtcatt    240
gtttttctcg cctcactttc caccaagtgt ctagagtcat gtgagcctcg tgtcatctcc    300
ggggtggacc t                                                        311

<210> SEQ ID NO 232
<211> LENGTH: 351
<212> TYPE: DNA
<213> ORGANISM: Homo sapiens

<400> SEQUENCE: 232
tcgtttagct aataatccct tccttgatga tacactccaa cttcttgttt ttctttattt      60
ctaaaaagcg gttctgtaac tctcaatcca gagatgttaa aaatgtttct aggcacggta    120
ttagtaaatc aagtaaattt catgtcctct aaaggacaa acttccagag atttgaatat     180
aaatttttat atgtgttatt gattgtcgtg taacaaatgg cccccacaaa ttagtagctt    240
aaaatagcat ttatgatgtc actgttttct ttgccttttc attaatgttc tgtacagacc    300
tatgtaaaca acttttgtat atgcatatag gatagctttt ttgagggtat a             351

<210> SEQ ID NO 233
<211> LENGTH: 511
<212> TYPE: DNA
<213> ORGANISM: Homo sapiens

<400> SEQUENCE: 233
aggtctggat gtaaggatgg atgctctcta tacatgctgg gttggggatg ctgggactgc     60
acagccaccc ccagtatgcc gctccaggac tctgggacta gggcgccaaa gtgtgcaaat    120
gaaaatacag gataccagg gaactttgaa tttcagattg tgaaaagaaa acaaatcttg     180
agactccaca atcaccaagc taaggaaaa agtcaagctg ggaactgctt agggcaaagc    240
tgcctcccat tctattcaca gtcatccccc tgaggctcac ctgcatagct gattgcttcc    300
tttcccctat cgcttctgta aaaatgcaga ctcactgagc cagactaaat tgtgtgttca    360
gtggaaggct gatcaagaac tcaaaagaat gcaacctttt gtctcttatc tactacaacc    420
```

```
aggaagcccc cacttaaggg ttgtcccacc ttactggact gaaccaaggt acatcttaca    480
cctactgatt gatgtctcat gtcccccta g                                    511
```

<210> SEQ ID NO 234
<211> LENGTH: 221
<212> TYPE: DNA
<213> ORGANISM: Homo sapiens

<400> SEQUENCE: 234

```
caggtccagc gaagggcttt cataggctac accaagcatg tccacataac cgaggaagct     60
ctctccatca gcatagcctc cgatgaccat ggtgttccac aaagggttca tcttcgagcg    120
ccggctgtac atggccctgg tcagccatga atgaatagct ctaggactat agctgtgtcc    180
atctcccaga agctcctcat caatcaccat ctggccgaga c                        221
```

<210> SEQ ID NO 235
<211> LENGTH: 381
<212> TYPE: DNA
<213> ORGANISM: Homo sapiens
<220> FEATURE:
<221> NAME/KEY: misc_feature
<222> LOCATION: 33
<223> OTHER INFORMATION: n = A,T,C or G

<400> SEQUENCE: 235

```
ggtccaagaa agggacatct atgtgaaagt ganactgaga cagtgctggt cacaggtcat     60
gctgcagaat aatacattcc caggcactgt cacgtggggg acccaagagg ccccaggagt    120
gacctataac ctctccagaa agaccactct gtgtggcatc acagtccaca cagtttaagg    180
aaatatttag acttaacaat cagacaccag ctcttactca cacttacact cacagcccac    240
acacaagtgt gcaaacatac acacacatat atatttcctg atacattcat ggaatatcag    300
agccctgccc tgaagtcgtt agtgtctctg ctccccaaac cgctgctccc acattggcta    360
agctccctca agagacctca g                                              381
```

<210> SEQ ID NO 236
<211> LENGTH: 441
<212> TYPE: DNA
<213> ORGANISM: Homo sapiens

<400> SEQUENCE: 236

```
aggtcctgtt gcccctttct tttgcccaac ttcgccattt gggaattgga atatttaccc     60
aacacctgta ctgcattgaa tattggaagc aaataacttg gctttgatct tataggctca    120
cagatggagg aacgtacctt gaagttcaga tgagatttcg acttttgag ttgatgctga    180 aacagcttga gattttggg gactactgag agatgataat tgtattgtgc aatatgagaa    240
ggacatgaga tttggtgggc ataggtgtga aatgacattg tttggatgtg tttaccctcc    300
aaatctcttg ttgaatgtga tcttaaacgt tggtggtggg cctagtggaa ggtgttgaat    360 catggggtg gactcttcat aatttgctta gctccatccc cttggtgatg agcaagtcct    420
tgctctgttg tgtcacatga g                                              441
```

<210> SEQ ID NO 237
<211> LENGTH: 281
<212> TYPE: DNA
<213> ORGANISM: Homo sapiens
<220> FEATURE:
<221> NAME/KEY: misc_feature
<222> LOCATION: 81, 90, 194, 209, 210, 211, 219, 233
<223> OTHER INFORMATION: n = A,T,C or G

<400> SEQUENCE: 237

```
tcctaaaaaa ttagctgacc ttgttaaaaa tgttggcgtg agcagtatat tattacctat    60
cttttttat tgtgtgtgtg ngtgtgtgtn ttaaactaat tggctgaaat atctgcctgt   120
ttccctcttt acatttttct tgtttctttc cttatttatc tttgtccatc ttgagatcta   180
ctgtaaagtg aatnttttaa tgaaaacann nccaagttnt actctcactg ggnttgggac   240
atcagatgta attgagaggc aacaggtaa gtcttcatgt c                        281
```

<210> SEQ ID NO 238
<211> LENGTH: 141
<212> TYPE: DNA
<213> ORGANISM: Homo sapiens
<220> FEATURE:
<221> NAME/KEY: misc_feature
<222> LOCATION: 30, 85
<223> OTHER INFORMATION: n = A,T,C or G

<400> SEQUENCE: 238

```
gtctgcctcc tcctactgtt tccctctatn aaaaagcctc cttggcgcag gttccctgag    60
ctgtgggatt ctgcactggt gcttnggatt ccctgatatg ttccttcaaa tccactgaga   120
attaaataaa catcgctaaa g                                             141
```

<210> SEQ ID NO 239
<211> LENGTH: 501
<212> TYPE: DNA
<213> ORGANISM: Homo sapiens
<220> FEATURE:
<221> NAME/KEY: misc_feature
<222> LOCATION: 29, 30, 65, 86, 471, 489
<223> OTHER INFORMATION: n = A,T,C or G

<400> SEQUENCE: 239

```
aacaatctaa acaaatccct cggttctann atacaatgga ttccccatat tggaaggact    60
ctgangcttt attcccccac tatgcntatc ttatcatttt attattatac acacatccat   120
cctaaactat actaaagccc ttttcccatg catggatgga aatggaagat tttttttaa   180
cttgttctag aagtcttaat atgggctgtt gccatgaagg cttgcagaat tgagtccatt   240
ttctagctgc ctttattcac atagtgatgg ggtactaaaa gtactgggtt gactcagaga   300
gtcgctgtca ttctgtcatt gctgctactc taacactgag caacactctc ccagtggcag   360
atcccctgta tcattccaag aggagcattc atcccttttgc tctaatgatc aggaatgatg   420
cttattagaa aacaaactgc ttgacccagg aacaagtggc ttagcttaag naaacttggc   480
tttgctcana tccctgatcc t                                             501
```

<210> SEQ ID NO 240
<211> LENGTH: 451
<212> TYPE: DNA
<213> ORGANISM: Homo sapiens

<400> SEQUENCE: 240

```
tgtcctgaaa ggccattact aatagaaaca cagcctttcc aatcctctgg aacatattct    60
gtctgggttt ttaatgtctg tggaaaaaaa ctaaacaagt ctctgtctca gttaagagaa   120
atctattggt ctgaaggttt ctgaacctct ttctggttct cagcagaagt aactgaagta   180
gatcaggaag gggctgcctc aggaaaaattc ctagatccta ggaattcagt gagaccctgg   240
gaaggaccag catgctaatc agtgtcagtg aatccacagt ctttacttcc tgcctcataa   300
```

```
agggccaggt ctccccagta ccaagtcctt tcctcatgaa gttgtgttgc ctcaggctgt    360
ttagggacca ttgcctgtct tggtcacatg agtctgtctc cttactttag tccctgggca    420
atccttgctt aatgcttttg ttgactcaac g                                   451
```

```
<210> SEQ ID NO 241
<211> LENGTH: 411
<212> TYPE: DNA
<213> ORGANISM: Homo sapiens
<220> FEATURE:
<221> NAME/KEY: misc_feature
<222> LOCATION: 62, 82, 364, 370, 385
<223> OTHER INFORMATION: n = A,T,C or G

<400> SEQUENCE: 241
```

```
aatctccagt gtgatggtat cggggttaga gcttcaatct ccagtgtgat ggtactgcag    60
cnagagcttc aatctccagt gngatggtat tagggttaga tcttcaatct ccagtgtgat   120
ggtatcaggg ttagagcttc agcctccagt gtgatggtat cagggttaga gcttcagcct   180
ccagtgtgat ggtatcgggg ttagatcttc aatcccagt ggtggtggtt agagcttcaa    240
tctccagtgt gatggtattg gggttagagc ttcaatctcc agtctgatgg tgtttcggga   300
tggggctttt aagatgtaat tagggtttaa gatcataagg gacctggtct gatggggatt   360
agtncgcttn tatgaagaga cacangaggg cttgctctat ctctgactct c            411
```

```
<210> SEQ ID NO 242
<211> LENGTH: 351
<212> TYPE: DNA
<213> ORGANISM: Homo sapiens

<400> SEQUENCE: 242
```

```
ttccccttca caacagtaga gacctacaca gtgaactttg gggacttctg agatcagcgt    60
cctaccaaga ccccagccca actcaagcta cagcagcagc acttcccaag cctgctgacc   120
acagtcacat cacccatcag cacatggaag gcccctggta tggacactga aggaagggc    180 tggtcctgcc cctttgaggg ggtgcaaaca tgactgggac ctaagagcca gaggctgtgt   240
agaggctcct gctccacctg ccagtctcgt aagaaatggg gttgctgcag tgttggagta   300
ggggcagagg gagggagcca aggtcactcc aataaaacaa gctcatggca c             351
```

```
<210> SEQ ID NO 243
<211> LENGTH: 241
<212> TYPE: DNA
<213> ORGANISM: Homo sapiens

<400> SEQUENCE: 243
```

```
gtctgtgctt tatcaggaaa agcacaagaa tatgttttc tacctaaaac cctcttctac     60
tttaaaaatg gtttgctgaa ttttctatg tttttaaaat gttttatgc tttttttaa      120 acacgtaaag gatggaacct aatcctctcc cgagacgcct cctttgtgtt aatgcctatt   180
cttacaacag agaaacaagt acattaatat aaaaacgagt tgattattgg ggtataaaat   240
a                                                                    241
```

```
<210> SEQ ID NO 244
<211> LENGTH: 301
<212> TYPE: DNA
<213> ORGANISM: Homo sapiens

<400> SEQUENCE: 244
```

```
ggtccagagc aatagcgtct gtggtgaagc gcctgcactc ctcgggagac atgcctggct    60
```

```
tatatgctgc atccacataa ccatagataa aggtgctgcc ggagccacca atggcaaaag    120
gctgtcgagt cagcattcct cccagggttc catatacctg acctccttca cgttggtccc    180
agccagctac catgagatgt gcagacaagt cctctcgata tttatagctg atatttctca    240
ccacatttgc agcagccaaa acaagtggag gttcctccag ttctatccca tggagctcca    300
g                                                                    301

<210> SEQ ID NO 245
<211> LENGTH: 391
<212> TYPE: DNA
<213> ORGANISM: Homo sapiens

<400> SEQUENCE: 245
ctgacactgc tgatgtgggc cggggggcgc cgaggcacaa ctggtggccg gaccattgag     60
gcacctggag ggtaggcagc ttgtggtgca gacaccacag agagagaaaa gttggatgga    120
gtggtgggaa taatcagggt ggcacactgt gcctagaagc ttccagggcc accaagagaa    180
tgggaaggga aactacaaca ttcacaacag aaataggagt caattcactt agacccagaa    240
ctccagaaag ggggagtgta ggaatctaca atttcaaagc cagctcgtgt ctacctagag    300
ccccaaactg cataagcacc aggattgtac accttagtcc ctcaagatag tttcaagtga    360
gcgtgcaatt cactcttaca gaggagggcc t                                   391

<210> SEQ ID NO 246
<211> LENGTH: 291
<212> TYPE: DNA
<213> ORGANISM: Homo sapiens
<220> FEATURE:
<221> NAME/KEY: misc_feature
<222> LOCATION: 26, 80, 82, 185, 255, 259
<223> OTHER INFORMATION: n = A,T,C or G

<400> SEQUENCE: 246
tcctccacag gggaagcagg aagttngacc agcttcaggc tggaacgtgc ccagggcaca     60
gagctggcaa ggtgcaaagn cntctgcaga atattcacca ggttgacaca gacctccaca    120
ttcagacata ttccaagctt ctggggtctt cagggcccca gaatttcctg gtcttgggca    180
tggtncacaa gtcatttgtc cttcctcatt ttggaaggtt ccatttggac ataaaatgca    240
agcgttctcg tgctncatna taataggtcc cagcctgcac tgacacattt g             291

<210> SEQ ID NO 247
<211> LENGTH: 471
<212> TYPE: DNA
<213> ORGANISM: Homo sapiens
<220> FEATURE:
<221> NAME/KEY: misc_feature
<222> LOCATION: 80, 110, 125, 245, 249, 279, 318, 336, 339, 455, 471
<223> OTHER INFORMATION: n = A,T,C or G

<400> SEQUENCE: 247
cactgagtga atgagtatat aatttatgaa aacagaaaag tgctttggaa aaaaaaaag      60 acaacaggag tacatacagn gaaccaaaaa gagtgtacca ggaggagcan accctgaaca    120
gttanaacta tggaaatcgc tatgctttgt gttgtcacag gagttaaaat aggaatcccc    180
tgcatacaat aaatatttat tggataaata actaagcctg atacccttt caatgcgtta    240 tacanactnt atcatcacac cactaatcta agttctcana agttaaacat tacaagactt    300
cagaacaaca taggcgtntt tggctccatt taacanaana aggaccatag tgatcattta    360
```

```
atctctatga gtctgtctta tcttctggaa aagggggccta acaccatttc cttttgcaaa    420
aaggtagctg ccttgcttcc agttctacca tcctntagca acccatcttt n              471

<210> SEQ ID NO 248
<211> LENGTH: 551
<212> TYPE: DNA
<213> ORGANISM: Homo sapiens

<400> SEQUENCE: 248
ccatgggatc aggaatgggg tcaggtcagt tgacctgagc atacccatta aacatgttca    60
aatgtcccca tcccacccac tcacatgaca tggctcccga gccctgagat ctgtatccca    120
agaacctcag ttgagaaata tttatggcag cttcactgtt gctcaagagc ctgggtattg    180
tagcagcctg ggggcaggtt gtccctaatg ttctccaagt tcttcacatc agccagaatc    240
ccatctatgc ttgtctccag caaatggagg tggcccctct gctgacgtgc cctctcttcc    300
agctctgaca tcatgggccg cagttggctg ttgatctggg tcttggctcg ggaaagcttc    360
tgctccagta agaccagccc ctcttcatct acactgagag gctggtccat cagatgcagg    420
aggccgtcta atgtgttgag tgtgtcttgg attgtaaccc cagcgttctt ggctctggta    480
tcaaccttct gggcttctgt aatcaccatc tgtactgcat ccatattcgt gtcgaactcc    540
agctccttcc t                                                         551

<210> SEQ ID NO 249
<211> LENGTH: 181
<212> TYPE: DNA
<213> ORGANISM: Homo sapiens
<220> FEATURE:
<221> NAME/KEY: misc_feature
<222> LOCATION: 3, 96
<223> OTHER INFORMATION: n = A,T,C or G

<400> SEQUENCE: 249
atntccagag ggaccgtaag actggtacaa gtttacacca taagaggcga cgtggtcagc    60
cacaatgtct tcacctccac aggggctcat cacggnggtc agggcaaggg ccccagcat    120 cagagctttg tttaggatca tcctcttccc aaggcagcct tagcagttgc tgacctgccc    180
g                                                                    181

<210> SEQ ID NO 250
<211> LENGTH: 551
<212> TYPE: DNA
<213> ORGANISM: Homo sapiens

<400> SEQUENCE: 250
tctgtagcta ggatgagctg gctctcaagc aaaagtttgt cttcctgggt ccatttgtgg    60
ttatcacttg ttattgaatg tacatcacaa attaaagtct gcattgttgg acgtaagaga    120
atgtgccgac tttggtaacc aggagatttc atgttactgg actgcctgta gtcacgtatt    180
tctgctatga cacatccgca atgaaaaata ttaacctgag atttttctag gagatcaacc    240
aaaataggag gtaattcttc tgcatccaaa tattcaagca actctccttc ttcatagggc    300
agtcgaatgg tctcggaatc tgatccgttt ttccccctga gcatcagaga atatccctca    360
tttcctgggt atagattgac cactaaacat gacaaagtct cttgcataac aagcttctct    420
aacaagttca catttcttct taatttctta acttcaggtt cttttcaca ttcttcaata    480 tacaagtcat aaagttttg aaatacagat tttcttccac ttgataggta tttcctttta    540
ggaggtctct g                                                         551
```

<210> SEQ ID NO 251
<211> LENGTH: 441
<212> TYPE: DNA
<213> ORGANISM: Homo sapiens

<400> SEQUENCE: 251

```
tgtctgctct cccatcctgg ttactatgag tcgctcttgg cagaaaggac cacagatgga    60
gagcttggca ctcgctccaa cttttgccgaa aagaggacaa ccaccaaagt agtaggtaaa   120
aacacaattt tagcagcagt gaaataaaaa gaggaagtga ggatggggcc aggccgcaac   180
tataattaaa ctgtctgttt aggagaagct gaatccagaa gaaacacaag ctgtaaagtg   240
agagaggaca gggagcaggg cctttggaga gcaggagagg acaggctgtc accaagcgct   300
gctcggactc tgccctgaaa gatttgaatt ggacactgtc cagtcacgtg tgtggcaaac   360
cgtactccaa gcactttcct cacggcagag gaaggagctg ccatggctgt accccctgaac  420
gtttgtgggg ccagcgatgt g                                              441
```

<210> SEQ ID NO 252
<211> LENGTH: 406
<212> TYPE: DNA
<213> ORGANISM: Homo sapiens

<400> SEQUENCE: 252

```
tttttttttg aacaagtaaa aatttcttta tttgctgaca ataagataac ctacagggaa    60
aacctgatga aatctattaa aaagttacta aaactaataa aagaatttag gaaggttata   120
gaatgtaaga ccaagacaca aaatcaatt acatttctat ataatagcaa tgaacagata   180
ctgaaatttt aaaaactaaa tcattttaca aagtatcac aatatgaaac actccgggat   240
aaattggata aagatgtgc aagactgtac aaaagctaca aacatttat gaaggaaatt   300
ggaagataga aacaagatag aaaatgaaaa tattgtcaag agtttcagat agaaaatgaa   360
aaacaagcta agacaagtat tggagaagta tagaagatag aaaaat                  406
```

<210> SEQ ID NO 253
<211> LENGTH: 544
<212> TYPE: DNA
<213> ORGANISM: Homo sapiens
<220> FEATURE:
<221> NAME/KEY: misc_feature
<222> LOCATION: 224
<223> OTHER INFORMATION: n = A,T,C or G

<400> SEQUENCE: 253

```
gaaggagttc agtagcaaag tcacacctgt ccaattccct gagctttgct cactcagcta    60
atgggatggc aaaggtggtg gtgctttcat cttcaggcag aagcctctgc ccatccccct   120
caagggctgc aggcccagtt tcatgctgc ccttgggtgg gcatctgtta acagaggaga   180
acgtctgggt ggcggcagca gctttgctct gagtgcctac aaanctaatg cttggtgcta   240
gaaacatcat cattattaaa cttcagaaaa gcagcagcca tgttcagtca ggctcatgct   300
gcctcactgc ttaagtgcct gcaggagccg cctgccaagc tccccttcct acacctggca   360
cactgggtc tgcacaaggc tttgtcaacc aaagacagct tccccctttt gattgcctgt    420
agactttgga gccaagaaac actctgtgtg actctacaca cacttcaggt ggtttgtgct   480
tcaaagtcat tgatgcaact tgaaaggaaa cagtttaatg gtggaaatga actaccattt   540
ataa                                                                 544
```

<210> SEQ ID NO 254
<211> LENGTH: 339
<212> TYPE: DNA
<213> ORGANISM: Homo sapiens

<400> SEQUENCE: 254

```
tggcattcag ggcagtgtct tctgcatctc ctaggaacct cgggagcggc agctccggcg      60
cctggtagcg agaggcgggt tccggagatc ccggcctcac ttcgtcccac tgtgttagg     120
ggtgagtcct gcaaatgtta agtgatttgc tcaaggtgcc catttcgcag gaattggagc    180
ccaggccagt tctctgagcc tatcattagg gctaaaggag tgcgtgatca gaatggtgtc    240
tggacggttc tacttgtcct gcctgctgct ggggtccctg ggctctatgt gcatcctctt    300
cactatctac tggatgcagt actggcgtgg tggctttgc                           339
```

<210> SEQ ID NO 255
<211> LENGTH: 405
<212> TYPE: DNA
<213> ORGANISM: Homo sapiens
<220> FEATURE:
<221> NAME/KEY: misc_feature
<222> LOCATION: 11, 39, 70, 87, 103, 120, 177, 181, 220, 229, 233, 341,
      345, 366, 380, 402
<223> OTHER INFORMATION: n = A,T,C or G

<400> SEQUENCE: 255

```
gaggttttt nttttttttt tttttttttt caattaaana tttgatttat tcaagtatgt      60
gaaaacattn tacaatggaa acttttntta aatgctgcat gtnctgtgct atggaccacn    120
cacatacagc catgctgttt caaaaaactt gaaatgccat tgatagttta aaaactntac    180
ncccgatgga aaatcgagga aaacaattta atgtttcatn tgaatccana ggngcatcaa    240
attaaatgac agctccactt ggcaataat agctgttact tgatggtatc caaaaaaaaa    300
tggttgggga tggataaatt caaaaatgct tccccaaagg ngggnggttt ttaaaaagtt    360
tcaggncaca acccttgcan aaaacactga tgcccaacac antga                   405
```

<210> SEQ ID NO 256
<211> LENGTH: 209
<212> TYPE: DNA
<213> ORGANISM: Homo sapiens
<220> FEATURE:
<221> NAME/KEY: misc_feature
<222> LOCATION: 6
<223> OTHER INFORMATION: n = A,T,C or G

<400> SEQUENCE: 256

```
gggcangtct ggtcctctcc ccacatgtca cactctcctc agcctctccc ccaaccctgc     60
tctccctcct cccctgccct agcccaggga cagagtctag gaggagcctg ggcagagct    120
ggaggcagga agagagcact ggacagacag ctatggtttg gattggggaa gaggttagga   180
agtaggttct taaagacact tttttagta                                      209
```

<210> SEQ ID NO 257
<211> LENGTH: 343
<212> TYPE: DNA
<213> ORGANISM: Homo sapiens
<220> FEATURE:
<221> NAME/KEY: misc_feature
<222> LOCATION: 306, 311, 343
<223> OTHER INFORMATION: n = A,T,C or G

<400> SEQUENCE: 257

```
tctggacacc ataatccctt ttaagtggct ggatggtcac acctctccca ttgacaagct      60 ggggttaagtc aataggttga ctaggatcaa cacgacccaa atcaataaga tactgcagtc    120
tattgagact caaaggctta tactggcgtc tgaaactatg tccttcgtta aacccgtatt    180
ttgggattcg gatgtaaaat ggagtctggc ctccctcaaa gcccaagcgg ggccgggttc    240
ctctttgcct ttctccttta tggcctctgc cacattttct acctcttctc cgacctcttg    300
gtcttntctc nggtttcttg gagccgggat tcggctttaa gtn                     343
```

<210> SEQ ID NO 258
<211> LENGTH: 519
<212> TYPE: DNA
<213> ORGANISM: Homo sapiens

<400> SEQUENCE: 258

```
gcggcttctg acttctagaa gactaaggct ggtctgtgtt tgcttgtttg cccacctttg      60
gctgataccc agagaacctg gcacttgct gcctgatgcc caccctgcc agtcattcct      120 ccattcaccc agcgggaggt gggatgtgag acagcccaca ttggaaaatc cagaaaaccg    180
ggaacaggga tttgcccttc acaattctac tccccagatc ctctcccctg gacacaggag    240
acccacaggg caggacccta agatctgggg aaaggaggtc ctgagaacct tgaggtaccc    300
ttagatcctt tctacccac tttcctatgg aggattccaa gtcaccactt ctctcaccgg    360
cttctaccag ggtccaggac taaggcgttt tctccatagc ctcaacattt gggaatctt     420 cccttaatca cccttgctcc tcctgggtgc ctggaagatg gactggcaga gacctctttg    480
ttgcgttttg tgctttgatg ccaggaatgc cgcctagtt                         519
```

<210> SEQ ID NO 259
<211> LENGTH: 371
<212> TYPE: DNA
<213> ORGANISM: Homo sapiens

<400> SEQUENCE: 259

```
attgtcaact atatacacag tagtgaggaa taaaatgcac acaaaacaat ggatagaata      60
tgaaaatgtc ttctaaatat gaccagtcta gcatagaacc ttcttctctt ccttctcagg    120
tcttccagct ccatgtcatc taacccactt aacaaacgtg gacgtatcgc ttccagaggc    180
cgtcttaaca actccattc caaaagtcat ctccagaaga catgtatttt ctatgatttc    240
ttttaaacaa atgagaattt acaagatgtg taactttcta actctatttt atcatacgtc    300
ggcaacctct ttccatctag aagggctaga tgtgacaaat gttttctatt aaaaggttgg    360
ggtggagttg a                                                       371
```

<210> SEQ ID NO 260
<211> LENGTH: 430
<212> TYPE: DNA
<213> ORGANISM: Homo sapiens
<220> FEATURE:
<221> NAME/KEY: misc_feature
<222> LOCATION: 57, 189, 208, 256, 426
<223> OTHER INFORMATION: n = A,T,C or G

<400> SEQUENCE: 260

```
ttggattttt tgacttgcga tttcagtttt tttactttt tttttttttt ttttganaaa      60
tactatattt attgtcaaag agtggtacat aggtgagtgt tcatcttccc tctcatgccg    120
gtatactctg cttcgctgtt tcagtaaaag ttttccgtag ttctgaacgt cccttgacca    180
caccataana caagcgcaag tcactcanaa ttgccactgg aaaactggct caactatcat    240
```

```
ttgaggaaag actganaaag cctatcccaa agtaatggac atgcaccaac atcgcggtac        300
ctacatgttc ccgtttttct gccaatctac ctgtgtttcc aagataaatt accacccagg        360
gagtcacttc ctgctatgtg aacaaaaacc cggtttcttt ctggaggtgc ttgactactc        420 tctcgngagc                                                                430
```

```
<210> SEQ ID NO 261
<211> LENGTH: 365
<212> TYPE: DNA
<213> ORGANISM: Homo sapiens
<220> FEATURE:
<221> NAME/KEY: misc_feature
<222> LOCATION: 178
<223> OTHER INFORMATION: n = A,T,C or G

<400> SEQUENCE: 261
tcctgacgat agccatggct gtaccactta actatgattc tattccaact gttcagaatc        60
atatcacaaa atgacttgta cacagtagtt tacaacgact cccaagagag gaaaaaaaaa       120
aaaaaagacg cctcaaaatt cactcaactt ttgagacagc aatggcaata ggcagcanag       180
aagctatgct gcaactgagg gcacatatca ttgaagatgt cacaggagtt taagagacag       240
gctggaaaaa atctcatact aagcaaacag tagtatctca taccaagcaa aaccaagtag       300
tatctgctca gcctgccgct aacagatctc acaatcacca actgtgcttt aggactgtca       360
ccaaa                                                                    365
```

```
<210> SEQ ID NO 262
<211> LENGTH: 500
<212> TYPE: DNA
<213> ORGANISM: Homo sapiens

<400> SEQUENCE: 262
cctagatgtc atttgggacc cttcacaacc attttgaagc cctgtttgag tccctgggat        60
atgtgagctg tttctatgca taatggatat tcggggttaa caacagtccc ctgcttggct       120
tctattctga atccttttct ttcaccatgg ggtgcctgaa gggtggctga tgcatatggt       180
acaatggcac ccagtgtaaa gcagctacaa ttaggagtgg atgtgttctg tagcatccta       240
tttaaataag cctattttat cctttggccc gtcaactctg ttatctgctg cttgtactgg       300
tgcctgtact tttctgactc tcattgacca tattccacga ccatggttgt catccattac       360
ttgatcctac tttacatgtc tagtctgtgt ggttggtggt gaataggctt cttttttacat      420 ggtgctgcca gcccagctaa ttaatggtgc acgtggactt ttagcaagcg ggctcactgg       480
aagagactga acctggcatg                                                    500
```

```
<210> SEQ ID NO 263
<211> LENGTH: 413
<212> TYPE: DNA
<213> ORGANISM: Homo sapiens

<400> SEQUENCE: 263
ctcagagagg ttgaaagatt tgcctacgaa agggacagtg atgaagctaa gctctagatc        60
caggatgtct gacttcaaat tgaaactccc aaagtaatga gtttggaagg gtggggtgtg       120
gcctttccag gatgggggtc ttttctgctc ccagcggata gtgaaacccc tgtctgcacc       180
tggttgggcg tgttgctttc ccaaaggttt ttttttttagg tccgtcgctg tcttgtggat       240
taggcattat tatcctttact ttgtctccaa ataacctgga gaatgagag agtagtgacc       300
```

```
agctcagggc cacagtgcga tgaggaccat cttctcacct ctctaaatgc aggaagaaac    360
gcagagtaac gtggaagtgg tccacaccta ccgccagcac attgtgaatg aca           413
```

<210> SEQ ID NO 264
<211> LENGTH: 524
<212> TYPE: DNA
<213> ORGANISM: Homo sapiens

<400> SEQUENCE: 264

```
tccaatgggg ccctgagagc tgtgacagga actcacactc tggcactggc agcaaaacac    60
cattccaccc cactcatcgt ctgtgcacct atgttcaaac tttctccaca gttcccaat    120 gaagaagact catttcataa gtttgtggct cctgaagaag tcctgccatt cacagaaggg   180
gacattctgg agaaggtcag cgtgcattgc cctgtgtttg actacgttcc cccagagctc   240
attaccctct ttatctccaa cattggtggg aatgcacctt cctacatcta ccgcctgatg   300
agtgaactct accatcctga tgatcatgtt ttatgaccga ccacacgtgt cctaagcaga   360
ttgcttaggc agatacagaa tgaagaggag acttgagtgt tgctgctgaa gcacatcctt   420
gcaatgtggg agtgcacagg agtccaccta aaaaaaaaaa tccttgatac tgttgcctgc   480 cttttttagtc accccgtaac aagggcacac atccaggact gtgt                   524
```

<210> SEQ ID NO 265
<211> LENGTH: 344
<212> TYPE: DNA
<213> ORGANISM: Homo sapiens

<400> SEQUENCE: 265

```
tcctttcttc tacttcagga gatgattcaa agttacttgt ggacatttct ttaagttctg    60
aagacaaatg agacaggatt tggcctgcgg gttcttcaga cttctctacc acctccatta   120
actcttcatc ttggcttgac gtaggcaatg cactattttg ctcttttgtt tctggagatg   180
acccagcacc acttctttct cttggcgggg ttctaagtgt gtctttgaat accagtgaag   240
actcaggcct atcctgtact ggaaagggac taaatttgtc tttctgtcta ggaggtgatg   300
cagtagcatc ctcctgaggg ggtaaggcca ttttctcttt ttga                    344
```

<210> SEQ ID NO 266
<211> LENGTH: 210
<212> TYPE: DNA
<213> ORGANISM: Homo sapiens
<220> FEATURE:
<221> NAME/KEY: misc_feature
<222> LOCATION: 78
<223> OTHER INFORMATION: n = A,T,C or G

<400> SEQUENCE: 266

```
ccacaatgtc cataacttga gcaggctttg gcatcccacc accccttca gaccaataca     60 cactatgttg gaggaacnac tttaaaatgt aaaatgagaa atgggcactg aacactccat   120
cctcactccc aacagcccac ccacacacct cttcaactgc tatccaaaca tggaggagct   180
cttgtggaag agaggctcaa caccaaataa                                    210
```

<210> SEQ ID NO 267
<211> LENGTH: 238
<212> TYPE: DNA
<213> ORGANISM: Homo sapiens
<220> FEATURE:
<221> NAME/KEY: misc_feature
<222> LOCATION: 5, 19, 31
<223> OTHER INFORMATION: n = A,T,C or G

<400> SEQUENCE: 267

```
tcggncctcc caccctctna ctgaaattct ntgaaattct cccctttggg atgaggatgg     60
caacccagg catgtaccct cccaacctgg gacccgacct aatacccctaa catcctgctg   120
```

```
tcggncctcc caccctctna ctgaaattct ntgaaattct cccctttggg atgaggatgg     60
caacccagg catgtaccct cccaacctgg gacccgacct aatacccctaa catcctgctg   120
acagtggctg ttctcgctgg gcaggcgtcc caaagcacat cgagccagat tcaggcagag   180
tggaactggc ccctcagcca tcagtggagg tggcctggga ggctctaccc tgaacggg     238
```

<210> SEQ ID NO 268
<211> LENGTH: 461
<212> TYPE: DNA
<213> ORGANISM: Homo sapiens
<220> FEATURE:
<221> NAME/KEY: misc_feature
<222> LOCATION: 459
<223> OTHER INFORMATION: n = A,T,C or G

<400> SEQUENCE: 268

```
tcctcaagga catgcccctt gatagaaact cagttcctgt ctccagttcc ctcctggacc     60
tgatccccca aatgcagggc ctgggactat atccagttcc ttattttcag aggcccatgc   120
acaagatgca cagcaaataa gtgctgaata aagacccagc tactgctagc ttaccctgct   180
ccaaacattc accaagtcct cagcaaagag ggccatccat tcacctcttc taaaaacaca   240
ctgagctccc cagtctatac cccaagatat gcttggctcc caactatccc tcctctctca   300
tctccaagcc agtttcccct ttctaagtat actgatatta ccaaagacac tgacaatctt   360
cttttcctac ctctccccag tgactaggtt tgcagcagga gctctataag tcctagtata   420
cagcagaagc tccataaatg tgtgctgacc taacattang c                       461
```

<210> SEQ ID NO 269
<211> LENGTH: 434
<212> TYPE: DNA
<213> ORGANISM: Homo sapiens

<400> SEQUENCE: 269

```
ctgtgttggt gagcaccgat tcccactcaa tatggcgtgg cttacagtct tcattaggtt     60
cccgctccca accagaatga ggaatgatca cttcatctgt caaggcatgc agtgcatggt   120
ccacaatctc cattttgatt gagtcatggg atgaaagatt ccacagggtt ccggtaataa   180
cttcagtaag gtccatatca cgagcctttc gaagcaatcg cacaagggca ggcacaccat   240
cacagttttt tatggcaatc ttgttatcct ggtcacgtcc aaaagagata ttcttgagag   300
ctccacaggc tccaaggtgc acttccttt tgggatggtc taacaatccc accagtactg   360
ggatgccctt gagcttccgc acgtcagtct tcaccttgtc attgcggtag cataagtgtt   420
gcaggtatgc aaga                                                    434
```

<210> SEQ ID NO 270
<211> LENGTH: 156
<212> TYPE: DNA
<213> ORGANISM: Homo sapiens

<400> SEQUENCE: 270

```
ctgcaccagc gattaccagt ggcattcaaa tactgtgtga ctaaggattt tgtatgctcc     60
ccagtagaac cagaatcaga caggtatgag ctagtcaaca gcaagtcttt gttggattcg   120
agtaggctca ggatctgctg aaggtcggag gagtta                             156
```

<210> SEQ ID NO 271

```
<211> LENGTH: 533
<212> TYPE: DNA
<213> ORGANISM: Homo sapiens
<220> FEATURE:
<221> NAME/KEY: misc_feature
<222> LOCATION: 100, 137, 383, 385, 411
<223> OTHER INFORMATION: n = A,T,C or G

<400> SEQUENCE: 271
ccactgtcac ggtctgtctg acacttactg ccaaacgcat ggcaaggaaa aactgcttag      60
tgaagaactt agaagctgtg gagaccttgg ggtccacgtn caccatctgc tctgataaaa     120
ctggaactct gactcanaac cggatgacag tggcccacat gtggtttgac aatcaaatcc     180
atgaagctga tacgacagag aatcagagtg gtgtctcttt tgacaagact tcagctacct     240
ggcttgctct gtccagaatt gcaggtcttt gtaacagggc agtgtttcag gctaaccagg     300
aaaacctacc tattcttaag cgggcagttg caggagatgc ctctgagtca gcactcttaa     360
agtgcataga gctgtgctgt ggntncgtga aggagatgag agaaagatac nccaaaatcg     420
tcgagatacc cttcaactcc accaacaagt accagttgtc tattcataag aaccccaaca     480
catcggagcc ccaacacctg ttggtgatga agggcgcccc agaaaggatc cta            533

<210> SEQ ID NO 272
<211> LENGTH: 630
<212> TYPE: DNA
<213> ORGANISM: Homo sapiens

<400> SEQUENCE: 272
tggtattttt cttttctttt tggatgtttt atactttttt ttcttttttc ttctctattc      60
ttttcttcgc cttcccgtac ttctgtcttc cagttttcca cttcaaactt ctatcttctc     120
caaattgttt catcctacca ctcccaatta atctttccat tttcgtctgc gtttagtaaa     180
tgcgttaact aggctttaaa tgacgcaatt ctccctgcgt catggatttc aaggtctttt     240
aatcaccttc ggtttaatct cttttaaaa gatcgccttc aaattatttt aatcacctac      300
aacttttaaa ctaaacttta agctgtttaa gtcaccttca ttttaatcta aaagcattgc     360
ccttctattg gtattaattc ggggctctgt agtcctttct ctcaattttc ttttaaatac     420 atttttact ccatgaagaa gcttcatctc aacctccgtc atgttttaga aacctttat       480 cttttccttc ctcatgctac tcttctaagt cttcatattt tctcttaaaa tcttaagcta     540
ttaaaattac gttaaaaact taacgctaag caatatctta gtaacctatt gactatattt     600
tttaagtagt tgtattaatc tctatctttc                                      630

<210> SEQ ID NO 273
<211> LENGTH: 400
<212> TYPE: DNA
<213> ORGANISM: Homo sapiens

<400> SEQUENCE: 273 tctggttgc cctccagttc attctgaatc tagacttgct cagcctaatc aagttcctgt       60
acaaccagaa gcgacacagg ttcctttggt atcatccaca agtgagggt acacagcatc      120 tcaacccttg taccagcctt ctcatgctac agagcaacga ccacagaagg aaccaattga     180
tcagattcag gcaacaatct ctttaaatac agaccagact cagcatcat catcccttcc      240 tgctgcgtct cagcctcaag tatttcaggc tgggacaagc aaacctttac atagcagtgg     300
aatcaatgta aatgcagctc cattccaatc catgcaaacg tgttcaata tgaatgcccc      360 agttcctcct gttaatgaac cagaaacttt aaaacagcaa                           400
```

<210> SEQ ID NO 274
<211> LENGTH: 351
<212> TYPE: DNA
<213> ORGANISM: Homo sapiens
<220> FEATURE:
<221> NAME/KEY: misc_feature
<222> LOCATION: 2
<223> OTHER INFORMATION: n = A,T,C or G

<400> SEQUENCE: 274
tntgagtatg tcccagagaa ggtgaagaaa gcggaaaaga aattagaaga gaatccatat      60
gaccttgatg cttggagcat tctcattcga gaggcacaga atcaacctat agacaaagca     120
cggaagactt atgaacgcct tgttgcccag ttccccagtt ctggcagatt ctggaaactg     180
tacattgaag cagaggttac tattttattt tattttttct tatatcagta ttgcagcatt     240
cactgtagtg atagaaaaca agttaggaac atagccaatt aggacaagga ggatttaaat     300
gtgtcttacc tttatttttgt aaaataggta taaaggagta attaaaatga a             351

<210> SEQ ID NO 275
<211> LENGTH: 381
<212> TYPE: DNA
<213> ORGANISM: Homo sapiens
<220> FEATURE:
<221> NAME/KEY: misc_feature
<222> LOCATION: 4, 11, 12, 13
<223> OTHER INFORMATION: n = A,T,C or G

<400> SEQUENCE: 275
gcgnggtcgc nnncgaggtc tgagaagccc ataccactat ttgttgagaa atgtgtggaa      60
tttattgaag atacagggtt atgtaccgaa ggactctacc gtgtcagcgg gaataaaact     120
gaccaagaca atattcaaaa gcagtttgat caagatcata atatcaatct agtgtcaatg     180
gaagtaacag taaatgctgt agctggagcc cttaaagctt tctttgcaga tctgccagat     240
cctttaattc catattctct tcatccagaa ctattggaag cagcaaaaat cccggataaa     300
acagaacgtc ttcatgcctt gaaagaaatt gttaagaaat tcatcctgt aaactatgat      360 gtattcagat acgtgataac a                                                381

<210> SEQ ID NO 276
<211> LENGTH: 390
<212> TYPE: DNA
<213> ORGANISM: Homo sapiens
<220> FEATURE:
<221> NAME/KEY: misc_feature
<222> LOCATION: 5
<223> OTHER INFORMATION: n = A,T,C or G

<400> SEQUENCE: 276
gctcngactc cggcgggacc tgctcggagg aatggcgccg ccgggttcaa gcactgtctt      60
cctgttggcc ctgacaatca tagccagcac ctgggctctg acgcccactc actacctcac     120
caagcatgac gtggagagac taaaagcctc gctggatcgc cctttcacaa atttggaatc     180
tgccttctac tccatcgtgg gactcagcag ccttggtgct caggtgccag atgcaaagaa     240
agcatgtacc tacatcagat ctaaccttga tcccagcaat gtggattccc tcttctacgc     300
tgcccaggcc agccaggccc tctcaggatg tgagatctct atttcaaatg agaccaaaga     360
tctgcttctg gcagacctcg gccgcgacca                                       390

<210> SEQ ID NO 277

<211> LENGTH: 378
<212> TYPE: DNA
<213> ORGANISM: Homo sapiens

<400> SEQUENCE: 277

```
tgggaacttc tggggtagga cgttgtctgc tatctccagt tccacagacc caaccagtta      60
cgatggtttt ggaccattta tgccgggatt cgacatcatt ccctataatg atctgcccgc     120
actggagcgt gctcttcagg atccaaatgt ggctgcgttc atggtagaac caattcaggg     180
tgaagcaggc gttgttgttc cggatccagg ttacctaatg ggagtgcgag agctctgcac     240
caggcaccag gttctctttta ttgctgatga aatacagaca ggattggcca gaactggtag     300
atggctggct gttgattatg aaaatgtcag acctgatata gtcctccttg aaaggccct      360
ttctgggggc ttataccc                                                   378
```

<210> SEQ ID NO 278
<211> LENGTH: 366
<212> TYPE: DNA
<213> ORGANISM: Homo sapiens

<400> SEQUENCE: 278

```
ggagggcaca ttccttttca cctcagagtc ggtcgggaa ggccacccag ataagatttg       60
tgaccaaacc agtgatgctg tccttgatgc ccaccttcag caggatcctg atgccaaagt     120
agcttgtgaa actgttgcta aaactggaat gatccttctt gctggggaaa ttacatccag     180
agctgctgtt gactaccaga agtggttcg tgaagctgtt aaacacattg gatatgatga      240
ttcttccaaa ggttttgact acaagacttg taacgtgctg gtagccttgg agcaacagtc     300
accagatatt gctcaaggtg ttcatcttga cagaaatgaa gaagacattg gtgctggaga     360
ccaggg                                                                366
```

<210> SEQ ID NO 279
<211> LENGTH: 435
<212> TYPE: DNA
<213> ORGANISM: Homo sapiens

<400> SEQUENCE: 279

```
cctaagaact gagacttgtg acacaaggcc aacgacctaa gattagccca gggttgtagc      60
tggaagacct acaacccaag gatggaaggc ccctgtcaca aagcctacct agatggatag     120
aggacccaag cgaaaaagat atctcaagac taacggccgg aatctggagg cccatgaccc     180
agaacccagg aaggatagaa gcttgaagac ctggggaaat cccaagatga aaccctaaa      240
ccctacctct tttctattgt ttacacttct tactcttaga tatttccagt tctcctgttt     300
atctttaagc ctgattcttt tgagatgtac tttttgatgt tgccggttac ctttagattg     360
acaagtatta tgcctggcca gtcttgagcc agctttaaat cacagctttt acctatttgt     420
taggctatag tgttt                                                      435
```

<210> SEQ ID NO 280
<211> LENGTH: 435
<212> TYPE: DNA
<213> ORGANISM: Homo sapiens

<400> SEQUENCE: 280

```
tctggatgag ctgctaactg agcacaggat gacctgggac ccagcccagc caccccgaga      60
cctgactgag gccttcctgg caaagaagga gaaggcaag gggagccctg agagcagctt      120
caatgatgag aacctgcgca gtgtggtggg taacctgttc cttgccggga tggtgaccac     180
```

```
ctcgaccacg ctggcctggg gcctcctgct catgatccta cacctggatg tgcagcgtga      240
gcccagacct gtccgggcgg ccgctcgaaa ttccagcaca ctggcggccg ttactagtgg      300
atccgagctc ggtaccaagc ttggcgtaat catggtcata gctgtttcct gtgtgaaatt      360
gttatccgct cacaattcca cacaacatac gagccggaag cataaagtgt aaagcctggg      420
gtgcctaatg agtga                                                       435
```

<210> SEQ ID NO 281
<211> LENGTH: 440
<212> TYPE: DNA
<213> ORGANISM: Homo sapiens

<400> SEQUENCE: 281

```
catctgatct ataaatgcgg tggcatcgac aaaagaacca ttgaaaaatt tgagaaggag      60
gctgctgaga tgggaaaggg ctccttcaag tatgcctggg tcttggataa actgaaagct     120
gagcgtgaac gtggtatcac cattgatatc tccttgtgga aatttgagac cagcaagtac     180
tatgtgacta tcattgatgc cccaggacac agagacttta tcaaaaacat gattacaggg     240
acatctcagg ctgactgtgc tgtcctgatt gttgctgctg tgttggtga atttgaagct      300 ggtatctcca agaatgggca gacccgagag catgcccttc tggcttacac actgggtgtg     360
aaacaactaa ttgtcggtgt taacaaaatg gattccactg agccccctac agccagaaga     420
gatatgagga aattgttaag                                                  440
```

<210> SEQ ID NO 282
<211> LENGTH: 502
<212> TYPE: DNA
<213> ORGANISM: Homo sapiens

<400> SEQUENCE: 282

```
tctgtggcgc aggagccccc tcccccggca gctctgacgt ctccaccgca gggactggtg      60
cttctcggag ctcccactcc tcagactccg gtggaagtga cgtggacctg atcccactg      120 atggcaagct cttccccagc gatggttttc gtgactgcaa gaaggggat cccaagcacg      180 ggaagcggaa acgaggccgg ccccgaaagc tgagcaaaga gtactgggac tgtctcgagg     240
gcaagaagag caagcacgcg cccagaggca cccacctgtg ggagttcatc cgggacatcc     300
tcatccaccc ggagctcaac gagggcctca tgaagtggga gaatcggcat gaaggcgtct     360
tcaagttcct gcgctccgag gctgtggccc aactatgggg ccaaaagaaa agaacagca     420 acatgaccta cgagaagctg agccgggcca tgaggtacta ctacaaacgg gagatcctgg     480
aacgggtgga tggccggcga ct                                              502
```

<210> SEQ ID NO 283
<211> LENGTH: 433
<212> TYPE: DNA
<213> ORGANISM: Homo sapiens
<220> FEATURE:
<221> NAME/KEY: misc_feature
<222> LOCATION: 130, 147, 221, 225, 242, 246, 261, 279, 292, 294, 298,
      314, 323, 332, 339, 342, 343, 350, 351, 356, 361, 362, 368, 372,
      375, 379, 380, 382, 387, 390, 392, 394, 401, 404, 406, 409,
      413, 423, 431, 433
<223> OTHER INFORMATION: n = A,T,C or G

<400> SEQUENCE: 283

```
ccatattaga ttactggaac atctaagcat cagtgtgtga ccatgcgaac aaaagacttc      60
ggggagtgtc tatttttaaa aaggtttatg tgtgtcgagg cagttgtaaa agatttactg     120
```

```
cagaatcaan cccacttttta ggcttangac caggttctaa ctatctaaaa atattgactg    180
ataacaaaaa gtgttctaaa tgtggctatt ctgatccata nttgntttttt aaagaaaaaa    240 antgtntata cagaaagagt ntaaaagttc tgtgaattna atgcaaatta gncnccantc    300
ttgactcccc aaanacttga ttnatacctt tnactcctnt cnnttcctgn ncttcttaa     360 nntcaatnat tnggnagtnn anggccntcn gnanaacacc nttncncgnt ccncgcaatc    420
canccgcctt nan                                                       433

<210> SEQ ID NO 284
<211> LENGTH: 479
<212> TYPE: DNA
<213> ORGANISM: Homo sapiens

<400> SEQUENCE: 284
tctggaagga tcagggatct gagcaaagcc aagtttactt aagctaagcc acttgttcct    60
gggtcaagca gtttgttttc taataagcat cattcctgat cattagagca aagggatgaa    120
tgctcctctt ggaatgatac agggatctg ccactgggag agtgttgctc agtgttagag     180
tagcagcaat gacagaatga cagcgactct ctgagtcaac ccagtacttt tagtaccccg    240
tcactatgtg aataaaggca gctagaaaat ggactcaatt ctgcaagcct tcatggcaac    300
agcccatatt aagacttcta gaacaagtta aaaaaaaatc ttccatttcc atccatgcat    360
gggaaaaggg ctttagtata gtttaggatg gatgtgtgta taataataaa atgataagat    420
atgcatagtg ggggaataaa gcctcagagt ccttccagta tggggaatcc attgtatct    479

<210> SEQ ID NO 285
<211> LENGTH: 435
<212> TYPE: DNA
<213> ORGANISM: Homo sapiens
<220> FEATURE:
<221> NAME/KEY: misc_feature
<222> LOCATION: 27, 83, 90, 93, 96, 184, 207, 227, 232, 293, 306, 307,
      328, 331, 339, 343, 347, 349, 350, 370, 371, 382, 383, 414, 418,
      434
<223> OTHER INFORMATION: n = A,T,C or G

<400> SEQUENCE: 285
tttttttttt tttttttttt tcaatanaaa tgccataatt tattccattg tataaaaaag    60
tcatccttat gtaacaaaat gtnttcttan aanaanaaat atattatttc aggtcataaa    120
taatcagcaa acatacaact gttggcaact aaaaaaaaac ccaacactgg tattttccat    180
cagngctgaa acaaacctg cttaaanata tatttacagg datagtncag tnctcaaaaa     240
caaaaattga ggtattttgg ttcttctagg agtagacaat gacatttgg gangggcaga    300 ccctnncc aaaaaataaa ataagggnat nttcttcant atngaanann ggggcgccc      360 cggggaaaan naaaccttgg gnngggggtt tggcccaagc ccttgaaaaa aaantttntt    420
tcccaaaaaa aacng                                                    435

<210> SEQ ID NO 286
<211> LENGTH: 301
<212> TYPE: DNA
<213> ORGANISM: Homo sapiens

<400> SEQUENCE: 286
cctggtttct ggtggcctct atgaatccca tgtagggtgc agaccgtact ccatccctcc    60
ctgtgagcac cacgtcaacg gctcccggcc cccatgcacg ggggagggag atacccccaa    120
```

```
gtgtagcaag atctgtgagc ctggctacag cccgacctac aaacaggaca agcactacgg      180
atacaattcc tacagcgtct ccaatagcga gaaggacatc atggccgaga tctacaaaaa      240 cggcccgtg gagggagctt tctctgtgta ttcggacttc ctgctctaca agtcaggagt       300
g                                                                     301

<210> SEQ ID NO 287
<211> LENGTH: 432
<212> TYPE: DNA
<213> ORGANISM: Homo sapiens

<400> SEQUENCE: 287
tccagcttgt tgccagcatg agaaccgcca ttgatgacat tgaacgccgg gactggcagg      60
atgacttcag agttgccagc caagtcagcg atgtggcggt acaggggac cccttctca       120 acggcaccag ctttgcagac ggcaagggac acccccagaa tggcgttcgc accaaactta     180
gatttatttt ctgttccatc catctcgatc atcagtttgt caatcttctc ttgttctgtg     240
acgttcagtt tcttgctaac cagggcaggc gcaatagttt tattgatgtg ctcaacagcc     300
tttgagacac ccttccccat atagcgagtc ttatcattgt cccggagctc tagggcctca    360
tagataccag ttgaagcacc actgggcaca gcagctctga agagaccttt tgaggtgaag    420
agatcaacct ca                                                        432

<210> SEQ ID NO 288
<211> LENGTH: 326
<212> TYPE: DNA
<213> ORGANISM: Homo sapiens
<220> FEATURE:
<221> NAME/KEY: misc_feature
<222> LOCATION: 254
<223> OTHER INFORMATION: n = A,T,C or G

<400> SEQUENCE: 288
tctggctcaa gtcaaagtcc tggtcctctt ctccgcctcc ttcttcatca tagtaataaa     60
cgttgtcccg ggtgtcatcc tctgggggca gtaagggctc tttgaccacc gctctcctcc    120
gaagaaacag caagagcagc agaatcagaa ttagcaaagc aagaattcct ccaagaatcc    180
ccagaatggc aggaatttgc aatcctgctt cgacaggctg tgccttccta cagacgccgg    240
cggccccttc acantcacac acgctgacct ctaaggtggt cacttggtct ttattctggt    300
tatccatgag cttgagattg attttg                                         326

<210> SEQ ID NO 289
<211> LENGTH: 451
<212> TYPE: DNA
<213> ORGANISM: Homo sapiens

<400> SEQUENCE: 289
gtcccggtgt ggctgtgccg ttggtcctgt gcggtcactt agccaagatg cctgaggaaa    60
cccagaccca agaccaaccg atggaggagg aggaggttga gacgttcgcc tttcaggcag    120
aaattgccca gttgatgtca ttgatcatca atactttcta ctcgaacaaa gagatctttc    180
tgagagagct catttcaaat tcatcagatg cattggacaa aatccggtat gaaagcttga    240
cagatcccag taaattagac tctggaaag agctgcatat taaccttata ccgaacaaac    300
aagatcgaac tctcactatt gtggatactg gaattggaat gaccaaggct gacttgatca    360
ataaccttgg tactatcgcc aagtctggga ccaaagcgtt catggaagct ttgcaggctg   420
gtgcagatat ctctatgatt ggacctcggc c                                  451
```

<210> SEQ ID NO 290
<211> LENGTH: 494
<212> TYPE: DNA
<213> ORGANISM: Homo sapiens
<220> FEATURE:
<221> NAME/KEY: misc_feature
<222> LOCATION: 421
<223> OTHER INFORMATION: n = A,T,C or G

<400> SEQUENCE: 290

```
tttttttttt tcaaaacagt atatttt att ttacaatagc aaccaactcc ccagtttgtt    60
tcaattgtga catctagatg gcttaagatt actttctggt ggtcacccat gctgaacaat   120
attttcaat cttccaaaca gcaaagactc aaaagagatt ctgcatttca catcagttca   180
caagttcaag agtcttccat ttatcttagc ttttggaata aattatcttt gaggtagaag   240
gacaatgacg aagccactta attccttgtg tctgcataaa agcagattta ttcatcacaa   300
cttcatttat gtgaataaag cagatgatga taaaatgttc tcttattctt gtttaatcag   360
tagtggtagt gatgccagaa acttgtaaat gcacttcaaa ccaattgtgg ctcaagtgta   420
ngtggttccc caaggctggt accaatgaga ctggggtttg ggaattagtt ggtcatcatc   480
cctcctgctg ccca                                                     494
```

<210> SEQ ID NO 291
<211> LENGTH: 535
<212> TYPE: DNA
<213> ORGANISM: Homo sapiens

<400> SEQUENCE: 291

```
tcgcgtgctt aacatgaaaa caaactttgt gctgtttggt tcattgtatg cattgatgga    60
gtcttgtctc tcatcatggg gtgtctgacc atccaacctg cagtactcat aatttctcca   120
catgcaataa tcttccaaaa tgtccaatac ccttgtcatt tgactgaaga ttagtactcg   180
tgaaccttgt tcttttaact tagggagcag cttgtctaaa accaccattt tgccactgtt   240
ggttactaga tgcatatctg ttgtataagg tggaccaggt tctgctccat caaagagata   300
tggatgatta caacattttc tcaactgcat taggatgttc ataaccctca ttttgtccat   360
cttgcctgct gagttgagta tatctatatc cttcattaat atccgagtat accattccct   420
ttgcattttg ctgaggccca catagatttt tacttccttc tttggaggca aactcttttc   480
aacatcagcc ttaattcgac gaaggaggaa tggacgcaaa accatatgaa gcctc         535
```

<210> SEQ ID NO 292
<211> LENGTH: 376
<212> TYPE: DNA
<213> ORGANISM: Homo sapiens
<220> FEATURE:
<221> NAME/KEY: misc_feature
<222> LOCATION: 4, 348
<223> OTHER INFORMATION: n = A,T,C or G

<400> SEQUENCE: 292

```
tacnagcccg tgctgatcga gatcctggtg gaggtgatgg atccttcctt cgtgtgcttg    60
aaaattggag cctgccccctc ggcccataag cccttgttgg gaactgagaa gtgtatatgg   120
ggcccaagct actggtgcca gaacacagag acagcagccc agtgcaatgc tgtcgagcat   180
tgcaaacgcc atgtgtggaa ctaggaggag gaatattcca tcttggcaga aaccacagca   240
ttggtttttt tctacttgtg tgtctggggg aatgaacgca cagatctgtt tgactttgtt   300
```

```
ataaaaatag ggctccccca cctcccccat ttttgtgtcc tttattgnag cattgctgtc      360
tgcaagggag ccccta                                                      376

<210> SEQ ID NO 293
<211> LENGTH: 320
<212> TYPE: DNA
<213> ORGANISM: Homo sapiens

<400> SEQUENCE: 293
tcggctgctt cctggtctgg cggggatggg tttgctttgg aaatcctcta ggaggctcct       60
cctcgcatgg cctgcagtct ggcagcagcc ccgagttgtt tcctcgctga tcgatttctt      120
tcctccaggt agagttttct ttgcttatgt tgaattccat tgcctctttt ctcatcacag      180
aagtgatgtt ggaatcgttt cttttgtttg tctgatttat ggttttttta agtataaaca      240
aaagtttttt attagcattc tgaaagaagg aaagtaaaat gtacaagttt aataaaaagg      300
ggccttcccc tttagaatag                                                  320

<210> SEQ ID NO 294
<211> LENGTH: 359
<212> TYPE: DNA
<213> ORGANISM: Homo sapiens

<400> SEQUENCE: 294
ctgtcataaa ctggtctgga gtttctgacg actccttgtt caccaaatgc accatttcct       60
gagacttgct ggcctctccg ttgagtccac ttggcttttct gtcctccaca gctccattgc     120
cactgttgat cactagcttt ttcttctgcc cacaccttct tcgactgttg actgcaatgc      180
aaactgcaag aatcaaagcc aaggccaaga gggatgccaa gatgatcagc cattctggaa      240
tttggggtgt ccttatagga ccagaggttg tgtttgctcc accttcttga ctcccatgtg      300
agtgtccatc tgattcagat ccatgagtgg tatgggaccc cccactgggg tggaatgtg       359

<210> SEQ ID NO 295
<211> LENGTH: 584
<212> TYPE: DNA
<213> ORGANISM: Homo sapiens
<220> FEATURE:
<221> NAME/KEY: misc_feature
<222> LOCATION: 558
<223> OTHER INFORMATION: n = A,T,C or G

<400> SEQUENCE: 295
cctgagttgg gctgactgcc agagacagac ccctctgggt ctcggtgaac cagccaggca       60
tttacctcag tggttggcac ctggaacctg tccagggccc tcacctgact gaggagccgc      120
cgggcagtga agtaattgtc caggtctatg ctcttggggt ggataccata gccatccaag      180
gtattcctca ggttgtggaa ctgggtctga gtataggcag aactgggccc caggatgatc      240
tcccggagtg ggggaagctg tgaggtcagg taagtatcca cgtccacccg taccccaatc      300
aaactcagca gaatggtgaa ctggagaagt ccttccgtta agtatttctt cagagaaagc      360
attgctgaag gaccagaatg tttatgcttt tggttttta aaatcttcca aaagacaaat       420
caaggccact gctctgccgc tccagccagc aggttaccct cctcagtgtc aaacccgta       480 ccccaccctg gcagaacaca agggatgagc tccctgacgg ccccagagga aagcacaccc      540
tgtggagcca aggccaanga cacactccag accacattca cttt                      584

<210> SEQ ID NO 296
<211> LENGTH: 287
```

```
<212> TYPE: DNA
<213> ORGANISM: Homo sapiens

<400> SEQUENCE: 296
ccttatcatt cattcttagc tcttaattgt tcatttttgag ctgaaatgct gcatttttaat      60
tttaaccaaa acatgtctcc tatcctggtt tttgtagcct tcctccacat cctttctaaa     120
caagattttta aagacatgta ggtgtttgtt catctgtaac tctaaaagat ccttttttaaa    180
ttcagtccta agaaagagga gtgcttgtcc cctaagagtg tttaatggca aggcagccct     240
gtctgaagga cacttcctgc ctaagggaga gtggtatttg cagacta                    287

<210> SEQ ID NO 297
<211> LENGTH: 457
<212> TYPE: DNA
<213> ORGANISM: Homo sapiens

<400> SEQUENCE: 297
ccaattgaaa caaacagttc tgagaccgtt cttccaccac tgattaagag tggggtggca      60
ggtattaggg ataatattca tttagccttc tgagctttct gggcagactt ggtgaccttg     120
ccagctccag cagccttctt gtccactgct ttgatgacac ccaccgcaac tgtctgtctc     180
atatcacgaa cagcaaagcg acccaaaggt ggatagtctg agaagctctc aacacacatg     240
ggcttgccag gaaccatatc aacaatggca gcatcaccag acttcaagaa tttagggcca     300
tcttccagct tttaccaga acggcgatca atctttttcct tcagctcagc aaacttgcat     360
gcaatgtgag ccgtgtggca atccaataca ggggcatagc cggcgcttat ttggcctgga     420
tggttcagga taatcacctg agcagtgaag ccagacc                              457

<210> SEQ ID NO 298
<211> LENGTH: 469
<212> TYPE: DNA
<213> ORGANISM: Homo sapiens

<400> SEQUENCE: 298
tctttgactt tccttgtcta cctcctctgg agatctcaaa ttctccaggt tccatgctcc      60
cagagatctc aatgattcct gattctcctc ttccaggagt ctgaatgtct cttggttcac     120
ttccacagac tccagtggtt cttgaatttc cttttctaga ggattcattg cccctgatt     180
tatttcttct ggagtccaca gtggtgcttg agtttctgga gatttcagtg tttccaggtt     240
ctcttgtccc gcagacttca gtgattctag gatctctgtt tctaaagatt ttactgcctc     300
tatgctctct tctttgagtg actttaagaa ctcttgattc tcatttttcaa gaggtctagc     360
tatctcctgg tcaagagact tcagtggttc tagatccact tttctggggg gtcttaatgt     420
catctgatcc tgttccccta gagacctccg tcgctgttga gtctctttt                  469

<210> SEQ ID NO 299
<211> LENGTH: 165
<212> TYPE: DNA
<213> ORGANISM: Homo sapiens
<220> FEATURE:
<221> NAME/KEY: misc_feature
<222> LOCATION: 37, 82, 144
<223> OTHER INFORMATION: n = A,T,C or G

<400> SEQUENCE: 299
tctgtggaga ggatgaggtt gagggaggtg gggtatntcg ctgctctgac cttaggtaga      60
gtcctccaca gaagcatcaa antggactgg cacatatgga ctcccttcac aggccacaat    120
```

```
gatgtgtctc tccttcgggc tggnccggta tgcacagttg gggta              165
```

<210> SEQ ID NO 300
<211> LENGTH: 506
<212> TYPE: DNA
<213> ORGANISM: Homo sapiens

<400> SEQUENCE: 300

```
tctgaggaaa gtttgggctt attagtattt gctccagcga acctccaagt tttctccatt    60
gcggacaacg taactaccag ctccttggct cagtggttcg cctccactca gaagttccca   120
gtaggttctg tcattattgt tggcacatag ccctgaata caggtgatat agggcccca    180 tgagcgctcc tccattgtga aaccaaatat agtatcattc attttctggg ctttctccat   240
cacactgagg aagacagaac catttagcac agtgacattg tgaaatatg tttcattgat    300 tctcacagag taattgacgg agatatatga ttgtgagtca ggaggtgtca cagttatagg   360
ctcatcagcg gagatgttga agttacctga agcagagacg caagaagagt ctttgttaat   420
atccaagaag gtctttccca tcagggcagg taagacctgg gctgcagcgt ttggattgct   480
gaatgctcct tgagaaattt ccgtga                                        506
```

<210> SEQ ID NO 301
<211> LENGTH: 304
<212> TYPE: DNA
<213> ORGANISM: Homo sapiens
<220> FEATURE:
<221> NAME/KEY: misc_feature
<222> LOCATION: 221, 223, 252, 275, 280
<223> OTHER INFORMATION: n = A,T,C or G

<400> SEQUENCE: 301

```
tcctaaggca gagcccccat cacctcaggc ttctcagttc ccttagccgt cttactcaac    60 tgccccttc ctctccctca gaatttgtgt ttgctgcctc tatcttgttt tttgttttt    120 cttctggggg gggtctagaa cagtgcctgg cacatagtag gcgctcaata aatacttgtt   180
tgttgaatgt ctcctctctc tttccactct gggaaaccta ngnttctgcc attctgggtg   240
accctgtatt tntttctggt gcccattcca tttgnccagn taatacttcc tcttaaaaat   300
ctcc                                                                304
```

<210> SEQ ID NO 302
<211> LENGTH: 492
<212> TYPE: DNA
<213> ORGANISM: Homo sapiens

<400> SEQUENCE: 302

```
ttttcagtaa gcaacttttc catgctctta atgtattcct ttttagtagg aatccggaag    60
tattagattg aatggaaaag cacttgccat ctctgtctag gggtcacaaa ttgaaatggc   120
tcctgtatca catacggagg tcttgtgtat ctgtggcaac agggagtttc cttattcact   180
ctttatttgc tgctgtttaa gttgccaacc tcccctccca ataaaaattc acttacacct   240
cctgcctttg tagttctggt attcacttta ctatgtgata gaagtagcat gttgctgcca   300
gaatacaagc attgcttttg gcaaattaaa gtgcatgtca tttcttaata cactagaaag   360
gggaaataaa ttaaagtaca caagtccaag tctaaaactt tagtactttt ccatgcagat   420
ttgtgcacat gtgagagggt gtccagtttg tctagtgatt gttatttaga gagttggacc   480
actattgtgt gt                                                       492
```

<210> SEQ ID NO 303
<211> LENGTH: 470
<212> TYPE: DNA
<213> ORGANISM: Homo sapiens

<400> SEQUENCE: 303

```
tctggggcag caggtactcc ctacggcact agtctacagg gggaaggacg ctctgtgctg      60
gcagcggtgg ctcacatggc ctgtctgcac tgtaaccaca ggctgggatg tagccaggac     120
ttggtctcct tggaagacag gtctgatgtt tggccaatcc agtccttcag accctgcctg     180
aaacttgtat cttacgtgaa cttaaagaat aaaatgcatt tctacccgga tctcgccccc     240
aggactggca cgacaggccc acggcagatt agatcttttc ccagtactga tcggtgcgtg     300
gaattccagc caccacttct gattcgattc cacagtgatc ctgtcctctg agtattttaa     360
agaagccatt gtcaccccag tcagtgttcc aggagttggc aaccagccag tagggtgtgc     420
cattctccac tccccagccc aggatgcgga tggcatggac ctcggccgcg                470
```

<210> SEQ ID NO 304
<211> LENGTH: 79
<212> TYPE: DNA
<213> ORGANISM: Homo sapiens

<400> SEQUENCE: 304

```
tgtcccattg ttaactcagc ctcaaatctc aactgtcagg ccctacaaag aaaatggaga      60
gcctcttctg gtggatgcg                                                    79
```

<210> SEQ ID NO 305
<211> LENGTH: 476
<212> TYPE: DNA
<213> ORGANISM: Homo sapiens

<400> SEQUENCE: 305

```
tcactgagcc accctacagc cagaagagat atgaggaaat tgttaaggaa gtcagcactt      60
acattaagaa aattggctac aaccccgaca cagtagcatt tgtgccaatt tctggttgga     120
atggtgacaa catgctggag ccaagtgcta acgtaagtgg cttTcaagac cattgttaaa     180
aagctctggg aatggcgatt tcatgcttac acaaattggc atgcttgtgt tcagatgcc     240
ttggttcaag ggatggaaag tcacccgtaa ggatggcaat gccagtggaa ccacgctgct     300
tgaggctctg gactgcatcc taccaccaac tcgtccaact gacaagccct gcgcctgcc     360
tctccaggat gtctacaaaa ttggtggtaa gttggctgta aacaaagttg aatttgagtt     420
gatagagtac tgtctgcctt cataggtatt tagtatgctg taaatatttt taggta         476
```

<210> SEQ ID NO 306
<211> LENGTH: 404
<212> TYPE: DNA
<213> ORGANISM: Homo sapiens

<400> SEQUENCE: 306

```
tctgtctcgg agctcagggc gcagccagca cacacaggag cccacaggac agccacgtct      60
tcacagaaac tacagaagtc aggacccagg cgaggacctc aggaacaagt gcccctgca     120
gacagagaga cgcagtagca acagcttctg aacaactaca taataatgcg gggagaatcc     180
tgaagaccac tgcatcccac aagcactgac aaccacttca ggattttatt tcctccactc     240
taaccccag atccatttat gagaagtgag tgaggatggc aggggcatgg agggtgaagg     300
gacagcaagg atggtctgag ggcctggaaa caatagaaaa tcttcgtcct ttagcatatc     360
```

```
ctggactaga aaacaagagt tggagaagag gggggttgat acta                      404
```

<210> SEQ ID NO 307
<211> LENGTH: 260
<212> TYPE: DNA
<213> ORGANISM: Homo sapiens
<220> FEATURE:
<221> NAME/KEY: misc_feature
<222> LOCATION: 10, 255, 257
<223> OTHER INFORMATION: n = A,T,C or G

<400> SEQUENCE: 307

```
tcctgcctan acatctgtga gggcctcaag ggctgctgcc tcgactttct ccctagctaa     60
gtccacccgt ccagggacac agccagggca ctgctctgtg ctgacttcca ctgcagccaa    120
gggtcaaaat gaagcatctg cggaggccag gactccttgg catcggacac agtcaggga    180
aaagccaccc tgactctgca ggacagaggg tctagggtca tttggcagga gaacactggt   240
gtgccaaggg aagcnancat                                                260
```

<210> SEQ ID NO 308
<211> LENGTH: 449
<212> TYPE: DNA
<213> ORGANISM: Homo sapiens

<400> SEQUENCE: 308

```
tctgtgctcc cgactcctcc atctcaggta ccaccgactg cactgggcgg ggccctctgg     60
ggggaaaggc tccacggggc agggatacat ctcgaggcca gtcatcctct ggaggcagcc    120
caatcaggtc aaagattttg cccaactggt cggcttcaga gtttccacag aagagaggct    180
ttcgacgaaa catctctgca aagatacagc caacactcca catgtccaca ggtgttgcat    240
atgtggactg cagaagaact tcgggagctc ggtaccgagt gtaacaacct tgatcgtttt   300
cggctggcaa gcctggtggg ggtgccttgt ccagatatgt ccttaggtcc tggtctacat    360
gctcaaacac cagggttacc ttgatctccc ggtcagttcg ggatgtggca cagacgtcca    420
tcagccggac aacattggga tgctcaaaa                                      449
```

<210> SEQ ID NO 309
<211> LENGTH: 411
<212> TYPE: DNA
<213> ORGANISM: Homo sapiens
<220> FEATURE:
<221> NAME/KEY: misc_feature
<222> LOCATION: 384
<223> OTHER INFORMATION: n = A,T,C or G

<400> SEQUENCE: 309

```
ctgtggaaac ctggggtgcc gggtaaatgg agaactccag cttggatttc ttgccataat     60
caactgagag acgttccatg agcagggagg tgaacccaga accagttccc ccaccaaagc    120
tgtgaaaac caagaagccc tgaagaccgg tgcactggtc agccagcttg cgaattcggt     180
ccaacacaag gtcaatgatc tccttgccaa tggtgtagtg ccctcgggca tagttattgg    240
cagcatcttc cttgcctgtg atgagctgct cagggtggaa gagctggcgg taggtgccag    300
tgcgaacttc atcaatgact gtgggttcca agtctacaaa cacagcccgg ggcacgtgct    360
tgccagcgcc cgtctcactt gaanaagggt gtttgaagga agtcatctcc t             411
```

<210> SEQ ID NO 310
<211> LENGTH: 320
<212> TYPE: DNA
<213> ORGANISM: Homo sapiens

```
<220> FEATURE:
<221> NAME/KEY: misc_feature
<222> LOCATION: 250
<223> OTHER INFORMATION: n = A,T,C or G

<400> SEQUENCE: 310
tcctcgtcca gcttgactcg attagtcctc ataaggtaag caaggcagat ggtggctgac      60
cgggaaatgc ctgcctggca gtggacaaac cccttcctc cagcattctt gatggagtct      120
atgaagtcaa tggcctcgtt gaaccaggag ctgatgtctg ccttgtggtt gtcctccaca      180
gggatgctct tgtactggta gtgaccctca aaatggttgg acaattggc tgagacgttg       240 atcaaggcan ttatgcccaa ggcatccagc atgtccttgc gggaagcgtg atacgcactg      300
cccaggtaca gaaagggcag                                                  320

<210> SEQ ID NO 311
<211> LENGTH: 539
<212> TYPE: DNA
<213> ORGANISM: Homo sapiens

<400> SEQUENCE: 311
tctggcccat gaagctgaag ttgggagaga tgatgcttcg cctctgcttc acaaactcaa      60
aggcctcgtc cagcttgact cgattagtcc tcataaggta agcaaggcag atggtggctg      120
accgggaaat gcctgcctgg cagtggacaa acacccttcc tccagcattc ttgatggagt      180
ctatgaagtc aatggcctcg ttgaaccagg agctgatgtc tgccttgtgg ttgtcctcca      240
cagggatgct cttgtactgg tagtgaccct caaaatggtt gggacaattg ctgagacgt       300 tgatcaaggc agttatgccc aaggcatcca gcatgtcctt gcgggaagcg tgatacgcac      360
tgcccaggta cagaaagggc aggatttcca ccgggccacc ctgaaatcca gaatatcca      420 acattcatca gcttgctca aagccaaggc cagtgcccat acccacaaaa actttctgct       480
ggaaaagtca atttcagata ccgagtgaac tcagttctgt tgctggagga taaataaat       539

<210> SEQ ID NO 312
<211> LENGTH: 475
<212> TYPE: DNA
<213> ORGANISM: Homo sapiens

<400> SEQUENCE: 312
tcaaggatct tcctaaagcc accatgtgag aggattcgga cgagagtctg agctgtatgg      60
cagaccatgt cctgctgttc tagggtcatg actgtgtgta ctctaaagtt gccactctca      120
caggggtcag tgatacccac tgaacctggc aggaacagtc ctgcagccag aatctgcaag      180
cagcgcctgt atgcaacgtt tagggccaaa ggctgtctgg tggggttgtt catcacagca      240
taatggccta gtaggtcaag gatccagggt gtgagggggct caaagccagg aaaacgaatc     300
ctcaagtcct tcagtagtct gatgagaact ttaactgtgg actgagaagc attttcctcg      360
aaccagcggg catgtcggat ggctgctaag gcactctgca atactttgat atccaaatgg      420
agttctggat ccagttttcg aagattgggt ggcactgttg taatgagaat cttca          475

<210> SEQ ID NO 313
<211> LENGTH: 456
<212> TYPE: DNA
<213> ORGANISM: Homo sapiens

<400> SEQUENCE: 313
tccacttaaa gggtgcctct gccaactggt ggaatcatcg ccacttccag caccacgcca      60
```

| | |
|---|---|
| agcctaacat cttccacaag gatcccgatg tgaacatgct gcacgtgttt gttctgggcg | 120 |
| aatggcagcc catcgagtac ggcaagaaga agctgaaata cctgccctac aatcaccagc | 180 |
| acgaatactt cttcctgatt gggccgccgc tgctcatccc catgtatttc cagtaccaga | 240 |
| tcatcatgac catgatcgtc cataagaact gggtggaccct ggcctgggcc gtcagctact | 300 |
| acatccggtt cttcatcacc tacatcccctt tctacggcat cctgggagcc ctccttttcc | 360 |
| tcaacttcat caggttcctg gagagccact ggtttgtgtg ggtcacacag atgaatcaca | 420 |
| tcgtcatgga gattgaccag gaggacctcg gcccgc | 456 |

<210> SEQ ID NO 314
<211> LENGTH: 477
<212> TYPE: DNA
<213> ORGANISM: Homo sapiens

<400> SEQUENCE: 314

| | |
|---|---|
| tgcgtgggct tctggaagcc tggatctgga atcattcacc agattattct ggaaaactat | 60 |
| gcgtaccctg gtgttcttct gattggcact gactcccaca cccccaatgg tggcggcctt | 120 |
| gggggcatct gcattggagt tgggggtgcc gatgctgtgg atgtcatggc tgggatcccc | 180 |
| tgggagctga agtgccccaa ggtgattggc gtgaagctga cgggctctct ctccggttgg | 240 |
| tcctcaccca agatgtgat cctgaaggtg gcaggcatcc tcacggtgaa aggtggcaca | 300 |
| ggtgcaatcg tggaatacca cgggcctggt gtagactcca tctcctgcac tggcatggcg | 360 |
| acaatctgca acatgggtgc agaaattggg gccaccactt ccgtgttccc ttacaaccac | 420 |
| aggatgaaga agtatctgag caagaccggc cgggaagaca ttgccaatct agctgat | 477 |

<210> SEQ ID NO 315
<211> LENGTH: 241
<212> TYPE: DNA
<213> ORGANISM: Homo sapiens
<220> FEATURE:
<221> NAME/KEY: misc_feature
<222> LOCATION: 35
<223> OTHER INFORMATION: n = A,T,C or G

<400> SEQUENCE: 315

| | |
|---|---|
| caggtactgg atgtcaggtc tgcgaaactt cttanatttt gacctcagtc cataaaccac | 60 |
| actatcacct cggccatcat atgtgtctac tgtggggaca actggagtga aaacttcggt | 120 |
| tgctgcaggt ccgtgggaaa atcagtgacc agttcatcag attcatcaga atggtgagac | 180 |
| tcatcagact ggtgagaatc atcagtgtca tctacatcat cagagtcgtt cgagtcaatg | 240 |
| g | 241 |

<210> SEQ ID NO 316
<211> LENGTH: 241
<212> TYPE: DNA
<213> ORGANISM: Homo sapiens
<220> FEATURE:
<221> NAME/KEY: misc_feature
<222> LOCATION: 1, 4, 32, 39, 68, 77, 82, 94, 166, 172, 195, 196
<223> OTHER INFORMATION: n = A,T,C or G

<400> SEQUENCE: 316

| | |
|---|---|
| nttntgtgat agtgtggttt atggactgag gncaaaatnt aagaagtttc gcagacctga | 60 |
| catccaance tgcccgngcg gncgctcgaa aggncgaatt ctgcagatat ccatcacact | 120 |
| ggcggccgct cgagcatgca tctagagggc ccaattcgcc ctatantgag tnatattaca | 180 |
| attcactggc cgtcnnttta caacgtcgtg actgggaaaa ccctggcgtt acccaactta | 240 | a                                                                          241

<210> SEQ ID NO 317
<211> LENGTH: 241
<212> TYPE: DNA
<213> ORGANISM: Homo sapiens
<220> FEATURE:
<221> NAME/KEY: misc_feature
<222> LOCATION: 15, 25, 135, 154, 193
<223> OTHER INFORMATION: n = A,T,C or G

<400> SEQUENCE: 317
aggtaccctg ctcancagcc tgggngcctg ggttgtctcc ttgtccatcc actggtccat     60
tctgctctgc atttttttgt tcctcttttg gaggttccac tttgggtttg ggctttgaaa    120
ttatagggct acaantacct cggccgaaac cacnctaagg gcgaattctg cagatatcca    180
tcacactggc ggncgctcga gcatgcatct agagggccca attcgcccta tagtgagtcg    240
t                                                                          241

<210> SEQ ID NO 318
<211> LENGTH: 241
<212> TYPE: DNA
<213> ORGANISM: Homo sapiens
<220> FEATURE:
<221> NAME/KEY: misc_feature
<222> LOCATION: 3, 5, 10, 11, 24, 28, 31, 34, 40, 42, 47, 53, 74, 80,
      96, 101, 127, 129, 136, 138, 205, 241
<223> OTHER INFORMATION: n = A,T,C or G

<400> SEQUENCE: 318
cgngnacaan ntacattgat gganggtntg nggntctgan tntttantta cantggagca     60
ttaatatttt cttnaacgtn cctcaccttc ctgaantaaa nactctgggt tgtagcgctc    120
tgtgctnana accacntnaa ctttacatcc ctcttttgga ttaatccact gcgcggccac    180
ctctgccgcg accacgctaa gggcnaattc tgcagatatc catcacactg gcggccgctc    240 n                                                                          241

<210> SEQ ID NO 319
<211> LENGTH: 241
<212> TYPE: DNA
<213> ORGANISM: Homo sapiens
<220> FEATURE:
<221> NAME/KEY: misc_feature
<222> LOCATION: 24, 36, 39
<223> OTHER INFORMATION: n = A,T,C or G

<400> SEQUENCE: 319
caggtactga tcggtgcgtg gaantccagc caccanttnt gattcgattc cacagtgatc     60
ctgtcctctg agtattttaa agaagccatt gtcaccccag tcagtgttcc aggagttggc    120
aaccagccag tagggtgtgc cattctccac tccccagccc aggatgcgga tggcatggcc    180
acccatcatc tctccggtga cgtgttggta cctcggccgc gaccacgcta agggcgaatt    240
c                                                                          241

<210> SEQ ID NO 320
<211> LENGTH: 241
<212> TYPE: DNA
<213> ORGANISM: Homo sapiens
<220> FEATURE:
<221> NAME/KEY: misc_feature
<222> LOCATION: 27, 215, 216, 217, 220, 222, 235
<223> OTHER INFORMATION: n = A,T,C or G

<400> SEQUENCE: 320

```
ggcaggtacc aacagagctt agtaatntct aaaaagaaaa aatgatcttt ttccgacttc      60
taaacaagtg actatactag cataaatcat tctagtaaaa cagctaaggt atagacattc     120
taataatttg ggaaaaccta tgattacaag tgaaaactca gaaatgcaaa gatgttggtt     180
ttttgtttct cagtctgctt tagcttttaa ctctnnnaan cncatgcaca cttgnaactc     240
t                                                                    241
```

<210> SEQ ID NO 321
<211> LENGTH: 241
<212> TYPE: DNA
<213> ORGANISM: Homo sapiens
<220> FEATURE:
<221> NAME/KEY: misc_feature
<222> LOCATION: 2, 25, 26, 228
<223> OTHER INFORMATION: n = A,T,C or G

<400> SEQUENCE: 321

```
angtaccaac agagcttagt aattnntaaa agaaaaaat gatcttttc cgacttctaa       60
acaagtgact atactagcat aaatcattct agtaaaacag ctaaggtata gacattctaa    120
taatttggga aacctatga ttacaagtga aactcagaa atgcaaagat gttggttttt     180
tgtttctcag tctgctttag cttttaactc tggaagcgca tgcacacntg aactctgctc    240
a                                                                    241
```

<210> SEQ ID NO 322
<211> LENGTH: 241
<212> TYPE: DNA
<213> ORGANISM: Homo sapiens

<400> SEQUENCE: 322

```
ggtaccaaca gagcttagta atttctaaaa agaaaaaatg atctttttcc gacttctaaa     60
caagtgacta tactagcata atcattcttt ctagtaaaac agctaaggta tagacattct    120
aataatttgg gaaacctat gattacaagt aaaaactcag aaatgcaaag atgttggttt    180
tttgtttctc agtctgcttt agcttttaac tctggaagcg catgcacact gaactctgct    240
c                                                                    241
```

<210> SEQ ID NO 323
<211> LENGTH: 241
<212> TYPE: DNA
<213> ORGANISM: Homo sapiens

<400> SEQUENCE: 323

```
cgaggtactg tcgtatcctc agccttgttc tatttcttta ttttagcttt acagagatta     60
ggtctcaagt tatgagaatc tccatggctt caggggcta aacttttctg ccattctttt    120
gctcttaccg ggctcagaag gacatgtcag gtgggatacg tgtttctctt tcagagctga    180
agaaagggtc tgagctgcgg aatcagtaga gaaagccttg gtctcagtga ctccttggct    240
t                                                                    241
```

<210> SEQ ID NO 324
<211> LENGTH: 241
<212> TYPE: DNA
<213> ORGANISM: Homo sapiens

<400> SEQUENCE: 324

```
aggtactgtc gtatcctcag ccttgttcta tttctttatt ttagctttac agagattagg    60
tctcaagtta tgagaatctc catggctttc aggggctaaa cttttctgcc attcttttgc   120
tcttaccggg ctcagaagga catgtcaggt gggatacgtg tttctctttc agagctgaag   180
aaagggtctg agctgcggaa tcagtagaga aagccttggt ctcagtgact ccttggcttt   240
c                                                                   241
```

<210> SEQ ID NO 325
<211> LENGTH: 241
<212> TYPE: DNA
<213> ORGANISM: Homo sapiens

<400> SEQUENCE: 325

```
ggcaggtaca tttgttttgc ccagccatca ctctttttgt gaggagcct  aaatacattc    60 ttcctggggt ccagagtccc cattcaaggc agtcaagtta agacactaac ttggcccttt   120
cctgatggaa atatttcctc catagcagaa gttgtgttct gacaagactg agagagttac   180
atgttgggaa aaaaaagaa gcattaactt agtagaactg aaccaggagc attaagttct   240
g                                                                   241
```

<210> SEQ ID NO 326
<211> LENGTH: 241
<212> TYPE: DNA
<213> ORGANISM: Homo sapiens

<400> SEQUENCE: 326

```
gcaggtacat ttgttttgcc cagccatcac tctttttgt gaggagccta atacattct     60 tcctggggtc cagagtcccc attcaaggca gtcaagttaa gacactaact tggcccttc    120 ctgatggaaa tatttcctcc atagcagaag ttgtgttctg acaagactga gagagttaca  180
tgttgggaaa aaaagaagc attaacttag tagaactgat ccaggagcat taagttctga   240
a                                                                   241
```

<210> SEQ ID NO 327
<211> LENGTH: 241
<212> TYPE: DNA
<213> ORGANISM: Homo sapiens

<400> SEQUENCE: 327

```
ggtaccagac caagtgaatg cgacagggaa ttatttcctg tgttgataat tcatgaagta    60
gaacagtata atcaaaatca attgtatcat cattagtttt ccactgcctc acactagtga   120
gctgtgccaa gtagtagtgt gacacctgtg ttgtcatttc ccacatcacg taagagcttc   180
caaggaaagc caaatcccag atgagtctca gagagggatc aatatgtcca tgattatcag   240
g                                                                   241
```

<210> SEQ ID NO 328
<211> LENGTH: 241
<212> TYPE: DNA
<213> ORGANISM: Homo sapiens
<220> FEATURE:
<221> NAME/KEY: misc_feature
<222> LOCATION: 6, 19, 66, 232, 240
<223> OTHER INFORMATION: n = A,T,C or G

<400> SEQUENCE: 328

```
ggtacnagac caaatgaang ccacagggaa ttatttcctg tgttgataat tcatgaagta    60
gaacantata atcaaaatca attgtatcat cattagtttt ccactgcctc acactagtga   120
```

```
gctgtgccaa gtagtagtgt gacacctgtg ttgtcatttc ccacatcacg taagagcttc    180
caaggaaagc caaatcccag atgagtctca gagagggatc aatatgtcca tnatcatcan    240
g                                                                    241
```

<210> SEQ ID NO 329
<211> LENGTH: 241
<212> TYPE: DNA
<213> ORGANISM: Homo sapiens
<220> FEATURE:
<221> NAME/KEY: misc_feature
<222> LOCATION: 33, 61, 220, 228, 229, 240, 241
<223> OTHER INFORMATION: n = A,T,C or G

<400> SEQUENCE: 329

```
ttcaggtcga gttggctgca gatttgtggt gcnttctgag ccgtctgtcc tgcgccaaaa    60
ngcttcaaag tattattaaa aacatatgga tccccatgaa gccctactac accaaagttt    120
accaggagat ttggatagga atggggctga tgggcttcat cgtttataaa atccgggctg    180
ctgataagaa gtaaggcttt gaaagcttca gcgcctgctn ctggtcanna ctaaccatan    240 n                                                                    241
```

<210> SEQ ID NO 330
<211> LENGTH: 241
<212> TYPE: DNA
<213> ORGANISM: Homo sapiens

<400> SEQUENCE: 330

```
ttttgtgcag atttgtggtg cgttctgagc cgtctgtcct gcgccaagat gcttcaaagt    60
attattaaaa acatatggat ccccatgaag ccctactaca ccaaagttta ccaggagatt    120
tggataggaa tggggctgat gggcttcatc gtttataaaa tccgggctgc tgataaagga    180
agtaaggctt tgaaagcttc agcgcctgct cctggtcatc actaaccaga tttacttgga    240
g                                                                    241
```

<210> SEQ ID NO 331
<211> LENGTH: 241
<212> TYPE: DNA
<213> ORGANISM: Homo sapiens
<220> FEATURE:
<221> NAME/KEY: misc_feature
<222> LOCATION: 1, 9, 41, 60, 61, 119, 124, 132, 139, 141, 153, 168
<223> OTHER INFORMATION: n = A,T,C or G

<400> SEQUENCE: 331

```
nttttaggna ctttgggctc cagacttcac tggtcttagg nattgaaacc atcacctggn    60
ntgcattcct catgactgag gttaacttaa aacaaaaatg gtaggaaagc tttcctatnc    120
ttcnggtaag anacaaatnt ncttaaaaa aangtgaag gcatgacnta cgtgagaact    180
gcacaaactg gccactgaca aaaatgaccc ccatttgtgt gacttcattg agacacatta    240
c                                                                    241
```

<210> SEQ ID NO 332
<211> LENGTH: 241
<212> TYPE: DNA
<213> ORGANISM: Homo sapiens

<400> SEQUENCE: 332

```
tgtgaggaga gggaacatgc tgagaaactg atgaagctgc agaaccaacg aggtggccga    60
```

```
atcttccttc aggatatcaa gaaaccagac tgtgatgact gggagagcgg gctgaatgca    120
atggagtgtg cattacattt ggaaaaaaat gtgaatcagt cactactgga actgcacaaa    180
ctggccactg acaaaaatga cccccatttg tgtgacttca ttgagacaca ttacctgaat    240
g                                                                   241
```

```
<210> SEQ ID NO 333
<211> LENGTH: 241
<212> TYPE: DNA
<213> ORGANISM: Homo sapiens
<220> FEATURE:
<221> NAME/KEY: misc_feature
<222> LOCATION: 44, 52, 60, 98, 104, 108, 124, 126, 190, 198, 206, 214
<223> OTHER INFORMATION: n = A,T,C or G

<400> SEQUENCE: 333
caggtacaag cttttttttt tttttttttt ttgnaaatac tntttattgn    60
aaatattcta tcctaaattc catatagcca attaattntt acanaatntt ttgttaattt    120
ttgngngtat aaattttaca aaaataaagg gtatgtttgt tgcacacaac ttacaaataa    180
taataaactn tttattgnaa atattnttta ttgnaaatat tctttatcct aaattccata    240
t                                                                   241
```

```
<210> SEQ ID NO 334
<211> LENGTH: 241
<212> TYPE: DNA
<213> ORGANISM: Homo sapiens
<220> FEATURE:
<221> NAME/KEY: misc_feature
<222> LOCATION: 10, 16, 22, 24, 49, 158, 159, 237
<223> OTHER INFORMATION: n = A,T,C or G

<400> SEQUENCE: 334
tacctgctgn aggggntgaa gncntctctg ctgccccagg catctgcanc ccctgctgct    60
ggttctgccc ctgctgcagc agaggagaag aaagatgaga agaaggagga gtctgaagag    120
tcagatgatg acatgggatt tggccttttt gattaaannc ctgctcccct gcaaataaag    180 ccttttaca caaaaaaaaa aaaaaaaaaa aaaaaaaaaa aagcttgtac ctgcccngc    240 g                                                                   241
```

```
<210> SEQ ID NO 335
<211> LENGTH: 241
<212> TYPE: DNA
<213> ORGANISM: Homo sapiens
<220> FEATURE:
<221> NAME/KEY: misc_feature
<222> LOCATION: 39
<223> OTHER INFORMATION: n = A,T,C or G

<400> SEQUENCE: 335
ctatgtgctg ggatgactat ggagacccaa atgtctcana atgtatgtcc cagaaacctg    60
tggctgcttc aaccattgac agttttgctg ctgctggctt ctgcagacag tcaagctgca    120
gctcccccaa aggctgtgct gaaacttgag ccccgtgga tcaacgtgct ccaggaggac    180
tctgtgactc tgacatgcca gggggctcgc agccctgaga gcgactccat tcagtggttc    240
c                                                                   241
```

```
<210> SEQ ID NO 336
<211> LENGTH: 241
<212> TYPE: DNA
<213> ORGANISM: Homo sapiens
```

<400> SEQUENCE: 336

```
taccaaccta tgcagccaag caacctcagc agttcccatc aaggccacct ccaccacaac    60
cgaaagtatc atctcaggga aacttaattc ctgcccgtcc tgctcctgca cctcctttat   120
atagttccct cacttgattt ttttaacctt cttttttgcaa atgtcttcag ggaactgagc   180
taatactttt ttttttcttg atgttttctt gaaaagcctt tctgttgcaa ctatgaatga   240
a                                                                    241
```

<210> SEQ ID NO 337
<211> LENGTH: 241
<212> TYPE: DNA
<213> ORGANISM: Homo sapiens
<220> FEATURE:
<221> NAME/KEY: misc_feature
<222> LOCATION: 47, 56, 69, 228
<223> OTHER INFORMATION: n = A,T,C or G

<400> SEQUENCE: 337

```
ggtactgtat gtagctgcac tacaacagat tcttaccgtc tccacanagg tcatanattg    60
taaatggtna atactgactt ttttttttatt cccttgactc aagacagcta acttcatttt   120
cagaactgtt ttaaacctttt gtgtgctggt ttataaaata atgtgtgtaa tccttgttgc   180
tttcctgata ccagactgtt tcccgtggtt ggttagaata tattttgntt tgatgcttat   240
a                                                                    241
```

<210> SEQ ID NO 338
<211> LENGTH: 241
<212> TYPE: DNA
<213> ORGANISM: Homo sapiens

<400> SEQUENCE: 338

```
aggtacaggt gtgcgctgag ccgagtttac acggaaagga taaagcccat ttagtttctt    60
ctcaaatgga gttttccact ttcctttgaa gtagacagca ttcaccagga tcatcctggt   120
atccccatct acagaaacctt caggtaacaa gtttgggatt ttgcctttgg tttgagtctt   180
gacccaggaa ttaatctttt ttctagcttc ttctgcacat tctaggaagt ctactgcctg   240
g                                                                    241
```

<210> SEQ ID NO 339
<211> LENGTH: 241
<212> TYPE: DNA
<213> ORGANISM: Homo sapiens

<400> SEQUENCE: 339

```
taccgacggc tcctggaggg agagagtgaa gggacacggg aagaatcaaa gtcgagcatg    60
aaagtgtctg caactccaaa gatcaaggcc ataacccagg agaccatcaa cggaagatta   120
gttctttgtc aagtgaatga aatccaaaag cacgcatgag accaatgaaa gtttccgcct   180
gttgtaaaat ctattttccc ccaaggaaag tccttgcaca gacaccagtg agtgagttct   240
a                                                                    241
```

<210> SEQ ID NO 340
<211> LENGTH: 241
<212> TYPE: DNA
<213> ORGANISM: Homo sapiens

<400> SEQUENCE: 340

```
gtagccctca cacacacatg cccgtaacag gatttatcac aagacacgcc tgcatgtaga      60
ccagacacag ggcgtatgga aagcacgtcc tcaagactgt agtattccag atgagctgca     120
gatgcttacc taccacggcc gtctccacca gaaaaccatc gccaactcct gcgatcagct     180
tgtgacttac aaaccttgtt taaaagctgc ttacatggac ttctgtcctt aaaagcttc     240 c                                                                     241
```

<210> SEQ ID NO 341
<211> LENGTH: 241
<212> TYPE: DNA
<213> ORGANISM: Homo sapiens

<400> SEQUENCE: 341

```
gtaccgccta ctttcgtctc atgtctccga acttcttgct gatggccgtt ccaacgttgc      60
tgaaagctgc agttgccttt tgccctgcgt gactcagggt tcatgtgtt ttcttgtagg      120 cagtggtagt ctgcatgtca tgccagcttt tgctgaagtt ctgttttaat tcattcatca     180
ggttcatgcc gagttttgtt ttatctcaac tagatgcctt tctttcgctg acaaaacttg     240
t                                                                     241
```

<210> SEQ ID NO 342
<211> LENGTH: 241
<212> TYPE: DNA
<213> ORGANISM: Homo sapiens

<400> SEQUENCE: 342

```
gtacattggt gctataaata taaatgctac ttatgaagca tgaaattaag cttctttttt      60
cttcaagttt tttctcttgt ctagcaatct gttaggcttc tgaaccaaga ccaaatgttt     120
acgttcctct gctgcatacc aacgttactc caaacaataa aaatctatca tttctgctct     180
gtgctgagga atggaaaatg aaaccccccac cccctgaccc ctaggactat acagtggaaa    240
c                                                                     241
```

<210> SEQ ID NO 343
<211> LENGTH: 241
<212> TYPE: DNA
<213> ORGANISM: Homo sapiens

<400> SEQUENCE: 343

```
gtacatgtgg tagcagtaat ttttttgaag caactgcact gacattcatt tgagttttct      60
ctcattatca gattctgttc caaacaagta ttctgtagat ccaaatggat taccagtgtg     120
ctacagactt cttattatag aacagcattc tattctacat caaaaatagt ttgtgtaagt     180
tagttttggt taccatctaa aatattttta aatgttcttt acataaaaat ttatgttgtg     240
t                                                                     241
```

<210> SEQ ID NO 344
<211> LENGTH: 241
<212> TYPE: DNA
<213> ORGANISM: Homo sapiens

<400> SEQUENCE: 344

```
ggtacaaaat tgttggaatt tagctaatag aaaaacatag taaatattta caaaaacgtt      60
gataacatta ctcaagtcac acacatataa caatgtagac aggtcttaac aaagtttaca     120
aattgaaatt atgagatttt cccaaaatga atctaatagc tcattgctga gcatggttat     180
caatataaca tttaagatct tggatcaaat gttgtccccg agtcttctgc aatccagtcc     240
``` t 241

<210> SEQ ID NO 345
<211> LENGTH: 241
<212> TYPE: DNA
<213> ORGANISM: Homo sapiens

<400> SEQUENCE: 345
ggtacgaagc tgagcgcacg ggggttgccc cagcgtggag cctggacctc aaacttcacg    60
gaaaatgctc tctctctttg acaggcttcc agctgtctcc taatttcctg gatgaactct   120
ccccggcgat ttaactgatc ctgaaaagtg gtgagaggac tgaggaagac aaccaggtca   180
gcgttagatc ggcctctgag ggtggtgccc ttgcctgagg agccacccct taccaccttg   240
g                                                                   241

<210> SEQ ID NO 346
<211> LENGTH: 241
<212> TYPE: DNA
<213> ORGANISM: Homo sapiens

<400> SEQUENCE: 346
caggtaccac tgagcctgag atggggatga gggcagagag aggggagccc cctcttccac    60
tcagttgttc ctactcagac tgttgcactc taaacctagg gaggttgaag aatgagaccc   120
ttaggtttta acacgaatcc tgacaccacc atctataggg tcccaacttg gttattgtag   180
gcaaccttcc ctctctcctt ggtgaagaac atcccaagcc agaagaagt taactacagt    240 g                                                                   241

<210> SEQ ID NO 347
<211> LENGTH: 241
<212> TYPE: DNA
<213> ORGANISM: Homo sapiens

<400> SEQUENCE: 347
aggtacatct aaaggcatga agcactcaat tgggcaatta acattagtgt ttgttctctg    60
atggtatctc tgagaatact ggttgtagga ctggccagta gtgccttcgg gactgggttc   120 accccccaggt ctgcggcagt tgtcacagcg ccagccccgc tggcctccaa agcatgtgca   180
ggagcaaatg gcaccgagat attccttctg ccactgttct cctacgtggt atgtcttccc   240
a                                                                   241

<210> SEQ ID NO 348
<211> LENGTH: 241
<212> TYPE: DNA
<213> ORGANISM: Homo sapiens
<220> FEATURE:
<221> NAME/KEY: misc_feature
<222> LOCATION: 2, 18, 29, 35, 56, 57, 64, 76, 77, 85, 102, 103, 104,
      189, 232
<223> OTHER INFORMATION: n = A,T,C or G

<400> SEQUENCE: 348
angtacttgg caagattnga tgctcttgng ctcantgaca tcattcataa cttgtnngtg    60
tgancagagg aggagnncat catcntgtcc tcattcgtca gnnncctctc ctctctgaat   120
ctcaaacaag ttgataatgg agaaaaattt gaattctcag gattgaggct ggactggttc   180
cgcctacang catacactag cgtggctaag gcccctctgc accctgcatg anaaccctga   240
c                                                                   241

<210> SEQ ID NO 349
<211> LENGTH: 241
<212> TYPE: DNA
<213> ORGANISM: Homo sapiens

<400> SEQUENCE: 349

| | | | | | |
|---|---|---|---|---|---|
| gcaggtacca | tttgtctgac | ctctgtaaaa | aatgtgatcc | tacagaagtg | gagctggata | 60 |
| atcagatagt | tactgctacc | cagagcaata | tctgtgatga | agacagtgct | acagagacct | 120 |
| gctacactta | tgacagaaac | aagtgctaca | cagctgtggt | cccactcgta | tatggtggtg | 180 |
| agaccaaaat | ggtggaaaca | gccttaaccc | cagatgcctg | ctatcctgac | taatttaagt | 240 |
| c | | | | | | 241 |

<210> SEQ ID NO 350
<211> LENGTH: 241
<212> TYPE: DNA
<213> ORGANISM: Homo sapiens

<400> SEQUENCE: 350

| | | | | | |
|---|---|---|---|---|---|
| aggtactgtg | gatatttaaa | atatcacagt | aacaagatca | tgcttgttcc | tacagtattg | 60 |
| cgggccagac | acttaagtga | aagcagaagt | gtttgggtga | cttttcctact | taaaattttg | 120 |
| gtcatatcat | ttcaaaacat | ttgcatcttg | gttggctgca | tatgctttcc | tattgatccc | 180 |
| aaaccaaatc | ttagaatcac | ttcatttaaa | atactgagcg | gtattgaata | cttcgaagca | 240 |
| g | | | | | | 241 |

<210> SEQ ID NO 351
<211> LENGTH: 241
<212> TYPE: DNA
<213> ORGANISM: Homo sapiens

<400> SEQUENCE: 351

| | | | | | |
|---|---|---|---|---|---|
| tacagaaatc | atttggagcc | gttttgagac | agaagtagag | gctctgtcaa | gtcaatactg | 60 |
| cattgcagct | tggtccactg | aagaagccac | gcctgagata | caaaagatgc | actacacttg | 120 |
| acccgctttta | tgttcgcttc | ctctcccctt | ctctctcatc | aactttatta | ggttaaaaca | 180 |
| ccacatacag | gctttctcca | aatgactccc | tatgtctggg | gtttggttag | aattttatgc | 240 |
| c | | | | | | 241 |

<210> SEQ ID NO 352
<211> LENGTH: 241
<212> TYPE: DNA
<213> ORGANISM: Homo sapiens
<220> FEATURE:
<221> NAME/KEY: misc_feature
<222> LOCATION: 10, 28, 29, 49, 54, 59, 72, 127, 148, 150, 160, 166, 182
<223> OTHER INFORMATION: n = A,T,C or G

<400> SEQUENCE: 352

| | | | | | |
|---|---|---|---|---|---|
| gtaccctgtn | gagctgcacc | aagattannt | ggggccatca | tgactgcanc | cacnacgang | 60 |
| acgcaggcgt | gnagtgcatc | gtctgacccg | gaaacccttt | cacttctctg | ctcccgaggt | 120 |
| gtcctcnggc | tcatatgtgg | gaaggcanan | gatctctgan | gagttncctg | gggacaactg | 180 |
| ancagcctct | ggagagggc | cattaataaa | gctcaacatc | attggcaaaa | aaaaaaaaaa | 240 |
| a | | | | | | 241 |

<210> SEQ ID NO 353

<211> LENGTH: 241
<212> TYPE: DNA
<213> ORGANISM: Homo sapiens

<400> SEQUENCE: 353

```
aggtaccagt gcattaattt gggcaaggaa agtgtcataa tttgatactg tatctgtttt    60
ccttcaaagt atagagcttt tggggaagga aagtattgaa ctgggggttg gtctggccta   120
ctgggctgac attaactaca attatgggaa atgcaaaagt tgtttggata tggtagtgtg   180
tggttctctt ttggaatttt tttcaggtga tttaataata atttaaaact actataaaaa   240
c                                                                   241
```

<210> SEQ ID NO 354
<211> LENGTH: 241
<212> TYPE: DNA
<213> ORGANISM: Homo sapiens
<220> FEATURE:
<221> NAME/KEY: misc_feature
<222> LOCATION: 1
<223> OTHER INFORMATION: n = A,T,C or G

<400> SEQUENCE: 354

```
ngcaggtccg ggcaggtacc aagattcatt ctcatcaaaa actagaaaca gaagggcaaa    60
ttccagtttc cttctgggat tgaatacttt caagtaaggt cttcgacaaa caatcagggg   120
gccaattaat ccactgtaga ggtccttaac ttgatccaca gttgaataat aagcccatgg   180
aatacaagca gaatcctctg ttccagctcc agatctttct gggattttcc atacgtaagt   240
g                                                                   241
```

<210> SEQ ID NO 355
<211> LENGTH: 241
<212> TYPE: DNA
<213> ORGANISM: Homo sapiens

<400> SEQUENCE: 355

```
ggtacccacc ctaaatttga actcttatca agaggctgat gaatctgacc atcaaatagg    60
ataggatgga ccttttttg agttcattgt ataaacaaat tttctgattt ggacttaatt    120
cccaaaggat taggtctact cctgctcatt cactctttca aagctctgtc cactctaact   180
tttctccagt gtcatagata gggaattgct cactgcgtgc ctagtctttc ttcacttacc   240
t                                                                   241
```

<210> SEQ ID NO 356
<211> LENGTH: 241
<212> TYPE: DNA
<213> ORGANISM: Homo sapiens
<220> FEATURE:
<221> NAME/KEY: misc_feature
<222> LOCATION: 27
<223> OTHER INFORMATION: n = A,T,C or G

<400> SEQUENCE: 356

```
aggtactgta attgagcatc cggaatntgg agaagtaatt tagctacagg gtgaccaacg    60
caagaacata tgccagttcc tcgtagagat tggactggct aaggacgatc agctgaaggt   120
tcatgggttt taagtgcttg tggctcactg aagcttaagt gaggatttcc ttgcaatgag   180
tagaatttcc cttctctccc ttgtcacagg tttaaaaacc tcacagcttg tataatgtaa   240
c                                                                   241
```

<210> SEQ ID NO 357
<211> LENGTH: 241
<212> TYPE: DNA
<213> ORGANISM: Homo sapiens

<400> SEQUENCE: 357

```
ttttgtacca ccgatatgat caaggaaaat tctgcccatt tttatggctg aagttctaaa      60
aacctaattc aaagttcttc catgatccta cactgcctcc aagatggtcc aggctggcat     120
aaggcctgag cggcggtgag atccgcggct gccagcagct tgtcgctctt cagctggtat     180
gaagcccctc ggccacccga gtctccagga cctgcccggg cgccgctcga aagggcgaat     240
t                                                                    241
```

<210> SEQ ID NO 358
<211> LENGTH: 241
<212> TYPE: DNA
<213> ORGANISM: Homo sapiens
<220> FEATURE:
<221> NAME/KEY: misc_feature
<222> LOCATION: 25, 57
<223> OTHER INFORMATION: n = A,T,C or G

<400> SEQUENCE: 358

```
aggtacgggg agtggggtg aagcntgttc tctacatagg caacacagcc gcctaantca       60
caaagtcagt ggtcggccgc ttcgaccaac atgtggtgag cattccacgg gcgcatgaag     120
tctgggtgct gtgctcgagt ctctgaatat tttgatagga agcgacaaga aaattcaaac     180
tgctctttgc tgactactgg aaagtgaaaa gatgctcaag tttaccattc aaagaaacca     240
t                                                                    241
```

<210> SEQ ID NO 359
<211> LENGTH: 241
<212> TYPE: DNA
<213> ORGANISM: Homo sapiens

<400> SEQUENCE: 359

```
gaggtacaca aaaggaatac cttctgagag ccagggagtg aggaaagggg aaggagactt      60
gacgtcaagg gtgcttttga ggaacatgac gggccagcca gcctgcccca actttgaggc     120
cctgctgggc tcttgtgact ataaatatac tgtctatttc taatgcaatc cgtctttcct     180
gaaagatctt gttatctttt actattgaga catgctttca tttttgtggt cctgtttcca     240
a                                                                    241
```

<210> SEQ ID NO 360
<211> LENGTH: 241
<212> TYPE: DNA
<213> ORGANISM: Homo sapiens
<220> FEATURE:
<221> NAME/KEY: misc_feature
<222> LOCATION: 1
<223> OTHER INFORMATION: n = A,T,C or G

<400> SEQUENCE: 360

```
ngtactctat actaattctg cctttttata cttaattcta aatttctccc ctctaattta      60
caacaaattt tgtgatttt ataagaatct atgcctcccc aattctcaga ttcttctctt     120
ttctccttta tttctttgct taaattcagt ataagctttc ttggtatttt aggcttcatg     180
cacattctta ttcctaaaca ccagcagttc ttcagagacc taaaatccag tataggaata     240
a                                                                    241
```

<210> SEQ ID NO 361
<211> LENGTH: 241
<212> TYPE: DNA
<213> ORGANISM: Homo sapiens

<400> SEQUENCE: 361

```
aggtactctc cgtgccccga cactgaacat tatccagcca gatctgccca gtgccagctc    60
ccactttgta cttttcttac tatcctgtct agaatcatgt cttatgattt aacagatat   120
agaaccactc ctagaaaatg ttctttcact ttctcgtttc cttttttaatc tatcatcctg   180
actactgaac ttaaaatctt tttcttccct tttttgtttc tcttttcttt tatcctgttc   240
a                                                                  241
```

<210> SEQ ID NO 362
<211> LENGTH: 241
<212> TYPE: DNA
<213> ORGANISM: Homo sapiens
<220> FEATURE:
<221> NAME/KEY: misc_feature
<222> LOCATION: 17, 23
<223> OTHER INFORMATION: n = A,T,C or G

<400> SEQUENCE: 362

```
aggtactttt atacctngct tangtcagtg acagatttac caatgacaac acaattttaa    60
aattccaaca catatattac tttgtcctat gaagggcaaa aagtcaatat attttaaatt   120
ttaaaaacag aatggatata atgacctttt tacacatcag tgatatttaa aagacttaaa   180
gagacaatac tatggttgag acactggctt cctattccag ccctaattaa agaaaaaata   240
g                                                                  241
```

<210> SEQ ID NO 363
<211> LENGTH: 241
<212> TYPE: DNA
<213> ORGANISM: Homo sapiens
<220> FEATURE:
<221> NAME/KEY: misc_feature
<222> LOCATION: 4
<223> OTHER INFORMATION: n = A,T,C or G

<400> SEQUENCE: 363

```
ttangtacta aaacaaaat cctaattctg ttttaaagag ctgggagatg ttaatcatat    60
gctcagtttt tccacgttat aatttcctaa atgcaaactt ttcaatcagg gcagttcaaa   120
ttcattacat cacagtaaat aacagtagcc aactttgatt ttatgcttat aggaaaaaaa   180
atcctgtaga tataaaaaca gcaaattttg acaaataaaa ctcaaaccat tcatccctaa   240
a                                                                  241
```

<210> SEQ ID NO 364
<211> LENGTH: 241
<212> TYPE: DNA
<213> ORGANISM: Homo sapiens

<400> SEQUENCE: 364

```
ggtacaagca gttagtcctg aaggcccctg ataagaatgt catcttctcc ccactgagca    60
tctccaccgc cttggccttc ctgtctctgg gggcccataa taccaccctg acagagattc   120
tcaaaggcct caagttcaac ctcacggaga cttctgaggc agaaattcac cagagcttcc   180
agcacctcct gcgcaccctc aatcagtcca gcgatgagct gcagctgagt atgggaaatg   240
c                                                                  241
```

<210> SEQ ID NO 365
<211> LENGTH: 241
<212> TYPE: DNA
<213> ORGANISM: Homo sapiens

<400> SEQUENCE: 365

```
cgaggtactg agattacagg catgagccac cacgcccggc caaaaacatt taaaaaatga      60
ctgtccctgc tcaaatactg cagtaggaaa tgtaatttga catatatcac ttccagaaaa     120
aaactttaaa tctttctata aaatgaattt gatacatcat cagcatgaag tgaagttaaa     180
atctcttaca aagtaaattc aggtatatca acaatgagat ccaaaagtat cggttcaaga     240
t                                                                      241
```

<210> SEQ ID NO 366
<211> LENGTH: 241
<212> TYPE: DNA
<213> ORGANISM: Homo sapiens

<400> SEQUENCE: 366

```
ggcaggtaca catcaaacac ttcattgcct aaatgcaggg acatgcttcc atctgaccac      60
ttgactatcc gagcattgct ttctttaatt tcatttcctt cttcatctcg gcgtatcctc     120
catcttatag tattttctac ctttaatttt aacctggttc taccttcttc atccagcatt     180
tcttcatctt caaattcatc ttcataatac tgggctctac acttgagaaa gttgggcagt     240
t                                                                      241
```

<210> SEQ ID NO 367
<211> LENGTH: 241
<212> TYPE: DNA
<213> ORGANISM: Homo sapiens
<220> FEATURE:
<221> NAME/KEY: misc_feature
<222> LOCATION: 25
<223> OTHER INFORMATION: n = A,T,C or G

<400> SEQUENCE: 367

```
gcaggtacaa ataattcctg ttgtnacatt tagtggacgc gattatctgt atacctcaaa      60
ttttaattta agaaagtatc acttaaagag catctcattt tctatagatt gaggcttaat     120
tactgaaaag tgactcaacc aaaaagcaca taacctttta aaggagctac acctaccgca     180
gaaagtcaga tgccctgtaa ataactttgg tctttcaaaa tagtggcaat gcttaagata     240
c                                                                      241
```

<210> SEQ ID NO 368
<211> LENGTH: 241
<212> TYPE: DNA
<213> ORGANISM: Homo sapiens

<400> SEQUENCE: 368

```
tttgtacatt gttaatagtg accctcggag gaaatggatt tctcttctat taaaaactct      60
atggtatata agcattacat aataatgcta cttaaccacc ttttgtctca agaattatca     120
ccaaagtttt ctggaaataa gtccacataa gaattaaata tttaaaaggt gaaatgttcc     180
ttattttaac tttagcaaga tcttttcttt ttcattaaga aacactttaa taattttaaa     240
g                                                                      241
```

<210> SEQ ID NO 369

```
<211> LENGTH: 241
<212> TYPE: DNA
<213> ORGANISM: Homo sapiens

<400> SEQUENCE: 369
gcaggtactt tattcttatt tcttatccta tattctgtgt tacagaaaaa ctactaccat    60
aaacaaaaca ccaaccagcc acagcagttg tgtcaagcat gacaattggt ctagtcttca   120
cattttatta gtaagtctat caagtaagag atgaagggtc tagaaaacta gacacaaagc   180
aaccagggtc caaatcacca aggtagatct gtgcttagct aaagggaaac acccgaagat   240
t                                                                   241

<210> SEQ ID NO 370
<211> LENGTH: 241
<212> TYPE: DNA
<213> ORGANISM: Homo sapiens
<220> FEATURE:
<221> NAME/KEY: misc_feature
<222> LOCATION: 1
<223> OTHER INFORMATION: n = A,T,C or G

<400> SEQUENCE: 370
ngttcacagt gcccctccgg cctcgccatg aggctcttcc tgtcgctccc ggtcctggtg    60
gtggttctgt cgatcgtctt ggaaggccca gccccagccc aggggacccc agacgtctcc   120
agtgccttgg ataagctgaa ggagtttgga acacactgg aggacaaggc tcgggaactc    180
atcagccgca tcaaacagag tgaactttct gccaagatgc gggagtggtt ttcagaagac   240
a                                                                   241

<210> SEQ ID NO 371
<211> LENGTH: 241
<212> TYPE: DNA
<213> ORGANISM: Homo sapiens
<220> FEATURE:
<221> NAME/KEY: misc_feature
<222> LOCATION: 227
<223> OTHER INFORMATION: n = A,T,C or G

<400> SEQUENCE: 371
ggcaggtcat cttgagcctt gcacatgata ctcagattcc tcacccttgc ttaggagtaa    60
aacaatatac tttacagggt gataataatc tccatagtta tttgaagtgg cttgaaaaag   120
gcaagattga cttttatgac attggataaa atctacaaat cagccctcga gttattcaat   180
gataactgac aaactaaatt atttccctag aaaggaagat gaaaggnagt ggagtgtggt   240
t                                                                   241

<210> SEQ ID NO 372
<211> LENGTH: 241
<212> TYPE: DNA
<213> ORGANISM: Homo sapiens
<220> FEATURE:
<221> NAME/KEY: misc_feature
<222> LOCATION: 26, 27, 59
<223> OTHER INFORMATION: n = A,T,C or G

<400> SEQUENCE: 372
aggtacagca aagcgaccct tggtgnnata gatcagacgg aaattctctc ccgtcttgnc    60
aatgctgatg acatccatga atccagcagg gtaggttata tcagttcgga ccttgccatc   120
gattttaatg aaccgctgca tgcaaatctt ctttacttca tctcctgtca gggcatactt   180
aagtctgttc ctcaggaaaa tgatgagggg gagacactct ctcaacttgt ggggaccggt   240
``` g                                                                    241

<210> SEQ ID NO 373
<211> LENGTH: 241
<212> TYPE: DNA
<213> ORGANISM: Homo sapiens

<400> SEQUENCE: 373
tactgaaaca gaaaaaatgt attcccacaa aagctgttac acagcggttt cccgtcccca    60
gaagcagtag aaaatcttag cattccaatg gaaggcatgt atttgtaaaa tattctaaaa   120
tcagctctat agtttccttg tcctctttga taagggatca gacagagggt gtgtcccct   180 tcagcagcta cccttcttga caaactggtc tccaataata cctttcagaa acttacaaga   240
c                                                                    241

<210> SEQ ID NO 374
<211> LENGTH: 241
<212> TYPE: DNA
<213> ORGANISM: Homo sapiens

<400> SEQUENCE: 374
caggtactaa aacttacaat aaatatcaga gaagccgtta gttttttacag catcgtctgc    60 ttaaaagcta agttgaccag gtgcataatt tcccatcagt ctgtccttgt agtaggcagg   120
gcaatttctg ttttcatgat cggaatactc aaatatatcc aaacatcttt ttaaaacttt   180
gatttatagc tcctagaaag ttatgttttt taatagtcac tctactctaa tcaggcctag   240
c                                                                    241

<210> SEQ ID NO 375
<211> LENGTH: 241
<212> TYPE: DNA
<213> ORGANISM: Homo sapiens

<400> SEQUENCE: 375
aggtacaaag gaccagtatc cctacctgaa gtctgtgtgt gagatggcag agaacggtgt    60
gaagaccatc acctccgtgg ccatgaccag tgctctgccc atcatccaga agctagagcc   120
gcaaattgca gttgccaata cctatgcctg taagggcta gacaggattg aggagagact    180
gcctattctg aatcagccat caactcagat tgttgccaat gccaaaggcg ctgtgactgg   240
g                                                                    241

<210> SEQ ID NO 376
<211> LENGTH: 241
<212> TYPE: DNA
<213> ORGANISM: Homo sapiens

<400> SEQUENCE: 376
ggtacatttt actttccttc tttcagaatg ctaataaaaa acttttgttt atacttaaaa    60
aaaccataaa tcagacaaac aaaagaaacg attccaacat cacttctgtg atgagaaaag   120
aggcaatgga attcaacata agcaaagaaa actctacctg gaggaaagaa atcgatcagc   180
gaagaaacaa ctcggggctg ctgccagact gcaggccatg cgaggaggag cctcctagag   240
g                                                                    241

<210> SEQ ID NO 377
<211> LENGTH: 241
<212> TYPE: DNA

<213> ORGANISM: Homo sapiens
<220> FEATURE:
<221> NAME/KEY: misc_feature
<222> LOCATION: 234
<223> OTHER INFORMATION: n = A,T,C or G

<400> SEQUENCE: 377
tcctttctgt ccaggtgatt cacagactag acctttctta tcctcctcct agagttttga    60
cttgggactc tagtgttaag atgatgagcc cgtgcatcag gtccttctgc actttggtgg   120
aagtctccca gggtaggttt cctatttgaa acagtggaat catgtttcca gtgataaagt   180
ttaatgacct catcctttt ttttttttc tcatctgcca tttgtgtgtc ttanatgggt   240
t                                                                 241

<210> SEQ ID NO 378
<211> LENGTH: 241
<212> TYPE: DNA
<213> ORGANISM: Homo sapiens

<400> SEQUENCE: 378
aggtcagcga tcaggtcctt tatgggcagc tgctgggcag ccccacaagc ccagggccag    60
ggcactatct ccgctgcgac tccactcagc ccctcttggc gggcctcacc cccagcccca   120
agtcctatga gaacctctgg ttccaggcca gccccttggg gaccctggta accccagccc   180
caagccagga ggacgactgt gtctttgggc cactgctcaa cttcccctc ctgcagggga   240 t                                                                 241

<210> SEQ ID NO 379
<211> LENGTH: 241
<212> TYPE: DNA
<213> ORGANISM: Homo sapiens

<400> SEQUENCE: 379
tacggagcaa tcgaagaggc atatccacac ttggggtggc tatagggctg gaaaatgctg    60
aagatgactg ctttcactga ggtcaaggat tgtaatattg ccagctttgt aaagccatta   120
aagcagaagt tcttcagtg atcttctctc taagaaacac catcacctcc atgtgcctta   180
cagaggcccc ctgcgttctg ctgcattgct tttgcgcaat cccttgatga tgaagatggt   240
c                                                                 241

<210> SEQ ID NO 380
<211> LENGTH: 241
<212> TYPE: DNA
<213> ORGANISM: Homo sapiens
<220> FEATURE:
<221> NAME/KEY: misc_feature
<222> LOCATION: 24, 25, 26, 34, 36, 56, 113, 129, 137, 184, 185, 208,
       210, 237, 240
<223> OTHER INFORMATION: n = A,T,C or G

<400> SEQUENCE: 380
acgtacacgc agaccgacat gggnnnttca ggcntnagat caaactcaaa acctgnaatg    60
atatccactc tcttttttctt aagctcaggg aaatattcca agtagaagtc canaaagtca   120
tcggctaana tgcttcngaa tttgaattca tgcacatagg ccttgaaaaa actgtcaaac   180
tgannctgat cacccaccaa gtgggccntn tatgacacaa agcagaaacc tttctcntan   240
g                                                                 241

<210> SEQ ID NO 381

<211> LENGTH: 241
<212> TYPE: DNA
<213> ORGANISM: Homo sapiens

<400> SEQUENCE: 381

```
aggtacaact taatggatta gcttttgggt ttaactgaat atatgaagaa attgggtctg      60
tctaaagaga gggtatttca tatggctttt agttcacttg tttgtatttc atcttgattt     120
ttttctttgg aaaataaagc attctatttg gttcagattt ctcagatttg aaaaggctc     180
tatctcagat gtagtaaatt atttcctttc agtttgtgaa agcaggattt gactctgaaa     240
g                                                                    241
```

<210> SEQ ID NO 382
<211> LENGTH: 241
<212> TYPE: DNA
<213> ORGANISM: Homo sapiens

<400> SEQUENCE: 382

```
gtactgctat aatcaatacg tctgatagac aggtttatcc actatattga ccctacctct      60
aaaaggattg tcataattta tatgctttat gtttacacct atgatacagt tgccttggaa     120
cacaaaattt ttcattgtaa ttaaaaaaag aagagttgtg cagacagaag aaatcaaatc     180
taagaaaatc acaggagtag ataaatactc tagaattcat ataccttgg aagatgggtt     240
t                                                                    241
```

<210> SEQ ID NO 383
<211> LENGTH: 241
<212> TYPE: DNA
<213> ORGANISM: Homo sapiens

<400> SEQUENCE: 383

```
ggcaggtaca aagtcttctc tttgcttttt ataattttaa agcaaataac acatttaact      60
gtatttaagt ctgtgcaaat aatccttcag aagaaatatc caagattctg tttgcagagg     120
tcattttgtc tctcaaagat gattaaatga gtttgtcttc agataaagtg ctcctgtcca     180
gcagaactca aaaggccttc aagctgttca gtaagtgtag ttcagataag actccgtcat     240
a                                                                    241
```

<210> SEQ ID NO 384
<211> LENGTH: 241
<212> TYPE: DNA
<213> ORGANISM: Homo sapiens

<400> SEQUENCE: 384

```
ggtacacaaa atacacttgc aagcttgctt acagagacct gttaaacaaa gaacagacag      60
attctataaa atcagttata tcaacatata aaggagtgtg attttcagtt tgttttttta     120
agtaaatatg accaaactga ctaaataaga aggcaaaaca aaaaattatg cttccttgac     180
aaggcctttg gagtaaacaa aatgctttaa ggctcctggt gaatgggtt gcaaggatga     240
a                                                                    241
```

<210> SEQ ID NO 385
<211> LENGTH: 241
<212> TYPE: DNA
<213> ORGANISM: Homo sapiens

<400> SEQUENCE: 385

```
ggcaggtcta caatggctct gtcccttctg tggaatcgtt acaccaagag gtctcagtcc      60
```

```
tggtccctga ccccacagtg agctgtttag atgatccttc acatcttcct gatcaactgg    120
aagacactcc aatcctcagt gaagactctc tggagccctt caactctctg gcaccaggta    180
ggtttggagg ctatgtccct ttaacttatc catgcagagt agccaaactt tacctgaaag    240
a                                                                    241

<210> SEQ ID NO 386
<211> LENGTH: 241
<212> TYPE: DNA
<213> ORGANISM: Homo sapiens

<400> SEQUENCE: 386
aggtaccttt ttcctctcca aggaacagt ttctaaagtt ttctgggggg aaaaaaaact    60
tacatcaaat ttaaaccata tgttaaactg catattagtt gtgttacacc aaaaaattgc    120
ctcagctgat ctacacaagt ttcaaagtca ttaatgcttg atataaattt actcaacatt    180
aaattatctt aaattattaa ttaaaaaaaa aactttctaa gggaaaaata aacaaatgta    240
g                                                                    241

<210> SEQ ID NO 387
<211> LENGTH: 241
<212> TYPE: DNA
<213> ORGANISM: Homo sapiens

<400> SEQUENCE: 387
accccactgg ccgctgtgga gtatctccac tctcccctcg tgagggccgc tcccaccgac    60
cagtcgaact ttcgtaaatg gagttaatgt gtttccactc ccctttccc ctttctggcc    120 ttttggtcca gaatttcctg gccttccggc atatcctggg agtcctcgac ttccaggaaa    180
gccaattgct ccccgatcac ctttaagacc cggaggacct attggacctg gaaatcctcg    240
t                                                                    241

<210> SEQ ID NO 388
<211> LENGTH: 241
<212> TYPE: DNA
<213> ORGANISM: Homo sapiens

<400> SEQUENCE: 388
tttgtactct tgtccacagc agagacattg agtataccat ggcatcaat gtcaaaagtg     60 acttcaatct gaggaacacc tcggggtgca ggaggtatgc ctgtgagttc aaacttgcca    120
agcaggttgt tatcctttgt catggcacgc tcgccttcat aaacctgaat aagtacacca    180
ggctggttgt cagaataggt agtgaaggtc tgtgtctgct tggtaggaat ggtggtatta    240
c                                                                    241

<210> SEQ ID NO 389
<211> LENGTH: 241
<212> TYPE: DNA
<213> ORGANISM: Homo sapiens
<220> FEATURE:
<221> NAME/KEY: misc_feature
<222> LOCATION: 6, 28, 38, 43
<223> OTHER INFORMATION: n = A,T,C or G

<400> SEQUENCE: 389
tacctntgtt agtgagcacc ttgtcttntg tgcttatntc ttnaagataa atacatggaa     60
ggatgtgaaa atcggaacac caactatgtg tctcactgca tctaagtgaa gcagccacag    120
```

```
ctgtgagagt tttcaaagca gaaagatgct gatgtgacct ctggaattca gacatactga      180
gctatgggtc agaagtgttt tacttaaaaa gcaaacaatc cccaggaaat actgaatagg      240
a                                                                      241
```

<210> SEQ ID NO 390
<211> LENGTH: 241
<212> TYPE: DNA
<213> ORGANISM: Homo sapiens

<400> SEQUENCE: 390

```
gcaggtacat ccacatgttc ctccaaatga cgtttggggt cctgcttgcc aacattcttt       60
attgccagct gttcaggtgt catcttatct tcttcttcta cagccttatt gtaattcttg      120
gctaattcca acatctcttt taccactgat tcattgcgtt tacaatgttc actgtagtcc      180
tgaagtgtca aaccttccat ccaactcttc ttatgcaaat ttagcaacat cttctgttcc      240
a                                                                      241
```

<210> SEQ ID NO 391
<211> LENGTH: 241
<212> TYPE: DNA
<213> ORGANISM: Homo sapiens
<220> FEATURE:
<221> NAME/KEY: misc_feature
<222> LOCATION: 2, 10, 14, 22, 23, 25, 40, 50, 57, 59, 65, 71, 72, 73,
      76, 77, 78, 82, 83, 84, 95, 98, 100, 101, 102, 107, 148, 152,
      155, 158, 163, 169, 170, 172, 180, 182, 192, 193, 198, 200,
      202, 203, 206, 207, 208, 213, 214, 218, 220, 224, 225
<223> OTHER INFORMATION: n = A,T,C or G
<221> NAME/KEY: misc_feature
<222> LOCATION: 235, 236
<223> OTHER INFORMATION: n = A,T,C or G

<400> SEQUENCE: 391

```
cnggcacaan cttntgtttt tnntnttttt tttttttttn tctttatttn tttttantnt       60
taaanaaaaa nnntannnaa annngggttt aaatnctntn nncagancat taaaactgaa      120
ggggaaaaaa aaaccaaaaa cgagcttntt anttnacntg ggnttgggnn gntgctgatn      180
tnaagaagca annttttanan cnngcnnnat ganngagngn tcannttgaa atttnnaccc      240
t                                                                      241
```

<210> SEQ ID NO 392
<211> LENGTH: 241
<212> TYPE: DNA
<213> ORGANISM: Homo sapiens

<400> SEQUENCE: 392

```
gaggtactaa atggtatcct tagattaaaa ttttgtgctt gataacagct gttttttcta       60
cattagaaat aagatgccac acaaggaact acattccaga tttaaagaaa tgaaaggata      120
ccattagtgt gtataacaga ttattgttca tacttgtaaa gcatcttatg tcattgagaa      180
tataaagaac agtgccttag aagacagtga aaggtaagct ctagcttaat gtctatgatt      240
t                                                                      241
```

<210> SEQ ID NO 393
<211> LENGTH: 241
<212> TYPE: DNA
<213> ORGANISM: Homo sapiens
<220> FEATURE:
<221> NAME/KEY: misc_feature
<222> LOCATION: 57, 75, 224
<223> OTHER INFORMATION: n = A,T,C or G

<400> SEQUENCE: 393

```
ggcaggtaca taagcataat cagttatgga cagcttcttg tataaattgc tattcancaa      60
tacataaact gcctnaaaga tttatgctta caggtagaca ttcaatttac caataaaaca     120
gcatgttctg aaaatatggg cacattttaa aacatattaa gacagttctg ttaaccataa     180
tagtcccaca gtatgactga gtaataagaa tctacttcaa aagnaaaaaa aaaattaatc     240
a                                                                     241
```

<210> SEQ ID NO 394
<211> LENGTH: 241
<212> TYPE: DNA
<213> ORGANISM: Homo sapiens

<400> SEQUENCE: 394

```
aggtacagca gcagtagatg gctgcaacaa ccttcctcct accccagccc agaaaatatt      60
tctgccccac cccaggatcc gggaccaaaa taaagagcaa gcaggccccc ttcactgagg     120
tgctgggtag ggctcagtgc cacattactg tgctttgaga aagaggaagg ggatttgttt     180
ggcactttaa aaatagagga gtaagcagga ctggagaggc cagagaagat accaaaattg     240
g                                                                     241
```

<210> SEQ ID NO 395
<211> LENGTH: 241
<212> TYPE: DNA
<213> ORGANISM: Homo sapiens
<220> FEATURE:
<221> NAME/KEY: misc_feature
<222> LOCATION: 1, 5, 8, 9, 14, 24, 26, 28, 32, 42, 54
<223> OTHER INFORMATION: n = A,T,C or G

<400> SEQUENCE: 395

```
nggcnggnnc caanatatga aatntnanta tnatacatga tnaaaagctt tatntatttt      60
agtgagtaat taagtttaca ctgtgaataa ggattaattc ccagatgacc atctacagtt     120
actaccacat agagggtata cacgatgga tcgattacaa gaatataaaa cttattttcc      180
ttcctgtatc cacatttctt tgcaatgtga atttgcaggc cctctcaaga agtggagtct     240
a                                                                     241
```

<210> SEQ ID NO 396
<211> LENGTH: 241
<212> TYPE: DNA
<213> ORGANISM: Homo sapiens
<220> FEATURE:
<221> NAME/KEY: misc_feature
<222> LOCATION: 26
<223> OTHER INFORMATION: n = A,T,C or G

<400> SEQUENCE: 396

```
gaggtacacc ttgaatgaca atgctnggag ccccccctgtg gtcatcgacg cctccactgc     60
cattgatgca ccatccaacc tgcgtttcct ggccaccaca cccaattcct tgctggtatc     120
atggcagccg ccacgtgcca ggattaccgg ctacatcatc aagtatgaga agcctgggtc     180
tcctcccaga gaagtggtcc ctcggccccg ccctggtgtc acagaggcta ctattactgg     240
c                                                                     241
```

<210> SEQ ID NO 397
<211> LENGTH: 241
<212> TYPE: DNA

```
<213> ORGANISM: Homo sapiens
<220> FEATURE:
<221> NAME/KEY: misc_feature
<222> LOCATION: 90
<223> OTHER INFORMATION: n = A,T,C or G

<400> SEQUENCE: 397
ggcaggtacc agcagggga tgtgtttctg gggaattgtg gctctggaag cttcacggtt      60
tcccagaatg tggaaaatat atctgtgcan gatagaaatc ctgcccagag gctgtttctg    120
tctcatttga gctctccttc atgtggcaga gctgactgtg gcggtttagg agcctacatt    180
ttagaaaagc ttacctcaaa gttctgcatt gagcctgagc actggaaagg agataaaata    240
a                                                                    241

<210> SEQ ID NO 398
<211> LENGTH: 241
<212> TYPE: DNA
<213> ORGANISM: Homo sapiens
<220> FEATURE:
<221> NAME/KEY: misc_feature
<222> LOCATION: 3, 11, 22, 27, 38, 41, 53, 59, 63, 69, 77, 78, 94, 131,
      133, 137, 149, 154, 162, 166, 167, 172, 175, 176, 179, 191, 230
<223> OTHER INFORMATION: n = A,T,C or G

<400> SEQUENCE: 398
gangtgacca ngacatcacc tnacacntgg aaagcganga nttgaatggt gcntacaang     60
ccntacccnt tgcccannac ctgaacgcgc cttntgattg gacagccgt gggaaggaca    120 gttatgaaac nantcanctg gatgaccana gtgntgaaac cnacanncac angcnntcna    180
cattatataa ncggaaagct aatgatgaga gcaatgatca ttccgatgtn attgatagtc    240
a                                                                    241

<210> SEQ ID NO 399
<211> LENGTH: 241
<212> TYPE: DNA
<213> ORGANISM: Homo sapiens
<220> FEATURE:
<221> NAME/KEY: misc_feature
<222> LOCATION: 212, 226
<223> OTHER INFORMATION: n = A,T,C or G

<400> SEQUENCE: 399
cagagtgaga tgggagtggg agggccaatc tgatacagaa gggggtgaag ggtagggccc     60
ctgagcagcc caccccttac cctgacgaag gcaatcctcc tctggaatgt ctcttccctc   120
ttcagtctgg gttctgcctc agccacgaac tgggaaggag tgaggaacat cccaacggca   180
atgagagtat cccagtgact ccaaacagga angaatcagt gttcanaaag tcagggccct   240
t                                                                    241

<210> SEQ ID NO 400
<211> LENGTH: 241
<212> TYPE: DNA
<213> ORGANISM: Homo sapiens

<400> SEQUENCE: 400
ggtactcttg ctcttttagc tagagtgtat gtgaaaataa agaaatacat cattgtattc     60
acaaccatgt gtcttcattt ataacttttt gtttaaaaaa ttttttagttc aagtttagtt   120 cattgatatt atcctctgaa tgcagttaag gctgggcaga aattctactc atgtgacatc    180
tgccacaggt ctattttgaa gcttttcttc taatgggcaa tgtttgtcct taccaggatt   240
```

-continued

| | |
|---|---|
| t | 241 |

<210> SEQ ID NO 401
<211> LENGTH: 241
<212> TYPE: DNA
<213> ORGANISM: Homo sapiens
<220> FEATURE:
<221> NAME/KEY: misc_feature
<222> LOCATION: 1, 2
<223> OTHER INFORMATION: n = A,T,C or G

<400> SEQUENCE: 401

| | |
|---|---|
| nncaggtact tgtagagca gagagaggct ttggttcctc ctttcttcaa tcacgtggag | 60 |
| atgtgtcatc acctgggatt tcatctgggc cgccttttct gggtcaacag ccaacacatg | 120 |
| ctggtaatga cggatggtat gtaagcgatc tttgttctca gcacggacat aacgccgtaa | 180 |
| ggcctggaga atgcgatgag gccgtggcgg gtcagactgc aaggcagcca ggtagttctc | 240 |
| c | 241 |

<210> SEQ ID NO 402
<211> LENGTH: 241
<212> TYPE: DNA
<213> ORGANISM: Homo sapiens
<220> FEATURE:
<221> NAME/KEY: misc_feature
<222> LOCATION: 26, 27
<223> OTHER INFORMATION: n = A,T,C or G

<400> SEQUENCE: 402

| | |
|---|---|
| ggcaggtcca aaaaaaacct aaaaanngtt tcaggaatgt agagaaatat ccaacttaaa | 60 |
| tagcgaaaaa gtgcaccata attactgctg cactgcagtc atttctgcaa ttcccatgtt | 120 |
| tcttaaataa ctatcttgtc agataacaca caatataaag agcaattatg aaaaacagac | 180 |
| atttacatat acttctaaag tcttattggg aatatcctgt ttggccattg ggataaccaa | 240 |
| t | 241 |

<210> SEQ ID NO 403
<211> LENGTH: 241
<212> TYPE: DNA
<213> ORGANISM: Homo sapiens
<220> FEATURE:
<221> NAME/KEY: misc_feature
<222> LOCATION: 49
<223> OTHER INFORMATION: n = A,T,C or G

<400> SEQUENCE: 403

| | |
|---|---|
| aggtgttaac tacccgctcc gagacgggat tgatgacgag tcctatgang ccattttcaa | 60 |
| gccggtcatg tccaaagtaa tggagatgtt ccagcctagt gcggtggtct tacagtgtgg | 120 |
| ctcagactcc ctatctgggg atcggttagg ttgcttcaat ctaactatca aaggacacgc | 180 |
| caagtgtgtg gaatttgtca agagctttaa cctgcctatg ctgatgctgg gaggcggtgg | 240 |
| t | 241 |

<210> SEQ ID NO 404
<211> LENGTH: 241
<212> TYPE: DNA
<213> ORGANISM: Homo sapiens

<400> SEQUENCE: 404

| | |
|---|---|
| caggtactgc aacccataaa atactgtttc ctcatatttc accttcctta atttggagtt | 60 |
| ttctgtcttc ttttcacggc attcaaagta ggaataaaact ttgcttgtgt tgggtggata | 120 |

```
ttgtttatag tgagtaacct tgtaggagtc ggtggccagg aggatgttga actcggcttc    180
tgccgcagga ttcatctcgg gccggaggac aagggggccg cgcgccgcga gctccctgac    240
c                                                                    241

<210> SEQ ID NO 405
<211> LENGTH: 266
<212> TYPE: DNA
<213> ORGANISM: Homo sapiens

<400> SEQUENCE: 405
ttctgggctg gggagtggag agaaagaagt tgcagggctt acaggaaatc ccagagcctg     60
aggttttctc ccagatttga gaactctaga ttctgcatca ttatctttga gtctatattc    120
tcttgggctg taagaagatg aggaatgtaa taggtctgcc ccaagccttt catgccttct    180
gtaccaagct tgtttccttg tgcatccttc ccaggctctg gctgccccct attggagaat    240
gtgatttcca agacaatcaa tccaca                                         266

<210> SEQ ID NO 406
<211> LENGTH: 231
<212> TYPE: DNA
<213> ORGANISM: Homo sapiens

<400> SEQUENCE: 406
ttggtgaaga accattcctc ggcatccttg cggttcttct ctgccatctt ctcatactgg     60
tcacgcatct cgttcagaat gcggctcagg tccacgccag gtgcagcgtc catctccaca    120
ttgacatctc cacccacctg gcctctcagg gcattcatct cctcctcgtg gttcttcttc    180
aggtaggcca gctcctcctt caggctctca atctgcatct ccaggtcagc t             231

<210> SEQ ID NO 407
<211> LENGTH: 266
<212> TYPE: DNA
<213> ORGANISM: Homo sapiens

<400> SEQUENCE: 407
cagcatcatt gtttataatc agaaactctg gtccttctgt ctggtggcac ttagagtctt     60
ttgtgccata atgcagcagt atggagggag gattttatgg agaaatgggg atagtcttca    120
tgaccacaaa taaataaagg aaaactaagc tgcattgtgg gttttgaaaa ggttattata    180
cttcttaaca attcttttt tcagggactt ttctagctgt atgactgtta cttgaccttc    240
tttgaaaagc attcccaaaa tgctct                                         266

<210> SEQ ID NO 408
<211> LENGTH: 261
<212> TYPE: DNA
<213> ORGANISM: Homo sapiens

<400> SEQUENCE: 408
ctgtgtcagc gagcctcggt acactgattt ccgatcaaaa gaatcatcat ctttaccttg     60
acttttcagg gaattactga actttcttct cagaagatag ggcacagcca ttgccttggc    120
ctcacttgaa gggtctgcat ttgggtcctc tggtctcttg ccaagtttcc cagccactcg    180
agggagtaat atctggaggg caagaagag acttatgtta ttgttgaacc tccagccaca    240
gggaggagca tgggcatggg t                                              261

<210> SEQ ID NO 409
```

```
<211> LENGTH: 266
<212> TYPE: DNA
<213> ORGANISM: Homo sapiens

<400> SEQUENCE: 409
gctgacagta atacactgcc acatcttcag cctgcaggct gctgatggtg agagtgaaat      60
ctgtcccaga cccgctgcca ctgaatcggt cagggatccc ggattccgg gtagatgccc      120 agtaaatgag cagtttagga ggctgtcctg gtttctgctg gtaccaagct aagtagttct      180
tattgttgga gctgtctaaa acactctggc tggtcttgca gttgatggtg ccctctcgc      240 ccagagacac agccagggag tgtgga                                           266

<210> SEQ ID NO 410
<211> LENGTH: 181
<212> TYPE: DNA
<213> ORGANISM: Homo sapiens
<220> FEATURE:
<221> NAME/KEY: misc_feature
<222> LOCATION: 9, 17, 24, 26, 65, 97, 98, 99, 100, 103, 105, 106, 107,
      108, 120, 121, 123, 142, 145, 149, 162, 177
<223> OTHER INFORMATION: n = A,T,C or G

<400> SEQUENCE: 410
caaaaggtnc tttttgntca aaancnattt ttattccttg atattttct tttttttttt      60 tttgnggatg gggacttgtg aattttttcta aggggnnnn ttnannnngg aagaaaaccn    120
ngntccggtt ccagccaaac cngtngctna cttccacct tntttccacc tccctcnggt    180
t                                                                      181

<210> SEQ ID NO 411
<211> LENGTH: 261
<212> TYPE: DNA
<213> ORGANISM: Homo sapiens

<400> SEQUENCE: 411
gcccctgcag tacttggccg atgtggacac ctctgatgag gaaagcatcc gggctcacgt      60
gatggcctcc caccattcca gcggagagg ccgggcgtct tctgagagtc agggtctagg      120
tgctggagtg cgcacggagg ccgatgtaga ggaggaggcc ctgaggagga agctggagga    180
gctggccagc aacgtcagtg accaggagac ctcgtccgag gaggaggaag ccaaggacga    240
aaaggcagag cccaacaggg a                                               261

<210> SEQ ID NO 412
<211> LENGTH: 171
<212> TYPE: DNA
<213> ORGANISM: Homo sapiens
<220> FEATURE:
<221> NAME/KEY: misc_feature
<222> LOCATION: 1, 6, 53, 79, 91, 96, 114, 132
<223> OTHER INFORMATION: n = A,T,C or G

<400> SEQUENCE: 412
nttttntctt tacaattcag tcttcaacaa cttgagagct ttcttcatgt tgncaagcaa      60
cagagctgta tctgcaggnt cgtaagcata nagacngttt gaatatcttc cagngatatc    120
ggctctaact gncagagatg ggtcaacaaa cataatcctg gggacatact g              171

<210> SEQ ID NO 413
<211> LENGTH: 266
<212> TYPE: DNA
<213> ORGANISM: Homo sapiens
```

<400> SEQUENCE: 413

```
ttaggaccaa agatagcatc aactgtattt gaaggaactg tagtttgcgc attttatgac    60
attttataa agtactgtaa ttctttcatt gagggctat gtgatggaga cagactaact    120
cattttgtta tttgcattaa aattattttg ggtctctgtt caaatgagtt tggagaatgc    180
ttgacttgtt ggtctgtgta aatgtgtata tatatatacc tgaatacagg aacatcggag    240
acctattcac tcccacacac tctgct                                         266
```

<210> SEQ ID NO 414
<211> LENGTH: 266
<212> TYPE: DNA
<213> ORGANISM: Homo sapiens
<220> FEATURE:
<221> NAME/KEY: misc_feature
<222> LOCATION: 86, 153, 162, 178, 184, 205
<223> OTHER INFORMATION: n = A,T,C or G

<400> SEQUENCE: 414

```
tttgccataa ttgagtgaaa agtggcagat ggcattaact ctgctccgct tcaagctggc    60
tccatgacca ctcaaggcct ccccancctg ttcgtcaagt tgtcctcaag tccaagcaat    120
ggaatccatg tgtttgcaaa aaaagtgtgc tanttttaag gnctttcgta taagaatnaa    180
tganacaatt ttcctaccaa aggangaaca aaggataaa tataatacaa aatatatgta    240
tatggttgtt tgacaaatta tataac                                         266
```

<210> SEQ ID NO 415
<211> LENGTH: 266
<212> TYPE: DNA
<213> ORGANISM: Homo sapiens
<220> FEATURE:
<221> NAME/KEY: misc_feature
<222> LOCATION: 37, 103, 223
<223> OTHER INFORMATION: n = A,T,C or G

<400> SEQUENCE: 415

```
cctccatcca gtctattaat tgttgccggg aagctanagt aagtagttcg ccagttaata    60
gtttgcgcaa cgttgttgcc attgctacag gcatcgtggt gtnacgctcg tcgattggta    120
tggcttcatt cagctccggt tcccaacgat caaggcgagt tacatgatcc cccatgttgt    180
gcaaaaaagc ggttagctcc ttcggtcctc cgatcgttgt canaagtaag ttggccgcag    240
tgttatcact catggttatg gcagca                                         266
```

<210> SEQ ID NO 416
<211> LENGTH: 878
<212> TYPE: DNA
<213> ORGANISM: Homo sapiens

<400> SEQUENCE: 416

```
cctgacgata gccatggctg taccacttaa ctatgattct attccaactg ttcagaatca    60
tatcacaaaa tgacttgtac acagtagttt acaacgactc ccaagagagg aaaaaaaaaa    120
aaaaagacgc ctcaaaattc actcaacttt tgagacagca atggcaatag gcagcagaga    180
agctatgctg caactgaggg cacatatcat tgaagatgtc acaggagttt aagagacagg    240
ctggaaaaaa tctcatacta agcaaacagt agtatctcat accaagcaaa accaagtagt    300
atctgctcag cctgccgcta acagatctca caatcaccaa ctgtgcttta ggactgtcac    360
caaagtcaga ttcggtgcta accaggtggc atctatgatc aacgtcgccc tcttatttta    420
acaaagggct ctgaaggagg tgttctccaa gcaacaagga gactgcttca gtacaagact    480
```

| | |
|---|---|
| ttgcaccttg aattcaattg catcaagtgt ggatagcaaa ataagtatct taccattgaa | 540 |
| atatgtgttc agcctaagat tttacccacc agcagaacaa aagtgagggt gagagggatg | 600 |
| ggccagtgag gggatggggg agaaaaaaaa atcacaggat taccaccaaa gccttgtttt | 660 |
| aaaagggctc ccttcactat tcaggaaggg aagtggaagg agaaattaac caattcctgc | 720 |
| cacagcagcc cttttggct gcttccacaa tagatacttt atggagtggc acagccaacc | 780 |
| ctatctgtga cctgccctgc ggataaacac agccaagcag gtttaattag atcaaagaca | 840 |
| caaagggcta ttccctcctt tcataacaac gcagacct | 878 |

<210> SEQ ID NO 417
<211> LENGTH: 514
<212> TYPE: DNA
<213> ORGANISM: Homo sapiens

<400> SEQUENCE: 417

| | |
|---|---|
| ttctgacttc tagaagacta aggctggtct gtgtttgctt gtttgcccac ctttggctga | 60 |
| tacccagaga acctgggcac ttgctgcctg atgcccaccc ctgccagtca ttcctccatt | 120 |
| cacccagcgg gaggtgggat gtgagacagc ccacattgga aaatccagaa aaccgggaac | 180 |
| agggatttgc ccttcacaat tctactcccc agatcctctc ccctggacac aggagaccca | 240 |
| cagggcagga ccctaagatc tggggaaagg aggtcctgag aaccttgagg tacccttaga | 300 |
| tccttttcta cccactttcc tatggaggat tccaagtcac cacttctctc accggcttct | 360 |
| accagggtcc aggactaagg cgttttctcc atagcctcaa cattttggga atcttcccttt | 420 |
| aatcacccttt gctcctcctg ggtgcctgga agatggactg gcagagacct ctttgttgcg | 480 |
| ttttgtgctt tgatgccagg aatgccgcct agtt | 514 |

<210> SEQ ID NO 418
<211> LENGTH: 352
<212> TYPE: DNA
<213> ORGANISM: Homo sapiens

<400> SEQUENCE: 418

| | |
|---|---|
| ctgcaccagc gattaccagt ggcattcaaa tactgtgtga ctaaggattt tgtatgctcc | 60 |
| ccagtagaac cagaatcaga caggtatgag ctagtcaaca gcaagtcttt gttggattcg | 120 |
| agtaggctca ggatctgctg aaggtcggag gagttagtcc ccgcaatcaa gagcctgtct | 180 |
| tcctgaagcc cttggtgata ttttgccact cagccaagaa tgaggatgca tccttcagat | 240 |
| tctctatgtc ccgaacctgg aacccatcca cgccagcttg cagccaaaac tccagagcat | 300 |
| ccttcacctt ggtggaaaaa aaaaaaaaaa aaaaaaaaaa aaaaaaaaaa aa | 352 |

<210> SEQ ID NO 419
<211> LENGTH: 344
<212> TYPE: DNA
<213> ORGANISM: Homo sapiens

<400> SEQUENCE: 419

| | |
|---|---|
| ctggacacca taatcccttt taagtggctg gatggtcaca cctctcccat tgacaagctg | 60 |
| ggttaagtca ataggttgac taggatcaac acgacccaaa tcaataagat actgcagtct | 120 |
| attgagactc aaaggcttat actggcgtct gaaactatgt ccttcgttaa acccgtattt | 180 |
| tgggattcgg atgtaaaatg gagtctggcc tccctcaaag cccaagcggg gccgggttcc | 240 |
| tctttgcctt tctcctttat ggcctctgcc acattttcta cctcttctcc gacctcttgg | 300 | tcttctctcc ggtttcttgg agccgggatt cggctttaag ttgg          344

<210> SEQ ID NO 420
<211> LENGTH: 935
<212> TYPE: DNA
<213> ORGANISM: Homo sapiens

<400> SEQUENCE: 420
cgaaagtcaa cgttaagggg ctcaggtgaa ccatgatgat gaccttctgt tgactttgaa     60
atattggctc ttgtgggtga caaaagccag acaagctgtg gctgtggtcc gatttttaaga  120
cgaggttctc aaagatccaa aggagggaaa gggtattgga acactgtgt atcatctgag    180
acacacgtgt cctcatgatc ttaaatgcct actttaaagc cacctaatac tgcccttcat   240
tgtggtcaga agagatttct acaaaagcac tcagaattct ggaggcagtt gtgatttgc    300
catgtggcag ttggtttgtg agttgggca ggtgtgaaag ggtaaaactc cacttctgaa   360
tgctgcttct gcccctggg acccagcaca ttgttagacc atcttcttga ctgaaaattc   420
tctcctgatg ctgagccctg caccaccacc ttccttttcc taactatgaa ttgatggcaa  480
agtccactca aaacaaccag ttaagtgctc acgagagagt agtcaagcac ctccagaaag  540
aaaccgggtt tttgttcaca tagcaggaag tgactccctg ggtggtaatt tatcttggaa  600
acacaggtag attggcagaa aaacgggaac atgtaggtac cgcgatgttg gtgcatgtcc  660
attactttgg gataggcttt ctcagtcttt cctcaaatga tagttgagcc agttttccag  720
tggcaattct gagtgacttg cgcttgtctt atggtgtggt caaggacgt tcagaactac   780
ggaaaacttt tactgaaaca gcgaagcaga gtataccggc atgagaggga agatgaacac  840
tcacctatgt accactcttt gacaataaat atagtatttc tcaaaaaaaa aaaaaaaaa   900
agtaaaaaaa ctgaaatcgc aagtcaaaaa atcca                              935

<210> SEQ ID NO 421
<211> LENGTH: 745
<212> TYPE: DNA
<213> ORGANISM: Homo sapiens

<400> SEQUENCE: 421
ggcttcgagc ggccgcccgg gcaggtccta gatgtcattt gggacccttc acaaccattt     60
tgaagccctg tttgagtccc tgggatatgt gagctgtttc tatgcataat ggatattcgg   120
ggttaacaac agtcccctgc ttggcttcta ttctgaatcc ttttctttca ccatggggtg   180
cctgaagggt ggctgatgca tatggtacaa tggcacccag tgtaaagcag ctacaattag   240
gagtggatgt gttctgtagc atcctattta aataagccta ttttatcctt ggcccgtca    300
actctgttat ctgctgcttg tactggtgcc tgtacttttc tgactctcat tgaccatatt   360
ccacgaccat ggttgtcatc cattacttga tcctacttta catgtctagt ctgtgtggtt   420
ggtggtgaat aggcttcttt ttacatggtg ctgccagccc agctaattaa tggtgcacgt  480
ggacttttag caagcgggct cactggaaga gactgaacct ggcatggaat tcctgaagat  540
gtttggggtt ttttttcttc ttaatcgaaa gttaacattg tctgaaaagt tttgttagaa  600
ctactgcgga acctcaaaat cagtagattt ggaagtgatt caaagctaaa cttttttcctt  660
ggccctcctt gtgttctaat tgcttgcaag tgtaatacta ggatgtccaa gatgccagtt   720
tttgcttctt tgttagttgt cagac                                          745

<210> SEQ ID NO 422
<211> LENGTH: 764

<210> SEQ ID NO 422
<211> LENGTH: 764
<212> TYPE: DNA
<213> ORGANISM: Homo sapiens

<400> SEQUENCE: 422

```
gagttcagta gcaaagtcac acctgtccaa ttccctgagc tttgctcact cagctaatgg      60
gatggcaaag gtggtggtgc tttcatcttc aggcagaagc ctctgcccat ccccctcaag     120
ggctgcaggc ccagttctca tgctgccctt ggtgggcat ctgttaacag aggagaacgt     180
ctgggtggcg gcagcagctt tgctctgagt gcctacaaag ctaatgcttg gtgctagaaa     240
catcatcatt attaaacttc agaaaagcag cagccatgtt cagtcaggct catgctgcct     300
cactgcttaa gtgcctgcag gagccgcctg ccaagctccc cttcctacac ctggcacact     360
ggggtctgca caaggctttg tcaaccaaag acagcttccc ccttttgatt gcctgtagac     420
tttggagcca agaaacactc tgtgtgactc tacacacact tcaggtggtt tgtgcttcaa     480
agtcattgat gcaacttgaa aggaaacagt ttaatggtgg aaatgaacta ccatttataa     540
cttctgtttt tttattgaga aaatgattca cgaattccaa atcagattgc caggaagaaa     600
taggacgtga cggtactggg ccctgtgatt ctcccagccc ttgcagtccg ctaggtgaga     660
ggaaaagctc tttacttccg cccctggcag ggacttctgg gttatgggag aaaccagaga     720
tgggaatgag gaaaatatga actacagcag aagcccctgg gcag                      764
```

<210> SEQ ID NO 423
<211> LENGTH: 1041
<212> TYPE: DNA
<213> ORGANISM: Homo sapiens

<400> SEQUENCE: 423

```
ctcagagagg ttgaaagatt tgcctacgaa agggacagtg atgaagctaa gctctagatc      60
caggatgtct gacttcaaat tgaaactccc aaagtaatga gtttggaagg gtggggtgtg     120
gcctttccag gatgggggtc ttttctgctc ccagcggata gtgaaacccc tgtctgcacc     180
tggttgggcg tgttgctttc ccaaaggttt ttttttttagg tccgtcgctg tcttgtggat     240
taggcattat tatctttact ttgtctccaa ataacctgga gaatggagag agtagtgacc     300
agctcagggc cacagtgcga tgaggaccat cttctcacct ctctaaatgc aggaagaaac     360
gcagagtaac gtggaagtgg tccacaccta ccgccagcac attgtgaatg acatgaaccc     420
cggcaacctg cacctgttca tcaatgccta caacaggtat gggatgtag ttcagccaca     480
tcattgctat ttatgaggtg tcttctgtag atccgaaatg tgggacagat gagagggaga     540
gtataaaatg agcggaagag gcaggctctg agtttgagca aatagattaa taggacaggt     600
gtccccagga aggacacctg gcctgtaagc tggttcctgg cattcagctc gccttgcagg     660
gatctgaaca aacactccag accactgggg gtgcagacgt gagagggacg cagtcgcaca     720
ctcagaggt tgagagtaaa tatgtgtgcc cgctgctgac cttcacgaaa ggccaaatgt     780
aagaagagct aagtgagaga gcagcaaagc actcctggag gccggggata atccaggcag     840
gcttctggga gtttgtcatt ccaaggataa ggaggacctg aacatggcct ttgcctaagg     900
cgtggccctc tcaaccagca ctaggtgctt atctggagct cagctagggg aggagacagc     960
tcagggccat tggtgtcagc cagagactct gtaatcttcc agggagctcg ctcaacctgc    1020
tgagctcgct ctgccacgca c                                               1041
```

<210> SEQ ID NO 424
<211> LENGTH: 1288
<212> TYPE: DNA

<213> ORGANISM: Homo sapiens

<400> SEQUENCE: 424

```
ctaagaactg agacttgtga cacaaggcca acgacctaag attagcccag ggttgtagct      60
ggaagaccta caacccaagg atggaaggcc cctgtcacaa agcctaccta gatggataga     120
ggacccaagc gaaaaaggta tctcaagact aacggccgga atctggaggc ccatgaccca     180
gaacccagga aggatagaag cttgaagacc tggggaaatc ccaagatgag aaccctaaac     240
cctacctctt ttctattgtt tacacttctt actcttagat atttccagtt ctcctgttta     300
tctttaagcc tgattctttt gagatgtact ttttgatgtt gccggttacc tttagattga     360
cagtattatg cctgggccag tcttgagcca gctttaaatc acagctttta cctatttgtt     420
aggctatagt gttttgtaaa cttctgtttc tattcacatc ttctccactt gagagagaca     480
ccaaaatcca gtcagtatct aatctggctt ttgttaactt ccctcaggag cagacattca     540
tataggtgat actgtatttc agtcctttct tttgacccca gaagccctag actgagaaga     600
taaaatggtc aggttgttgg ggaaaaaaaa gtgccaggct ctctagagaa aaatgtgaag     660
agatgctcca ggccaatgag aagaattaga caagaaatac acagatgtgc cagacttctg     720
agaagcacct gccagcaaca gcttccttct ttgagcttag tccatccctc atgaaaaatg     780
actgaccact gctgggcagc aggagggatg atgaccaact aattcccaaa ccccagtctc     840
attggtacca gccttgggga accacctaca cttgagccac aattggtttt gaagtgcatt     900
tacaagtttc tggcatcact accactactg attaaacaag aataagagaa cattttatca     960
tcatctgctt tattcacata aatgaagttg tgatgaataa atctgctttt atgcagacac    1020
aaggaattaa gtggcttcgt cattgtcctt ctacctcaaa gataatttat tccaaaagct    1080
aagataaatg gaagactctt gaacttgtga actgatgtga aatgcagaat ctcttttgag    1140
tctttgctgt ttggaagatt gaaaaatatt gttcagcatg ggtgaccacc agaaagtaat    1200
cttaagccat ctagatgtca caattgaaac aaactgggga gttggttgct attgtaaaat    1260
aaaatatact gttttgaaaa aaaaaaac                                        1288
```

<210> SEQ ID NO 425
<211> LENGTH: 446
<212> TYPE: DNA
<213> ORGANISM: Homo sapiens

<400> SEQUENCE: 425

```
ccacttaaag ggtgcctctg ccaactggtg gaatcatcgc cacttccagc accacgccaa      60
gcctaacatc ttccacaagg atcccgatgt gaacatgctg cacgtgtttg ttctgggcga     120
atggcagccc atcgagtacg gcaagaagaa gctgaaatac ctgccctaca atcaccagca     180
cgaatacttc ttcctgattg ggccgccgct gctcatcccc atgtatttcc agtaccagat     240
catcatgacc atgatcgtcc ataagaactg ggtggacctg gcctgggccg tcagctacta     300
catccggttc ttcatcacct acatcccttt ctacggcatc ctgggagccc tccttttcct     360
caacttcatc aggttcctgg agagccactg gtttgtgtgg gtcacacaga tgaatcacat     420
cgtcatggag attgaccagg aggacc                                          446
```

<210> SEQ ID NO 426
<211> LENGTH: 874
<212> TYPE: DNA
<213> ORGANISM: Homo sapiens

<400> SEQUENCE: 426

```
ttttttttttt ttttttttttt tttttttcaat taaagatttg atttattcaa gtatgtgaaa      60
acattctaca atggaaactt ttattaaatg ctgcatgtac tgtgctatgg accacgcaca        120
tacagccatg ctgtttcaga agacttgaaa tgccattgat agtttaaaaa ctctacaccc        180
gatggagaat cgaggaagac aatttaatgt ttcatctgaa tccagaggtg catcaaatta       240
aatgacagct ccacttggca ataatagct gttacttgat ggtatccaag aagaaatggt        300
tggtgatgga taaattcaga aatgcttccc caaaggtggg tggttttttaa aaagttttca     360 ggtcacaacc cttgcagaaa acactgatgc ccaacacact gattcgcggt ccaggaaaca      420
cgggtcttcc aagttccaag gggctggggt tccccaacga tcaagttcct gtgctgtaat      480
caagagggtc ctttggactg atagggagc acttgggagc tgtacaccat cagtcataat       540
ggatggcagt gtaaagatg atccaaatga cctgagatgc tcctgaggag tggtgcacca      600
gacccaggag tgccactgta gggctgcttc tttgctttag tcatcacaca cacacacagc     660
tccagagcag caatggcctt tcctgtaaca ggaaaaaagc ctcctgctat tcccaagaac    720
cctcgtaatg gcaaaactcc ccaaatgaca cccaggacca cagcaatgat ctgtcggaac   780
cagtagatca catctaaaaa ttcatcctta tcctcccagg ccgcgtcgct ccgcagcacc    840
ttactccaga cggagacttt gagggccccg ttgg                                874

<210> SEQ ID NO 427
<211> LENGTH: 638
<212> TYPE: DNA
<213> ORGANISM: Homo sapiens

<400> SEQUENCE: 427
acttgtaatt agcacttggt gaaagctgga aggaagataa ataacactaa actatgctat       60
ttgatttttc ttcttgaaag agtaaggttt acctgttaca ttttcaagtt aattcatgta      120
aaaaatgata gtgattttga tgtaatttat ctcttgtttg aatctgtcat tcaaaggcca     180
ataatttaag ttgctatcag ctgatattag tagctttgca accctgatag agtaaataaa    240
ttttatgggc gggtgccaaa tactgctgtg aatctatttg tatagtatcc atgaatgaat    300
ttatggaaat agatatttgt gcagctcaat ttatgcagag attaaatgac atcataatac   360
tggatgaaaa cttgcataga attctgatta aataagtgggt ctgttcaca tgtgcagttt   420 gaagtattta ataaccact cctttcacag tttatttttct tctcaagcgt tttcaagatc    480
tagcatgtgg attttaaaag attttgccctc attaacaaga ataacattta aaggagattg   540
tttcaaaata tttttgcaaa ttgagataag gacagaaaga ttgagaaaca ttgtatattt   600
tgcaaaaaca agatgtttgt agctgtttca gagagagt                           638

<210> SEQ ID NO 428
<211> LENGTH: 535
<212> TYPE: DNA
<213> ORGANISM: Homo sapiens

<400> SEQUENCE: 428
acaagatgat tcttcctcct caatttgaca gatcaaagaa gtatcccttg ctaattcaag      60
tgtatggtgg tccctgcagt cagagtgtaa ggtctgtatt tgctgttaat tggatatctt    120
atcttgcaag taaggaaggg atggtcattg ccttggtgga tggtcgagga acagctttcc    180
aaggtgacaa actcctctat gcagtgtatc gaaagctggg tgtttatgaa gttgaagacc    240
agattacagc tgtcagaaaa ttcatagaaa tgggtttcat tgatgaaaaa agaatagcca    300
```

| | |
|---|---|
| tatggggctg gtcctatgga ggatacgttt catcactggc ccttgcatct ggaactggtc | 360 |
| ttttcaaatg tggtatagca gtggctccag tctccagctg gaatattac gcgtctgtct | 420 |
| acacagagag attcatgggt ctcccaacaa aggatgataa tcttgagcac tataagaatt | 480 |
| caactgtgat ggcaagagca gaatatttca gaaatgtaga ctatcttctc atcca | 535 |

<210> SEQ ID NO 429
<211> LENGTH: 675
<212> TYPE: DNA
<213> ORGANISM: Homo sapiens

<400> SEQUENCE: 429

| | |
|---|---|
| actattttca accctgagca ttaacactgc ataccaaggg ggggtgggtc aagaagctgg | 60 |
| ttagatcgaa gcacaagcac aagccactga tattctctat gtgatcaggt ttttacaaaa | 120 |
| aaatacatag ttttcaataa ataatgctta attttacaac tttgatacag caatgtcata | 180 |
| caccgtttca acacactaca ctctgcatgc tagatagtct acgagaagac gaaactttgc | 240 |
| catgcatttt ctttcccccc tagtgctatc aaacacttca tcctccagcg cactgcctca | 300 |
| ggtagcttta ccttctctct gtttcacagc aataggccgt cgctggcat gcaaactcta | 360 |
| aaaaaggtcc cccccacaaa ccactcagac ttctacacaa aagggttttt cagcttttct | 420 |
| gctcccaaac ctggagtggc taagaaagta agtttcatgt ggccttggaa aatacacact | 480 |
| tgttaacagt gtcatgctga aaactgctct aaaacatcag gtggttctgt cctggtggcc | 540 |
| gtcacgaagc attatgggat gccataacca ctaggagtcc caaaccggaa aaaataggcc | 600 |
| tccgttttaa aacagtcaat tcaaaaaagg tgtcacagaa caaatgcaaa agactcttaa | 660 |
| acccacaaca tatgt | 675 |

<210> SEQ ID NO 430
<211> LENGTH: 434
<212> TYPE: DNA
<213> ORGANISM: Homo sapiens

<400> SEQUENCE: 430

| | |
|---|---|
| acctctgcca gaagtccagc gagaggacct cacagtagag cacaggccac tccgggagtg | 60 |
| catcagaaga ttcatcctca tggaggaaga aggcttcaaa cgtgaatggg taggagaagt | 120 |
| gagccacctt gtccattgcc agggacttgg tggtgcaggt ctgtgttact cctgagagct | 180 |
| gctggaatgc tgggcttgac cagtgagcag ttggcaattc tacaaagaag tggacgtaga | 240 |
| gattgtcata ctccatagcct tgggctgaaa cgacctctcc atttacaaag agccggaggg | 300 |
| cacctgggac agtcatctca aagtcggtgc ctacgaggct gctgagatac tccttgtgcc | 360 |
| ggccataaag atccttgaac actcgccgtt cccgctcctc ctcctccggc tgtgcgtggg | 420 |
| gggaaacatt gtcg | 434 |

<210> SEQ ID NO 431
<211> LENGTH: 581
<212> TYPE: DNA
<213> ORGANISM: Homo sapiens

<400> SEQUENCE: 431

| | |
|---|---|
| acacaagcct ccagcccgac ccagcggcct aatgaaactc tggcaaccta tcctgggcgt | 60 |
| ggccacgagt atccagctcc aagcccaagt gaggcgggga gtcaacttcc ccatgattgc | 120 |
| caagtgacca agaccagaag cagggacgat taggctagtt ctgcggcaag gtgaactgga | 180 |
| gaccctgtct ctgccctcct tccctggcct gtcccacaga catcccgttg tttaacccac | 240 |

```
tgcctttgca aggacctgct ctgtccactc caaatcaaag gatacttgca tccttcttac    300
acagactccc atctctctgc tcatagtggt cccaggctgc ccgagaaaaa gaaacttggg    360
tcagtagaag gctcattagt gtgaaggagt gagaggccag gccttcctgt gacataatgc    420
ttctatgctt gtttcctaaa cacttggtcc acacacaata cctgggcagg aagagagaac    480
caagcaccac tggatggctc tggagccagg ggacttctat gcacatacaa ccaacatcac    540
cccactctgc tcatctgtgc ctccaccctg aacagcagag t                       581

<210> SEQ ID NO 432
<211> LENGTH: 532
<212> TYPE: DNA
<213> ORGANISM: Homo sapiens

<400> SEQUENCE: 432
actccaactc aagtttacaa gttacacctt tgccacagcc ttggctaaat cttgaactag     60
tgcagaattc agctgtggta gagtgctgat cttagcatgc ttcgatgtgg catacttgtt    120
cttgacagtc atgtgctttg taagtccttg atttaccatg actacattct tagccaggtg    180
ctgcataact ggaagaagag attcttcagt atatgacagg taatgttgta gagttggtgt    240
ccattcacca ttatccagaa ttttcagtgc taagcaaaaa gctcctgctg caatttgaga    300
aggaggaaag tgcaccatgt catagtccaa catagttagt tccatcaggt atttggccaa    360
agtatgttgc tcgacatcaa cctctccaat cttagatgct ctccgaagga agtgcaaagg    420
tagaggccga cccagaccaa agtttaaagc tcttagaatc ttcatttcca tctgtctgat    480
ttggtgctta gtataagtgt tgtcagtcac aaaagcaaag tcaccaattt ct            532

<210> SEQ ID NO 433
<211> LENGTH: 531
<212> TYPE: DNA
<213> ORGANISM: Homo sapiens

<400> SEQUENCE: 433
acttggtttt acagctcctt tgaaaactct gtgtttggaa tatctctaaa aacatagaaa     60
acactacagt ggtttagaaa ttactaattt tacttctaag tcattcataa accttgtcta    120
tgaaatgact tcttaaatat ttagttgata gactgctaca ggtaataggg acttagcaag    180 ctctttata tgctaaagga gcatctatca gattaagtta gaacatttgc tgtcagccac     240
atattgagat gacactaggt gcaatagcag ggatagattt tgttggtgag tagtctcatg    300
ccttgagatc tgtggtggtc ttcaaaatgg tggccagcca gatcaaggat gtagtatctc    360
atagttccca ggtgatattt ttcttattag aaaaatatta taactcattt gttgtttgac    420
acttatagat tgaaatttcc taatttattc taaattttaa gtggttcttt ggttccagtg    480
ctttatgttg ttgttgtttt tggatggtgt tacatattat atgttctaga a             531

<210> SEQ ID NO 434
<211> LENGTH: 530
<212> TYPE: DNA
<213> ORGANISM: Homo sapiens

<400> SEQUENCE: 434
acaagagaaa accccctaaaa aaaggatggc tttagatgac aagctctacc agagagactt     60
agaagttgca ctagctttat cagtgaagga acttccaaca gtcaccacta atgtgcagaa    120
ctctcaagat aaaagcattg aaaaacatgg cagtagtaaa atagaaacaa tgaataagtc    180
```

```
tcctcatatc tctaattgca gtgtagccag tgattattta gatttggata agattactgt    240
ggaagatgat gttggtggtg ttcaagggaa aagaaaagca gcatctaaag ctgcagcaca    300
gcagaggaag attcttctgg aaggcagtga tggtgatagt gctaatgaca ctgaaccaga    360 cttttgcacct ggtgaagatt ctgaggatga ttctgatttt tgtgagagtg aggataatga   420
cgaagacttc tctatgagaa aaagtaaagt taaagaaatt aaaaagaaag aagtgaaggt    480
aaaatcccca gtagaaaaga aagagaagaa atctaaatcc aaatgtaatg                530
```

```
<210> SEQ ID NO 435
<211> LENGTH: 677
<212> TYPE: DNA
<213> ORGANISM: Homo sapiens

<400> SEQUENCE: 435
accttatgat ctaattaata gatattagaa acagtagaaa gacaagttac acgtcaatgc     60
ccaatgacta gagtcaacat taaagagttg taatttaagt aatccaaact gacatctaat    120
tccaaaatca tttataaaat gtatttggct ttggaatcca caggacttca acaagcaaa    180 gtttcactgc agatagtcac aaagatgcag atacactgaa atacttaaga gccttattaa    240
tgatttttgt tattttggat cttctgtttt tttcttatta tggtccgaag cctccttaat    300
accaatttat cagacagaag catgtcatct tgttgttcaa gataatccag taaattttca    360
gtccattcaa gtgccgcttt atggctaata cgcttctctg gattcagttc tgttttttcta   420 ctcttactgg aaggcttttg ctcagcagcc ttggtctggt cctcagcact ttcactgtca    480
gtcagcacct gacagcttga gtcactgctc cgagagtcga accactgatc aatattctca    540
atgtcaacat gttcacattc ttctgtgttc tgtaaaactg ttgctaaatt agctgctaaa    600
atggctcctt catcaatgtt catacctgaa ttctcttcat tgccagggaa aagtttttc    660 catgctttgg ttatggt                                                   677
```

```
<210> SEQ ID NO 436
<211> LENGTH: 573
<212> TYPE: DNA
<213> ORGANISM: Homo sapiens

<400> SEQUENCE: 436
acctcttagg gtgggagaaa tggtgaagag ttgttcctac aacttgctaa cctagtggac     60
agggtagtag attagcatca tccggataga tgtgaagagg acggctgttt ggataataat    120
taaggataaa atttggccag ttgacagatt ctgtttccag cagtttttac agcaacagtg    180
gagtgcttca gtattgtgtt cctgtaaatt taattttgat ccgcaatcat ttggtataca    240
atgctgtttg aagttttgtc ctattggaaa agtcttgtgt tgcaggggtg cagttaagat    300
ctttgtgatg aggaatggga tgggctaatt ttttgccgtt ttcttggaat tggggggcatg   360 gcaaatacag tagggtagtt tagttctta cacagaacat gataaactac acctgttgat     420
gtcaccgtct gtcaatgaat attatagaag gtatgaaggt gtaattacca taataacaaa    480
acaccctgtc tttagggctg acctttcgtc ctttgacctc ctcagcctcc attcccatct    540
tcgctcagac tgcaagtatg tttgtattaa tgt                                 573
```

```
<210> SEQ ID NO 437
<211> LENGTH: 645
<212> TYPE: DNA
<213> ORGANISM: Homo sapiens
<220> FEATURE:
<221> NAME/KEY: misc_feature
```

<222> LOCATION: 605
<223> OTHER INFORMATION: n = A,T,C or G

<400> SEQUENCE: 437

```
acaattggta tccatatctt gttgaaattg taatgggaaa acaatatatt tcaatctcta      60
tgtagatagt gggttttgt tttcataata tattctttta gtttactgta tgagttttgc     120
aggactgcat aatagatcac cacaatcata acatcttagg accacagaca tttatgagat    180
catggcttct gtgggttaga agtatgctca tgtcttaact gggtcctctg ctcagtctta    240
tctggctgca atcaaggtgt cagctgggct gaattttcat ttggaatctt gactgggaaa    300
gagtctgctt ccaaggtcat gaagtttgct ggcaaaatgt atgtttttat gacagtatga    360
ctgaaatccc aagctatctc ctgactttta gctgggtaat ctcaggccct aaatgttgcc    420
tacagttcct agaggctggt cacagttctt agccatgtgg atttcctcaa catggctgct    480
tgcttcatca gtcagcaag aatagcctgt catatcagtg tatatcaggc tcactcagga    540
taatttccct actgatgagc caaacactaa ctgattttag agcttaacta catctgcaaa    600
attcngttca ccagaggcaa gtcatattca gggaaggaga agtgt                    645
```

<210> SEQ ID NO 438
<211> LENGTH: 485
<212> TYPE: DNA
<213> ORGANISM: Homo sapiens

<400> SEQUENCE: 438

```
acagaattga gagacaagat tgcttgtaat ggagatgctt ctagctctca gataatacat     60
atttctgatg aaaatgaagg aaaagaaatg tgtgttctgc gaatgactcg agctagacgt    120
tcccaggtag aacagcagca gctcatcact gttgaaaagg ctttggcaat tctttctcag    180
cctacaccct cacttgttgt ggatcatgag cgattaaaaa atcttttgaa gactgttgtt    240
aaaaaagtc aaaactacaa catatttcag ttggaaaatt tgtatgcagt aatcagccaa    300
tgtatttatc ggcatcgcaa ggaccatgat aaaacatcac ttattcagaa atggagcaa    360
gaggtagaaa acttcagttg ttccagatga tgatgtcatg gtatcgagta ttctttatat    420
tcagttccta tttaagtcat ttttgtcatg tccgcctaat tgatgtagta tgaaaccctg    480
catct                                                                485
```

<210> SEQ ID NO 439
<211> LENGTH: 533
<212> TYPE: DNA
<213> ORGANISM: Homo sapiens

<400> SEQUENCE: 439

```
acagcagttt cctcatccct gcagctgtgt ttgaacaggt catttaccat actgtcctcc     60
aggttcaaca gtatggctcc aaatgatgaa atttcattct gattttctgg ctgaagacta    120
ttctgtttgt gtatgtccac cacagttact ttatcccttc atctgtggat gggcagaatg    180
aaacatatat ggaaatgttc tgtgcaataa aaacagcagt ggtaacacag atgtaggctc    240
tgagtgtctc actggagact gaagtccaca gatatgcaac aaagcctttg tctccctgat    300
gttttgcct cctgctggtc atgtgctttc acacatcaag agaggacatt taacatttga    360
gccacagtgt catttgctgt tgtctgatgg ttggttggca gagaatttga actggagatg    420
aactttatta tccaggacgc tgagagtata acatgcatga cagagctttt agagcactgt    480
gatgtaacat gtcaagcaga aatagggagc atgtttacag ccattctatg aaa           533
```

<210> SEQ ID NO 440
<211> LENGTH: 341
<212> TYPE: DNA
<213> ORGANISM: Homo sapiens

<400> SEQUENCE: 440

```
catggggtag gggggtcggg gattcattga attgtggttg gcaggagcaa gccctgctca      60
cactctcaca ctcgcaccca gaattgtcaa agatacagat tgtaaaaatc tacgatccct     120
cagtctcact cacaaaaaat aaaatctcat gtccccaacg aacccagagt cagacgacag     180
ctggagcatt gcagggaca gtcagaaagg agacaagtga aacggtcag atggacacag       240
gcggaggaga aaagacagag ggagagagac catcgggaac aatcagaggg gccgagacga     300
tcagaaaagg gtcagcccga gacaggctga gccagagttt c                         341
```

<210> SEQ ID NO 441
<211> LENGTH: 572
<212> TYPE: DNA
<213> ORGANISM: Homo sapiens
<220> FEATURE:
<221> NAME/KEY: misc_feature
<222> LOCATION: 53, 84, 132, 138, 148
<223> OTHER INFORMATION: n = A,T,C or G

<400> SEQUENCE: 441

```
aagtttgggg ataatttatt atgcagcaag agataataca caggacttct canagcactt      60
aatatgttaa tataaatctc caanaaaaaa gatatacaat gaaacattcc tcttagttat     120
ctggccaagg anactttntt tttttganaa tattcttcaa aaagctgatc taatgatatg     180
gctctggtcc tacaattcca tgtaacttct aaccttgatt ttatctcatg agcaaatcat     240
ttatccttcc agaacctcaa cttttccctt ttacaaagta gaaataaacc atctgccttt     300
acataaaatca ttaatacagc cctggatggg cagattctga gctatttttg gctgggggt     360
gggaaatagc ctgtggaggt cctaaaaaga tctacggggc tcgagatggt tctctgcaag     420
gtagcaggtg ggctcagggc ccatttcagt ctttgttccc caggccattt ccacaaaatg     480
gtgagaaata gtgtcttctt ttagcttgct cataactcaa agatggggggg catggacctg     540
ggccttctcta ggctagggca tgaacctcct cc                                   572
```

<210> SEQ ID NO 442
<211> LENGTH: 379
<212> TYPE: DNA
<213> ORGANISM: Homo sapiens
<220> FEATURE:
<221> NAME/KEY: misc_feature
<222> LOCATION: 34, 67
<223> OTHER INFORMATION: n = A,T,C or G

<400> SEQUENCE: 442

```
tcccagctgc actgcttaca cgtcttcctt cgtnttcacc taccccgagg ctgactcctt      60
ccccagntgt gcagctgccc accgcaaggg cagcagcagc aatgagcctt cctctgactc     120
gctcagctca cccacgctgc tggccctgtg aggggcagg gaaggggagg cagccggcac     180
ccacaagtgc cactgcccga gctggtgcat tacagagagg agaaacacat cttccctaga     240
gggttcctgt agacctaggg aggacctat ctgtgcgtga acacaccag gctgtgggcc      300
tcaaggactt gaaagcatcc atgtgtggac tcaagtcctt acctcttccg gagatgtagc     360
aaaacgcatg gagtgtgta                                                   379
```

```
<210> SEQ ID NO 443
<211> LENGTH: 511
<212> TYPE: DNA
<213> ORGANISM: Homo sapiens
<220> FEATURE:
<221> NAME/KEY: misc_feature
<222> LOCATION: 444
<223> OTHER INFORMATION: n = A,T,C or G

<400> SEQUENCE: 443
acatgccccc aaaggctcgc ttcattgcta cgattctcta cttaaatcca cattcacagc      60
tattgcctca gaccctctgg aggaggggcc aggggttagc tggctttgaa tagcatgtag     120
agcacaggca gtgtggccac aaatgtcaca caggtgacca gggtgctata gatggtgttc     180
ctgttgactt gggcttctag tctctgctcc gtgtctgaca gtgccaagat catgctcccc     240
tgctccagca agaagctggg catagccccg tctgctggtt ccaccaggcc tgggtgtgct     300
gcagacttta caagctgaac caccccagcc atttggctac aagtcttttc taggccatca     360
agctgctctc gtaagccttc tagacatgaa tggacttgcc tggaatgact aagctgctct     420
ttcaaggcag ctgaaaggac atcnacatct ctgtctctgg tcggggact acctgcctgt      480 gacccagagt cctgccctgg cccagcagca t                                    511

<210> SEQ ID NO 444
<211> LENGTH: 612
<212> TYPE: DNA
<213> ORGANISM: Homo sapiens
<220> FEATURE:
<221> NAME/KEY: misc_feature
<222> LOCATION: 547
<223> OTHER INFORMATION: n = A,T,C or G

<400> SEQUENCE: 444
acaggaagaa ttctacagtt aatctatcac agtgttccag caaagcatat gttgaaaact      60
acagttttca atctaacatc taaattttaa aaagtagcat ttcagcaaca aacaagctca     120
gagaggctca tggcaaaagt gaaataacag aactattgct cagatgtctg caaagtcaag     180
ctgctgccct cagctccgcc cacttgaagg cttaggcaga cacgtaaggt ggcggtggct     240
ccttggcagc accattcaca gtggcatcat catacggagg tagcagcacc gtagtgtcat     300
tgctggtaac ataaaccagg acatcagagg agttcctacc attgatgtat cggtagcagt     360
tccaaacaca gctaatcaag taacccttaa aagtcaagat aatgctaata aacagaagaa     420
taataaggac caaacaggta ggattcactg acatgacatc atctctgtag ggaaaattag     480
gaggcagttg ccgtatgtat tcctgaatgg agtttggata aataagcaca gtgattgcaa     540 ccaacancttt cagggcaaag tcaaagatct ggtaacagaa gaatgggatg atccaggctg     600
cgcgttgctt gt                                                         612

<210> SEQ ID NO 445
<211> LENGTH: 708
<212> TYPE: DNA
<213> ORGANISM: Homo sapiens
<220> FEATURE:
<221> NAME/KEY: misc_feature
<222> LOCATION: 643, 676
<223> OTHER INFORMATION: n = A,T,C or G

<400> SEQUENCE: 445
accatcctgt tccaacagag ccattgccta ttcctaaatt gaatctgact gggtgtgccc      60
ctcctcggaa cacaacagta gaccttaata gtggaaacat cgatgtgcct cccaacatga     120
```

```
caagctgggc cagctttcat aatggtgtgg ctgctggcct gaagatagct cctgcctccc    180
agatcgactc agcttggatt gtttacaata agcccaagca tgctgagttg gccaatgagt    240
atgctggctt tctcatggct ctgggtttga atgggcacct taccaagctg gcgactctca    300
atatccatga ctacttgacc aagggccatg aaatgacaag cattggactg ctacttggtg    360
tttctgctgc aaaactaggc accatggata tgtctattac tcggcttgtt agcattcgca    420
ttcctgctct cttaccccca acgtccacag agttggatgt tcctcacaat gtccaagtgg    480
ctgcagtggt tggcattggc cttgtatatc aagggacagc tcacagacat actgcagaag    540
tcctgttggc tgagatagga cggcctcctg gtcctgaaat ggaatactgc actgacagag    600
agtcatactc cttagctgct ggcttggccc tgggcatggt ctncttgggg catggcagca    660
atttgatagg tatgtntgat ctcaatgtgc ctgagcagct ctatcagt                 708

<210> SEQ ID NO 446
<211> LENGTH: 612
<212> TYPE: DNA
<213> ORGANISM: Homo sapiens

<400> SEQUENCE: 446
acaagcaacg cgcagcctgg atcatcccat tcttctgtta ccagatcttt gactttgccc    60
tgaacatgtt ggttgcaatc actgtgctta tttatccaaa ctccattcag gaatacatac    120
ggcaactgcc tcctaatttt ccctacagag atgatgtcat gtcagtgaat cctacctgtt    180
tggtccttat tattcttctg tttattagca ttatcttgac ttttaagggt tacttgatta    240
gctgtgtttg gaactgctac cgatacatca atggtaggaa ctcctctgat gtcctggttt    300
atgttaccag caatgacact acggtgctgc taccccgta tgatgatgcc actgtgaatg    360
gtgctgccaa ggagccaccg ccaccttacg tgtctgccta agccttcaag tgggcggagc    420
tgagggcagc agcttgactt tgcagacatc tgagcaatag ttctgttatt tcacttttgc    480
catgagcctc tctgagcttg tttgttgctg aaatgctact ttttaaaatt tagatgttag    540
attgaaaact gtagttttca acatatgctt tgctggaaca ctgtgataga ttaactgtag    600
aattcttcct gt                                                        612

<210> SEQ ID NO 447
<211> LENGTH: 642
<212> TYPE: DNA
<213> ORGANISM: Homo sapiens

<400> SEQUENCE: 447
actgaaagaa ttaaagtcag aagtcttccc aaaacaaaaa gaactgccca cagagaaaat    60
cctttctgat acttttcatt gctaaaataa acaggcggg aaatgtggaa agaaattca     120 acaaaataat gtagcaccag aagaacaagt cctagatgat tcaagttcaa aaggtaagct    180
ccagcaatgt ggaagaggta aagaccatg tagacaagct gacgaggaat atcttctttt    240
ttggttttct ggaagtagag ttcaggaaaa gcatgaagcc agtaagccag ctgtgatatg    300
tagaaaaact tcatttgaaa tgtcatcagg ttatggggat aagccctcca taagatagtt    360
gggtctgaga tgtagttttc agagatgaga atgaatgtgc cccaaacaca ggcaaaaagg    420
tagaacgcac taagctgacc agattcatta aacttgctgt gttttgtttt ggagaagtgc    480
attcgcctgt taattttatc caacatatac tcttgaatta cggcatgaat aattatcgcc    540
actagcatgt agaagaaaac agtagccaaa tctttgatgc catagtaata aagggacact    600
gattcagtag cttgttcttc tgttgctggg agggtgacat tg                       642
```

<210> SEQ ID NO 448
<211> LENGTH: 394
<212> TYPE: DNA
<213> ORGANISM: Homo sapiens
<220> FEATURE:
<221> NAME/KEY: misc_feature
<222> LOCATION: 66
<223> OTHER INFORMATION: n = A,T,C or G

<400> SEQUENCE: 448

```
accagaagac cttagaaaaa ggaggaaagg aggagaggca gataatttgg atgaattcct      60
caaagngttt gaaaatccag aggttcctag agaggaccag caacagcagc atcagcagcg     120
tgatgttatc gatgagccca ttattgaaga gccaagccgc ctccaggagt cagtgatgga     180
ggccagcaga acaaacatag atgagtcagc tatgcctcca ccaccacctc agggagttaa     240
gcgaaaagct ggacaaattg acccagagcc tgtgatgcct cctcagcagg tagagcagat     300
ggaaatacca cctgtagagc ttcccccaga agaacctcca aatatctgtc agctaatacc     360
agagttagaa cttctgccag aaaaagagaa ggag                                 394
```

<210> SEQ ID NO 449
<211> LENGTH: 494
<212> TYPE: DNA
<213> ORGANISM: Homo sapiens
<220> FEATURE:
<221> NAME/KEY: misc_feature
<222> LOCATION: 66
<223> OTHER INFORMATION: n = A,T,C or G

<400> SEQUENCE: 449

```
acaaaaaaca caaggaatac aacccaatag aaaatagtcc tgggaatgtg gtcagaagca      60
aaggcntgag tgtcttttctc aaccgtgcaa aagccgtgtt cttcccggga aaccaggaaa    120
aggatccgct actcaaaaac caagaattta aggagtttc ttaaatttcg accttgtttc     180
tgaagctcac ttttcagtgc cattgatgtg agatgtgctg gagtggctat taaccttttt    240
ttcctaaaga ttattgttaa atagatattg tggtttgggg aagttgaatt ttttataggt    300
taaatgtcat tttagagatg gggagaggga ttatactgca ggcagcttca gccatgttgt    360
gaaactgata aaagcaactt agcaaggctt cttttcatta ttttttatgt ttcacttata    420
aagtcttagg taactagtag gatagaaaca ctgtgtcccg agagtaagga gagaagctac    480
tattgattag agcc                                                       494
```

<210> SEQ ID NO 450
<211> LENGTH: 547
<212> TYPE: DNA
<213> ORGANISM: Homo sapiens

<400> SEQUENCE: 450

```
actttgggct ccagacttca ctgtccttag gcattgaaac catcacctgg tttgcattct      60
tcatgactga ggttaactta aaacaaaaat ggtaggaaag cttttcctatg cttcgggtaa    120 gagacaaatt tgcttttgta gaattggtgg ctgagaaagg cagacagggc ctgattaaag    180 aagcatttg tcaccactag ccaccaagtt aagttgtgga acccaaaggt gacggccatg     240
gaaacgtaga tcatcagctc tgctaagtag ttaggggaag aaacatattc aaaccagtct    300
ccaaatggga tcctgtggtt acagtgaatg gccactcctg cttttatttt cctgagattg    360
ccgagaataa catggcactt atactgatgg gcagatgacc agatgaacat catcatccca    420
```

```
agaatatgga accaccgtgc ttgcatcaat agattttcc ctgttatgta ggcattcctg    480
ccatccattg gcacttggct cagcacagtt aggccaacaa ggacataata gacaagtcca    540
aaacagt                                                              547
```

<210> SEQ ID NO 451
<211> LENGTH: 384
<212> TYPE: DNA
<213> ORGANISM: Homo sapiens
<220> FEATURE:
<221> NAME/KEY: misc_feature
<222> LOCATION: 8, 9, 19, 41
<223> OTHER INFORMATION: n = A,T,C or G

<400> SEQUENCE: 451

```
actacttnnt ggttaaaang ccactggtag agtcatctga ntgtaaacaa tgtccctgca     60
ctgctggaaa atccactgg ctcccaagaa aagaaaatgg tctgaagcct ctgttgtggc    120
tctcacaact catctttccc taagtcatca agctccacat cactgaggtc aatgtcatcc    180
tccacgggaa gctcgccatc cctgccgtcc caaggctctc tctcaacgat ggtagggaaa    240
gccccgcctc ctacaggtgc cgtggagcca cgcccaaaag agagctccct gagaaactcg    300
ttgatgcctt gctcactgaa ggagccttt agcagagcaa atttcatctt gcgtgcattg    360
atggcggcca tggcggggta ccca                                          384
```

<210> SEQ ID NO 452
<211> LENGTH: 381
<212> TYPE: DNA
<213> ORGANISM: Homo sapiens
<220> FEATURE:
<221> NAME/KEY: misc_feature
<222> LOCATION: 291, 341, 368
<223> OTHER INFORMATION: n = A,T,C or G

<400> SEQUENCE: 452

```
actctaaagt tgccactctc acagggtca gtgatacca ctgaacctgg caggaacagt      60
cctgcagcca gaatctgcaa gcagcgcctg tatgcaacgt ttagggccaa aggctgtctg    120
gtggggttgt tcatcacagc ataatggcct agtaggtcaa ggatccaggg tgtgaggggc    180
tcaaagccag gaaaacgaat cctcaagtcc ttcagtagtc tgatgagaac tttaactgtg    240
gactgagaag cattttcctc gaaccagcgg gcatgtcgga tggctgctaa ngcactctgc    300
aatactttga tatccaaatg gagttctgga tccagttttc naagattggg tggcactgtt    360
gtaatganaa tcttcactgt a                                             381
```

<210> SEQ ID NO 453
<211> LENGTH: 455
<212> TYPE: DNA
<213> ORGANISM: Homo sapiens

<400> SEQUENCE: 453

```
actgtgctaa acagcctata gccaagtttt aaagagttac aggaacaact gctacacatt     60
caaagaacag gcattcactg cagcctcctg atttgacctg atgggaggga caggagaatg    120
agtcactctg ccaccacttt tcctgccttg gatttgtaga ggatttgttt tgctctaatt    180
tgtttttcct atatctgccc tactaaggta cacagtctgg gcactttgaa aatgttaaag    240 ttttttaacgt ttgactgaca gaagcagcac ttaaaggctt catgaatcta ttttccaaaa    300
aaagtatgct ttcagtaaaa cattttacca ttttatctaa ctatgcactg acattttgt     360 tcttcctgaa aaggggattt atgctaacac tgtatttta atgtaaaaat atacgtgtag    420
```
agatatttta acttcctgag tgacttatac ctcaa 455

<210> SEQ ID NO 454
<211> LENGTH: 383
<212> TYPE: DNA
<213> ORGANISM: Homo sapiens
<220> FEATURE:
<221> NAME/KEY: misc_feature
<222> LOCATION: 9
<223> OTHER INFORMATION: n = A,T,C or G

<400> SEQUENCE: 454
acagagcanc tttacaagtt gtcacatttc tttataaatt tttttaaagc tacagtttaa    60
tacaaaatga attgcggttt tattacatta ataaccttc acctcagggt tttatgaaga    120
ggaaagggtt ttatgcaaaa gaaagtgcta caattcctaa tcattttaga cactttagga    180
gggggtgaag ttgtatgata aagcagatat tttaattatt tgttatcttt ttgtattgca    240
agaaatttct tgctagtgaa tcaagaaaac atccagattg acagtctaaa atggctactg    300
gtattttagt taattcaaaa atgaaacttt tcagtgattc actttactaa cattctattt    360
gagaaggctt attggtaaag ttt    383

<210> SEQ ID NO 455
<211> LENGTH: 383
<212> TYPE: DNA
<213> ORGANISM: Homo sapiens
<220> FEATURE:
<221> NAME/KEY: misc_feature
<222> LOCATION: 10
<223> OTHER INFORMATION: n = A,T,C or G

<400> SEQUENCE: 455
actcctttan gacaaggaaa caggtatcag catgatggta gcagaaacct tatccaccaag    60 gtgcaggagc tgacttcttc caaagagttg tggttccggg cagcggtcat tgccgtgccc    120
attgctggag ggctgatttt agtgttgctt attatgttgg ccctgaggat gcttcgaagt    180
gaaaataaga ggctgcagga tcagcggcaa cagatgctct cccgtttgca ctacagcttt    240
cacggacacc attccaaaaa ggggcaggtt gcaaagttag acttggaatg catggtgccg    300
gtcagtgggc acgagaactg ctgtctgacc tgtgataaaa tgagacaagc agacctcagc    360
aacgataaga tcctctcgct tgt    383

<210> SEQ ID NO 456
<211> LENGTH: 543
<212> TYPE: DNA
<213> ORGANISM: Homo sapiens
<220> FEATURE:
<221> NAME/KEY: misc_feature
<222> LOCATION: 64
<223> OTHER INFORMATION: n = A,T,C or G

<400> SEQUENCE: 456
acaaacattt tacaaaaaag aacattacca atatcagtgg cagtaagggc aagctgaaga    60
atangtagac tgagtttccg ggcaatgtct gtcctcaaag acatccaaac tgcgttcagg    120
cagctgaaac aggcttcttt cccagtgaca agcatatgtg gtcagtaata caaacgatgg    180
taaatgaggc tactacatag gcccagttaa caaactcctc ttctcctcgg gtaggccatg    240
atacaagtgg aactcatcaa ataatttaaa cccaaggcga taacaacact atttcccatc    300
taaactcatt taagccttca caatgtcgca atggattcag ttacttgcaa acgatcccgg    360

```
gttgtcatac agatacttgt tttttacaca taacgctgtg ccatcccttc cttcactgcc    420
ccagtcaggt ttcctgttgt tggaccgaaa ggggatacat tttagaaatg cttccctcaa    480
gacagaagtg agaaagaaag gagaccctga ggccaggatc tattaaacct ggtgtgtgcg    540
caa                                                                  543
```

<210> SEQ ID NO 457
<211> LENGTH: 544
<212> TYPE: DNA
<213> ORGANISM: Homo sapiens
<220> FEATURE:
<221> NAME/KEY: misc_feature
<222> LOCATION: 17
<223> OTHER INFORMATION: n = A,T,C or G

<400> SEQUENCE: 457

```
actggtgcca atattgncat ggtgagctcc tctctaatgt cttccagggc accaatatct     60
gcccatgtca cattagggac agtgacaaag ccttcccttt tggcagaggg ttggactgag    120
gatagagcaa caatgaaatc attcagttca atgcacagtc cttgcatctg ctcctctgag    180
aggggatctt ggtctcttag caacccagc agcctttgta attcatcctg tgtttcagaa     240
gtgggctcag ttcccagcct ttcctcctgg actcctttag atggcaaatc ttccatttca    300
ggatttttct tctgctgttc ctgtagcttc attaagactc tattgactgc acacattgct    360
gcctctcggc acagtgccat gagatcagca ccaacaaagc ctggagttag gtgtgctaag    420
tgacagaaat caaaagcttg aggaagcctc agttttctgc acaatgtttg aagtattctt    480
tccctggatg cttcatctgg gataccttagg catatttctc ggtcgaacct tcccgcacgt    540
ctca                                                                 544
```

<210> SEQ ID NO 458
<211> LENGTH: 382
<212> TYPE: DNA
<213> ORGANISM: Homo sapiens
<220> FEATURE:
<221> NAME/KEY: misc_feature
<222> LOCATION: 5, 23
<223> OTHER INFORMATION: n = A,T,C or G

<400> SEQUENCE: 458

```
acctntaggc tcaacggcag aancttcacc acaaaagcga atgggcaca ccacagggag      60
aaaactggtt gtcctggatg tttgaaaagt tggtcgttgt catggtgtgt tacttcatcc    120
tatctatcat taactccatg gcacaaagtt atgccaaacg aatccagcag cggttgaact    180
cagaggagaa aactaaataa gtagagaaag ttttaaactg cagaaattgg agtggatggg    240
ttctgcctta aattgggagg actccaagcc gggaaggaaa attccctttt ccaacctgta    300
tcaattttta caacttttt cctgaaagca gtttagtcca tactttgcac tgacatactt     360
tttccttctg tgctaaggta ag                                             382
```

<210> SEQ ID NO 459
<211> LENGTH: 168
<212> TYPE: DNA
<213> ORGANISM: Homo sapiens

<400> SEQUENCE: 459

```
ctcgtactct agccaggcac gaaaccatga agtagcctga tccttcttag ccatcctggc     60
cgccttagcg gtagtaactt tgtgttatga atcacatgaa agcatggaat cttatgaact    120
taatcccttc attaacagga gaaatgcaaa taccttcata tcccctca                 168
```

<210> SEQ ID NO 460
<211> LENGTH: 190
<212> TYPE: DNA
<213> ORGANISM: Homo sapiens
<220> FEATURE:
<221> NAME/KEY: misc_feature
<222> LOCATION: 4
<223> OTHER INFORMATION: n = A,T,C or G

<400> SEQUENCE: 460

| | | |
|---|---|---|
| acanctgcta ccagggagcc gagagctgac tatcccagcc tcggctaatg tattctacgc | 60 |
| catggatgga gcttcacacg atttcctcct gcggcagcgg cgaaggtcct ctactgctac | 120 |
| acctggcgtc accagtggcc cgtctgcctc aggaactcct ccgagtgagg gaggagggggg | 180 |
| ctcctttccc | 190 |

<210> SEQ ID NO 461
<211> LENGTH: 495
<212> TYPE: DNA
<213> ORGANISM: Homo sapiens

<400> SEQUENCE: 461

| | | |
|---|---|---|
| acagacaggc ttctctgcta tcctccaggc agtgtaatag tcaaggaaaa gggcaacagt | 60 |
| attggatcat tccttagaca ctaatcagct ggggaaagag ttcattggca aaagtgtcct | 120 |
| cccaagaatg gtttacacca agcagagagg acatgtcact gaatggggaa agggaacccc | 180 |
| cgtatccaca gtcactgtaa gcatccagta ggcaggaaga tggctttggg cagtggctgg | 240 |
| atgaaagcag atttgagata cccagctccg gaacgaggtc atcttctaca ggttcttcct | 300 |
| tcactgagac aatgaattca gggtgatcat tctctgaggg gctgagaggt gcttcctcga | 360 |
| ttttcactac cacattagct tggctctctg tctcagaggg tatctctaag actaggggct | 420 |
| tggtatatat gtggtcaaaa cgaattagtt cattaatggc ttccagcttg gctgatgacg | 480 |
| tccccactga cagag | 495 |

<210> SEQ ID NO 462
<211> LENGTH: 493
<212> TYPE: DNA
<213> ORGANISM: Homo sapiens
<220> FEATURE:
<221> NAME/KEY: misc_feature
<222> LOCATION: 68
<223> OTHER INFORMATION: n = A,T,C or G

<400> SEQUENCE: 462

| | | |
|---|---|---|
| acactgaaac ataaatccgc aagtcaccac acatacaaca cccggcagga aaaaaacaaa | 60 |
| aacagggngt ttacatgatc cctgtaacag ccatggtctc aaactcagat gcttcctcca | 120 |
| tctgccaagt gtgttttgga tacagagcac atcgtggctt ctggggtcac actcagctta | 180 |
| ggctgtgggt ccacagagca ctcatctggc tgggctatgg tggtggtggc tctactcaag | 240 |
| aagcaaagca gttaccagca cattcaaaca gtgtattgaa catctttta atatcaaagt | 300 |
| gagaaacaag aaggcaacat aataatgtta tcagaaagat gttaggaagt aaggacagct | 360 |
| gtgtaaagct tgaggctgaa aagtagcttg ccagcttcat ttctttggtt tcttgggtag | 420 |
| tgggcgccgg aacagcaaga tgtgaggttc tggttcatgg atcatataat ggacccatcc | 480 |
| ctgactctgc tga | 493 |

<210> SEQ ID NO 463

<211> LENGTH: 3681
<212> TYPE: DNA
<213> ORGANISM: Homo sapiens

<400> SEQUENCE: 463

```
tccgagctga ttacagacac caaggaagat gctgtaaaga gtcagcagcc acagccctgg      60
ctagctggcc ctgtgggcat ttattagtaa agttttaatg acaaaagctt tgagtcaaca     120
cacccgtggg taattaacct ggtcatcccc accctggaga gccatcctgc ccatgggtga     180
tcaaagaagg aacatctgca ggaacacctg atgaggctgc acccttggcg aaagaacac      240
ctgacacagc tgaaagcttg gtggaaaaaa cacctgatga ggctgcaccc ttggtggaaa     300
gaacacctga cacggctgaa agcttggtgg aaaaaacacc tgatgaggct gcatccttgg     360
tggagggaac atctgacaaa attcaatgtt tggagaaagc gacatctgga aagttcgaac     420
agtcagcaga agaaacacct agggaaatta cgagtcctgc aaaagaaaca tctgagaaat     480
ttacgtggcc agcaaaagga agacctagga agatcgcatg ggagaaaaaa gaagacacac     540
ctagggaaat tatgagtccc gcaaaagaaa catctgagaa atttacgtgg gcagcaaaag     600
gaagacctag gaagatcgca tgggagaaaa aagaaacacc tgtaaagact ggatgcgtgg     660
caagagtaac atctaataaa actaaagttt ggaaaaagg aagatctaag atgattgcat      720
gtcctacaaa agaatcatct acaaaagcaa gtgccaatga tcagaggttc ccatcagaat     780
ccaaacaaga ggaagatgaa gaatattctt gtgattctcg gagtctcttt gagagttctg     840
caaagattca agtgtgtata cctgagtcta tatcaaaa agtaatggag ataaatagag       900
aagtagaaga gcctcctaag aagccatctg ccttcaagcc tgccattgaa atgcaaaact     960
ctgttccaaa taaagccttt gaattgaaga atgaacaaac attgagagca gatccgatgt    1020
tcccaccaga atccaaacaa aaggactatg aagaaaattc ttgggattct gagagtctct    1080
gtgagactgt ttcacagaag gatgtgtgtt tacccaaggc tacacatcaa aaagaaatag    1140
ataaaataaa tggaaaatta aagagtctc ctaataaaga tggtcttctg aaggctacct     1200
gcggaatgaa agtttctatt ccaactaaag ccttagaatt gaaggacatg caaactttca    1260
aagcagagcc tccggggaag ccatctgcct tcgagcctgc cactgaaatg caaaagtctg    1320
tcccaaataa agccttggaa ttgaaaaatg aacaaacatt gagagcagat gagatactcc    1380
catcagaatc caaacaaaag gactatgaag aaagttcttg ggattctgag agtctctgtg    1440
agactgtttc acagaaggat gtgtgtttac ccaaggctrc rcatcaaaaa gaaatagata    1500
aaataaatgg aaaattagaa gggtctcctg ttaaagatgt tcttctgaag gctaactgcg    1560
gaatgaaagt ttctattcca actaaagcct tagaattgat ggacatgcaa actttcaaag    1620
cagagcctcc cgagaagcca tctgccttcg agcctgccat tgaaatgcaa aagtctgttc    1680
caaataaagc cttggaattg aagaatgaac aaacattgag agcagatgag atactcccat    1740
cagaatccaa acaaaaggac tatgaagaaa gttcttggga ttctgagagt ctctgtgaga    1800
ctgtttcaca gaaggatgtg tgtttaccca aggctrcrca tcaaaaagaa atagataaaa    1860
taaatggaaa attagaagag tctcctgata atgatggttt tctgaaggct ccctgcagaa    1920
tgaaagtttc tattccaact aaagccttag aattgatgga catgcaaact ttcaaagcag    1980
agcctcccga gaagccatct gccttcgagc ctgccattga atgcaaaag tctgttccaa     2040
ataaagcctt ggaattgaag aatgaacaaa cattgagagc agatcagatg ttcccttcag    2100
aatcaaaaca aaagaasgtt gaagaaaatt cttgggattc tgagagtctc cgtgagactg    2160
tttcacagaa ggatgtgtgt gtacccaagg ctacacatca aaaagaaatg gataaaataa    2220
```

-continued

```
gtggaaaatt agaagattca actagcctat caaaaatctt ggatacagtt cattcttgtg    2280
aaagagcaag ggaacttcaa aaagatcact gtgaacaacg tacaggaaaa atggaacaaa    2340
tgaaaaagaa gttttgtgta ctgaaaaaga aactgtcaga agcaaaagaa ataaaatcac    2400
agttagagaa ccaaaaagtt aaatgggaac aagagctctg cagtgtgagg tttctcacac    2460
tcatgaaaat gaaaattatc tcttacatga aaattgcatg ttgaaaaagg aaattgccat    2520
gctaaaactg gaaatagcca cactgaaaca ccaataccag gaaaaggaaa ataaatactt    2580
tgaggacatt aagattttaa agaaaaagaa tgctgaactt cagatgaccc taaaactgaa    2640
agaggaatca ttaactaaaa gggcatctca atatagtggg cagcttaaag ttctgatagc    2700
tgagaacaca atgctcactt ctaaattgaa ggaaaaacaa gacaaagaaa tactagaggc    2760
agaaattgaa tcacaccatc ctagactggc ttctgctgta caagaccatg atcaaattgt    2820
gacatcaaga aaaagtcaag aacctgcttt ccacattgca ggagatgctt gtttgcaaag    2880
aaaaatgaat gttgatgtga gtagtacgat atataacaat gaggtgctcc atcaaccact    2940
ttctgaagct caaggaaat ccaaaagcct aaaaattaat ctcaattatg cmggagatgc    3000
tctaagagaa aatacattgg tttcagaaca tgcacaaaga gaccaacgtg aaacacagtg    3060
tcaaatgaag gaagctgaac acatgtatca aaacgaacaa gataatgtga acaaacacac    3120
tgaacagcag gagtctctag atcagaaatt atttcaacta caaagcaaaa atatgtggct    3180
tcaacagcaa ttagttcatg cacataagaa agctgacaac aaaagcaaga taacaattga    3240
tattcatttt cttgagagga aaatgcaaca tcatctccta aaagagaaaa atgaggagat    3300
atttaattac aataaccatt taaaaaaccg tatatatcaa tatgaaaaag agaaagcaga    3360
aacagaaaac tcatgagaga caagcagtaa gaaacttctt ttggagaaac aacagaccag    3420
atctttactc acaactcatg ctaggaggcc agtcctagca tcaccttatg ttgaaaatct    3480
taccaatagt ctgtgtcaac agaatactta ttttagaaga aaaattcatg atttcttcct    3540
gaagcctaca gacataaaat aacagtgtga agaattactt gttcacgaat tgcataaagc    3600
tgcacaggat tcccatctac cctgatgatg cagcagacat cattcaatcc aaccagaatc    3660
tcgctctgtc actcaggctg g                                              3681
```

<210> SEQ ID NO 464
<211> LENGTH: 1424
<212> TYPE: DNA
<213> ORGANISM: Homo sapiens

<400> SEQUENCE: 464

```
tccgagctga ttacagacac caaggaagat gctgtaaaga gtcagcagcc acagccctgg      60
ctagctggcc ctgtgggcat ttattagtaa agttttaatg acaaaagctt tgagtcaaca     120
cacccgtggg taattaacct ggtcatcccc accctggaga gccatcctgc ccatgggtga     180
tcaaagaagg aacatctgca ggaacacctg atgaggctgc acccttggcg gaaagaacac     240
ctgacacagc tgaaagcttg gtggaaaaaa cacctgatga ggctgcaccc ttggtggaaa     300
gaacacctga cacggctgaa agcttggtgg aaaaaacacc tgatgaggct gcatccttgg     360
tggagggaac atctgacaaa attcaatgtt tggagaaagc gacatctgga aagttcgaac     420
agtcagcaga agaaacacct agggaaatta cgagtcctgc aaaagaaaca tctgagaaat     480
ttacgtggcc agcaaaagga agacctagga agatcgcatg ggagaaaaaa gaagacacac     540
ctagggaaat tatgagtccc gcaaaagaaa catctgagaa atttacgtgg gcagcaaaag     600
```

| | |
|---|---|
| gaagacctag gaagatcgca tgggagaaaa aagaaacacc tgtaaagact ggatgcgtgg | 660 |
| caagagtaac atctaataaa actaaagttt tggaaaaagg aagatctaag atgattgcat | 720 |
| gtcctacaaa agaatcatct acaaaagcaa gtgccaatga tcagaggttc ccatcagaat | 780 |
| ccaaacaaga ggaagatgaa gaatattctt gtgattctcg gagtctcttt gagagttctg | 840 |
| caaagattca agtgtgtata cctgagtcta tatatcaaaa agtaatggag ataaatagag | 900 |
| aagtagaaga gcctcctaag aagccatctg ccttcaagcc tgccattgaa atgcaaaact | 960 |
| ctgttccaaa taaagccttt gaattgaaga tgaacaaac attgagagca gatccgatgt | 1020 |
| tcccaccaga atccaaacaa aaggactatg aagaaaattc ttgggattct gagagtctct | 1080 |
| gtgagactgt ttcacagaag gatgtgtgtt tacccaaggc tacacatcaa aaagaaatag | 1140 |
| ataaaataaa tggaaaatta gaaggtaaga accgtttttt atttaaaaat cagttgaccg | 1200 |
| aatatttctc taaactgatg aggagggata tcctctagta gctgaagaaa attacctcct | 1260 |
| aaaatgcaaac catggaaaaa aagagaagtg caatggtcgt aagttgtatg tctcatcagg | 1320 |
| tgttggcaac agactatatt gagagtgctg aaaaggagct gaattattag tttgaattca | 1380 |
| agatattgca agacctgaga gaaaaaaaaa aaaaaaaaa aaaa | 1424 |

<210> SEQ ID NO 465
<211> LENGTH: 674
<212> TYPE: DNA
<213> ORGANISM: Homo sapiens

<400> SEQUENCE: 465

| | |
|---|---|
| attccgagct gattacagac accaaggaag atgctgtaaa gagtcagcag ccacagccct | 60 |
| ggctagctgg ccctgtgggc atttattagt aaagttttaa tgacaaaagc tttgagtcaa | 120 |
| cacacccgtg ggtaattaac ctggtcatcc ccaccctgga gagccatcct gcccatgggt | 180 |
| gatcaaagaa ggaacatctg caggaacacc tgatgaggct gcaccttgg cggaaagaac | 240 |
| acctgacaca gctgaaagct tggtggaaaa aacacctgat gaggctgcac ccttggtgga | 300 |
| aagaacaccct gacacggctg aaagcttggt ggaaaaaaca cctgatgagg ctgcatcctt | 360 |
| ggtggaggga acatctgaca aaattcaatg tttggagaaa gcgacatctg aaagttcga | 420 |
| acagtcagca gaagaaacac ctagggaaat tacgagtcct gcaaaagaaa catctgagaa | 480 |
| atttacgtgg ccagcaaaag gaagacctag gaagatcgca tgggagaaaa aagatgactc | 540 |
| agttaaggca aaaaaaaaaa aaaaaaaaaa aaaaaaaaaa aaaaaaaaaa aaaaaaaaa | 600 |
| aaaaaaaaaa aaaaaaaaaa aaaaaaaaa aaaaaaaaa aaaaaaaaaa aaaaaaaaa | 660 |
| aaaaaaaaaa aaaa | 674 |

<210> SEQ ID NO 466
<211> LENGTH: 1729
<212> TYPE: DNA
<213> ORGANISM: Homo sapiens
<220> FEATURE:
<221> NAME/KEY: misc_feature
<222> LOCATION: 11, 1128
<223> OTHER INFORMATION: n = A,T,C or G

<400> SEQUENCE: 466

| | |
|---|---|
| gaaagttcga ncagtcagca gaagaaacac ctagggaaat tacgagtcct gcaaaagaaa | 60 |
| catctgagaa atttacgtgg ccagcaaaag gaagacctag gaagatcgca tgggagaaaa | 120 |
| aagaagacac acctagggaa attatgagtc ccgcaaaaga aacatctgag aaatttacgt | 180 |
| gggcagcaaa aggaagacct aggaagatcg catgggagaa aaagaaaaca cctgtaaaga | 240 |

-continued

| | |
|---|---|
| ctggatgcgt ggcaagagta acatctaata aaactaaagt tttggaaaaa ggaagatcta | 300 |
| agatgattgc atgtcctaca aaagaatcat ctacaaaagc aagtgccaat gatcagaggt | 360 |
| tcccatcaga atccaaacaa gaggaagatg aagaatattc ttgtgattct cggagtctct | 420 |
| ttgagagttc tgcaaagatt caagtgtgta tacctgagtc tatatatcaa aaagtaatgg | 480 |
| agataaatag agaagtagaa gagcctccta agaagccatc tgccttcaag cctgccattg | 540 |
| aaatgcaaaa ctctgttcca aataaagcct ttgaattgaa gaatgaacaa acattgagag | 600 |
| cagatccgat gttcccacca gaatccaaac aaaaggacta tgaagaaaat tcttgggatt | 660 |
| ctgagagtct ctgtgagact gtttcacaga aggatgtgtg tttacccaag gctacacatc | 720 |
| aaaaagaaat agataaaata aatggaaaat tagaagagtc tcctaataaa gatggtcttc | 780 |
| tgaaggctac ctgcggaatg aaagtttcta ttccaactaa agccttagaa ttgaaggaca | 840 |
| tgcaaacttt caaagcagag cctccgggga agccatctgc cttcgagcct gccactgaaa | 900 |
| tgcaaaagtc tgtcccaaat aaagccttgg aattgaaaaa tgaacaaaca ttgagagcag | 960 |
| atgagatact cccatcagaa tccaaacaaa aggactatga agaaaattct tgggatactg | 1020 |
| agagtctctg tgagactgtt tcacagaagg atgtgtgttt acccaaggct gcgcatcaaa | 1080 |
| aagaaataga taaataaat ggaaaattag aagggtctcc tggtaaanat ggtcttctga | 1140 |
| aggctaactg cggaatgaaa gtttctattc caactaaagc cttagaattg atggacatgc | 1200 |
| aaactttcaa agcagagcct cccgagaagc catctgcctt cgagcctgcc attgaaatgc | 1260 |
| aaaagtctgt tccaaataaa gccttggaat tgaagaatga acaaacattg agagcagatg | 1320 |
| agatactccc atcagaatcc aaacaaaagg actatgaaga agttcttgg gattctgaga | 1380 |
| gtctctgtga gactgtttca gaaggatg tgtgtttacc caaggctgcg catcaaaaag | 1440 |
| aaatagataa aataaatgga aaattagaag gtaagaaccg ttttttattt aaaaatcatt | 1500 |
| tgaccaaata tttctctaaa ttgatgagga aggatatcct ctagtagctg aagaaaatta | 1560 |
| cctcctaaat gcaaaccatg gaaaaaagaa gaagtgcaat ggtcataagc tatgtgtctc | 1620 |
| atcaggcatt ggcaacagac tatattgtga gtgctgaaga ggagctgaat tactagttta | 1680 |
| aattcaagat attccaagac gtgaggaaaa tgagaaaaaa aaaaaaaaa | 1729 |

<210> SEQ ID NO 467
<211> LENGTH: 1337
<212> TYPE: DNA
<213> ORGANISM: Homo sapiens

<400> SEQUENCE: 467

| | |
|---|---|
| aaaaagaaat agataaaata aatggaaaat tagaagggtc tcctgttaaa gatggtcttc | 60 |
| tgaaggctaa ctgcggaatg aaagtttcta ttccaactaa agccttagaa ttgatggaca | 120 |
| tgcaaacttt caaagcagag cctcccgaga agccatctgc cttcgagcct gccattgaaa | 180 |
| tgcaaaagtc tgttccaaat aaagccttgg aattgaagaa tgaacaaaca ttgagagcag | 240 |
| atgagatact cccatcagaa tccaaacaaa aggactatga agaaagttct tgggattctg | 300 |
| agagtctctg tgagactgtt tcacagaagg atgtgtgttt acccaaggct gcgcatcaaa | 360 |
| aagaaataga taaataaat ggaaaattag aagagtctcc tgataatgat ggttttctga | 420 |
| aggctccctg cagaatgaaa gtttctattc aactaaagc cttagaattg atggacatgc | 480 |
| aaactttcaa agcagagcct cccgagaagc catctgcctt cgagcctgcc attgaaatgc | 540 |
| aaaagtctgt tccaaataaa gccttggaat tgaagaatga acaaacattg agagcagatc | 600 |

| | |
|---|---:|
| agatgttccc ttcagaatca aaacaaaaga aggttgaaga aaattcttgg gattctgaga | 660 |
| gtctccgtga gactgtttca cagaaggatg tgtgtgtacc caaggctaca catcaaaaag | 720 |
| aaatggataa aataagtgga aaattagaag attcaactag cctatcaaaa atcttggata | 780 |
| cagttcattc ttgtgaaaga gcaagggaac ttcaaaaaga tcactgtgaa caacgtacag | 840 |
| gaaaaatgga acaaatgaaa aagaagtttt gtgtactgaa aaagaaactg tcagaagcaa | 900 |
| aagaaataaa atcacagtta gagaaccaaa agtaaatg gaacaagag ctctgcagtg | 960 |
| tgagattgac tttaaaccaa gaagaagaga agagaagaaa tgccgatata ttaaatgaaa | 1020 |
| aaattaggga agaattagga agaatcgaag agcagcatag gaaagagtta gaagtgaaac | 1080 |
| aacaacttga acaggctctc agaatacaag atatagaatt gaagagtgta gaaagtaatt | 1140 |
| tgaatcaggt ttctcacact catgaaaatg aaaattatct cttacatgaa aattgcatgt | 1200 |
| tgaaaaagga aattgccatg ctaaaactgg aaatagccac actgaaacac caataccagg | 1260 |
| aaaaggaaaa taaatacttt gaggacatta agattttaaa agaaaagaat gctgaacttc | 1320 |
| agatgacccc tcgtgcc | 1337 |

```
<210> SEQ ID NO 468
<211> LENGTH: 2307
<212> TYPE: DNA
<213> ORGANISM: Homo sapiens

<400> SEQUENCE: 468
```

| | |
|---|---:|
| attgagagca gatgagatac tcccatcaga atccaaacaa aaggactatg aagaaagttc | 60 |
| ttgggattct gagagtctct gtgagactgt ttcacagaag gatgtgtgtt tacccaaggc | 120 |
| tacacatcaa aaagaaatag ataaaataaa tggaaaatta aagggtctc ctgttaaaga | 180 |
| tggtcttctg aaggctaact gcggaatgaa agtttctatt ccaactaaag ccttagaatt | 240 |
| gatggacatg caaactttca aagcagagcc tcccgagaag ccatctgcct tcgagcctgc | 300 |
| cattgaaatg caaaagtctg ttccaaataa agccttggaa ttgaagaatg aacaaacatt | 360 |
| gagagcagat gagatactcc catcagaatc caaacaaaag gactatgaag aaagttcttg | 420 |
| ggattctgag agtctctgtg agactgtttc acagaaggat gtgtgtttac ccaaggctac | 480 |
| acatcaaaaa gaaatagata aataaatgg aaaattagaa gagtctcctg ataatgatgg | 540 |
| ttttctgaag tctccctgca gaatgaaagt ttctattcca actaaagcct tagaattgat | 600 |
| ggacatgcaa actttcaaag cagagcctcc cgagaagcca tctgccttcg agcctgccat | 660 |
| tgaaatgcaa aagtctgttc caaataaagc cttggaattg aagaatgaac aaacattgag | 720 |
| agcagatcag atgttcccct tcagaatcaaa acaaagaac gttgaagaaa attcttggga | 780 |
| ttctgagagt ctccgtgaga ctgtttcaca gaaggatgtg tgtgtaccca aggctacaca | 840 |
| tcaaaaagaa atggataaaa taagtggaaa attagaagat caactagcc tatcaaaaat | 900 |
| cttggataca gttcattctt gtgaaagagc aagggaactt caaaaagatc actgtgaaca | 960 |
| acgtacagga aaatggaac aaatgaaaaa gaagttttgt gtactgaaaa agaaactgtc | 1020 |
| agaagcaaaa gaaataaaat cacagttaga gaaccaaaaa gttaaatggg aacaagagct | 1080 |
| ctgcagtgtg aggtttctca cactcatgaa aatgaaaatt atctcttaca tgaaaattgc | 1140 |
| atgttgaaaa aggaaattgc catgctaaaa ctggaaatag ccacactgaa acaccaatac | 1200 |
| caggaaaagg aaaataaata ctttgaggac attaagattt taaagaaaa gaatgctgaa | 1260 |
| cttcagatga ccctaaaact gaaagaggaa tcattaacta aaagggcatc tcaatatagt | 1320 |
| gggcagctta agttctgat agctgagaac acaatgctca cttctaaatt gaaggaaaaa | 1380 |

-continued

```
caagacaaag aaatactaga ggcagaaatt gaatcacacc atcctagact ggcttctgct   1440
gtacaagacc atgatcaaat tgtgacatca agaaaaagtc aagaacctgc tttccacatt   1500
gcaggagatg cttgtttgca agaaaaatg aatgttgatg tgagtagtac gatatataac    1560
aatgaggtgc tccatcaacc actttctgaa gctcaaagga atccaaaag cctaaaaatt    1620 aatctcaatt atgcaggaga tgctctaaga gaaaatacat tggtttcaga acatgcacaa   1680
agagaccaac gtgaaacaca gtgtcaaatg aaggaagctg aacacatgta tcaaaacgaa   1740
caagataatg tgaacaaaca cactgaacag caggagtctc tagatcagaa attatttcaa   1800
ctacaaagca aaatatgtg gcttcaacag caattagttc atgcacataa gaaagctgac     1860
aacaaaagca agataacaat tgatattcat tttcttgaga ggaaaatgca acatcatctc   1920
ctaaaagaga aaatgagga gatatttaat tacaataacc atttaaaaaa ccgtatatat    1980
caatatgaaa aagagaaagc agaaacagaa aactcatgag agacaagcag taagaaactt   2040
cttttggaga acaacagac cagatcttta ctcacaactc atgctaggag gccagtccta    2100
gcatcacctt atgttgaaaa tcttaccaat agtctgtgtc aacagaatac ttattttaga   2160
agaaaaattc atgatttctt cctgaagcct acagacataa aataacagtg tgaagaatta   2220
cttgttcacg aattgcataa agctgcacag gattcccatc taccctgatg atgcagcaga   2280
catcattcaa tccaaccaga atctcgc                                        2307
```

<210> SEQ ID NO 469
<211> LENGTH: 650
<212> TYPE: PRT
<213> ORGANISM: Homo sapiens
<220> FEATURE:
<221> NAME/KEY: VARIANT
<222> LOCATION: 310, 429, 522
<223> OTHER INFORMATION: Xaa = Any Amino Acid

<400> SEQUENCE: 469

```
Met Ser Pro Ala Lys Glu Thr Ser Glu Lys Phe Thr Trp Ala Ala Lys
 1               5                  10                  15

Gly Arg Pro Arg Lys Ile Ala Trp Glu Lys Lys Glu Thr Pro Val Lys
            20                  25                  30

Thr Gly Cys Val Ala Arg Val Thr Ser Asn Lys Thr Lys Val Leu Glu
        35                  40                  45

Lys Gly Arg Ser Lys Met Ile Ala Cys Pro Thr Lys Glu Ser Ser Thr
    50                  55                  60

Lys Ala Ser Ala Asn Asp Gln Arg Phe Pro Ser Glu Ser Lys Gln Glu
65                  70                  75                  80

Glu Asp Glu Glu Tyr Ser Cys Asp Ser Arg Ser Leu Phe Glu Ser Ser
                85                  90                  95

Ala Lys Ile Gln Val Cys Ile Pro Glu Ser Ile Tyr Gln Lys Val Met
            100                 105                 110

Glu Ile Asn Arg Glu Val Glu Glu Pro Pro Lys Lys Pro Ser Ala Phe
        115                 120                 125

Lys Pro Ala Ile Glu Met Gln Asn Ser Val Pro Asn Lys Ala Phe Glu
    130                 135                 140

Leu Lys Asn Glu Gln Thr Leu Arg Ala Asp Pro Met Phe Pro Pro Glu
145                 150                 155                 160

Ser Lys Gln Lys Asp Tyr Glu Glu Asn Ser Trp Asp Ser Glu Ser Leu
                165                 170                 175

Cys Glu Thr Val Ser Gln Lys Asp Val Cys Leu Pro Lys Ala Thr His
```

```
                180                185                190
Gln Lys Glu Ile Asp Lys Ile Asn Gly Lys Leu Glu Glu Ser Pro Asn
            195                200                205
Lys Asp Gly Leu Leu Lys Ala Thr Cys Gly Met Lys Val Ser Ile Pro
        210                215                220
Thr Lys Ala Leu Glu Leu Lys Asp Met Gln Thr Phe Lys Ala Glu Pro
225                230                235                240
Pro Gly Lys Pro Ser Ala Phe Glu Pro Ala Thr Glu Met Gln Lys Ser
                245                250                255
Val Pro Asn Lys Ala Leu Glu Leu Lys Asn Glu Gln Thr Leu Arg Ala
            260                265                270
Asp Glu Ile Leu Pro Ser Glu Ser Lys Gln Lys Asp Tyr Glu Glu Ser
        275                280                285
Ser Trp Asp Ser Glu Ser Leu Cys Glu Thr Val Ser Gln Lys Asp Val
    290                295                300
Cys Leu Pro Lys Ala Xaa His Gln Lys Glu Ile Asp Lys Ile Asn Gly
305                310                315                320
Lys Leu Glu Gly Ser Pro Val Lys Asp Gly Leu Leu Lys Ala Asn Cys
                325                330                335
Gly Met Lys Val Ser Ile Pro Thr Lys Ala Leu Glu Leu Met Asp Met
            340                345                350
Gln Thr Phe Lys Ala Glu Pro Pro Glu Lys Pro Ser Ala Phe Glu Pro
        355                360                365
Ala Ile Glu Met Gln Lys Ser Val Pro Asn Lys Ala Leu Glu Leu Lys
    370                375                380
Asn Glu Gln Thr Leu Arg Ala Asp Glu Ile Leu Pro Ser Glu Ser Lys
385                390                395                400
Gln Lys Asp Tyr Glu Glu Ser Ser Trp Asp Ser Glu Ser Leu Cys Glu
                405                410                415
Thr Val Ser Gln Lys Asp Val Cys Leu Pro Lys Ala Xaa His Gln Lys
            420                425                430
Glu Ile Asp Lys Ile Asn Gly Lys Leu Glu Glu Ser Pro Asp Asn Asp
        435                440                445
Gly Phe Leu Lys Ala Pro Cys Arg Met Lys Val Ser Ile Pro Thr Lys
    450                455                460
Ala Leu Glu Leu Met Asp Met Gln Thr Phe Lys Ala Glu Pro Pro Glu
465                470                475                480
Lys Pro Ser Ala Phe Glu Pro Ala Ile Glu Met Gln Lys Ser Val Pro
                485                490                495
Asn Lys Ala Leu Glu Leu Lys Asn Glu Gln Thr Leu Arg Ala Asp Gln
            500                505                510
Met Phe Pro Ser Glu Ser Lys Gln Lys Xaa Val Glu Glu Asn Ser Trp
        515                520                525
Asp Ser Glu Ser Leu Arg Glu Thr Val Ser Gln Lys Asp Val Cys Val
    530                535                540
Pro Lys Ala Thr His Gln Lys Glu Met Asp Lys Ile Ser Gly Lys Leu
545                550                555                560
Glu Asp Ser Thr Ser Leu Ser Lys Ile Leu Asp Thr Val His Ser Cys
                565                570                575
Glu Arg Ala Arg Glu Leu Gln Lys Asp His Cys Glu Gln Arg Thr Gly
            580                585                590
Lys Met Glu Gln Met Lys Lys Phe Cys Val Leu Lys Lys Lys Leu
        595                600                605
```

```
Ser Glu Ala Lys Glu Ile Lys Ser Gln Leu Glu Asn Gln Lys Val Lys
    610                 615                 620
Trp Glu Gln Glu Leu Cys Ser Val Arg Phe Leu Thr Leu Met Lys Met
625                 630                 635                 640
Lys Ile Ile Ser Tyr Met Lys Ile Ala Cys
                645                 650

<210> SEQ ID NO 470
<211> LENGTH: 228
<212> TYPE: PRT
<213> ORGANISM: Homo sapiens

<400> SEQUENCE: 470

Met Ser Pro Ala Lys Glu Thr Ser Glu Lys Phe Thr Trp Ala Ala Lys
1               5                   10                  15
Gly Arg Pro Arg Lys Ile Ala Trp Glu Lys Lys Glu Thr Pro Val Lys
                20                  25                  30
Thr Gly Cys Val Ala Arg Val Thr Ser Asn Lys Thr Lys Val Leu Glu
            35                  40                  45
Lys Gly Arg Ser Lys Met Ile Ala Cys Pro Thr Lys Glu Ser Ser Thr
50                  55                  60
Lys Ala Ser Ala Asn Asp Gln Arg Phe Pro Ser Glu Ser Lys Gln Glu
65                  70                  75                  80
Glu Asp Glu Glu Tyr Ser Cys Asp Ser Arg Ser Leu Phe Glu Ser Ser
                85                  90                  95
Ala Lys Ile Gln Val Cys Ile Pro Glu Ser Ile Tyr Gln Lys Val Met
            100                 105                 110
Glu Ile Asn Arg Glu Val Glu Glu Pro Pro Lys Lys Pro Ser Ala Phe
        115                 120                 125
Lys Pro Ala Ile Glu Met Gln Asn Ser Val Pro Asn Lys Ala Phe Glu
130                 135                 140
Leu Lys Asn Glu Gln Thr Leu Arg Ala Asp Pro Met Phe Pro Pro Glu
145                 150                 155                 160
Ser Lys Gln Lys Asp Tyr Glu Glu Asn Ser Trp Asp Ser Glu Ser Leu
                165                 170                 175
Cys Glu Thr Val Ser Gln Lys Asp Val Cys Leu Pro Lys Ala Thr His
            180                 185                 190
Gln Lys Glu Ile Asp Lys Ile Asn Gly Lys Leu Glu Gly Lys Asn Arg
        195                 200                 205
Phe Leu Phe Lys Asn Gln Leu Thr Glu Tyr Phe Ser Lys Leu Met Arg
210                 215                 220
Arg Asp Ile Leu
225

<210> SEQ ID NO 471
<211> LENGTH: 154
<212> TYPE: PRT
<213> ORGANISM: Homo sapiens
<220> FEATURE:
<221> NAME/KEY: VARIANT
<222> LOCATION: 148
<223> OTHER INFORMATION: Xaa = Any Amino Acid

<400> SEQUENCE: 471

Met Arg Leu His Pro Trp Arg Lys Glu His Leu Thr Gln Leu Lys Ala
1               5                   10                  15
Trp Trp Lys Lys His Leu Met Arg Leu His Pro Trp Trp Lys Glu His
```

-continued

```
                    20                  25                  30
Leu Thr Arg Leu Lys Ala Trp Trp Lys Lys His Leu Met Arg Leu His
             35                  40                  45

Pro Trp Trp Arg Glu His Leu Thr Lys Phe Asn Val Trp Arg Lys Arg
         50                  55                  60

His Leu Glu Ser Ser Asn Ser Gln Gln Lys Lys His Leu Gly Lys Leu
 65                  70                  75                  80

Arg Val Leu Gln Lys Lys His Leu Arg Asn Leu Arg Gly Gln Gln Lys
                 85                  90                  95

Glu Asp Leu Gly Arg Ser His Gly Arg Lys Lys Met Thr Gln Leu Arg
            100                 105                 110

Gln Lys Lys Lys Lys Lys Lys Lys Lys Lys Lys Lys Lys Lys Lys Lys
            115                 120                 125

Lys Lys Lys Lys Lys Lys Lys Lys Lys Lys Lys Lys Lys Lys Lys Lys
        130                 135                 140

Lys Lys Lys Xaa Lys Lys Lys Lys Lys Lys
145                 150

<210> SEQ ID NO 472
<211> LENGTH: 466
<212> TYPE: PRT
<213> ORGANISM: Homo sapiens
<220> FEATURE:
<221> NAME/KEY: VARIANT
<222> LOCATION: 329
<223> OTHER INFORMATION: Xaa = Any Amino Acid

<400> SEQUENCE: 472

Met Ser Pro Ala Lys Glu Thr Ser Glu Lys Phe Thr Trp Ala Ala Lys
 1               5                  10                  15

Gly Arg Pro Arg Lys Ile Ala Trp Glu Lys Lys Glu Thr Pro Val Lys
                20                  25                  30

Thr Gly Cys Val Ala Arg Val Thr Ser Asn Lys Thr Lys Val Leu Glu
            35                  40                  45

Lys Gly Arg Ser Lys Met Ile Ala Cys Pro Thr Lys Glu Ser Ser Thr
 50                  55                  60

Lys Ala Ser Ala Asn Asp Gln Arg Phe Pro Ser Glu Ser Lys Gln Glu
 65                  70                  75                  80

Glu Asp Glu Glu Tyr Ser Cys Asp Ser Arg Ser Leu Phe Glu Ser Ser
                 85                  90                  95

Ala Lys Ile Gln Val Cys Ile Pro Glu Ser Ile Tyr Gln Lys Val Met
            100                 105                 110

Glu Ile Asn Arg Glu Val Glu Glu Pro Pro Lys Lys Pro Ser Ala Phe
        115                 120                 125

Lys Pro Ala Ile Glu Met Gln Asn Ser Val Pro Asn Lys Ala Phe Glu
130                 135                 140

Leu Lys Asn Glu Gln Thr Leu Arg Ala Asp Pro Met Phe Pro Pro Glu
145                 150                 155                 160

Ser Lys Gln Lys Asp Tyr Glu Glu Asn Ser Trp Asp Ser Glu Ser Leu
                165                 170                 175

Cys Glu Thr Val Ser Gln Lys Asp Val Cys Leu Pro Lys Ala Thr His
            180                 185                 190

Gln Lys Glu Ile Asp Lys Ile Asn Gly Lys Leu Glu Glu Ser Pro Asn
        195                 200                 205

Lys Asp Gly Leu Leu Lys Ala Thr Cys Gly Met Lys Val Ser Ile Pro
210                 215                 220
```

```
Thr Lys Ala Leu Glu Leu Lys Asp Met Gln Thr Phe Lys Ala Glu Pro
225                 230                 235                 240

Pro Gly Lys Pro Ser Ala Phe Glu Pro Ala Thr Glu Met Gln Lys Ser
                245                 250                 255

Val Pro Asn Lys Ala Leu Glu Leu Lys Asn Glu Gln Thr Leu Arg Ala
            260                 265                 270

Asp Glu Ile Leu Pro Ser Glu Ser Lys Gln Lys Asp Tyr Glu Glu Asn
            275                 280                 285

Ser Trp Asp Thr Glu Ser Leu Cys Glu Thr Val Ser Gln Lys Asp Val
290                 295                 300

Cys Leu Pro Lys Ala Ala His Gln Lys Glu Ile Asp Lys Ile Asn Gly
305                 310                 315                 320

Lys Leu Glu Gly Ser Pro Gly Lys Xaa Gly Leu Leu Lys Ala Asn Cys
                325                 330                 335

Gly Met Lys Val Ser Ile Pro Thr Lys Ala Leu Glu Leu Met Asp Met
                340                 345                 350

Gln Thr Phe Lys Ala Glu Pro Pro Glu Lys Pro Ser Ala Phe Glu Pro
                355                 360                 365

Ala Ile Glu Met Gln Lys Ser Val Pro Asn Lys Ala Leu Glu Leu Lys
            370                 375                 380

Asn Glu Gln Thr Leu Arg Ala Asp Glu Ile Leu Pro Ser Glu Ser Lys
385                 390                 395                 400

Gln Lys Asp Tyr Glu Glu Ser Ser Trp Asp Ser Glu Ser Leu Cys Glu
                405                 410                 415

Thr Val Ser Gln Lys Asp Val Cys Leu Pro Lys Ala Ala His Gln Lys
            420                 425                 430

Glu Ile Asp Lys Ile Asn Gly Lys Leu Glu Gly Lys Asn Arg Phe Leu
            435                 440                 445

Phe Lys Asn His Leu Thr Lys Tyr Phe Ser Lys Leu Met Arg Lys Asp
            450                 455                 460

Ile Leu
465

<210> SEQ ID NO 473
<211> LENGTH: 445
<212> TYPE: PRT
<213> ORGANISM: Homo sapiens

<400> SEQUENCE: 473

Lys Glu Ile Asp Lys Ile Asn Gly Lys Leu Glu Gly Ser Pro Val Lys
1               5                   10                  15

Asp Gly Leu Leu Lys Ala Asn Cys Gly Met Lys Val Ser Ile Pro Thr
                20                  25                  30

Lys Ala Leu Glu Leu Met Asp Met Gln Thr Phe Lys Ala Glu Pro Pro
                35                  40                  45

Glu Lys Pro Ser Ala Phe Glu Pro Ala Ile Glu Met Gln Lys Ser Val
            50                  55                  60

Pro Asn Lys Ala Leu Glu Leu Lys Asn Glu Gln Thr Leu Arg Ala Asp
65                  70                  75                  80

Glu Ile Leu Pro Ser Glu Ser Lys Gln Lys Asp Tyr Glu Glu Ser Ser
                85                  90                  95

Trp Asp Ser Glu Ser Leu Cys Glu Thr Val Ser Gln Lys Asp Val Cys
            100                 105                 110

Leu Pro Lys Ala Ala His Gln Lys Glu Ile Asp Lys Ile Asn Gly Lys
```

```
            115                 120                 125
Leu Glu Glu Ser Pro Asp Asn Asp Gly Phe Leu Lys Ala Pro Cys Arg
    130                 135                 140

Met Lys Val Ser Ile Pro Thr Lys Ala Leu Glu Leu Met Asp Met Gln
145                 150                 155                 160

Thr Phe Lys Ala Glu Pro Pro Glu Lys Pro Ser Ala Phe Glu Pro Ala
                165                 170                 175

Ile Glu Met Gln Lys Ser Val Pro Asn Lys Ala Leu Glu Leu Lys Asn
                    180                 185                 190

Glu Gln Thr Leu Arg Ala Asp Gln Met Phe Pro Ser Glu Ser Lys Gln
                195                 200                 205

Lys Lys Val Glu Glu Asn Ser Trp Asp Ser Glu Ser Leu Arg Glu Thr
    210                 215                 220

Val Ser Gln Lys Asp Val Cys Val Pro Lys Ala Thr His Gln Lys Glu
225                 230                 235                 240

Met Asp Lys Ile Ser Gly Lys Leu Glu Asp Ser Thr Ser Leu Ser Lys
                    245                 250                 255

Ile Leu Asp Thr Val His Ser Cys Glu Arg Ala Arg Glu Leu Gln Lys
                260                 265                 270

Asp His Cys Glu Gln Arg Thr Gly Lys Met Glu Gln Met Lys Lys Lys
    275                 280                 285

Phe Cys Val Leu Lys Lys Leu Ser Glu Ala Lys Glu Ile Lys Ser
290                 295                 300

Gln Leu Glu Asn Gln Lys Val Lys Trp Glu Gln Glu Leu Cys Ser Val
305                 310                 315                 320

Arg Leu Thr Leu Asn Gln Glu Glu Glu Lys Arg Arg Asn Ala Asp Ile
                    325                 330                 335

Leu Asn Glu Lys Ile Arg Glu Glu Leu Gly Arg Ile Glu Glu Gln His
                340                 345                 350

Arg Lys Glu Leu Glu Val Lys Gln Gln Leu Glu Gln Ala Leu Arg Ile
    355                 360                 365

Gln Asp Ile Glu Leu Lys Ser Val Glu Ser Asn Leu Asn Gln Val Ser
    370                 375                 380

His Thr His Glu Asn Glu Asn Tyr Leu Leu His Glu Asn Cys Met Leu
385                 390                 395                 400

Lys Lys Glu Ile Ala Met Leu Lys Leu Glu Ile Ala Thr Leu Lys His
                    405                 410                 415

Gln Tyr Gln Glu Lys Glu Asn Lys Tyr Phe Glu Asp Ile Lys Ile Leu
                420                 425                 430

Lys Glu Lys Asn Ala Glu Leu Gln Met Thr Pro Arg Ala
    435                 440                 445

<210> SEQ ID NO 474
<211> LENGTH: 3865
<212> TYPE: DNA
<213> ORGANISM: Homo sapiens

<400> SEQUENCE: 474
tccgagctga ttacagacac caaggaagat gctgtaaaga gtcagcagcc acagccctgg      60
ctagctggcc ctgtgggcat ttattagtaa agttttaatg acaaaagctt tgagtcaaca     120
cacccgtggg taattaacct ggtcatcccc accctggaga gccatcctgc ccatgggtga     180
tcaaagaagg aacatctgca ggaacacctg atgaggctgc acccttggcg gaaagaacac     240
ctgacacagc tgaaagcttg gtggaaaaaa cacctgatga ggctgcaccc ttggtggaaa     300
```

```
gaacacctga cacggctgaa agcttggtgg aaaaaacacc tgatgaggct gcatccttgg      360
tggagggaac atctgacaaa attcaatgtt tggagaaagc gacatctgga aagttcgaac      420
agtcagcaga agaaacacct agggaaatta cgagtcctgc aaaagaaaca tctgagaaat      480
ttacgtggcc agcaaaagga agacctagga agatcgcatg ggagaaaaaa gaagacacac      540
ctagggaaat tatgagtccc gcaaaagaaa catctgagaa atttacgtgg gcagcaaaag      600
gaagacctag gaagatcgca tgggagaaaa aagaaacacc tgtaaagact ggatgcgtgg      660
caagagtaac atctaataaa actaaagttt tggaaaaagg aagatctaag atgattgcat      720
gtcctacaaa agaatcatct acaaaagcaa gtgccaatga tcagaggttc ccatcagaat      780
ccaaacaaga ggaagatgaa gaatattctt gtgattctcg gagtctcttt gagagttctg      840
caaagattca agtgtgtata cctgagtcta tatcaaaaa agtaatggag ataaatagag      900
aagtagaaga gcctcctaag aagccatctg ccttcaagcc tgccattgaa atgcaaaact      960
ctgttccaaa taaagccttt gaattgaaga atgaacaaac attgagagca gatccgatgt     1020
tcccaccaga atccaaacaa aaggactatg aagaaaattc ttgggattct gagagtctct     1080
gtgagactgt ttcacagaag gatgtgtgtt tacccaaggc tacacatcaa aaagaaatag     1140
ataaaataaa tggaaaatta gaagagtctc taataaaga tggtcttctg aaggctacct     1200
gcggaatgaa agtttctatt ccaactaaag ccttagaatt gaaggacatg caaactttca     1260
aagcagagcc tccggggaag ccatctgcct tcgagcctgc cactgaaatg caaaagtctg     1320
tcccaaataa agccttggaa ttgaaaaatg aacaaacatt gagagcagat gagatactcc     1380
catcagaatc caaacaaaag gactatgaag aaagttcttg ggattctgag agtctctgtg     1440
agactgtttc acagaaggat gtgtgtttac ccaaggctrc rcatcaaaaa gaaatagata     1500
aaataaatgg aaaattagaa gggtctcctg ttaaagatgg tcttctgaag gctaactgcg     1560
gaatgaaagt ttctattcca actaaagcct tagaattgat ggacatgcaa actttcaaag     1620
cagagcctcc cgagaagcca tctgccttcg agcctgccat tgaaatgcaa aagtctgttc     1680
caaataaagc cttggaattg aagaatgaac aaacattgag agcagatgag atactcccat     1740
cagaatccaa acaaaaggac tatgaagaaa gttcttggga ttctgagagt ctctgtgaga     1800
ctgtttcaca gaaggatgtg tgtttaccca aggctcrca tcaaaaagaa atagataaaa     1860
taaatggaaa attagaagag tctcctgata tgatggtttt tctgaaggct ccctgcagaa     1920
tgaaagtttc tattccaact aaagccttag aattgatgga catgcaaact ttcaaagcag     1980
agcctcccga gaagccatct gccttcgagc tgccattgaa atgcaaaag tctgttccaa     2040 ataaagccttt ggaattgaag aatgaacaaa cattgagagc agatcagatg ttcccttcag     2100
aatcaaaaca aagaasgtt gaagaaaatt cttgggattc tgagagtctc cgtgagactg     2160
tttcacagaa ggatgtgtgt gtacccaagg ctacacatca aaagaaatg gataaaataa     2220 gtggaaaatt agaagattca actagcctat caaaaatctt ggatacagtt cattcttgtg     2280
aaagagcaag ggaacttcaa aaagatcact gtgaacaacg tacaggaaaa atggaacaaa     2340
tgaaaaagaa gttttgtgta ctgaaaaaga aactgtcaga agcaaaagaa ataaaatcac     2400
agttagagaa ccaaaaagtt aaatgggaac aagagctctg cagtgtgaga ttgactttaa     2460
accaagaaga agagaagaga agaaatgccg atatattaaa tgaaaaaatt agggaagaat     2520
taggaagaat cgaagagcag cataggaaag agttagaagt gaaacaacaa cttgaacagg     2580
ctctcagaat acaagatata gaattgaaga gtgtagaaag taatttgaat caggtttctc     2640
```

-continued

```
acactcatga aaatgaaaat tatctcttac atgaaaattg catgttgaaa aaggaaattg    2700
ccatgctaaa actggaaata gccacactga acaccaata ccaggaaaag gaaaataaat    2760
actttgagga cattaagatt ttaaaagaaa agaatgctga acttcagatg accctaaaac    2820
tgaaagagga atcattaact aaaagggcat ctcaatatag tgggcagctt aaagttctga    2880
tagctgagaa cacaatgctc acttctaaat tgaaggaaaa acaagacaaa gaaatactag    2940
aggcagaaat tgaatcacac catcctagac tggcttctgc tgtacaagac catgatcaaa    3000
ttgtgacatc aagaaaaagt caagaacctg cttccacat tgcaggagat gcttgtttgc    3060
aaagaaaaat gaatgttgat gtgagtagta cgatatataa caatgaggtg ctccatcaac    3120
cactttctga agctcaaagg aaatccaaaa gcctaaaaat taatctcaat tatgcmggag    3180
atgctctaag agaaaataca ttggtttcag aacatgcaca aagagaccaa cgtgaaacac    3240
agtgtcaaat gaaggaagct gaacacatgt atcaaaacga acaagataat gtgaacaaac    3300
acactgaaca gcaggagtct ctagatcaga aattatttca actacaaagc aaaaatatgt    3360
ggcttcaaca gcaattagtt catgcacata agaaagctga caacaaaagc aagataacaa    3420
ttgatattca ttttcttgag aggaaaatgc aacatcatct cctaaaagag aaaaatgagg    3480
agatatttaa ttacaataac catttaaaaa accgtatata tcaatatgaa aaagagaaag    3540
cagaaacaga aaactcatga gagacaagca gtaagaaact tcttttggag aaacaacaga    3600
ccagatcttt actcacaact catgctagga ggccagtcct agcatcacct tatgttgaaa    3660
atcttaccaa tagtctgtgt caacagaata cttattttag aagaaaaatt catgatttct    3720
tcctgaagcc tacagacata aaataacagt gtgaagaatt acttgttcac gaattgcata    3780
aagctgcaca ggattcccat ctaccctgat gatgcagcag acatcattca atccaaccag    3840
aatctcgctc tgtcactcag gctgg                                         3865
```

<210> SEQ ID NO 475
<211> LENGTH: 1002
<212> TYPE: PRT
<213> ORGANISM: Homo sapiens
<220> FEATURE:
<221> NAME/KEY: VARIANT
<222> LOCATION: 310, 429, 522
<223> OTHER INFORMATION: Xaa = Any Amino Acid

<400> SEQUENCE: 475

```
Met Ser Pro Ala Lys Glu Thr Ser Glu Lys Phe Thr Trp Ala Ala Lys
  1               5                  10                  15

Gly Arg Pro Arg Lys Ile Ala Trp Glu Lys Lys Glu Thr Pro Val Lys
                 20                  25                  30

Thr Gly Cys Val Ala Arg Val Thr Ser Asn Lys Thr Lys Val Leu Glu
             35                  40                  45

Lys Gly Arg Ser Lys Met Ile Ala Cys Pro Thr Lys Glu Ser Ser Thr
         50                  55                  60

Lys Ala Ser Ala Asn Asp Gln Arg Phe Pro Ser Glu Ser Lys Gln Glu
 65                  70                  75                  80

Glu Asp Glu Glu Tyr Ser Cys Asp Ser Arg Ser Leu Phe Glu Ser Ser
                 85                  90                  95

Ala Lys Ile Gln Val Cys Ile Pro Glu Ser Ile Tyr Gln Lys Val Met
            100                 105                 110

Glu Ile Asn Arg Glu Val Glu Glu Pro Pro Lys Lys Pro Ser Ala Phe
        115                 120                 125

Lys Pro Ala Ile Glu Met Gln Asn Ser Val Pro Asn Lys Ala Phe Glu
```

-continued

```
            130                 135                 140
Leu Lys Asn Glu Gln Thr Leu Arg Ala Asp Pro Met Phe Pro Pro Glu
145                 150                 155                 160

Ser Lys Gln Lys Asp Tyr Glu Glu Asn Ser Trp Asp Ser Glu Ser Leu
                165                 170                 175

Cys Glu Thr Val Ser Gln Lys Asp Val Cys Leu Pro Lys Ala Thr His
            180                 185                 190

Gln Lys Glu Ile Asp Lys Ile Asn Gly Lys Leu Glu Ser Pro Asn
        195                 200                 205

Lys Asp Gly Leu Leu Lys Ala Thr Cys Gly Met Lys Val Ser Ile Pro
210                 215                 220

Thr Lys Ala Leu Glu Leu Lys Asp Met Gln Thr Phe Lys Ala Glu Pro
225                 230                 235                 240

Pro Gly Lys Pro Ser Ala Phe Glu Pro Ala Thr Glu Met Gln Lys Ser
                245                 250                 255

Val Pro Asn Lys Ala Leu Glu Leu Lys Asn Glu Gln Thr Leu Arg Ala
                260                 265                 270

Asp Glu Ile Leu Pro Ser Glu Ser Lys Gln Lys Asp Tyr Glu Glu Ser
            275                 280                 285

Ser Trp Asp Ser Glu Ser Leu Cys Glu Thr Val Ser Gln Lys Asp Val
        290                 295                 300

Cys Leu Pro Lys Ala Xaa His Gln Lys Glu Ile Asp Lys Ile Asn Gly
305                 310                 315                 320

Lys Leu Glu Gly Ser Pro Val Lys Asp Gly Leu Leu Lys Ala Asn Cys
                325                 330                 335

Gly Met Lys Val Ser Ile Pro Thr Lys Ala Leu Glu Leu Met Asp Met
                340                 345                 350

Gln Thr Phe Lys Ala Glu Pro Pro Glu Lys Pro Ser Ala Phe Glu Pro
            355                 360                 365

Ala Ile Glu Met Gln Lys Ser Val Pro Asn Lys Ala Leu Glu Leu Lys
        370                 375                 380

Asn Glu Gln Thr Leu Arg Ala Asp Glu Ile Leu Pro Ser Glu Ser Lys
385                 390                 395                 400

Gln Lys Asp Tyr Glu Glu Ser Ser Trp Asp Ser Glu Ser Leu Cys Glu
                405                 410                 415

Thr Val Ser Gln Lys Asp Val Cys Leu Pro Lys Ala Xaa His Gln Lys
                420                 425                 430

Glu Ile Asp Lys Ile Asn Gly Lys Leu Glu Glu Ser Pro Asp Asn Asp
            435                 440                 445

Gly Phe Leu Lys Ala Pro Cys Arg Met Lys Val Ser Ile Pro Thr Lys
        450                 455                 460

Ala Leu Glu Leu Met Asp Met Gln Thr Phe Lys Ala Glu Pro Pro Glu
465                 470                 475                 480

Lys Pro Ser Ala Phe Glu Pro Ala Ile Glu Met Gln Lys Ser Val Pro
                485                 490                 495

Asn Lys Ala Leu Glu Leu Lys Asn Glu Gln Thr Leu Arg Ala Asp Gln
                500                 505                 510

Met Phe Pro Ser Glu Ser Lys Gln Lys Xaa Val Glu Glu Asn Ser Trp
            515                 520                 525

Asp Ser Glu Ser Leu Arg Glu Thr Val Ser Gln Lys Asp Val Cys Val
        530                 535                 540

Pro Lys Ala Thr His Gln Lys Glu Met Asp Lys Ile Ser Gly Lys Leu
545                 550                 555                 560
```

-continued

```
Glu Asp Ser Thr Ser Leu Ser Lys Ile Leu Asp Thr Val His Ser Cys
                565                 570                 575
Glu Arg Ala Arg Glu Leu Gln Lys Asp His Cys Glu Gln Arg Thr Gly
            580                 585                 590
Lys Met Glu Gln Met Lys Lys Lys Phe Cys Val Leu Lys Lys Lys Leu
        595                 600                 605
Ser Glu Ala Lys Glu Ile Lys Ser Gln Leu Glu Asn Gln Lys Val Lys
    610                 615                 620
Trp Glu Gln Glu Leu Cys Ser Val Arg Leu Thr Leu Asn Gln Glu Glu
625                 630                 635                 640
Glu Lys Arg Arg Asn Ala Asp Ile Leu Asn Glu Lys Ile Arg Glu Glu
                645                 650                 655
Leu Gly Arg Ile Glu Glu Gln His Arg Lys Glu Leu Glu Val Lys Gln
            660                 665                 670
Gln Leu Glu Gln Ala Leu Arg Ile Gln Asp Ile Glu Leu Lys Ser Val
        675                 680                 685
Glu Ser Asn Leu Asn Gln Val Ser His Thr His Glu Asn Glu Asn Tyr
    690                 695                 700
Leu Leu His Glu Asn Cys Met Leu Lys Lys Glu Ile Ala Met Leu Lys
705                 710                 715                 720
Leu Glu Ile Ala Thr Leu Lys His Gln Tyr Gln Glu Lys Glu Asn Lys
                725                 730                 735
Tyr Phe Glu Asp Ile Lys Ile Leu Lys Glu Lys Asn Ala Glu Leu Gln
            740                 745                 750
Met Thr Leu Lys Leu Lys Glu Glu Ser Leu Thr Lys Arg Ala Ser Gln
        755                 760                 765
Tyr Ser Gly Gln Leu Lys Val Leu Ile Ala Glu Asn Thr Met Leu Thr
    770                 775                 780
Ser Lys Leu Lys Glu Lys Gln Asp Lys Glu Ile Leu Glu Ala Glu Ile
785                 790                 795                 800
Glu Ser His His Pro Arg Leu Ala Ser Ala Val Gln Asp His Asp Gln
                805                 810                 815
Ile Val Thr Ser Arg Lys Ser Gln Glu Pro Ala Phe His Ile Ala Gly
            820                 825                 830
Asp Ala Cys Leu Gln Arg Lys Met Asn Val Asp Val Ser Ser Thr Ile
        835                 840                 845
Tyr Asn Asn Glu Val Leu His Gln Pro Leu Ser Glu Ala Gln Arg Lys
    850                 855                 860
Ser Lys Ser Leu Lys Ile Asn Leu Asn Tyr Ala Gly Asp Ala Leu Arg
865                 870                 875                 880
Glu Asn Thr Leu Val Ser Glu His Ala Gln Arg Asp Gln Arg Glu Thr
                885                 890                 895
Gln Cys Gln Met Lys Glu Ala Glu His Met Tyr Gln Asn Glu Gln Asp
            900                 905                 910
Asn Val Asn Lys His Thr Glu Gln Gln Glu Ser Leu Asp Gln Lys Leu
        915                 920                 925
Phe Gln Leu Gln Ser Lys Asn Met Trp Leu Gln Gln Gln Leu Val His
    930                 935                 940
Ala His Lys Lys Ala Asp Asn Lys Ser Lys Ile Thr Ile Asp Ile His
945                 950                 955                 960
Phe Leu Glu Arg Lys Met Gln His His Leu Leu Lys Glu Lys Asn Glu
                965                 970                 975
```

Glu Ile Phe Asn Tyr Asn Asn His Leu Lys Asn Arg Ile Tyr Gln Tyr
          980                 985                 990

Glu Lys Glu Lys Ala Glu Thr Glu Asn Ser
        995                 1000

<210> SEQ ID NO 476
<211> LENGTH: 356
<212> TYPE: DNA
<213> ORGANISM: Homo sapiens

<400> SEQUENCE: 476

| | | | | | | |
|---|---|---|---|---|---|---|
| aggtctgccg | gaaatgttag | gcaccccaac | tcaagtccca | ggccccaggc | atctttcctg | 60 |
| ccctgccttg | cttggcccat | ccagtccagg | cgcctggagc | aagtgctcag | ctacttctcc | 120 |
| tgcactttga | agacccctc | ccactcctgg | cctcacattt | ctctgtgtga | tccccactt | 180 |
| ctgggctctg | ccaccccaca | gtgggaaagg | ccaccctaga | agaagtccg | ctggcaccca | 240 |
| taggaagggg | cctcaggagc | aggaagggcc | aggaccagaa | ccttgcccac | ggcaactgcc | 300 |
| ttcctgcctc | tccccttcct | cctctgctct | tgatctgtgt | ttcaataaat | taatgt | 356 |

<210> SEQ ID NO 477
<211> LENGTH: 1876
<212> TYPE: DNA
<213> ORGANISM: Homo sapiens

<400> SEQUENCE: 477

| | | | | | | |
|---|---|---|---|---|---|---|
| atgacctgcg | gatcaggatt | tggtgggcgc | gccttcagct | gcatctcggc | ctgcgggccg | 60 |
| cgccccggcc | gctgctgcat | caccgccgcc | ccctaccgtg | gcatctcctg | ctaccgcggc | 120 |
| ctcaccgggg | gcttcggcag | ccacagcgtg | tgcggaggct | ttcgggccgg | ctcctgcgga | 180 |
| cgcagcttcg | gctaccgctc | cggggcgtg | tgcgggccca | gtcccccatg | catcaccacc | 240 |
| gtgtcggtca | acgagagcct | cctcacgccc | ctcaacctgg | agatcgaccc | caacgcgcag | 300 |
| tgcgtgaagc | aggaggagaa | ggagcagatc | aagtccctca | acagcaggtt | cgcggccttc | 360 |
| atcgacaagg | tgcgcttcct | ggagcagcag | aacaaactgc | tggagacaaa | gctgcagttc | 420 |
| taccagaacc | gcgagtgttg | ccagagcaac | ctggagcccc | tgtttgaggg | ctacatcgag | 480 |
| actctgcggc | gggaggccga | gtgcgtggag | gccgacagcg | gaggctggc | ctcagagctt | 540 |
| aaccacgtgc | aggaggtgct | ggagggctac | aagaagaagt | atgaggagga | ggtttctctg | 600 |
| agagcaacag | ctgagaacga | gtttgtggct | ctgaagaagg | atgtggactg | cgcctacctc | 660 |
| cgcaagtcag | acctggaggc | caacgtggag | gccctgatcc | aggagatcga | cttcctgagg | 720 |
| cggctgtatg | aggaggagat | ccgcattctc | cagtcgcaca | tctcagacac | ctccgtggtt | 780 |
| gtcaagctgg | acaacagccg | ggacctgaac | atggactgca | tcattgccga | gattaaggca | 840 |
| cagtatgacg | acattgtcac | ccgcagccgg | gccgaggccg | agtcctggta | ccgcagcaag | 900 |
| tgtgaggaga | tgaaggccac | ggtgatcagg | cacggggaga | ccctgcgccg | caccaaggag | 960 |
| gagatcaatg | agctgaaccg | catgatccaa | aggctgacgg | ccgaggtgga | gaatgccaag | 1020 |
| tgccagaact | ccaagctgga | ggccgcggtg | gctcagtctg | agcagcaggg | tgaggcagcc | 1080 |
| ctcagtgatg | cccgctgcaa | gctggccgag | ctggagggcg | ccctgcagaa | ggccaagcag | 1140 |
| gacatggcct | gcctgatcag | ggagtaccag | gaggtgatga | actccaagct | gggcctggac | 1200 |
| atcgagatcg | ccacctacag | gcgcctgctg | gagggcgagg | agcagaggct | atgtgaaggc | 1260 |
| attggggctg | tgaatgtctg | tgtcagcagc | tcccggggcg | gggtcgtgtg | cggggaccct | 1320 |
| tgcgtgtcag | gctcccggcc | agtgactggc | agtgtctgca | gcgctccgtg | caacgggaac | 1380 |

-continued

```
gtggcggtga gcaccggcct gtgtgcgccc tgcggccaat tgaacaccac ctgcggaggg    1440
ggttcctgcg gcgtgggctc ctgtggtatc agctccctgg gtgtggggtc ttgcggcagc    1500
agctgccgga aatgttaggc accccaactc aagtcccagg ccccaggcat ctttcctgcc    1560
ctgccttgct tggcccatcc agtccaggcg cctggagcaa gtgctcagct acttctcctg    1620
cactttgaaa gacccctccc actcctggcc tcacatttct ctgtgtgatc ccccacttct    1680
gggctctgcc accccacagt gggaaaggcc accctagaaa gaagtccgct ggcacccata    1740
ggaaggggcc tcaggagcag gaagggccag gaccagaacc ttgcccacgg caactgccttt   1800 cctgcctctc cccttcctcc tctgctcttg atctgtgttt caataaatta atgtagccaa    1860
aaaaaaaaaa aaaaa                                                     1876
```

<210> SEQ ID NO 478
<211> LENGTH: 505
<212> TYPE: PRT
<213> ORGANISM: Homo sapiens

<400> SEQUENCE: 478

```
Met Thr Cys Gly Ser Gly Phe Gly Gly Arg Ala Phe Ser Cys Ile Ser
  1               5                   10                  15

Ala Cys Gly Pro Arg Pro Gly Arg Cys Cys Ile Thr Ala Ala Pro Tyr
             20                  25                  30

Arg Gly Ile Ser Cys Tyr Arg Gly Leu Thr Gly Gly Phe Gly Ser His
         35                  40                  45

Ser Val Cys Gly Gly Phe Arg Ala Gly Ser Cys Gly Arg Ser Phe Gly
     50                  55                  60

Tyr Arg Ser Gly Gly Val Cys Gly Pro Ser Pro Cys Ile Thr Thr
 65                  70                  75                  80

Val Ser Val Asn Glu Ser Leu Leu Thr Pro Leu Asn Leu Glu Ile Asp
                 85                  90                  95

Pro Asn Ala Gln Cys Val Lys Gln Glu Glu Lys Glu Gln Ile Lys Ser
            100                 105                 110

Leu Asn Ser Arg Phe Ala Ala Phe Ile Asp Lys Val Arg Phe Leu Glu
        115                 120                 125

Gln Gln Asn Lys Leu Leu Glu Thr Lys Leu Gln Phe Tyr Gln Asn Arg
    130                 135                 140

Glu Cys Cys Gln Ser Asn Leu Glu Pro Leu Phe Glu Gly Tyr Ile Glu
145                 150                 155                 160

Thr Leu Arg Arg Glu Ala Glu Cys Val Glu Ala Asp Ser Gly Arg Leu
                165                 170                 175

Ala Ser Glu Leu Asn His Val Gln Glu Val Leu Glu Gly Tyr Lys Lys
            180                 185                 190

Lys Tyr Glu Glu Glu Val Ser Leu Arg Ala Thr Ala Glu Asn Glu Phe
        195                 200                 205

Val Ala Leu Lys Lys Asp Val Asp Cys Ala Tyr Leu Arg Lys Ser Asp
    210                 215                 220

Leu Glu Ala Asn Val Glu Ala Leu Ile Gln Glu Ile Asp Phe Leu Arg
225                 230                 235                 240

Arg Leu Tyr Glu Glu Glu Ile Arg Ile Leu Gln Ser His Ile Ser Asp
                245                 250                 255

Thr Ser Val Val Val Lys Leu Asp Asn Ser Arg Asp Leu Asn Met Asp
            260                 265                 270

Cys Ile Ile Ala Glu Ile Lys Ala Gln Tyr Asp Asp Ile Val Thr Arg
```

|  | | | 275 | | | | 280 | | | | 285 | | |
|---|---|---|---|---|---|---|---|---|---|---|---|---|---|

Ser Arg Ala Glu Ala Glu Ser Trp Tyr Arg Ser Lys Cys Glu Glu Met
290                 295                 300

Lys Ala Thr Val Ile Arg His Gly Glu Thr Leu Arg Arg Thr Lys Glu
305                 310                 315                 320

Glu Ile Asn Glu Leu Asn Arg Met Ile Gln Arg Leu Thr Ala Glu Val
            325                 330                 335

Glu Asn Ala Lys Cys Gln Asn Ser Lys Leu Glu Ala Ala Val Ala Gln
                340                 345                 350

Ser Glu Gln Gln Gly Glu Ala Ala Leu Ser Asp Ala Arg Cys Lys Leu
            355                 360                 365

Ala Glu Leu Glu Gly Ala Leu Gln Lys Ala Lys Gln Asp Met Ala Cys
370                 375                 380

Leu Ile Arg Glu Tyr Gln Glu Val Met Asn Ser Lys Leu Gly Leu Asp
385                 390                 395                 400

Ile Glu Ile Ala Thr Tyr Arg Arg Leu Leu Glu Gly Glu Glu Gln Arg
                405                 410                 415

Leu Cys Glu Gly Ile Gly Ala Val Asn Val Cys Val Ser Ser Ser Arg
            420                 425                 430

Gly Gly Val Val Cys Gly Asp Leu Cys Val Ser Gly Ser Arg Pro Val
            435                 440                 445

Thr Gly Ser Val Cys Ser Ala Pro Cys Asn Gly Asn Val Ala Val Ser
450                 455                 460

Thr Gly Leu Cys Ala Pro Cys Gly Gln Leu Asn Thr Thr Cys Gly Gly
465                 470                 475                 480

Gly Ser Cys Gly Val Gly Ser Cys Gly Ile Ser Ser Leu Gly Val Gly
                485                 490                 495

Ser Cys Gly Ser Ser Cys Arg Lys Cys
            500                 505

<210> SEQ ID NO 479
<211> LENGTH: 221
<212> TYPE: DNA
<213> ORGANISM: Homo sapiens
<220> FEATURE:
<221> NAME/KEY: misc_feature
<222> LOCATION: 22
<223> OTHER INFORMATION: n = A,T,C or G

<400> SEQUENCE: 479
ggtccattcc tttcctcgcg tnggggtttc tctgtgtcag cgagcctcgg tacactgatt      60
tccgatcaaa agaatcatca tctttacctt gactttt cag ggaattactg aactttcttc     120
tcagaagata gggcacagcc attgccttgg cctcacttga agggtctgca tttgggtcct     180
ctggtctctt gccaagtttc ccagccactc gagggagaaa t                         221

<210> SEQ ID NO 480
<211> LENGTH: 36
<212> TYPE: DNA
<213> ORGANISM: Artificial Sequence
<220> FEATURE:
<223> OTHER INFORMATION: PCR primer

<400> SEQUENCE: 480
cggcgaattc accatgggaa caagagctct gcagtg                                36

<210> SEQ ID NO 481
<211> LENGTH: 62

<212> TYPE: DNA
<213> ORGANISM: Artificial Sequence
<220> FEATURE:
<223> OTHER INFORMATION: PCR primer

<400> SEQUENCE: 481

```
cggcaagctt ttaatggtga tggtgatgat gtataacttc tgtttctgct ttctcttttt    60
ca                                                                    62
```

<210> SEQ ID NO 482
<211> LENGTH: 972
<212> TYPE: DNA
<213> ORGANISM: Homo sapiens

<400> SEQUENCE: 482

```
atgggaacaa gagctctgca gtgtgaggtt tctcacactc atgaaaatga aaattatctc    60
ttacatgaaa attgcatgtt gaaaaaggaa attgccatgc taaaactgga atagccaca    120
ctgaaacacc aataccagga aaggaaaat aaatactttg aggacattaa gattttaaaa    180
gaaaagaatg ctgaacttca gatgacccta aaactgaaag aggaatcatt aactaaaagg    240
gcatctcaat atagtgggca gcttaaagtt ctgatagctg agaacacaat gctcacttct    300
aaattgaagg aaaacaaga caaagaaata ctagaggcag aaattgaatc acaccatcct    360
agactggctt ctgctgtaca agaccatgat caaattgtga catcaagaaa aagtcaagaa    420
cctgctttcc acattgcagg agatgcttgt ttgcaaagaa aaatgaatgt tgatgtgagt    480
agtacgatat ataacaatga ggtgctccat caaccacttt ctgaagctca aggaaatcc    540
aaaagcctaa aaattaatct caattatgcc ggagatgctc taagagaaaa tacattggtt    600
tcagaacatg cacaaagaga ccaacgtgaa acacagtgtc aaatgaagga agctgaacac    660
atgtatcaaa acgaacaaga taatgtgaac aaacacactg aacagcagga gtctctagat    720
cagaaattat ttcaactaca aagcaaaaat atgtggcttc aacagcaatt agttcatgca    780
cataagaaag ctgacaacaa agcaagata acaattgata ttcatttct tgagaggaaa    840
atgcaacatc atctcctaaa agagaaaaat gaggagatat ttaattacaa taaccattta    900
aaaaaccgta tatcaata tgaaaagag aaagcagaaa cagaagttat acatcatcac    960
catcaccatt aa                                                        972
```

<210> SEQ ID NO 483
<211> LENGTH: 323
<212> TYPE: PRT
<213> ORGANISM: Homo sapiens

<400> SEQUENCE: 483

```
Met Gly Thr Arg Ala Leu Gln Cys Glu Val Ser His Thr His Glu Asn
 1               5                  10                  15

Glu Asn Tyr Leu Leu His Glu Asn Cys Met Leu Lys Lys Glu Ile Ala
            20                  25                  30

Met Leu Lys Leu Glu Ile Ala Thr Leu Lys His Gln Tyr Gln Glu Lys
        35                  40                  45

Glu Asn Lys Tyr Phe Glu Asp Ile Lys Ile Leu Lys Glu Lys Asn Ala
    50                  55                  60

Glu Leu Gln Met Thr Leu Lys Leu Lys Glu Ser Leu Thr Lys Arg
65                  70                  75                  80

Ala Ser Gln Tyr Ser Gly Gln Leu Lys Val Leu Ile Ala Glu Asn Thr
                85                  90                  95
```

```
Met Leu Thr Ser Lys Leu Lys Glu Lys Gln Asp Lys Glu Ile Leu Glu
                100                 105                 110
Ala Glu Ile Glu Ser His His Pro Arg Leu Ala Ser Ala Val Gln Asp
            115                 120                 125
His Asp Gln Ile Val Thr Ser Arg Lys Ser Gln Glu Pro Ala Phe His
        130                 135                 140
Ile Ala Gly Asp Ala Cys Leu Gln Arg Lys Met Asn Val Asp Val Ser
145                 150                 155                 160
Ser Thr Ile Tyr Asn Asn Glu Val Leu His Gln Pro Leu Ser Glu Ala
                165                 170                 175
Gln Arg Lys Ser Lys Ser Leu Lys Ile Asn Leu Asn Tyr Ala Gly Asp
            180                 185                 190
Ala Leu Arg Glu Asn Thr Leu Val Ser Glu His Ala Gln Arg Asp Gln
        195                 200                 205
Arg Glu Thr Gln Cys Gln Met Lys Glu Ala Glu His Met Tyr Gln Asn
    210                 215                 220
Glu Gln Asp Asn Val Asn Lys His Thr Glu Gln Gln Glu Ser Leu Asp
225                 230                 235                 240
Gln Lys Leu Phe Gln Leu Gln Ser Lys Asn Met Trp Leu Gln Gln Gln
                245                 250                 255
Leu Val His Ala His Lys Lys Ala Asp Asn Lys Ser Lys Ile Thr Ile
            260                 265                 270
Asp Ile His Phe Leu Glu Arg Lys Met Gln His His Leu Leu Lys Glu
        275                 280                 285
Lys Asn Glu Glu Ile Phe Asn Tyr Asn Asn His Leu Lys Asn Arg Ile
    290                 295                 300
Tyr Gln Tyr Glu Lys Glu Lys Ala Glu Thr Glu Val Ile His His His
305                 310                 315                 320
His His His

<210> SEQ ID NO 484
<211> LENGTH: 1518
<212> TYPE: DNA
<213> ORGANISM: Homo sapiens

<400> SEQUENCE: 484
atgacctgcg atcaggatt tggtgggcgc gccttccgct gcatctcggc ctgcgggccg    60
cggcccggcc gctgctgcat caccgccgcc ccctaccgtg gcatctcctg ctaccgcggc   120
ctcaccgggg gcttcggcag ccacagcgtg tgcggaggct ttcgggccgg ctcctgcgga   180
cgcagcttcg gctaccgctc cggggggcgtg tgcgggccca gtcccccatg catcaccacc   240
gtgtcggtca acgagagcct cctcacgccc ctcaacctgg agatcgaccc caacgcgcag   300
tgcgtgaagc aggaggagaa ggagcagatc aagtccctca cagcaggtt cgcggccttc   360 atcgacaagg tgcgcttcct ggagcagcag aacaaactgc tggagacaaa gctgcagttc   420
taccagaacc gcgagtgttg ccagagcaac ctggagcccc tgtttgaggg ctacatcgag   480
actctgcggc gggaggccga gtgcgtggag gccgacagcg gaggctggc ctcagagctt   540 aaccacgtgc aggaggtgct ggagggctac aagaagaagt atgaggagga ggtttctctg   600
agagcaacag ctgagaacga gtttgtggct ctgaagaagg atgtgactg cgcctacctc   660 cgcaagtcag acctggaggc caacgtggag gccctgatcc aggagatcga cttcctgagg   720
cggctgtatg aggaggagat ccgcattctc cagtcgcaca tctcagacac ctccgtggtt   780
gtcaagctgg acaacagccg ggacctgaac atggactgca tcattgccga gattaaggca   840
```

```
cagtatgacg acattgtcac ccgcagccgg gccgaggccg agtcctggta ccgcagcaag      900
tgtgaggaga tgaaggccac ggtgatcagg cacggggaga ccctgcgccg caccaaggag      960
gagatcaatg agctgaaccg catgatccaa aggctgacgg ccgaggtgga aatgccaag     1020 tgccagaact ccaagctgga ggccgcggtg gcccagtctg agcagcaggg tgaggcagcc     1080
ctcagtgatg cccgctgcaa gctggccgag ctggagggcg ccctgcagaa ggccaagcag     1140
gacatggcct gcctgatcag ggagtaccag gaggtgatga actccaagct gggcctggac     1200
atcgagatcg ccacctacag cgcctgctg gagggcgagg agcagaggct atgtgaaggc     1260 attgggctg tgaatgtctg tgtcagcagc tcccgggcg gggtcgtgtg cggggacctc     1320
tgcgtgtcag gctcccggcc agtgactgg agtgtctgca cgctccgtg caacgggaac     1380 gtggcggtga gcaccggcct gtgtgcgccc tgcggccaat tgaacaccac ctgcggaggg     1440
ggttcctgcg cgtgggctc ctgtggtatc agctccctgg gtgtggggtc ttgcggcagc     1500
agctgccgga aatgttag                                                   1518
```

<210> SEQ ID NO 485
<211> LENGTH: 505
<212> TYPE: PRT
<213> ORGANISM: Homo sapiens

<400> SEQUENCE: 485

```
Met Thr Cys Gly Ser Gly Phe Gly Gly Arg Ala Phe Arg Cys Ile Ser
1               5                   10                  15

Ala Cys Gly Pro Arg Pro Gly Arg Cys Cys Ile Thr Ala Ala Pro Tyr
                20                  25                  30

Arg Gly Ile Ser Cys Tyr Arg Gly Leu Thr Gly Gly Phe Gly Ser His
            35                  40                  45

Ser Val Cys Gly Gly Phe Arg Ala Gly Ser Cys Gly Arg Ser Phe Gly
        50                  55                  60

Tyr Arg Ser Gly Gly Val Cys Gly Pro Ser Pro Cys Ile Thr Thr
65                  70                  75                  80

Val Ser Val Asn Glu Ser Leu Leu Thr Pro Leu Asn Leu Glu Ile Asp
                85                  90                  95

Pro Asn Ala Gln Cys Val Lys Gln Glu Glu Lys Glu Gln Ile Lys Ser
            100                 105                 110

Leu Asn Ser Arg Phe Ala Ala Phe Ile Asp Lys Val Arg Phe Leu Glu
        115                 120                 125

Gln Gln Asn Lys Leu Leu Glu Thr Lys Leu Gln Phe Tyr Gln Asn Arg
    130                 135                 140

Glu Cys Cys Gln Ser Asn Leu Glu Pro Leu Phe Glu Gly Tyr Ile Glu
145                 150                 155                 160

Thr Leu Arg Arg Glu Ala Glu Cys Val Glu Ala Asp Ser Gly Arg Leu
                165                 170                 175

Ala Ser Glu Leu Asn His Val Gln Glu Val Leu Glu Gly Tyr Lys Lys
            180                 185                 190

Lys Tyr Glu Glu Glu Val Ser Leu Arg Ala Thr Ala Glu Asn Glu Phe
        195                 200                 205

Val Ala Leu Lys Lys Asp Val Asp Cys Ala Tyr Leu Arg Lys Ser Asp
    210                 215                 220

Leu Glu Ala Asn Val Glu Ala Leu Ile Gln Glu Ile Asp Phe Leu Arg
225                 230                 235                 240

Arg Leu Tyr Glu Glu Glu Ile Arg Ile Leu Gln Ser His Ile Ser Asp
```

```
                245                 250                 255
Thr Ser Val Val Val Lys Leu Asp Asn Ser Arg Asp Leu Asn Met Asp
                260                 265                 270
Cys Ile Ile Ala Glu Ile Lys Ala Gln Tyr Asp Asp Ile Val Thr Arg
                275                 280                 285
Ser Arg Ala Glu Ala Glu Ser Trp Tyr Arg Ser Lys Cys Glu Glu Met
                290                 295                 300
Lys Ala Thr Val Ile Arg His Gly Glu Thr Leu Arg Arg Thr Lys Glu
305                 310                 315                 320
Glu Ile Asn Glu Leu Asn Arg Met Ile Gln Arg Leu Thr Ala Glu Val
                325                 330                 335
Glu Asn Ala Lys Cys Gln Asn Ser Lys Leu Glu Ala Ala Val Ala Gln
                340                 345                 350
Ser Glu Gln Gln Gly Glu Ala Ala Leu Ser Asp Ala Arg Cys Lys Leu
                355                 360                 365
Ala Glu Leu Glu Gly Ala Leu Gln Lys Ala Lys Gln Asp Met Ala Cys
                370                 375                 380
Leu Ile Arg Glu Tyr Gln Glu Val Met Asn Ser Lys Leu Gly Leu Asp
385                 390                 395                 400
Ile Glu Ile Ala Thr Tyr Arg Arg Leu Leu Glu Gly Glu Glu Gln Arg
                405                 410                 415
Leu Cys Glu Gly Ile Gly Ala Val Asn Val Cys Val Ser Ser Ser Arg
                420                 425                 430
Gly Gly Val Val Cys Gly Asp Leu Cys Val Ser Gly Ser Arg Pro Val
                435                 440                 445
Thr Gly Ser Val Cys Ser Ala Pro Cys Asn Gly Asn Val Ala Val Ser
                450                 455                 460
Thr Gly Leu Cys Ala Pro Cys Gly Gln Leu Asn Thr Thr Cys Gly Gly
465                 470                 475                 480
Gly Ser Cys Gly Val Gly Ser Cys Gly Ile Ser Ser Leu Gly Val Gly
                485                 490                 495
Ser Cys Gly Ser Ser Cys Arg Lys Cys
                500                 505

<210> SEQ ID NO 486
<211> LENGTH: 827
<212> TYPE: DNA
<213> ORGANISM: Homo sapiens

<400> SEQUENCE: 486
gcattctcca gtcgcacatc tcagacacct ccgtggttgt caagctggac aacagccggg    60
acctgaacat ggactgcatc attgccgaga ttaaggcaca gtatgacgac attgtcaccc   120
gcagccgggc cgaggccgag tcctggtacc gcagcaagtg tgaggagatg aaggccacgg   180
tgatcaggca cggggagacc ctgcgccgca ccaaggagga gatcaatgag ctgaaccgca   240
tgatccaaag gctgacggcc gaggtggaga tgccaagtgc cagaactcc aagctggagg   300
ccgcggtggc ccagtctgag cagcagggtg aggcagccct cagtgatgcc cgctgcaagc   360
tggccgagct ggagggcgcc ctgcagaagg ccaagcagga catggcctgc ctgatcaggg   420
agtaccagga ggtgatgaac tccaagctgg gcctggacat cgagatcgcc acctacaggc   480
gcctgctgga gggcgaggag cagaggctat gtgaaggcat tggggctgtg aatgtctgtg   540
tcagcagctc ccggggcggg gtcgtgtgcg gggacctctg cgtgtcaggc tcccggccag   600
tgactggcag tgtctgcagc gctccgtgca acgggaacgt ggcggtgagc accggcctgt   660
```

```
gtgcgccctg cggccaattg aacaccacct gcggagggg ttcctgcggc gtgggctcct    720
gtggtatcag ctccctgggt gtggggtctt gcggcagcag ctgccggaaa tgttaggcac    780
cccaactcaa gtcccaggcc ccaggcatct ttcctgccct gccttgc                 827
```

<210> SEQ ID NO 487
<211> LENGTH: 235
<212> TYPE: PRT
<213> ORGANISM: Homo sapiens

<400> SEQUENCE: 487

```
Met Asp Cys Ile Ile Ala Glu Ile Lys Ala Gln Tyr Asp Asp Ile Val
1               5                   10                  15

Thr Arg Ser Arg Ala Glu Ala Glu Ser Trp Tyr Arg Ser Lys Cys Glu
            20                  25                  30

Glu Met Lys Ala Thr Val Ile Arg His Gly Glu Thr Leu Arg Arg Thr
        35                  40                  45

Lys Glu Glu Ile Asn Glu Leu Asn Arg Met Ile Gln Arg Leu Thr Ala
    50                  55                  60

Glu Val Glu Asn Ala Lys Cys Gln Asn Ser Lys Leu Glu Ala Ala Val
65                  70                  75                  80

Ala Gln Ser Glu Gln Gln Gly Glu Ala Ala Leu Ser Asp Ala Arg Cys
                85                  90                  95

Lys Leu Ala Glu Leu Glu Gly Ala Leu Gln Lys Ala Lys Gln Asp Met
            100                 105                 110

Ala Cys Leu Ile Arg Glu Tyr Gln Glu Val Met Asn Ser Lys Leu Gly
        115                 120                 125

Leu Asp Ile Glu Ile Ala Thr Tyr Arg Arg Leu Leu Glu Gly Glu Glu
    130                 135                 140

Gln Arg Leu Cys Glu Gly Ile Gly Ala Val Asn Val Cys Val Ser Ser
145                 150                 155                 160

Ser Arg Gly Gly Val Val Cys Gly Asp Leu Cys Val Ser Gly Ser Arg
                165                 170                 175

Pro Val Thr Gly Ser Val Cys Ser Ala Pro Cys Asn Gly Asn Val Ala
            180                 185                 190

Val Ser Thr Gly Leu Cys Ala Pro Cys Gly Gln Leu Asn Thr Thr Cys
        195                 200                 205

Gly Gly Gly Ser Cys Gly Val Gly Ser Cys Gly Ile Ser Ser Leu Gly
    210                 215                 220

Val Gly Ser Cys Gly Ser Ser Cys Arg Lys Cys
225                 230                 235
```

<210> SEQ ID NO 488
<211> LENGTH: 9
<212> TYPE: PRT
<213> ORGANISM: Homo sapiens

<400> SEQUENCE: 488

```
Ser Leu Thr Lys Arg Ala Ser Gln Tyr
1               5
```

<210> SEQ ID NO 489
<211> LENGTH: 27
<212> TYPE: DNA
<213> ORGANISM: Homo sapiens

<400> SEQUENCE: 489

<210> SEQ ID NO 490
<211> LENGTH: 3288
<212> TYPE: DNA
<213> ORGANISM: Homo sapiens

<400> SEQUENCE: 490

| | | | | | |
|---|---|---|---|---|---|
| tcattaacta aaagggcatc tcaatat | | | | | 27 |

| | | | | | |
|---|---|---|---|---|---|
| atgaagttgc | tgatggtcct | catgctggcg | gccctctccc | agcactgcta | cgcaggctct | 60 |
| ggctgcccct | tattggagaa | tgtgatttcc | aagacaatca | atccacaagt | gtctaagact | 120 |
| gaatacaaag | aacttcttca | agagttcata | gacgacaatg | ccactacaaa | tgccatagat | 180 |
| gaattgaagg | aatgttttct | taaccaaacg | gatgaaactc | tgagcaatgt | tgaggtgttt | 240 |
| atgcaattaa | tatatgacag | cagtctttgt | gatttattta | tgagtccgc | aaagaaaca | 300 |
| tctgagaaat | ttacgtgggc | agcaaaagga | agacctagga | agatcgcatg | ggagaaaaaa | 360 |
| gaaacacctg | taaagactgg | atgcgtggca | agagtaacat | ctaataaaac | taagttttg | 420 |
| gaaaaaggaa | gatctaagat | gattgcatgt | cctacaaaag | aatcatctac | aaaagcaagt | 480 |
| gccaatgatc | agaggttccc | atcagaatcc | aaacaagagg | aagatgaaga | atattcttgt | 540 |
| gattctcgga | gtctctttga | gagttctgca | aagattcaag | tgtgtatacc | tgagtctata | 600 |
| tatcaaaaag | taatggagat | aaatagaaa | gtagaagagc | ctcctaagaa | gccatctgcc | 660 |
| ttcaagcctg | ccattgaaat | gcaaaactct | gttccaaata | aagcctttga | attgaagaat | 720 |
| gaacaaacat | tgagagcaga | tccgatgttc | ccaccagaat | ccaaacaaaa | ggactatgaa | 780 |
| gaaaattctt | gggattctga | gagtctctgt | gagactgttt | cacagaagga | tgtgtgttta | 840 |
| cccaaggcta | cacatcaaaa | agaaatagat | aaaataaatg | gaaaattaga | agagtctcct | 900 |
| aataaagatg | gtcttctgaa | ggctacctgc | ggaatgaaag | tttctattcc | aactaaagcc | 960 |
| ttagaattga | aggacatgca | aactttcaaa | gcagagcctc | cggggaagcc | atctgccttc | 1020 |
| gagcctgcca | ctgaaatgca | aaagtctgtc | ccaataaag | ccttggaatt | gaaaaatgaa | 1080 |
| caaacattga | gagcagatga | gatactccca | tcagaatcca | acaaaagga | ctatgaagaa | 1140 |
| agttcttggg | attctgagag | tctctgtgag | actgtttcac | agaaggatgt | gtgtttaccc | 1200 |
| aaggctrcrc | atcaaaaaga | aatagataaa | ataaatggaa | aattagaagg | gtctcctgtt | 1260 |
| aaagatggtc | ttctgaaggc | taactgcgga | atgaaagttt | ctattccaac | taaagcctta | 1320 |
| gaattgatgg | acatgcaaac | tttcaaagca | gagcctcccg | agaagccatc | tgccttcgag | 1380 |
| cctgccattg | aaatgcaaaa | gtctgttcca | aataaagcct | tggaattgaa | gatgaacaa | 1440 |
| acattgagag | cagatgagat | actcccatca | gaatccaaac | aaaaggacta | tgaagaaagt | 1500 |
| tcttgggatt | ctgagagtct | ctgtgagact | gtttcacaga | aggatgtgtg | tttacccaag | 1560 |
| gctrcrcatc | aaaagaaat | agataaaata | aatggaaaat | tagaagagtc | tcctgataat | 1620 |
| gatggttttc | tgaaggctcc | ctgcagaatg | aaagtttcta | ttccaactaa | agccttagaa | 1680 |
| ttgatggaca | tgcaaacttt | caaagcagag | cctcccgaga | agccatctgc | cttcgagcct | 1740 |
| gccattgaaa | tgcaaaagtc | tgttccaaat | aaagccttgg | aattgaagaa | tgaacaaaca | 1800 |
| ttgagagcag | atcagatgtt | cccttcagaa | tcaaacaaa | agaasgttga | agaaaattct | 1860 |
| tgggattctg | agagtctccg | tgagactgtt | tcacagaagg | atgtgtgtgt | acccaaggct | 1920 |
| acacatcaaa | agaaatgga | taaataagt | ggaaaattag | aagattcaac | tagcctatca | 1980 |
| aaaatcttgg | atacagttca | ttcttgtgaa | agagcaaggg | aacttcaaaa | agatcactgt | 2040 |
| gaacaacgta | caggaaaaat | ggaacaaatg | aaaagaagt | tttgtgtact | gaaaaagaaa | 2100 |

```
ctgtcagaag caaagaaat aaaatcacag ttagagaacc aaaaagttaa atgggaacaa    2160
gagctctgca gtgtgagatt gactttaaac caagaagaag agaagagaag aaatgccgat    2220
atattaaatg aaaaaattag ggaagaatta ggaagaatcg aagagcagca taggaaagag    2280
ttagaagtga acaacaact tgaacaggct ctcagaatac aagatataga attgaagagt    2340
gtagaaagta atttgaatca ggtttctcac actcatgaaa atgaaaatta tctcttacat    2400
gaaaattgca tgttgaaaaa ggaaattgcc atgctaaaac tggaaatagc cacactgaaa    2460
caccaatacc aggaaaagga aaataaatac tttgaggaca ttaagatttt aaaagaaaag    2520
aatgctgaac ttcagatgac cctaaaactg aaagaggaat cattaactaa aagggcatct    2580
caatatagtg ggcagcttaa agttctgata gctgagaaca caatgctcac ttctaaattg    2640
aaggaaaaac aagacaaaga aatactagag gcagaaattg aatcacacca tcctagactg    2700
gcttctgctg tacaagacca tgatcaaatt gtgacatcaa gaaaaagtca agaacctgct    2760
ttccacattg caggagatgc ttgtttgcaa agaaaaatga atgttgatgt gagtagtacg    2820
atatataaca atgaggtgct ccatcaacca ctttctgaag ctcaaaggaa atccaaaagc    2880
ctaaaaatta atctcaatta tgcmggagat gctctaagag aaaatacatt ggtttcagaa    2940
catgcacaaa gagaccaacg tgaaacacag tgtcaaatga aggaagctga acacatgtat    3000
caaaacgaac aagataatgt gaacaaacac actgaacagc aggagtctct agatcagaaa    3060
ttatttcaac tacaaagcaa aaatatgtgg cttcaacagc aattagttca tgcacataag    3120
aaagctgaca caaaagcaa gataacaatt gatattcatt ttcttgagag gaaaatgcaa    3180
catcatctcc taaaagagaa aaatgaggag atatttaatt acaataacca tttaaaaaac    3240
cgtatatatc aatatgaaaa agagaaagca gaaacagaaa actcatga                3288

<210> SEQ ID NO 491
<211> LENGTH: 2232
<212> TYPE: DNA
<213> ORGANISM: Homo sapiens

<400> SEQUENCE: 491
atgaagttgc tgatggtcct catgctggcg gccctctccc agcactgcta cgcaggctct     60
ggctgcccct tattggagaa tgtgatttcc aagacaatca atccacaagt gtctaagact    120
gaatacaaag aacttcttca agagttcata gacgacaatg ccactacaaa tgccatagat    180
gaattgaagg aatgttttct taaccaaacg gatgaaactc tgagcaatgt tgaggtgttt    240
atgcaattaa tatatgacag cagtcttttgt gatttattta tgagtcccgc aaaagaaaca    300
tctgagaaat ttacgtgggc agcaaaagga gacctagga agatcgcatg ggagaaaaaa    360
gaaacacctg taaagactgg atgcgtggca agagtaacat ctaataaaac taaagttttg    420
gaaaaaggaa gatctaagat gattgcatgt cctacaaaag aatcatctac aaaagcaagt    480
gccaatgatc agaggttccc atcagaatcc aaacaagagg aagatgaaga atattcttgt    540
gattctcgga gtctctttga gagttctgca aagattcaag tgtgtatacc tgagtctata    600
tatcaaaaag taatggagat aaatagagaa gtagaagagc tcctaagaa gccatctgcc    660 ttcaagcctg ccattgaaat gcaaaactct gttccaaata agcctttga attgaagaat    720 gaacaaacat tgagagcaga tccgatgttc ccaccagaat ccaaacaaaa ggactatgaa    780
gaaaattctt gggattctga gagtctctgt gagactgttt cacagaagga tgtgtgttta    840
cccaaggcta cacatcaaaa agaaatagat aaaataaatg gaaaattaga gagtctcct     900
```

```
aataaagatg gtcttctgaa ggctacctgc ggaatgaaag tttctattcc aactaaagcc      960
ttagaattga aggacatgca aactttcaaa gcagagcctc cggggaagcc atctgccttc     1020
gagcctgcca ctgaaatgca aaagtctgtc ccaaataaag ccttggaatt gaaaaatgaa     1080
caaacattga gagcagatga gatactccca tcagaatcca acaaaagga ctatgaagaa      1140
agttcttggg attctgagag tctctgtgag actgtttcac agaaggatgt gtgtttaccc     1200
aaggctrcrc atcaaaaaga aatagataaa ataaatggaa aattagaagg gtctcctgtt     1260
aaagatggtc ttctgaaggc taactgcgga atgaaagttt ctattccaac taaagcctta     1320
gaattgatgg acatgcaaac tttcaaagca gagcctcccg agaagccatc tgccttcgag     1380
cctgccattg aaatgcaaaa gtctgttcca aataaagcct tggaattgaa gatgaacaa      1440
acattgagag cagatgagat actcccatca gaatccaaac aaaaggacta tgaagaaagt     1500
tcttgggatt ctgagagtct ctgtgagact gtttcacaga aggatgtgtg tttacccaag     1560
gctrcrcatc aaaaagaaat agataaata atgggaaaat tagaagagtc tcctgataat     1620
gatggttttc tgaaggctcc ctgcagaatg aaagtttcta ttccaactaa agccttagaa     1680
ttgatggaca tgcaaacttt caaagcagag cctcccgaga gccatctgc cttcgagcct     1740
gccattgaaa tgcaaaagtc tgttccaaat aaagccttgg aattgaagaa tgaacaaaca     1800
ttgagagcag atcagatgtt cccttcgaaa tcaaaacaaa agaasgttga agaaaattct     1860
tgggattctg agagtctccg tgagactgtt tcacagaagg atgtgtgtgt acccaaggct     1920
acacatcaaa aagaaatgga taaaataagt ggaaaattag aagattcaac tagcctatca     1980
aaaatcttgg atacagttca ttcttgtgaa agagcaaggg aacttcaaaa agatcactgt     2040
gaacaacgta caggaaaaat ggaacaaatg aaaaagaagt tttgtgtact gaaaagaaaa     2100
ctgtcagaag caaagaaat aaaatcacag ttagagaacc aaaaagttaa atgggaacaa     2160
gagctctgca gtgtgaggtt tctcacactc atgaaaatga aaattatctc ttacatgaaa     2220
attgcatgtt ga                                                        2232

<210> SEQ ID NO 492
<211> LENGTH: 1233
<212> TYPE: DNA
<213> ORGANISM: Homo sapiens

<400> SEQUENCE: 492
atgaagttgc tgatggtcct catgctggcg ccctctccc agcactgcta cgcaggctct       60
ggctgcccct tattggagaa tgtgatttcc aagcaatca atccacaagt gtctaagact      120
gaatacaaag aacttcttca agagttcata gacgacaatg ccactacaaa tgccatagat      180
gaattgaagg aatgttttct taaccaaacg gatgaaactc tgagcaatgt tgaggtgttt      240
atgcaattaa tatatgacag cagtctttgt gatttattta tgggaacaag agctctgcag      300
tgtgaggttt ctcacactca tgaaaatgaa aattatctct tacatgaaaa ttgcatgttg      360
aaaaaggaaa ttgccatgct aaaactggaa atagccacac tgaaacacca ataccaggaa      420
aaggaaaata aatactttga ggacattaag attttaaaag aaaagaatgc tgaacttcag      480
atgaccctaa aactgaaaga ggaatcatta actaaaggg catctcaata tagtgggcag      540
cttaaagttc tgatagctga gaacacaatg ctcacttcta aattgaagga aaacaagac       600
aaagaaatac tagaggcaga aattgaatca caccatccta gactggcttc tgctgtacaa      660
gaccatgatc aaattgtgac atcaagaaaa agtcaagaac ctgcttttcca cattgcagga     720
gatgcttgtt tgcaaagaaa aatgaatgtt gatgtgagta gtacgataaa taacaatgag     780
```

```
gtgctccatc aaccactttc tgaagctcaa aggaaatcca aaagcctaaa aattaatctc    840
aattatgccg gagatgctct aagagaaaat acattggttt cagaacatgc acaaagagac    900
caacgtgaaa cacagtgtca aatgaaggaa gctgaacaca tgtatcaaaa cgaacaagat    960
aatgtgaaca acacactga acagcaggag tctctagatc agaaattatt tcaactacaa   1020
agcaaaaata tgtggcttca acagcaatta gttcatgcac ataagaaagc tgacaacaaa   1080
agcaagataa caattgatat tcattttctt gagaggaaaa tgcaacatca tctcctaaaa   1140
gagaaaaatg aggagatatt taattacaat aaccatttaa aaaccgtat atatcaatat    1200 gaaaaagaga agcagaaac agaagttata taa                                 1233
```

<210> SEQ ID NO 493
<211> LENGTH: 1095
<212> TYPE: PRT
<213> ORGANISM: Homo sapiens
<220> FEATURE:
<221> NAME/KEY: VARIANT
<222> LOCATION: 403, 522, 615
<223> OTHER INFORMATION: Xaa = Any Amino Acid

<400> SEQUENCE: 493

```
Met Lys Leu Leu Met Val Leu Met Leu Ala Ala Leu Ser Gln His Cys
 1               5                  10                  15

Tyr Ala Gly Ser Gly Cys Pro Leu Leu Glu Asn Val Ile Ser Lys Thr
             20                  25                  30

Ile Asn Pro Gln Val Ser Lys Thr Glu Tyr Lys Glu Leu Leu Gln Glu
         35                  40                  45

Phe Ile Asp Asp Asn Ala Thr Thr Asn Ala Ile Asp Glu Leu Lys Glu
     50                  55                  60

Cys Phe Leu Asn Gln Thr Asp Glu Thr Leu Ser Asn Val Glu Val Phe
 65                  70                  75                  80

Met Gln Leu Ile Tyr Asp Ser Ser Leu Cys Asp Leu Phe Met Ser Pro
                 85                  90                  95

Ala Lys Glu Thr Ser Glu Lys Phe Thr Trp Ala Ala Lys Gly Arg Pro
            100                 105                 110

Arg Lys Ile Ala Trp Glu Lys Lys Glu Thr Pro Val Lys Thr Gly Cys
        115                 120                 125

Val Ala Arg Val Thr Ser Asn Lys Thr Lys Val Leu Glu Lys Gly Arg
    130                 135                 140

Ser Lys Met Ile Ala Cys Pro Thr Lys Glu Ser Ser Thr Lys Ala Ser
145                 150                 155                 160

Ala Asn Asp Gln Arg Phe Pro Ser Glu Ser Lys Gln Glu Glu Asp Glu
                165                 170                 175

Glu Tyr Ser Cys Asp Ser Arg Ser Leu Phe Glu Ser Ala Lys Ile
            180                 185                 190

Gln Val Cys Ile Pro Glu Ser Ile Tyr Gln Lys Val Met Glu Ile Asn
        195                 200                 205

Arg Glu Val Glu Glu Pro Pro Lys Lys Pro Ser Ala Phe Lys Pro Ala
    210                 215                 220

Ile Glu Met Gln Asn Ser Val Pro Asn Lys Ala Phe Glu Leu Lys Asn
225                 230                 235                 240

Glu Gln Thr Leu Arg Ala Asp Pro Met Phe Pro Glu Ser Lys Gln
                245                 250                 255

Lys Asp Tyr Glu Glu Asn Ser Trp Asp Ser Glu Ser Leu Cys Glu Thr
            260                 265                 270
```

-continued

```
Val Ser Gln Lys Asp Val Cys Leu Pro Lys Ala Thr His Gln Lys Glu
        275                 280                 285
Ile Asp Lys Ile Asn Gly Lys Leu Glu Glu Ser Pro Asn Lys Asp Gly
        290                 295                 300
Leu Leu Lys Ala Thr Cys Gly Met Lys Val Ser Ile Pro Thr Lys Ala
305                 310                 315                 320
Leu Glu Leu Lys Asp Met Gln Thr Phe Lys Ala Glu Pro Pro Gly Lys
                325                 330                 335
Pro Ser Ala Phe Glu Pro Ala Thr Glu Met Gln Lys Ser Val Pro Asn
                340                 345                 350
Lys Ala Leu Glu Leu Lys Asn Glu Gln Thr Leu Arg Ala Asp Glu Ile
                355                 360                 365
Leu Pro Ser Glu Ser Lys Gln Lys Asp Tyr Glu Glu Ser Ser Trp Asp
        370                 375                 380
Ser Glu Ser Leu Cys Glu Thr Val Ser Gln Lys Asp Val Cys Leu Pro
385                 390                 395                 400
Lys Ala Xaa His Gln Lys Glu Ile Asp Lys Ile Asn Gly Lys Leu Glu
                405                 410                 415
Gly Ser Pro Val Lys Asp Gly Leu Leu Lys Ala Asn Cys Gly Met Lys
                420                 425                 430
Val Ser Ile Pro Thr Lys Ala Leu Glu Leu Met Asp Met Gln Thr Phe
                435                 440                 445
Lys Ala Glu Pro Pro Glu Lys Pro Ser Ala Phe Glu Pro Ala Ile Glu
        450                 455                 460
Met Gln Lys Ser Val Pro Asn Lys Ala Leu Glu Leu Lys Asn Glu Gln
465                 470                 475                 480
Thr Leu Arg Ala Asp Glu Ile Leu Pro Ser Glu Ser Lys Gln Lys Asp
                485                 490                 495
Tyr Glu Glu Ser Ser Trp Asp Ser Glu Ser Leu Cys Glu Thr Val Ser
                500                 505                 510
Gln Lys Asp Val Cys Leu Pro Lys Ala Xaa His Gln Lys Glu Ile Asp
        515                 520                 525
Lys Ile Asn Gly Lys Leu Glu Glu Ser Pro Asp Asn Asp Gly Phe Leu
        530                 535                 540
Lys Ala Pro Cys Arg Met Lys Val Ser Ile Pro Thr Lys Ala Leu Glu
545                 550                 555                 560
Leu Met Asp Met Gln Thr Phe Lys Ala Glu Pro Pro Glu Lys Pro Ser
                565                 570                 575
Ala Phe Glu Pro Ala Ile Glu Met Gln Lys Ser Val Pro Asn Lys Ala
                580                 585                 590
Leu Glu Leu Lys Asn Glu Gln Thr Leu Arg Ala Asp Gln Met Phe Pro
                595                 600                 605
Ser Glu Ser Lys Gln Lys Xaa Val Glu Glu Asn Ser Trp Asp Ser Glu
        610                 615                 620
Ser Leu Arg Glu Thr Val Ser Gln Lys Asp Val Cys Val Pro Lys Ala
625                 630                 635                 640
Thr His Gln Lys Glu Met Asp Lys Ile Ser Gly Lys Leu Glu Asp Ser
                645                 650                 655
Thr Ser Leu Ser Lys Ile Leu Asp Thr Val His Ser Cys Glu Arg Ala
                660                 665                 670
Arg Glu Leu Gln Lys Asp His Cys Glu Gln Arg Thr Gly Lys Met Glu
                675                 680                 685
```

```
Gln Met Lys Lys Lys Phe Cys Val Leu Lys Lys Leu Ser Glu Ala
    690                 695                 700
Lys Glu Ile Lys Ser Gln Leu Glu Asn Gln Lys Val Lys Trp Glu Gln
705                 710                 715                 720
Glu Leu Cys Ser Val Arg Leu Thr Leu Asn Gln Glu Glu Lys Arg
                725                 730                 735
Arg Asn Ala Asp Ile Leu Asn Glu Lys Ile Arg Glu Glu Leu Gly Arg
                740                 745                 750
Ile Glu Glu Gln His Arg Lys Glu Leu Glu Val Lys Gln Gln Leu Glu
            755                 760                 765
Gln Ala Leu Arg Ile Gln Asp Ile Glu Leu Lys Ser Val Glu Ser Asn
    770                 775                 780
Leu Asn Gln Val Ser His Thr His Glu Asn Glu Asn Tyr Leu Leu His
785                 790                 795                 800
Glu Asn Cys Met Leu Lys Lys Glu Ile Ala Met Leu Lys Leu Glu Ile
                805                 810                 815
Ala Thr Leu Lys His Gln Tyr Gln Glu Lys Glu Asn Lys Tyr Phe Glu
                820                 825                 830
Asp Ile Lys Ile Leu Lys Glu Lys Asn Ala Glu Leu Gln Met Thr Leu
            835                 840                 845
Lys Leu Lys Glu Glu Ser Leu Thr Lys Arg Ala Ser Gln Tyr Ser Gly
850                 855                 860
Gln Leu Lys Val Leu Ile Ala Glu Asn Thr Met Leu Thr Ser Lys Leu
865                 870                 875                 880
Lys Glu Lys Gln Asp Lys Glu Ile Leu Glu Ala Ile Glu Ser His
                885                 890                 895
His Pro Arg Leu Ala Ser Ala Val Gln Asp His Asp Gln Ile Val Thr
                900                 905                 910
Ser Arg Lys Ser Gln Glu Pro Ala Phe His Ile Ala Gly Asp Ala Cys
                915                 920                 925
Leu Gln Arg Lys Met Asn Val Asp Val Ser Ser Thr Ile Tyr Asn Asn
    930                 935                 940
Glu Val Leu His Gln Pro Leu Ser Glu Ala Gln Arg Lys Ser Lys Ser
945                 950                 955                 960
Leu Lys Ile Asn Leu Asn Tyr Ala Gly Asp Ala Leu Arg Glu Asn Thr
                965                 970                 975
Leu Val Ser Glu His Ala Gln Arg Asp Gln Arg Glu Thr Gln Cys Gln
                980                 985                 990
Met Lys Glu Ala Glu His Met Tyr Gln Asn Glu Gln Asp Asn Val Asn
                995                 1000                1005
Lys His Thr Glu Gln Gln Glu Ser Leu Asp Gln Lys Leu Phe Gln Leu
    1010                1015                1020
Gln Ser Lys Asn Met Trp Leu Gln Gln Gln Leu Val His Ala His Lys
1025                1030                1035                1040
Lys Ala Asp Asn Lys Ser Lys Ile Thr Ile Asp Ile His Phe Leu Glu
                1045                1050                1055
Arg Lys Met Gln His His Leu Leu Lys Glu Lys Asn Glu Glu Ile Phe
                1060                1065                1070
Asn Tyr Asn Asn His Leu Lys Asn Arg Ile Tyr Gln Tyr Glu Lys Glu
                1075                1080                1085
Lys Ala Glu Thr Glu Asn Ser
1090                1095
```

```
<210> SEQ ID NO 494
<211> LENGTH: 743
<212> TYPE: PRT
<213> ORGANISM: Homo sapiens
<220> FEATURE:
<221> NAME/KEY: VARIANT
<222> LOCATION: 403, 522, 615
<223> OTHER INFORMATION: Xaa = Any Amino Acid

<400> SEQUENCE: 494
```

Met Lys Leu Leu Met Val Leu Met Leu Ala Ala Leu Ser Gln His Cys
 1               5                  10                  15

Tyr Ala Gly Ser Gly Cys Pro Leu Leu Glu Asn Val Ile Ser Lys Thr
             20                  25                  30

Ile Asn Pro Gln Val Ser Lys Thr Glu Tyr Lys Glu Leu Leu Gln Glu
         35                  40                  45

Phe Ile Asp Asp Asn Ala Thr Thr Asn Ala Ile Asp Glu Leu Lys Glu
     50                  55                  60

Cys Phe Leu Asn Gln Thr Asp Glu Thr Leu Ser Asn Val Glu Val Phe
 65                  70                  75                  80

Met Gln Leu Ile Tyr Asp Ser Ser Leu Cys Asp Leu Phe Met Ser Pro
                 85                  90                  95

Ala Lys Glu Thr Ser Glu Lys Phe Thr Trp Ala Ala Lys Gly Arg Pro
            100                 105                 110

Arg Lys Ile Ala Trp Glu Lys Glu Thr Pro Val Lys Thr Gly Cys
        115                 120                 125

Val Ala Arg Val Thr Ser Asn Lys Thr Lys Val Leu Glu Lys Gly Arg
    130                 135                 140

Ser Lys Met Ile Ala Cys Pro Thr Lys Glu Ser Ser Thr Lys Ala Ser
145                 150                 155                 160

Ala Asn Asp Gln Arg Phe Pro Ser Glu Ser Lys Gln Glu Glu Asp Glu
                165                 170                 175

Glu Tyr Ser Cys Asp Ser Arg Ser Leu Phe Glu Ser Ser Ala Lys Ile
            180                 185                 190

Gln Val Cys Ile Pro Glu Ser Ile Tyr Gln Lys Val Met Glu Ile Asn
        195                 200                 205

Arg Glu Val Glu Glu Pro Pro Lys Lys Pro Ser Ala Phe Lys Pro Ala
    210                 215                 220

Ile Glu Met Gln Asn Ser Val Pro Asn Lys Ala Phe Glu Leu Lys Asn
225                 230                 235                 240

Glu Gln Thr Leu Arg Ala Asp Pro Met Phe Pro Pro Gly Ser Lys Gln
                245                 250                 255

Lys Asp Tyr Glu Glu Asn Ser Trp Asp Ser Glu Ser Leu Cys Glu Thr
            260                 265                 270

Val Ser Gln Lys Asp Val Cys Leu Pro Lys Ala Thr His Gln Lys Glu
        275                 280                 285

Ile Asp Lys Ile Asn Gly Lys Leu Glu Glu Ser Pro Asn Lys Asp Gly
    290                 295                 300

Leu Leu Lys Ala Thr Cys Gly Met Lys Val Ser Ile Pro Thr Lys Ala
305                 310                 315                 320

Leu Glu Leu Lys Asp Met Gln Thr Phe Lys Ala Glu Pro Pro Gly Lys
                325                 330                 335

Pro Ser Ala Phe Glu Pro Ala Thr Glu Met Gln Lys Ser Val Pro Asn
            340                 345                 350

Lys Ala Leu Glu Leu Lys Asn Glu Gln Thr Leu Arg Ala Asp Glu Ile
        355                 360                 365

-continued

```
Leu Pro Ser Glu Ser Lys Gln Lys Asp Tyr Glu Glu Ser Ser Trp Asp
    370                 375                 380

Ser Glu Ser Leu Cys Glu Thr Val Ser Gln Lys Asp Val Cys Leu Pro
385                 390                 395                 400

Lys Ala Xaa His Gln Lys Glu Ile Asp Lys Ile Asn Gly Lys Leu Glu
            405                 410                 415

Gly Ser Pro Val Lys Asp Gly Leu Leu Lys Ala Asn Cys Gly Met Lys
            420                 425                 430

Val Ser Ile Pro Thr Lys Ala Leu Glu Leu Met Asp Met Gln Thr Phe
            435                 440                 445

Lys Ala Glu Pro Pro Glu Lys Pro Ser Ala Phe Glu Pro Ala Ile Glu
    450                 455                 460

Met Gln Lys Ser Val Pro Asn Lys Ala Leu Glu Leu Lys Asn Glu Gln
465                 470                 475                 480

Thr Leu Arg Ala Asp Glu Ile Leu Pro Ser Glu Ser Lys Gln Lys Asp
                485                 490                 495

Tyr Glu Glu Ser Ser Trp Asp Ser Glu Ser Leu Cys Glu Thr Val Ser
            500                 505                 510

Gln Lys Asp Val Cys Leu Pro Lys Ala Xaa His Gln Lys Glu Ile Asp
    515                 520                 525

Lys Ile Asn Gly Lys Leu Glu Glu Ser Pro Asn Asp Gly Phe Leu
530                 535                 540

Lys Ala Pro Cys Arg Met Lys Val Ser Ile Pro Thr Lys Ala Leu Glu
545                 550                 555                 560

Leu Met Asp Met Gln Thr Phe Lys Ala Glu Pro Pro Glu Lys Pro Ser
                565                 570                 575

Ala Phe Glu Pro Ala Ile Glu Met Gln Lys Ser Val Pro Asn Lys Ala
            580                 585                 590

Leu Glu Leu Lys Asn Glu Gln Thr Leu Arg Ala Asp Gln Met Phe Pro
            595                 600                 605

Ser Glu Ser Lys Gln Lys Xaa Val Glu Glu Asn Ser Trp Asp Ser Glu
    610                 615                 620

Ser Leu Arg Glu Thr Val Ser Gln Lys Asp Val Cys Val Pro Lys Ala
625                 630                 635                 640

Thr His Gln Lys Glu Met Asp Lys Ile Ser Gly Lys Leu Glu Asp Ser
                645                 650                 655

Thr Ser Leu Ser Lys Ile Leu Asp Thr Val His Ser Cys Glu Arg Ala
            660                 665                 670

Arg Glu Leu Gln Lys Asp His Cys Glu Gln Arg Thr Gly Lys Met Glu
            675                 680                 685

Gln Met Lys Lys Lys Phe Cys Val Leu Lys Lys Leu Ser Glu Ala
    690                 695                 700

Lys Glu Ile Lys Ser Gln Leu Glu Asn Gln Lys Val Lys Trp Glu Gln
705                 710                 715                 720

Glu Leu Cys Ser Val Arg Phe Leu Thr Leu Met Lys Met Lys Ile Ile
                725                 730                 735

Ser Tyr Met Lys Ile Ala Cys
            740

<210> SEQ ID NO 495
<211> LENGTH: 410
<212> TYPE: PRT
<213> ORGANISM: Homo sapiens
```

-continued

```
<400> SEQUENCE: 495

Met Lys Leu Leu Met Val Leu Met Leu Ala Ala Leu Ser Gln His Cys
 1               5                  10                  15

Tyr Ala Gly Ser Gly Cys Pro Leu Leu Glu Asn Val Ile Ser Lys Thr
             20                  25                  30

Ile Asn Pro Gln Val Ser Lys Thr Glu Tyr Lys Glu Leu Leu Gln Glu
         35                  40                  45

Phe Ile Asp Asp Asn Ala Thr Thr Asn Ala Ile Asp Glu Leu Lys Glu
 50                  55                  60

Cys Phe Leu Asn Gln Thr Asp Glu Thr Leu Ser Asn Val Glu Val Phe
 65                  70                  75                  80

Met Gln Leu Ile Tyr Asp Ser Ser Leu Cys Asp Leu Phe Met Gly Thr
                 85                  90                  95

Arg Ala Leu Gln Cys Glu Val Ser His Thr His Glu Asn Glu Asn Tyr
            100                 105                 110

Leu Leu His Glu Asn Cys Met Leu Lys Lys Glu Ile Ala Met Leu Lys
        115                 120                 125

Leu Glu Ile Ala Thr Leu Lys His Gln Tyr Gln Glu Lys Glu Asn Lys
130                 135                 140

Tyr Phe Glu Asp Ile Lys Ile Leu Lys Glu Lys Asn Ala Glu Leu Gln
145                 150                 155                 160

Met Thr Leu Lys Leu Lys Glu Glu Ser Leu Thr Lys Arg Ala Ser Gln
                165                 170                 175

Tyr Ser Gly Gln Leu Lys Val Leu Ile Ala Glu Asn Thr Met Leu Thr
            180                 185                 190

Ser Lys Leu Lys Glu Lys Gln Asp Lys Glu Ile Leu Glu Ala Glu Ile
        195                 200                 205

Glu Ser His His Pro Arg Leu Ala Ser Ala Val Gln Asp His Asp Gln
210                 215                 220

Ile Val Thr Ser Arg Lys Ser Gln Glu Pro Ala Phe His Ile Ala Gly
225                 230                 235                 240

Asp Ala Cys Leu Gln Arg Lys Met Asn Val Asp Val Ser Ser Thr Ile
                245                 250                 255

Tyr Asn Asn Glu Val Leu His Gln Pro Leu Ser Glu Ala Gln Arg Lys
            260                 265                 270

Ser Lys Ser Leu Lys Ile Asn Leu Asn Tyr Ala Gly Asp Ala Leu Arg
        275                 280                 285

Glu Asn Thr Leu Val Ser Glu His Ala Gln Arg Asp Gln Arg Glu Thr
290                 295                 300

Gln Cys Gln Met Lys Glu Ala Glu His Met Tyr Gln Asn Glu Gln Asp
305                 310                 315                 320

Asn Val Asn Lys His Thr Glu Gln Glu Ser Leu Asp Gln Lys Leu
                325                 330                 335

Phe Gln Leu Gln Ser Lys Asn Met Trp Leu Gln Gln Leu Val His
            340                 345                 350

Ala His Lys Lys Ala Asp Asn Lys Ser Lys Ile Thr Ile Asp Ile His
        355                 360                 365

Phe Leu Glu Arg Lys Met Gln His His Leu Leu Lys Glu Lys Asn Glu
370                 375                 380

Glu Ile Phe Asn Tyr Asn Asn His Leu Lys Asn Arg Ile Tyr Gln Tyr
385                 390                 395                 400

Glu Lys Glu Lys Ala Glu Thr Glu Val Ile
                405                 410
```

<210> SEQ ID NO 496
<211> LENGTH: 20
<212> TYPE: PRT
<213> ORGANISM: Homo sapiens

<400> SEQUENCE: 496

Ile Asp Glu Leu Lys Glu Cys Phe Leu Asn Gln Thr Asp Glu Thr Leu
1               5                   10                  15
Ser Asn Val Glu
            20

<210> SEQ ID NO 497
<211> LENGTH: 15
<212> TYPE: PRT
<213> ORGANISM: Homo sapiens

<400> SEQUENCE: 497

Thr Thr Asn Ala Ile Asp Glu Leu Lys Glu Cys Phe Leu Asn Gln
1               5                   10                  15

<210> SEQ ID NO 498
<211> LENGTH: 21
<212> TYPE: PRT
<213> ORGANISM: Homo sapiens

<400> SEQUENCE: 498

Ser Gln His Cys Tyr Ala Gly Ser Gly Cys Pro Leu Leu Glu Asn Val
1               5                   10                  15
Ile Ser Lys Thr Ile
            20

<210> SEQ ID NO 499
<211> LENGTH: 20
<212> TYPE: PRT
<213> ORGANISM: Homo sapiens

<400> SEQUENCE: 499

Glu Tyr Lys Glu Leu Leu Gln Glu Phe Ile Asp Asp Asn Ala Thr Thr
1               5                   10                  15
Asn Ala Ile Asp
            20

<210> SEQ ID NO 500
<211> LENGTH: 9
<212> TYPE: PRT
<213> ORGANISM: Homo sapiens

<400> SEQUENCE: 500

Lys Leu Leu Met Val Leu Met Leu Ala
1               5

<210> SEQ ID NO 501
<211> LENGTH: 13
<212> TYPE: PRT
<213> ORGANISM: Homo sapiens

<400> SEQUENCE: 501

Gln Glu Phe Ile Asp Asp Asn Ala Thr Thr Asn Ala Ile
1               5                   10

<210> SEQ ID NO 502
<211> LENGTH: 13

<212> TYPE: PRT
<213> ORGANISM: Homo sapiens

<400> SEQUENCE: 502

Leu Lys Glu Cys Phe Leu Asn Gln Thr Asp Glu Thr Leu
1               5                   10

<210> SEQ ID NO 503
<211> LENGTH: 93
<212> TYPE: PRT
<213> ORGANISM: Homo sapiens

<400> SEQUENCE: 503

Met Lys Leu Leu Met Val Leu Met Leu Ala Ala Leu Ser Gln His Cys
1               5                   10                  15

Tyr Ala Gly Ser Gly Cys Pro Leu Leu Glu Asn Val Ile Ser Lys Thr
            20                  25                  30

Ile Asn Pro Gln Val Ser Lys Thr Glu Tyr Lys Glu Leu Leu Gln Glu
        35                  40                  45

Phe Ile Asp Asp Asn Ala Thr Thr Asn Ala Ile Asp Glu Leu Lys Glu
    50                  55                  60

Cys Phe Leu Asn Gln Thr Asp Glu Thr Leu Ser Asn Val Glu Val Phe
65                  70                  75                  80

Met Gln Leu Ile Tyr Asp Ser Ser Leu Cys Asp Leu Phe
            85                  90

<210> SEQ ID NO 504
<211> LENGTH: 1964
<212> TYPE: DNA
<213> ORGANISM: Homo sapiens

<400> SEQUENCE: 504
gcatgctcga cgccccatgt gctgaaaggg cgaggagcct cctgcggcgg ccccctgtgtc     60
cctgcctcta cctgcgcacc tgcatgtgtt caaccccgg gagaacacct ggcggcccct     120
gacccaggtg cccgaggagg ccccgcttcg gggctgcgt ctctgcacca tgcacaacta     180
cctgtttctg gcgggggca tccgtggctc cggtgccaag gccgtctgct ccaacgaggt     240
cttctgctac aaccctctga ccaacatctg gagccaggtt cggcccatgc agcaggcccg     300
agcccagctc aagctggtgg ccctggacgg gctgctctat gccatcggtg gcgaatgcct     360
gtacagcatg gagtgctacg acccgcgaac agacgcctgg accccacgcg cgccactccc     420
cgcaggcacc ttccctgtgg cccacgaggc tgtggcctgc cgtggggaca tctacgtcac     480
cggggggtcac ctcttctacc gcctgctcag gtacagcccc gtgaaggatg cttgggacga     540
gtgcccatac agtgccagcc accggcgttc agcgacatc gttgcactgg ggggcttcct     600
gtaccgcttc gacctgctgc ggggcgtggg cgccgccgtg atgcgctaca acacagtgac     660
cggctcctgg agcagggctg cctccctgcc cctgcccgcc ccgcccac tgcgctgcac     720
caccctgggc aacaccattt actgcctcaa cccccaggtc actgccacct tcacggtctc     780
tgggggggact gccagttcc aggccaagga gctgcagccc ttcccccttgg ggagcaccgg     840
ggtcctcagt ccattcatcc tgactctgcc ccctgaggac cggctgcaga cctcactctg     900
agtggcagga agagaaccaa agctgcttcg ctgctctcca gggagaccct cctgggatgg     960
gcctgagagg ccggggctca gggaaggggc tgggatcgga acttcctgct cttgtttctg    1020
gacaactttc cccttctgct ttaaaggttg tcgattattt tgaagccag actccctcag    1080
cctcttctg ccccctcactc cacacccaga ctgtttcctg actcaattcc gtacctactt    1140

| | | |
|---|---|---|
| acagaccctc tcagcttgct gacaccccc tgtctgtggg actccctatt ccctagagcc | | 1200 |
| agggactgat gcgtctccac agacaaggac ttggctcgct ggagctctgc tgagccgaga | | 1260 |
| gaggaggggg tagaaaacat tcacacttcc tatgctctgt cagcaggaca gggagcaaaa | | 1320 |
| acgtccccag gcaacgccct cgcctctggg actttctgcc tgtcctaagg cctcccagg | | 1380 |
| taccaacccc gtagctatct gggtctgttt ggcactgtgg attctcaagg cctagaacc | | 1440 |
| cttgcctctg aaactggtcc gctggtgcag ccctgctgtc tgcagctcct gcccataccc | | 1500 |
| ccagcccaca ccaggccagg cccactccgg gctcaccacc ctctgcagcc ttgtggggct | | 1560 |
| ctcccagccc ctccagaagc ccaccccact tctcgccaac cccgatctc taaatgaggc | | 1620 |
| ctgagcgtca ccctagttct gccccttttt agctgtgtag acttggacga gacatttgac | | 1680 |
| ttccctttct ccttgtctat aaaatgtgga cagtggacgt ctgtcaccca agagagttgt | | 1740 |
| gggagacaag atcacagcta tgagcacctc gcacggtgtc caggatgcac agcacaatcc | | 1800 |
| atgatgcgtt ttctcccctt acgcactttg aaacccatgc tagaaaagtg aatacatctg | | 1860 |
| actgtgctcc actccaacct ccagcctgga tgtccctgtc tgggccctttt ttctgttttt | | 1920 |
| tattctatgt tcagcaccac tggcaccaaa tacatttaa ttca | | 1964 |

<210> SEQ ID NO 505
<211> LENGTH: 732
<212> TYPE: DNA
<213> ORGANISM: Homo sapiens

<400> SEQUENCE: 505

| | | |
|---|---|---|
| atgcacaact acctgtttct ggcgggggc atccgtggct ccggtgccaa ggccgtctgc | | 60 |
| tccaacgagg tcttctgcta caaccctctg accaacatct ggagccaggt tcggcccatg | | 120 |
| cagcaggccc gagcccagct caagctggtg gccctggacg ggctgctcta tgccatcggt | | 180 |
| ggcgaatgcc tgtacagcat ggagtgctac gaccgcgaa cagacgcctg gacccccacgc | | 240 |
| gcgccactcc ccgcaggcac cttccctgtg gcccacgagg ctgtggcctg ccgtggggac | | 300 |
| atctacgtca ccggggggtca cctcttctac cgcctgctca ggtacagccc cgtgaaggat | | 360 |
| gcttgggacg agtgcccata cagtgccagc caccggcgtt ccagcgacat cgttgcactg | | 420 |
| ggggcttcc tgtaccgctt cgacctgctg cggggcgtgg gcgccgccgt gatgcgctac | | 480 |
| aacacagtga ccggctcctg gagcagggct gcctccctgc ccctgcccgc cccgcccca | | 540 |
| ctgcgctgca ccaccctggg caacaccatt tactgcctca accccaggt cactgccacc | | 600 |
| ttcacggtct ctgggggggac tgcccagttc caggccaagg agctgcagcc cttccccttg | | 660 |
| gggagcaccg gggtcctcag tccattcatc ctgactctgc ccctgagga ccggctgcag | | 720 |
| acctcactct ga | | 732 |

<210> SEQ ID NO 506
<211> LENGTH: 729
<212> TYPE: DNA
<213> ORGANISM: Homo sapiens

<400> SEQUENCE: 506

| | | |
|---|---|---|
| atgcacaact acctgtttct ggcgggggc atccgtggct ccggtgccaa ggccgtctgc | | 60 |
| tccaacgagg tcttctgcta caaccctctg accaacatct ggagccaggt tcggcccatg | | 120 |
| cagcaggccc gagcccagct caagctggtg gccctggacg ggctgctcta tgccatcggt | | 180 |
| ggcgaatgcc tgtacagcat ggagtgctac gaccgcgaa cagacgcctg gacccccacgc | | 240 |

```
gcgccactcc ccgcaggcac cttccctgtg gcccacgagg ctgtggcctg ccgtggggac    300
atctacgtca ccgggggtca cctcttctac cgcctgctca ggtacagccc cgtgaaggat    360
gcttgggacg agtgcccata cagtgccagc caccggcgtt ccagcgacat cgttgcactg    420
gggggcttcc tgtaccgctt cgacctgctg cggggcgtgg cgccgccgt gatgcgctac     480 aacacagtga ccggctcctg gagcagggct gcctccctgc ccctgccgc ccccgcccca     540 ctgcgctgca ccaccctggg caacaccatt tactgcctca accccaggt cactgccacc     600 ttcacggtct ctgggggggac tgcccagttc caggccaagg agctgcagcc cttcccttg    660 gggagcaccg gggtcctcag tccattcatc ctgactctgc ccctgagga ccggctgcag    720 acctcactc                                                            729
```

<210> SEQ ID NO 507
<211> LENGTH: 243
<212> TYPE: PRT
<213> ORGANISM: Homo sapiens

<400> SEQUENCE: 507

```
Met His Asn Tyr Leu Phe Leu Ala Gly Gly Ile Arg Gly Ser Gly Ala
 1               5                  10                  15

Lys Ala Val Cys Ser Asn Glu Val Phe Cys Tyr Asn Pro Leu Thr Asn
            20                  25                  30

Ile Trp Ser Gln Val Arg Pro Met Gln Gln Ala Arg Ala Gln Leu Lys
        35                  40                  45

Leu Val Ala Leu Asp Gly Leu Leu Tyr Ala Ile Gly Gly Glu Cys Leu
    50                  55                  60

Tyr Ser Met Glu Cys Tyr Asp Pro Arg Thr Asp Ala Trp Thr Pro Arg
65                  70                  75                  80

Ala Pro Leu Pro Ala Gly Thr Phe Pro Val Ala His Glu Ala Val Ala
                85                  90                  95

Cys Arg Gly Asp Ile Tyr Val Thr Gly Gly His Leu Phe Tyr Arg Leu
            100                 105                 110

Leu Arg Tyr Ser Pro Val Lys Asp Ala Trp Asp Glu Cys Pro Tyr Ser
        115                 120                 125

Ala Ser His Arg Arg Ser Ser Asp Ile Val Ala Leu Gly Gly Phe Leu
    130                 135                 140

Tyr Arg Phe Asp Leu Leu Arg Gly Val Gly Ala Ala Val Met Arg Tyr
145                 150                 155                 160

Asn Thr Val Thr Gly Ser Trp Ser Arg Ala Ala Ser Leu Pro Leu Pro
                165                 170                 175

Ala Pro Ala Pro Leu Arg Cys Thr Thr Leu Gly Asn Thr Ile Tyr Cys
            180                 185                 190

Leu Asn Pro Gln Val Thr Ala Thr Phe Thr Val Ser Gly Gly Thr Ala
        195                 200                 205

Gln Phe Gln Ala Lys Glu Leu Gln Pro Phe Pro Leu Gly Ser Thr Gly
    210                 215                 220

Val Leu Ser Pro Phe Ile Leu Thr Leu Pro Pro Glu Asp Arg Leu Gln
225                 230                 235                 240

Thr Ser Leu
```

<210> SEQ ID NO 508
<211> LENGTH: 158
<212> TYPE: PRT
<213> ORGANISM: Homo sapiens

<400> SEQUENCE: 508

Met His Asn Tyr Leu Phe Leu Ala Gly Gly Ile Arg Gly Ser Gly Ala
1               5                   10                  15

Lys Ala Val Cys Ser Asn Glu Val Phe Cys Tyr Asn Pro Leu Thr Asn
            20                  25                  30

Ile Trp Ser Gln Val Arg Pro Met Gln Gln Ala Arg Ala Gln Leu Lys
        35                  40                  45

Leu Val Ala Leu Asp Gly Leu Leu Tyr Ala Ile Gly Gly Glu Cys Leu
    50                  55                  60

Tyr Ser Met Glu Cys Tyr Asp Pro Arg Thr Asp Ala Trp Thr Pro Arg
65                  70                  75                  80

Ala Pro Leu Pro Ala Gly Thr Phe Pro Val Ala His Glu Ala Val Ala
                85                  90                  95

Cys Arg Gly Asp Ile Tyr Val Thr Gly Gly His Leu Phe Tyr Arg Leu
            100                 105                 110

Leu Arg Tyr Ser Pro Val Lys Asp Ala Trp Asp Glu Cys Pro Tyr Ser
        115                 120                 125

Ala Ser His Arg Arg Ser Ser Asp Ile Val Ala Leu Gly Gly Phe Leu
    130                 135                 140

Tyr Arg Phe Asp Leu Leu Arg Gly Val Gly Ala Ala Val Met
145                 150                 155

<210> SEQ ID NO 509
<211> LENGTH: 85
<212> TYPE: PRT
<213> ORGANISM: Homo sapiens

<400> SEQUENCE: 509

Arg Tyr Asn Thr Val Thr Gly Ser Trp Ser Arg Ala Ala Ser Leu Pro
1               5                   10                  15

Leu Pro Ala Pro Ala Pro Leu Arg Cys Thr Thr Leu Gly Asn Thr Ile
            20                  25                  30

Tyr Cys Leu Asn Pro Gln Val Thr Ala Thr Phe Thr Val Ser Gly Gly
        35                  40                  45

Thr Ala Gln Phe Gln Ala Lys Glu Leu Gln Pro Phe Pro Leu Gly Ser
    50                  55                  60

Thr Gly Val Leu Ser Pro Phe Ile Leu Thr Leu Pro Pro Glu Asp Arg
65                  70                  75                  80

Leu Gln Thr Ser Leu
                85

<210> SEQ ID NO 510
<211> LENGTH: 732
<212> TYPE: DNA
<213> ORGANISM: Homo sapiens

<400> SEQUENCE: 510
atgcgacccc agggccccgc cgcctccccg cagcggctcc gcggcctcct gctgctcctg      60
ctgctgcagc tgcccgcgcc gtcgagcgcc tctgagatcc ccaagggaa gcaaaaggcg     120 cagctccggc agaggaggt ggtggacctg tataatggaa tgtgcttaca agggccagca     180
ggagtgcctg gtcgagacgg gagccctggg gccaatgtta ttccgggtac acctgggatc     240
ccaggtcggg atggattcaa aggagaaaag ggggaatgtc tgagggaaag ctttgaggag     300
tcctggacac ccaactacaa gcagtgttca tggagttcat tgaattatgg catagatctt     360
gggaaaattg cggagtgtac atttacaaag atgcgttcaa atagtgctct aagagttttg     420

| | |
|---|---|
| ttcagtggct cacttcggct aaaatgcaga atgcatgct gtcagcgttg gtatttcaca | 480 |
| ttcaatggag ctgaatgttc aggacctctt cccattgaag ctataattta tttggaccaa | 540 |
| ggaagccctg aaatgaattc aacaattaat attcatcgca cttcttctgt ggaaggactt | 600 |
| tgtgaaggaa ttggtgctgg attagtggat gttgctatct gggttggcac ttgttcagat | 660 |
| tacccaaaag gagatgcttc tactggatgg aattcagttt ctcgcatcat tattgaagaa | 720 |
| ctaccaaaat aa | 732 |

<210> SEQ ID NO 511
<211> LENGTH: 729
<212> TYPE: DNA
<213> ORGANISM: Homo sapiens

<400> SEQUENCE: 511

| | |
|---|---|
| atgcgacccc agggccccgc cgcctccccg cagcggctcc gcggcctcct gctgctcctg | 60 |
| ctgctgcagc tgcccgcgcc gtcgagcgcc tctgagatcc caaggggaa gcaaaaggcg | 120 |
| cagctccggc agagggaggt ggtggacctg tataatggaa tgtgcttaca agggccagca | 180 |
| ggagtgcctg gtcgagacgg gagccctggg gccaatgtta ttccgggtac acctgggatc | 240 |
| ccaggtcggg atggattcaa aggagaaaag gggaatgtc tgaggaaag ctttgaggag | 300 |
| tcctggacac ccaactacaa gcagtgttca tggagttcat tgaattatgg catagatctt | 360 |
| gggaaaattg cggagtgtac atttacaaag atgcgttcaa atagtgctct aagagttttg | 420 |
| ttcagtggct cacttcggct aaaatgcaga atgcatgct gtcagcgttg gtatttcaca | 480 |
| ttcaatggag ctgaatgttc aggacctctt cccattgaag ctataattta tttggaccaa | 540 |
| ggaagccctg aaatgaattc aacaattaat attcatcgca cttcttctgt ggaaggactt | 600 |
| tgtgaaggaa ttggtgctgg attagtggat gttgctatct gggttggcac ttgttcagat | 660 |
| tacccaaaag gagatgcttc tactggatgg aattcagttt ctcgcatcat tattgaagaa | 720 |
| ctaccaaaa | 729 |

<210> SEQ ID NO 512
<211> LENGTH: 837
<212> TYPE: DNA
<213> ORGANISM: Homo sapiens

<400> SEQUENCE: 512

| | |
|---|---|
| atgcagcctg cggcggcctc ggagcgcggc ggagcagacg ctgaccacgt tcctctcctc | 60 |
| ggtctcctcc gcctccagct ccgcgctgcc cggcagccgg agccatgcg accccagggc | 120 |
| cccgccgcct ccccgcagcg gctccgcggc ctcctgctgc tcctgctgct gcagctgccc | 180 |
| gcgccgtcga gcgcctctga gatccccaag gggaagcaaa aggcgcagct ccggcagagg | 240 |
| gaggtggtgg acctgtataa tggaatgtgc ttacaagggc agcaggagt gcctggtcga | 300 |
| gacgggagcc ctggggccaa tgttattccg gtacacctg gatcccagg tcgggatgga | 360 |
| ttcaaaggag aaaagggga atgtctgagg gaaagctttg aggagtcctg gacacccaac | 420 |
| tacaagcagt gttcatggag ttcattgaat tatggcatag atcttgggaa aattgcggag | 480 |
| tgtacattta caaagatgcg ttcaaatagt gctctaagag ttttgttcag tggctcactt | 540 |
| cggctaaaat gcagaaatgc atgctgtcag cgttggtatt tcacattcaa tggagctgaa | 600 |
| tgttcaggac ctcttcccat tgaagctata atttatttgg accaaggaag ccctgaaatg | 660 |
| aattcaacaa ttaatattca tcgcacttct tctgtggaag gactttgtga aggaattggt | 720 |

```
                                       gctggattag tggatgttgc tatctgggtt ggcacttgtt cagattaccc aaaaggagat       780
gcttctactg gatggaattc agtttctcgc atcattattg aagaactacc aaaataa         837

<210> SEQ ID NO 513
<211> LENGTH: 837
<212> TYPE: DNA
<213> ORGANISM: Homo sapiens

<400> SEQUENCE: 513
atgcagcctg cggcggcctc ggagcgcggc ggagcagacg ctgaccacgt tcctctcctc        60
ggtctcctcc gcctccagct ccgcgctgcc cggcagccgg gagccatgcg accccagggc       120
cccgccgcct cccgcagcg gctccgcggc ctcctgctgc tcctgctgct gcagctgccc        180
gcgccgtcga gcgcctctga gatccccaag gggaagcaaa aggcgcagct ccggcagagg       240
gaggtggtgg acctgtataa tggaatgtgc ttacaagggc cagcaggagt gcctggtcga       300
gacgggagcc ctggggccaa tgttattccg ggtacacctg gatcccagg tcggatgga        360 ttcaaaggag aaaaggggga atgtctgagg gaaagctttg aggagtcctg gacacccaac       420
tacaagcagt gttcatggag ttcattgaat tatggcatag atcttgggaa aattgcggag       480
tgtacattta caagatgcg ttcaaatagt gctctaagag ttttgttcag tggctcactt        540
cggctaaaat gcagaaatgc atgctgtcag cgttggtatt tcacattcaa tggagctgaa       600
tgttcaggac ctcttcccat tgaagctata atttatttgg accaaggaag ccctgaaatg       660
aattcaacaa ttaatattca tcgcacttct tctgtggaag actttgtga aggaattggt        720 gctggattag tggatgttgc tatctgggtt ggcacttgtt cagattaccc aaaaggagat       780
gcttctactg gatggaattc agtttctcgc atcattattg aagaactacc aaaataa         837

<210> SEQ ID NO 514
<211> LENGTH: 243
<212> TYPE: PRT
<213> ORGANISM: Homo sapiens

<400> SEQUENCE: 514

Met Arg Pro Gln Gly Pro Ala Ala Ser Pro Gln Arg Leu Arg Gly Leu
 1               5                  10                  15

Leu Leu Leu Leu Leu Leu Gln Leu Pro Ala Pro Ser Ser Ala Ser Glu
             20                  25                  30

Ile Pro Lys Gly Lys Gln Lys Ala Gln Leu Arg Gln Arg Glu Val Val
         35                  40                  45

Asp Leu Tyr Asn Gly Met Cys Leu Gln Gly Pro Ala Gly Val Pro Gly
     50                  55                  60

Arg Asp Gly Ser Pro Gly Ala Asn Val Ile Pro Gly Thr Pro Gly Ile
 65                  70                  75                  80

Pro Gly Arg Asp Gly Phe Lys Gly Glu Lys Gly Glu Cys Leu Arg Glu
                 85                  90                  95

Ser Phe Glu Glu Ser Trp Thr Pro Asn Tyr Lys Gln Cys Ser Trp Ser
            100                 105                 110

Ser Leu Asn Tyr Gly Ile Asp Leu Gly Lys Ile Ala Glu Cys Thr Phe
        115                 120                 125

Thr Lys Met Arg Ser Asn Ser Ala Leu Arg Val Leu Phe Ser Gly Ser
    130                 135                 140

Leu Arg Leu Lys Cys Arg Asn Ala Cys Cys Gln Arg Trp Tyr Phe Thr
145                 150                 155                 160

Phe Asn Gly Ala Glu Cys Ser Gly Pro Leu Pro Ile Glu Ala Ile Ile
```

```
                165                 170                 175
Tyr Leu Asp Gln Gly Ser Pro Glu Met Asn Ser Thr Ile Asn Ile His
            180                 185                 190
Arg Thr Ser Ser Val Glu Gly Leu Cys Glu Gly Ile Gly Ala Gly Leu
        195                 200                 205
Val Asp Val Ala Ile Trp Val Gly Thr Cys Ser Asp Tyr Pro Lys Gly
    210                 215                 220
Asp Ala Ser Thr Gly Trp Asn Ser Val Ser Arg Ile Ile Ile Glu Glu
225                 230                 235                 240
Leu Pro Lys

<210> SEQ ID NO 515
<211> LENGTH: 278
<212> TYPE: PRT
<213> ORGANISM: Homo sapiens

<400> SEQUENCE: 515

Met Gln Pro Ala Ala Ala Ser Glu Arg Gly Gly Ala Asp Ala Asp His
                5                  10                  15
Val Pro Leu Leu Gly Leu Leu Arg Leu Gln Leu Arg Ala Ala Arg Gln
            20                  25                  30
Pro Gly Ala Met Arg Pro Gln Gly Pro Ala Ala Ser Pro Gln Arg Leu
        35                  40                  45
Arg Gly Leu Leu Leu Leu Leu Leu Gln Leu Pro Ala Pro Ser Ser
    50                  55                  60
Ala Ser Glu Ile Pro Lys Gly Lys Gln Lys Ala Gln Leu Arg Gln Arg
65                  70                  75                  80
Glu Val Val Asp Leu Tyr Asn Gly Met Cys Leu Gln Gly Pro Ala Gly
                85                  90                  95
Val Pro Gly Arg Asp Gly Ser Pro Gly Ala Asn Val Ile Pro Gly Thr
            100                 105                 110
Pro Gly Ile Pro Gly Arg Asp Gly Phe Lys Gly Glu Lys Gly Glu Cys
        115                 120                 125
Leu Arg Glu Ser Phe Glu Glu Ser Trp Thr Pro Asn Tyr Lys Gln Cys
    130                 135                 140
Ser Trp Ser Ser Leu Asn Tyr Gly Ile Asp Leu Gly Lys Ile Ala Glu
145                 150                 155                 160
Cys Thr Phe Thr Lys Met Arg Ser Asn Ser Ala Leu Arg Val Leu Phe
                165                 170                 175
Ser Gly Ser Leu Arg Leu Lys Cys Arg Asn Ala Cys Cys Gln Arg Trp
            180                 185                 190
Tyr Phe Thr Phe Asn Gly Ala Glu Cys Ser Gly Pro Leu Pro Ile Glu
        195                 200                 205
Ala Ile Ile Tyr Leu Asp Gln Gly Ser Pro Glu Met Asn Ser Thr Ile
    210                 215                 220
Asn Ile His Arg Thr Ser Ser Val Glu Gly Leu Cys Glu Gly Ile Gly
225                 230                 235                 240
Ala Gly Leu Val Asp Val Ala Ile Trp Val Gly Thr Cys Ser Asp Tyr
                245                 250                 255
Pro Lys Gly Asp Ala Ser Thr Gly Trp Asn Ser Val Ser Arg Ile Ile
            260                 265                 270
Ile Glu Glu Leu Pro Lys
        275
```

<210> SEQ ID NO 516
<211> LENGTH: 197
<212> TYPE: PRT
<213> ORGANISM: Homo sapiens

<400> SEQUENCE: 516

Met Arg Pro Gln Gly Pro Ala Ala Ser Pro Gln Arg Leu Arg Gly Leu
1               5                   10                  15

Leu Leu Leu Leu Leu Leu Gln Leu Pro Ala Pro Ser Ser Ala Ser Glu
            20                  25                  30

Ile Pro Lys Gly Lys Gln Lys Ala Gln Leu Arg Gln Arg Glu Val Val
        35                  40                  45

Asp Leu Tyr Asn Gly Met Cys Leu Gln Gly Pro Ala Gly Val Pro Gly
    50                  55                  60

Arg Asp Gly Ser Pro Gly Ala Asn Val Ile Pro Gly Thr Pro Gly Ile
65                  70                  75                  80

Pro Gly Arg Asp Gly Phe Lys Gly Glu Lys Gly Glu Cys Leu Arg Glu
                85                  90                  95

Ser Phe Glu Glu Ser Trp Thr Pro Asn Tyr Lys Gln Cys Ser Trp Ser
            100                 105                 110

Ser Leu Asn Tyr Gly Ile Asp Leu Gly Lys Ile Ala Glu Cys Thr Phe
        115                 120                 125

Thr Lys Met Arg Ser Asn Ser Ala Leu Arg Val Leu Phe Ser Gly Ser
    130                 135                 140

Leu Arg Leu Lys Cys Arg Asn Ala Cys Cys Gln Arg Trp Tyr Phe Thr
145                 150                 155                 160

Phe Asn Gly Ala Glu Cys Ser Gly Pro Leu Pro Ile Glu Ala Ile Ile
                165                 170                 175

Tyr Leu Asp Gln Gly Ser Pro Glu Met Asn Ser Thr Ile Asn Ile His
            180                 185                 190

Arg Thr Ser Ser Val
        195

<210> SEQ ID NO 517
<211> LENGTH: 232
<212> TYPE: PRT
<213> ORGANISM: Homo sapiens

<400> SEQUENCE: 517

Met Gln Pro Ala Ala Ala Ser Glu Arg Gly Gly Ala Asp Ala Asp His
1               5                   10                  15

Val Pro Leu Leu Gly Leu Leu Arg Leu Gln Leu Arg Ala Ala Arg Gln
            20                  25                  30

Pro Gly Ala Met Arg Pro Gln Gly Pro Ala Ala Ser Pro Gln Arg Leu
        35                  40                  45

Arg Gly Leu Leu Leu Leu Leu Leu Gln Leu Pro Ala Pro Ser Ser Ser
    50                  55                  60

Ala Ser Glu Ile Pro Lys Gly Lys Gln Lys Ala Gln Leu Arg Gln Arg
65                  70                  75                  80

Glu Val Val Asp Leu Tyr Asn Gly Met Cys Leu Gln Gly Pro Ala Gly
                85                  90                  95

Val Pro Gly Arg Asp Gly Ser Pro Gly Ala Asn Val Ile Pro Gly Thr
            100                 105                 110

Pro Gly Ile Pro Gly Arg Asp Gly Phe Lys Gly Glu Lys Gly Glu Cys
        115                 120                 125

Leu Arg Glu Ser Phe Glu Glu Ser Trp Thr Pro Asn Tyr Lys Gln Cys

```
                130                 135                 140
Ser Trp Ser Ser Leu Asn Tyr Gly Ile Asp Leu Gly Lys Ile Ala Glu
145                 150                 155                 160

Cys Thr Phe Thr Lys Met Arg Ser Asn Ser Ala Leu Arg Val Leu Phe
                165                 170                 175

Ser Gly Ser Leu Arg Leu Lys Cys Arg Asn Ala Cys Cys Gln Arg Trp
            180                 185                 190

Tyr Phe Thr Phe Asn Gly Ala Glu Cys Ser Gly Pro Leu Pro Ile Glu
                195                 200                 205

Ala Ile Ile Tyr Leu Asp Gln Gly Ser Pro Glu Met Asn Ser Thr Ile
210                 215                 220

Asn Ile His Arg Thr Ser Ser Val
225                 230

<210> SEQ ID NO 518
<211> LENGTH: 46
<212> TYPE: PRT
<213> ORGANISM: Homo sapiens

<400> SEQUENCE: 518

Glu Gly Leu Cys Glu Gly Ile Gly Ala Gly Leu Val Asp Val Ala Ile
                5                   10                  15

Trp Val Gly Thr Cys Ser Asp Tyr Pro Lys Gly Asp Ala Ser Thr Gly
            20                  25                  30

Trp Asn Ser Val Ser Arg Ile Ile Ile Glu Glu Leu Pro Lys
        35                  40                  45

<210> SEQ ID NO 519
<211> LENGTH: 26
<212> TYPE: PRT
<213> ORGANISM: Homo sapiens

<400> SEQUENCE: 519

Cys Ser Asp Tyr Pro Lys Gly Asp Ala Ser Thr Gly Trp Asn Ser Val
                5                   10                  15

Ser Arg Ile Ile Ile Glu Glu Leu Pro Lys
            20                  25

<210> SEQ ID NO 520
<211> LENGTH: 60
<212> TYPE: DNA
<213> ORGANISM: Homo sapiens

<400> SEQUENCE: 520
aaaaatgagg agatatttaa ttacaataac catttaaaaa accgtatata tcaatatgaa    60

<210> SEQ ID NO 521
<211> LENGTH: 60
<212> TYPE: DNA
<213> ORGANISM: Homo sapiens

<400> SEQUENCE: 521
atgcaacatc atctcctaaa agagaaaaat gaggagatat taattacaa taaccattta    60

<210> SEQ ID NO 522
<211> LENGTH: 60
<212> TYPE: DNA
<213> ORGANISM: Homo sapiens

<400> SEQUENCE: 522
```
gacaacaaaa gcaagataac aattgatatt cattttcttg agaggaaaat gcaacatcat    60

<210> SEQ ID NO 523
<211> LENGTH: 60
<212> TYPE: DNA
<213> ORGANISM: Homo sapiens

<400> SEQUENCE: 523
aaaaatatgt ggcttcaaca gcaattagtt catgcacata agaaagctga caacaaaagc    60

<210> SEQ ID NO 524
<211> LENGTH: 63
<212> TYPE: DNA
<213> ORGANISM: Homo sapiens

<400> SEQUENCE: 524
gatcagaaat tatttcaact acaaagcaaa aatatgtggc ttcaacagca attagttcat    60
gca    63

<210> SEQ ID NO 525
<211> LENGTH: 60
<212> TYPE: DNA
<213> ORGANISM: Homo sapiens

<400> SEQUENCE: 525
actgaacagc aggagtctct agatcagaaa ttatttcaac tacaaagcaa aaatatgtgg    60

<210> SEQ ID NO 526
<211> LENGTH: 63
<212> TYPE: DNA
<213> ORGANISM: Homo sapiens

<400> SEQUENCE: 526
gctcaaagga atccaaaag cctaaaaatt aatctcaatt atgccggaga tgctctaaga    60
gaa    63

<210> SEQ ID NO 527
<211> LENGTH: 60
<212> TYPE: DNA
<213> ORGANISM: Homo sapiens

<400> SEQUENCE: 527
agtacgatat ataacaatga ggtgctccat caaccacttt ctgaagctca aggaaatcc    60

<210> SEQ ID NO 528
<211> LENGTH: 60
<212> TYPE: DNA
<213> ORGANISM: Homo sapiens

<400> SEQUENCE: 528
agaaaaatga atgttgatgt gagtagtacg atatataaca atgaggtgct ccatcaacca    60

<210> SEQ ID NO 529
<211> LENGTH: 60
<212> TYPE: DNA
<213> ORGANISM: Homo sapiens

<400> SEQUENCE: 529
attgcaggag atgcttgttt gcaaagaaaa atgaatgttg atgtgagtag tacgatatat    60

<210> SEQ ID NO 530
<211> LENGTH: 60

```
<212> TYPE: DNA
<213> ORGANISM: Homo sapiens

<400> SEQUENCE: 530
aaaagtcaag aacctgcttt ccacattgca ggagatgctt gtttgcaaag aaaaatgaat    60

<210> SEQ ID NO 531
<211> LENGTH: 60
<212> TYPE: DNA
<213> ORGANISM: Homo sapiens

<400> SEQUENCE: 531 gaaataaat actttgagga cattaagatt ttaaagaaa agaatgctga acttcagatg       60

<210> SEQ ID NO 532
<211> LENGTH: 60
<212> TYPE: DNA
<213> ORGANISM: Homo sapiens

<400> SEQUENCE: 532
ctgaaacacc aataccagga aaggaaaat aaatactttg aggacattaa gattttaaaa     60

<210> SEQ ID NO 533
<211> LENGTH: 63
<212> TYPE: DNA
<213> ORGANISM: Homo sapiens

<400> SEQUENCE: 533
aattgcatgt tgaaaaagga aattgccatg ctaaaactgg aaatagccac actgaaacac    60
caa                                                                  63

<210> SEQ ID NO 534
<211> LENGTH: 21
<212> TYPE: PRT
<213> ORGANISM: Homo sapiens

<400> SEQUENCE: 534

Asn Cys Met Leu Lys Lys Glu Ile Ala Met Leu Lys Leu Glu Ile Ala
                 5                  10                  15

Thr Leu Lys His Gln
             20

<210> SEQ ID NO 535
<211> LENGTH: 20
<212> TYPE: PRT
<213> ORGANISM: Homo sapiens

<400> SEQUENCE: 535

Leu Lys His Gln Tyr Gln Glu Lys Glu Asn Lys Tyr Phe Glu Asp Ile
                 5                  10                  15

Lys Ile Leu Lys
             20

<210> SEQ ID NO 536
<211> LENGTH: 20
<212> TYPE: PRT
<213> ORGANISM: Homo sapiens

<400> SEQUENCE: 536

Glu Asn Lys Tyr Phe Glu Asp Ile Lys Ile Leu Lys Glu Lys Asn Ala
                 5                  10                  15

Glu Leu Gln Met
```

-continued

<210> SEQ ID NO 537
<211> LENGTH: 20
<212> TYPE: PRT
<213> ORGANISM: Homo sapiens

<400> SEQUENCE: 537

Lys Ser Gln Glu Pro Ala Phe His Ile Ala Gly Asp Ala Cys Leu Gln
                5                  10                  15

Arg Lys Met Asn
            20

<210> SEQ ID NO 538
<211> LENGTH: 20
<212> TYPE: PRT
<213> ORGANISM: Homo sapiens

<400> SEQUENCE: 538

Ile Ala Gly Asp Ala Cys Leu Gln Arg Lys Met Asn Val Asp Val Ser
                5                  10                  15

Ser Thr Ile Tyr
            20

<210> SEQ ID NO 539
<211> LENGTH: 20
<212> TYPE: PRT
<213> ORGANISM: Homo sapiens

<400> SEQUENCE: 539

Arg Lys Met Asn Val Asp Val Ser Ser Thr Ile Tyr Asn Asn Glu Val
                5                  10                  15

Leu His Gln Pro
            20

<210> SEQ ID NO 540
<211> LENGTH: 20
<212> TYPE: PRT
<213> ORGANISM: Homo sapiens

<400> SEQUENCE: 540

Ser Thr Ile Tyr Asn Asn Glu Val Leu His Gln Pro Leu Ser Glu Ala
                5                  10                  15

Gln Arg Lys Ser
            20

<210> SEQ ID NO 541
<211> LENGTH: 21
<212> TYPE: PRT
<213> ORGANISM: Homo sapiens

<400> SEQUENCE: 541

Ala Gln Arg Lys Ser Lys Ser Leu Lys Ile Asn Leu Asn Tyr Ala Gly
                5                  10                  15

Asp Ala Leu Arg Glu
            20

<210> SEQ ID NO 542
<211> LENGTH: 20
<212> TYPE: PRT
<213> ORGANISM: Homo sapiens

<400> SEQUENCE: 542

```
Thr Glu Gln Gln Glu Ser Leu Asp Gln Lys Leu Phe Gln Leu Gln Ser
  1               5                  10                  15

Lys Asn Met Trp
            20

<210> SEQ ID NO 543
<211> LENGTH: 21
<212> TYPE: PRT
<213> ORGANISM: Homo sapiens

<400> SEQUENCE: 543

Asp Gln Lys Leu Phe Gln Leu Gln Ser Lys Asn Met Trp Leu Gln Gln
  1               5                  10                  15

Gln Leu Val His Ala
            20

<210> SEQ ID NO 544
<211> LENGTH: 20
<212> TYPE: PRT
<213> ORGANISM: Homo sapiens

<400> SEQUENCE: 544

Lys Asn Met Trp Leu Gln Gln Gln Leu Val His Ala His Lys Lys Ala
  1               5                  10                  15

Asp Asn Lys Ser
            20

<210> SEQ ID NO 545
<211> LENGTH: 20
<212> TYPE: PRT
<213> ORGANISM: Homo sapiens

<400> SEQUENCE: 545

Asp Asn Lys Ser Lys Ile Thr Ile Asp Ile His Phe Leu Glu Arg Lys
  1               5                  10                  15

Met Gln His His
            20

<210> SEQ ID NO 546
<211> LENGTH: 20
<212> TYPE: PRT
<213> ORGANISM: Homo sapiens

<400> SEQUENCE: 546

Met Gln His His Leu Leu Lys Glu Lys Asn Glu Glu Ile Phe Asn Tyr
  1               5                  10                  15

Asn Asn His Leu
            20

<210> SEQ ID NO 547
<211> LENGTH: 20
<212> TYPE: PRT
<213> ORGANISM: Homo sapiens

<400> SEQUENCE: 547

Lys Asn Glu Glu Ile Phe Asn Tyr Asn Asn His Leu Lys Asn Arg Ile
  1               5                  10                  15

Tyr Gln Tyr Glu
            20

<210> SEQ ID NO 548
```

<211> LENGTH: 3045
<212> TYPE: DNA
<213> ORGANISM: Homo sapiens

<400> SEQUENCE: 548

```
atgcagcatc accaccatca ccacgtcggc tccatgagtc ccgcaaaaga aacatctgag     60
aaatttacgt gggcagcaaa aggaagacct aggaagatcg catgggagaa aaagaaaca    120
cctgtaaaga ctggatgcgt ggcaagagta acatctaata aaactaaagt tttggaaaaa    180
ggaagatcta agatgattgc atgtcctaca aagaatcat ctacaaaagc aagtgccaat    240
gatcagaggt tcccatcaga atccaaacaa gaggaagatg aagaatattc ttgtgattct    300
cggagtctct ttgagagttc tgcaaagatt caagtgtgta tacctgagtc tatatatcaa    360
aaagtaatgg agataaatag agaagtagaa gagcctccta agaagccatc tgccttcaag    420
cctgccattg aaatgcaaaa ctctgttcca aataaagcct ttgaattgaa gaatgaacaa    480
acattgagag cagatccgat gttcccacca gaatccaaac aaaaggacta tgaagaaaat    540
tcttgggatt ctgagagtct ctgtgagact gtttcacaga aggatgtgtg tttacccaag    600
gctacacatc aaaagaaat agataaaata aatggaaaat tagaagagtc tcctaataaa    660
gatggtcttc tgaaggctac ctgcggaatg aaagtttcta ttccaactaa agccttagaa    720
ttgaaggaca tgcaaacttt caaagcagag cctccgggga agccatctgc cttcgagcct    780
gccactgaaa tgcaaaagtc tgtcccaaat aaagccttgg aattgaaaaa tgaacaaaca    840
ttgagagcag atgagatact cccatcagaa tccaaacaaa aggactatga agaaaattct    900
tgggatactg agagtctctg tgagactgtt tcacagaagg atgtgtgttt acccaaggct    960
gcgcatcaaa agaaataga taaataaat ggaaaattag aagggtctcc tggtaaagat   1020
ggtcttctta aggctaactg cggaatgaaa gtttctattc caactaaagc cttagaattg   1080
atggacatgc aaactttcaa agcagagcct cccgagaagc catctgcctt cgagcctgcc   1140
attgaaatgc aaaagtctgt tccaaataaa gccttggaat tgaagaatga acaaacattg   1200
agagcagatg agatactccc atcagaatcc aaacaaaagg actatgaaga agttcttgg   1260
gattctgaga gtctctgtga gactgtttca gaaggatg tgtgtttacc caaggctgcg   1320
catcaaaaag aaatagataa aataaatgga aaattagaag agtctcctga taatgatggt   1380
tttctgaagt ctccctgcag aatgaaagtt tctattccaa ctaaagcctt agaattgatg   1440
gacatgcaaa ctttcaaagc agagcctccc gagaagccat ctgccttcga gcctgccatt   1500
gaaatgcaaa agtctgttcc aaataaagcc ttggaattga agaatgaaca acattgaga   1560
gcagatcaga tgttcccttc agaatcaaaa caaaagaacg ttgaagaaaa ttcttgggat   1620
tctgagagtc tccgtgagac tgtttcacag aaggatgtgt gtgtacccaa ggctacacat   1680
caaaagaaa tggataaaat aagtggaaaa ttagaagatt caactagcct atcaaaaatc   1740
ttggatacag ttcattcttg tgaaagagca agggaacttc aaaaagatca ctgtgaacaa   1800
cgtacaggaa aaatggaaca aatgaaaaag aagttttgtg tactgaaaaa gaaactgtca   1860
gaagcaaaag aaataaaatc acagttagag aaccaaaaag ttaaatggga caagagctc   1920
tgcagtgtga gattgacttt aaaccaagaa gagagaaga gaagaaatgc cgatatatta   1980
aatgaaaaaa ttagggaaga attaggaaga atcgaagagc agcataggaa agagttagaa   2040
gtgaaacaac aacttgaaca ggctctcaga atacaagata tagaattgaa gagtgtagaa   2100
agtaatttaa atcaggtttc tcacactcat gaaaatgaaa attatctctt acatgaaaat   2160
tgcatgttga aaaggaaat tgccatgcta aaactggaaa tagccacact gaaacaccaa   2220
```

| | |
|---|---|
| taccaggaaa aggaaaataa atactttgag gacattaaga ttttaaaaga aaagaatgct | 2280 |
| gaacttcaga tgaccctaaa actgaaagag gaatcattaa ctaaaagggc atctcaatat | 2340 |
| agtgggcagc ttaaagttct gatagctgag aacacaatgc tcacttctaa attgaaggaa | 2400 |
| aaacaagaca aagaaatact agaggcagaa attgaatcac accatcctag actggcttct | 2460 |
| gctgtacaag accatgatca aattgtgaca tcaagaaaaa gtcaagaacc tgctttccac | 2520 |
| attgcaggag atgcttgttt gcaaagaaaa atgaatgttg atgtgagtag tacgatatat | 2580 |
| aacaatgagg tgctccatca accactttct gaagctcaaa ggaaatccaa aagcctaaaa | 2640 |
| attaatctca attatgccgg agatgctcta agagaaaata cattggtttc agaacatgca | 2700 |
| caaagagacc aacgtgaaac acagtgtcaa atgaaggaag ctgaacacat gtatcaaaac | 2760 |
| gaacaagata atgtgaacaa acacactgaa cagcaggagt ctctagatca gaaattattt | 2820 |
| caactacaaa gcaaaaatat gtggcttcaa cagcaattag ttcatgcaca taagaaagct | 2880 |
| gacaacaaaa gcaagataac aattgatatt cattttcttg agaggaaaat gcaacatcat | 2940 |
| ctcctaaaag agaaaaatga ggagatattt aattacaata accatttaaa aaccgtata | 3000 |
| tatcaatatg aaaagagaa agcagaaaca gaagttatat aatag | 3045 |

<210> SEQ ID NO 549
<211> LENGTH: 1953
<212> TYPE: DNA
<213> ORGANISM: Homo sapiens
<220> FEATURE:
<221> NAME/KEY: misc_feature
<222> LOCATION: 985
<223> OTHER INFORMATION: n = A,T,C or G

<400> SEQUENCE: 549

| | |
|---|---|
| atgagtcccg caaaagaaac atctgagaaa tttacgtggg cagcaaaagg aagacctagg | 60 |
| aagatcgcat gggagaaaaa agaaacacct gtaaagactg gatgcgtggc aagagtaaca | 120 |
| tctaataaaa ctaaagtttt ggaaaaagga agatctaaga tgattgcatg tcctacaaaa | 180 |
| gaatcatcta caaaagcaag tgccaatgat cagaggttcc catcagaatc caacaagag | 240 |
| gaagatgaag aatattcttg tgattctcgg agtctctttg agagttctgc aaagattcaa | 300 |
| gtgtgtatac ctgagtctat atatcaaaaa gtaatggaga taaatagaga agtagaagag | 360 |
| cctcctaaga agccatctgc cttcaagcct gccattgaaa tgcaaaactc tgttccaaat | 420 |
| aaagcctttg aattgaagaa tgaacaaaca ttgagagcag atccgatgtt cccaccagaa | 480 |
| tccaaacaaa aggactatga agaaaattct tgggattctg agagtctctg tgagactgtt | 540 |
| tcacagaagg atgtgtgttt acccaaggct acacatcaaa aagaaataga taaataaat | 600 |
| ggaaaattag aagagtctcc taataaagat ggtcttctga aggctacctg cggaatgaaa | 660 |
| gtttctattc caactaaagc cttagaattg aaggacatgc aaactttcaa agcagagcct | 720 |
| ccggggaagc catctgcctt cgagcctgcc actgaaatgc aaaagtctgt cccaaataaa | 780 |
| gccttggaat tgaaaaatga acaaacattg agagcagatg agatactccc atcagaatcc | 840 |
| aaacaaaagg actatgaaga aaattcttgg gatactgaga gtctctgtga gactgtttca | 900 |
| cagaaggatg tgtgtttacc caaggctgcg catcaaaaag aaatagataa aataaatgga | 960 |
| aaattagaag ggtctcctgg taaanatggt cttctgaagg ctaactgcgg aatgaaagtt | 1020 |
| tctattccaa ctaaagcctt agaattgatg gacatgcaaa cttttcaaagc agagcctccc | 1080 |
| gagaagccat ctgccttcga gcctgccatt gaaatgcaaa agtctgttcc aaataaagcc | 1140 |

```
ttggaattga agaatgaaca aacattgaga gcagatgaga tactcccatc agaatccaaa    1200
caaaaggact atgaagaaag ttcttgggat tctgagagtc tctgtgagac tgtttcacag    1260
aaggatgtgt gtttacccaa ggctgcgcat caaaaagaaa tagataaaat aaatggaaaa    1320
ttagaagagt ctcctgataa tgatggtttt ctgaagtctc cctgcagaat gaaagtttct    1380
attccaacta aagccttaga attgatggac atgcaaactt tcaaagcaga gcctcccgag    1440
aagccatctg ccttcgagcc tgccattgaa atgcaaaagt ctgttccaaa taaagccttg    1500
gaattgaaga tgaacaaac attgagagca gatcagatgt tcccttcaga atcaaaacaa     1560
aagaacgttg aagaaaattc ttgggattct gagagtctcc gtgagactgt tcacagaag     1620 gatgtgtgtg tacccaaggc tacacatcaa aaagaaatgg ataaaataag tggaaaatta    1680
gaagattcaa ctagcctatc aaaaatcttg gatacagttc attcttgtga agagcaagg     1740 gaacttcaaa agatcactg tgaacaacgt acaggaaaaa tggaacaaat gaaaaagaag     1800
ttttgtgtac tgaaaagaa actgtcagaa gcaaagaaa taaatcaca gttagagaac       1860 caaaagtta atgggaaca agagctctgc agtgtgaggt ttctcacact catgaaaatg       1920
aaaattatct cttacatgaa aattgcatgt tga                                  1953

<210> SEQ ID NO 550
<211> LENGTH: 978
<212> TYPE: DNA
<213> ORGANISM: Homo sapiens

<400> SEQUENCE: 550
atgcagcatc accaccatca ccacggcaca agagctctgc agtgtgaggt ttctcacact      60
catgaaaatg aaaattatct cttacatgaa aattgcatgt tgaaaaagga aattgccatg     120
ctaaaactgg aaatagccac actgaaacac caataccagg aaaaggaaaa taaatacttt     180
gaggacatta agattttaaa agaaaagaat gctgaacttc agatgaccct aaaactgaaa     240
gaggaatcat taactaaaag ggcatctcaa tatagtgggc agcttaaagt tctgatagct     300
gagaacacaa tgctcacttc taaattgaag gaaaaacaag acaaagaaat actagaggca     360
gaaattgaat cacaccatcc tagactggct tctgctgtac aagaccatga tcaaattgtg     420
acatcaagaa aaagtcaaga acctgctttc cacattgcag gagatgcttg tttgcaaaga     480
aaaatgaatg ttgatgtgag tagtacgata tataacaatg aggtgctcca tcaaccactt     540
tctgaagctc aaaggaaatc caaagcccta aaaattaatc tcaattatgc cggagatgct     600
ctaagagaaa atacattggt ttcagaacat gcacaaagag accaacgtga acacagtgt      660 caaatgaagg aagctgaaca catgtatcaa aacgaacaag ataatgtgaa caaacacact     720
gaacagcagg agtctctaga tcagaaatta tttcaactac aaagcaaaaa tatgtggctt     780
caacagcaat tagttcatgc acataagaaa gctgacaaca aaagcaagat aacaattgat     840
attcattttc ttgagaggaa aatgcaacat catctcctaa aagagaaaaa tgaggagata     900
tttaattaca ataaccatt aaaaaaccgt atatcaat atgaaaaaga gaaagcagaa        960
acagaagtta tataatag                                                    978

<210> SEQ ID NO 551
<211> LENGTH: 324
<212> TYPE: PRT
<213> ORGANISM: Homo sapiens

<400> SEQUENCE: 551

Met Gln His His His His His His Gly Thr Arg Ala Leu Gln Cys Glu
```

-continued

```
                 5                  10                   15
Val Ser His Thr His Glu Asn Glu Asn Tyr Leu Leu His Glu Asn Cys
             20                  25                  30

Met Leu Lys Lys Glu Ile Ala Met Leu Lys Leu Glu Ile Ala Thr Leu
             35                  40                  45

Lys His Gln Tyr Gln Glu Lys Glu Asn Lys Tyr Phe Glu Asp Ile Lys
         50                  55                  60

Ile Leu Lys Glu Lys Asn Ala Glu Leu Gln Met Thr Leu Lys Leu Lys
     65                  70                  75                  80

Glu Glu Ser Leu Thr Lys Arg Ala Ser Gln Tyr Ser Gly Gln Leu Lys
                 85                  90                  95

Val Leu Ile Ala Glu Asn Thr Met Leu Thr Ser Lys Leu Lys Glu Lys
             100                 105                 110

Gln Asp Lys Glu Ile Leu Glu Ala Glu Ile Glu Ser His His Pro Arg
         115                 120                 125

Leu Ala Ser Ala Val Gln Asp His Asp Gln Ile Val Thr Ser Arg Lys
     130                 135                 140

Ser Gln Glu Pro Ala Phe His Ile Ala Gly Asp Ala Cys Leu Gln Arg
145                 150                 155                 160

Lys Met Asn Val Asp Val Ser Ser Thr Ile Tyr Asn Asn Glu Val Leu
                 165                 170                 175

His Gln Pro Leu Ser Glu Ala Gln Arg Lys Ser Lys Ser Leu Lys Ile
             180                 185                 190

Asn Leu Asn Tyr Ala Gly Asp Ala Leu Arg Glu Asn Thr Leu Val Ser
         195                 200                 205

Glu His Ala Gln Arg Asp Gln Arg Glu Thr Gln Cys Gln Met Lys Glu
     210                 215                 220

Ala Glu His Met Tyr Gln Asn Glu Gln Asp Asn Val Asn Lys His Thr
225                 230                 235                 240

Glu Gln Gln Glu Ser Leu Asp Gln Lys Leu Phe Gln Leu Gln Ser Lys
                 245                 250                 255

Asn Met Trp Leu Gln Gln Gln Leu Val His Ala His Lys Lys Ala Asp
             260                 265                 270

Asn Lys Ser Lys Ile Thr Ile Asp Ile His Phe Leu Glu Arg Lys Met
         275                 280                 285

Gln His His Leu Leu Lys Glu Lys Asn Glu Glu Ile Phe Asn Tyr Asn
     290                 295                 300

Asn His Leu Lys Asn Arg Ile Tyr Gln Tyr Glu Lys Glu Lys Ala Glu
305                 310                 315                 320

Thr Glu Val Ile
```

<210> SEQ ID NO 552
<211> LENGTH: 661
<212> TYPE: PRT
<213> ORGANISM: Homo sapiens

<400> SEQUENCE: 552

```
Met Gln His His His His His His Val Gly Ser Met Ser Pro Ala Lys
                 5                  10                  15

Glu Thr Ser Glu Lys Phe Thr Trp Ala Ala Lys Gly Arg Pro Arg Lys
             20                  25                  30

Ile Ala Trp Glu Lys Lys Glu Thr Pro Val Lys Thr Gly Cys Val Ala
         35                  40                  45

Arg Val Thr Ser Asn Lys Thr Lys Val Leu Glu Lys Gly Arg Ser Lys
```

-continued

```
            50                  55                  60
Met Ile Ala Cys Pro Thr Lys Glu Ser Ser Thr Lys Ala Ser Ala Asn
 65                  70                  75                  80

Asp Gln Arg Phe Pro Ser Glu Ser Lys Gln Glu Glu Asp Glu Glu Tyr
                 85                  90                  95

Ser Cys Asp Ser Arg Ser Leu Phe Glu Ser Ser Ala Lys Ile Gln Val
                100                 105                 110

Cys Ile Pro Glu Ser Ile Tyr Gln Lys Val Met Glu Ile Asn Arg Glu
            115                 120                 125

Val Glu Glu Pro Pro Lys Lys Pro Ser Ala Phe Lys Pro Ala Ile Glu
130                 135                 140

Met Gln Asn Ser Val Pro Asn Lys Ala Phe Glu Leu Lys Asn Glu Gln
145                 150                 155                 160

Thr Leu Arg Ala Asp Pro Met Phe Pro Pro Glu Ser Lys Gln Lys Asp
                165                 170                 175

Tyr Glu Glu Asn Ser Trp Asp Ser Glu Ser Leu Cys Glu Thr Val Ser
                180                 185                 190

Gln Lys Asp Val Cys Leu Pro Lys Ala Thr His Gln Lys Glu Ile Asp
            195                 200                 205

Lys Ile Asn Gly Lys Leu Glu Glu Ser Pro Asn Lys Asp Gly Leu Leu
210                 215                 220

Lys Ala Thr Cys Gly Met Lys Val Ser Ile Pro Thr Lys Ala Leu Glu
225                 230                 235                 240

Leu Lys Asp Met Gln Thr Phe Lys Ala Glu Pro Pro Gly Lys Pro Ser
                245                 250                 255

Ala Phe Glu Pro Ala Thr Glu Met Gln Lys Ser Val Pro Asn Lys Ala
                260                 265                 270

Leu Glu Leu Lys Asn Glu Gln Thr Leu Arg Ala Asp Glu Ile Leu Pro
            275                 280                 285

Ser Glu Ser Lys Gln Lys Asp Tyr Glu Glu Asn Ser Trp Asp Thr Glu
290                 295                 300

Ser Leu Cys Glu Thr Val Ser Gln Lys Asp Val Cys Leu Pro Lys Ala
305                 310                 315                 320

Ala His Gln Lys Glu Ile Asp Lys Ile Asn Gly Lys Leu Glu Gly Ser
                325                 330                 335

Pro Gly Lys Asp Gly Leu Leu Lys Ala Asn Cys Gly Met Lys Val Ser
            340                 345                 350

Ile Pro Thr Lys Ala Leu Glu Leu Met Asp Met Gln Thr Phe Lys Ala
            355                 360                 365

Glu Pro Pro Glu Lys Pro Ser Ala Phe Glu Pro Ala Ile Glu Met Gln
370                 375                 380

Lys Ser Val Pro Asn Lys Ala Leu Glu Leu Lys Asn Glu Gln Thr Leu
385                 390                 395                 400

Arg Ala Asp Glu Ile Leu Pro Ser Glu Ser Lys Gln Lys Asp Tyr Glu
                405                 410                 415

Glu Ser Ser Trp Asp Ser Glu Ser Leu Cys Glu Thr Val Ser Gln Lys
                420                 425                 430

Asp Val Cys Leu Pro Lys Ala Ala His Gln Lys Glu Ile Asp Lys Ile
            435                 440                 445

Asn Gly Lys Leu Glu Glu Ser Pro Asp Asn Asp Gly Phe Leu Lys Ser
            450                 455                 460

Pro Cys Arg Met Lys Val Ser Ile Pro Thr Lys Ala Leu Glu Leu Met
465                 470                 475                 480
```

```
Asp Met Gln Thr Phe Lys Ala Glu Pro Pro Glu Lys Pro Ser Ala Phe
                485                 490                 495

Glu Pro Ala Ile Glu Met Gln Lys Ser Val Pro Asn Lys Ala Leu Glu
            500                 505                 510

Leu Lys Asn Glu Gln Thr Leu Arg Ala Asp Gln Met Phe Pro Ser Glu
        515                 520                 525

Ser Lys Gln Lys Asn Val Glu Glu Asn Ser Trp Asp Ser Glu Ser Leu
    530                 535                 540

Arg Glu Thr Val Ser Gln Lys Asp Val Cys Val Pro Lys Ala Thr His
545                 550                 555                 560

Gln Lys Glu Met Asp Lys Ile Ser Gly Lys Leu Glu Asp Ser Thr Ser
                565                 570                 575

Leu Ser Lys Ile Leu Asp Thr Val His Ser Cys Glu Arg Ala Arg Glu
            580                 585                 590

Leu Gln Lys Asp His Cys Glu Gln Arg Thr Gly Lys Met Glu Gln Met
        595                 600                 605

Lys Lys Lys Phe Cys Val Leu Lys Lys Lys Leu Ser Glu Ala Lys Glu
    610                 615                 620

Ile Lys Ser Gln Leu Glu Asn Gln Lys Val Lys Trp Glu Gln Glu Leu
625                 630                 635                 640

Cys Ser Val Arg Phe Leu Thr Leu Met Lys Met Lys Ile Ile Ser Tyr
                645                 650                 655

Met Lys Ile Ala Cys
                660

<210> SEQ ID NO 553
<211> LENGTH: 1013
<212> TYPE: PRT
<213> ORGANISM: Homo sapiens

<400> SEQUENCE: 553

Met Gln His His His His His Val Gly Ser Met Ser Pro Ala Lys
                5                  10                  15

Glu Thr Ser Glu Lys Phe Thr Trp Ala Ala Lys Gly Arg Pro Arg Lys
            20                  25                  30

Ile Ala Trp Glu Lys Lys Glu Thr Pro Val Lys Thr Gly Cys Val Ala
        35                  40                  45

Arg Val Thr Ser Asn Lys Thr Lys Val Leu Glu Lys Gly Arg Ser Lys
    50                  55                  60

Met Ile Ala Cys Pro Thr Lys Glu Ser Ser Thr Lys Ala Ser Ala Asn
65                  70                  75                  80

Asp Gln Arg Phe Pro Ser Glu Ser Lys Gln Glu Glu Asp Glu Glu Tyr
                85                  90                  95

Ser Cys Asp Ser Arg Ser Leu Phe Glu Ser Ala Lys Ile Gln Val
                100                 105                 110

Cys Ile Pro Glu Ser Ile Tyr Gln Lys Val Met Glu Ile Asn Arg Glu
        115                 120                 125

Val Glu Glu Pro Pro Lys Lys Pro Ser Ala Phe Lys Pro Ala Ile Glu
    130                 135                 140

Met Gln Asn Ser Val Pro Asn Lys Ala Phe Glu Leu Lys Asn Glu Gln
145                 150                 155                 160

Thr Leu Arg Ala Asp Pro Met Phe Pro Pro Glu Ser Lys Gln Lys Asp
                165                 170                 175

Tyr Glu Glu Asn Ser Trp Asp Ser Glu Ser Leu Cys Glu Thr Val Ser
```

-continued

```
                180                 185                 190
Gln Lys Asp Val Cys Leu Pro Lys Ala Thr His Gln Lys Glu Ile Asp
        195                 200                 205
Lys Ile Asn Gly Lys Leu Glu Glu Ser Pro Asn Lys Asp Gly Leu Leu
    210                 215                 220
Lys Ala Thr Cys Gly Met Lys Val Ser Ile Pro Thr Lys Ala Leu Glu
225                 230                 235                 240
Leu Lys Asp Met Gln Thr Phe Lys Ala Glu Pro Pro Gly Lys Pro Ser
                245                 250                 255
Ala Phe Glu Pro Ala Thr Glu Met Gln Lys Ser Val Pro Asn Lys Ala
        260                 265                 270
Leu Glu Leu Lys Asn Glu Gln Thr Leu Arg Ala Asp Glu Ile Leu Pro
    275                 280                 285
Ser Glu Ser Lys Gln Lys Asp Tyr Glu Glu Asn Ser Trp Asp Thr Glu
    290                 295                 300
Ser Leu Cys Glu Thr Val Ser Gln Lys Asp Val Cys Leu Pro Lys Ala
305                 310                 315                 320
Ala His Gln Lys Glu Ile Asp Lys Ile Asn Gly Lys Leu Glu Gly Ser
                325                 330                 335
Pro Gly Lys Asp Gly Leu Leu Lys Ala Asn Cys Gly Met Lys Val Ser
        340                 345                 350
Ile Pro Thr Lys Ala Leu Glu Leu Met Asp Met Gln Thr Phe Lys Ala
    355                 360                 365
Glu Pro Pro Glu Lys Pro Ser Ala Phe Glu Pro Ala Ile Glu Met Gln
370                 375                 380
Lys Ser Val Pro Asn Lys Ala Leu Glu Leu Lys Asn Glu Gln Thr Leu
385                 390                 395                 400
Arg Ala Asp Glu Ile Leu Pro Ser Glu Ser Lys Gln Lys Asp Tyr Glu
                405                 410                 415
Glu Ser Ser Trp Asp Ser Glu Ser Leu Cys Glu Thr Val Ser Gln Lys
        420                 425                 430
Asp Val Cys Leu Pro Lys Ala Ala His Gln Lys Glu Ile Asp Lys Ile
    435                 440                 445
Asn Gly Lys Leu Glu Glu Ser Pro Asp Asn Asp Gly Phe Leu Lys Ser
    450                 455                 460
Pro Cys Arg Met Lys Val Ser Ile Pro Thr Lys Ala Leu Glu Leu Met
465                 470                 475                 480
Asp Met Gln Thr Phe Lys Ala Glu Pro Pro Glu Lys Pro Ser Ala Phe
                485                 490                 495
Glu Pro Ala Ile Glu Met Gln Lys Ser Val Pro Asn Lys Ala Leu Glu
        500                 505                 510
Leu Lys Asn Glu Gln Thr Leu Arg Ala Asp Gln Met Phe Pro Ser Glu
    515                 520                 525
Ser Lys Gln Lys Asn Val Glu Glu Asn Ser Trp Asp Ser Glu Ser Leu
    530                 535                 540
Arg Glu Thr Val Ser Gln Lys Asp Val Cys Val Pro Lys Ala Thr His
545                 550                 555                 560
Gln Lys Glu Met Asp Lys Ile Ser Gly Lys Leu Glu Asp Ser Thr Ser
                565                 570                 575
Leu Ser Lys Ile Leu Asp Thr Val His Ser Cys Glu Arg Ala Arg Glu
        580                 585                 590
Leu Gln Lys Asp His Cys Glu Gln Arg Thr Gly Lys Met Glu Gln Met
    595                 600                 605
```

-continued

```
Lys Lys Lys Phe Cys Val Leu Lys Lys Leu Ser Glu Ala Lys Glu
    610             615                 620
Ile Lys Ser Gln Leu Glu Asn Gln Lys Val Lys Trp Glu Gln Glu Leu
625                 630                 635                 640
Cys Ser Val Arg Leu Thr Leu Asn Gln Glu Glu Lys Arg Arg Asn
            645                 650                 655
Ala Asp Ile Leu Asn Glu Lys Ile Arg Glu Glu Leu Gly Arg Ile Glu
                660                 665                 670
Glu Gln His Arg Lys Glu Leu Glu Val Lys Gln Gln Leu Glu Gln Ala
            675                 680                 685
Leu Arg Ile Gln Asp Ile Glu Leu Lys Ser Val Glu Ser Asn Leu Asn
            690                 695                 700
Gln Val Ser His Thr His Glu Asn Glu Asn Tyr Leu Leu His Glu Asn
705                 710                 715                 720
Cys Met Leu Lys Lys Glu Ile Ala Met Leu Lys Leu Glu Ile Ala Thr
                725                 730                 735
Leu Lys His Gln Tyr Gln Glu Lys Glu Asn Lys Tyr Phe Glu Asp Ile
            740                 745                 750
Lys Ile Leu Lys Glu Lys Asn Ala Glu Leu Gln Met Thr Leu Lys Leu
            755                 760                 765
Lys Glu Glu Ser Leu Thr Lys Arg Ala Ser Gln Tyr Ser Gly Gln Leu
770                 775                 780
Lys Val Leu Ile Ala Glu Asn Thr Met Leu Thr Ser Lys Leu Lys Glu
785                 790                 795                 800
Lys Gln Asp Lys Glu Ile Leu Glu Ala Glu Ile Glu Ser His His Pro
                805                 810                 815
Arg Leu Ala Ser Ala Val Gln Asp His Asp Gln Ile Val Thr Ser Arg
            820                 825                 830
Lys Ser Gln Glu Pro Ala Phe His Ile Ala Gly Asp Ala Cys Leu Gln
            835                 840                 845
Arg Lys Met Asn Val Asp Val Ser Ser Thr Ile Tyr Asn Asn Glu Val
850                 855                 860
Leu His Gln Pro Leu Ser Glu Ala Gln Arg Lys Ser Lys Ser Leu Lys
865                 870                 875                 880
Ile Asn Leu Asn Tyr Ala Gly Asp Ala Leu Arg Glu Asn Thr Leu Val
                885                 890                 895
Ser Glu His Ala Gln Arg Asp Gln Arg Glu Thr Gln Cys Gln Met Lys
            900                 905                 910
Glu Ala Glu His Met Tyr Gln Asn Glu Gln Asp Asn Val Asn Lys His
            915                 920                 925
Thr Glu Gln Gln Glu Ser Leu Asp Gln Lys Leu Phe Gln Leu Gln Ser
930                 935                 940
Lys Asn Met Trp Leu Gln Gln Gln Leu Val His Ala His Lys Lys Ala
945                 950                 955                 960
Asp Asn Lys Ser Lys Ile Thr Ile Asp Ile His Phe Leu Glu Arg Lys
                965                 970                 975
Met Gln His His Leu Leu Lys Glu Lys Asn Glu Glu Ile Phe Asn Tyr
            980                 985                 990
Asn Asn His Leu Lys Asn Arg Ile Tyr Gln Tyr Glu Lys Glu Lys Ala
            995                 1000                1005
Glu Thr Glu Val Ile
    1010
```

<210> SEQ ID NO 554
<211> LENGTH: 25
<212> TYPE: DNA
<213> ORGANISM: Artificial Sequence
<220> FEATURE:
<223> OTHER INFORMATION: PCR primer

<400> SEQUENCE: 554
gtcggctcca tgagtcccgc aaaag                                              25

<210> SEQ ID NO 555
<211> LENGTH: 36
<212> TYPE: DNA
<213> ORGANISM: Artificial Sequence
<220> FEATURE:
<223> OTHER INFORMATION: PCR primer

<400> SEQUENCE: 555
cgagaattca atacttaaga agaccatctt taccag                                  36

<210> SEQ ID NO 556
<211> LENGTH: 31
<212> TYPE: DNA
<213> ORGANISM: Artificial Sequence
<220> FEATURE:
<223> OTHER INFORMATION: PCR primer

<400> SEQUENCE: 556
cataagctta aggctaactg cggaatgaaa g                                       31

<210> SEQ ID NO 557
<211> LENGTH: 35
<212> TYPE: DNA
<213> ORGANISM: Artificial Sequence
<220> FEATURE:
<223> OTHER INFORMATION: PCR primer

<400> SEQUENCE: 557
cccgcagaat tcaacatgca attttcatgt aagag                                   35

<210> SEQ ID NO 558
<211> LENGTH: 25
<212> TYPE: DNA
<213> ORGANISM: Artificial Sequence
<220> FEATURE:
<223> OTHER INFORMATION: PCR primer

<400> SEQUENCE: 558
ctaaatgccg gcacaagagc tctgc                                              25

<210> SEQ ID NO 559
<211> LENGTH: 35
<212> TYPE: DNA
<213> ORGANISM: Artificial Sequence
<220> FEATURE:
<223> OTHER INFORMATION: PCR primer

<400> SEQUENCE: 559
cgcgcagaat tctattatat aacttctgtt tctgc                                   35

<210> SEQ ID NO 560
<211> LENGTH: 26
<212> TYPE: DNA
<213> ORGANISM: Artificial Sequence
<220> FEATURE:
<223> OTHER INFORMATION: PCR primer -continued

<400> SEQUENCE: 560
ggggaattgt gagcggataa caattc        26

<210> SEQ ID NO 561
<211> LENGTH: 36
<212> TYPE: DNA
<213> ORGANISM: Artificial Sequence
<220> FEATURE:
<223> OTHER INFORMATION: PCR primer

<400> SEQUENCE: 561
cgtagaattc aacctgattt aaattacttt ctacac        36

<210> SEQ ID NO 562
<211> LENGTH: 31
<212> TYPE: DNA
<213> ORGANISM: Artificial Sequence
<220> FEATURE:
<223> OTHER INFORMATION: PCR primer

<400> SEQUENCE: 562
gaaagtaatt taaatcaggt ttctcacact c        31

<210> SEQ ID NO 563
<211> LENGTH: 23
<212> TYPE: DNA
<213> ORGANISM: Artificial Sequence
<220> FEATURE:
<223> OTHER INFORMATION: PCR primer

<400> SEQUENCE: 563
gaggccccaa ggggttatgc tag        23

<210> SEQ ID NO 564
<211> LENGTH: 4458
<212> TYPE: DNA
<213> ORGANISM: Homo sapiens

<400> SEQUENCE: 564
ctagtctata ccagcaacga ctcctacatc gtccactctg ggatcttag aaagatccat        60
aaagctgcct cccggggaca agtccggaag ctggagaaga tgacaaagag gaagaagacc        120
atcaacctta atatacaaga cgcccagaag aggactgctc tacactgggc ctgtgtcaat        180
ggccatgagg aagtagtaac atttctggta gacagaaagt gccagcttga cgtccttgat        240
ggcgaacaca ggacacctct gatgaaggct ctacaatgcc atcaggaggc ttgtgcaaat        300
attctgatag attctggtgc cgatataaat ctcgtagatg tgtatggcaa catggctctc        360
cattatgctg tttatagtga gattttgtca gtggtggcaa aactgctgtc ccatggtgca        420
gtcatcgaag tgcacaacaa ggctagcctc acaccacttt tactatccat aacgaaaaga        480
agtgagcaaa ttgtggaatt tttgctgata aaaatgcaa atgcgaatgc agttaataag        540
tataaatgca cagcccctcat gcttgctgta tgtcatggat catcagagat agttggcatg        600
cttcttcagc aaaatgttga cgtctttgct gcagatatat gtggagtaac tgcagaacat        660
tatgctgtta cttgtggatt tcatcacatt catgaacaaa ttatgaata tatacgaaaa        720
ttatctaaaa atcatcaaaa taccaatcca gaaggaacat ctgcaggaac acctgatgag        780
gctgcaccct tggcgaaaag aacacctgac acagctgaaa gcttggtgga aaaaacacct        840
gatgaggctg caccccttggt ggaaagaaca cctgacacgg ctgaaagctt ggtggaaaaa        900

```
acacctgatg aggctgcatc cttggtggag ggaacatctg acaaaattca atgtttggag    960
aaagcgacat ctggaaagtt cgaacagtca gcagaagaaa cacctaggga aattacgagt   1020
cctgcaaaag aaacatctga gaaatttacg tggccagcaa aaggaagacc taggaagatc   1080
gcatgggaga aaaagaaga cacacctagg gaaattatga gtcccgcaaa agaaacatct   1140
gagaaattta cgtgggcagc aaaaggaaga cctaggaaga tcgcatggga gaaaaagaa   1200
acacctgtaa agactggatg cgtggcaaga gtaacatcta ataaaactaa agttttggaa   1260
aaaggaagat ctaagatgat tgcatgtcct acaaaagaat catctacaaa agcaagtgcc   1320
aatgatcaga ggttcccatc agaatccaaa caagaggaag atgaagaata ttcttgtgat   1380
tctcggagtc tctttgagag ttctgcaaag attcaagtgt gtatacctga gtctatatat   1440
caaaaagtaa tggagataaa tagaagta gaagagcctc taagaagcc atctgccttc   1500
aagcctgcca ttgaaatgca aaactctgtt ccaaataaag cctttgaatt gaagaatgaa   1560
caaacattga gagcagatcc gatgttccca ccagaatcca acaaaagga ctatgaagaa   1620
aattcttggg attctgagag tctctgtgag actgtttcac agaaggatgt gtgtttaccc   1680
aaggctacac atcaaaaaga aatagataaa ataaatggaa aattagaaga gtctcctaat   1740
aaagatggtc ttctgaaggc tacctgcgga atgaaagttt ctattccaac taaagcctta   1800
gaattgaagg acatgcaaac tttcaaagcg agcctccgg ggaagccatc tgccttcgag   1860
cctgccactg aaatgcaaaa gtctgtccca ataaagcct tggaattgaa aaatgaacaa   1920
acatggagag cagatgagat actcccatca gaatccaaac aaaaggacta tgaagaaaat   1980
tcttgggata ctgagagtct ctgtgagact gtttcacaga aggatgtgtg tttacccaag   2040
gctgcgcatc aaaagaaat agataaaata aatggaaaat tagaagggtc tcctgttaaa   2100
gatggtcttc tgaaggctaa ctgcggaatg aaagtttcta ttccaactaa agccttagaa   2160
ttgatggaca tgcaaacttt caaagcagag cctcccgaga agccatctgc cttcgagcct   2220
gccattgaaa tgcaaaagtc tgttccaaat aaagccttgg aattgaagaa tgaacaaaca   2280
ttgagagcag atgagatact cccatcagaa tccaaacaaa aggactatga agaaagttct   2340
tgggattctg agagtctctg tgagactgtt tcacagaagg atgtgtgttt acccaaggct   2400
acacatcaaa agaaatagaa taaaataaat ggaaaattag aagagtctcc tgataatgat   2460
ggttttctga aggctccctg cagaatgaaa gtttctattc caactaaagc cttagaattg   2520
atggacatgc aaactttcaa agcagagcct cccgagaagc catctgcctt cgagcctgcc   2580
attgaaatgc aaaagtctgt tccaaataaa gccttggaat tgaagaatga acaaacattg   2640
agagcagatc agatgttccc ttcagaatca aaacaaaaga aggttgaaga aaattcttgg   2700
gattctgaga gtctccgtga gactgtttca cagaaggatg tgtgtgtacc caaggctaca   2760
catcaaaaag aaatggataa aataagtgga aaattagaag attcaactag cctatcaaaa   2820
atcttggata cagttcattc ttgtgaaaga gcaagggaac ttcaaaaaga tcactgtgaa   2880
caacgtacag gaaaaatgga acaaatgaaa agaagttttt gtgtactgaa aagaaactg   2940
tcagaagcaa aagaaataaa atcacagtta gagaaccaaa agttaaatg ggaacaagag   3000
ctctgcagtg tgagattgac tttaaaccaa gaagaagaga agagaagaaa tgccgatata   3060
ttaaatgaaa aaattaggga agaattagga agaatcgaag agcagcatag gaaagagtta   3120
gaagtgaaac aacaacttga acaggctctc agaatacaag atatagaatt gaagagtgta   3180
gaaagtaatt tgaatcaggt ttctcacact catgaaaatg aaaattatct cttacatgaa   3240
aattgcatgt tgaaaaagga aattgccatg ctaaaactgg aaatagccac actgaaacac   3300
```

```
caataccagg aaaaggaaaa taaatacttt gaggacatta agattttaaa agaaaagaat    3360
gctgaacttc agatgaccct aaaactgaaa gaggaatcat taactaaaag gcatctcaa     3420 tatagtgggc agcttaaagt tctgatagct gagaacacaa tgctcacttc taaattgaag    3480
gaaaaacaag acaaagaaat actagaggca gaaattgaat cacaccatcc tagactggct    3540
tctgctgtac aagaccatga tcaaattgtg acatcaagaa aaagtcaaga acctgctttc    3600
cacattgcag gagatgcttg tttgcaaaga aaatgaatg ttgatgtgag tagtacgata     3660
tataacaatg aggtgctcca tcaaccactt tctgaagctc aaaggaaatc caaaagccta    3720
aaaattaatc tcaattatgc aggagatgct ctaagagaaa atacattggt ttcagaacat    3780
gcacaaagag accaacgtga aacacagtgt caaatgaagg aagctgaaca catgtatcaa    3840
aacgaacaag ataatgtgaa caaacacact gaacagcagg agtctctaga tcagaaatta    3900
tttcaactac aaagcaaaaa tatgtggctt caacagcaat tagttcatgc acataagaaa    3960
gctgacaaca aaagcaagat aacaattgat attcattttc ttgagaggaa aatgcaacat    4020
catctcctaa aagagaaaaa tgaggagata tttaattaca ataaccattt aaaaaaccgt    4080
atatatcaat atgaaaaaga gaaagcagaa acagaaaact catgagagac aagcagtaag    4140
aaacttcttt tggagaaaca acagaccaga tctttactca caactcatgc taggaggcca    4200
gtcctagcat caccttatgt tgaaaatctt accaatagtc tgtgtcaaca gaatacttat    4260
tttagaagaa aaattcatga tttcttcctg aagcctacag acataaaata acagtgtgaa    4320
gaattacttg ttcacgaatt gcataaagct gcacaggatt cccatctacc ctgatgatgc    4380
agcagacatc attcaatcca accagaatct cgctctgcac tccagcctag gtgacagagt    4440
gagactccac ctcggaaa                                                  4458
```

<210> SEQ ID NO 565
<211> LENGTH: 1341
<212> TYPE: PRT
<213> ORGANISM: Homo sapiens

<400> SEQUENCE: 565

```
Met Thr Lys Arg Lys Lys Thr Ile Asn Leu Asn Ile Gln Asp Ala Gln
             5                  10                  15

Lys Arg Thr Ala Leu His Trp Ala Cys Val Asn Gly His Glu Val
         20                  25                  30

Val Thr Phe Leu Val Asp Arg Lys Cys Gln Leu Asp Val Leu Asp Gly
         35                  40                  45

Glu His Arg Thr Pro Leu Met Lys Ala Leu Gln Cys His Gln Glu Ala
     50                  55                  60

Cys Ala Asn Ile Leu Ile Asp Ser Gly Ala Asp Ile Asn Leu Val Asp
 65                  70                  75                  80

Val Tyr Gly Asn Met Ala Leu His Tyr Ala Val Tyr Ser Glu Ile Leu
                 85                  90                  95

Ser Val Val Ala Lys Leu Leu Ser His Gly Ala Val Ile Glu Val His
            100                 105                 110

Asn Lys Ala Ser Leu Thr Pro Leu Leu Leu Ser Ile Thr Lys Arg Ser
        115                 120                 125

Glu Gln Ile Val Glu Phe Leu Leu Ile Lys Asn Ala Asn Ala Asn Ala
    130                 135                 140

Val Asn Lys Tyr Lys Cys Thr Ala Leu Met Leu Ala Val Cys His Gly
145                 150                 155                 160
```

-continued

```
Ser Ser Glu Ile Val Gly Met Leu Leu Gln Gln Asn Val Asp Val Phe
            165                 170                 175
Ala Ala Asp Ile Cys Gly Val Thr Ala Glu His Tyr Ala Val Thr Cys
            180                 185                 190
Gly Phe His His Ile His Glu Gln Ile Met Glu Tyr Ile Arg Lys Leu
            195                 200                 205
Ser Lys Asn His Gln Asn Thr Asn Pro Glu Gly Thr Ser Ala Gly Thr
210                 215                 220
Pro Asp Glu Ala Ala Pro Leu Ala Glu Arg Thr Pro Asp Thr Ala Glu
225                 230                 235                 240
Ser Leu Val Glu Lys Thr Pro Asp Glu Ala Ala Pro Leu Val Glu Arg
            245                 250                 255
Thr Pro Asp Thr Ala Glu Ser Leu Val Glu Lys Thr Pro Asp Glu Ala
            260                 265                 270
Ala Ser Leu Val Glu Gly Thr Ser Asp Lys Ile Gln Cys Leu Glu Lys
            275                 280                 285
Ala Thr Ser Gly Lys Phe Glu Gln Ser Ala Glu Thr Pro Arg Glu
            290                 295                 300
Ile Thr Ser Pro Ala Lys Glu Thr Ser Glu Lys Phe Thr Trp Pro Ala
305                 310                 315                 320
Lys Gly Arg Pro Arg Lys Ile Ala Trp Glu Lys Lys Glu Asp Thr Pro
            325                 330                 335
Arg Glu Ile Met Ser Pro Ala Lys Glu Thr Ser Glu Lys Phe Thr Trp
            340                 345                 350
Ala Ala Lys Gly Arg Pro Arg Lys Ile Ala Trp Glu Lys Lys Glu Thr
            355                 360                 365
Pro Val Lys Thr Gly Cys Val Ala Arg Val Thr Ser Asn Lys Thr Lys
            370                 375                 380
Val Leu Glu Lys Gly Arg Ser Lys Met Ile Ala Cys Pro Thr Lys Glu
385                 390                 395                 400
Ser Ser Thr Lys Ala Ser Ala Asn Asp Gln Arg Phe Pro Ser Glu Ser
            405                 410                 415
Lys Gln Glu Glu Asp Glu Glu Tyr Ser Cys Asp Ser Arg Ser Leu Phe
            420                 425                 430
Glu Ser Ser Ala Lys Ile Gln Val Cys Ile Pro Glu Ser Ile Tyr Gln
            435                 440                 445
Lys Val Met Glu Ile Asn Arg Glu Val Glu Glu Pro Pro Lys Lys Pro
            450                 455                 460
Ser Ala Phe Lys Pro Ala Ile Glu Met Gln Asn Ser Val Pro Asn Lys
465                 470                 475                 480
Ala Phe Glu Leu Lys Asn Glu Gln Thr Leu Arg Ala Asp Pro Met Phe
            485                 490                 495
Pro Pro Glu Ser Lys Gln Lys Asp Tyr Glu Glu Asn Ser Trp Asp Ser
            500                 505                 510
Glu Ser Leu Cys Glu Thr Val Ser Gln Lys Asp Val Cys Leu Pro Lys
            515                 520                 525
Ala Thr His Gln Lys Glu Ile Asp Lys Ile Asn Gly Lys Leu Glu Glu
            530                 535                 540
Ser Pro Asn Lys Asp Gly Leu Leu Lys Ala Thr Cys Gly Met Lys Val
545                 550                 555                 560
Ser Ile Pro Thr Lys Ala Leu Glu Leu Lys Asp Met Gln Thr Phe Lys
            565                 570                 575
Ala Glu Pro Pro Gly Lys Pro Ser Ala Phe Glu Pro Ala Thr Glu Met
```

-continued

```
                580                 585                 590
Gln Lys Ser Val Pro Asn Lys Ala Leu Glu Leu Lys Asn Glu Gln Thr
            595                 600                 605

Trp Arg Ala Asp Glu Ile Leu Pro Ser Glu Ser Lys Gln Lys Asp Tyr
610                 615                 620

Glu Glu Asn Ser Trp Asp Thr Glu Ser Leu Cys Glu Thr Val Ser Gln
625                 630                 635                 640

Lys Asp Val Cys Leu Pro Lys Ala Ala His Gln Lys Glu Ile Asp Lys
                645                 650                 655

Ile Asn Gly Lys Leu Glu Gly Ser Pro Val Lys Asp Gly Leu Leu Lys
            660                 665                 670

Ala Asn Cys Gly Met Lys Val Ser Ile Pro Thr Lys Ala Leu Glu Leu
        675                 680                 685

Met Asp Met Gln Thr Phe Lys Ala Glu Pro Glu Lys Pro Ser Ala
    690                 695                 700

Phe Glu Pro Ala Ile Glu Met Gln Lys Ser Val Pro Asn Lys Ala Leu
705                 710                 715                 720

Glu Leu Lys Asn Glu Gln Thr Leu Arg Ala Asp Glu Ile Leu Pro Ser
                725                 730                 735

Glu Ser Lys Gln Lys Asp Tyr Glu Glu Ser Ser Trp Asp Ser Glu Ser
            740                 745                 750

Leu Cys Glu Thr Val Ser Gln Lys Asp Val Cys Leu Pro Lys Ala Thr
        755                 760                 765

His Gln Lys Glu Ile Asp Lys Ile Asn Gly Lys Leu Glu Glu Ser Pro
    770                 775                 780

Asp Asn Asp Gly Phe Leu Lys Ala Pro Cys Arg Met Lys Val Ser Ile
785                 790                 795                 800

Pro Thr Lys Ala Leu Glu Leu Met Asp Met Gln Thr Phe Lys Ala Glu
                805                 810                 815

Pro Pro Glu Lys Pro Ser Ala Phe Glu Pro Ala Ile Glu Met Gln Lys
            820                 825                 830

Ser Val Pro Asn Lys Ala Leu Glu Leu Lys Asn Glu Gln Thr Leu Arg
        835                 840                 845

Ala Asp Gln Met Phe Pro Ser Glu Ser Lys Gln Lys Val Glu Glu
    850                 855                 860

Asn Ser Trp Asp Ser Glu Ser Leu Arg Glu Thr Val Ser Gln Lys Asp
865                 870                 875                 880

Val Cys Val Pro Lys Ala Thr His Gln Lys Glu Met Asp Lys Ile Ser
                885                 890                 895

Gly Lys Leu Glu Asp Ser Thr Ser Leu Ser Lys Ile Leu Asp Thr Val
            900                 905                 910

His Ser Cys Glu Arg Ala Arg Glu Leu Gln Lys Asp His Cys Glu Gln
        915                 920                 925

Arg Thr Gly Lys Met Glu Gln Met Lys Lys Phe Cys Val Leu Lys
    930                 935                 940

Lys Lys Leu Ser Glu Ala Lys Glu Ile Lys Ser Gln Leu Glu Asn Gln
945                 950                 955                 960

Lys Val Lys Trp Glu Gln Glu Leu Cys Ser Val Arg Leu Thr Leu Asn
                965                 970                 975

Gln Glu Glu Glu Lys Arg Arg Asn Ala Asp Ile Leu Asn Glu Lys Ile
            980                 985                 990

Arg Glu Glu Leu Gly Arg Ile Glu Glu Gln His Arg Lys Glu Leu Glu
        995                 1000                1005
```

Val Lys Gln Gln Leu Glu Gln Ala Leu Arg Ile Gln Asp Ile Glu Leu
    1010                1015                1020

Lys Ser Val Glu Ser Asn Leu Asn Gln Val Ser His Thr His Glu Asn
1025                1030                1035                1040

Glu Asn Tyr Leu Leu His Glu Asn Cys Met Leu Lys Lys Glu Ile Ala
                1045                1050                1055

Met Leu Lys Leu Glu Ile Ala Thr Leu Lys His Gln Tyr Gln Glu Lys
            1060                1065                1070

Glu Asn Lys Tyr Phe Glu Asp Ile Lys Ile Leu Lys Glu Lys Asn Ala
        1075                1080                1085

Glu Leu Gln Met Thr Leu Lys Leu Lys Glu Glu Ser Leu Thr Lys Arg
    1090                1095                1100

Ala Ser Gln Tyr Ser Gly Gln Leu Lys Val Leu Ile Ala Glu Asn Thr
1105                1110                1115                1120

Met Leu Thr Ser Lys Leu Lys Glu Lys Gln Asp Lys Glu Ile Leu Glu
                1125                1130                1135

Ala Glu Ile Glu Ser His His Pro Arg Leu Ala Ser Ala Val Gln Asp
            1140                1145                1150

His Asp Gln Ile Val Thr Ser Arg Lys Ser Gln Glu Pro Ala Phe His
        1155                1160                1165

Ile Ala Gly Asp Ala Cys Leu Gln Arg Lys Met Asn Val Asp Val Ser
    1170                1175                1180

Ser Thr Ile Tyr Asn Asn Glu Val Leu His Gln Pro Leu Ser Glu Ala
1185                1190                1195                1200

Gln Arg Lys Ser Lys Ser Leu Lys Ile Asn Leu Asn Tyr Ala Gly Asp
                1205                1210                1215

Ala Leu Arg Glu Asn Thr Leu Val Ser Glu His Ala Gln Arg Asp Gln
            1220                1225                1230

Arg Glu Thr Gln Cys Gln Met Lys Glu Ala Glu His Met Tyr Gln Asn
        1235                1240                1245

Glu Gln Asp Asn Val Asn Lys His Thr Glu Gln Glu Ser Leu Asp
    1250                1255                1260

Gln Lys Leu Phe Gln Leu Gln Ser Lys Asn Met Trp Leu Gln Gln Gln
1265                1270                1275                1280

Leu Val His Ala His Lys Lys Ala Asp Asn Lys Ser Lys Ile Thr Ile
                1285                1290                1295

Asp Ile His Phe Leu Glu Arg Lys Met Gln His His Leu Leu Lys Glu
            1300                1305                1310

Lys Asn Glu Glu Ile Phe Asn Tyr Asn Asn His Leu Lys Asn Arg Ile
        1315                1320                1325

Tyr Gln Tyr Glu Lys Glu Lys Ala Glu Thr Glu Asn Ser
    1330                1335                1340

<210> SEQ ID NO 566
<211> LENGTH: 4047
<212> TYPE: DNA
<213> ORGANISM: Homo sapiens

<400> SEQUENCE: 566
atgcagcatc accaccatca ccaccacaca aagaggaaga agaccatcaa ccttaatata      60
caagacgccc agaagaggac tgctctacac tgggcctgtg tcaatggcca tgaggaagta     120
gtaacatttc tggtagacag aaagtgccag cctgacgtcc ttgatggcga acacaggaca     180
cctctgatga aggctctaca atgccatcag gaggcttgtg caaatattct gatagattct     240

```
ggtgccgata taaatctcgt agatgtgtat ggcaacatgg ctctccatta tgctgtttat    300
agtgagattt tgtcagtggt ggcaaaactg ctgtcccatg gtgcagtcat cgaagtgcac    360
aacaaggcta gcctcacacc acttttacta tccataacga aaagaagtga gcaaattgtg    420
gaattttgc tgataaaaaa tgcaaatgcg aatgcagtta ataagtataa atgcacagcc    480
ctcatgcttg ctgtatgtca tggattatca gagatagttg gcatgcttct tcagcaaaat    540
gttgacgtct ttgctgcaga tatatgtgga gtaactgcag acattatgc tgttacttgt    600
ggatttcatc acattcatga acaaattatg gaatatatac gaaaattatc taaaaatcat    660
caaaatacca atccagaagg aacatctgca ggaacacctg atgaggctgc acccttggcg    720
gaaagaacac ctgacacagc tgaaagcttg gtggaaaaaa cacctgatga ggctgcaccc    780
ttggtggaaa gaacacctga cacggctgaa agcttggtgg aaaaaacacc tgatgaggct    840
gcatccttgg tggagggaac atctgacaaa attcaatgtt tggagaaagc gacatctgga    900
aagttcgaac agtcagcaga agaaacacct agggaaatta cgagtcctgc aaaagaaaca    960
tctgagaaat ttacgtggcc agcaaaagga agacctagga agatcgcatg ggagaaaaaa   1020
gaagacacac ctagggaaat tatgagtccc gcaaaagaaa catctgagaa atttacgtgg   1080
gcagcaaaag gaagacctag gaagatcgca tgggagaaaa agaaacacc tgtaaagact   1140
ggatgcgtgg caagagtaac atctaataaa actaaagttt tggaaaaagg aagatctaag   1200
atgattgcat gtcctacaaa agaatcatct acaaaagcaa gtgccaatga tcagaggttc   1260
ccatcagaat ccaaacaaga ggaagatgaa gaatattctt gtgattctcg gagtctcttt   1320
gagagttctg caaagattca agtgtgtata cctgagtcta tatatcaaaa agtaatggag   1380
ataaatagag aagtagaaga gcctcctaag aagccatctg ccttcaagcc tgccattgaa   1440
atgcaaaact ctgttccaaa taaagccttt gaattgaaga tgaacaaac attgagagca   1500
gatccgatgt tcccaccaga atccaaacaa aaggactatg aagaaaattc ttgggattct   1560
gagagtctct gtgagactgt ttcacagaag gatgtgtgtt tacccaaggc tacacatcaa   1620
aaagaaatag ataaaataaa tggaaaatta gaagagtctc ctaataaaga tggtcttctg   1680
aaggctacct gcggaatgaa agtttctatt ccaactaaag ccttagaatt gaaggacatg   1740
caaactttca agcggagcc tccggggaag ccatctgcct tcgagcctgc cactgaaatg   1800
caaaagtctg tcccaaataa agccttggaa ttgaaaaatg aacaaacatg gagagcagat   1860
gagatactcc catcagaatc caaacaaaag gactatgaag aaaattcttg ggatactgag   1920
agtctctgtg agactgtttc acagaaggat gtgtgtttac ccaaggctgc gcatcaaaaa   1980
gaaatagata aaataaatgg aaaattagaa gggtctcctg ttaaagatgg tcttctgaag   2040
gctaactgcg gaatgaaagt ttctattcca actaaagcct tagaattgat ggacatgcaa   2100
actttcaaag cagagcctcc cgagaagcca tctgccttcg agcctgccat tgaaatgcaa   2160
aagtctgttc caaataaagc cttggaattg aagaatgaac aaacattgag agcagatgag   2220
atactcccat cagaatccaa acaaaaggac tatgaagaaa gttcttggga ttctgagagt   2280
ctctgtgaga ctgtttcaca gaaggatgtg tgtttaccca aggctacaca tcaaaaagaa   2340
atagataaaa taaatggaaa attagaagag tctcctgata tgatggttt tctgaaggct   2400
ccctgcagaa tgaaagtttc tattccaact aaagccttag aattgatgga catgcaaact   2460
ttcaaagcag agcctcccga gaagccatct gccttcgagc tgccattga atgcaaaag   2520
tctgttccaa ataaagcctt ggaattgaag aatgaacaaa cattgagagc agatcagatg   2580
```

-continued

```
ttcccttcag aatcaaaaca aaagaaggtt gaagaaaatt cttgggattc tgagagtctc    2640
cgtgagactg tttcacagaa ggatgtgtgt gtacccaagg ctacacatca aaaagaaatg    2700
gataaaataa gtggaaaatt agaagattca actagcctat caaaaatctt ggatacagtt    2760
cattcttgtg aaagagcaag ggaacttcaa aaagatcact gtgaacaacg tacaggaaaa    2820
atggaacaaa tgaaaagaa gttttgtgta ctgaaaaaga aactgtcaga agcaaaagaa    2880
ataaaatcac agttagagaa ccaaaaagtt aaatgggaac aagagctctg cagtgtgaga    2940
ttgactttaa accaagaaga agagaagaga agaaatgccg atatattaaa tgaaaaaatt    3000
agggaagaat taggaagaat cgaagagcag cataggaaag agttagaagt gaaacaacaa    3060
cttgaacagg ctctcagaat acaagatata gaattgaaga gtgtagaaag taatttgaat    3120
caggtttctc acactcatga aaatgaaaat tatctcttac atgaaaattg catgttgaaa    3180
aaggaaattg ccatgctaaa actggaaata gccacactga acaccaata ccaggaaaag    3240
gaaaataaat actttgagga cattaagatt ttaaagaaa agaatgctga acttcagatg    3300
accctaaaac tgaaagagga atcattaact aaaagggcat ctcaatatag tgggcagctt    3360
aaagttctga tagctgagaa cacaatgctc acttctaaat tgaaggaaaa acaagacaaa    3420
gaaatactag aggcagaaat tgaatcacac catcctagac tggcttctgc tgtacaagac    3480
catgatcaaa ttgtgacatc aagaaaaagt caagaacctg ctttccacat tgcaggagat    3540
gcttgtttgc aaagaaaaat gaatgttgat gtgagtagta cgatatataa caatgaggtg    3600
ctccatcaac cactttctga agctcaaagg aaatccaaaa gcctaaaaat taatctcaat    3660
tatgcaggag atgctctaag agaaaataca ttggtttcag aacatgcaca aagagaccaa    3720
cgtgaaacac agtgtcaaat gaaggaagct gaacacatgt atcaaaacga acaagataat    3780
gtgaacaaac acactgaaca gcaggagtct ctagatcaga aattatttca actacaaagc    3840
aaaaatatgt ggcttcaaca gcaattagtt catgcacata agaaagctga caacaaaagc    3900
aagataacaa ttgatattca ttttcttgag aggaaaatgc aacatcatct cctaaaagag    3960
aaaaatgagg agatatttaa ttacaataac catttaaaaa accgtatata tcaatatgaa    4020
aaagagaaag cagaaacaga agttata                                         4047
```

<210> SEQ ID NO 567
<211> LENGTH: 1199
<212> TYPE: DNA
<213> ORGANISM: Homo sapiens

<400> SEQUENCE: 567

```
acaaagagga agaagaccat caaccttaat atacaagacg cccagaagag gactgctcta     60
cactgggcct gtgtcaatgg ccatgaggaa gtagtaacat ttctggtaga cagaaagtgc    120
cagcctgacg tccttgatgg cgaacacagg acacctctga tgaaggctct acaatgccat    180
caggaggctt gtgcaaatat tctgatagat tctggtgccg atataaatct cgtagatgtg    240
tatggcaaca tggctctcca ttatgctgtt tatagtgaga ttttgtcagt ggtggcaaaa    300
ctgctgtccc atggtgcagt catcgaagtg cacaacaagg ctagcctcac accacttta     360
ctatccataa cgaaaagaag tgagcaaatt gtggaatttt tgctgataaa aaatgcaaat    420
gcgaatgcag ttaataagta taatgcaca gccctcatgc ttgctgtatg tcatggatta    480
tcagagatag ttggcatgct tcttcagcaa aatgttgacg tctttgctgc agatatatgt    540
ggagtaactg cagaacatta tgctgttact tgtggatttc atcacattca tgaacaaatt    600
atggaatata tacgaaaatt atctaaaaat catcaaaata ccaatccaga aggaacatct    660
```

```
gcaggaacac ctgatgaggc tgcacccttg gcggaaagaa cacctgacac agctgaaagc    720
ttggtggaaa aaacacctga tgaggctgca cccttggtgg aaagaacacc tgacacggct    780
gaaagcttgg tggaaaaaac acctgatgag gctgcatcct tggtggaggg aacatctgac    840
aaaattcaat gtttggagaa agcgacatct ggaaagttcg aacagtcagc agaagaaaca    900
cctagggaaa ttacgagtcc tgcaaaagaa acatctgaga aatttacgtg gccagcaaaa    960
ggaagaccta ggaagatcgc atgggagaaa aagaagaca cacctaggga aattatgagt    1020
cccgcaaaag aaacatctga gaaatttacg tgggcagcaa aaggaagacc taggaagatc    1080
gcatgggaga aaaagaaac acctgtaaag actggatgcg tggcaagagt aacatctaat    1140
aaaactaaag ttttggaaaa aggaagatct aagatgattg catgtcctac aaaagaatc    1199
```

<210> SEQ ID NO 568
<211> LENGTH: 1199
<212> TYPE: DNA
<213> ORGANISM: Homo sapiens

<400> SEQUENCE: 568

```
acaaagagga agaagaccat caaccttaat atacaagacg cccagaagag gactgctcta    60
cactgggcct gtgtcaatgg ccatgaggaa gtagtaacat ttctggtaga cagaaagtgc    120
cagcttgacg tccttgatgg cgaacacagg acacctctga tgaaggctct acaatgccat    180
caggaggctt gtgcaaatat tctgatagat tctggtgccg atataaatct cgtagatgtg    240
tatgacaaca cggctctcca ttatgctgtt tatagtgaga ttttgtcagt ggtggcaaaa    300
ctgctgtccc atggtgcagt catctaagcg cacaacaagg ctagcctcac accacttta    360 ctatccataa cgaaaagaag tgagcaaatt gtggaatttt tgctgataaa aaatgcaaat    420
gcgaatgcag ttaataagta taaatgcaca gccctcatgc ttgctgtatg tcatggatca    480
tcagagatag ttggcatgct tcttcagcaa aatgttgacg tctttgctgc agatatatgt    540
ggagtaactg cagaacatta tgctgttact tgtggatttc atcacattca tgaacaaatt    600
atggaatata tacgaaaatt atctaaaaat catcaaaata ccaatccaga aggaacatct    660
gcaggaacac ctgatgaggc tgcacccttg gcggaaagaa cacctgacac agctgaaagc    720
ttggtggaaa aaacacctga tgaggctgca cccttggtgg aaagaacacc tgacacggct    780
gaaagcttgg tggaaaaaac acctgatgag gctgcatcct tggtggaggg aacatctgac    840
aaaattcaat gtttggagaa agcgacatct ggaaagttcg aacagtcagc agaagaaaca    900
cctagggaaa ttacgagtcc tgcaaaagaa acatctgaga aatttacgtg gccagcaaaa    960
ggaagaccta ggaagatcgc atgggagaaa aagaagaca cacctaggga aattatgagt    1020
cccgcaaaag aaacatctga gaaatttacg tgggcagcaa aaggaagacc taggaagatc    1080
gcatgggaga aaaagaaac acctgtaaag actggatgcg tggcaagagt aacatctaat    1140
aaaactaaag ttttggaaaa aggaagatct aagatgattg catgtcctac aaaagaatc    1199
```

<210> SEQ ID NO 569
<211> LENGTH: 1199
<212> TYPE: DNA
<213> ORGANISM: Homo sapiens

<400> SEQUENCE: 569

```
acaaagagga agaagaccat caaccttaat atacaagacg cccagaagag gactgctcta    60
cactgggcct gtgtcaatgg ccatgaggaa gtagtaacat ttctggtaga cagaaagtgc    120
```

```
cagcttgacg tccttgatgg cgaacacagg acacctctga tgaaggctct acaatgccat    180
caggaggctt gtgcaaatat tctgatagat tctggtgccg atataaatct cgtagatgtg    240
tatggcaaca tggctctcca ttatgctgtt tatagtgaga ttttgtcagt ggtggcaaaa    300
ctgctgtccc atggtgcagt catcgaagtg cacaacaagg ctagcctcac accacttta    360 ctatccataa cgaaaagaag tgagcaaatt gtggaatttt tgctgataaa aaatgcaaat    420
gcgaatgcag ttaataagta taaatgcaca gccctcatgc ttgctgtatg tcatggatca    480
tcagagatag ttggcatgct tcttcagcaa aatgttgacg tctttgctgc agatatatgt    540
ggagtaactg cagaacatta tgctgttact tgtggatttc atcacattca tgaacaaatt    600
atggaatata tacgaaaatt atctaaaaat catcaaaata ccaatccaga aggaacatct    660
gcaggaacac ctgatgaggc tgcacccttg gcggaaagaa cacctgacac agctgaaagc    720
ttggtggaaa aaacacctga tgaggctgca cccttggtgg aaagaacacc tgacacggct    780
gaaagcttgg tggaaaaaac acctgatgag gctgcatcct tggtggaggg aacatctgac    840
aaaattcaat gtttggagaa agcgacatct ggaaagttcg aacagtcagc agaagaaaca    900
cctagggaaa ttacgagtcc tgcaaaagaa acatctgaga aatttacgtg gccagcaaaa    960
ggaagaccta ggaagatcgc atgggagaaa aagaagaca cacctaggga aattatgagt   1020
cccgcaaaag aaacatctga gaatttacg tgggcagcaa aaggaagacc taggaagatc   1080
gcatgggaga aaaagaaac acctgtaaag actggatgcg tggcaagagt aacatctaat   1140
aaaactaaag ttttggaaaa aggaagatct aagatgattg catgtcctac aaaagaatc   1199

<210> SEQ ID NO 570
<211> LENGTH: 399
<212> TYPE: PRT
<213> ORGANISM: Homo sapiens

<400> SEQUENCE: 570

Thr Lys Arg Lys Lys Thr Ile Asn Leu Asn Ile Gln Asp Ala Gln Lys
                 5                  10                  15

Arg Thr Ala Leu His Trp Ala Cys Val Asn Gly His Glu Glu Val Val
             20                  25                  30

Thr Phe Leu Val Asp Arg Lys Cys Gln Leu Asp Val Leu Asp Gly Glu
         35                  40                  45

His Arg Thr Pro Leu Met Lys Ala Leu Gln Cys His Gln Glu Ala Cys
     50                  55                  60

Ala Asn Ile Leu Ile Asp Ser Gly Ala Asp Ile Asn Leu Val Asp Val
 65                  70                  75                  80

Tyr Gly Asn Met Ala Leu His Tyr Ala Val Tyr Ser Glu Ile Leu Ser
                 85                  90                  95

Val Val Ala Lys Leu Leu Ser His Gly Ala Val Ile Glu Val His Asn
            100                 105                 110

Lys Ala Ser Leu Thr Pro Leu Leu Leu Ser Ile Thr Lys Arg Ser Glu
        115                 120                 125

Gln Ile Val Glu Phe Leu Leu Ile Lys Asn Ala Asn Ala Asn Ala Val
    130                 135                 140

Asn Lys Tyr Lys Cys Thr Ala Leu Met Leu Ala Val Cys His Gly Ser
145                 150                 155                 160

Ser Glu Ile Val Gly Met Leu Leu Gln Gln Asn Val Asp Val Phe Ala
                165                 170                 175

Ala Asp Ile Cys Gly Val Thr Ala Glu His Tyr Ala Val Thr Cys Gly
            180                 185                 190
```

```
Phe His His Ile His Glu Gln Ile Met Glu Tyr Ile Arg Lys Leu Ser
            195                 200                 205

Lys Asn His Gln Asn Thr Asn Pro Glu Gly Thr Ser Ala Gly Thr Pro
210                 215                 220

Asp Glu Ala Ala Pro Leu Ala Glu Arg Thr Pro Asp Thr Ala Glu Ser
225                 230                 235                 240

Leu Val Glu Lys Thr Pro Asp Glu Ala Ala Pro Leu Val Glu Arg Thr
            245                 250                 255

Pro Asp Thr Ala Glu Ser Leu Val Glu Lys Thr Pro Asp Glu Ala Ala
            260                 265                 270

Ser Leu Val Glu Gly Thr Ser Asp Lys Ile Gln Cys Leu Glu Lys Ala
            275                 280                 285

Thr Ser Gly Lys Phe Glu Gln Ser Ala Glu Glu Thr Pro Arg Glu Ile
            290                 295                 300

Thr Ser Pro Ala Lys Glu Thr Ser Glu Lys Phe Thr Trp Pro Ala Lys
305                 310                 315                 320

Gly Arg Pro Arg Lys Ile Ala Trp Glu Lys Lys Glu Asp Thr Pro Arg
            325                 330                 335

Glu Ile Met Ser Pro Ala Lys Glu Thr Ser Glu Lys Phe Thr Trp Ala
            340                 345                 350

Ala Lys Gly Arg Pro Arg Lys Ile Ala Trp Glu Lys Lys Glu Thr Pro
            355                 360                 365

Val Lys Thr Gly Cys Val Ala Arg Val Thr Ser Asn Lys Thr Lys Val
            370                 375                 380

Leu Glu Lys Gly Arg Ser Lys Met Ile Ala Cys Pro Thr Lys Glu
385                 390                 395

<210> SEQ ID NO 571
<211> LENGTH: 247
<212> TYPE: PRT
<213> ORGANISM: Homo sapiens

<400> SEQUENCE: 571

Met Leu Ala Val Cys His Gly Ser Ser Glu Ile Val Gly Met Leu Leu
                5                   10                  15

Gln Gln Asn Val Asp Val Phe Ala Ala Asp Ile Cys Gly Val Thr Ala
            20                  25                  30

Glu His Tyr Ala Val Thr Cys Gly Phe His His Ile His Glu Gln Ile
        35                  40                  45

Met Glu Tyr Ile Arg Lys Leu Ser Lys Asn His Gln Asn Thr Asn Pro
    50                  55                  60

Glu Gly Thr Ser Ala Gly Thr Pro Asp Glu Ala Ala Pro Leu Ala Glu
65                  70                  75                  80

Arg Thr Pro Asp Thr Ala Glu Ser Leu Val Glu Lys Thr Pro Asp Glu
                85                  90                  95

Ala Ala Pro Leu Val Glu Arg Thr Pro Asp Thr Ala Glu Ser Leu Val
            100                 105                 110

Glu Lys Thr Pro Asp Glu Ala Ala Ser Leu Val Glu Gly Thr Ser Asp
        115                 120                 125

Lys Ile Gln Cys Leu Glu Lys Ala Thr Ser Gly Lys Phe Glu Gln Ser
    130                 135                 140

Ala Glu Glu Thr Pro Arg Glu Ile Thr Ser Pro Ala Lys Glu Thr Ser
145                 150                 155                 160

Glu Lys Phe Thr Trp Pro Ala Lys Gly Arg Pro Arg Lys Ile Ala Trp
```

-continued

```
                165                 170                 175
Glu Lys Lys Glu Asp Thr Pro Arg Glu Ile Met Ser Pro Ala Lys Glu
            180                 185                 190

Thr Ser Glu Lys Phe Thr Trp Ala Ala Lys Gly Arg Pro Arg Lys Ile
        195                 200                 205

Ala Trp Glu Lys Lys Glu Thr Pro Val Lys Thr Gly Cys Val Ala Arg
    210                 215                 220

Val Thr Ser Asn Lys Thr Lys Val Leu Glu Lys Gly Arg Ser Lys Met
225                 230                 235                 240

Ile Ala Cys Pro Thr Lys Glu
                245

<210> SEQ ID NO 572
<211> LENGTH: 399
<212> TYPE: PRT
<213> ORGANISM: Homo sapiens

<400> SEQUENCE: 572

Thr Lys Arg Lys Lys Thr Ile Asn Leu Asn Ile Gln Asp Ala Gln Lys
                    5                  10                  15

Arg Thr Ala Leu His Trp Ala Cys Val Asn Gly His Glu Glu Val Val
                20                  25                  30

Thr Phe Leu Val Asp Arg Lys Cys Gln Pro Asp Val Leu Asp Gly Glu
            35                  40                  45

His Arg Thr Pro Leu Met Lys Ala Leu Gln Cys His Gln Glu Ala Cys
        50                  55                  60

Ala Asn Ile Leu Ile Asp Ser Gly Ala Asp Ile Asn Leu Val Asp Val
65                  70                  75                  80

Tyr Gly Asn Met Ala Leu His Tyr Ala Val Tyr Ser Glu Ile Leu Ser
                85                  90                  95

Val Val Ala Lys Leu Leu Ser His Gly Ala Val Ile Glu Val His Asn
                100                 105                 110

Lys Ala Ser Leu Thr Pro Leu Leu Leu Ser Ile Thr Lys Arg Ser Glu
            115                 120                 125

Gln Ile Val Glu Phe Leu Leu Ile Lys Asn Ala Asn Ala Asn Ala Val
        130                 135                 140

Asn Lys Tyr Lys Cys Thr Ala Leu Met Leu Ala Val Cys His Gly Leu
145                 150                 155                 160

Ser Glu Ile Val Gly Met Leu Leu Gln Gln Asn Val Asp Val Phe Ala
                165                 170                 175

Ala Asp Ile Cys Gly Val Thr Ala Glu His Tyr Ala Val Thr Cys Gly
            180                 185                 190

Phe His His Ile His Glu Gln Ile Met Glu Tyr Ile Arg Lys Leu Ser
        195                 200                 205

Lys Asn His Gln Asn Thr Asn Pro Glu Gly Thr Ser Ala Gly Thr Pro
    210                 215                 220

Asp Glu Ala Ala Pro Leu Ala Glu Arg Thr Pro Asp Thr Ala Glu Ser
225                 230                 235                 240

Leu Val Glu Lys Thr Pro Asp Glu Ala Ala Pro Leu Val Glu Arg Thr
                245                 250                 255

Pro Asp Thr Ala Glu Ser Leu Val Glu Lys Thr Pro Asp Glu Ala Ala
            260                 265                 270

Ser Leu Val Glu Gly Thr Ser Asp Lys Ile Gln Cys Leu Glu Lys Ala
        275                 280                 285
```

```
Thr Ser Gly Lys Phe Glu Gln Ser Ala Glu Glu Thr Pro Arg Glu Ile
        290                 295                 300

Thr Ser Pro Ala Lys Glu Thr Ser Glu Lys Phe Thr Trp Pro Ala Lys
305                 310                 315                 320

Gly Arg Pro Arg Lys Ile Ala Trp Glu Lys Lys Glu Asp Thr Pro Arg
                325                 330                 335

Glu Ile Met Ser Pro Ala Lys Glu Thr Ser Glu Lys Phe Thr Trp Ala
            340                 345                 350

Ala Lys Gly Arg Pro Arg Lys Ile Ala Trp Glu Lys Lys Glu Thr Pro
        355                 360                 365

Val Lys Thr Gly Cys Val Ala Arg Val Thr Ser Asn Lys Thr Lys Val
370                 375                 380

Leu Glu Lys Gly Arg Ser Lys Met Ile Ala Cys Pro Thr Lys Glu
385                 390                 395

<210> SEQ ID NO 573
<211> LENGTH: 1349
<212> TYPE: PRT
<213> ORGANISM: Homo sapiens

<400> SEQUENCE: 573

Met Gln His His His His His His Thr Lys Arg Lys Lys Thr Ile
                5                  10                  15

Asn Leu Asn Ile Gln Asp Ala Gln Lys Arg Thr Ala Leu His Trp Ala
            20                  25                  30

Cys Val Asn Gly His Glu Glu Val Val Thr Phe Leu Val Asp Arg Lys
        35                  40                  45

Cys Gln Pro Asp Val Leu Asp Gly Glu His Arg Thr Pro Leu Met Lys
    50                  55                  60

Ala Leu Gln Cys His Gln Glu Ala Cys Ala Asn Ile Leu Ile Asp Ser
65                  70                  75                  80

Gly Ala Asp Ile Asn Leu Val Asp Val Tyr Gly Asn Met Ala Leu His
                85                  90                  95

Tyr Ala Val Tyr Ser Glu Ile Leu Ser Val Val Ala Lys Leu Leu Ser
            100                 105                 110

His Gly Ala Val Ile Glu Val His Asn Lys Ala Ser Leu Thr Pro Leu
        115                 120                 125

Leu Leu Ser Ile Thr Lys Arg Ser Glu Gln Ile Val Glu Phe Leu Leu
    130                 135                 140

Ile Lys Asn Ala Asn Ala Asn Ala Val Asn Lys Tyr Lys Cys Thr Ala
145                 150                 155                 160

Leu Met Leu Ala Val Cys His Gly Leu Ser Glu Ile Val Gly Met Leu
                165                 170                 175

Leu Gln Gln Asn Val Asp Val Phe Ala Ala Asp Ile Cys Gly Val Thr
            180                 185                 190

Ala Glu His Tyr Ala Val Thr Cys Gly Phe His His Ile His Glu Gln
        195                 200                 205

Ile Met Glu Tyr Ile Arg Lys Leu Ser Lys Asn His Gln Asn Thr Asn
    210                 215                 220

Pro Glu Gly Thr Ser Ala Gly Thr Pro Asp Glu Ala Ala Pro Leu Ala
225                 230                 235                 240

Glu Arg Thr Pro Asp Thr Ala Glu Ser Leu Val Lys Thr Pro Asp
                245                 250                 255

Glu Ala Ala Pro Leu Val Glu Arg Thr Pro Asp Thr Ala Glu Ser Leu
            260                 265                 270
```

```
Val Glu Lys Thr Pro Asp Glu Ala Ala Ser Leu Val Glu Gly Thr Ser
        275                 280                 285
Asp Lys Ile Gln Cys Leu Glu Lys Ala Thr Ser Gly Lys Phe Glu Gln
290                 295                 300
Ser Ala Glu Glu Thr Pro Arg Glu Ile Thr Ser Pro Ala Lys Glu Thr
305                 310                 315                 320
Ser Glu Lys Phe Thr Trp Pro Ala Lys Gly Arg Pro Arg Lys Ile Ala
                325                 330                 335
Trp Glu Lys Lys Glu Asp Thr Pro Arg Glu Ile Met Ser Pro Ala Lys
            340                 345                 350
Glu Thr Ser Glu Lys Phe Thr Trp Ala Ala Lys Gly Arg Pro Arg Lys
        355                 360                 365
Ile Ala Trp Glu Lys Lys Glu Thr Pro Val Lys Thr Gly Cys Val Ala
        370                 375                 380
Arg Val Thr Ser Asn Lys Thr Lys Val Leu Glu Lys Gly Arg Ser Lys
385                 390                 395                 400
Met Ile Ala Cys Pro Thr Lys Glu Ser Thr Lys Ala Ser Ala Asn
                405                 410                 415
Asp Gln Arg Phe Pro Ser Glu Ser Lys Gln Glu Asp Glu Glu Tyr
                420                 425                 430
Ser Cys Asp Ser Arg Ser Leu Phe Glu Ser Ser Ala Lys Ile Gln Val
                435                 440                 445
Cys Ile Pro Glu Ser Ile Tyr Gln Lys Val Met Glu Ile Asn Arg Glu
        450                 455                 460
Val Glu Glu Pro Pro Lys Lys Pro Ser Ala Phe Lys Pro Ala Ile Glu
465                 470                 475                 480
Met Gln Asn Ser Val Pro Asn Lys Ala Phe Glu Leu Lys Asn Glu Gln
                485                 490                 495
Thr Leu Arg Ala Asp Pro Met Phe Pro Pro Glu Ser Lys Gln Lys Asp
                500                 505                 510
Tyr Glu Glu Asn Ser Trp Asp Ser Glu Ser Leu Cys Glu Thr Val Ser
                515                 520                 525
Gln Lys Asp Val Cys Leu Pro Lys Ala Thr His Gln Lys Glu Ile Asp
                530                 535                 540
Lys Ile Asn Gly Lys Leu Glu Glu Ser Pro Asn Lys Asp Gly Leu Leu
545                 550                 555                 560
Lys Ala Thr Cys Gly Met Lys Val Ser Ile Pro Thr Lys Ala Leu Glu
                565                 570                 575
Leu Lys Asp Met Gln Thr Phe Lys Ala Glu Pro Pro Gly Lys Pro Ser
                580                 585                 590
Ala Phe Glu Pro Ala Thr Glu Met Gln Lys Ser Val Pro Asn Lys Ala
                595                 600                 605
Leu Glu Leu Lys Asn Glu Gln Thr Trp Arg Ala Asp Glu Ile Leu Pro
                610                 615                 620
Ser Glu Ser Lys Gln Lys Asp Tyr Glu Glu Asn Ser Trp Asp Thr Glu
625                 630                 635                 640
Ser Leu Cys Glu Thr Val Ser Gln Lys Asp Val Cys Leu Pro Lys Ala
                645                 650                 655
Ala His Gln Lys Glu Ile Asp Lys Ile Asn Gly Lys Leu Glu Gly Ser
                660                 665                 670
Pro Val Lys Asp Gly Leu Leu Lys Ala Asn Cys Gly Met Lys Val Ser
                675                 680                 685
```

-continued

Ile Pro Thr Lys Ala Leu Glu Leu Met Asp Met Gln Thr Phe Lys Ala
    690                 695                 700
Glu Pro Pro Glu Lys Pro Ser Ala Phe Glu Pro Ala Ile Glu Met Gln
705                 710                 715                 720
Lys Ser Val Pro Asn Lys Ala Leu Glu Leu Lys Asn Glu Gln Thr Leu
                725                 730                 735
Arg Ala Asp Glu Ile Leu Pro Ser Glu Ser Lys Gln Lys Asp Tyr Glu
            740                 745                 750
Glu Ser Ser Trp Asp Ser Glu Ser Leu Cys Glu Thr Val Ser Gln Lys
        755                 760                 765
Asp Val Cys Leu Pro Lys Ala Thr His Gln Lys Glu Ile Asp Lys Ile
    770                 775                 780
Asn Gly Lys Leu Glu Glu Ser Pro Asp Asn Asp Gly Phe Leu Lys Ala
785                 790                 795                 800
Pro Cys Arg Met Lys Val Ser Ile Pro Thr Lys Ala Leu Glu Leu Met
                805                 810                 815
Asp Met Gln Thr Phe Lys Ala Glu Pro Pro Glu Lys Pro Ser Ala Phe
            820                 825                 830
Glu Pro Ala Ile Glu Met Gln Lys Ser Val Pro Asn Lys Ala Leu Glu
        835                 840                 845
Leu Lys Asn Glu Gln Thr Leu Arg Ala Asp Gln Met Phe Pro Ser Glu
    850                 855                 860
Ser Lys Gln Lys Lys Val Glu Glu Asn Ser Trp Asp Ser Glu Ser Leu
865                 870                 875                 880
Arg Glu Thr Val Ser Gln Lys Asp Val Cys Val Pro Lys Ala Thr His
                885                 890                 895
Gln Lys Glu Met Asp Lys Ile Ser Gly Lys Leu Glu Asp Ser Thr Ser
            900                 905                 910
Leu Ser Lys Ile Leu Asp Thr Val His Ser Cys Glu Arg Ala Arg Glu
        915                 920                 925
Leu Gln Lys Asp His Cys Glu Gln Arg Thr Gly Lys Met Glu Gln Met
    930                 935                 940
Lys Lys Lys Phe Cys Val Leu Lys Lys Lys Leu Ser Glu Ala Lys Glu
945                 950                 955                 960
Ile Lys Ser Gln Leu Glu Asn Gln Lys Val Lys Trp Glu Gln Glu Leu
                965                 970                 975
Cys Ser Val Arg Leu Thr Leu Asn Gln Glu Glu Glu Lys Arg Arg Asn
            980                 985                 990
Ala Asp Ile Leu Asn Glu Lys Ile Arg Glu Glu Leu Gly Arg Ile Glu
        995                 1000                1005
Glu Gln His Arg Lys Glu Leu Glu Val Lys Gln Gln Leu Glu Gln Ala
    1010                1015                1020
Leu Arg Ile Gln Asp Ile Glu Leu Lys Ser Val Glu Ser Asn Leu Asn
1025                1030                1035                1040
Gln Val Ser His Thr His Glu Asn Glu Asn Tyr Leu Leu His Glu Asn
                1045                1050                1055
Cys Met Leu Lys Lys Glu Ile Ala Met Leu Lys Leu Glu Ile Ala Thr
            1060                1065                1070
Leu Lys His Gln Tyr Gln Glu Lys Glu Asn Lys Tyr Phe Glu Asp Ile
        1075                1080                1085
Lys Ile Leu Lys Glu Lys Asn Ala Glu Leu Gln Met Thr Leu Lys Leu
    1090                1095                1100
Lys Glu Glu Ser Leu Thr Lys Arg Ala Ser Gln Tyr Ser Gly Gln Leu

-continued

```
              1105                1110                1115                1120
Lys Val Leu Ile Ala Glu Asn Thr Met Leu Thr Ser Lys Leu Lys Glu
                    1125                1130                1135
Lys Gln Asp Lys Glu Ile Leu Glu Ala Glu Ile Glu Ser His His Pro
            1140                1145                1150
Arg Leu Ala Ser Ala Val Gln Asp His Asp Gln Ile Val Thr Ser Arg
        1155                1160                1165
Lys Ser Gln Glu Pro Ala Phe His Ile Ala Gly Asp Ala Cys Leu Gln
    1170                1175                1180
Arg Lys Met Asn Val Asp Val Ser Ser Thr Ile Tyr Asn Asn Glu Val
1185                1190                1195                1200
Leu His Gln Pro Leu Ser Glu Ala Gln Arg Lys Ser Lys Ser Leu Lys
                    1205                1210                1215
Ile Asn Leu Asn Tyr Ala Gly Asp Ala Leu Arg Glu Asn Thr Leu Val
            1220                1225                1230
Ser Glu His Ala Gln Arg Asp Gln Arg Glu Thr Gln Cys Gln Met Lys
        1235                1240                1245
Glu Ala Glu His Met Tyr Gln Asn Glu Gln Asp Asn Val Asn Lys His
    1250                1255                1260
Thr Glu Gln Gln Glu Ser Leu Asp Gln Lys Leu Phe Gln Leu Gln Ser
1265                1270                1275                1280
Lys Asn Met Trp Leu Gln Gln Gln Leu Val His Ala His Lys Lys Ala
                    1285                1290                1295
Asp Asn Lys Ser Lys Ile Thr Ile Asp Ile His Phe Leu Glu Arg Lys
            1300                1305                1310
Met Gln His His Leu Leu Lys Glu Lys Asn Glu Glu Ile Phe Asn Tyr
        1315                1320                1325
Asn Asn His Leu Lys Asn Arg Ile Tyr Gln Tyr Glu Lys Glu Lys Ala
    1330                1335                1340
Glu Thr Glu Val Ile
1345

<210> SEQ ID NO 574
<211> LENGTH: 24
<212> TYPE: DNA
<213> ORGANISM: Artificial Sequence
<220> FEATURE:
<223> OTHER INFORMATION: PCR primer

<400> SEQUENCE: 574
cacacaaaga ggaagaagac catc                                          24

<210> SEQ ID NO 575
<211> LENGTH: 27
<212> TYPE: DNA
<213> ORGANISM: Artificial Sequence
<220> FEATURE:
<223> OTHER INFORMATION: PCR primer

<400> SEQUENCE: 575
gattcttttg taggacatgc aatcatc                                       27

<210> SEQ ID NO 576
<211> LENGTH: 3720
<212> TYPE: DNA
<213> ORGANISM: Homo sapiens
<220> FEATURE:
<221> NAME/KEY: misc_feature
<222> LOCATION: 1149
```

<223> OTHER INFORMATION: n = A,T,C or G

<400> SEQUENCE: 576

```
atggtggcaa cactgctgtc ctatggtgca gtcatcgagg tgcaaaacaa ggctagcctc      60
acacccctttt tactggccat acagaaaaga agcaagcaaa ctgtggaatt tttactaaca    120
aaaaatgcaa atgcaaacgc atttaatgag tctaaatgca cagccctcat gcttgccata    180
tgtgaaggct catcagagat agtcggcatg cttcttcagc aaaatgttga cgtctttgct    240
gaagacatac atggaataac tgcagaacgt tatgctgctg ctcgtggagt taattacatt    300
catcaacaac ttttggaaca tatacgaaaa ttacctaaaa atcctcaaaa taccaatcca    360
gaaggaacat ctacaggaac acctgatgag gctgcaccct tggcggaaag aacacctgac    420
acggctgaaa gcttgctgga aaaacacct gacgaggctg cacgcttggt ggagggaacg    480
tctgccaaaa ttcaatgtct ggggaaagca acatctggaa agtttgaaca gtcaacagaa    540
gaaacaccta ggaaaattttt gaggcctaca aagaaacat ctgagaaatt ttcatggcca    600
gcaaaagaaa gatctaggaa gatcacatgg gaggaaaaag aaacatctgt aaagactgaa    660
tgcgtggcag gagtaacacc taataaaact gaagttttgg aaaaaggaac atctaatatg    720
attgcatgtc ctacaaaaga aacatctaca aaagcaagta caaatgtgga tgtgagttct    780
gtagagccta tattcagtct tttttggcaca cggactattg aaaattcaca gtgtacaaaa    840
gttgaggaag actttaatct tgctaccaag attatctcta agagtgctgc acagaattat    900
acgtgtttac ctgatgctac atatcaaaaa gatatcaaaa caataaatca caaaatagaa    960
gatcagatgt tcccatcaga atccaaacga gaggaagatg aagaatattc ttgggattct   1020
gggagtctct ttgagagttc tgcaaagact caagtgtgta tacctgagtc tatgtatcag   1080
aaagtaatgg agataaatag agaagtagaa gagcttcctg agaagccatc tgccttcaag   1140
cctgccgtng aaatgcaaaa gactgttcca aataaagcct ttgaattgaa gaatgaacaa   1200
acattgagag cagctcagat gttcccatca gaatccaaac aaaaggacga tgaagaaaat   1260
tcttgggatt ctgagagtcc ctgtgagacg gtttcacaga aggatgtgta tttacccaaa   1320
gctacacatc aaaaagaatt cgataccta agtggaaaat tagaagagtc tcctgttaaa   1380
gatggtcttc tgaagcctac ctgtggaagg aaagtttctc ttccaaataa agccttagaa   1440
ttaaaggaca gagaaacatt caaagcagag tctcctgata agatggtct tctgaagcct   1500
acctgtggaa ggaaagtttc tcttccaaat aaagccttag aattaaagga cagagaaaca   1560
ctcaaagcag agtctcctga taatgatggt cttctgaagc taccttgtgg aaggaaagtt   1620
tctcttccaa ataaagcttt agaattgaag gacagagaaa cattcaaagc agctcagatg   1680
ttcccatcag aatccaaaca aaaggatgat gaagaaaatt cttgggattt tgagagtttc   1740
cttgagactc tcttacagaa tgatgtgtgt ttacccaagg ctacacatca aaaagaattc   1800
gataccttaa gtgaaaatt agaagagtct cctgataag atggtcttct gaagcctacc   1860
tgtggaatga aaatttctct tccaaataaa gccttagaat tgaaggacag agaaacattc   1920
aaagcagagg atgtgagttc tgtagagtcc acattcagtc ttttttggcaa accgactact   1980
gaaaattcac agtctacaaa agttgaggaa gactttaatc ttactaccaa ggagggagca   2040
acaaagacag taactggaca acaggaacgt gatattggca ttattgaacg agctccacaa   2100
gatcaaacaa ataagatgcc cacatcagaa ttaggaagaa aagaagatac aaaatcaact   2160
tcagattctg agattatctc tgtgagtgat acacagaatt atgagtgttt acctgaggct   2220
acatatcaaa aagaaataaa gacaacaaat ggcaaaatag aagagtctcc tgaaaagcct   2280
```

-continued

```
tctcactttg agcctgccac tgaaatgcaa aactctgttc caaataaagg cttagaatgg    2340
aagaataaac aaacattgag agcagattca actaccctat caaaaatctt ggatgcactt    2400
ccttcttgtg aaagaggaag ggaacttaaa aaagataact gtgaacaaat tacagcaaaa    2460
atggaacaaa tgaaaaataa gttttgtgta ctacaaaagg aactgtcaga agcgaaagaa    2520
ataaaatcac agttagagaa ccaaaaagct aaatgggaac aagagctctg cagtgtgaga    2580
ttgcctttaa atcaagaaga agagaagaga agaaatgtcg atatattaaa agaaaaaatt    2640
agacccgaag agcaacttag gaaaagtta gaagtgaaac accaacttga acagactctc    2700
agaatacaag atatagaatt gaaaagtgta acaagtaatt tgaatcaggt ttctcacact    2760
catgaaagtg aaaatgatct ctttcatgaa aattgcatgt tgaaaaagga aattgccatg    2820
ctaaaactgg aagtagccac actgaaacat caacaccagg tgaaggaaaa taaatacttt    2880
gaggacatta agattttaca agaaaagaat gctgaacttc aaatgaccct aaaactgaaa    2940
cagaaaacag taacaaaaag ggcatctcag tatagagagc agcttaaagt tctgacggca    3000
gagaacacga tgctgacttc taaattgaag gaaaaacaag acaaagaaat actggagaca    3060
gaaattgaat cacaccatcc tagactggct tctgctttac aagaccatga tcaaagtgtc    3120
acatcaagaa aaaaccaaga acttgctttc cacagtgcag gagatgctcc tttgcaagga    3180
ataatgaatg ttgatgtgag taatacaata tataacaatg aggtgctcca tcaaccactt    3240
tatgaagctc aaaggaaatc caaaagccca aaaattaatc tcaattatgc aggagatgat    3300
ctaagagaaa atgcattggt ttcagaacat gcacaaagag accgatgtga acacagtgt     3360 caaatgaaga aagctgaaca catgtatcaa aatgaacaag ataatgtgga caaacacact    3420
gaacagcagg agtctctgga gcagaaatta tttcaactag aaagcaaaaa taggtggctt    3480
cgacagcaat tagtttatgc acataagaaa gttaacaaaa gcaaggtaac aattaatatt    3540
cagtttcctg agatgaaaat gcaacgtcat ctaaaagaga aaaatgagga ggtattcaat    3600
tatggtaacc atttaaaaga acgtatagat caatatgaaa aagagaaagc agaaagagaa    3660
gtaagtatca aaaatataaa atactttca aacttcctga agaaagtgg ccttggctaa     3720
```

<210> SEQ ID NO 577
<211> LENGTH: 1239
<212> TYPE: PRT
<213> ORGANISM: Homo sapiens

<400> SEQUENCE: 577

```
Met Val Ala Thr Leu Leu Ser Tyr Gly Ala Val Ile Glu Val Gln Asn
                5                  10                  15

Lys Ala Ser Leu Thr Pro Leu Leu Ala Ile Gln Lys Arg Ser Lys
             20                  25                  30

Gln Thr Val Glu Phe Leu Leu Thr Lys Asn Ala Asn Ala Asn Ala Phe
         35                  40                  45

Asn Glu Ser Lys Cys Thr Ala Leu Met Leu Ala Ile Cys Glu Gly Ser
     50                  55                  60

Ser Glu Ile Val Gly Met Leu Leu Gln Gln Asn Val Asp Val Phe Ala
 65                  70                  75                  80

Glu Asp Ile His Gly Ile Thr Ala Glu Arg Tyr Ala Ala Ala Arg Gly
                 85                  90                  95

Val Asn Tyr Ile His Gln Gln Leu Leu Glu His Ile Arg Lys Leu Pro
            100                 105                 110

Lys Asn Pro Gln Asn Thr Asn Pro Glu Gly Thr Ser Thr Gly Thr Pro
```

-continued

```
            115                 120                 125
Asp Glu Ala Ala Pro Leu Ala Glu Arg Thr Pro Asp Thr Ala Glu Ser
    130                 135                 140

Leu Leu Glu Lys Thr Pro Asp Glu Ala Ala Arg Leu Val Glu Gly Thr
145                 150                 155                 160

Ser Ala Lys Ile Gln Cys Leu Gly Lys Ala Thr Ser Gly Lys Phe Glu
                165                 170                 175

Gln Ser Thr Glu Glu Thr Pro Arg Lys Ile Leu Arg Pro Thr Lys Glu
            180                 185                 190

Thr Ser Glu Lys Phe Ser Trp Pro Ala Lys Glu Arg Ser Arg Lys Ile
        195                 200                 205

Thr Trp Glu Glu Lys Glu Thr Ser Val Lys Thr Glu Cys Val Ala Gly
    210                 215                 220

Val Thr Pro Asn Lys Thr Glu Val Leu Glu Lys Gly Thr Ser Asn Met
225                 230                 235                 240

Ile Ala Cys Pro Thr Lys Glu Thr Ser Thr Lys Ala Ser Thr Asn Val
                245                 250                 255

Asp Val Ser Ser Val Glu Pro Ile Phe Ser Leu Phe Gly Thr Arg Thr
            260                 265                 270

Ile Glu Asn Ser Gln Cys Thr Lys Val Glu Glu Asp Phe Asn Leu Ala
        275                 280                 285

Thr Lys Ile Ile Ser Lys Ser Ala Ala Gln Asn Tyr Thr Cys Leu Pro
    290                 295                 300

Asp Ala Thr Tyr Gln Lys Asp Ile Lys Thr Ile Asn His Lys Ile Glu
305                 310                 315                 320

Asp Gln Met Phe Pro Ser Glu Ser Lys Arg Glu Glu Asp Glu Glu Tyr
                325                 330                 335

Ser Trp Asp Ser Gly Ser Leu Phe Glu Ser Ser Ala Lys Thr Gln Val
            340                 345                 350

Cys Ile Pro Glu Ser Met Tyr Gln Lys Val Met Glu Ile Asn Arg Glu
        355                 360                 365

Val Glu Glu Leu Pro Glu Lys Pro Ser Ala Phe Lys Pro Ala Val Glu
    370                 375                 380

Met Gln Lys Thr Val Pro Asn Lys Ala Phe Glu Leu Lys Asn Glu Gln
385                 390                 395                 400

Thr Leu Arg Ala Ala Gln Met Phe Pro Ser Glu Ser Lys Gln Lys Asp
                405                 410                 415

Asp Glu Glu Asn Ser Trp Asp Ser Glu Ser Pro Cys Glu Thr Val Ser
            420                 425                 430

Gln Lys Asp Val Tyr Leu Pro Lys Ala Thr His Gln Lys Glu Phe Asp
        435                 440                 445

Thr Leu Ser Gly Lys Leu Glu Glu Ser Pro Val Lys Asp Gly Leu Leu
    450                 455                 460

Lys Pro Thr Cys Gly Arg Lys Val Ser Leu Pro Asn Lys Ala Leu Glu
465                 470                 475                 480

Leu Lys Asp Arg Glu Thr Phe Lys Ala Glu Ser Pro Asp Lys Asp Gly
                485                 490                 495

Leu Leu Lys Pro Thr Cys Gly Arg Lys Val Ser Leu Pro Asn Lys Ala
            500                 505                 510

Leu Glu Leu Lys Asp Arg Glu Thr Leu Lys Ala Glu Ser Pro Asp Asn
        515                 520                 525

Asp Gly Leu Leu Lys Pro Thr Cys Gly Arg Lys Val Ser Leu Pro Asn
    530                 535                 540
```

-continued

```
Lys Ala Leu Glu Leu Lys Asp Arg Glu Thr Phe Lys Ala Ala Gln Met
545                 550                 555                 560

Phe Pro Ser Glu Ser Lys Gln Lys Asp Asp Glu Asn Ser Trp Asp
                565                 570                 575

Phe Glu Ser Phe Leu Glu Thr Leu Leu Gln Asn Asp Val Cys Leu Pro
                580                 585                 590

Lys Ala Thr His Gln Lys Glu Phe Asp Thr Leu Ser Gly Lys Leu Glu
                595                 600                 605

Glu Ser Pro Asp Lys Asp Gly Leu Leu Lys Pro Thr Cys Gly Met Lys
610                 615                 620

Ile Ser Leu Pro Asn Lys Ala Leu Glu Leu Lys Asp Arg Glu Thr Phe
625                 630                 635                 640

Lys Ala Glu Asp Val Ser Ser Val Glu Ser Thr Phe Ser Leu Phe Gly
                645                 650                 655

Lys Pro Thr Thr Glu Asn Ser Gln Ser Thr Lys Val Glu Glu Asp Phe
                660                 665                 670

Asn Leu Thr Thr Lys Glu Gly Ala Thr Lys Thr Val Thr Gly Gln Gln
                675                 680                 685

Glu Arg Asp Ile Gly Ile Ile Glu Arg Ala Pro Gln Asp Gln Thr Asn
690                 695                 700

Lys Met Pro Thr Ser Glu Leu Gly Arg Lys Glu Asp Thr Lys Ser Thr
705                 710                 715                 720

Ser Asp Ser Glu Ile Ile Ser Val Ser Asp Thr Gln Asn Tyr Glu Cys
                725                 730                 735

Leu Pro Glu Ala Thr Tyr Gln Lys Glu Ile Lys Thr Thr Asn Gly Lys
                740                 745                 750

Ile Glu Glu Ser Pro Glu Lys Pro Ser His Phe Glu Pro Ala Thr Glu
                755                 760                 765

Met Gln Asn Ser Val Pro Asn Lys Gly Leu Glu Trp Lys Asn Lys Gln
                770                 775                 780

Thr Leu Arg Ala Asp Ser Thr Thr Leu Ser Lys Ile Leu Asp Ala Leu
785                 790                 795                 800

Pro Ser Cys Glu Arg Gly Arg Glu Leu Lys Lys Asp Asn Cys Glu Gln
                805                 810                 815

Ile Thr Ala Lys Met Glu Gln Met Lys Asn Lys Phe Cys Val Leu Gln
                820                 825                 830

Lys Glu Leu Ser Glu Ala Lys Glu Ile Lys Ser Gln Leu Glu Asn Gln
                835                 840                 845

Lys Ala Lys Trp Glu Gln Glu Leu Cys Ser Val Arg Leu Pro Leu Asn
850                 855                 860

Gln Glu Glu Glu Lys Arg Arg Asn Val Asp Ile Leu Lys Glu Lys Ile
865                 870                 875                 880

Arg Pro Glu Glu Gln Leu Arg Lys Lys Leu Glu Val Lys His Gln Leu
                885                 890                 895

Glu Gln Thr Leu Arg Ile Gln Asp Ile Glu Leu Lys Ser Val Thr Ser
                900                 905                 910

Asn Leu Asn Gln Val Ser His Thr His Glu Ser Glu Asn Asp Leu Phe
                915                 920                 925

His Glu Asn Cys Met Leu Lys Lys Glu Ile Ala Met Leu Lys Leu Glu
930                 935                 940

Val Ala Thr Leu Lys His Gln His Gln Val Lys Glu Asn Lys Tyr Phe
945                 950                 955                 960
```

```
Glu Asp Ile Lys Ile Leu Gln Glu Lys Asn Ala Glu Leu Gln Met Thr
                965                 970                 975
Leu Lys Leu Lys Gln Lys Thr Val Thr Lys Arg Ala Ser Gln Tyr Arg
            980                 985                 990
Glu Gln Leu Lys Val Leu Thr Ala Glu Asn Thr Met Leu Thr Ser Lys
        995                 1000                1005
Leu Lys Glu Lys Gln Asp Lys Glu Ile Leu Glu Thr Glu Ile Glu Ser
    1010                1015                1020
His His Pro Arg Leu Ala Ser Ala Leu Gln Asp His Asp Gln Ser Val
1025                1030                1035                1040
Thr Ser Arg Lys Asn Gln Glu Leu Ala Phe His Ser Ala Gly Asp Ala
                1045                1050                1055
Pro Leu Gln Gly Ile Met Asn Val Asp Val Ser Asn Thr Ile Tyr Asn
            1060                1065                1070
Asn Glu Val Leu His Gln Pro Leu Tyr Glu Ala Gln Arg Lys Ser Lys
        1075                1080                1085
Ser Pro Lys Ile Asn Leu Asn Tyr Ala Gly Asp Asp Leu Arg Glu Asn
    1090                1095                1100
Ala Leu Val Ser Glu His Ala Gln Arg Asp Arg Cys Glu Thr Gln Cys
1105                1110                1115                1120
Gln Met Lys Lys Ala Glu His Met Tyr Gln Asn Glu Gln Asp Asn Val
                1125                1130                1135
Asp Lys His Thr Glu Gln Gln Glu Ser Leu Glu Gln Lys Leu Phe Gln
            1140                1145                1150
Leu Glu Ser Lys Asn Arg Trp Leu Arg Gln Gln Leu Val Tyr Ala His
        1155                1160                1165
Lys Lys Val Asn Lys Ser Lys Val Thr Ile Asn Ile Gln Phe Pro Glu
    1170                1175                1180
Met Lys Met Gln Arg His Leu Lys Glu Lys Asn Glu Glu Val Phe Asn
1185                1190                1195                1200
Tyr Gly Asn His Leu Lys Glu Arg Ile Asp Gln Tyr Glu Lys Glu Lys
                1205                1210                1215
Ala Glu Arg Glu Val Ser Ile Lys Lys Tyr Lys Tyr Phe Ser Asn Phe
            1220                1225                1230
Leu Lys Glu Ser Gly Leu Gly
        1235

<210> SEQ ID NO 578
<211> LENGTH: 20
<212> TYPE: PRT
<213> ORGANISM: Homo sapiens

<400> SEQUENCE: 578

Lys Asn Glu Glu Ile Phe Asn Tyr Asn Asn His Leu Lys Asn Arg Ile
                5                   10                  15
Tyr Gln Tyr Glu
            20

<210> SEQ ID NO 579
<211> LENGTH: 20
<212> TYPE: PRT
<213> ORGANISM: Homo sapiens

<400> SEQUENCE: 579

Glu Gln Asp Asn Val Asn Lys His Thr Glu Gln Gln Glu Ser Leu Asp
                5                   10                  15
```

Gln Lys Leu Phe
          20

<210> SEQ ID NO 580
<211> LENGTH: 20
<212> TYPE: PRT
<213> ORGANISM: Homo sapiens

<400> SEQUENCE: 580

Thr Glu Gln Gln Glu Ser Leu Asp Gln Lys Leu Phe Gln Leu Gln Ser
                5                   10                  15

Lys Asn Met Trp
          20

<210> SEQ ID NO 581
<211> LENGTH: 20
<212> TYPE: PRT
<213> ORGANISM: Homo sapiens

<400> SEQUENCE: 581

Lys Glu Glu Ser Leu Thr Lys Arg Ala Ser Gln Tyr Ser Gly Gln Leu
                5                   10                  15

Lys Val Leu Ile
          20

<210> SEQ ID NO 582
<211> LENGTH: 20
<212> TYPE: PRT
<213> ORGANISM: Homo sapiens

<400> SEQUENCE: 582

Ile Ala Gly Asp Ala Cys Leu Gln Arg Lys Met Asn Val Asp Val Ser
                5                   10                  15

Ser Thr Ile Tyr
          20

<210> SEQ ID NO 583
<211> LENGTH: 20
<212> TYPE: PRT
<213> ORGANISM: Homo sapiens

<400> SEQUENCE: 583

Arg Lys Met Asn Val Asp Val Ser Ser Thr Ile Tyr Asn Asn Glu Val
                5                   10                  15

Leu His Gln Pro
          20

<210> SEQ ID NO 584
<211> LENGTH: 20
<212> TYPE: PRT
<213> ORGANISM: Homo sapiens

<400> SEQUENCE: 584

Met Gly Thr Arg Ala Leu Gln Cys Glu Val Ser His Thr His Glu Asn
                5                   10                  15

Glu Asn Tyr Leu
          20

<210> SEQ ID NO 585
<211> LENGTH: 20
<212> TYPE: PRT
<213> ORGANISM: Homo sapiens -continued

```
<400> SEQUENCE: 585

Glu Val Ser His Thr His Glu Asn Glu Asn Tyr Leu Leu His Glu Asn
                 5                  10                  15

Cys Met Leu Lys
         20

<210> SEQ ID NO 586
<211> LENGTH: 20
<212> TYPE: PRT
<213> ORGANISM: Homo sapiens

<400> SEQUENCE: 586

Glu Asn Tyr Leu Leu His Glu Asn Leu Met Leu Lys Lys Glu Ile Ala
                 5                  10                  15

Met Leu Lys Leu
         20

<210> SEQ ID NO 587
<211> LENGTH: 21
<212> TYPE: PRT
<213> ORGANISM: Homo sapiens

<400> SEQUENCE: 587

Asn Cys Met Leu Lys Lys Glu Ile Ala Met Leu Lys Leu Glu Ile Ala
                 5                  10                  15

Thr Leu Lys His Gln
         20

<210> SEQ ID NO 588
<211> LENGTH: 20
<212> TYPE: PRT
<213> ORGANISM: Homo sapiens

<400> SEQUENCE: 588

Met Leu Thr Ser Lys Leu Lys Glu Lys Gln Asp Lys Glu Ile Leu Glu
                 5                  10                  15

Ala Glu Ile Glu
         20

<210> SEQ ID NO 589
<211> LENGTH: 20
<212> TYPE: PRT
<213> ORGANISM: Homo sapiens

<400> SEQUENCE: 589

Lys Gln Asp Lys Glu Ile Leu Glu Ala Glu Ile Glu Ser His His Pro
                 5                  10                  15

Arg Leu Ala Ser
         20

<210> SEQ ID NO 590
<211> LENGTH: 20
<212> TYPE: PRT
<213> ORGANISM: Homo sapiens

<400> SEQUENCE: 590

Ala Glu Ile Glu Ser His His Pro Arg Leu Ala Ser Ala Val Gln Asp
                 5                  10                  15

His Asp Gln Ile
         20
```

```
<210> SEQ ID NO 591
<211> LENGTH: 20
<212> TYPE: PRT
<213> ORGANISM: Homo sapiens

<400> SEQUENCE: 591

Arg Leu Ala Ser Ala Val Gln Asp His Asp Gln Ile Val Thr Ser Arg
                 5                  10                  15

Lys Ser Gln Glu
            20

<210> SEQ ID NO 592
<211> LENGTH: 20
<212> TYPE: PRT
<213> ORGANISM: Homo sapiens

<400> SEQUENCE: 592

His Asp Gln Ile Val Thr Ser Arg Lys Ser Gln Glu Pro Ala Phe His
                 5                  10                  15

Ile Ala Gly Asp
            20

<210> SEQ ID NO 593
<211> LENGTH: 20
<212> TYPE: PRT
<213> ORGANISM: Homo sapiens

<400> SEQUENCE: 593

Lys Ser Gln Glu Pro Ala Phe His Ile Ala Gly Asp Ala Cys Leu Gln
                 5                  10                  15

Arg Lys Met Asn
            20
```